(12) United States Patent
Fisher et al.

(10) Patent No.: US 11,285,158 B2
(45) Date of Patent: Mar. 29, 2022

(54) USES OF PYRIMIDOPYRIMIDINONES AS SIK INHIBITORS

(71) Applicants: The General Hospital Corporation, Boston, MA (US); Dana-Farber Cancer Institute, Inc., Boston, MA (US)

(72) Inventors: David E. Fisher, Newton, MA (US); Nisma Mujahid, Spencerport, NY (US); Ryo Murakami, Tokyo (JP); Nathanael S. Gray, Boston, MA (US); Yanke Liang, Belmont, MA (US); Hwan Geun Choi, Chestnut Hill, MA (US)

(73) Assignees: The General Hospital Corporation, Boston, MA (US); Dana-Farber Cancer Institute, Inc., Boston, MA (US)

( * ) Notice: Subject to any disclaimer, the term of this patent is extended or adjusted under 35 U.S.C. 154(b) by 70 days.

(21) Appl. No.: 16/489,462

(22) PCT Filed: Feb. 28, 2018

(86) PCT No.: PCT/US2018/020335
§ 371 (c)(1),
(2) Date: Aug. 28, 2019

(87) PCT Pub. No.: WO2018/160774
PCT Pub. Date: Sep. 7, 2018

(65) Prior Publication Data
US 2020/0253981 A1    Aug. 13, 2020

Related U.S. Application Data

(60) Provisional application No. 62/472,468, filed on Mar. 16, 2017, provisional application No. 62/464,675, filed on Feb. 28, 2017.

(51) Int. Cl.
*A61K 31/5377* (2006.01)
*A61K 31/519* (2006.01)
(Continued)

(52) U.S. Cl.
CPC ........ *A61K 31/5377* (2013.01); *A61K 31/519* (2013.01); *A61P 17/00* (2018.01); *A61P 35/00* (2018.01)

(58) Field of Classification Search
CPC ............... A61K 31/505; A61K 31/519; A61K 31/5377; A61K 31/5365; A61K 9/0014
See application file for complete search history.

(56) References Cited

U.S. PATENT DOCUMENTS 6,150,373 A    11/2000 Harris et al.
6,217,875 B1    4/2001 Murai et al.
(Continued)

FOREIGN PATENT DOCUMENTS

CN    104 482 860 A    4/2015
EP    1 544 295 A1    6/2005
(Continued)

OTHER PUBLICATIONS

B. Rodriguez-Spong et al. (Advanced Drug Delivery Reviews, 2004, 56, p. 263).*
(Continued)

*Primary Examiner* — Valerie Rodriguez-Garcia
(74) *Attorney, Agent, or Firm* — Burns & Levinson, LLP; Daniel W. Clarke

(57) ABSTRACT

The present disclosure provides methods of increasing skin pigmentation in a subject in need thereof using salt-inducible kinase (SIK) inhibitors, such as macrocyclic compounds of Formula (I), bicyclic urea compounds of Formula (II), (III), and (IV), and compounds of Formula (V), (VI), (VI-A), or (VII). Also provided are pharmaceutical compositions, methods, and uses that include or involve a compound described herein.

(Continued)

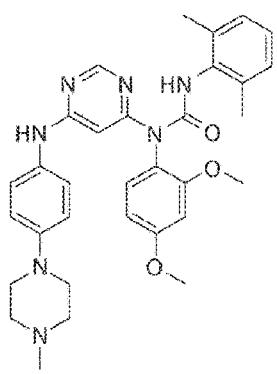

HG-9-91-01
SIK1/2/3: 4.29/4.02/8.37 nM

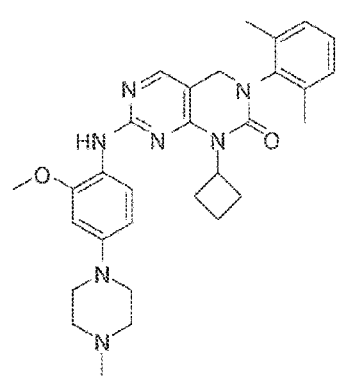

YKL-06-061
SIK1/2/3: 6.56/1.77/20.5 nM

YKL-06-062
SIK1/2/3: 2.12/1.40/2.86

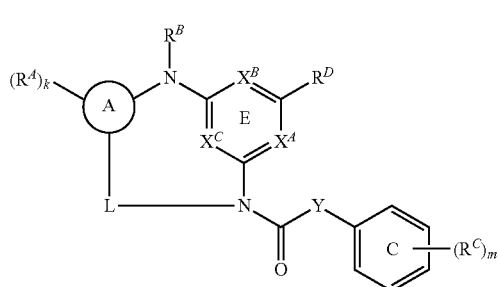

(I)

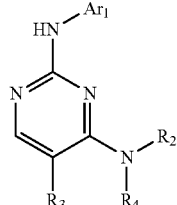

(VI-A)

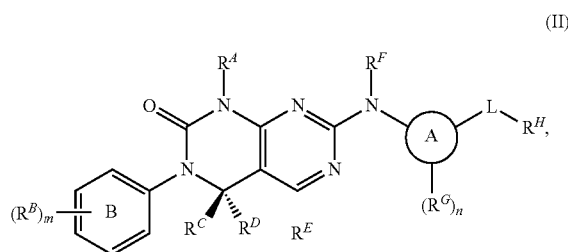

(II)

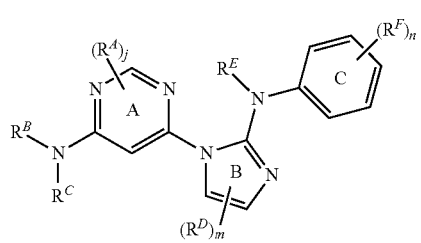

(VII)

47 Claims, 30 Drawing Sheets

Specification includes a Sequence Listing.

(III)

(51) Int. Cl.
A61P 17/00 (2006.01)
A61P 35/00 (2006.01)

(56) References Cited

U.S. PATENT DOCUMENTS (IV)

(V)

(VI)

| | | |
|---|---|---|
| 6,451,804 B1 | 9/2002 | Dunn et al. |
| 7,084,270 B2 | 8/2006 | Chen et al. |
| 7,112,676 B2 | 9/2006 | Dermatakis et al. |
| 7,312,225 B2 | 12/2007 | Luecking et al. |
| 8,921,336 B2 | 12/2014 | Gray et al. |
| 9,586,936 B2 | 3/2017 | Sim et al. |
| 9,663,524 B2 | 5/2017 | Barrague et al. |
| 9,670,165 B2 | 6/2017 | Cohen et al. |
| 9,783,504 B2 | 10/2017 | Gray et al. |
| 9,925,188 B2 | 3/2018 | Charifson et al. |
| 10,233,157 B2 | 3/2019 | Cohen et al. |
| 10,265,321 B2 | 4/2019 | Shamji et al. |
| 10,287,268 B2 | 5/2019 | Gray et al. |
| 10,457,691 B2 | 10/2019 | Gray et al. |
| 10,954,242 B2 * | 3/2021 | Gray ............ A61P 19/00 |
| 10,975,058 B2 | 4/2021 | Gray et al. |
| 2004/0204427 A1 | 10/2004 | Chen et al. |
| 2005/0026914 A1 | 2/2005 | Buchanan et al. |
| 2005/0202001 A1 | 9/2005 | Shen et al. |
| 2006/0258687 A1 | 11/2006 | Boehm et al. |
| 2007/0225286 A1 | 9/2007 | Ren et al. |
| 2008/0221098 A1 * | 9/2008 | Sim ............ A61P 27/02 |
| | | 514/234.2 |
| 2008/0249079 A1 | 10/2008 | Chen et al. |
| 2009/0137804 A1 | 5/2009 | Ding et al. |
| 2009/0312321 A1 * | 12/2009 | Ren ............ A61P 9/12 |
| | | 514/234.5 |
| 2010/0056524 A1 | 3/2010 | McIver et al. |
| 2011/0086858 A1 | 4/2011 | Wang et al. |

(56) References Cited

U.S. PATENT DOCUMENTS

| | | | |
|---|---|---|---|
| 2011/0207711 | A1 | 8/2011 | Katz et al. |
| 2014/0296216 | A1* | 10/2014 | Ding .................... A61K 31/551 514/218 |
| 2015/0094275 | A1 | 4/2015 | Gray et al. |
| 2016/0176825 | A1* | 6/2016 | Gray ...................... A61P 35/04 514/236.5 |
| 2017/0204082 | A1 | 7/2017 | Gray et al. |
| 2017/0204116 | A1 | 7/2017 | Gray et al. |
| 2017/0224700 | A1 | 8/2017 | Shamji et al. |
| 2017/0342036 | A1 | 11/2017 | Cohen et al. |
| 2018/0221379 | A1 | 8/2018 | Shamji et al. |
| 2019/0315752 | A1 | 10/2019 | Gray et al. |
| 2019/0343842 | A1 | 11/2019 | Shamji et al. |
| 2019/0367487 | A1 | 12/2019 | Gray et al. |
| 2020/0179387 | A1 | 6/2020 | Wein et al. |
| 2020/0317675 | A9 | 10/2020 | Gray et al. |
| 2021/0147388 | A1 | 5/2021 | Gray et al. |
| 2021/0147425 | A1 | 5/2021 | Gray et al. |

FOREIGN PATENT DOCUMENTS

| | | |
|---|---|---|
| EP | 2 746 283 A1 | 6/2014 |
| JP | 2002-516327 A | 6/2002 |
| JP | 2002-528455 A | 9/2002 |
| JP | 2006-522756 A | 10/2006 |
| JP | 2007-500725 A | 1/2007 |
| JP | 2008-510690 A | 4/2008 |
| WO | WO 2000/024744 A1 | 5/2000 |
| WO | WO 2004/041821 A1 | 5/2004 |
| WO | WO 2004/041822 A1 | 5/2004 |
| WO | WO 2004/048343 A1 | 6/2004 |
| WO | WO 2004/089955 A1 | 10/2004 |
| WO | WO 2005/009443 A1 | 2/2005 |
| WO | WO 2005/009978 A1 | 2/2005 |
| WO | WO 2005/011597 A2 | 2/2005 |
| WO | WO 2005/123719 A1 | 12/2005 |
| WO | WO 2006/000420 A1 | 1/2006 |
| WO | WO 2006/024545 A1 | 3/2006 |
| WO | WO 2007/071752 A2 | 6/2007 |
| WO | WO 2007/136465 A2 | 11/2007 |
| WO | WO 2008/060248 A1 | 5/2008 |
| WO | WO 2009/073153 A2 | 6/2009 |
| WO | WO 2009/122180 A1 | 10/2009 |
| WO | WO 2009/152027 A1 | 12/2009 |
| WO | WO 2013/045653 A1 | 4/2013 |
| WO | WO 2013/074986 A1 | 5/2013 |
| WO | WO 2013/136070 A1 | 9/2013 |
| WO | WO 2014/093383 A1 | 6/2014 |
| WO | WO 2014/140313 A1 | 9/2014 |
| WO | WO 2014/144737 A1 | 9/2014 |
| WO | WO 2015/006492 A1 | 1/2015 |
| WO | WO 2016/014542 A1 | 1/2016 |
| WO | WO 2016/014551 A1 | 1/2016 |
| WO | WO 2016/023014 A2 | 2/2016 |
| WO | WO 2018/009544 A1 | 1/2018 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*
Kubinyi (3D QSAR in Drug Design: Ligand-Protein Interactions and Molecular Similarity, vol. 2-3, Springer, 1998; see p. 243).*
Wermuth, The Practice of Medicinal Chemsitry, 2d ed. (2003), 768 pages, for example p. 142.*
U.S. Appl. No. 16/333,546, filed Mar. 14, 2019, Wein et al.
PCT/US2017/040722, Oct. 18, 2017, Invitation to Pay Additional Fees.
PCT/US2017/040722, Dec. 12, 2017, International Search Report and Written Opinion.
PCT/US2017/040722, Jan. 17, 2019, International Preliminary Report on Patentability.
EP 15824907.8, Jan. 2, 2018, Extended European Search Report.
PCT/US2015/041360, Sep. 24, 2015, Invitation to Pay Additional Fees.
PCT/US2015/041360, Dec. 15, 2015, International Search Report and Written Opinion.
PCT/US2015/041360, Feb. 2, 2017, International Preliminary Report on Patentability.
EP 15824975.5, Nov. 27, 2017, Extended European Search Report.
PCT/US2015/41348, Oct. 28, 2015, International Search Report and Written Opinion.
PCT/US2015/41348, Feb. 2, 2017, International Preliminary Report on Patentability.
EP 15829427.2, Feb. 8, 2018, Partial Supplementary European Search Report.
EP 15829427.2, May 14, 2018, Extended European Search Report.
EP 19164054.9, Jul. 31, 2019, Extended European Search Report.
PCT/US2015/04438, Jan. 28, 2016, Invitation to Pay Additional Fees.
PCT/US2015/04438, Mar. 25, 2016, International Search Report and Written Opinion.
PCT/US2015/04438, Feb. 23, 2017, International Preliminary Report on Patentability.
PCT/GB2013/050618, May 17, 2013, International Search Report and Written Opinion.
PCT/GB2013/050618, Sep. 25, 2014, International Preliminary Report on Patentability.
PCT/US2018/020335, May 17, 2018, International Search Report and Written Opinion.
PCT/US2018/020335, Sep. 12, 2019, International Preliminary Report on Patentability.
PCT/US2017/051937, Dec. 28, 2017, International Search Report and Written Opinion.
PCT/US2017/051937, Mar. 28, 2019, International Preliminary Report on Patentability.
Extended European Search Report for EP 15824907.8, dated Jan. 2, 2018.
Invitation to Pay Additional Fees for PCT/US2015/041360 mailed Sep. 24, 2015.
International Search Report and Written Opinion for PCT/US2015/041360 dated Dec. 15, 2015.
International Preliminary Report on Patentability for PCT/US2015/041360 dated Feb. 2, 2017.
Extended European Search Report for EP 15824975.5, dated Nov. 27, 2017.
International Search Report and Written Opinion for PCT/US2015/41348 dated Oct. 28, 2015.
International Preliminary Report on Patentability for PCT/US2015/41348 dated Feb. 2, 2017.
Partial Supplementary European Search Report for EP 15829427.2, dated Feb. 8, 2018.
Extended European Search Report for EP 15829427.2, dated May 15, 2018.
Invitation to Pay Additional Fees for PCT/US2015/044387, mailed Jan. 28, 2016.
International Search Report and Written Opinion for PCT/US2015/044387, dated Mar. 25, 2016.
International Preliminary Report on Patentability for PCT/US2015/044387, dated Feb. 23, 2017.
International Preliminary Report on Patentability for PCT/GB2013/050618, dated Sep. 25, 2014.
International Search Report and Written Opinion for PCT/GB2013/050618, dated May 17, 2013.
Invitation to Pay Additional Fees for PCT/US2017/040722, mailed Oct. 18, 2017.
International Search Report and Written Opinion for PCT/US2017/040722, dated Dec. 12, 2017.
International Preliminary Report on Patentability for PCT/US2017/040722, dated Jan. 17, 2019.
International Search Report and Written Opinion for PCT/US2018/020335, dated May 17, 2018.
Extended European Search Report for EP 19164054.9, dated Jul. 31, 2019.

(56) References Cited

OTHER PUBLICATIONS

International Preliminary Report on Patentability for PCT/US2018/020335, dated Sep. 12, 2019.
International Search Report and Written Opinion for PCT/US2017/051937, dated Dec. 28, 2017.
International Preliminary Report on Patentability for PCT/US2017/051937, dated Mar. 28, 2019.
Altarejos et al., CREB and the CRTC co-activators: sensors for hormonal and metabolic signals. Nat Rev Mol Cell Biol. Mar. 2011;12(3):141-51. doi: 10.1038/nrm3072.
Ananieva et al., The kinases MSK1 and MSK2 act as negative regulators of Toll-like receptor signaling. Nat Immunol. Sep. 2008;9(9):1028-36. doi: 10.1038/ni.1644.
Antiga et al., Serum levels of the regulatory cytokines transforming growth factor-β and interleukin-10 are reduced in patients with discoid lupus erythematosus. Lupus. May 2011;20(6):556-60. doi: 10.1177/0961203310392424. Epub Mar. 3, 2011.
Armstrong et al., The epidemiology of UV induced skin cancer. J Photochem Photobiol B. Oct. 2001;63(1-3):8-18.
Baertschi et al., Class I and IIa histone deacetylases have opposite effects on sclerostin gene regulation. J Biol Chem. Sep. 5, 2014;289(36):24995-5009. doi: 10.1074/jbc.M114.564997. Epub Jul. 10, 2014.
Bain et al., The selectivity of protein kinase inhibitors: a further update. Biochem J. Dec. 15, 2007;408(3):297-315.
Baron et al., WNT signaling in bone homeostasis and disease: from human mutations to treatments. Nat Med. Feb. 2013;19(2):179-92. doi: 10.1038/nm.3074. Epub Feb. 6, 2013.
Benoit et al., Macrophage polarization in bacterial infections. J Immunol. Sep. 15, 2008;181(6):3733-9.
Berdesux et al., SIK1 is a class II HDAC kinase that promotes survival of skeletal myocytes. Nat Med. May 2007;13(5):597-603. Epub Apr. 29, 2007.
Bergwitz et al., Regulation of phosphate homeostasis by PTH, vitamin D, and FGF23. Annu Rev Med. 2010;61:91-104. doi: 10.1146/annurev.med.051308.111339.
Bertolotto et al., Microphthalmia gene product as a signal transducer in cAMP-induced differentiation of melanocytes. J Cell Biol. Aug. 10, 1998;142(3):827-35.
Bettencourt-Dias et al., Genome-wide survey of protein kinases required for cell cycle progression. Nature. Dec. 23, 2004;432(7020):980-7.
Bonewald et al., The amazing osteocyte. J Bone Miner Res. Feb. 2011;26(2):229-38. doi: 10.1002/jbmr.320.
Bonnet et al., Regulation of beta catenin signaling and parathyroid hormone anabolic effects in bone by the matricellular protein periostin. Proc Natl Acad Sci U S A. Sep. 11, 2012;109(37):15048-53. doi: 10.1073/pnas.1203085109. Epub Aug. 27, 2012.
Bos et al., The 500 Dalton rule for the skin penetration of chemical compounds and drugs. Exp Dermatol. Jun. 2000;9(3):165-9.
Bouxsein et al., Guidelines for assessment of bone microstructure in rodents using micro-computed tomography. J Bone Miner Res. Jul. 2010;25(7):1468-86. doi: 10.1002/jbmr.141.
Chang et al., Histone deacetylases 5 and 9 govern responsiveness of the heart to a subset of stress signals and play redundant roles in heart development. Mol Cell Biol. Oct. 2004;24(19):8467-76.
Cheloha et al., PTH receptor-1 signalling-mechanistic insights and therapeutic prospects. Nat Rev Endocrinol. Dec. 2015;11(12):712-24. doi: 10.1038/nrendo.2015.139. Epub Aug. 25, 2015.
Clark et al., Novel cross-talk within the IKK family controls innate immunity. Biochem J. Feb. 15, 2011;434(1):93-104. doi: 10.1042/BJ20101701.
Clark et al., Phosphorylation of CRTC3 by the salt-inducible kinases controls the interconversion of classically activated and regulatory macrophages. Proc Natl Acad Sci U S A. Oct. 16, 2012;109(42):16986-91. doi: 10.1073/pnas.1215450109. Epub Oct. 2, 2012. With Supporting Information.
Clark et al., The TRAF-associated protein TANK facilitates cross-talk within the IkappaB kinase family during Toll-like receptor signaling. Proc Natl Acad Sci U S A. Oct. 11, 2011;108(41):17093-8. doi: 10.1073/pnas.1114194108. Epub Sep. 23, 2011.
Clark et al., Use of the pharmacological inhibitor BX795 to study the regulation and physiological roles of TBK1 and IkappaB kinase epsilon: a distinct upstream kinase mediates Ser-172 phosphorylation and activation. J Biol Chem. May 22, 2009;284(21):14136-46. doi: 10.1074/jbc.M109.000414. Epub Mar. 22, 2009.
Collette et al., Targeted deletion of Sost distal enhancer increases bone formation and bone mass. Proc Natl Acad Sci U S A. Aug. 28, 2012;109(35):14092-7. doi: 10.1073/pnas.1207188109. Epub Aug. 10, 2012.
Cui et al., Central role of p53 in the suntan response and pathologic hyperpigmentation. Cell. Mar. 9, 2007;128(5):853-64.
Cummings et al., Denosumab for prevention of fractures in postmenopausal women with osteoporosis. N Engl J Med. Aug. 20, 2009;361(8):756-65. doi: 10.1056/NEJMoa0809493. Epub Aug. 11, 2009.
Dempster et al., Standardized nomenclature, symbols, and units for bone histomorphometry: a 2012 update of the report of the ASBMR Histomorphometry Nomenclature Committee. J Bone Miner Res. Jan. 2013;28(1):2-17. doi: 10.1002/jbmr.1805.
Dentin et al., Insulin modulates gluconeogenesis by inhibition of the coactivator TORC2. Nature. Sep. 20, 2007;449(7160):366-9. Epub Sep. 5, 2007.
D'Orazio et al., Topical drug rescue strategy and skin protection based on the role of Mc1r in UV-induced tanning. Nature. Sep. 21, 2006;443(7109):340-4.
Ewald et al., Nucleic acid sensing Toll-like receptors in autoimmunity. Curr Opin Immunol. Feb. 2011;23(1):3-9. doi: 10.1016/j.coi.2010.11.006. Epub Dec. 14, 2010.
Eyers et al., Conversion of SB 203580-insensitive MAP kinase family members to drug-sensitive forms by a single amino-acid substitution. Chem Biol. Jun. 1998;5(6):321-8.
Fitzgerald et al., IKKepsilon and TBK1 are essential components of the IRF3 signaling pathway. Nat Immunol. May 2003;4(5):491-6.
Fleming et al., Regulatory macrophages: setting the threshold for therapy. Eur J Immunol. Sep. 2011;41(9):2498-502. doi: 10.1002/eji.201141717.
Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.
Fu et al., Parathyroid hormone controls receptor activator of NF-kappaB ligand gene expression via a distant transcriptional enhancer. Mol Cell Biol. Sep. 2006;26(17):6453-68.
Fu et al., Parathyroid hormone stimulates receptor activator of NFkappa B ligand and inhibits osteoprotegerin expression via protein kinase A activation of cAMP-response element-binding protein. J Biol Chem. Dec. 13, 2002;277(50):48868-75. Epub Oct. 2, 2002.
Fulzele et al., Myelopoiesis is regulated by osteocytes through Gsα-dependent signaling. Blood. Feb. 7, 2013;121(6):930-9. doi: 10.1182/blood-2012-06-437160. Epub Nov. 16, 2012.
Galli et al., Targeted deletion of a distant transcriptional enhancer of the receptor activator of nuclear factor-kappaB ligand gene reduces bone remodeling and increases bone mass. Endocrinology. Jan. 2008;149(1):146-53. Epub Oct. 11, 2007.
Garcia-Gomez et al., Dasatinib as a bone-modifying agent: anabolic and anti-resorptive effects. PLoS One. 2012;7(4):e34914. doi:10.1371/journal.pone.0034914. Epub Apr. 23, 2012.
Gendini et al., Meta-analysis of risk factors for cutaneous melanoma: III. Family history, actinic damage and phenotypic factors. Eur J Cancer. Sep. 2005;41(14):2040-59.
Ghoreschi et al., Janus kinases in immune cell signaling. Immunol Rev. Mar. 2009;228(1):273-87. doi: 10.1111/j.1600-065X.2008.00754.x.
Groztnger et al., Regulation of histone deacetylase 4 and 5 and transcriptional activity by 14-3-3-dependent cellular localization. Proc Natl Acad Sci U S A. Jul. 5, 2000;97(14):7835-40.
Haberland et al., Regulation of HDAC9 gene expression by MEF2 establishes a negative-feedback loop in the transcriptional circuitry of muscle differentiation. Mol Cell Biol. Jan. 2007;27(2):518-25. Epub Nov. 13, 2006.

(56) References Cited

OTHER PUBLICATIONS

Haberland et al., The many roles of histone deacetylases in development and physiology: implications for disease and therapy. Nat Rev Genet. Jan. 2009;10(1):32-42. doi: 10.1038/nrg2485.
Hadgraft et al., The selection and design of topical and transdermal agents: a review. J Investig Dermatol Symp Proc. Aug. 1998;3(2):131-5.
Hahn et al., Targeted therapies in systemic lupus erythematosus: successes, failures and future. Ann Rheum Dis. Mar. 2011;70 Suppl 1:i64-i66. doi: 10.1136/ard.2010.142208.
Harms et al., Mitigating photosensitivity of erythropoietic protoporphyria patients by an agonistic analog of alpha-melanocyte stimulating hormone. Photochem Photobiol. Nov.-Dec. 2009;85(6):1434-9. doi: 10.1111/j.1751-1097.2009.00595.x.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Hemmi et al., The roles of two IkappaB kinase-related kinases in lipopolysaccharide and double stranded RNA signaling and viral infection. J Exp Med. Jun. 21, 2004;199(12):1641-50.
Henriksson et al., SIK2 regulates CRTCs, HDAC4 and glucose uptake in adipocytes. J Cell Sci. Feb. 1, 2015;128(3):472-86.
Henriksson et al., The AMPK-related kinase SIK2 is regulated by cAMP via phosphorylation at Ser358 in adipocytes. Biochem J. Jun. 15, 2012;444(3):503-14. doi: 10.1042/BJ20111932.
Heppner et al., Immune attack: the role of inflammation in Alzheimer disease. Nat Rev Neurosci. Jun. 2015;16(6):358-72. doi: 10.1038/nrn3880.
Horike et al., Downregulation of SIK2 expression promotes the melanogenic program in mice. Pigment Cell Melanoma Res. Dec. 2010;23(6):809-19. doi: 10.1111/j.1755-148X.2010.00760.x. Epub Aug. 31, 2010.
Jansson et al., Glucose controls CREB activity in islet cells via regulated phosphorylation of TORC2. Proc Natl Acad Sci U S A. Jul. 22, 2008;105(29):10161-6. doi: 10.1073/pnas.0800796105. Epub Jul. 14, 2008.
Kantarjian et al., Dasatinib versus imatinib in newly diagnosed chronic-phase chronic myeloid leukemia. N Engl J Med. Jun. 17, 2010;362(24):2260-70.
Kawai et al., The role of pattern-recognition receptors in innate immunity: update on Toll-like receptors. Nat Immunol. May 2010;11(5):373-84. doi: 10.1038/ni.1863. Epub Apr. 20, 2010.
Keller et al., SOST is a target gene for PTH in bone. Bone. Aug. 2005;37(2):148-58.
Kennedy et al., The influence of painful sunburns and lifetime sun exposure on the risk of actinic keratoses, seborrheic warts, melanocytic nevi, atypical nevi, and skin cancer. J Invest Dermatol. Jun. 2003;120(6):1087-93.
Khaled et al., Control of melanocyte differentiation by a MITF-PDE4D3 homeostatic circuit. Genes Dev. Oct. 15, 2010;24(20):2276-81. doi: 10.1101/gad.1937710.
Kim et al., Activation of receptor activator of NF-kappaB ligand gene expression by 1,25-dihydroxyvitamin D3 is mediated through multiple long-range enhancers. Activation of receptor activator of NF-kappaB ligand gene expression by 1,25-dihydroxyvitamin D3 is mediated through multiple long-range enhancers Mol Cell Biol. Sep. 2006;26(17):6469-86.
Kim et al., An essential role for histone deacetylase 4 in synaptic plasticity and memory formation. J Neurosci. Aug. 8, 2012;32(32):10879-86. doi: 10.1523/JNEUROSCI.2089-12.2012.
Kim et al., Transcriptional control of receptor activator of nuclear factor-kappaB ligand by the protein kinase A activator forskolin and the transmembrane glycoprotein 130-activating cytokine, oncostatin M, is exerted through multiple distal enhancers. Mol Endocrinol. Jan. 2007;21(1):197-214. Epub Oct. 19, 2006.
Kir et al., Tumour-derived PTH-related protein triggers adipose tissue browning and cancer cachexia. Nature. Sep. 4, 2014;513(7516):100-4. doi: 10.1038/nature13528. Epub Jul. 13, 2014.

Kobayashi et al., Supranuclear melanin caps reduce ultraviolet induced DNA photoproducts in human epidermis. J Invest Dermatol. May 1998;110(5):806-10.
Kopf et al., Averting inflammation by targeting the cytokine environment. Nat Rev Drug Discov. Sep. 2010;9(9):703-18. doi: 10.1038/nrd2805.
Kozhemyakina et al., Parathyroid hormone-related peptide represses chondrocyte hypertrophy through a protein phosphatase 2A/histone deacetylase 4/MEF2 pathway. Mol Cell Biol. Nov. 2009;29(21):5751-62. doi: 10.1128/MCB.00415-09. Epub Aug. 24, 2009.
Kramer et al., Mef2c deletion in osteocytes results in increased bone mass. J Bone Miner Res. Feb. 2012;27(2):360-73. doi: 10.1002/jbmr.1492.
Kramer et al., Parathyroid hormone (PTH)-induced bone gain is blunted in SOST overexpressing and deficient mice. J Bone Miner Res. Feb. 2010;25(2):178-89. doi: 10.1359/jbmr.090730.
Kronenberg et al., Developmental regulation of the growth plate. Nature. May 15, 2003;423(6937):332-6.
Kuhn et al., Interleukin-10-deficient mice develop chronic enterocolitis. Cell. Oct. 22, 1993;75(2):263-74.
Kumagai et al., A potent inhibitor of SIK2, 3, 3', 7-trihydroxy-4'-methoxyflavon (4'-O-methylfisetin), promotes melanogenesis in B16F10 melanoma cells. PLoS One. 2011;6(10):e26148. doi: 10.1371/journal.pone.0026148. Epub Oct. 13, 2011.
Kunisada et al., Murine cutaneous mastocytosis and epidermal melanocytosis induced by keratinocyte expression of transgenic stem cell factor. J Exp Med. May 18, 1998; 87(10):1565-73.
Langendonk et al., Afamelanotide for Erythropoietic Protoporphyria. N Engl J Med. Jul. 2, 2015;373(1):48-59. doi: 10.1056/NEJMoa1411481.
Leupin et al., Control of the SOST bone enhancer by PTH using MEF2 transcription factors. J Bone Miner Res. Dec. 2007;22(12):1957-67.
Li et al., Lipoprotein receptor-related protein 6 is required for parathyroid hormone-induced Sost suppression. Ann N Y Acad Sci. Jan. 2016;1364:62-73. doi: 10.1111/nyas.12750. Epub Apr. 2, 2015.
Liu et al., Engineering Src family protein kinases with unnatural nucleotide specificity. Chem Biol. Feb. 1998;5(2):91-101.
Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.
Lizcano et al., LKB1 is a master kinase that activates 13 kinases of the AMPK subfamily, including MARK/PAR-1. EMBO J. Feb. 25, 2004;23(4):833-43. Epub Feb. 19, 2004.
Loots et al., Genomic deletion of a long-range bone enhancer misregulates sclerostin in Van Buchem disease. Genome Res. Jul. 2005;15(7):928-35. Epub Jun. 17, 2005.
Lu et al., DMP1-targeted Cre expression in odontoblasts and osteocytes. J Dent Res. Apr. 2007;86(4):320-5.
Maier et al., Development of N-4,6-pyrimidine-N-alkyl-N'-phenyl ureas as orally active inhibitors of lymphocyte specific tyrosine kinase. Bioorg Med Chem Lett. Jul. 15, 2006;16(14):3646-50. Epub May 8, 2006.
Mair et al., Lifespan extension induced by AMPK and calcineurin is mediated by CRTC-1 and CREB. Nature. Feb. 17, 2011;470(7334):404-8. doi: 10.1038/nature09706.
Mallison et al., Macrocycles in new drug discovery. Future Med Chem. Jul. 2012;4(11):1409-38. doi: 10.4155/fmc.12.93.
Manthey et al., JNJ-28312141, a novel orally active colony-stimulating factor-1 receptor/FMS-related receptor tyrosine kinase-3 receptor tyrosine kinase inhibitor with potential utility in solid tumors, bone metastases, and acute myeloid leukemia. Mol Cancer Ther. Nov. 2009;8(11):3151-61. doi:10.1158/1535-7163.MCT-09-0255. Epub Nov. 3, 2009.
Martin et al., Novel 2-aminopyrimidine carbamates as potent and orally active inhibitors of Lck: synthesis, SAR, and in vivo antiinflammatory activity. J Med Chem. Aug. 10, 2006;49(16):4981-91.
Martowicz et al., The mouse RANKL gene locus is defined by a broad pattern of histone H4 acetylation and regulated through distinct distal enhancers. J Cell Biochem. Aug. 2011;112(8):2030-45. doi: 10.1002/jcb.23123.

(56) References Cited

OTHER PUBLICATIONS

McClung et al., Romosozumab in postmenopausal women with low bone mineral density. N Engl J Med. Jan. 30, 2014;370(5):412-20. doi: 10.1056/NEJMoa1305224. Epub Jan. 1, 2014.

McKinsey et al., Signal-dependent nuclear export of a histone deacetylase regulates muscle differentiation. Nature. Nov. 2, 2000;408(6808):106-11.

McNulty et al., Hydrophilic interaction chromatography reduces the complexity of the phosphoproteome and improves global phosphopeptide isolation and detection. Mol Cell Proteomics. May 2008;7(5):971-80. doi: 10.1074/mcp.M700543-MCP200. Epub Jan. 22, 2008.

McWhirter et al., IFN-regulatory factor 3-dependent gene expression is defective in Tbk1-deficient mouse embryonic fibroblasts. Proc Natl Acad Sci U S A. Jan. 6, 2004;101(1):233-8. Epub Dec. 16, 2003.

Mosser et al., Interleukin-10: new perspectives on an old cytokine. Immunol Rev. Dec. 2008;226:205-18. doi: 10.1111/j.1600-065X.2008.00706.x.

Nakashima et al., Evidence for osteocyte regulation of bone homeostasis through RANKL expression. Nat Med. Sep. 11, 2011;17(10):1231-4. doi: 10.1038/nm.2452.

Navarro et al., Phosphoproteomic analysis reveals an intrinsic pathway for the regulation of histone deacetylase 7 that controls the function of cytotoxic T lymphocytes. Nat Immunol. Apr. 2011;12(4):352-61. doi: 10.1038/ni.2008. Epub Mar. 13, 2011.

Newton et al., Activation of the cAMP pathway by variant human MC1R alleles expressed in HEK and in melanoma cells. Peptides. Oct. 2005;26(10):1818-24.

Oancea et al., TRPM1 forms ion channels associated with melanin content in melanocytes. Sci Signal. May 12, 2009;2(70):ra21. doi: 10.1126/scisignal.2000146.

Obri et al., HDAC4 integrates PTH and sympathetic signaling in osteoblasts. J Cell Biol. Jun. 23, 2014;205(6):771-80. doi: 10.1083/jcb.201403138. Epub Jun. 16, 2014.

O'Garra et al., Strategies for use of IL-10 or its antagonists in human disease. Immunol Rev. Jun. 2008;223:114-31. doi: 10.1111/j.1600-065X.2008.00635.x.

Onal et al., Deletion of the Distal Tnfsf11 RL-D2 Enhancer That Contributes to PTH-Mediated RANKL Expression in Osteoblast Lineage Cells Results in a High Bone Mass Phenotype in Mice. J Bone Miner Res. Feb. 2016;31(2):416-29. doi: 10.1002/jbmr.2698.

Pacifici et al., Role of T cells in the modulation of PTH action: physiological and clinical significance. Endocrine. Dec. 2013;44(3):576-82. doi: 10.1007/s12020-013-9960-8. Epub Jun. 2, 2013.

Park et al., A long-term time course of colorimetric evaluation of ultraviolet light-induced skin reactions. Clin Exp Dermatol. Jul. 1999;24(4):315-20.

Park et al., SIK2 is critical in the regulation of lipid homeostasis and adipogenesis in vivo. Diabetes. Nov. 2014;63(11):3659-73. doi: 10.2337/db13-1423. Epub Jun. 4, 2014.

Parra et al., Regulatory signal transduction pathways for class IIa histone deacetylases. Curr Opin Pharmacol. Aug. 2010;10(4):454-60. doi: 10.1016/j.coph.2010.04.004. Epub May 4, 2010.

Patel et al., The LKB1-salt-inducible kinase pathway functions as a key gluconeogenic suppressor in the liver. Nat Commun. Aug. 4, 2014;5:4535. doi: 10.1038/ncomms5535.

Pennello et al., Association of surface ultraviolet B radiation levels with melanoma and nonmelanoma skin cancer in United States blacks. Cancer Epidemiol Biomarkers Prev. Mar. 2000;9(3):291-7.

Perry et al., Differential requirement for TANK-binding kinase-1 in type I interferon responses to toll-like receptor activation and viral infection. J Exp Med. Jun. 21, 2004;199(12):1651-8.

Pethe et al., A chemical genetic screen in Mycobacterium tuberculosis identifies carbon-source-dependent growth inhibitors devoid of in vivo efficacy. Nature Communications 2010;1:57. doi:10.1038/ncomms1060.

Pfaffl, A new mathematical model for relative quantification in real-time RT-PCR. Nucleic Acids Res. May 1, 2001;29(9):e45.

Pfeifer et al., Mutations induced by ultraviolet light. Mutat Res. Apr. 1, 2005;571(1-2):19-31. Epub Jan. 20, 2005.

Popov et al., Lack of salt-inducible kinase 2 (SIK2) prevents the development of cardiac hypertrophy in response to chronic high-salt intake. PLoS One. Apr. 21, 2014;9(4):e95771. doi: 10.1371/journal.pone.0095771. eCollection 2014.

Price et al., alpha-Melanocyte-stimulating hormone signaling regulates expression of microphthalmia, a gene deficient in Waardenburg syndrome. J Biol Chem. Dec. 4, 1998;273(49):33042-7.

Ran et al., Genome engineering using the CRISPR-Cas9 system. Nat Protoc. Nov. 2013;8(11):2281-308.doi: 10.1038/nprot.2013.143. Epub Oct. 24, 2013.

Rhee et al., PTH receptor signaling in osteocytes governs periosteal bone formation and intracortical remodeling. J Bone Miner Res. May 2011;26(5):1035-46. doi: 10.1002/jbmr.304.

Saidak et al., Low-dose PTH increases osteoblast activity via decreased Mef2c/Sost in senescent osteopenic mice. J Endocrinol. Oct. 2014;223(1):25-33. doi: 10.1530/JOE-14-0249. Epub Jul. 23, 2014.

Saini et al., Parathyroid hormone (PTH)/PTH-related peptide type 1 receptor (PPR) signaling in osteocytes regulates anabolic and catabolic skeletal responses to PTH. J Biol Chem. Jul. 12, 2013;288(28):20122-34. doi: 10.1074/jbc.M112.441360. Epub Jun. 2, 2013.

Sakamaki et al., Role of the SIK2-p35-PJA2 complex in pancreatic β-cell functional compensation. Nat Cell Biol. Mar. 2014;16(3):234-44. doi: 10.1038/ncb2919.

Santegoets et al., Toll-like receptors in rheumatic diseases: are we paying a high price for our defense against bugs? FEBS Lett. Dec. 1, 2011;585(23):3660-6. doi: 10.1016/j.febslet.2011.04.028. Epub Apr. 16, 2011.

Saraiva et al., The regulation of IL-10 production by immune cells. Nat Rev Immunol. Mar. 2010;10(3):170-81.doi: 10.1038/nri2711. Epub Feb. 15, 2010.

Sasagawa et al., SIK3 is essential for chondrocyte hypertrophy during skeletal development in mice. Development. Mar. 2012;139(6):1153-63. doi: 10.1242/dev.072652. Epub Feb. 8, 2012.

Sasaki et al., SIK2 is a key regulator for neuronal survival after ischemia via TORC1-CREB. Neuron. Jan. 13, 2011;69(1):106-19. doi: 10.1016/j.neuron.2010.12.004.

Scholz et al., A new method to customize protein expression vectors for fast, efficient and background free parallel cloning. BMC Biotechnol. Feb. 14, 2013;13:12. doi: 10.1186/1472-6750-13-12.

Screaton et al., The CREB coactivator TORC2 functions as a calcium- and cAMP-sensitive coincidence detector. Cell. Oct. 1, 2004;119(1):61-74.

Sharma et al., Triggering the interferon antiviral response through an IKK-related pathway. Science. May 16, 2003;300(5622):1148-51. Epub Apr. 17, 2003.

Shimizu et al., HDAC4 represses matrix metalloproteinase-13 transcription in osteoblastic cells, and parathyroid hormone controls this repression. J Biol Chem. Mar. 26, 2010;285(13):9616-26. doi: 10.1074/jbc.M109.094862. Epub Jan. 22, 2010.

Soriano et al., Targeted disruption of the c-src proto-oncogene leads to osteopetrosis in mice. Cell. Feb. 22, 1991;64(4):693-702.

Spatz et al., The Wnt Inhibitor Sclerostin Is Up-regulated by Mechanical Unloading in Osteocytes in Vitro. J Biol Chem. Jul. 3, 2015;290(27):16744-58. doi: 10.1074/jbc.M114.628313. Epub May 7, 2015.

St John et al., Analysis of SOST expression using large minigenes reveals the MEF2C binding site in the evolutionarily conserved region (ECR5) enhancer mediates forskolin, but not 1,25-dihydroxyvitamin D3 or TGFβ1 responsiveness. J Steroid Biochem Mol Biol. Nov. 2016;164:277-280. doi: 10.1016/j.jsbmb.2015.09.005. Epub Sep. 7, 2015.

Sundberg et al., Development of Chemical Probes for Investigation of Salt-Inducible Kinase Function in Vivo. ACS Chem Biol. Aug. 19, 2016;11(8):2105-11. doi: 10.1021/acschembio.6b00217. Epub Jun. 6, 2016.

Sundberg et al., Small-molecule screening identifies inhibition of salt-inducible kinases as a therapeutic strategy to enhance immunoregula-

(56) References Cited

OTHER PUBLICATIONS tory functions of dendritic cells. Proc Natl Acad Sci U S A. Aug. 26, 2014;111(34):12468-73. doi: 10.1073/pnas.1412308111. Epub Aug. 11, 2014.
Takemori et al., Inactivation of HDAC5 by SIK1 in AICAR-treated C2C12 myoblasts. Endocr J. 2009;56(1):121-30. Epub Oct. 22, 2008.
Taniguchi et al., Histone deacetylase 5 limits cocaine reward through cAMP-induced nuclear import. Neuron. Jan. 12, 2012;73(1):108-20. doi: 10.1016/j.neuron.2011.10.032.
Tella et al., Prevention and treatment of postmenopausal osteoporosis. J Steroid Biochem Mol Biol. Jul. 2014;142:155-70. doi:10.1016/j.jsbmb.2013.09.008. Epub Oct. 29, 2013.
Triantafillidis et al., Current and emerging drugs for the treatment of inflammatory bowel disease. Drug Des Devel Ther. Apr. 6, 2011;5:185-210. doi: 10.2147/DDDT.S11290.
Tsai et al., Teriparatide and denosumab, alone or combined, in women with postmenopausal osteoporosis: the DATA study randomised trial. Lancet. Jul. 6, 2013;382(9886):50-6. doi: 10.1016/S0140-6736(13)60856-9. Epub May 15, 2013.
Tsatmalia et al., Skin POMC peptides. Their binding affinities and activation of the human MC1 receptor. Ann N Y Acad Sci. Oct. 20, 1999;885:466-9.
Tu et al., Sost downregulation and local Wnt signaling are required for the osteogenic response to mechanical loading. Bone. Jan. 2012;50(1):209-17. doi: 10.1016/j.bone.2011.10.025. Epub Oct. 30, 2011.
Valverde et al., Variants of the melanocyte-stimulating hormone receptor gene are associated with red hair and fair skin in humans. Nat Genet. Nov. 1995;11(3):328-30.
Wakamatsu et al., Advanced chemical methods in melanin determination. Pigment Cell Res. Jun. 2002;15(3):174-83.
Walkinshaw et al., The tumor suppressor kinase LKB1 activates the downstream kinases SIK2 and SIK3 to stimulate nuclear export of class IIa histone deacetylases. J Biol Chem. Mar. 29, 2013;288(13):9345-62. doi: 10.1074/jbc.M113.456996. Epub Feb. 7, 2013.
Wang et al. Cloning of a novel kinase (SIK) of the SNF1/AMPK family from high salt diet-treated rat adrenal. FEBS Lett. Jun. 18, 1999;453(1-2):135-9.
Wang et al., A hormone-dependent module regulating energy balance. Cell. May 13, 2011;145(4):596-606. doi: 10.1016/j.cell.2011.04.013.
Wein et al., HDAC5 controls MEF2C-driven sclerostin expression in osteocytes. J Bone Miner Res. Mar. 2015;30(3):400-11. doi: 10.1002/jbmr.2381.
Weir et al., Targeted overexpression of parathyroid hormone-related peptide in chondrocytes causes chondrodysplasia and delayed endochondral bone formation. Proc Natl Acad Sci U S A. Sep. 17, 1996;93(19):10240-5.
Wu et al., Cumulative ultraviolet radiation flux in adulthood and risk of incident skin cancers in women. Br J Cancer. Apr. 2, 2014;110(7):1855-61. doi: 10.1038/bjc.2014.43. Epub Mar. 4, 2014.
Wu et al., Exploring the selectivity of PI3Kα and mTOR inhibitors by 3D-QSAR, molecular dynamics simulations and MM/GBSA binding free energy decomposition. Med. Chem. Commun., 2013;4:1482-1496. DOI: 10.1039/C3MD00157A.
Wu et al., Gsα enhances commitment of mesenchymal progenitors to the osteoblast lineage but restrains osteoblast differentiation in mice. J Clin Invest. Sep. 2011;121(9):3492-504. doi: 10.1172/JCI46406. Epub Aug. 1, 2011.
Xiong et al., Matrix-embedded cells control osteoclast formation. Nat Med. Sep. 11, 2011;17(10):1235-41. doi: 10.1038/nm.2448.
Yahara et al., Pterosin B prevents chondrocyte hypertrophy and osteoarthritis in mice by inhibiting Sik3. Nat Commun. Mar. 24, 2016;7:10959. doi: 10.1038/ncomms10959.
Yang et al., CBP/p300-interacting protein CITED1 modulates parathyroid hormone regulation of osteoblastic differentiation. Endocrinology. Apr. 2008;149(4):1728-35. doi: 10.1210/en.2007-0826. Epub Jan. 10, 2008.
Yasumoto et al., Microphthalmia-associated transcription factor as a regulator for melanocyte-specific transcription of the human tyrosinase gene. Mol Cell Biol. Dec. 1994;14(12):8058-70.
CAPLUS Accession No. 2015:690395. 2 pages. Reynolds et al., N-Aryl-heteroarylamines as FGFR4 inhibitors and their Preparation.
CAPLUS Accession No. 2015:453874. 12 pages. Ding et al., Pyrimido-heterocyclic compounds as EGFR protease inhibitors and their preparation, pharmaceutical compositions and use in the treatment of cancer.
CAPLUS Accession No. 2015:76117. 2 pages. Gray et al., Preparation of functionalized pyrimidine compounds as kinase inhibitors for the treatment of proliferative diseases.
CAPLUS Accession No. 2014:1815213. 3 pages. Tan et al., Development of covalent inhibitors that can overcome resistance to first-generation FGFR kinase inhibitors.
CAPLUS Accession No. 2014:1753550. 1 page. Huang et al., DFG-out Mode of Inhibition by an Irreversible Type-1 Inhibitor Capable of Overcoming Gate-Keeper Mutations.
CAPLUS Accession No. 2014:1558688. 10 pages. D'Agostino et al., Preparation of heteroaryl compounds as inhibitors of protein kinases.
CAPLUS Accession No. 2013:1609048. 10 pages. Xu et al., Design, Synthesis, and Biological Evaluation of 2-Oxo-3,4-dihydropyrimido[4,5 d]pyrimidinyl Derivatives as New Irreversible Epidermal Growth Factor Receptor Inhibitors with Improved Pharmacokinetic Properties.
CAPLUS Accession No. 2013:82305. 2 pages. Zender et al., Pharmaceutical compositions comprising sorafenib in combination with MAPK14 inhibitors for the treatment and prevention of liver cancer.
CAPLUS Accession No. 2013:51064. 2 pages. Zender et al., Pharmaceutical compositions comprising sorafenib in combination with MAPK14 inhibitors for the treatment and prevention of liver cancer.
CAPLUS Accession No. 2012:1832180. 2 pages. Ding et al., Pyrimidopyrimidone derivatives as EGFR inhibitors and their preparation, pharmaceutical compositions and use in the treatment of cancers.
CAPLUS Accession No. 2012:1816780. 5 pages. Ding et al., Pyrimidopyrimidone derivatives as EGFR inhibitors and their preparation, pharmaceutical compositions and use in the treatment of cancers.
CAPLUS Accession No. 2012:1191791. 1 page. Wan et al., Discovery of novel Bruton's tyrosine kinase inhibitors using a hybrid protocol of virtual screening approaches based on SVM model, pharmacophore and molecular docking.
CAPLUS Accession No. 2012:235081. 3 pages. Chang et al., Design, Synthesis, and Biological Evaluation of Novel Conformationally Constrained Inhibitors Targeting Epidermal Growth Factor Receptor Threonine790 ® Methionine790 Mutant.
CAPLUS Accession No. 2011:391484. 1 page. Kuglstatter et al., Insights into the conformational flexibility of Bruton's tyrosine kinase from multiple ligand complex structures.
CAPLUS Accession No. 2007:1363959. 4 page. Ren et al., Preparation of pyrimidopyrimidinones and analogs as FGF receptor kinases inhibitors.
CAPLUS Accession No. 2006:333232. 17 pages. Engh et al., Preparation of amide derivatives of 3-phenyl-dihydropyrimido[4,5-d]pyrimidines as antitumor agents.
CAPLUS Accession No. 2005:120672. 22 pages. Sim et al., Preparation of pyrimidopyrimidines as protein kinase inhibitors.
CAPLUS Accession No. 2004:412945. 5 pages. Luk et al., Preparation of pyrimido Src tyrosine kinase inhibitors as anti-proliferative agents for the treatment of cancer.
CAPLUS Accession No. 2000:291041. 11 pages. Harris et al., Preparation of pyrimidopyrimidinones as T-cell tyrosine kinase inhibitors.
CAPLUS Accession No. 1999:764041. 5 pages. Dobrusin et al., Preparation of oxopyrido- and -pyrimidopyrimidines as cellular proliferation inhibitors.
Extended European Search Report for EP 18760857.5, dated Nov. 12, 2020.
Mujahid et al., A UV-Independent Topical Small-Molecule Approach for Melanin Production in Human Skin. Cell Rep. Jun. 13,

(56) References Cited

OTHER PUBLICATIONS

2017;19(11):2177-2184. doi: 10.1016/j.celrep.2017.05.042. PMID: 28614705; PMCID: PMC5549921.
U.S. Appl. No. 16/953,984, filed Nov. 20, 2020, Gray et al.
EP 18760857.5, Nov. 12, 2020, Extended European Search Report.
Liang et al., Discovery of 2-((3-Amino-4-methylphenyl)amino)-N-(2-methyl-5-(3-(trifluoromethyl)benzamido)phenyl)-4-(methylamino)pyrimidine-5-carboxamide (CHMFL-ABL-053) as a Potent, Selective, and Orally Available BCR-ABL/SRC/p38 Kinase Inhibitor for Chronic Myeloid Leukemia. J Med Chem. Mar. 10, 2016;59(5):1984-2004. doi: 10.1021/acs.jmedchem.5b01618. Epub Feb. 5, 2016. PMID: 26789553.

* cited by examiner

| Kinase | % control at 1 µM | Enzymatic IC$_{50}$ (nM) |
|---|---|---|
| CSF1R | 0 | 9.66 |
| FRK | 0 | 1.10 |
| KIT | 0 | 153 |
| p38-alpha | 0 | 10.1 |
| p38-beta | 0 | 9.64 |
| SRC | 0.15 | 58.8 |
| BRK | 0.2 | 24.1 |
| PDGFRB | 0.25 | 103 |
| EPHB1 | 0.3 | 16.4 |
| SIK1 | 0.3 | 6.56 |
| TNK2 | 0.4 | 10.5 |
| RSK4 | 0.6 | >10000 |
| SIK2 | 0.7 | 1.77 |
| NLK | 0.95 | 132 |
| PRKR | 1 | >10000 |

YKL-06-061
468 Assays Tested
16 Interactions Mapped
S-Score(1) = 0.04

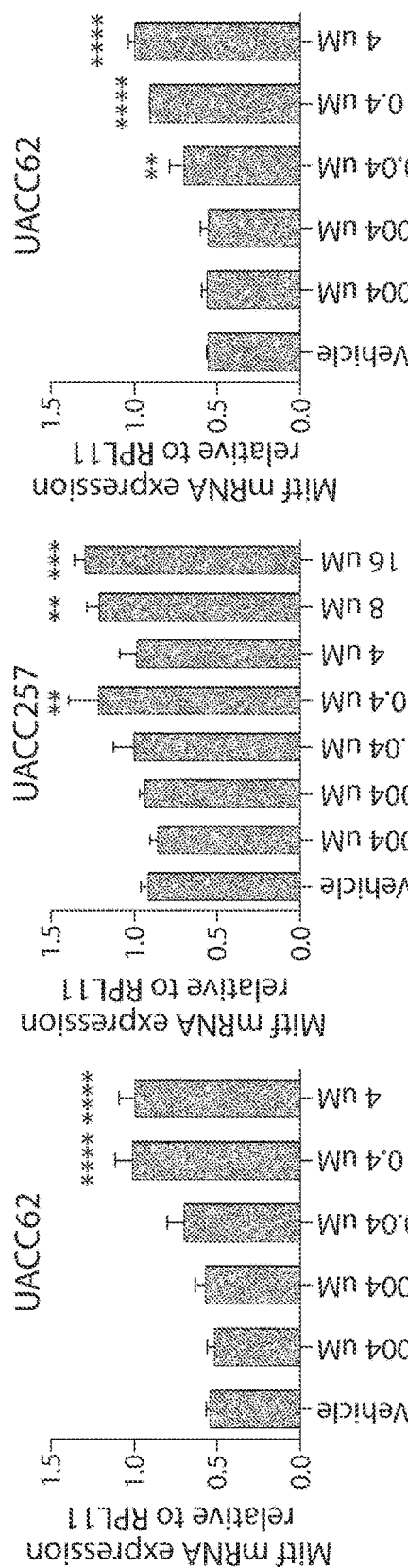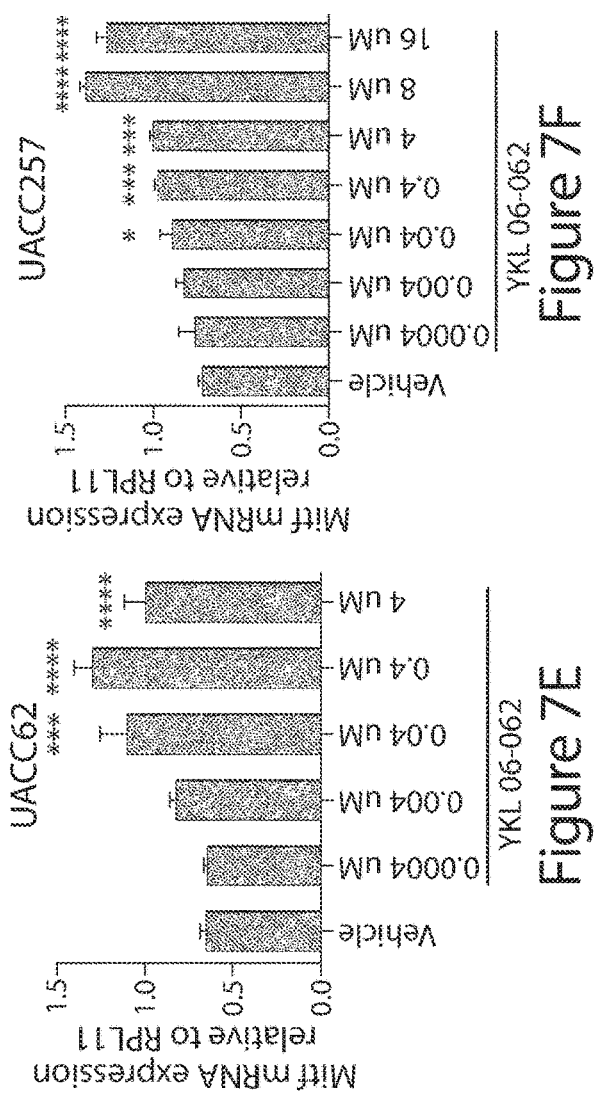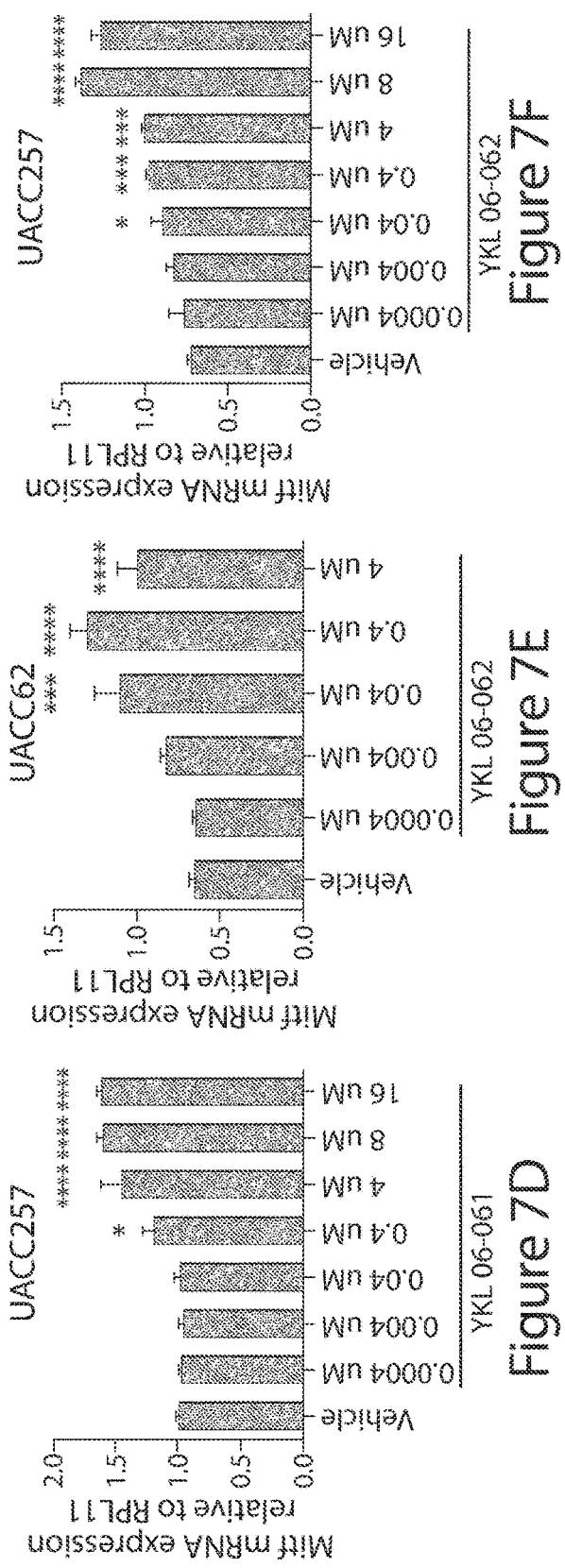

USES OF PYRIMIDOPYRIMIDINONES AS SIK INHIBITORS

RELATED APPLICATIONS

This application is a national stage filing under 35 U.S.C. § 371 of international PCT application, PCT/US2018/020335, filed Feb. 28, 2018, which claims priority under 35 U.S.C. § 119(e) to U.S. Provisional Applications, U.S. Ser. No. 62/464,675, filed Feb. 28, 2017, and U.S. Ser. No. 62/472,468, filed Mar. 16, 2017, each of which is incorporated herein by reference.

BACKGROUND OF THE INVENTION

A protein kinase inhibitor is an enzyme inhibitor that blocks the action of a protein kinase. A protein kinase is an enzyme that adds a phosphate group to a protein or other organic molecule. Phosphorylation is involved in a wide range of diseases, such as cancer. One protein kinase is a salt-inducible kinase (SIK), e.g., SIK1, SIK2 or SIK3). SIK's (e.g., SIK1, SIK2 or SIK3) are serine/threonine kinases in the adenosine monophosphate-activated protein kinase (AMPK) family. (See Altarejos et al. 2011, Patel et al. 2014, Park et al. 2014, and Henriksson et al. 2015).

The incidence of non-melanoma and melanoma skin cancers has been increasing in the United States over recent decades (Rogers et al. 2015; Ryerson et al. 2016; Watson et al. 2016). Epidemiological evidence suggests that there is a causal relationship between sun/UV exposure and the three major histologic forms of skin cancer: squamous cell carcinoma, basal cell carcinoma, and cutaneous melanoma (Wu et al. 2014; Kennedy et al. 2003; Gandini et al. 2005). Individuals with fair skin and/or poor tanning ability are at higher risk for developing these malignancies (Armstrong and Kricker 2001), which are uncommon in darkly pigmented individuals (Pennello, Devesa, and Gail 2000). During UV induced tanning, DNA damage in keratinocytes triggers p53 mediated transcription of the pro-opiomelanocortin (POMC) gene (Cui et al. 2007). Proteolytic cleavage of POMC, produces alpha-MSH, which binds to the melanocortin-receptor-1 (MC1R) on melanocytes, activating adenylate cyclase. Elevated cAMP activates protein kinase A (PKA), which phosphorylates the cAMP-responsive-element-binding protein (CREB) (Tsatmalia et al. 1999; Newton et al. 2005), resulting in stimulated transcription of the microphthalmia-associated transcription factor (MITF) gene (Price et al. 1998; Bertolotto et al. 1998). MC1R non-signaling variants are associated with lighter skin tones and red hair, and are linked to poor tanning responses (Valverde et al. 1995). Previously, topical application of the cAMP agonist forskolin was shown to rescue the cAMP-MITF-eumelanin pathway in Mc1r deficient mice (D'Orazio et al. 2006). Subsequent studies identified the phosphodiesterase PDE4d3 as a key regulator of melanocytic cAMP homeostasis, and its suppression produced similar hyperpigmentation as forskolin treatment in redhaired mice (Khaled, Levy, and Fisher 2010). However attempts to apply both of these small molecule approaches to human skin have been unsuccessful, likely related to poor skin penetration of the active species.

Genetic data in mice have suggested the presence of a pathway in which CREB-regulated transcription co-activator (CRTC) positively and salt-inducible kinase 2 (SIK2) negatively regulate MITF and pigment synthesis independently of CREB phosphorylation by PKA (Horike et al. 2010). In macrophages, the small molecule SIK inhibitor HG 9-91-01 has been shown to regulate CREB-dependent gene transcription by suppressing phosphorylation of CRTC (Clark et al. 2012), thereby inhibiting cytoplasmic sequestration and permitting its nuclear translocation. It was hypothesized that small molecule SIK inhibitors could be generated and optimized as topical agents capable of inducing cutaneous pigmentation independently of UV irradiation in human skin. There is a need for SIK inhibitors with good skin penetration for such a use in a subject.

SUMMARY OF THE INVENTION

The presence of dark melanin (eumelanin) within human epidermis represents one of the strongest predictors of protection from skin cancer and UV photodamage (Armstrong and Kricker 2001; Pennello, Devesa, and Gail 2000). Non-genotoxic topical rescue of eumelanin synthesis has been previously achieved in "redhaired" Mc1r deficient mice and exhibited significant protection against UV damage and skin carcinogenesis (D'Orazio et al. 2006). However, application of this topical strategy to human skin has not been achieved, in large part due to the profoundly greater barrier function of human stratum corneum and epidermis. Salt Inducible Kinase (SIK) is a serine threonine kinase (Dentin et al. 2007) that has been demonstrated to regulate MITF, the master regulator of pigment gene expression through its effects on CRTC and CREB activity (Horike et al. 2010). A flavonoid inhibitor of SIK2 has been reported to promote melanogenesis in B16F10 melanoma cells (See Kumagai et al.). Here, the development of small molecule SIK inhibitors that are useful for human skin penetration are described, resulting in MITF up-regulation and induction of melanogenesis. When topically applied, pigment production was induced in redhead mice harboring an inactivating mutation in Mc1r, as well as in normal human skin. These findings provide a realistic pathway towards topical modulation of human skin pigmentation without a requirement for UV irradiation, potentially impacting UV protection and skin cancer risk.

Described herein are compounds of Formula (I), (II), (III), (IV), (V)(VI), (VI-A), or (VII) that are salt-inducible kinase (SIK) inhibitors. The compounds include macrocyclic compounds of Formula (I), bicyclic urea compounds of Formulae (II), (III), and (IV), and compounds of Formulae (V), (VI), (VI-A), and (VII), and pharmaceutically acceptable salts, solvates, hydrates, polymorphs, co-crystals, tautomers, stereoisomers, isotopically labeled derivatives, and prodrugs thereof. The described compounds are able to inhibit the activity of a salt-inducible kinase (SIK, e.g., SIK1, SIK2, SIK3). Also provided in the present disclosure are methods of increasing skin pigmentation and/or reducing the risk of skin cancer in a subject in need thereof using the described compounds (e.g., via topical administration of the described compounds). In certain embodiments, provided herein are methods of increasing the appearance of skin darkening in a subject in need thereof using the described compounds (e.g., via topical administration of the described compounds).

In one aspect, the compound utilized in the present disclosure is of Formula (I):

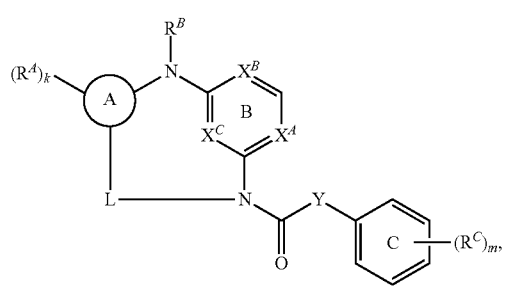

and pharmaceutically acceptable salts, solvates, hydrates, polymorphs, co-crystals, tautomers, stereoisomers, isotopically labeled derivatives, and prodrugs thereof. Exemplary compounds of Formula (I) useful in the present invention include, but are not limited to:

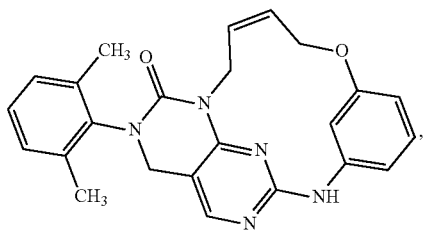

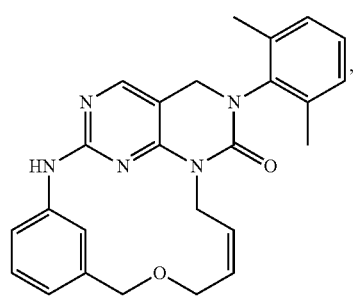

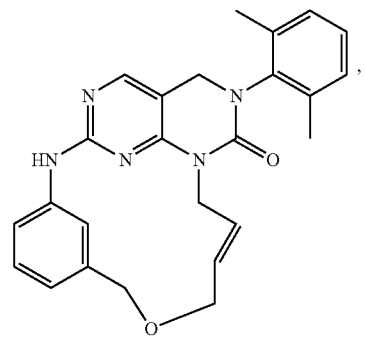

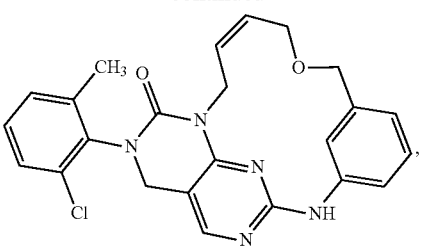

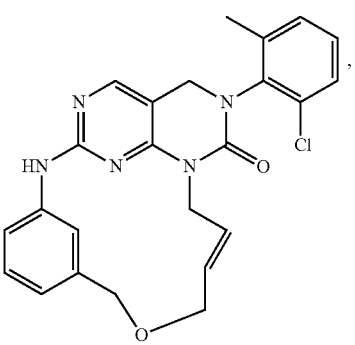

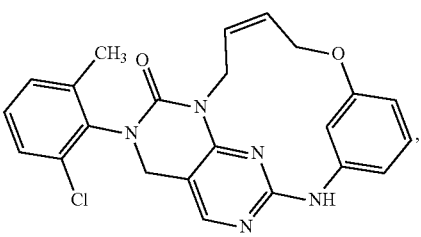

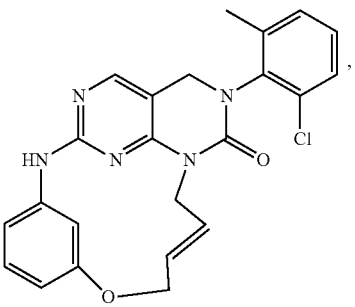

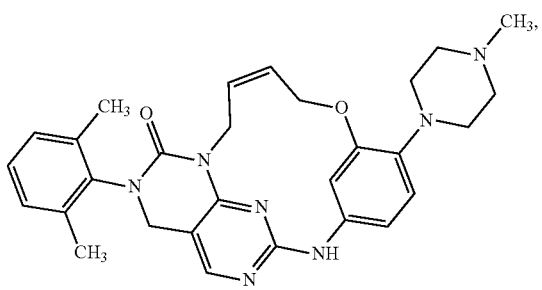

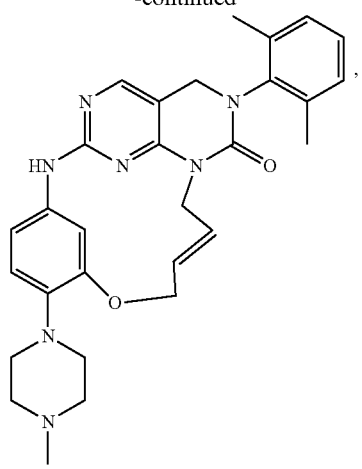

Exemplary compounds of Formula (I) useful in the present invention include, but are not limited to:

(HG-10-32-01)

(HG-10-88-02)

(HG-10-93-01)

and pharmaceutically acceptable salts, solvates, hydrates, polymorphs, co-crystals, tautomers, stereoisomers, isotopically labeled derivatives, and prodrugs thereof.

Exemplary compounds of Formula (I) useful in the present invention include, but are not limited to:

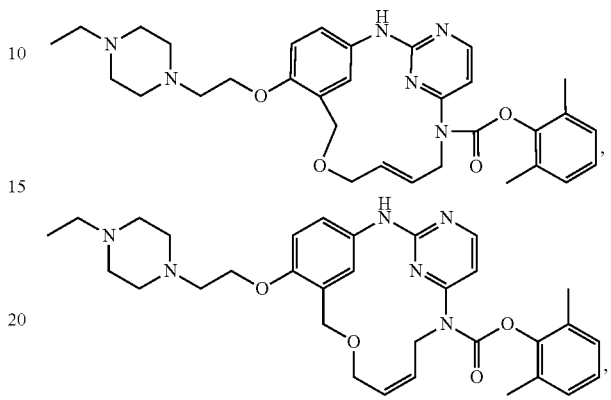

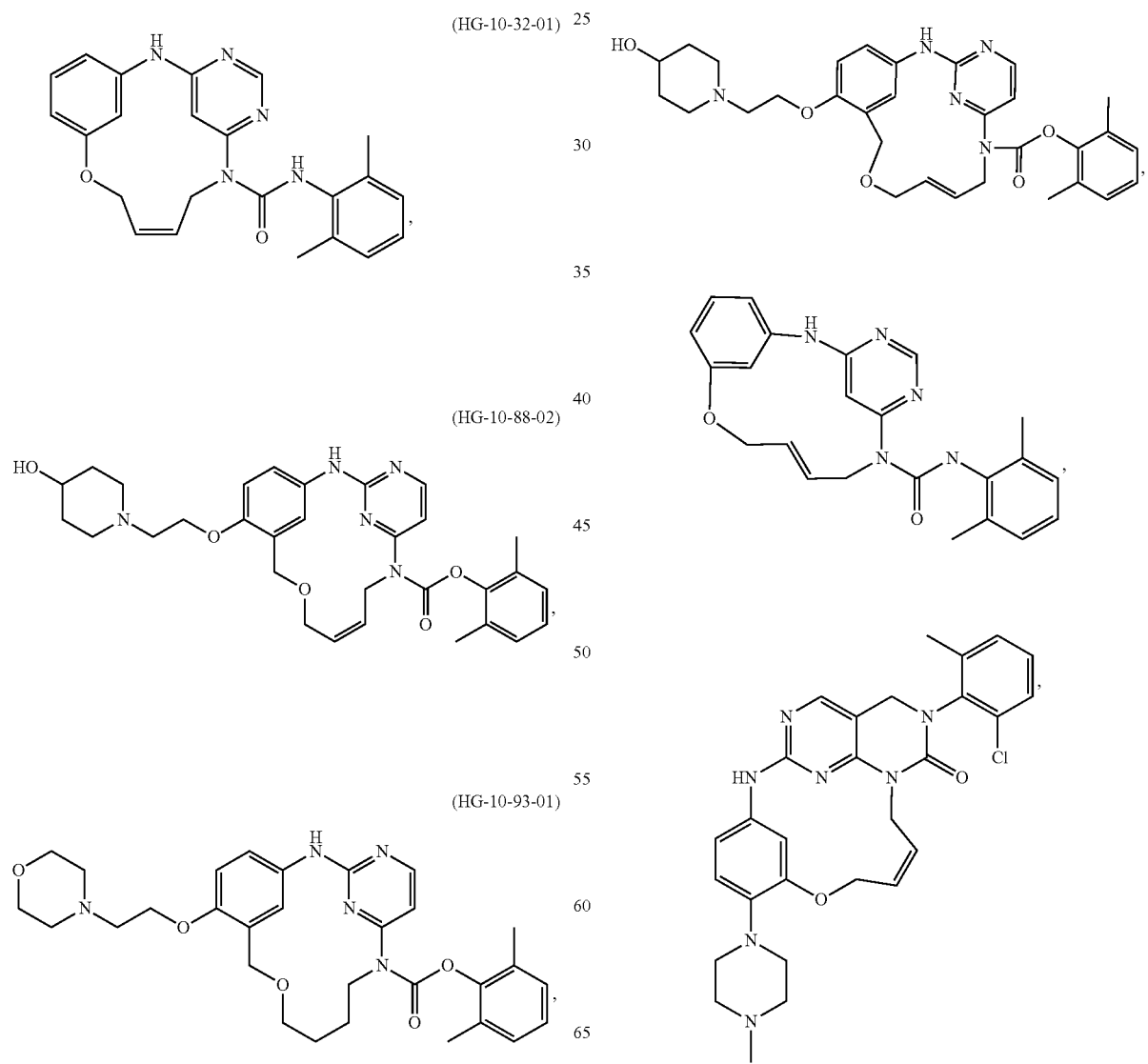

-continued

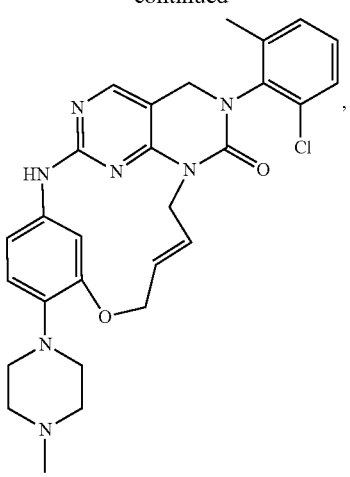

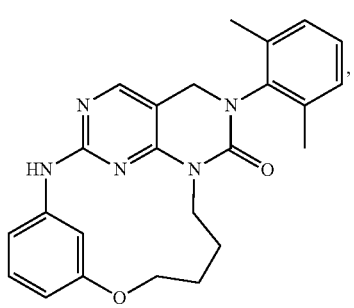

In another aspect, the compound utilized in the present disclosure is of Formula (II):

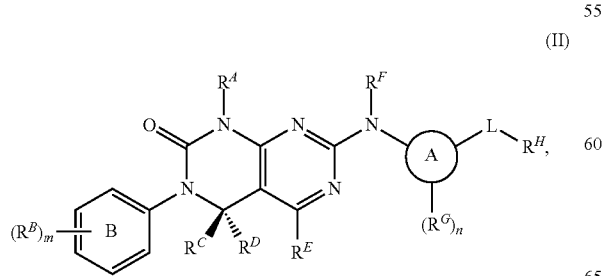

(II)

and pharmaceutically acceptable salts, solvates, hydrates, polymorphs, co-crystals, tautomers, stereoisomers, isotopically labeled derivatives, and prodrugs thereof. Exemplary compounds of Formula (II) useful in the present invention include, but are not limited to:

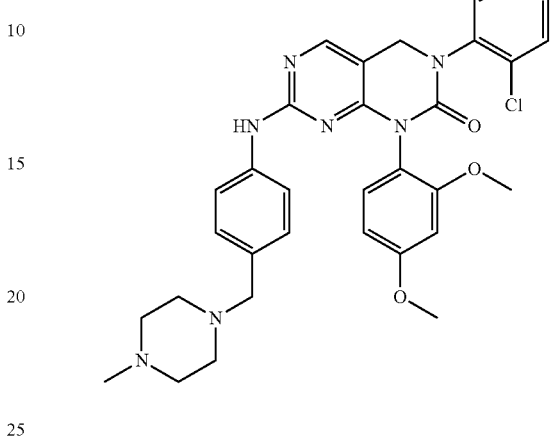

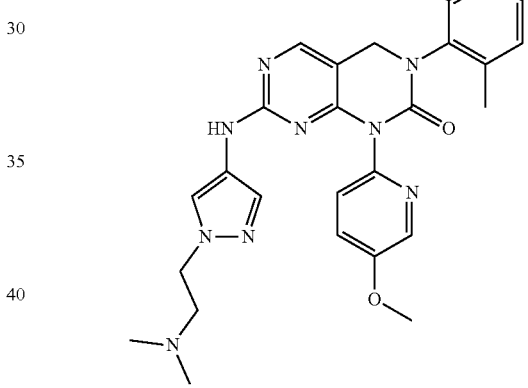

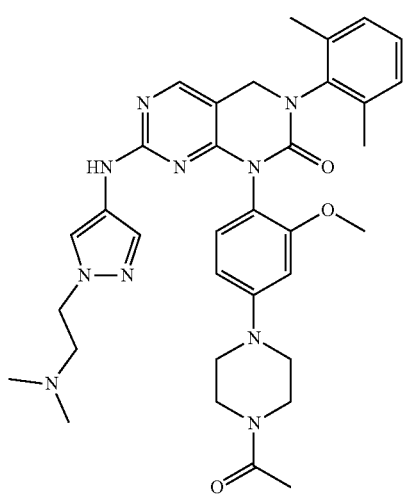

9
-continued
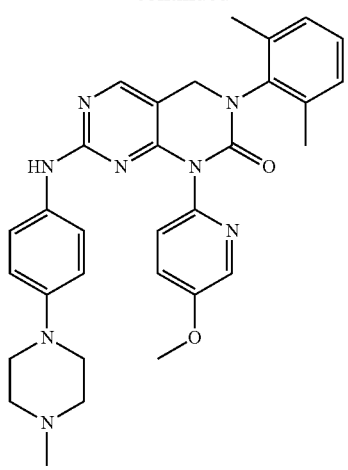
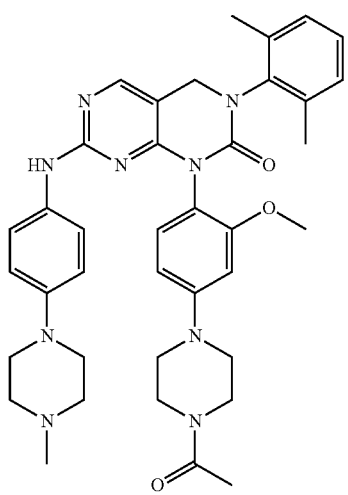
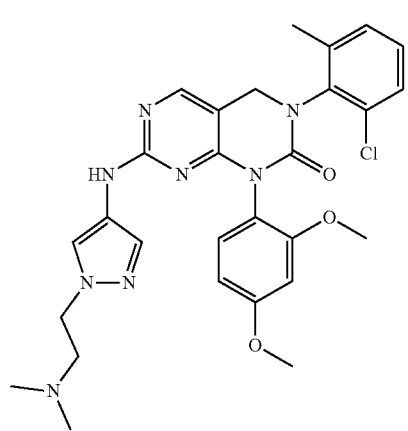
10
-continued
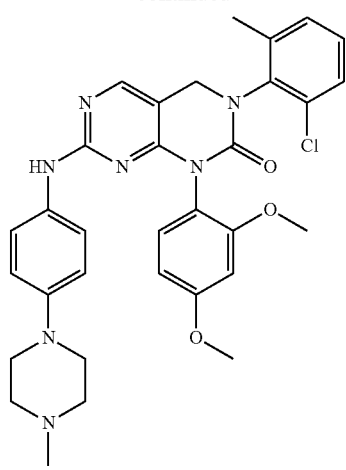
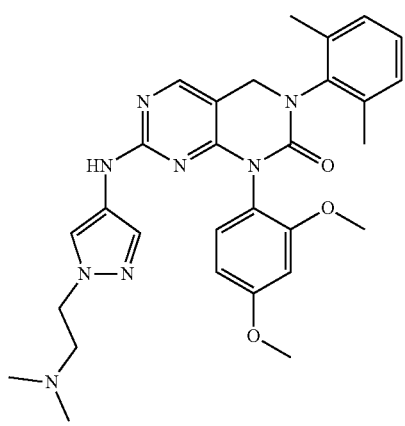
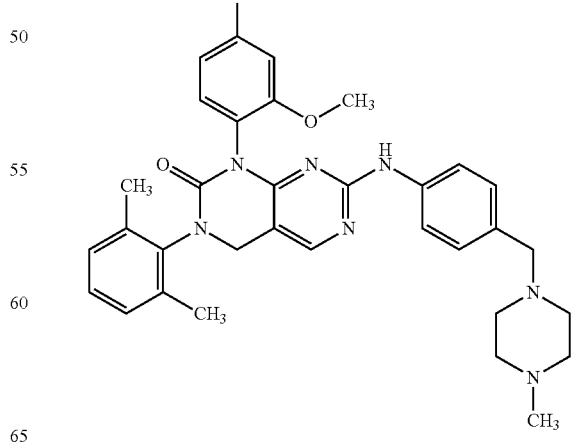

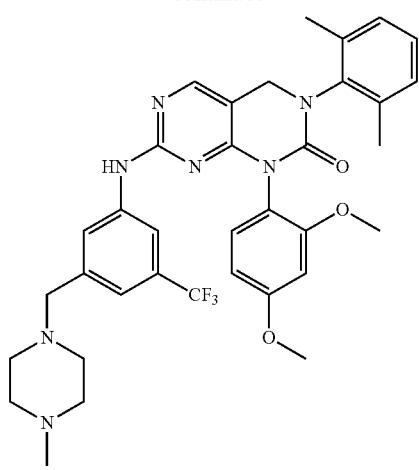
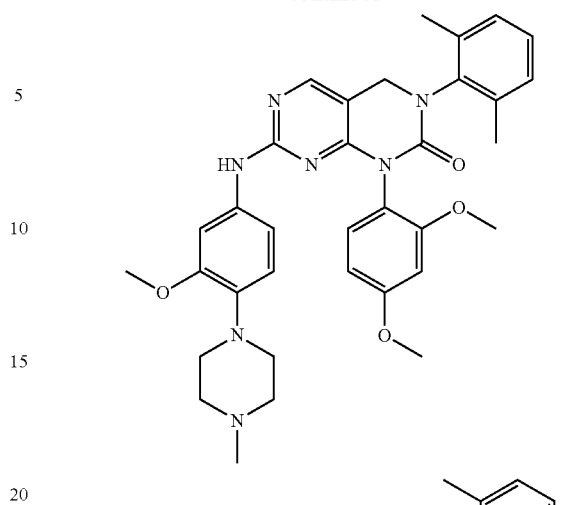
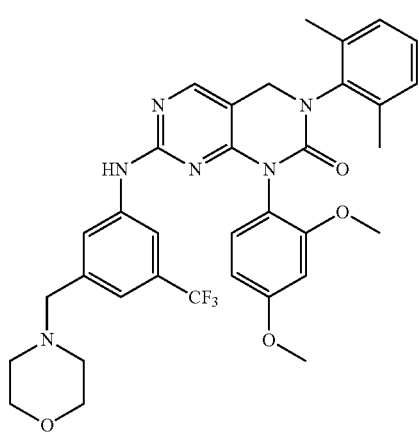
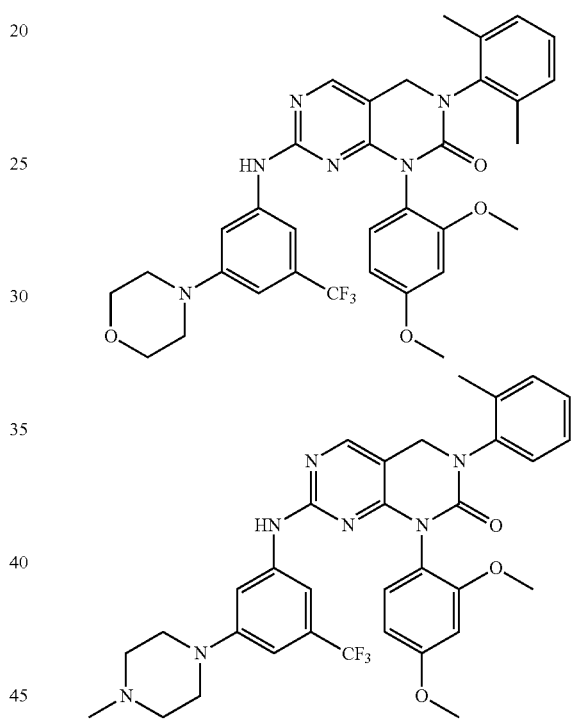
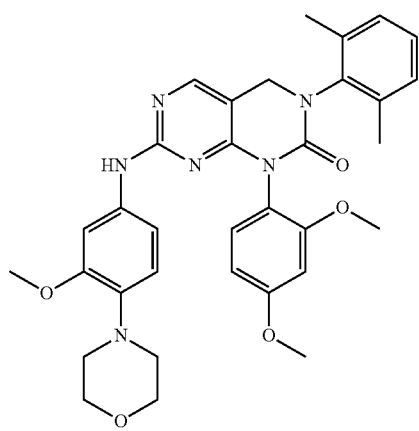
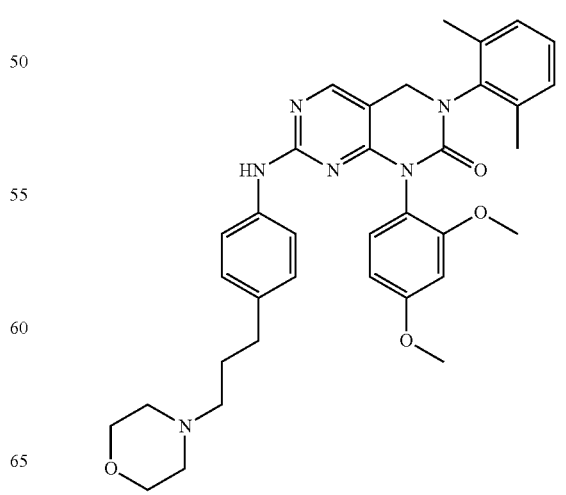

13
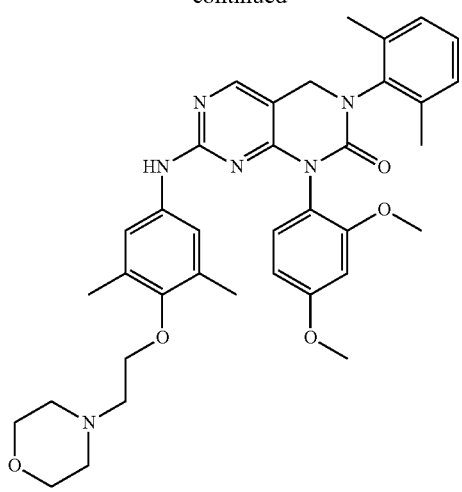
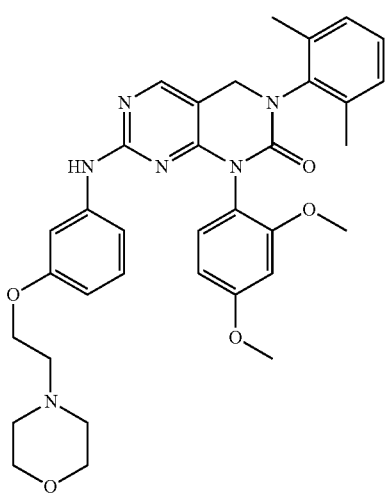
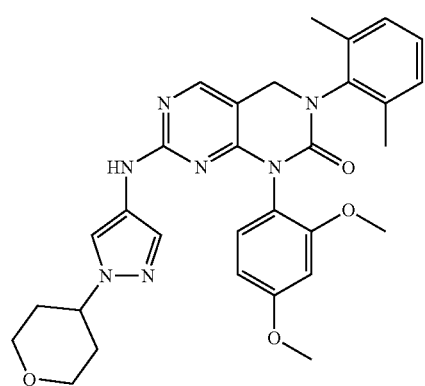
14
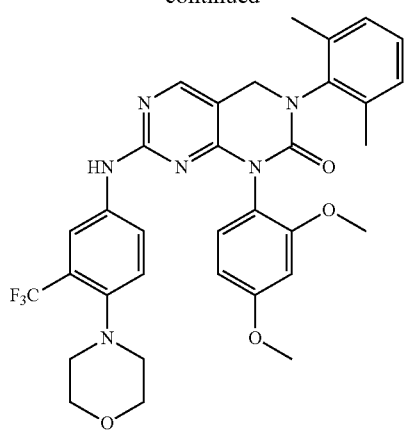
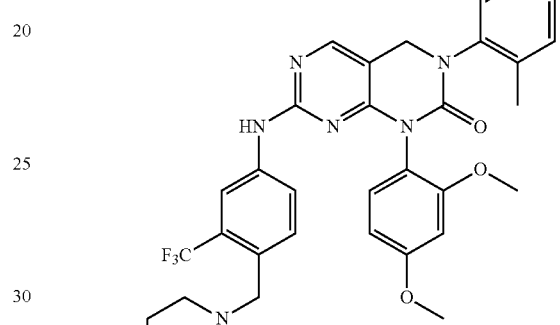
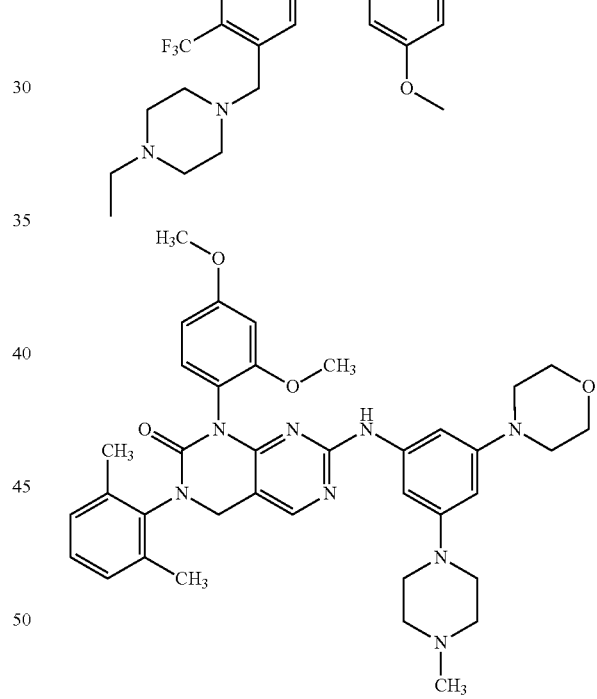
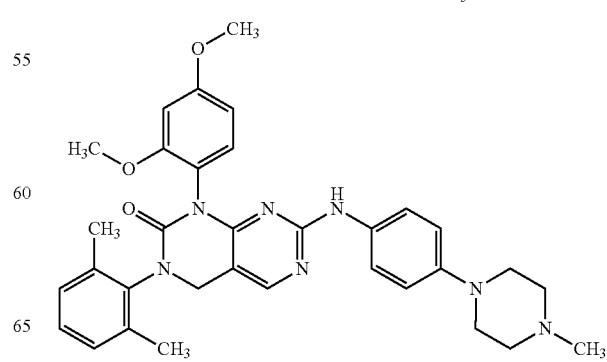

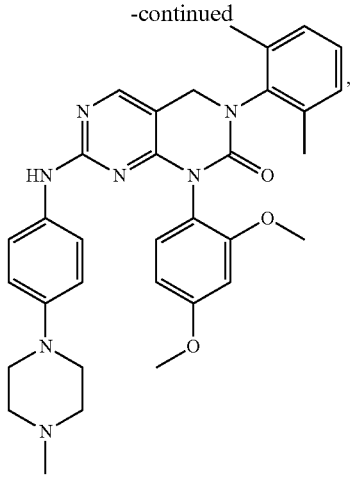

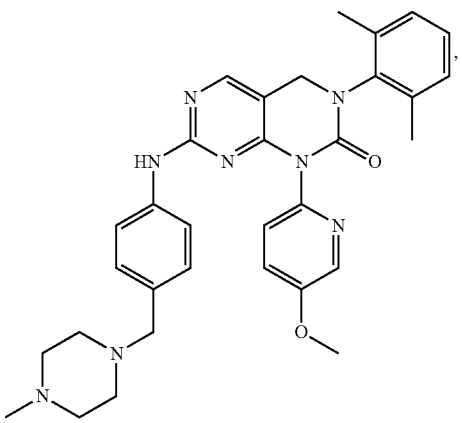 (YKL-04-136-10)

Exemplary compounds of Formula (II) useful in the present invention include, but are not limited to:

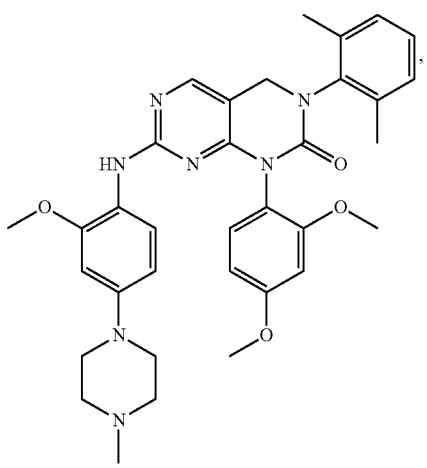 (HG-11-139-01)

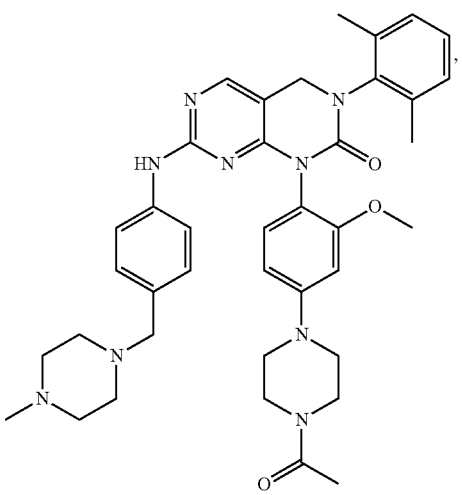 (YKL-04-136-11)

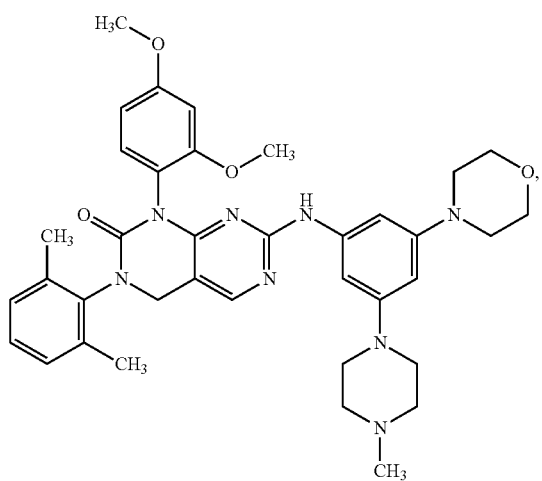 (HG-11-143-01)

In another aspect, the compound utilized in the present disclosure is of Formula (III):

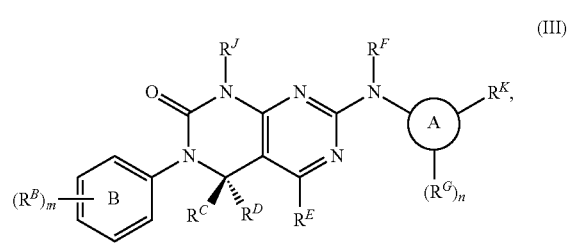 (III)

and pharmaceutically acceptable salts, solvates, hydrates, polymorphs, co-crystals, tautomers, stereoisomers, isotopically labeled derivatives, and prodrugs thereof. Exemplary compounds of Formula (III) useful in the present invention include, but are not limited to:

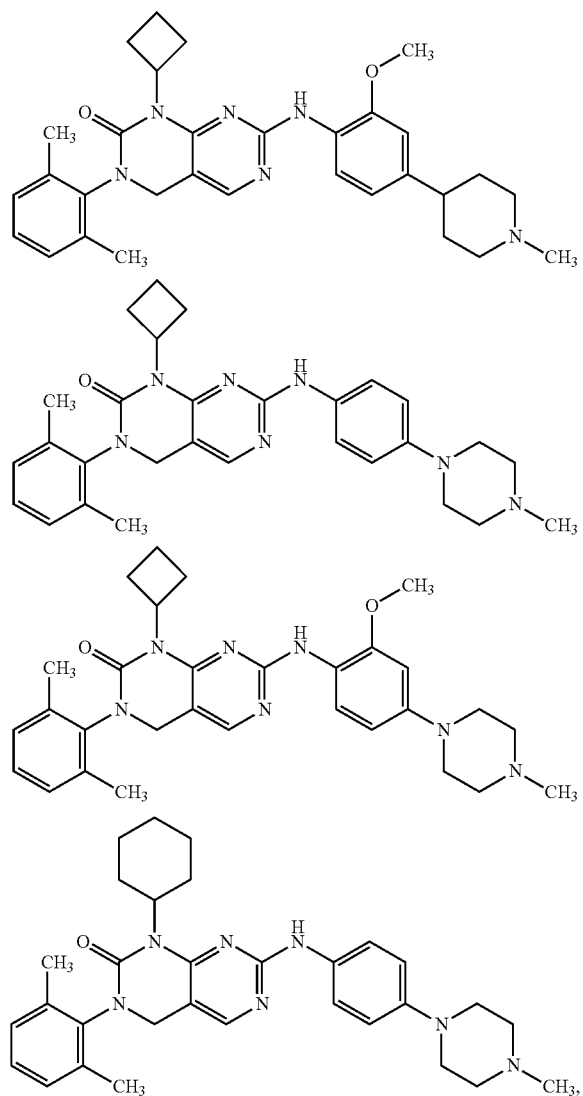
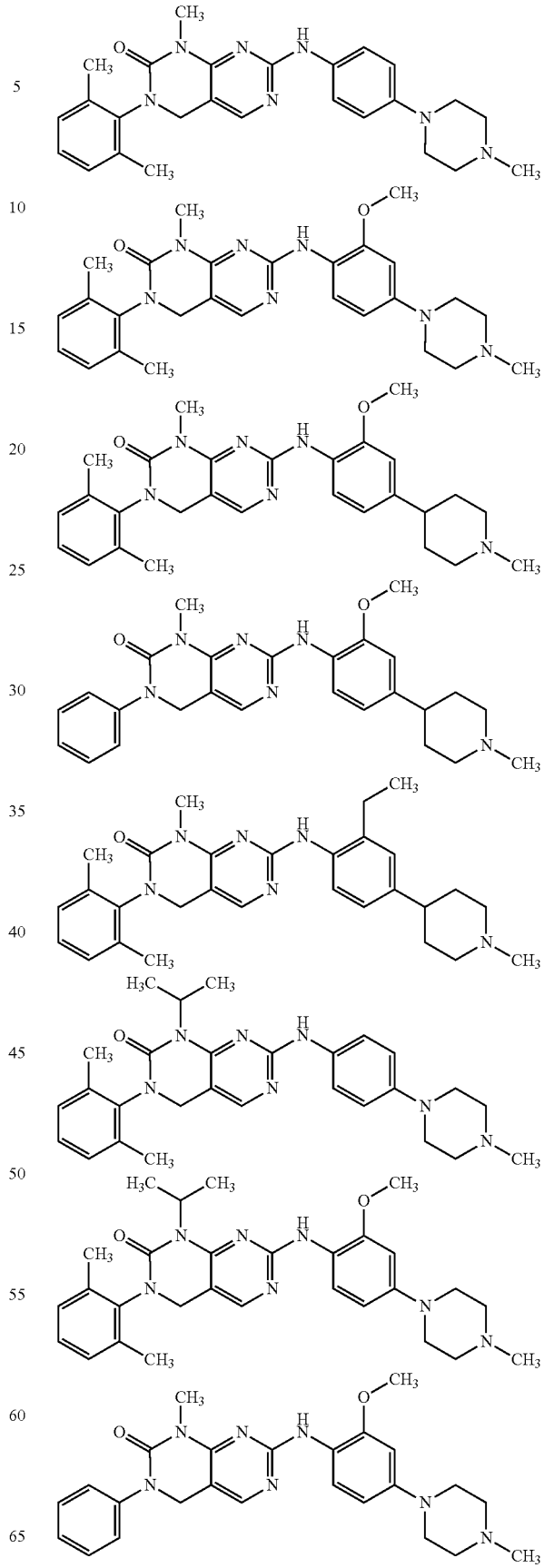
In another aspect, the compound utilized in the present disclosure is of Formula (IV):
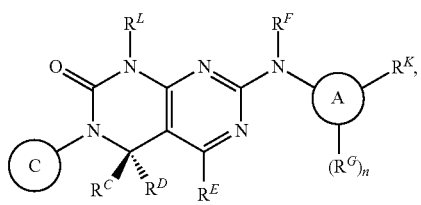
(IV)
and pharmaceutically acceptable salts, solvates, hydrates, polymorphs, co-crystals, tautomers, stereoisomers, isotopically labeled derivatives, and prodrugs thereof. Exemplary compounds of Formula (IV) useful in the present invention include, but are not limited to:

-continued

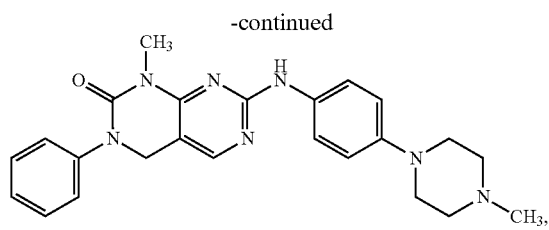

Exemplary compounds of Formula (IV) useful in the present invention include, but are not limited to:

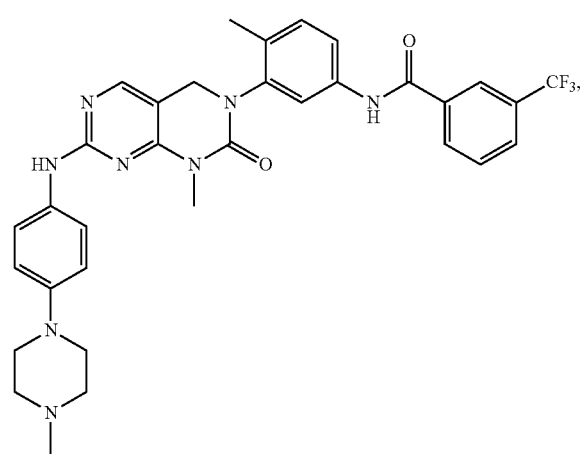

(HG-11-23-01)

and pharmaceutically acceptable salts, solvates, hydrates, polymorphs, co-crystals, tautomers, stereoisomers, isotopically labeled derivatives, and prodrugs thereof.

In another aspect, the compound utilized in the present disclosure is of Formula (V):

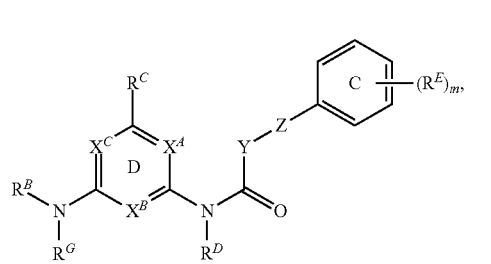

(V)

and pharmaceutically acceptable salts, solvates, hydrates, polymorphs, co-crystals, tautomers, stereoisomers, isotopically labeled derivatives, and prodrugs thereof. Exemplary compounds of Formula (V) useful in the present invention include, but are not limited to:

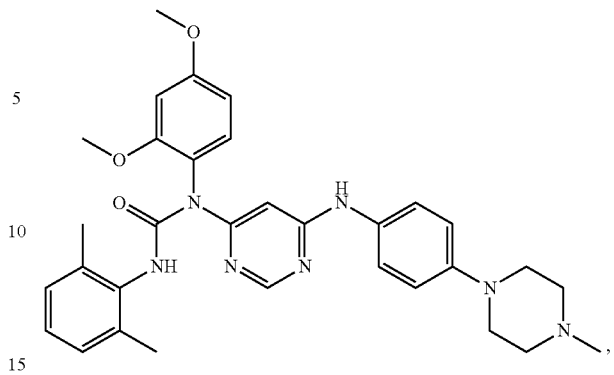

and pharmaceutically acceptable salts, solvates, hydrates, polymorphs, co-crystals, tautomers, stereoisomers, isotopically labeled derivatives, and prodrugs thereof.

In another aspect, the compound utilized in the present disclosure is of Formula (VI):

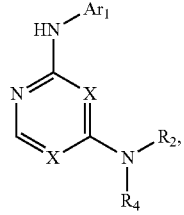

(VI)

and pharmaceutically acceptable salts, solvates, hydrates, polymorphs, co-crystals, tautomers, stereoisomers, isotopically labeled derivatives, and prodrugs thereof.

In another aspect, the compound utilized in the present disclosure is of Formula (VI-A):

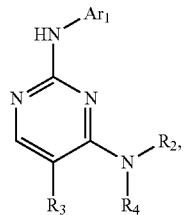

(VI-A)

and pharmaceutically acceptable salts, solvates, hydrates, polymorphs, co-crystals, tautomers, stereoisomers, isotopically labeled derivatives, and prodrugs thereof. Exemplary compounds of Formula (VI) and (VI-A) useful in the present invention include, but are not limited to:

(MRT67307)
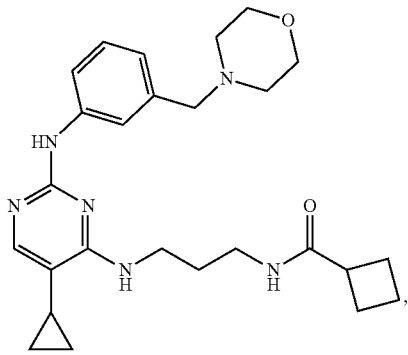

(KIN112)
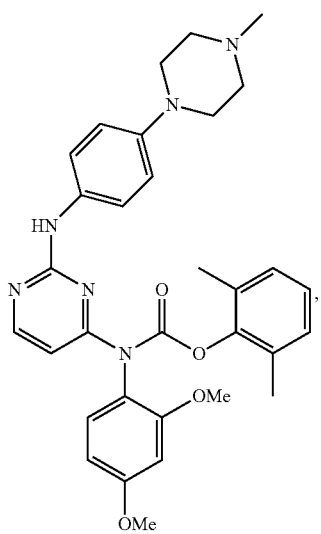

(MRT68771)
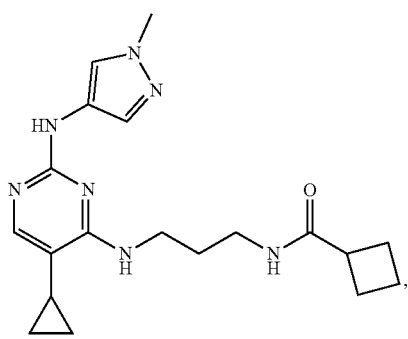

and pharmaceutically acceptable salts, solvates, hydrates, polymorphs, co-crystals, tautomers, stereoisomers, isotopically labeled derivatives, and prodrugs thereof.

In another aspect, the compound utilized in the present disclosure is of Formula (VII):

(VII)
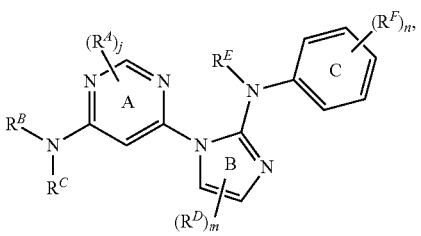

(MRT199665)
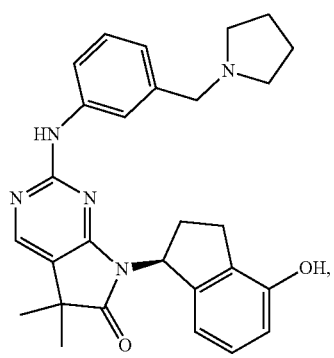

and pharmaceutically acceptable salts, solvates, hydrates, polymorphs, co-crystals, tautomers, stereoisomers, isotopically labeled derivatives, and prodrugs thereof. Exemplary compounds of Formula (VII) useful in the present invention include, but are not limited to:

(VII-5)
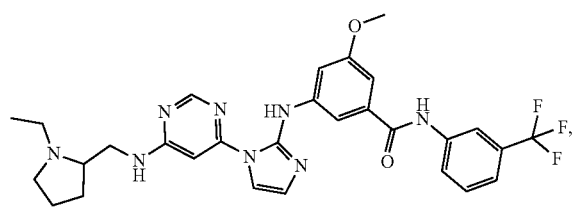

(VII-6)
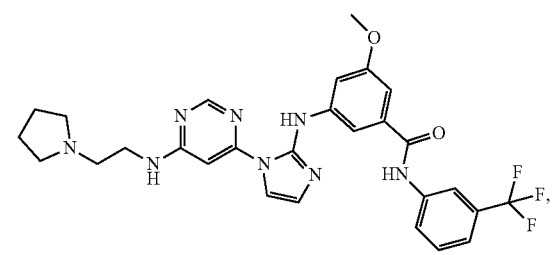

-continued (VII-7)
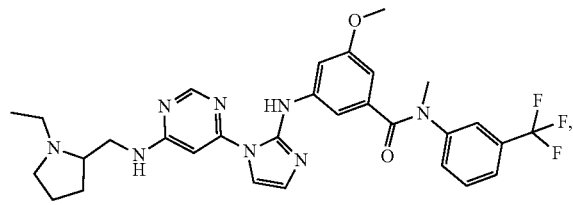

(VII-8)
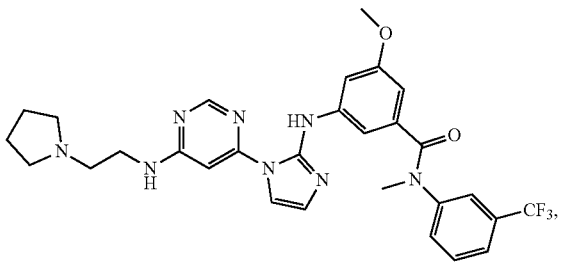

(VII-9)
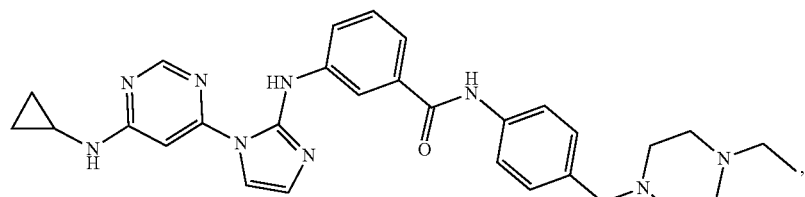

(VII-10)
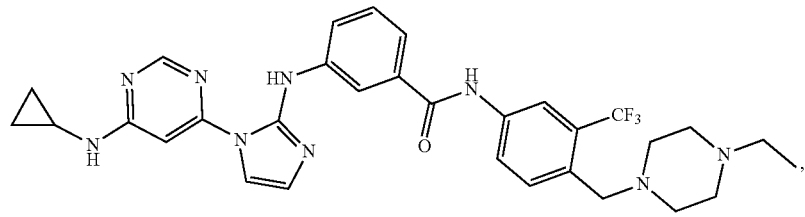

(VII-11)
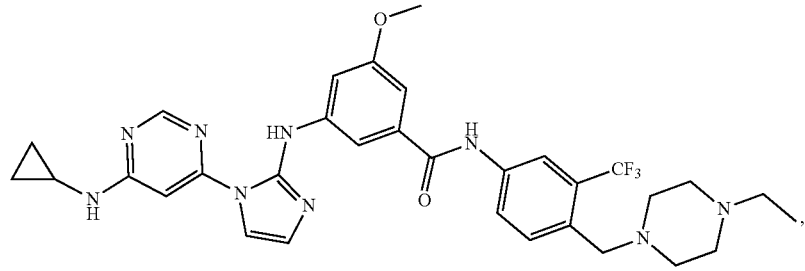

(VII-12)
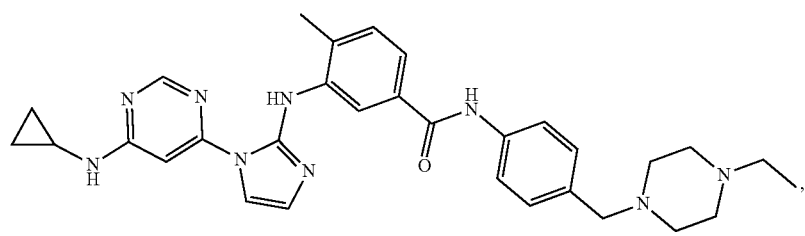

The pharmaceutical compositions including a compound described herein, and optionally a pharmaceutically acceptable excipient may be useful in increasing skin pigmentation and/or reducing the risk of skin cancer in a subject in need thereof. In certain embodiments, a pharmaceutical composition described herein includes an effective amount (e.g., a prophylactically effective) amount of a compound described herein. In certain embodiments, the compound being administered or used selectively inhibits the activity of a salt-inducible protein kinase (SIK) (e.g., SIK1, SIK2, or SIK3). In certain embodiments, the compound selectively inhibits SIK1. In certain embodiments, the compound selectively inhibits SIK2.

In certain embodiments, the subject being administered a compound or pharmaceutical composition described herein is a human. In certain embodiments, the subject being administered a compound or pharmaceutical composition described herein is a non-human animal.

In another aspect, the present disclosure provides methods of increasing skin pigmentation and/or reducing the risk of skin cancer in a subject in need thereof. In another aspect, the present disclosure provides methods of inhibiting SIK in the skin of a subject. In another aspect, the present disclosure provides methods of inducing eumelanin synthesis. In certain embodiments, the present disclosure provides methods of inducing melanosomal maturation, export, and localization. In certain embodiments, the present disclosure provides methods of inducing microphthalmia-associated transcription factor (MITF) expression.

In still another aspect, described herein are kits including a container with a compound or pharmaceutical composition described herein for use in a method described herein. A kit described herein may include a single dose or multiple doses of the compound or pharmaceutical composition. The described kits may be useful in increasing skin pigmentation in a subject in need thereof. In certain embodiments, a kit described herein further includes instructions for using the kit.

In another aspect, the present disclosure provides methods of inhibiting the activity of a SIK (e.g., SIK1, SIK2, or SIK3).

The methods of the present disclosure include administering to the subject an effective amount of a compound or pharmaceutical composition described herein for use in a method of the disclosure (e.g., a method of increasing skin pigmentation and/or reducing the risk of skin cancer in a subject in need thereof. In certain embodiments, the method comprises administering topically to the subject's skin an effective amount of a compound or pharmaceutical composition described herein.

In yet another aspect, the present disclosure provides compounds and pharmaceutical compositions described herein for use in a method of the disclosure (e.g., a method of increasing skin pigmentation and/or reducing the risk of skin cancer in a subject in need thereof.

The present application refers to various issued patent, published patent applications, journal articles, and other publications, all of which are incorporated herein by reference. The details of one or more embodiments of the invention are set forth herein. Other features, objects, and advantages of the invention will be apparent from the Detailed Description, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

In a formula, - - - is absent or a single bond, and ═ or ≡ is a single or double bond.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of)

and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and for 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is unspecified (e.g., —CH=CHCH$_3$ or

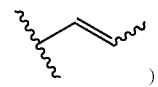
)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_3$-6 carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-8 carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, phthalimidyl, naphthalimidyl, chromanyl, chromenyl, and the like.

The term "aryl" refers to a radical of a monocyclic or polycyclic (e.g., bicyclic or tricyclic) 4n+2 aromatic ring system (e.g., having 6, 10, or 14 it electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 it electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{aa}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2$$R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)($R^{aa}$)$_2$, —P(=O)(O$R^{cc}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$$^+$X$^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)(O$R^{ee}$)$_2$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl), —N($C_{1-6}$ alkyl), —N($C_{1-6}$ alkyl)$_3$$^+$X$^-$, —NH($C_{1-6}$ alkyl)$_2$$^+$X$^-$, —NH$_2$($C_{1-6}$ alkyl)$^+$X$^-$, —NH$_3$$^+$X$^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O) ($C_{1-6}$ alkyl), —CO$_2$H, —OO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl), —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl), —C(=NH)NH($C_{1-6}$ alkyl), —C(=NH)NH$_2$, —OC(=NH)N($C_{1-6}$ alkyl), —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl), —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl), —OSi($C_{1-6}$ alkyl)$_3$-C(=S)N($C_{1-6}$ alkyl), C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl), —P(=O)($C_{1-6}$ alkyl), —OP(=O)($C_{1-6}$ alkyl)$_2$, —OP(=O)(O$C_{1-6}$ alkyl), $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

Exemplary carbon atom substituents include, but are not limited to, halogen, —CN, —NO$_2$, —N$_3$, —SO$_2$H, —SO$_3$H, —OH, —O$R^{aa}$, —ON($R^{bb}$)$_2$, —N($R^{bb}$)$_2$, —N(O$R^{cc}$)$R^{bb}$, —SH, —S$R^{aa}$, —C(=O)$R^{aa}$, —CO$_2$H, —CHO, —C(O$R^{cc}$)$_2$, —CO$_2$$R^{aa}$, —OC(=O)$R^{aa}$, —OCO$_2$$R^{aa}$, —C(=O)N($R^{bb}$)$_2$, —OC(=O)N($R^{bb}$)$_2$, —N$R^{bb}$C(=O)$R^{aa}$, —N$R^{bb}$CO$_2$$R^{aa}$, —N$R^{bb}$C(=O)N($R^{bb}$)$_2$, —C(=N$R^{bb}$)$R^{aa}$, —C(=N$R^{bb}$)O$R^{aa}$, —OC(=N$R^{bb}$)$R^{aa}$, —OC(=N$R^{bb}$)O$R^{aa}$, —C(=N$R^{bb}$)N($R^{bb}$)$_2$, —OC(=N$R^{bb}$)N($R^{bb}$)$_2$, —N$R^{bb}$C(=N$R^{bb}$)N($R^{66}$)$_2$, —C(=O)N$R^{bb}$SO$_2$$R^{aa}$, —SO$_2$$R^{aa}$, —SO$_2$O$R^{aa}$, —OSO$_2$$R^{aa}$, —S(=O)$R^{aa}$, or —OS(=O)$R^{aa}$.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —O$R^{aa}$, —ON($R^{bb}$)$_2$, —OC(=O) S$R^{aa}$, —OC(=O)$R^{aa}$, —OCO$_2$$R^{aa}$, —OC(=O)N($R^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(=O)(R$^{aa}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(R$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

The term "silyl" refers to the group —Si(R$^{aa}$)$_3$, wherein R$^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is a nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O) (R$^{aa}$)$_2$, —P(=O)(OR$_{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})$ $R^{aa}$, —$C(=NR^{bb})OR^{aa}$, —$C(=NR^{bb})N(R^{bb})_2$, —$S(=O)$ $R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)$ $(OR^{cc})_2$, and —$P(=O)(N(R^{bb})_2)_2$, wherein $R^{aa}$, $R^{bb}$, and $R^{cc}$ are as defined herein; wherein $X^-$ is a counterion. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

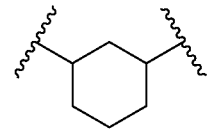 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

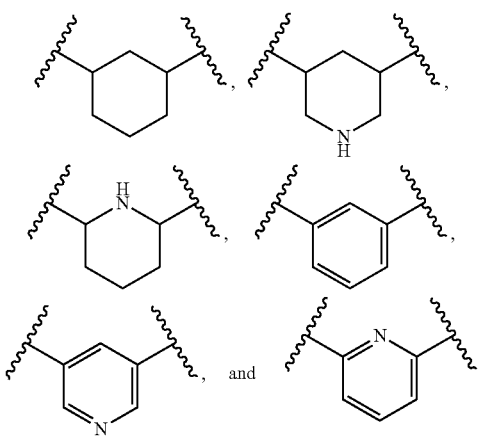

are all examples of a hydrocarbon chain. In contrast, in certain embodiments,

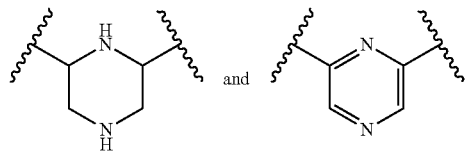 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

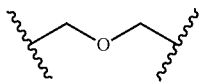

is a $C_3$ hydrocarbon chain wherein one chain atom is replaced with an oxygen atom.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March Advanced Organic Chemistry 6th ed. (501-502). Exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. In certain embodiments, a "pharmaceutically acceptable salt" is a "cosmetically acceptable salt."

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs, pp.* 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The "molecular weight" of a monovalent moiety —R is calculated by subtracting 1 from the molecular weight of the compound R-H. The "molecular weight" of a divalent moiety -L- is calculated by subtracting 2 from the molecular weight of the compound H-L-H.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. A "patient" refers to a human subject in need of treatment of a disease.

The term "topical" refers to local application of the compounds described herein to a body surface of a human or non-human animal. In certain embodiments, the body surface is skin. In certain embodiments, the skin is on a body part. In certain embodiments, the skin is on the face. In certain embodiments, the skin is on the neck. In certain embodiments, the skin is on the torso. In certain embodiments, the skin is on the chest. In certain embodiments, the skin is on the back. In certain embodiments, the skin is on the arms. In certain embodiments, the skin is on the legs.

The term "skin condition" or "skin disease" refers to a condition related to the skin. Exemplary skin conditions or skin diseases include, but are not limited to, skin cancers (e.g., non-melanoma and melanoma skin cancers, basal or squamous cell skin cancer, Merkel cell carcinoma, skin lymphoma, or Kaposi sarcoma), pruritus (itch), psoriasis, eczema, burns, or dermatitis.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent" refers to a prophylactic treatment of a subject who is not and did not have a disease but is at risk of developing the disease or who had a disease, does not have the disease, but is at risk of regression of the disease.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of skin cancer. The term "prophylactically effective amount" can encompass an amount that improves overall prophylaxis or enhances the prophylactic efficacy of another prophylactic agent.

A "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. Salt-inducible kinase (SIK) is one exemplary human protein kinase (e.g., SIK1, SIK2, or SIK3).

The term "salt-inducible kinase" or "SIK" refers to a subfamily of serine/threonine protein kinases including SIK1, SIK2, and SIK3 that belong to an AMP-activated protein kinase family. In certain embodiments, the SIK is SIK1. In certain embodiments, the SIK is SIK2. In certain embodiments, the SIK is SIK3.

The term "inhibition," "inhibiting," "inhibit," or "inhibitor" refer to the ability of a compound to reduce, slow, halt, and/or prevent activity of a particular biological process (e.g., SIK kinase activity) in a cell relative to vehicle.

When a compound, pharmaceutical composition, method, use, or kit is referred to as "selectively" or "specifically" modulating (e.g., increasing or inhibiting) the activity of a first protein kinase, the compound, pharmaceutical composition, method, use, or kit modulates the activity of the first protein kinase (e.g., SIK) to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of a second protein kinase that is different from the first protein kinase.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); and thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

(n=1). The image was taken 4 days after start of treatment. Panel F shows Fontana-masson (top panel) and hematoxylin and eosin (bottom panel) and staining (400× magnification) of human skin explants described in Panel E.

FIG. 6 shows characterization of SIK inhibitors. Panel A shows structures of HG-9-91-01, YKL-06-061 and YKL-06-062 and their biochemical $IC_{50}$ against SIKs. Panel B shows KinomeScan kinase selectivity profiles for YKL-06-061. YKL-06-061 was profiled at a concentration of 1 pM against a diverse panel of 468 kinases by DiscoverX. Kinases that exhibited a score of 1 or below (Score is percent relative to DMSO control. Smaller numbers indicate stronger binding) are marked in circles. Panel C shows biochemical kinase $IC_{50}$'s of YKL-06-061 top hits as shown in Panel B.

FIG. 7 shows that inhibition of SIK by HG 9-91-01, YKL 06-061, and YKL 06-062 in UACC62 and UACC257 melanoma cells induces Mitf expression. Panel A shows mRNA expression of Mitfrelative to Rpl11 mRNA quantified by QPCR in melanocytes, UACC62 melanoma cells (Panels A, C and E), and UACC257 melanoma cells (Panels B, D, and E) treated with HG 9-91-01 (Panels A and B), YKL 06-061 (Panels C and D), or YKL 06-062 (Panels E and F) (n=3, mean±SD). Panels G and H show mRNA expression of Mitf (Panel G) and Mitf-dependent gene, TRPM1 (Panel H), relative to Rpl11 and vehicle control (70% ethanol; 30% propylene glycol) treatment's Mitf or TRPM1 mRNA expression, respectively, in normal human melanocytes treated with 4 uM of SIK inhibitor quantified by QPCR.

Figure 2A:
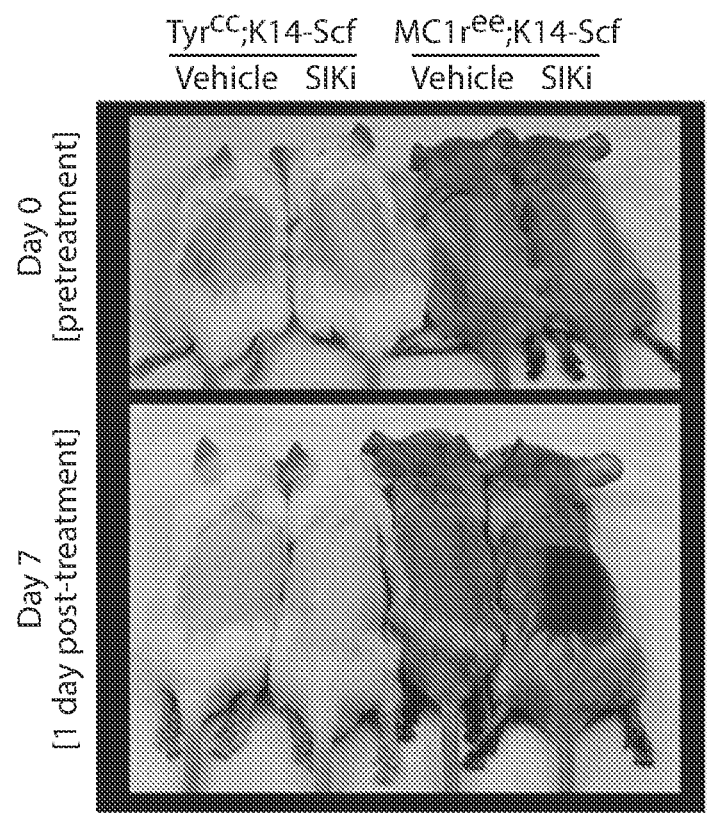
FIG. 2 shows that topical treatment with HG 9-91-01 caused robust darkening in MC1R$^{e/e}$;K14-Scf mice. Panel A shows MC1R$^{e/e}$;K14-Scf mice and Tyr$^{c/c}$;K14-Scf mice (albinos, which serve as negative controls) before treatment (Day 0) and after 7 days of treatment (Day 7) with 30 uL of vehicle control (70% ethanol; 30% propylene glycol) or 37.5 mM HG 9-91-01 (n=4). Panel B shows reflective colorimetry measurements (CIE L* white-black color axis), and Panel D shows melanin extraction of MC1R$^{e/e}$;K14-Scf mice and Tyr$_{c/c}$;K14-Scf mice described in Panel A (n=4, mean±SD). Fontana-Masson (eumelanin) (top two panels of C) and hematoxylin and eosin (bottom two panels of C)stained skin sections of MC1R$^{e/e}$;K14-Scf mice (×400 magnification) are described in Panel A. For all graphs, statistical significance is reported as follows: ****P<0.0001.

FIG. 8 shows $MC1R^{e/e}$;K14-Scf mice (Panel A) and $Tyr^{c/c}$;K14-Scf mice (Panel B) after treatment with vehicle control (70% ethanol; 30% propylene glycol) or 37.5 mM HG 9-91-01 before treatment (Day 0) and after 7 days of treatment (Day 7). Panel C shows fontana-masson (eumelanin) (top panel) and hematoxylin and eosin stain (bottom panel) of $Tyr_{c/c}$;K14-Scf mice (as described in FIG. 2A) after treatment with vehicle control (70% ethanol; 30% propylene glycol) or 37.5 mM HG 9-91-01 before treatment (Day 0) and after 7 days of treatment (Day 7) (n=4) (×630 magnification) (Panel C). Panel D shows fontana-masson (eumelanin) (left two panels) stained skin sections of $MC1R_{e/e}$;K14-Scf mice treated 37.5 mM for 7 days. Image is at the margin of treated and untreated area (×100 magnification) (Panel D). Panel E shows fontana-masson (eumelanin) (left panels) and hematoxylin and eosin stain (right panels) of $MC1R^{e/e}$;K14-Scf mice and Albino;K14-Scf mice with 6 days of treatment of vehicle control (70% ethanol; 30% propylene glycol) or 37.5 mM HG 9-91-01 after 46 days from start of treatment (200× magnification).

Figure 9:
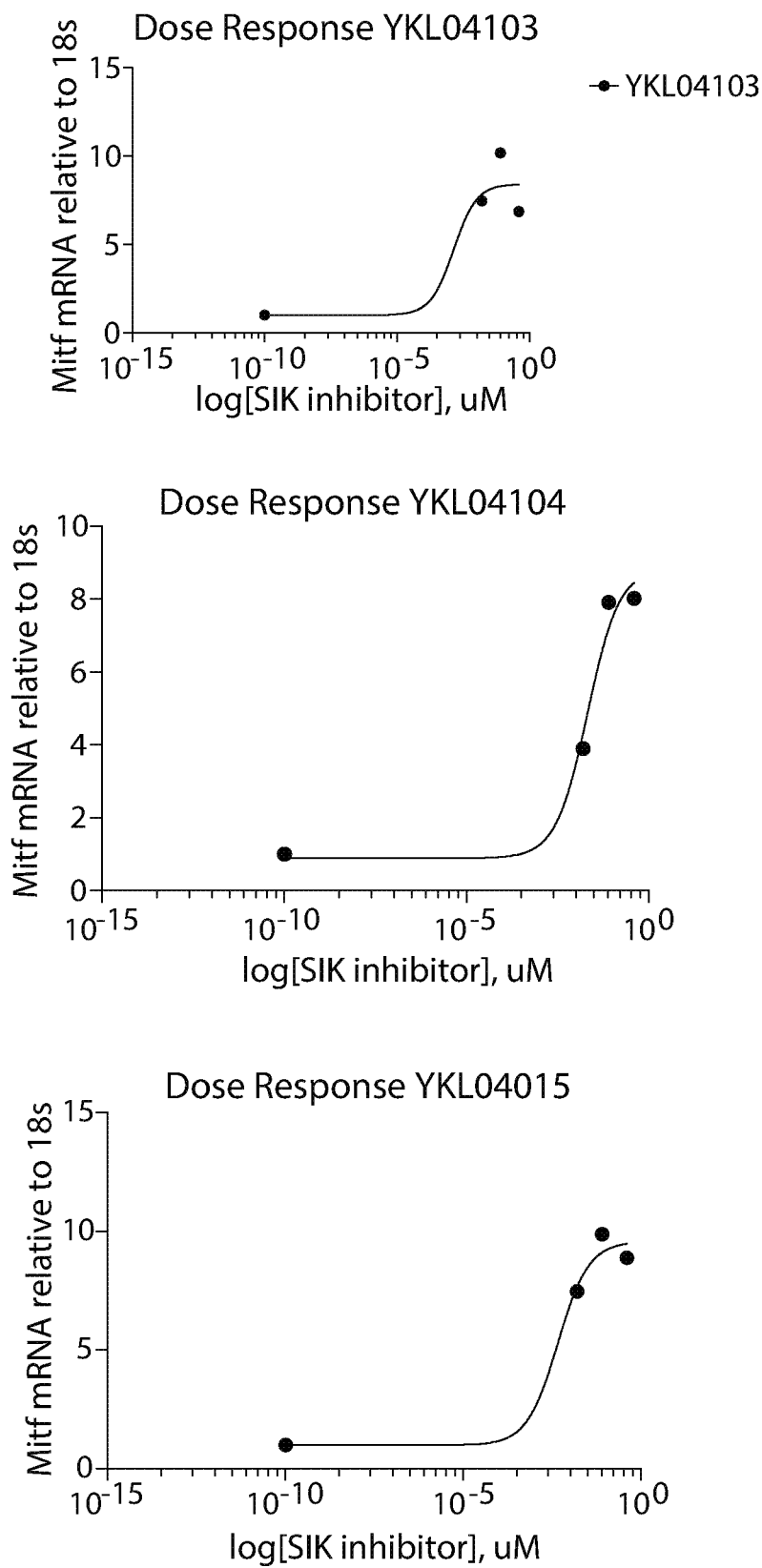
Figure 9:
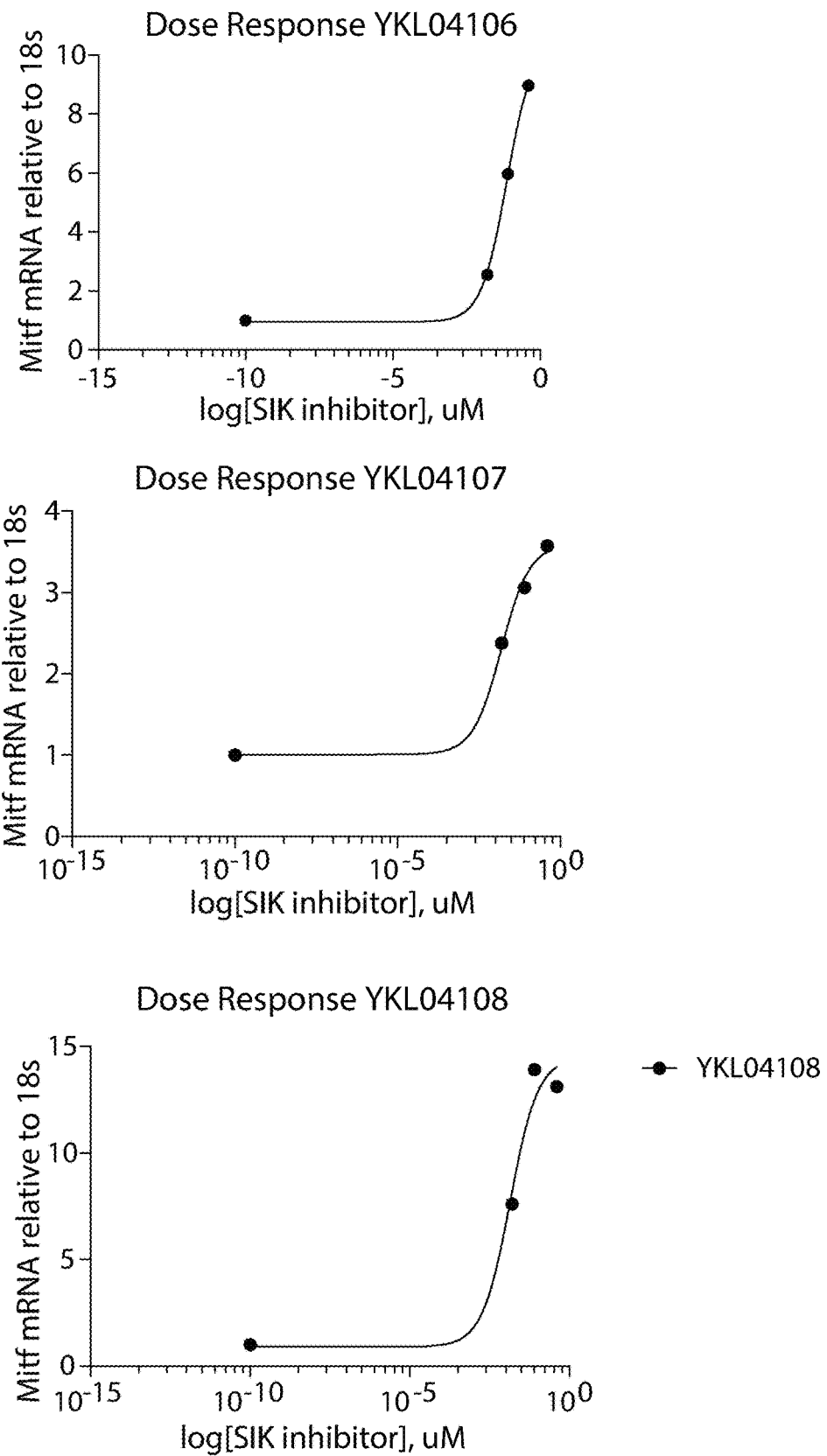
Figure 9:
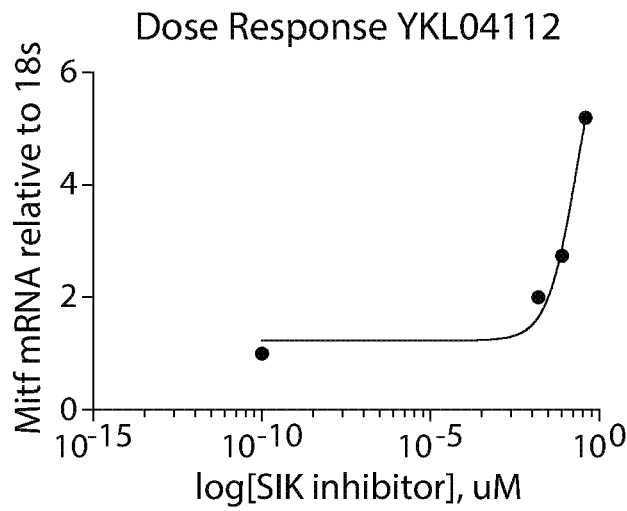
Figure 9:
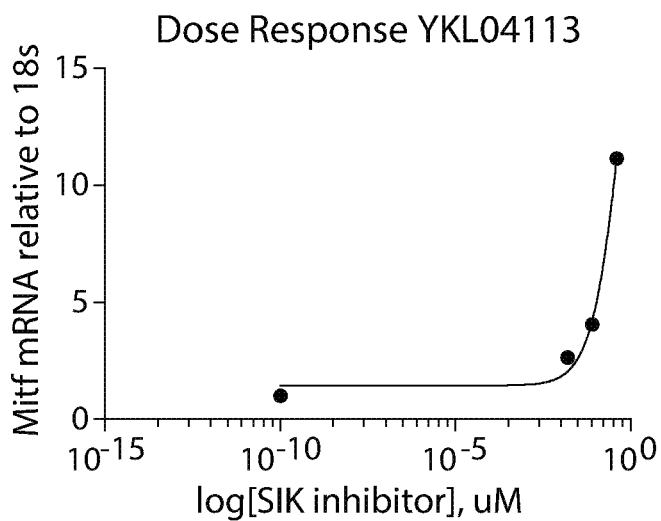
Figure 9:
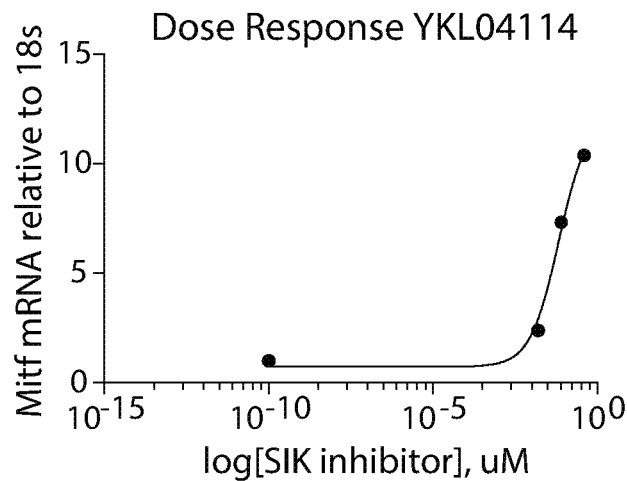
Figure 9:
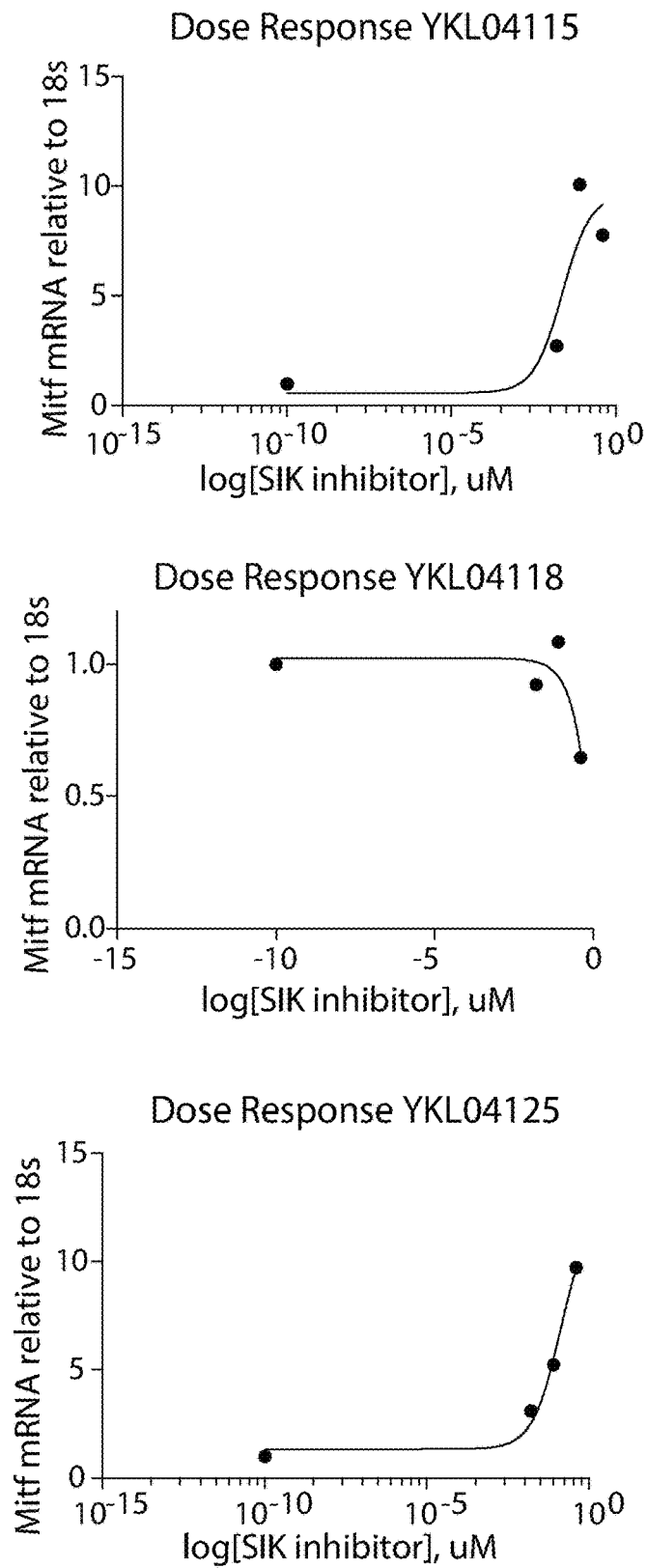
Figure 9:
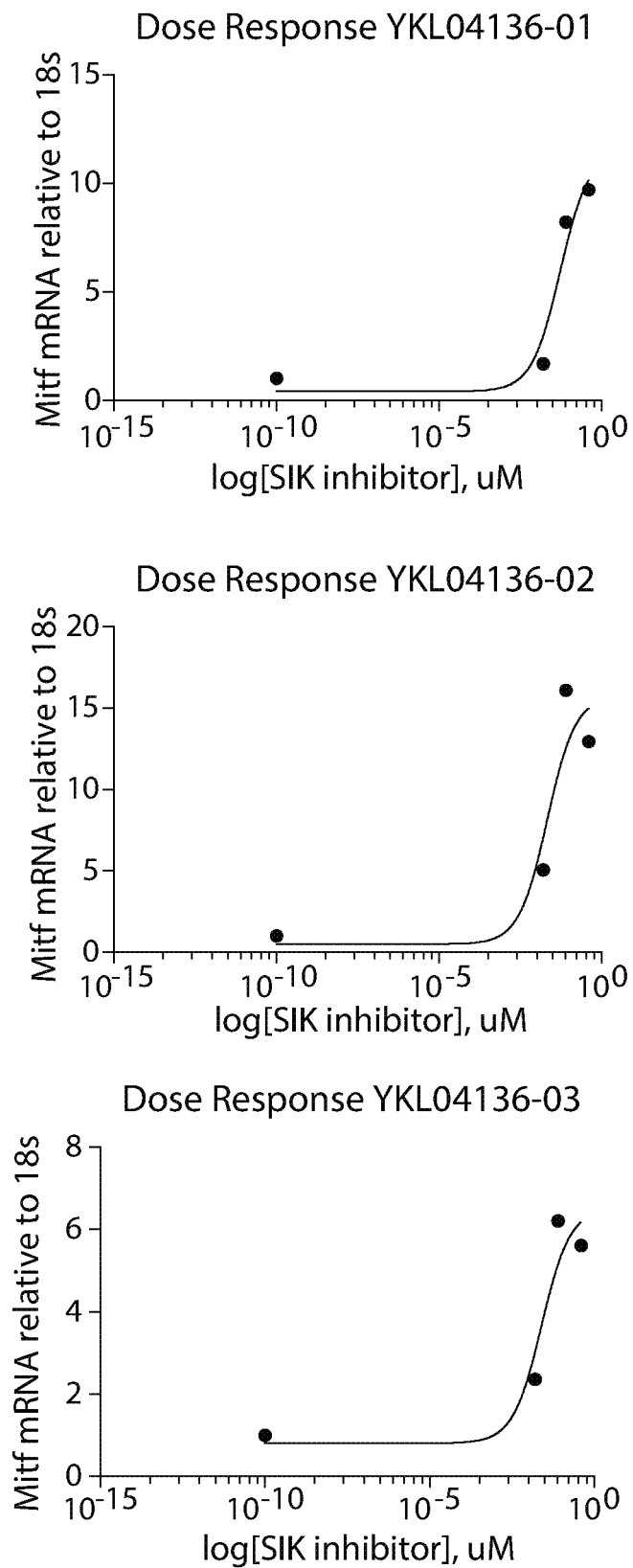
Figure 9:
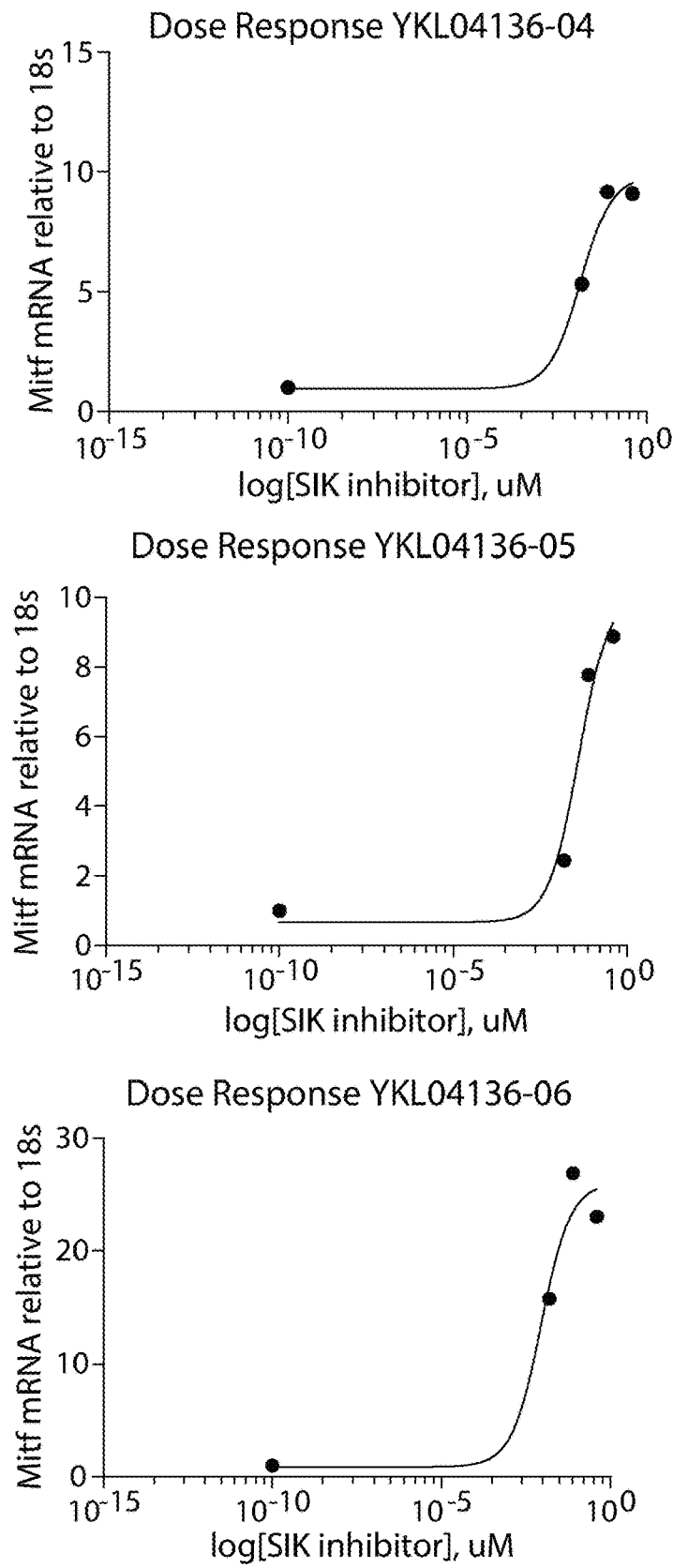
Figure 9:
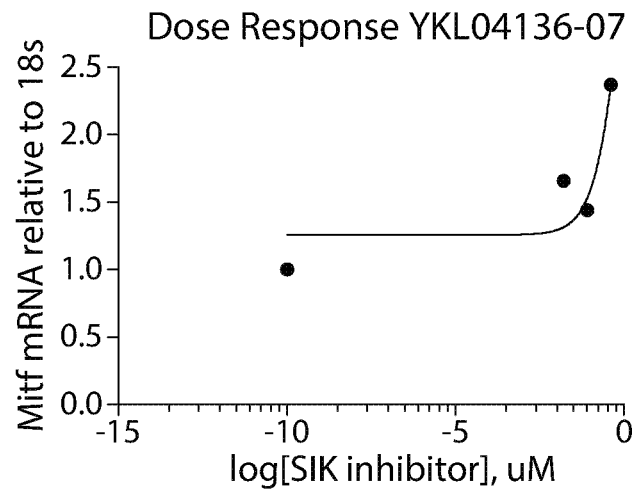
Figure 9:
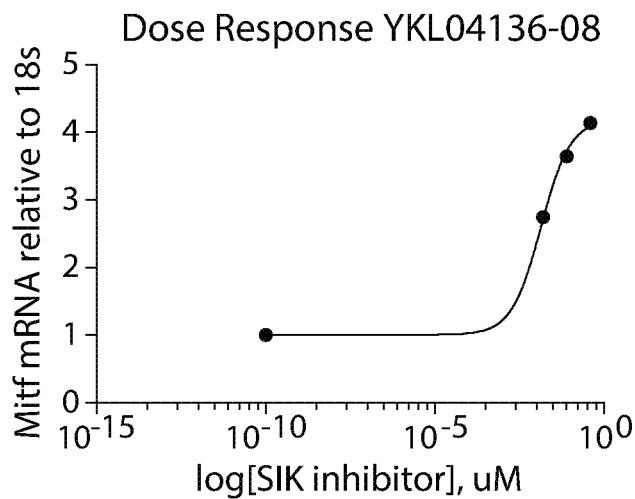
Figure 9:
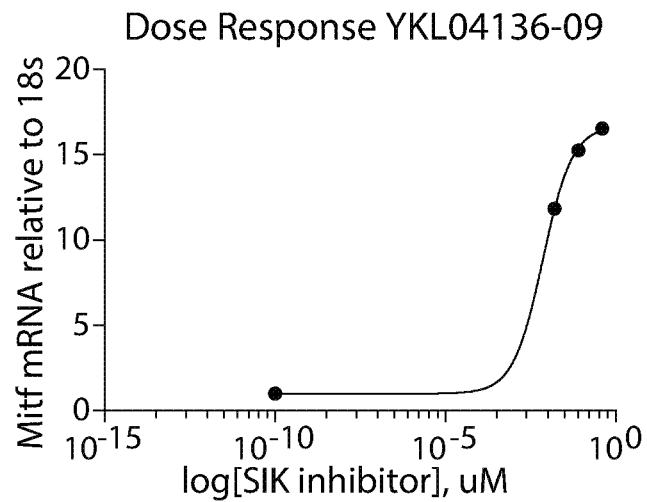
Figure 9:
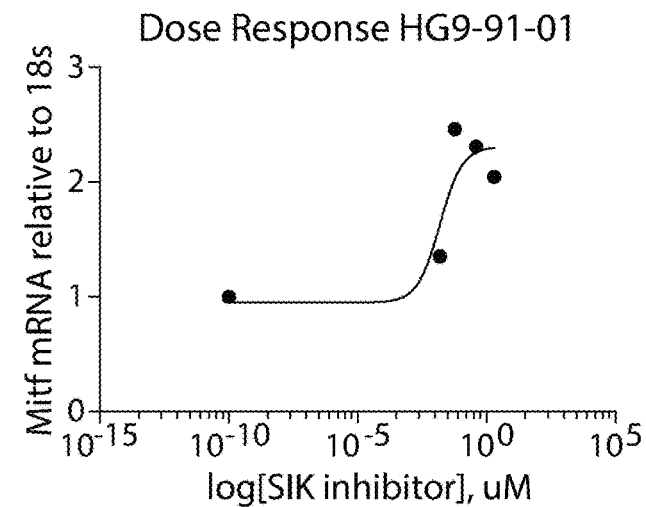
Figure 9:
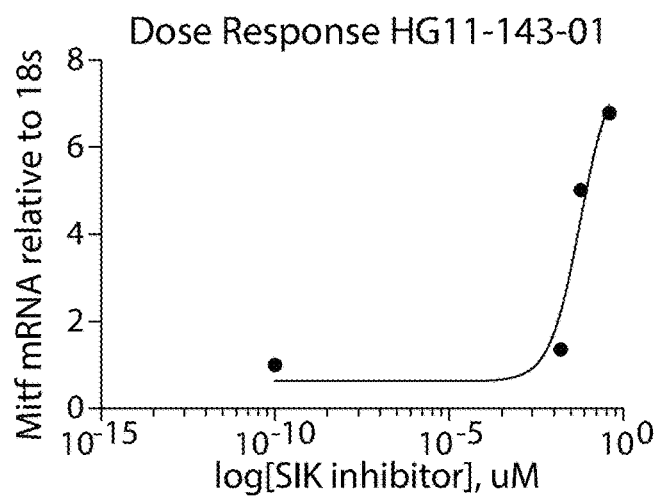
Figure 9:
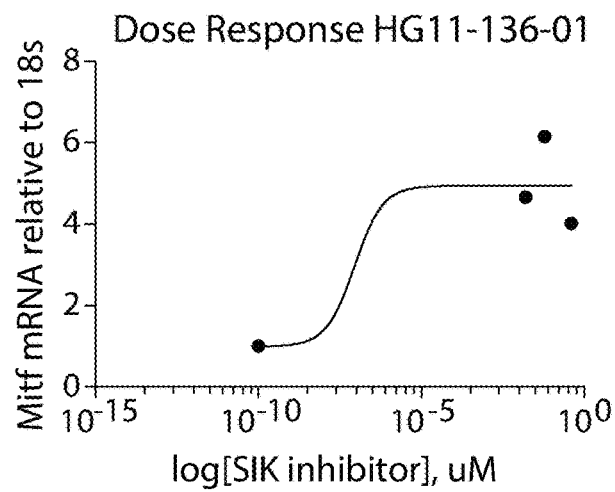
Figure 9:
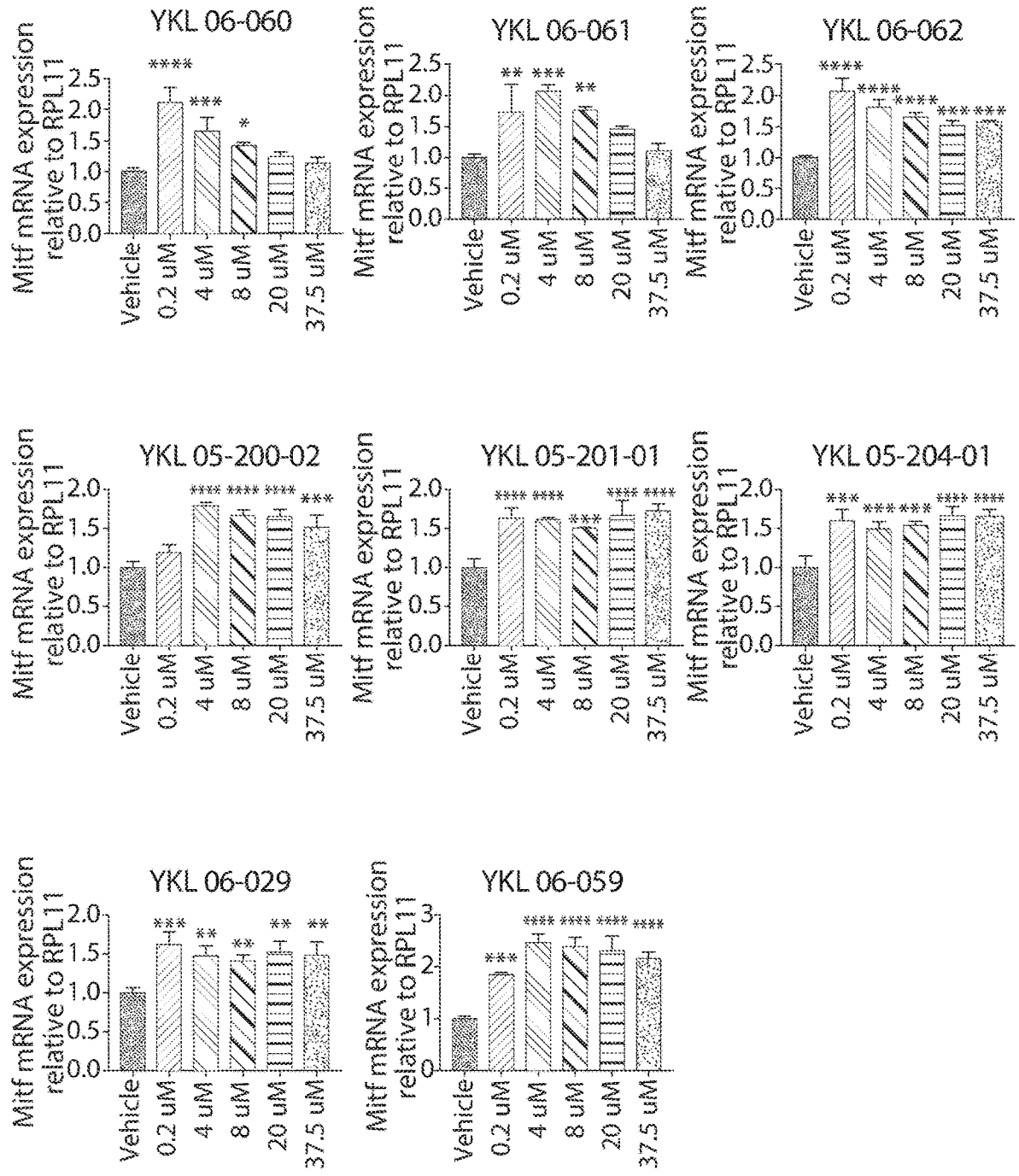

FIG. 9 shows induction of microphthalmia-associated transcription factor (MITF) by exemplary SIK inhibitor compounds in mouse melanoma and human melanoma cell lines.

Figure 10:
Figure 11:
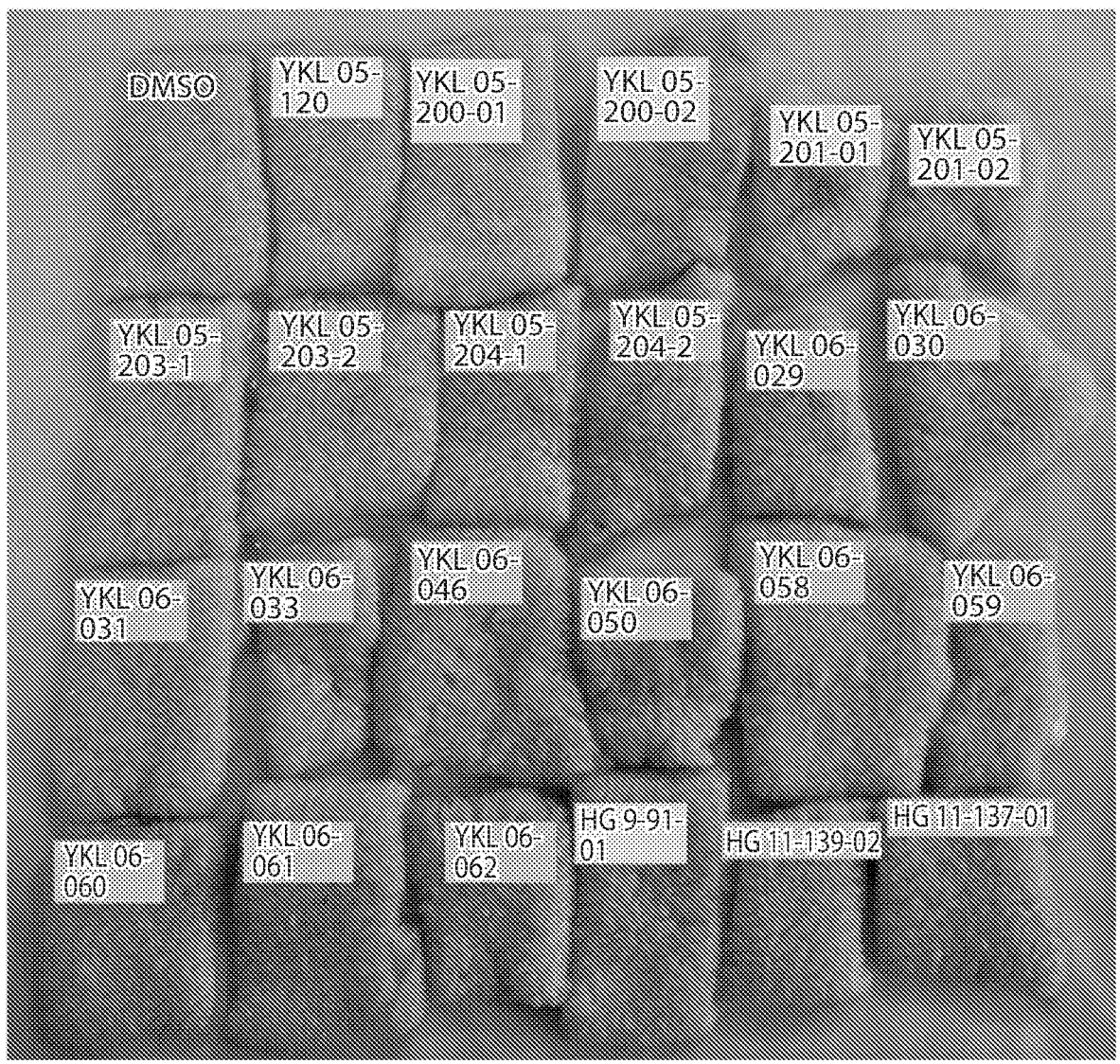
Figure 12:
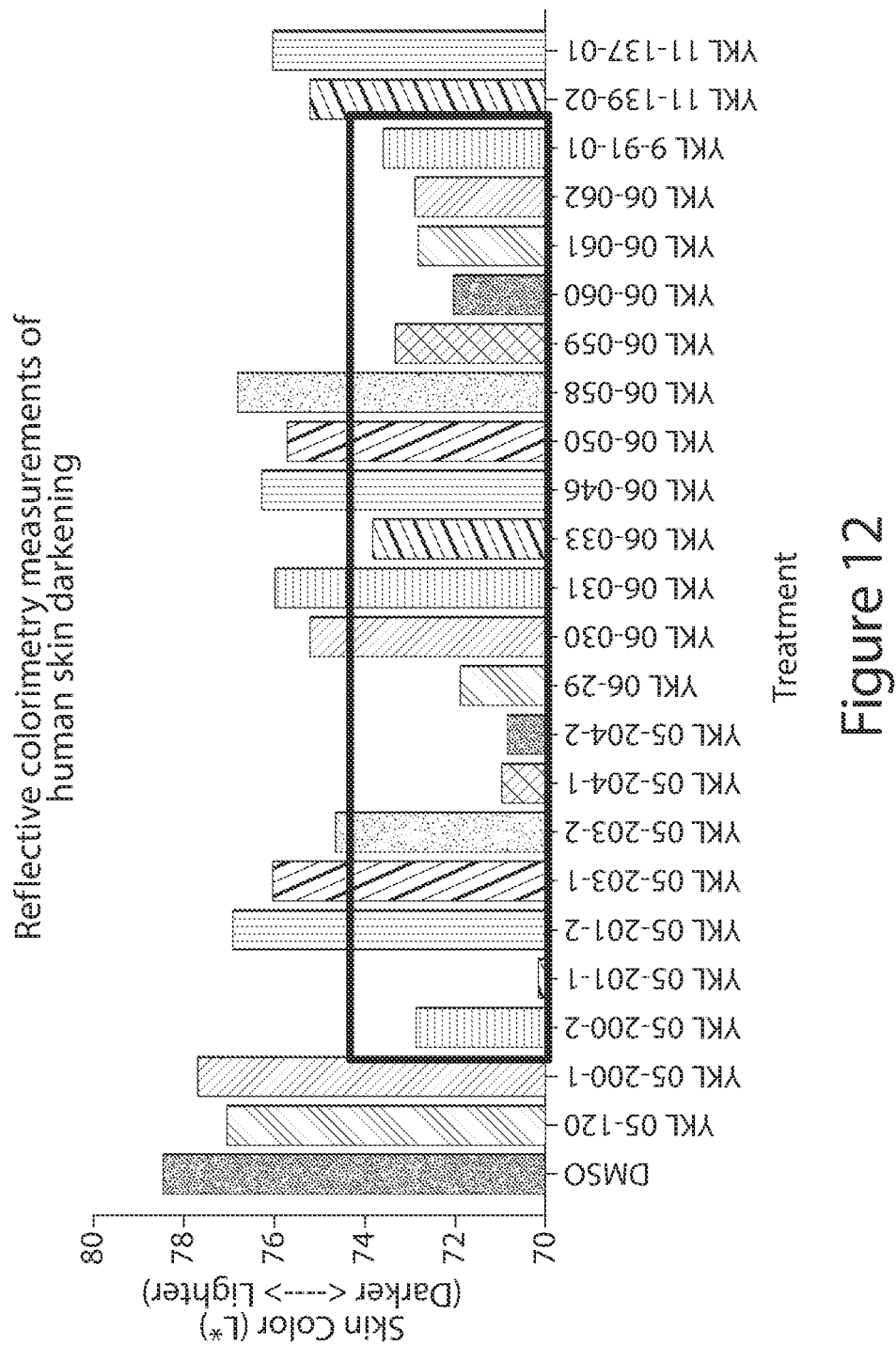

FIG. 10 shows a schematic of SIK inhibitor treatment regime for the skin experiments in FIG. 11 and in FIG. 12.

FIG. 11 shows skin darkening 9 days post treatment with exemplary compounds YKL-05-120, YKL-05-200-01, YKL-05-200-02, YKL-05-201-1, YKL-05-203-1, YKL-05-203-2, YKL-05-204-1, YKL-05-204-2, YKL-06-203-029, YKL-06-030, YKL-06-031, YKL-06-033, YKL-06-046, YKL-06-050, YKL-06-058, YKL-06-059, YKL-06-060, YKL-06-061, YKL-06-062, HG 9-91-01, HG 11-139-02, and HG 11-137-01, compared with DMSO treatment. Treatment of human skin explants 9 days after start of treatment with vehicle control (DMSO) or 10 mM SIK inhibitor solution for all SIK inhibitor compounds except HG 9-91-01, which was applied at a 37.5 mM concentration. Skin was treated with passive application as displayed in the schematic in FIG. 10: 1×/day for the first day, and 2×/day for the next three days with a 2 day break and another 2×/day treatment for the next three days. Image and Colorimeter analysis were conducted 24 hours after the last treatment.

FIG. 12 shows reflective colorimetry measurements of human skin darkening 9 days after treatment with exemplary compounds under the same conditions as for FIG. 11, with exemplary compounds YKL-05-120, YKL-05-200-01, YKL-05-200-02, YKL-05-201-1, YKL-05-203-1, YKL-05-203-2, YKL-05-204-1, YKL-05-204-2, YKL-06-203-029, YKL-06-030, YKL-06-031, YKL-06-033, YKL-06-046, YKL-06-050, YKL-06-058, YKL-06-059, YKL-06-060, YKL-06-061, YKL-06-062, HG 9-91-01, HG 11-139-02, and HG 11-137-01, compared with DMSO treatment.

DETAILED DESCRIPTION OF CERTAIN EMBODIMENTS OF THE INVENTION

Described herein are compounds of Formulas (I), (II), (III), (IV), (V), (VI), (VI-A), and (VII), and pharmaceutically acceptable salts, solvates, hydrates, polymorphs, co-crystals, tautomers, stereoisomers, isotopically labeled derivatives, and prodrugs thereof. Certain compounds described herein are useful in inhibiting the activity of SIK kinase, and are useful in increasing skin pigmentation in a subject in need thereof. Increasing the skin pigmentation in a subject may reduce the risk of developing skin cancer in the subject. Also provided are pharmaceutical compositions and kits including a compound described herein. In certain embodiments, compounds for use in this application are the compounds described in U.S. patent application U.S. Ser. No. 14/385,077, filed Sep. 12, 2014, U.S. Ser. No. 15/606,970, filed May 26, 2017, U.S. Ser. No. 62/027,099, filed Jul. 21, 2014, U.S. Ser. No. 15/327,690, filed Jan. 20, 2017, U.S. Ser. No. 62/358,524, filed Jul. 5, 2016, U.S. Ser. No. 62/027,122, filed Jul. 21, 2014, U.S. Ser. No. 15/327,705, filed Jan. 20, 2017, each of which is incorporated herein by reference.

Compounds Useful in the Invention

Compounds of Formula (I)

In one aspect, the compound utilized in the present disclosure is of Formula (I):

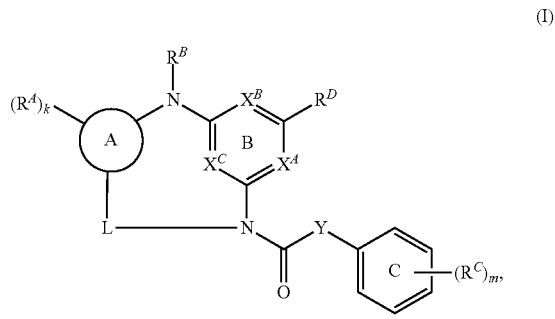

or a pharmaceutically acceptable salt thereof, wherein:

Ring A is a substituted or unsubstituted phenyl ring or a substituted or unsubstituted, monocyclic, 5- to 6-membered heteroaryl ring, wherein one, two, three, or four atoms in the heteroaryl ring system are independently nitrogen, oxygen, or sulfur;

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A1}$, —N(R$^{A1}$)$_2$, —SR$^{A1}$, —CN, —SCN, —C(=NR$^{A1}$)R$^{A1}$, —C(=NR$^{A1}$)OR$^{A1}$, —C(=NR$^{A1}$)N(R$^{A1}$)$_2$, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$C(=O)N(R$^{A1}$)$_2$, —OC(=O)R$^{A1}$, —OC(=O)OR$^{A1}$, or —OC(=O)N(R$^A$)$_2$, wherein each instance of R$^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{A1}$ groups are joined to form a substituted or unsubstituted heterocyclic or substituted or unsubstituted heteroaryl ring;

k is 0, 1, 2, 3, or 4;

L is a substituted or unsubstituted, saturated or unsaturated C$_{3-10}$ hydrocarbon chain, optionally wherein one or more chain atoms of the hydrocarbon chain are independently replaced with —O—, —S—, —NR$^N$—, —N=, or =N—, wherein each instance of R$^N$ is independently hydrogen, substituted or unsubstituted acyl, substituted or unsubstituted C$_{1-6}$ alkyl, or a nitrogen protecting group;

R$^B$ is hydrogen, substituted or unsubstituted acyl, substituted or unsubstituted C$_{1-6}$ alkyl, or a nitrogen protecting group;

each of X$^A$, X$^B$, and X$^C$ is independently N or CR$^X$, wherein R$^X$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{X1}$, —N(R$^{X1}$)$_2$, —SR$^{X1}$, —CN, —SCN, —C(=NR$^{X1}$)R$^{X1}$, —C(=NR$^{X1}$)OR$^{X1}$, —C(=NR$^{X1}$)N(R$^{X1}$)$_2$, —C(=O)R$^{X1}$, C(=O)OR$^{X1}$, —C(=O)N(R$^{X1}$)$_2$, —NO$_2$, —NR$^{X1}$C(=O)R$^{X1}$, —NR$^{X1}$C(=O)OR$^{X1}$, —NR$^{X1}$C(=O)N(R$^{X1}$)$_2$, —OC(=O)R$^{X1}$, —OC(=O)OR$^{X1}$, or —OC(=O)N(R$^{X1}$)$_2$, wherein each instance of R$^{X1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{X1}$ groups are joined to form a substituted or unsubstituted heterocyclic or substituted or unsubstituted heteroaryl ring;

Y is —O— or —NR$^Y$—, wherein R$^Y$ is hydrogen, substituted or unsubstituted acyl, substituted or unsubstituted C$_{1-6}$ alkyl, or a nitrogen protecting group;

or when Y is —NR$^Y$—, and X$^A$ is CR$^X$, R$^Y$ and R$^X$ of X$^A$ are joined to form a substituted or unsubstituted, monocyclic, 5- to 7-membered heterocyclic ring that is fused with Ring B;

each instance of R$^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{C1}$, —N(R$^{C1}$)$_2$, —SR$^{C1}$, —CN, —SCN, —C(=NR$^{C1}$)R$^{C1}$, —C(=NR$^{C1}$)OR$^{C1}$, —C(=NR$^{C1}$)N(R$^{C1}$)$_2$, —C(=O)R$_{C1}$, —C(=O)OR$^{C1}$, —C(=O)N(R$^{C1}$)$_2$, —NO$_2$, —NR$^{C1}$C(=O)R$^{C1}$, —NR$^{C1}$C(=O)OR$^{C1}$, —NR$^{C1}$C(=O)N(R$^{C1}$)$_2$, —OC(=O)R$^{C1}$, —OC(=O)OR$^{C1}$, or —OC(=O)N(R$^{C1}$)$_2$, wherein each instance of R$^{C1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{C1}$ groups are joined to form a substituted or unsubstituted heterocyclic or substituted or unsubstituted heteroaryl ring;

m is 0, 1, 2, 3, 4, or 5; and

R$^D$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{D1}$, —N(R$^{D1}$)$_2$, —SR$^{D1}$, —CN, —SCN, —C(=NR$^{D1}$)R$^{D1}$, —C(=NR$^{D1}$)OR$^{D1}$, C(=NR$^{D1}$)N(R$^{D1}$)$_2$, —C(=O)R$^{D1}$, —C(=O)OR$^{D1}$, —C(=O)N(R$^{D1}$)$_2$, —NO$_2$, —NR$^{D1}$C(=O)R$^{D1}$, —NR$^{D1}$C(=O)OR$^{D1}$, —NR$^{D1}$C(=O)N(R$^{D1}$)$_2$, —OC(=O)R$^{D1}$, —OC(=O)OR$^{D1}$, or —OC(=O)N(R$^{D1}$)$_2$, wherein each instance of R$^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{D1}$ are joined to form a substituted or unsubstituted heterocyclic or substituted or unsubstituted heteroaryl ring.

Formula (I) includes Ring A that is unsubstituted (e.g., when k is 0) or substituted with one or more substituents R$^A$ (e.g., when k is 1, 2, 3, or 4). In certain embodiments, Ring A is an unsubstituted phenyl ring. In certain embodiments, Ring A is a substituted phenyl ring. In certain embodiments, Ring A is a substituted or unsubstituted, monocyclic, 5-membered heteroaryl ring (e.g., furanyl, thienyl, pyrrolyl, imidazolyl, pyrazolyl, oxazolyl, isoxazolyl, thiazolyl, or isothiazolyl ring), wherein one, two, three, or four atoms in the heteroaryl ring system are independently nitrogen, oxygen, or sulfur. In certain embodiments, Ring A is substituted or unsubstituted pyrazolyl. In certain embodiments, Ring A is a substituted or unsubstituted, monocyclic, 6-membered heteroaryl ring (e.g., a pyridyl, pyrazinyl, pyrimidinyl, or pyridazinyl ring), wherein one, two, three, or four atoms in the heteroaryl ring system are independently nitrogen, oxygen, or sulfur. In certain embodiments, Ring A is substituted or unsubstituted pyridinyl. In certain embodiments, Ring A is of the formula:

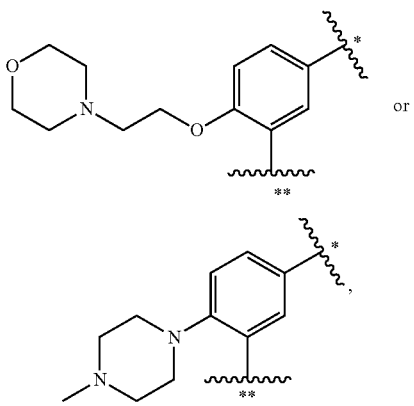

wherein the radical marked with "*" is directly attached to N(R$^B$), and the radical marked with "**" is directly attached to L.

In Formula (I), Ring A may include one or more substituents R$^A$. In certain embodiments, at least two instances of R$^A$ are different. In certain embodiments, all instances of R$^A$ are the same. In certain embodiments, at least one instance of R$^A$ is halogen. In certain embodiments, at least one instance of R$^A$ is F. In certain embodiments, at least one instance of R$^A$ is Cl. In certain embodiments, at least one instance of R$^A$ is Br. In certain embodiments, at least one instance of R$^A$ is I (iodine). In certain embodiments, at least one instance of R$^A$ is substituted alkyl. In certain embodiments, at least one instance of R$^A$ is unsubstituted alkyl. In certain embodiments, at least one instance of R$^A$ is unsubstituted C$_{1-6}$ alkyl. In certain embodiments, all instances of R$^A$ are unsubstituted C$_{1-6}$ alkyl. In certain embodiments, at least one instance of R$^A$ is substituted C$_{1-6}$ alkyl. In certain embodiments, at least one instance of R$^A$ is C$_{1-6}$ alkyl substituted with at least one halogen. In certain embodiments, at least one instance of R$^A$ is —CH$_3$. In certain embodiments, all instances of R$^A$ are —CH$_3$. In certain embodiments, at least one instance of R$^A$ is substituted methyl. In certain embodiments, at least one instance of R$^A$ is —CH$_2$F. In certain embodiments, at least one instance of R$^A$ is —CHF$_2$. In certain embodiments, at least one instance of R$^A$ is —CF$_3$. In certain embodiments, at least one instance of R$^A$ is ethyl. In certain embodiments, at least one instance of R$^A$ is propyl. In certain embodiments, at least one instance of R$^A$ is butyl. In certain embodiments, at least one instance of R$^A$ is pentyl. In certain embodiments, at least one instance of R$^A$ is hexyl. In certain embodiments, at least one instance of R$^A$ is substituted alkenyl. In certain embodiments, at least one instance of R$^A$ is unsubstituted alkenyl. In certain embodiments, at least one instance of R$^A$ is substituted alkynyl. In certain embodiments, at least one instance of R$^A$ is unsubstituted alkynyl. In certain embodiments, at least one instance of R$^A$ is substituted carbocyclyl. In certain embodiments, at least one instance of R$^A$ is unsubstituted carbocyclyl. In certain embodiments, at least one instance of R$^A$ is saturated carbocyclyl. In certain embodiments, at least one instance of R$^A$ is unsaturated carbocyclyl. In certain embodiments, at least one instance of R$^A$ is monocyclic carbocyclyl. In certain embodiments, at least one instance of R$^A$ is 3- to 7-membered, monocyclic carbocyclyl. In certain embodiments, at least one instance of R$^A$ is substituted heterocyclyl. In certain embodiments, at least one instance of R$^A$ is unsubstituted heterocyclyl. In certain embodiments, at least one instance of R$^A$ is saturated heterocyclyl. In certain embodiments, at least one instance of R$^A$ is unsaturated heterocyclyl. In certain embodiments, at least one instance of R$^A$ is heterocyclyl, wherein one, two, or three atoms in the heterocyclic ring system are independently selected from the group consisting of nitrogen, oxygen, and sulfur. In certain embodiments, at least one instance of R$^A$ is monocyclic heterocyclyl. In certain embodiments, at least one instance of R$^A$ is 3- to 7-membered, monocyclic heterocyclyl. In certain embodiments, at least one instance of R$^A$ is substituted or unsubstituted, monocyclic, 3- to 7-membered heterocyclyl, wherein one, two, or three atoms in the heterocyclic ring system are independently selected from the group consisting of nitrogen, oxygen, and sulfur. In certain embodiments, at least one instance of R$^A$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, at least one instance of R$^A$ is of the formula:

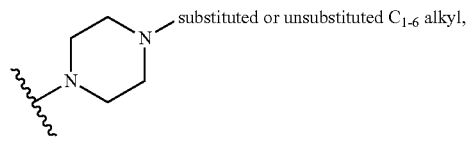

such as

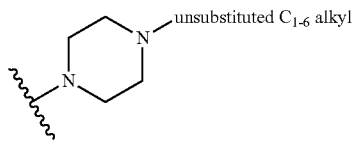

(e.g.,

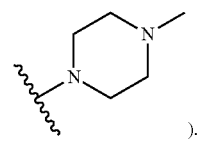 [SMILES: *N1CCN(C)CC1]

).

In certain embodiments, at least one instance of R$^A$ is of the formula

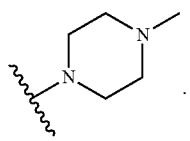 [SMILES: *N1CCN(C)CC1]

.

In certain embodiments, at least one instance of R$^A$ is substituted aryl. In certain embodiments, at least one instance of R$^A$ is unsubstituted aryl. In certain embodiments, at least one instance of R$^A$ is 6- to 10-membered aryl. In certain embodiments, at least one instance of R$^A$ is substituted phenyl. In certain embodiments, at least one instance of R$^A$ is unsubstituted phenyl. In certain embodiments, at least one instance of R$^A$ is substituted heteroaryl. In certain embodiments, at least one instance of R$^A$ is unsubstituted heteroaryl. In certain embodiments, at least one instance of $R^4$ is heteroaryl, wherein one, two, three, or four atoms in the heteroaryl ring system are independently selected from the group consisting of nitrogen, oxygen, and sulfur. In certain embodiments, at least one instance of $R^4$ is monocyclic heteroaryl. In certain embodiments, at least one instance of $R^4$ is 5-membered, monocyclic heteroaryl. In certain embodiments, at least one instance of $R^4$ is 6-membered, monocyclic heteroaryl. In certain embodiments, at least one instance of $R^4$ is bicyclic heteroaryl, wherein the point of attachment may be on any atom of the bicyclic heteroaryl ring system, as valency permits. In certain embodiments, at least one instance of $R^4$ is 9- or 10-membered, bicyclic heteroaryl. In certain embodiments, at least one instance of $R^4$ is —$OR^{41}$. In certain embodiments, at least one instance of $R^4$ is —OH. In certain embodiments, at least one instance of $R^4$ is —O(substituted or unsubstituted $C_{1-6}$ alkyl). In certain embodiments, at least one instance of $R^4$ is —OMe. In certain embodiments, at least one instance of $R^4$ is —OEt. In certain embodiments, at least one instance of $R^4$ is —OPr. In certain embodiments, at least one instance of $R^4$ is —OBu. In certain embodiments, at least one instance of $R^4$ is —OBn. In certain embodiments, at least one instance of $R^4$ is —OPh. In certain embodiments, at least one instance of $R^4$ is —$SR^{41}$. In certain embodiments, at least one instance of $R^4$ is —SH. In certain embodiments, at least one instance of $R^4$ is —SMe. In certain embodiments, at least one instance of $R^4$ is —$N(R^{41})_2$. In certain embodiments, at least one instance of $R^4$ is —$NH_2$. In certain embodiments, at least one instance of $R^4$ is —NHMe. In certain embodiments, at least one instance of $R^4$ is —$NMe_2$. In certain embodiments, at least one instance of $R^4$ is —CN. In certain embodiments, at least one instance of $R^4$ is —SCN. In certain embodiments, at least one instance of $R^4$ is —$C(=NR^{41})R^{41}$, —$C(=NR^{41})OR^{41}$, or —$C(=NR^{41})N(R^{41})_2$. In certain embodiments, at least one instance of $R^4$ is —$C(=O)R^{41}$ or —$C(=O)OR^{41}$. In certain embodiments, at least one instance of $R^4$ is —$C(=O)N(R^{41})_2$. In certain embodiments, at least one instance of $R^4$ is —$C(=O)NMe_2$, —$C(=O)NHMe$, or —$C(=O)NH_2$. In certain embodiments, at least one instance of $R^4$ is —$NO_2$. In certain embodiments, at least one instance of $R^4$ is —$NR^{41}C(=O)R^{41}$, —$NR^4C(=O)OR^{41}$, or —$NR^{41}C(=O)N(R^{41})_2$. In certain embodiments, at least one instance of $R^4$ is —$OC(=O)R^{41}$, —$OC(=O)OR^{41}$, or —$OC(=O)N(R^{41})_2$.

In certain embodiments, at least one instance of $R^{41}$ is H. In certain embodiments, at least one instance of $R^{41}$ is substituted acyl. In certain embodiments, at least one instance of $R^{41}$ is unsubstituted acyl. In certain embodiments, at least one instance of $R^{41}$ is acetyl. In certain embodiments, at least one instance of $R^{41}$ is substituted alkyl. In certain embodiments, at least one instance of $R^{41}$ is unsubstituted alkyl. In certain embodiments, at least one instance of $R^{41}$ is unsubstituted $C_{1-6}$ alkyl. In certain embodiments, at least one instance of $R^4$ is methyl. In certain embodiments, at least one instance of $R^{41}$ is ethyl. In certain embodiments, at least one instance of $R^{41}$ is propyl. In certain embodiments, at least one instance of $R^{41}$ is butyl. In certain embodiments, at least one instance of $R^{41}$ is pentyl. In certain embodiments, at least one instance of $R^{41}$ is hexyl. In certain embodiments, at least one instance of $R^{41}$ is substituted alkenyl. In certain embodiments, at least one instance of $R^{41}$ is unsubstituted alkenyl. In certain embodiments, at least one instance of $R^{41}$ is substituted alkynyl. In certain embodiments, at least one instance of $R^{41}$ is unsubstituted alkynyl. In certain embodiments, at least one instance of $R^{41}$ is substituted or unsubstituted carbocyclyl. In certain embodiments, at least one instance of $R^{41}$ is saturated carbocyclyl. In certain embodiments, at least one instance of $R^{41}$ is unsaturated carbocyclyl. In certain embodiments, at least one instance of $R^{41}$ is 3- to 7-membered, monocyclic carbocyclyl. In certain embodiments, at least one instance of $R^{41}$ is substituted or unsubstituted heterocyclyl. In certain embodiments, at least one instance of $R^{41}$ is saturated heterocyclyl. In certain embodiments, at least one instance of R is unsaturated heterocyclyl. In certain embodiments, at least one instance of $R^{41}$ is heterocyclyl, wherein one, two, or three atoms in the heterocyclic ring system are independently selected from the group consisting of nitrogen, oxygen, and sulfur. In certain embodiments, at least one instance of $R^{41}$ is 3- to 7-membered, monocyclic heterocyclyl. In certain embodiments, at least one instance of $R^{41}$ is substituted or unsubstituted aryl. In certain embodiments, at least one instance of $R^{41}$ is 6- to 10-membered aryl. In certain embodiments, at least one instance of $R^{41}$ is monocyclic aryl. In certain embodiments, at least one instance of $R^{41}$ is substituted phenyl. In certain embodiments, at least one instance of $R^{41}$ is unsubstituted phenyl. In certain embodiments, at least one instance of $R^{41}$ is bicyclic aryl. In certain embodiments, at least one instance of $R^{41}$ is substituted or unsubstituted heteroaryl. In certain embodiments, at least one instance of $R^{41}$ is heteroaryl, wherein one, two, three, or four atoms in the heteroaryl ring system are independently selected from the group consisting of nitrogen, oxygen, and sulfur. In certain embodiments, at least one instance of $R^{41}$ is monocyclic heteroaryl. In certain embodiments, at least one instance of $R^{41}$ is 5- or 6-membered, monocyclic heteroaryl. In certain embodiments, at least one instance of $R^{41}$ is bicyclic heteroaryl, wherein the point of attachment may be on any atom of the bicyclic heteroaryl ring system, as valency permits. In certain embodiments, at least one instance of $R^{41}$ is a nitrogen protecting group when attached to a nitrogen atom. In certain embodiments, at least one instance of $R^{41}$ is Bn, Boc, Cbz, Fmoc, trifluoroacetyl, triphenylmethyl, acetyl, or Ts when attached to a nitrogen atom. In certain embodiments, $R^{41}$ is an oxygen protecting group when attached to an oxygen atom. In certain embodiments, $R^{41}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{41}$ is a sulfur protecting group when attached to a sulfur atom. In certain embodiments, $R^{41}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{41}$ are joined to form a substituted or unsubstituted heterocyclic ring. In certain embodiments, two instances of $R^{41}$ are joined to form a saturated or unsaturated heterocyclic ring. In certain embodiments, two instances of $R^{41}$ are joined to form a heterocyclic ring, wherein one, two, or three atoms in the heterocyclic ring system are independently selected from the group consisting of nitrogen, oxygen, and sulfur. In certain embodiments, two instances of $R^{41}$ are joined to form a 3- to 7-membered, monocyclic heterocyclic ring. In certain embodiments, two instances of $R^{41}$ are joined to form a substituted or unsubstituted heteroaryl ring. In certain embodiments, two instances of $R^{41}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

In certain embodiments, k is 0. In certain embodiments, k is 1. In certain embodiments, k is 2. In certain embodiments, k is 3. In certain embodiments, k is 4. In certain embodiments, k is 1 and $R^A$ is

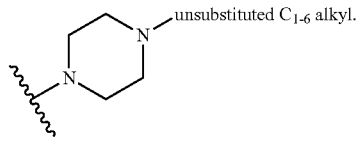

Formula (I) includes divalent linker L. L consists of a chain, and optionally one or more hydrogen atoms and/or one or more substituents (e.g., =O) on the chain, where any two substituents may optionally be joined to form a ring. In certain embodiments, the molecular weight of L is not more than about 300 g/mol, not more than about 200 g/mol, not more than about 150 g/mol, not more than about 100 g/mol, or not more than 80 g/mol. In certain embodiments, the molecular weight of L is between 50 and 150 g/mol, inclusive. In certain embodiments, L consists of not more than about 70 atoms, not more than about 50 atoms, not more than about 30 atoms, not more than about 20 atoms, or not more than 15 atoms. In certain embodiments, L consists of between 10 and 30 atoms, inclusive. In certain embodiments, L does not include unsaturated bonds in the chain. In certain embodiments, L consists of one unsaturated bond in the chain. In certain embodiments, L consists of 2, 3, or 4 unsaturated bonds in the chain. In certain embodiments, L is a substituted or unsubstituted, saturated or unsaturated $C_{3-10}$ hydrocarbon chain (e.g., a $C_{5-6}$ hydrocarbon chain). In certain embodiments, L is a substituted or unsubstituted, saturated or unsaturated $C_{3-10}$ hydrocarbon chain (e.g., a $C_{5-6}$ hydrocarbon chain), wherein one chain atom of the hydrocarbon chain is replaced with —O—, —S—, —NR$^N$—, —N=, or =N—. In certain embodiments, L is a substituted or unsubstituted, saturated or unsaturated, $C_{3-10}$ hydrocarbon chain (e.g., a $C_{5-6}$ hydrocarbon chain), wherein 2, 3, 4, or 5 chain atoms of the hydrocarbon chain are independently replaced with —O—, —S—, —NRN—, —N=, or =N—. In certain embodiments, L is a substituted or unsubstituted, saturated or unsaturated $C_{5-6}$ hydrocarbon chain, wherein one or two chain atoms of the hydrocarbon chain are independently replaced with —O—, —S—, or —NR$^N$—. In certain embodiments, L is of the formula:

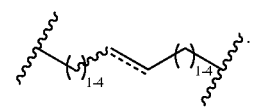

In certain embodiments, L is of the formula:

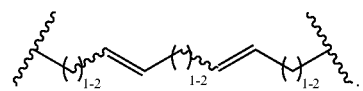

In certain embodiments, L is of the formula:

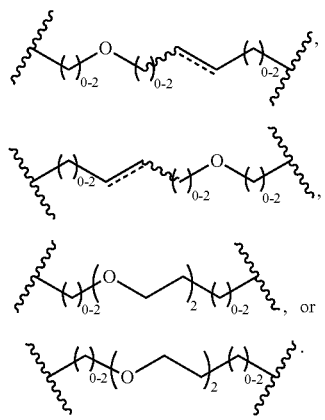

In certain embodiments, L is of the formula:

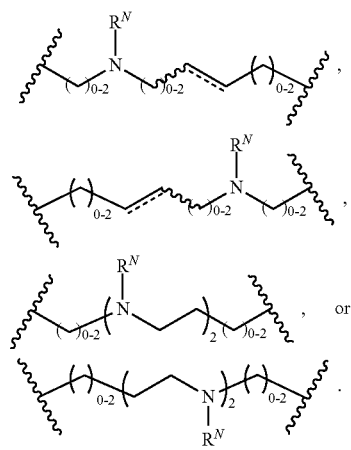

In certain embodiments, L is of the formula:

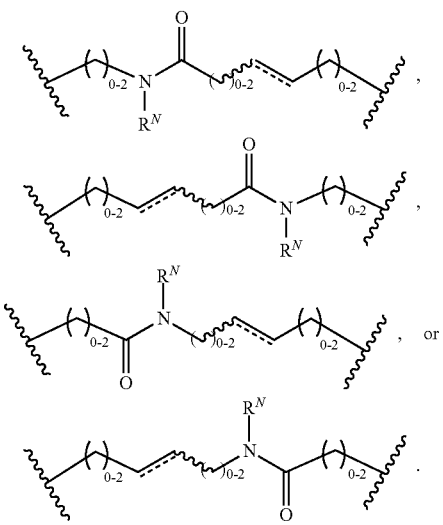

In certain embodiments, L is of the formula:

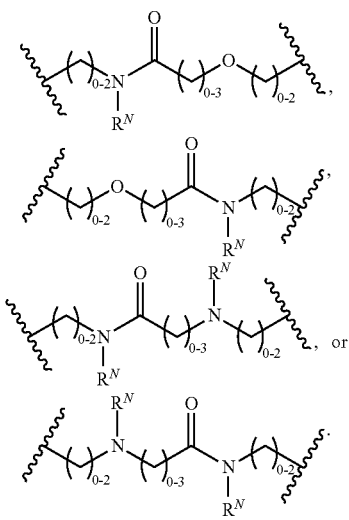

In certain embodiments, L is of the formula:

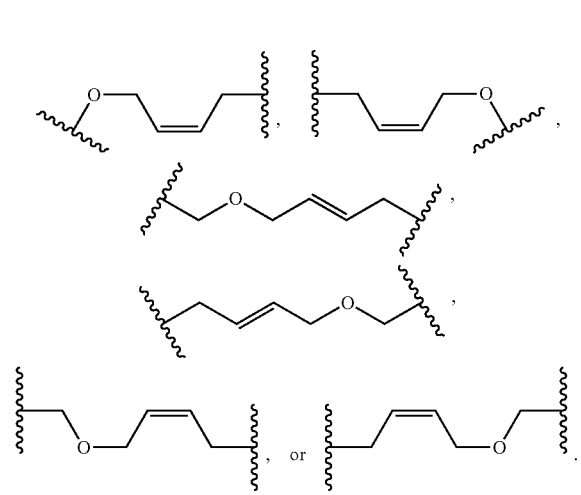

In certain embodiments, L is of the formula:

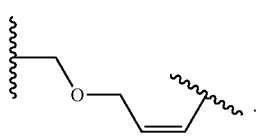 [SMILES: */C=C\COC*]

In certain embodiments, L is of the formula:

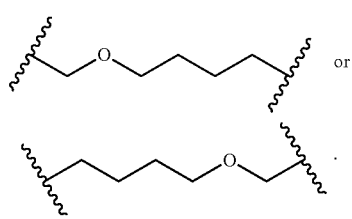

In certain embodiments, L is of the formula:

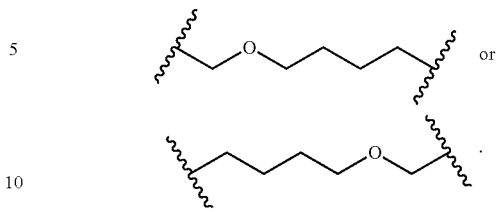

In certain embodiments, L is of the formula:

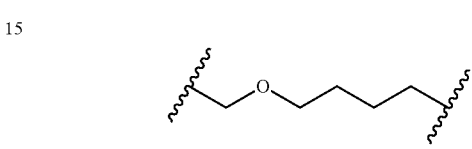

In certain embodiments, L is of the formula:

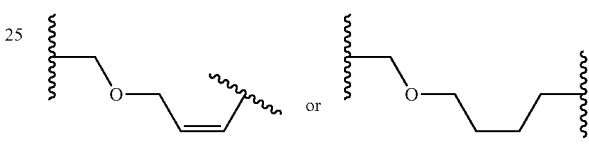

In certain embodiments, at least two instances of $R^N$ are different. In certain embodiments, all instances of $R^N$ are the same. In certain embodiments, at least one instance of $R^N$ is H. In certain embodiments, each instance of $R^N$ is H. In certain embodiments, at least one instance of $R^N$ is substituted acyl. In certain embodiments, at least one instance of $R^N$ is unsubstituted acyl. In certain embodiments, at least one instance of $R^N$ is acetyl. In certain embodiments, at least one instance of $R^N$ is unsubstituted $C_{1-6}$ alkyl. In certain embodiments, each instance of $R^N$ is independently unsubstituted $C_{1-6}$ alkyl. In certain embodiments, at least one instance of $R^N$ is substituted $C_{1-6}$ alkyl. In certain embodiments, at least one instance of $R^N$ is $C_{1-6}$ alkyl substituted with at least one halogen. In certain embodiments, at least one instance of $R^N$ is unsubstituted methyl. In certain embodiments, at least one instance of $R^N$ is substituted methyl. In certain embodiments, at least one instance of $R^N$ is —$CH_2F$. In certain embodiments, at least one instance of $R^N$ is —$CHF_2$. In certain embodiments, at least one instance of $R^N$ is —$CF_3$. In certain embodiments, at least one instance of $R^N$ is ethyl. In certain embodiments, at least one instance of $R^N$ is propyl. In certain embodiments, at least one instance of $R^N$ is butyl. In certain embodiments, at least one instance of $R^N$ is pentyl. In certain embodiments, at least one instance of $R^N$ is hexyl. In certain embodiments, at least one instance of $R^N$ is a nitrogen protecting group. In certain embodiments, at least one instance of $R^N$ is Bn, Boc, Cbz, Fmoc, trifluoroacetyl, triphenylmethyl, acetyl, or Ts.

Formula (I) includes substituent $R^B$ on a nitrogen atom. In certain embodiments, $R^B$ is H. In certain embodiments, $R^B$ is substituted acyl. In certain embodiments, $R^B$ is unsubstituted acyl. In certain embodiments, $R^B$ is acetyl. In certain embodiments, $R^B$ is unsubstituted $C_{1-6}$ alkyl. In certain embodiments, $R^B$ is substituted $C_{1-6}$ alkyl. In certain embodiments, $R^B$ is $C_{1-6}$ alkyl substituted with at least one halogen. In certain embodiments, $R^B$ is unsubstituted methyl. In certain embodiments, $R^B$ is substituted methyl. In certain embodiments, $R^B$ is —CH$_2$F. In certain embodiments, $R^B$ is —CHF$_2$. In certain embodiments, $R^B$ is —CF$_3$. In certain embodiments, $R^B$ is ethyl. In certain embodiments, $R^B$ is propyl. In certain embodiments, $R^B$ is butyl. In certain embodiments, $R^B$ is pentyl. In certain embodiments, $R^B$ is hexyl. In certain embodiments, $R^B$ is a nitrogen protecting group. In certain embodiments, $R^B$ is Bn, Boc, Cbz, Fmoc, trifluoroacetyl, triphenylmethyl, acetyl, or Ts.

Formula (I) includes Ring B that includes moieties $X^A$, $X^B$, and $X^C$ in the ring system. In certain embodiments, $X^A$ is $CR^X$, and each of $X^B$ and $X^C$ is N. In certain embodiments, $X^A$ is CH, and each of $X^B$ and $X^C$ is N. In certain embodiments, $X^B$ is $CR^X$, and each of $X^A$ and $X^C$ is N. In certain embodiments, $X^B$ is CH, and each of $X^A$ and $X^C$ is N. In certain embodiments, $X^C$ is $CR^X$, and each of $X^A$ and $X^B$ is N. In certain embodiments, $X^C$ is CH, and each of $X^A$ and $X^B$ is N. In certain embodiments, $X^A$ is N, and each of $X^B$ and $X^C$ is independently $CR^X$. In certain embodiments, $X^A$ is N, and each of $X^B$ and $X^C$ is CH. In certain embodiments, $X^B$ is N, and each of $X^A$ and $X^C$ is independently $CR^X$. In certain embodiments, $X^B$ is N, and each of $X^A$ and $X^C$ is CH. In certain embodiments, $X^C$ is N, and each of $X^A$ and $X^B$ is independently $CR^X$. In certain embodiments, $X^C$ is N, and each of $X^A$ and $X^B$ is CH. In certain embodiments, each of $X^A$, $X^B$, and $X^C$ is independently $CR^X$. In certain embodiments, each of $X^A$, $X^B$, and $X^C$ is CH.

In certain embodiments, when $X^A$, $X^B$, or $X^C$ is $CR^X$, $R^X$ is H. In certain embodiments, $R^X$ is halogen. In certain embodiments, $R^X$ is F. In certain embodiments, $R^X$ is Cl. In certain embodiments, $R^X$ is Br. In certain embodiments, $R^X$ is I (iodine). In certain embodiments, $R^X$ is substituted alkyl. In certain embodiments, $R^X$ is unsubstituted alkyl. In certain embodiments, $R^X$ is unsubstituted $C_{1-6}$ alkyl. In certain embodiments, $R^X$ is substituted $C_{1-6}$ alkyl. In certain embodiments, $R^X$ is $C_{1-6}$ alkyl substituted with at least one halogen. In certain embodiments, $R^X$ is —CH$_3$. In certain embodiments, $R^X$ is substituted methyl. In certain embodiments, $R^X$ is —CH$_2$F. In certain embodiments, $R^X$ is —CHF$_2$. In certain embodiments, $R^X$ is —CF$_3$. In certain embodiments, $R^X$ is ethyl. In certain embodiments, $R^X$ is propyl. In certain embodiments, $R^X$ is butyl. In certain embodiments, $R^X$ is pentyl. In certain embodiments, $R^X$ is hexyl. In certain embodiments, $R^X$ is substituted alkenyl. In certain embodiments, $R^X$ is unsubstituted alkenyl. In certain embodiments, $R^X$ is substituted alkynyl. In certain embodiments, $R^X$ is unsubstituted alkynyl. In certain embodiments, $R^X$ is substituted carbocyclyl. In certain embodiments, $R^X$ is unsubstituted carbocyclyl. In certain embodiments, $R^X$ is saturated carbocyclyl. In certain embodiments, $R^X$ is unsaturated carbocyclyl. In certain embodiments, $R^X$ is monocyclic carbocyclyl. In certain embodiments, $R^X$ is 3- to 7-membered, monocyclic carbocyclyl. In certain embodiments, $R^X$ is substituted heterocyclyl. In certain embodiments, $R^X$ is unsubstituted heterocyclyl. In certain embodiments, $R^X$ is saturated heterocyclyl. In certain embodiments, $R^X$ is unsaturated heterocyclyl. In certain embodiments, $R^X$ is heterocyclyl, wherein one, two, or three atoms in the heterocyclic ring system are independently selected from the group consisting of nitrogen, oxygen, and sulfur. In certain embodiments, $R^X$ is monocyclic heterocyclyl. In certain embodiments, $R^X$ is 3- to 7-membered, monocyclic heterocyclyl. In certain embodiments, $R^X$ is substituted aryl. In certain embodiments, $R^X$ is unsubstituted aryl. In certain embodiments, $R^X$ is 6- to 10-membered aryl. In certain embodiments, $R^X$ is substituted phenyl. In certain embodiments, $R^X$ is unsubstituted phenyl. In certain embodiments, $R^X$ is substituted heteroaryl. In certain embodiments, $R^X$ is unsubstituted heteroaryl. In certain embodiments, $R^X$ is heteroaryl, wherein one, two, three, or four atoms in the heteroaryl ring system are independently selected from the group consisting of nitrogen, oxygen, and sulfur. In certain embodiments, $R^X$ is monocyclic heteroaryl. In certain embodiments, $R^X$ is 5-membered, monocyclic heteroaryl. In certain embodiments, $R^X$ is 6-membered, monocyclic heteroaryl. In certain embodiments, $R^X$ is bicyclic heteroaryl, wherein the point of attachment may be on any atom of the bicyclic heteroaryl ring system, as valency permits. In certain embodiments, $R^X$ is —OR$^{X1}$. In certain embodiments, $R^X$ is —OH. In certain embodiments, $R^X$ is —O(substituted or unsubstituted $C_{1-6}$ alkyl). In certain embodiments, $R^X$ is —OMe. In certain embodiments, $R^X$ is —OEt. In certain embodiments, $R^X$ is —OPr. In certain embodiments, $R^X$ is —OBu. In certain embodiments, $R^X$ is —OBn. In certain embodiments, $R^X$ is —OPh. In certain embodiments, $R^X$ is —SRxI. In certain embodiments, $R^X$ is —SH. In certain embodiments, $R^X$ is —SMe. In certain embodiments, $R^X$ is —N(R$^{X1}$)$_2$. In certain embodiments, $R^X$ is —NH$_2$. In certain embodiments, RX is —NHMe. In certain embodiments, $R^X$ is —NMe$_2$. In certain embodiments, $R^X$ is —CN. In certain embodiments, $R^X$ is —SCN. In certain embodiments, $R^X$ is —C(=NR$^{X1}$)R$^{X1}$, —C(=NR$^{X1}$)OR$^{X1}$, or —C(=NR$^{X1}$)N(R$^{X1}$)$_2$. In certain embodiments, $R^X$ is —C(=O)R$^{X1}$ or —C(=O)OR$^{X1}$. In certain embodiments, $R^X$ is —C(=O)N(R$^{X1}$)$_2$. In certain embodiments, $R^X$ is —C(=O)NMe$_2$, —C(=O)NHMe, or —C(=O)NH$_2$. In certain embodiments, $R^X$ is —NO$_2$. In certain embodiments, RX is —NR$^{X1}$C(=O)R$^{X1}$, —NR$^{X1}$C(=O)OR$_{X1}$, or —NR$^{X1}$C(=O)N(R$^{X1}$)$_2$. In certain embodiments, $R^X$ is —OC(=O)R$^{X1}$, —OC(=O)OR$^{X1}$, or —OC(=O)N(R$^{X1)}$)$_2$.

In certain embodiments, $R^{x1}$ is H. In certain embodiments, $R^{x1}$ is substituted acyl. In certain embodiments, $R^{X1}$ is unsubstituted acyl. In certain embodiments, $R^{X1}$ is acetyl. In certain embodiments, $R^{X1}$ is substituted alkyl. In certain embodiments, $R^{X1}$ is unsubstituted alkyl. In certain embodiments, $R^{X1}$ is unsubstituted $C_{1-6}$ alkyl. In certain embodiments, $R^{X1}$ is methyl. In certain embodiments, $R^{X1}$ is ethyl. In certain embodiments, $R^{X1}$ is propyl. In certain embodiments, $R^{X1}$ is butyl. In certain embodiments, $R^{X1}$ is pentyl. In certain embodiments, $R^{X1}$ is hexyl. In certain embodiments, $R^{X1}$ is substituted alkenyl. In certain embodiments, $R^{X1}$ is unsubstituted alkenyl. In certain embodiments, $R^{X1}$ is substituted alkynyl. In certain embodiments, $R^{X1}$ is unsubstituted alkynyl. In certain embodiments, $R^{X1}$ is substituted or unsubstituted carbocyclyl. In certain embodiments, $R^{X1}$ is saturated carbocyclyl. In certain embodiments, $R^{X1}$ is unsaturated carbocyclyl. In certain embodiments, $R^{X1}$ is 3- to 7-membered, monocyclic carbocyclyl. In certain embodiments, $R^{X1}$ is substituted or unsubstituted heterocyclyl. In certain embodiments, $R^{X1}$ is saturated heterocyclyl. In certain embodiments, $R^{X1}$ is unsaturated heterocyclyl. In certain embodiments, $R^{X1}$ is heterocyclyl, wherein one, two, or three atoms in the heterocyclic ring system are independently selected from the group consisting of nitrogen, oxygen, and sulfur. In certain embodiments, $R^{X1}$ is 3- to 7-membered, monocyclic heterocyclyl. In certain embodiments, $R^{X1}$ is substituted or unsubstituted aryl. In certain embodiments, $R^{X1}$ is 6- to 10-membered aryl. In certain embodiments, $R^{X1}$ is monocyclic aryl. In certain embodiments, $R^{X1}$ is substituted phenyl. In certain embodiments, $R^{X1}$ is unsubstituted phenyl. In certain embodiments, $R^{X1}$ is bicyclic aryl. In certain embodiments, $R^{X1}$ is substituted or unsubstituted heteroaryl. In certain embodiments, $R_{X1}$ is heteroaryl, wherein one, two, three, or four atoms in the heteroaryl ring system are independently selected from the group consisting of nitrogen, oxygen, and sulfur. In certain embodiments, $R_{X1}$ is monocyclic heteroaryl. In certain embodiments, $R^{X1}$ is 5- or 6-membered, monocyclic heteroaryl. In certain embodiments, $R^{X1}$ is bicyclic heteroaryl, wherein the point of attachment may be on any atom of the bicyclic heteroaryl ring system, as valency permits. In certain embodiments, $R^{X1}$ is a nitrogen protecting group when attached to a nitrogen atom. In certain embodiments, $R^{X1}$ is Bn, Boc, Cbz, Fmoc, trifluoroacetyl, triphenylmethyl, acetyl, or Ts when attached to a nitrogen atom. In certain embodiments, $R^{X1}$ is an oxygen protecting group when attached to an oxygen atom. In certain embodiments, $R^{X1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{X1}$ is a sulfur protecting group when attached to a sulfur atom. In certain embodiments, $R^{X1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{X1}$ are joined to form a substituted or unsubstituted heterocyclic ring. In certain embodiments, two instances of $R^{X1}$ are joined to form a saturated or unsaturated heterocyclic ring. In certain embodiments, two instances of $R^{X1}$ are joined to form a heterocyclic ring, wherein one, two, or three atoms in the heterocyclic ring system are independently selected from the group consisting of nitrogen, oxygen, and sulfur. In certain embodiments, two instances of $R^{X1}$ are joined to form a 3- to 7-membered, monocyclic heterocyclic ring. In certain embodiments, two instances of $R^{X1}$ are joined to form a substituted or unsubstituted heteroaryl ring. In certain embodiments, two instances of $R^{X1}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

Formula (I) includes divalent moiety Y. In certain embodiments, Y is —O—. In certain embodiments, Y is —NR$^Y$—. In certain embodiments, Y is —NH—. In certain embodiments, Y is —NR$^Y$—; $X^A$ is CR$^X$; and R$^Y$ and R$^X$ of $X^A$ are joined to form a substituted or unsubstituted, monocyclic, 5- to 7-membered heterocyclic ring that is fused with Ring B, optionally wherein there are 2 or 3 nitrogen atoms, 0 or 1 oxygen atom, and 0 or 1 sulfur atom, in the monocyclic heterocyclic ring system. The monocyclic heterocyclic ring formed by joining R$^Y$ and R$^X$ of $X^A$ is fused with Ring B to form a substituted or unsubstituted, bicyclic, 9- to 11-membered ring. In certain embodiments, Y is —NR$^Y$—; $X^A$ is CR$^X$; and R$^Y$ and R$^X$ of $X^A$ are joined to form a substituted or unsubstituted, monocyclic, 6-membered heterocyclic ring that is fused with Ring B.

In certain embodiments, when Y is —NR$^Y$—, R$^Y$ is H. In certain embodiments, R$^Y$ is substituted acyl. In certain embodiments, R is unsubstituted acyl. In certain embodiments, R$^Y$ is acetyl. In certain embodiments, R$^Y$ is unsubstituted $C_{1-6}$ alkyl. In certain embodiments, R$^Y$ is substituted $C_{1-6}$ alkyl. In certain embodiments, R$^Y$ is $C_{1-6}$ alkyl substituted with at least one halogen. In certain embodiments, R$^Y$ is unsubstituted methyl. In certain embodiments, R$^Y$ is substituted methyl. In certain embodiments, R$^Y$ is —CH$_2$F. In certain embodiments, R$^Y$ is —CHF$_2$. In certain embodiments, R$^Y$ is —CF$_3$. In certain embodiments, R$^Y$ is ethyl. In certain embodiments, R$^Y$ is propyl. In certain embodiments, R$^Y$ is butyl. In certain embodiments, R$^Y$ is pentyl. In certain embodiments, R$^Y$ is hexyl. In certain embodiments, R$^Y$ is a nitrogen protecting group. In certain embodiments, R$^Y$ is Bn, Boc, Cbz, Fmoc, trifluoroacetyl, triphenylmethyl, acetyl, or Ts.

In Formula (I), Ring B includes substituent R$^D$. In certain embodiments, R$^D$ is H. In certain embodiments, R$^D$ is halogen. In certain embodiments, R$^D$ is F. In certain embodiments, R$^D$ is Cl. In certain embodiments, R$^D$ is Br. In certain embodiments, R$^D$ is I (iodine). In certain embodiments, R$^D$ is substituted alkyl. In certain embodiments, R$^D$ is unsubstituted alkyl. In certain embodiments, R$^D$ is unsubstituted $C_{1-6}$ alkyl. In certain embodiments, R$^D$ is substituted $C_{1-6}$ alkyl. In certain embodiments, R$^D$ is $C_{1-6}$ alkyl substituted with at least one halogen. In certain embodiments, R$^D$ is —CH$_3$. In certain embodiments, R$^D$ is substituted methyl. In certain embodiments, R$^D$ is —CH$_2$F. In certain embodiments, R$^D$ is —CHF$_2$. In certain embodiments, R$^D$ is —CF$_3$. In certain embodiments, R$^D$ is ethyl. In certain embodiments, R$^D$ is propyl. In certain embodiments, R$^D$ is butyl. In certain embodiments, R$^D$ is pentyl. In certain embodiments, R$^D$ is hexyl. In certain embodiments, R$^D$ is substituted alkenyl. In certain embodiments, R$^D$ is unsubstituted alkenyl. In certain embodiments, R$^D$ is substituted alkynyl. In certain embodiments, R$^D$ is unsubstituted alkynyl. In certain embodiments, R$^D$ is substituted carbocyclyl. In certain embodiments, R$^D$ is unsubstituted carbocyclyl. In certain embodiments, R$^D$ is saturated carbocyclyl. In certain embodiments, R$^D$ is unsaturated carbocyclyl. In certain embodiments, R$^D$ is monocyclic carbocyclyl. In certain embodiments, R$^D$ is 3- to 7-membered, monocyclic carbocyclyl. In certain embodiments, R$^D$ is substituted heterocyclyl. In certain embodiments, R$^D$ is unsubstituted heterocyclyl. In certain embodiments, R$^D$ is saturated heterocyclyl. In certain embodiments, R$^D$ is unsaturated heterocyclyl. In certain embodiments, R$^D$ is heterocyclyl, wherein one, two, or three atoms in the heterocyclic ring system are independently selected from the group consisting of nitrogen, oxygen, and sulfur. In certain embodiments, R$^D$ is monocyclic heterocyclyl. In certain embodiments, R$^D$ is 3- to 7-membered, monocyclic heterocyclyl. In certain embodiments, R$^D$ is substituted aryl. In certain embodiments, R$^D$ is unsubstituted aryl. In certain embodiments, R$^D$ is 6- to 10-membered aryl. In certain embodiments, R$^D$ is substituted phenyl. In certain embodiments, R$^D$ is unsubstituted phenyl. In certain embodiments, R$^D$ is substituted heteroaryl. In certain embodiments, R$^D$ is unsubstituted heteroaryl. In certain embodiments, R$^D$ is heteroaryl, wherein one, two, three, or four atoms in the heteroaryl ring system are independently selected from the group consisting of nitrogen, oxygen, and sulfur. In certain embodiments, R$^D$ is monocyclic heteroaryl. In certain embodiments, R$^D$ is 5-membered, monocyclic heteroaryl. In certain embodiments, R$^D$ is 6-membered, monocyclic heteroaryl. In certain embodiments, R$^D$ is bicyclic heteroaryl, wherein the point of attachment may be on any atom of the bicyclic heteroaryl ring system, as valency permits. In certain embodiments, R$^D$ is 9- or 10-membered, bicyclic heteroaryl. In certain embodiments, R$^D$ is —OR$^{D1}$. In certain embodiments, R$^D$ is —OH. In certain embodiments, R$^D$ is —O(substituted or unsubstituted $C_{1-6}$ alkyl). In certain embodiments, R$^D$ is —OMe. In certain embodiments, R$^D$ is —OEt. In certain embodiments, R$^D$ is —OPr. In certain embodiments, R$^D$ is —OBu. In certain embodiments, R$^D$ is —OBn. In certain embodiments, R$^D$ is —OPh. In certain embodiments, R$^D$ is —SR$^{D1}$. In certain embodiments, R$^D$ is —SH. In certain embodiments, R$^D$ is —SMe. In certain embodiments, R$^D$ is —N(R$^{D1}$)$_2$. In certain embodiments, R$^D$ is —NH$_2$. In certain embodiments, R$^D$ is —NHMe. In certain embodiments, R$^D$ is —NMe$_2$. In certain embodiments, R$^D$ is —CN. In certain embodiments, R$^D$ is —SCN. In certain embodiments, R$^D$ is —C(=NR$^{D1}$)R$^{D1}$, —C(=NR$^{D1}$)OR$^{D1}$, or —C(=NR$^{D1}$)N(R$^{D1}$)$_2$. In certain embodiments, $R^D$ is —C(=O)$R^{D1}$ or —C(=O)O$R^{D1}$. In certain embodiments, $R^D$ is —C(=O)N($R^{D1}$)$_2$. In certain embodiments, $R^D$ is —C(=O)NMe$_2$, —C(=O)NHMe, or —C(=O)NH$_2$. In certain embodiments, $R^D$ is —NO$_2$. In certain embodiments, $R^D$ is —N$R^{D1}$C(=O)$R^{D1}$, —N$R^{D1}$C(=O)O$R^{D1}$, or —N$R^{D1}$C(=O)N($R^{D1}$)$_2$. In certain embodiments, $R^D$ is —OC(=O)$R^{D1}$, —OC(=O)O$R^{D1}$, or —OC(=O)N($R^{D1}$)$_2$.

In certain embodiments, $R^{D1}$ is H. In certain embodiments, $R^{D1}$ is substituted acyl. In certain embodiments, $R^{D1}$ is unsubstituted acyl. In certain embodiments, $R^{D1}$ is acetyl. In certain embodiments, $R^{D1}$ is substituted alkyl. In certain embodiments, $R^{D1}$ is unsubstituted alkyl. In certain embodiments, $R^{D1}$ is unsubstituted $C_{1-6}$ alkyl. In certain embodiments, $R^{D1}$ is methyl. In certain embodiments, $R^{D1}$ is ethyl. In certain embodiments, $R^{D1}$ is propyl. In certain embodiments, $R^{D1}$ is butyl. In certain embodiments, $R^{D1}$ is pentyl. In certain embodiments, $R^{D1}$ is hexyl. In certain embodiments, $R^{D1}$ is substituted alkenyl. In certain embodiments, $R^{D1}$ is unsubstituted alkenyl. In certain embodiments, $R^{D1}$ is substituted alkynyl. In certain embodiments, $R^{D1}$ is unsubstituted alkynyl. In certain embodiments, $R^{D1}$ is substituted or unsubstituted carbocyclyl. In certain embodiments, $R^{D1}$ is saturated carbocyclyl. In certain embodiments, $R^{D1}$ is unsaturated carbocyclyl. In certain embodiments, $R^{D1}$ is 3- to 7-membered, monocyclic carbocyclyl. In certain embodiments, $R^{D1}$ is substituted or unsubstituted heterocyclyl. In certain embodiments, $R^{D1}$ is saturated heterocyclyl. In certain embodiments, $R^{D1}$ is unsaturated heterocyclyl. In certain embodiments, $R^{D1}$ is heterocyclyl, wherein one, two, or three atoms in the heterocyclic ring system are independently selected from the group consisting of nitrogen, oxygen, and sulfur. In certain embodiments, $R^{D1}$ is 3- to 7-membered, monocyclic heterocyclyl. In certain embodiments, $R^{D1}$ is substituted or unsubstituted aryl. In certain embodiments, $R^{D1}$ is 6- to 10-membered aryl. In certain embodiments, $R^{D1}$ is monocyclic aryl. In certain embodiments, $R^{D1}$ is substituted phenyl. In certain embodiments, $R^{D1}$ is unsubstituted phenyl. In certain embodiments, $R^{D1}$ is bicyclic aryl. In certain embodiments, $R^{D1}$ is substituted or unsubstituted heteroaryl. In certain embodiments, $R^{D1}$ is heteroaryl, wherein one, two, three, or four atoms in the heteroaryl ring system are independently selected from the group consisting of nitrogen, oxygen, and sulfur. In certain embodiments, $R^{D1}$ is monocyclic heteroaryl. In certain embodiments, $R^{D1}$ is 5- or 6-membered, monocyclic heteroaryl. In certain embodiments, $R^{D1}$ is bicyclic heteroaryl, wherein the point of attachment may be on any atom of the bicyclic heteroaryl ring system, as valency permits. In certain embodiments, $R^{D1}$ is a nitrogen protecting group when attached to a nitrogen atom. In certain embodiments, $R^{D1}$ is Bn, Boc, Cbz, Fmoc, trifluoroacetyl, triphenylmethyl, acetyl, or Ts when attached to a nitrogen atom. In certain embodiments, $R^{D1}$ is an oxygen protecting group when attached to an oxygen atom. In certain embodiments, $R^{D1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D1}$ is a sulfur protecting group when attached to a sulfur atom. In certain embodiments, $R^{D1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{D1}$ are joined to form a substituted or unsubstituted heterocyclic ring. In certain embodiments, two instances of $R^{D1}$ are joined to form a saturated or unsaturated heterocyclic ring. In certain embodiments, two instances of $R^{D1}$ are joined to form a heterocyclic ring, wherein one, two, or three atoms in the heterocyclic ring system are independently selected from the group consisting of nitrogen, oxygen, and sulfur. In certain embodiments, two instances of $R^{D1}$ are joined to form a 3- to 7-membered, monocyclic heterocyclic ring. In certain embodiments, two instances of $R^{D1}$ are joined to form a substituted or unsubstituted heteroaryl ring. In certain embodiments, two instances of $R^{D1}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

Formula (I) includes Ring C that is unsubstituted (e.g., when m is 0) or substituted with one or more substituents $R^C$ (e.g., when m is 1, 2, 3, 4, or 5). In certain embodiments, Ring C is of the formula:

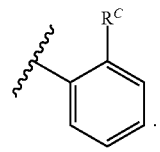

In certain embodiments, Ring C is of the formula:

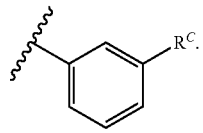

In certain embodiments, Ring C is of the formula:

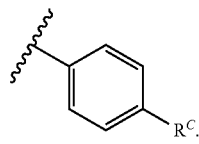

In certain embodiments, Ring C is of the formula:

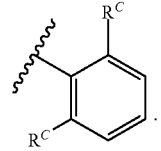

In certain embodiments, Ring C is of the formula:

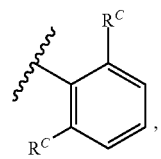

wherein each instance of $R^C$ is independently substituted or unsubstituted $C_{1-6}$ alkyl. In certain embodiments, Ring C is of the formula:

In certain embodiments, Ring C is of the formula:

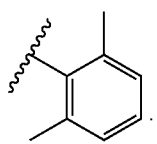 [SMILES: *c1c(C)cccc1C]

In certain embodiments, Ring C is of the formula:

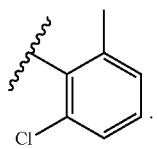 [SMILES: *c1c(C)cccc1Cl]

In certain embodiments, Ring C is of the formula:

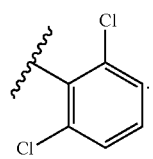

In certain embodiments, Ring C is of the formula:

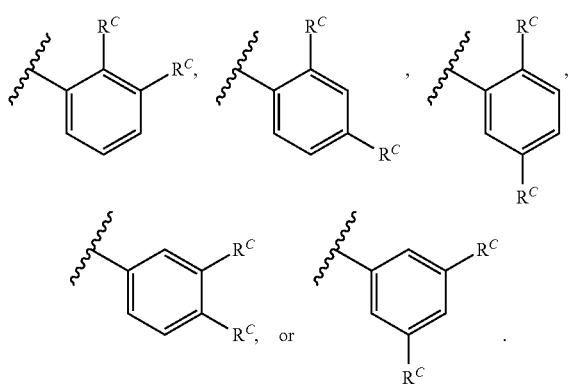

In certain embodiments, at least two instances of $R^C$ are different. In certain embodiments, all instances of $R^C$ are the same. In certain embodiments, at least one instance of $R^C$ is halogen. In certain embodiments, at least one instance of $R^C$ is F. In certain embodiments, at least one instance of $R^C$ is Cl. In certain embodiments, at least one instance of $R^C$ is Br. In certain embodiments, at least one instance of $R^C$ is I (iodine). In certain embodiments, at least one instance of $R^C$ is substituted alkyl. In certain embodiments, at least one instance of $R^C$ is unsubstituted alkyl. In certain embodiments, at least one instance of $R^C$ is unsubstituted $C_{1-6}$ alkyl. In certain embodiments, all instances of $R^C$ are unsubstituted $C_{1-6}$ alkyl. In certain embodiments, at least one instance of $R^C$ is substituted $C_{1-6}$ alkyl. In certain embodiments, at least one instance of $R^C$ is $C_{1-6}$ alkyl substituted with at least one halogen. In certain embodiments, at least one instance of $R^C$ is —$CH_3$. In certain embodiments, all instances of $R^C$ are —$CH_3$. In certain embodiments, at least one instance of $R^C$ is substituted methyl. In certain embodiments, at least one instance of $R^C$ is —$CH_2F$. In certain embodiments, at least one instance of $R^C$ is —$CHF_2$. In certain embodiments, at least one instance of $R^C$ is —$CF_3$. In certain embodiments, at least one instance of $R^C$ is ethyl. In certain embodiments, at least one instance of $R^C$ is propyl. In certain embodiments, at least one instance of $R^C$ is butyl. In certain embodiments, at least one instance of $R^C$ is pentyl. In certain embodiments, at least one instance of $R^C$ is hexyl. In certain embodiments, each instance of $R^C$ is independently halogen (e.g., Cl) or substituted or unsubstituted $C_{1-6}$ alkyl (e.g., unsubstituted $C_{1-6}$ alkyl (e.g., Me)). In certain embodiments, at least one instance of $R^C$ is substituted alkenyl. In certain embodiments, at least one instance of $R^C$ is unsubstituted alkenyl. In certain embodiments, at least one instance of $R^C$ is substituted alkynyl. In certain embodiments, at least one instance of $R^C$ is unsubstituted alkynyl. In certain embodiments, at least one instance of $R^C$ is substituted carbocyclyl. In certain embodiments, at least one instance of $R^C$ is unsubstituted carbocyclyl. In certain embodiments, at least one instance of $R^C$ is saturated carbocyclyl. In certain embodiments, at least one instance of $R^C$ is unsaturated carbocyclyl. In certain embodiments, at least one instance of $R^C$ is monocyclic carbocyclyl. In certain embodiments, at least one instance of $R^C$ is 3- to 7-membered, monocyclic carbocyclyl. In certain embodiments, at least one instance of $R^C$ is substituted heterocyclyl. In certain embodiments, at least one instance of $R^C$ is unsubstituted heterocyclyl. In certain embodiments, at least one instance of $R^C$ is saturated heterocyclyl. In certain embodiments, at least one instance of $R^C$ is unsaturated heterocyclyl. In certain embodiments, at least one instance of $R^C$ is heterocyclyl, wherein one, two, or three atoms in the heterocyclic ring system are independently selected from the group consisting of nitrogen, oxygen, and sulfur. In certain embodiments, at least one instance of $R^C$ is monocyclic heterocyclyl. In certain embodiments, at least one instance of $R^C$ is 3- to 7-membered, monocyclic heterocyclyl. In certain embodiments, at least one instance of $R^C$ is substituted aryl. In certain embodiments, at least one instance of $R^C$ is unsubstituted aryl. In certain embodiments, at least one instance of $R^C$ is 6- to 10-membered aryl. In certain embodiments, at least one instance of $R^C$ is substituted phenyl. In certain embodiments, at least one instance of $R^C$ is unsubstituted phenyl. In certain embodiments, at least one instance of $R^C$ is substituted heteroaryl. In certain embodiments, at least one instance of $R^C$ is unsubstituted heteroaryl. In certain embodiments, at least one instance of $R^C$ is heteroaryl, wherein one, two, three, or four atoms in the heteroaryl ring system are independently selected from the group consisting of nitrogen, oxygen, and sulfur. In certain embodiments, at least one instance of $R^C$ is monocyclic heteroaryl. In certain embodiments, at least one instance of $R^C$ is 5-membered, monocyclic heteroaryl. In certain embodiments, at least one instance of $R^C$ is 6-membered, monocyclic heteroaryl. In certain embodiments, at least one instance of $R^C$ is bicyclic heteroaryl, wherein the point of attachment may be on any atom of the bicyclic heteroaryl ring system, as valency permits. In certain embodiments, at least one instance of $R^C$ is 9- or 10-membered, bicyclic heteroaryl. In certain embodiments, at least one instance of $R^C$ is —$OR^{C1}$. In certain embodiments, at least one instance of $R^C$ is —OH. In certain embodiments, at least one instance of $R^C$ is —O(substituted or unsubstituted $C_{1-6}$ alkyl). In certain embodiments, at least one instance of $R^C$ is —OMe. In certain embodiments, at least one instance of $R^C$ is —OEt. In certain embodiments, at least one instance of $R^C$ is —OPr. In certain embodiments, at least one instance of $R^C$ is —OBu. In certain embodiments, at least one instance of $R^C$ is —OBn. In certain embodiments, at least one instance of $R^C$ is —OPh. In certain embodiments, at least one instance of $R^C$ is —$SR^{C1}$. In certain embodiments, at least one instance of $R^C$ is —SH. In certain embodiments, at least one instance of $R^C$ is —SMe. In certain embodiments, at least one instance of $R^C$ is —$N(R^{C1})_2$. In certain embodiments, at least one instance of $R^C$ is —$NH_2$. In certain embodiments, at least one instance of $R^C$ is —NHMe. In certain embodiments, at least one instance of $R^C$ is —$NMe_2$. In certain embodiments, at least one instance of $R^C$ is —CN. In certain embodiments, at least one instance of $R^C$ is —SCN. In certain embodiments, at least one instance of $R^C$ is —$C(=NR^{C1})R^{C1}$, —$C(=NR^{C1})OR^{C1}$, or —$C(=NR^{C1})N(R^{C1})_2$. In certain embodiments, at least one instance of $R^C$ is —$C(=O)R^{C1}$ or —$C(=O)OR^{C1}$. In certain embodiments, at least one instance of $R^C$ is —$C(=O)N(R^{C1})_2$. In certain embodiments, at least one instance of $R^C$ is —$C(=O)NMe_2$, —$C(=O)NHMe$, or —$C(=O)NH_2$. In certain embodiments, at least one instance of $R^C$ is —$NO_2$. In certain embodiments, at least one instance of $R^C$ is —$NR^{C1}C(=O)R^{C1}$, —$NR^{C1}C(=O)OR^{C1}$, or —$NR^{C1}C(=O)N(R^{C1})_2$. In certain embodiments, at least one instance of $R^C$ is —$OC(=O)R^{C1}$, —$OC(=O)OR^{C1}$, or —$OC(=O)N(R^{C1})_2$.

In certain embodiments, at least one instance of $R^{C1}$ is H. In certain embodiments, at least one instance of $R^{C1}$ is substituted acyl. In certain embodiments, at least one instance of $R^{C1}$ is unsubstituted acyl. In certain embodiments, at least one instance of $R^{C1}$ is acetyl. In certain embodiments, at least one instance of $R^{C1}$ is substituted alkyl. In certain embodiments, at least one instance of $R^{C1}$ is unsubstituted alkyl. In certain embodiments, at least one instance of $R^{C1}$ is unsubstituted $C_{1-6}$ alkyl. In certain embodiments, at least one instance of $R^{C1}$ is methyl. In certain embodiments, at least one instance of $R^{C1}$ is ethyl. In certain embodiments, at least one instance of $R^{C1}$ is propyl. In certain embodiments, at least one instance of $R^{C1}$ is butyl. In certain embodiments, at least one instance of $R^{C1}$ is pentyl. In certain embodiments, at least one instance of $R^{C1}$ is hexyl. In certain embodiments, at least one instance of $R^{C1}$ is substituted alkenyl. In certain embodiments, at least one instance of $R^{C1}$ is unsubstituted alkenyl. In certain embodiments, at least one instance of $R^{C1}$ is substituted alkynyl. In certain embodiments, at least one instance of $R^{C1}$ is unsubstituted alkynyl. In certain embodiments, at least one instance of $R^{C1}$ is substituted or unsubstituted carbocyclyl. In certain embodiments, at least one instance of $R^{C1}$ is saturated carbocyclyl. In certain embodiments, at least one instance of $R^{C1}$ is unsaturated carbocyclyl. In certain embodiments, at least one instance of $R^{C1}$ is 3- to 7-membered, monocyclic carbocyclyl. In certain embodiments, at least one instance of $R^{C1}$ is substituted or unsubstituted heterocyclyl. In certain embodiments, at least one instance of $R^{C1}$ is saturated heterocyclyl. In certain embodiments, at least one instance of $R^{C1}$ is unsaturated heterocyclyl. In certain embodiments, at least one instance of $R^{C1}$ is heterocyclyl, wherein one, two, or three atoms in the heterocyclic ring system are independently selected from the group consisting of nitrogen, oxygen, and sulfur. In certain embodiments, at least one instance of $R^{C1}$ is 3- to 7-membered, monocyclic heterocyclyl. In certain embodiments, at least one instance of $R^{C1}$ is substituted or unsubstituted aryl. In certain embodiments, at least one instance of $R^{C1}$ is 6- to 10-membered aryl. In certain embodiments, at least one instance of $R^{C1}$ is monocyclic aryl. In certain embodiments, at least one instance of $R^{C1}$ is substituted phenyl. In certain embodiments, at least one instance of $R^{C1}$ is unsubstituted phenyl. In certain embodiments, at least one instance of $R^{C1}$ is bicyclic aryl. In certain embodiments, at least one instance of $R^{C1}$ is substituted or unsubstituted heteroaryl. In certain embodiments, at least one instance of $R^{C1}$ is heteroaryl, wherein one, two, three, or four atoms in the heteroaryl ring system are independently selected from the group consisting of nitrogen, oxygen, and sulfur. In certain embodiments, at least one instance of $R^{C1}$ is monocyclic heteroaryl. In certain embodiments, at least one instance of $R^{C1}$ is 5- or 6-membered, monocyclic heteroaryl. In certain embodiments, at least one instance of $R^{C1}$ is bicyclic heteroaryl, wherein the point of attachment may be on any atom of the bicyclic heteroaryl ring system, as valency permits. In certain embodiments, at least one instance of $R^{C1}$ is a nitrogen protecting group when attached to a nitrogen atom. In certain embodiments, at least one instance of $R^{C1}$ is Bn, Boc, Cbz, Fmoc, trifluoroacetyl, triphenylmethyl, acetyl, or Ts when attached to a nitrogen atom. In certain embodiments, $R^{C1}$ is an oxygen protecting group when attached to an oxygen atom. In certain embodiments, $R^{C1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{C1}$ is a sulfur protecting group when attached to a sulfur atom. In certain embodiments, $R^{C1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{C1}$ are joined to form a substituted or unsubstituted heterocyclic ring. In certain embodiments, two instances of $R^{C1}$ are joined to form a saturated or unsaturated heterocyclic ring. In certain embodiments, two instances of $Rc^1$ are joined to form a heterocyclic ring, wherein one, two, or three atoms in the heterocyclic ring system are independently selected from the group consisting of nitrogen, oxygen, and sulfur. In certain embodiments, two instances of $Rc^i$ are joined to form a 3- to 7-membered, monocyclic heterocyclic ring. In certain embodiments, two instances of $R^{C1}$ are joined to form a substituted or unsubstituted heteroaryl ring. In certain embodiments, two instances of $R^{C1}$ are joined to form a substituted or unsubstituted, 5- to 6-membered, monocyclic heteroaryl ring, wherein one, two, three, or four atoms in the heteroaryl ring system are independently nitrogen, oxygen, or sulfur.

In certain embodiments, m is 0. In certain embodiments, m is 1. In certain embodiments, m is 2. In certain embodiments, m is 3. In certain embodiments, m is 4. In certain embodiments, m is 5.

In certain embodiments, m is 2; and each instance of $R^C$ is halogen (e.g., Cl). In certain embodiments, m is 2; and each instance of $R^C$ is substituted or unsubstituted $C_{1-6}$ alkyl. In certain embodiments, m is 2; and each instance of $R^C$ is methyl. In certain embodiments, m is 2; and each instance of $R^C$ is independently halogen (e.g., Cl) or substituted or unsubstituted $C_{1-6}$ alkyl (e.g., unsubstituted $C_{1-6}$ alkyl (e.g., Me)).

In certain embodiments, the compound of Formula (I) useful in the present invention is of the formula:

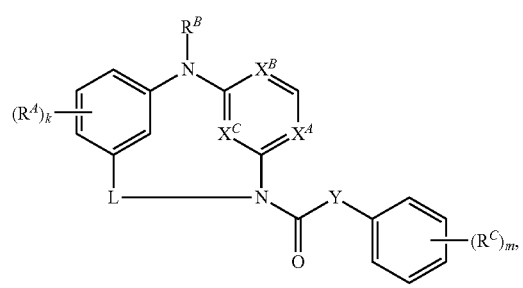

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

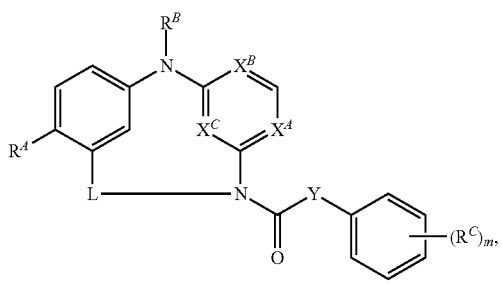

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

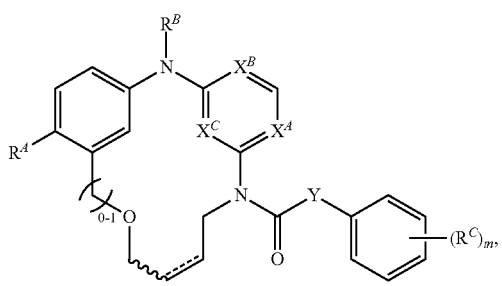

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

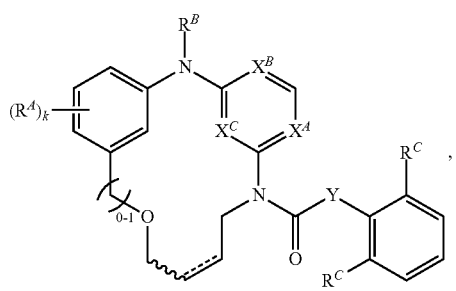

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

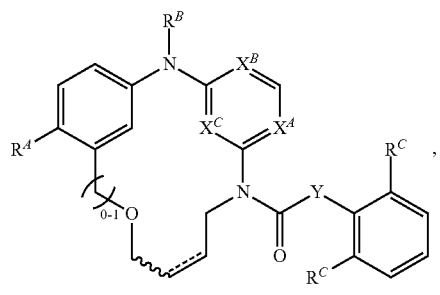

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

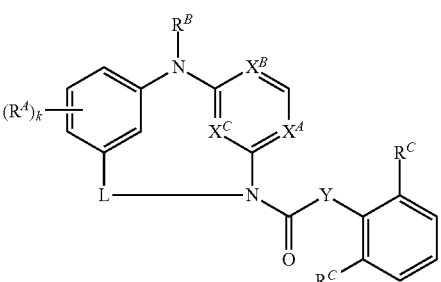

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

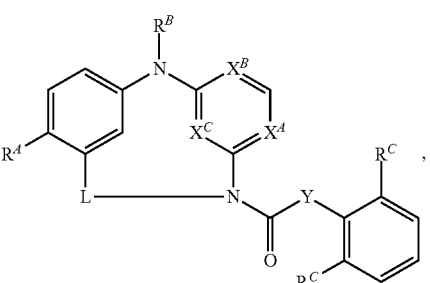

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

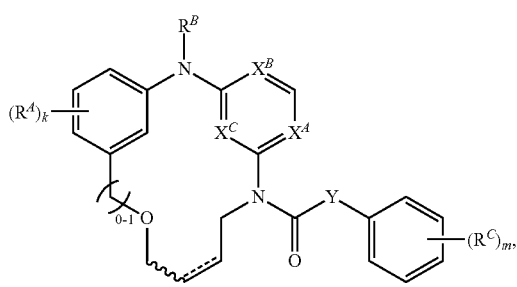

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

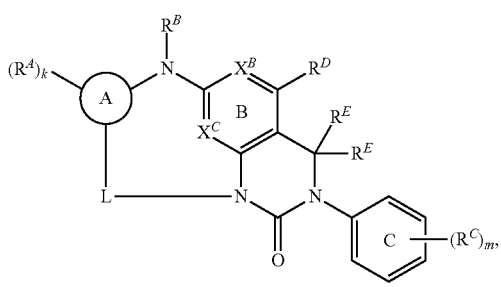

or a pharmaceutically acceptable salt, solvate, hydrate, polymorph, co-crystal, tautomer, stereoisomer, isotopically labeled derivative, or prodrug thereof, wherein each instance of $R^E$ is independently hydrogen, halogen, or substituted or unsubstituted $C_{1-6}$ alkyl. In certain embodiments, the two instances of $R^E$ are the same. In certain embodiments, the two instances of $R^E$ are not the same. In certain embodiments, at least one instance of $R^E$ is hydrogen. In certain embodiments, each instance of $R^E$ is hydrogen. In certain embodiments, at least one instance of $R^E$ is halogen (e.g., F, Cl, Br, or I). In certain embodiments, at least one instance of $R^E$ is substituted or unsubstituted $C_{1-6}$ alkyl. In certain embodiments, at least one instance of $R^E$ is Me. In certain embodiments, at least one instance of $R^E$ is substituted methyl (e.g., —$CF_3$ or Bn), Et, substituted ethyl (e.g., perfluoroethyl), Pr, substituted propyl (e.g., perfluoropropyl), Bu, or substituted butyl (e.g., perfluorobutyl).

In certain embodiments, the compound of Formula (I) useful in the present invention is of the formula:

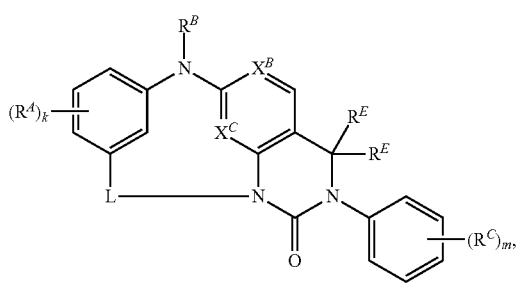

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

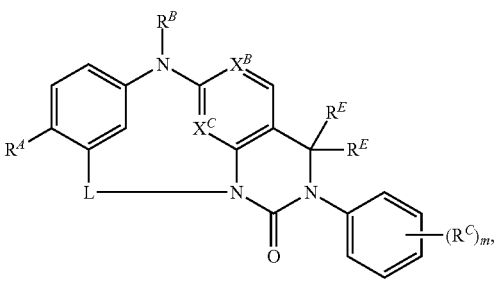

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

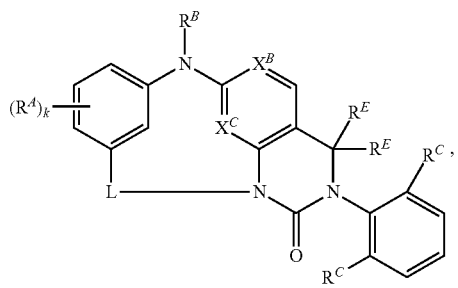

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

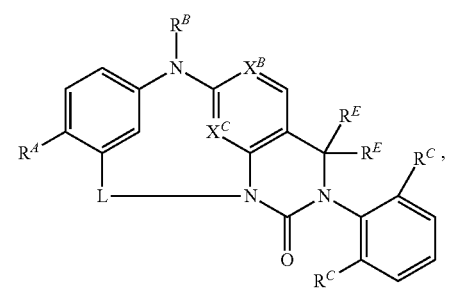

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

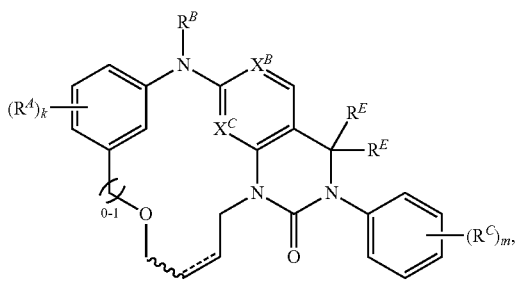

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

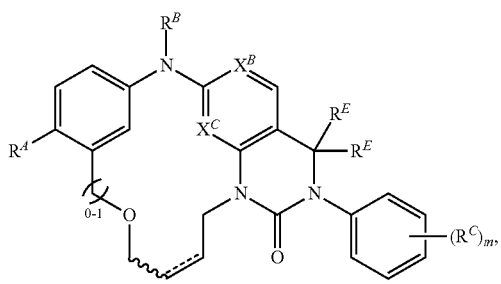

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

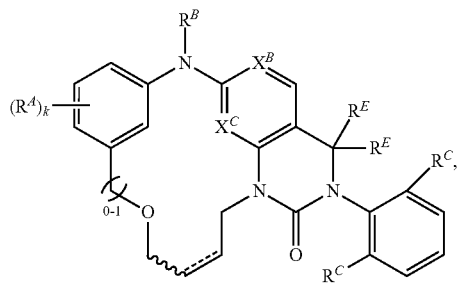

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

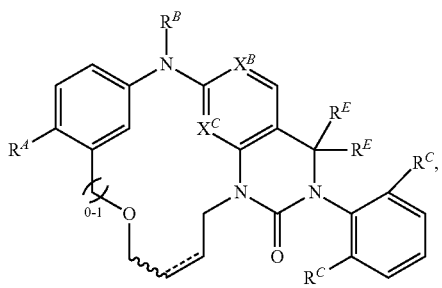

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

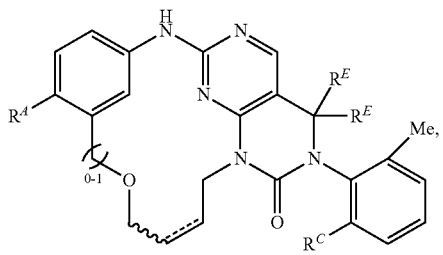

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

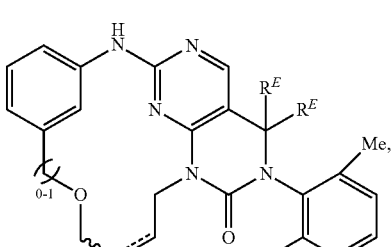

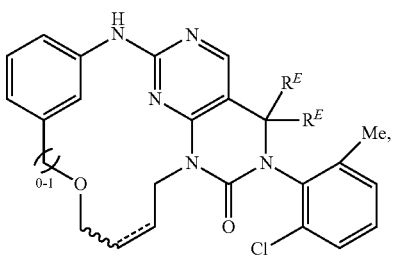

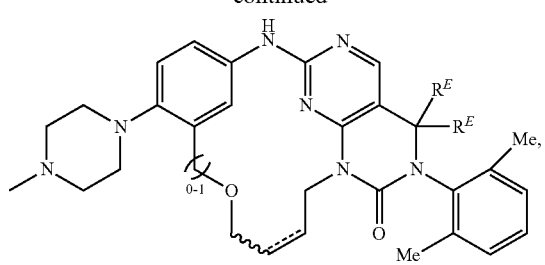

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

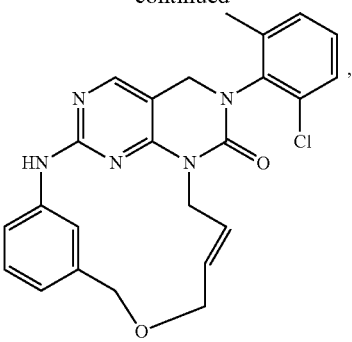

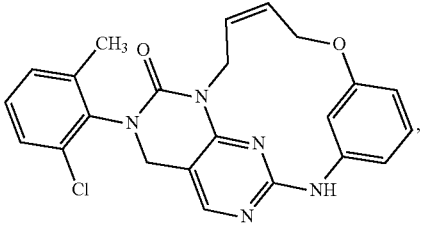

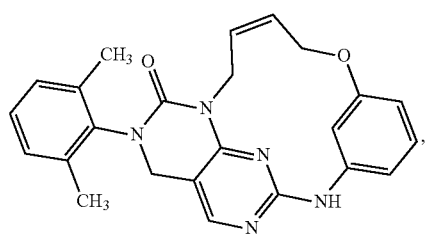

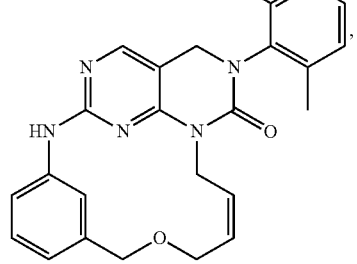

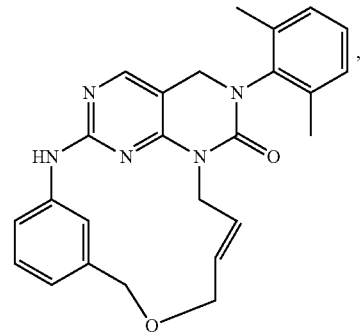

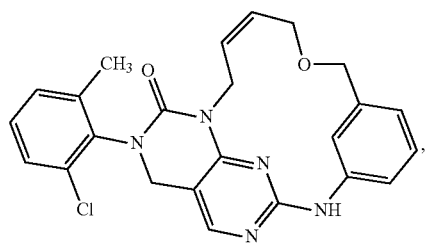

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:
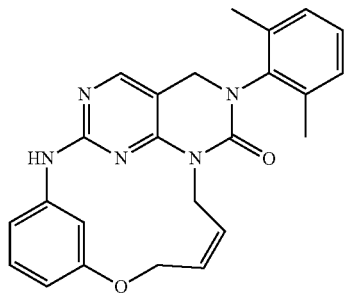
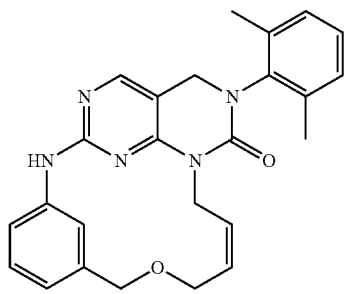
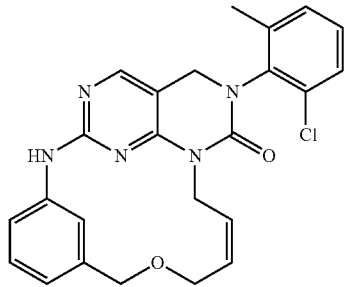
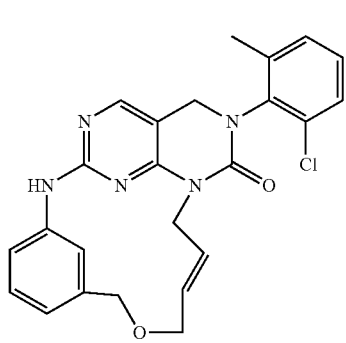
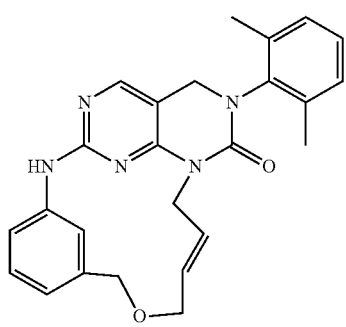
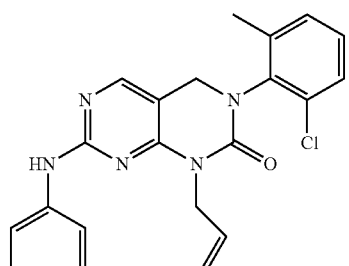
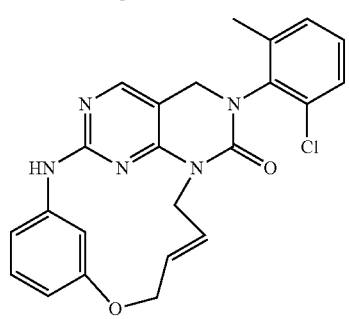
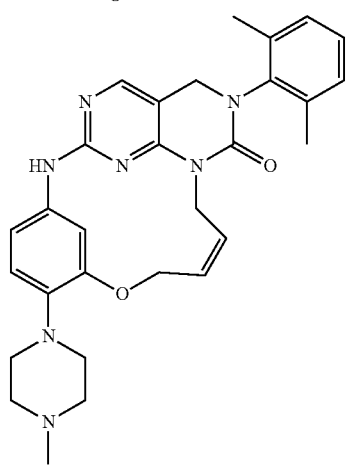
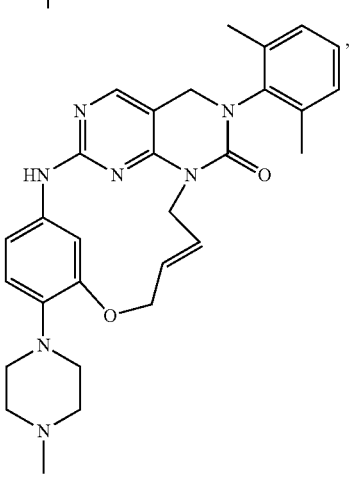
or a pharmaceutically acceptable salt, solvate, hydrate, polymorph, co-crystal, tautomer, stereoisomer, isotopically labeled derivative, or prodrug thereof.
In certain embodiments, the compound of Formula (I) useful in the present invention is of the formula:

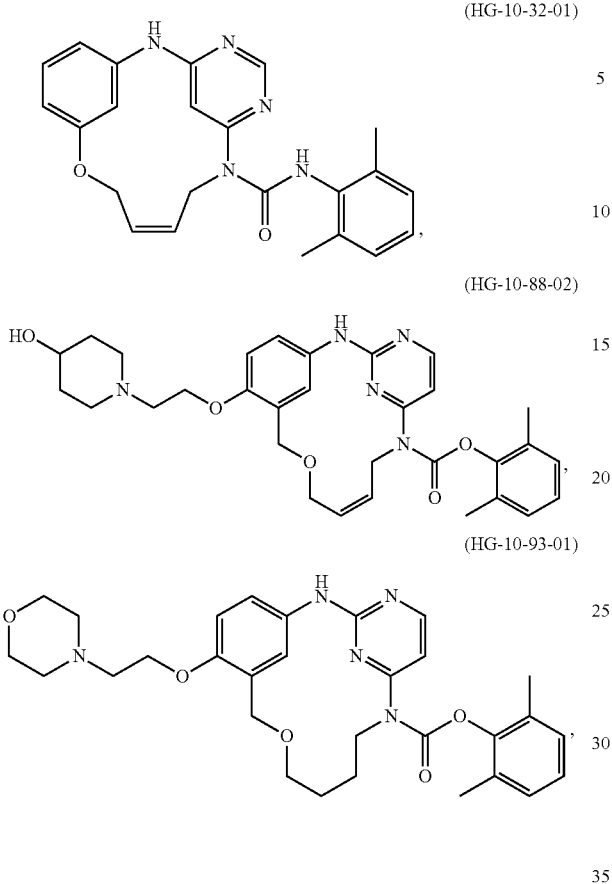

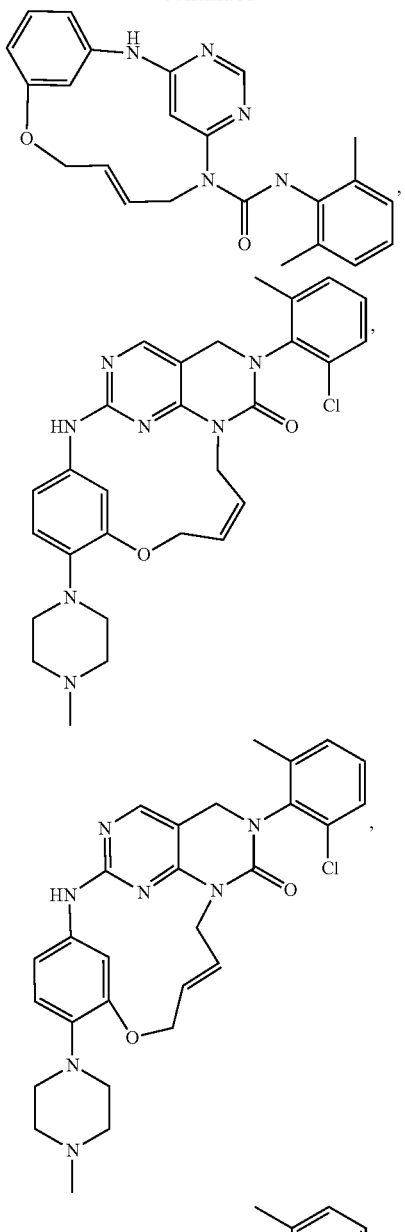

or a pharmaceutically acceptable salt, solvate, hydrate, polymorph, co-crystal, tautomer, stereoisomer, isotopically labeled derivative, or prodrug thereof.

In certain embodiments, the compound of Formula (I) useful in the present invention is of the formula:

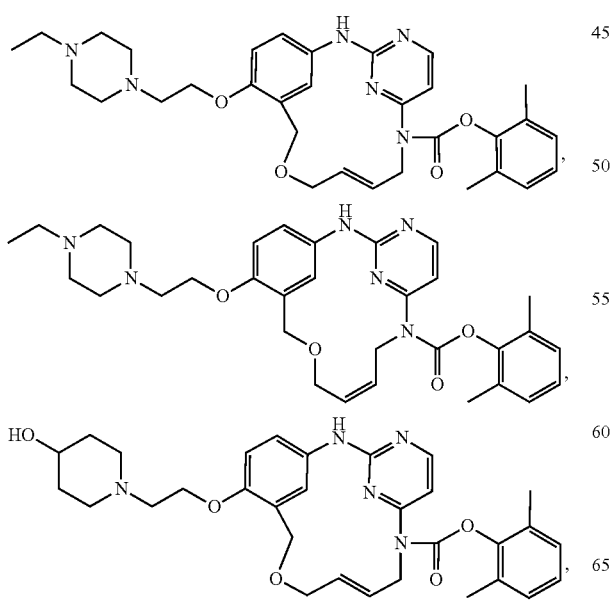

or a pharmaceutically acceptable salt, solvate, hydrate, polymorph, co-crystal, tautomer, stereoisomer, isotopically labeled derivative, or prodrug thereof.

Compounds of Formula (II)

In another aspect, the compound utilized in the present disclosure is of Formula (II):

(II)

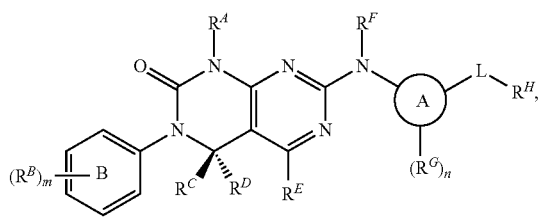

and pharmaceutically acceptable salts, solvates, hydrates, polymorphs, co-crystals, tautomers, stereoisomers, isotopically labeled derivatives, and prodrugs thereof, wherein:

$R^A$ is substituted or unsubstituted alkenyl, substituted or unsubstituted alkynyl,

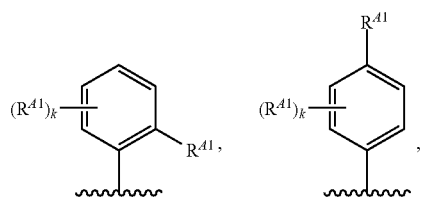

substituted or unsubstituted heteroaryl, or substituted or unsubstituted heterocyclyl;

each instance of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —C(=$NR^b$)$R^a$, —C(=$NR^b$)$OR^a$, —C(=$NR^b$)N($R^b$)$_2$, —C(=O)$R^a$, —C(=O)$OR^a$, —C(=O)N($R^b$)$_2$, —$NO_2$, —$NR^b$C(=O)$R^a$, —$NR^b$C(=O)$OR^a$, —$NR^b$C(=O)N($R^b$)$_2$, —OC(=O)$R^a$, —OC(=O)$OR^a$, or —OC(=O)N($R^b$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom, or two instances of Ra are joined to form a substituted or unsubstituted heterocyclic or substituted or unsubstituted heteroaryl ring;

each instance of $R^b$ is independently hydrogen, substituted or unsubstituted $C_{1-6}$ alkyl, or a nitrogen protecting group, or optionally two instances of $R^b$ are taken together with their intervening atoms to form a substituted or unsubstituted heterocyclic or substituted or unsubstituted heteroaryl ring;

k is 0, 1, 2, 3, or 4;

each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —C(=$NR^b$)$R^a$, —C(=$NR^b$)$OR^a$, —C(=$NR^b$)N($R^b$)$_2$, —C(=O)$R^a$, —C(=O)$OR^a$, —C(=O)N($R^b$)$_2$, —$NO_2$, —$NR^b$C(=O)$R^a$, —$NR^b$C(=O)$OR^a$, —$NR^b$C(=O)N($R^b$)$_2$, —OC(=O)$R^a$, —OC(=O)$OR^a$, or —OC(=O)N($R^b$)$_2$;

m is 0, 1, 2, 3, 4, or 5;

$R^C$ is hydrogen, halogen, or substituted or unsubstituted $C_{1-6}$ alkyl;

$R^D$ is hydrogen, halogen, or substituted or unsubstituted $C_{1-6}$ alkyl;

$R^E$ is hydrogen, halogen, or substituted or unsubstituted $C_{1-6}$ alkyl;

$R^F$ is hydrogen, substituted or unsubstituted $C_{1-6}$ alkyl, or a nitrogen protecting group;

Ring A is substituted or unsubstituted phenyl; substituted or unsubstituted, polycyclic aryl; substituted or unsubstituted, 5- or 6-membered, monocyclic heteroaryl; or substituted or unsubstituted, polycyclic heteroaryl;

each instance of $R^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —C(=$NR^b$)$R^a$, —C(=$NR^b$)$OR^a$, —C(=$NR^b$)N($R^b$)$_2$, —C(=O)$R^a$, —C(=O)$OR^a$, —C(=O)N($R^b$)$_2$, —$NO_2$, —$NR^b$C(=O)$R^a$, —$NR^b$C(=O)$OR^a$, —$NR^b$C(=O)N($R^b$)$_2$, —OC(=O)$R^a$, —OC(=O)$OR^a$, or —OC(=O)N($R^b$)$_2$;

n is 0, 1, 2, 3, or 4, as valency permits;

L is a bond or a substituted or unsubstituted $C_{1-6}$ hydrocarbon chain, optionally wherein one or more chain atoms of the hydrocarbon chain are independently replaced with —C(=O)—, —O—, —S—, —$NR^b$—, —N=, or =N—;

and $R^H$ is substituted or unsubstituted $C_{1-6}$ alkyl, substituted or unsubstituted heterocyclyl, —OH, or —N($R^c$)$_2$, wherein each instance of $R^c$ is independently hydrogen, substituted or unsubstituted $C_{1-6}$ alkyl, or a nitrogen protecting group, or optionally two instances of $R^c$ are taken together with their intervening atoms to form a substituted or unsubstituted heterocyclic or substituted or unsubstituted heteroaryl ring.

Formula (II) includes substituent $R^A$. In certain embodiments, $R^A$ is substituted alkenyl. In certain embodiments, $R^A$ is unsubstituted alkenyl. In certain embodiments, $R^A$ is substituted alkynyl. In certain embodiments, $R^A$ is unsubstituted alkynyl. In certain embodiments, $R^A$ is substituted phenyl. In certain embodiments, $R^A$ is of the formula:

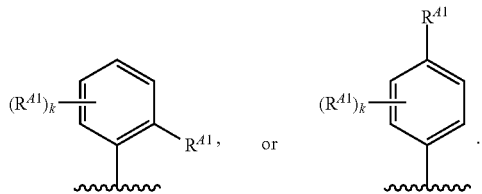

In certain embodiments, k is 0. In certain embodiments, $R^A$ is of the formula:

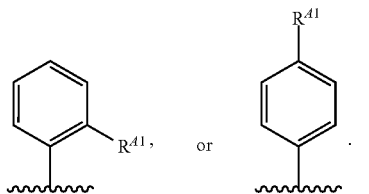

In certain embodiments, k is 1. In certain embodiments, $R^A$ is of the formula:

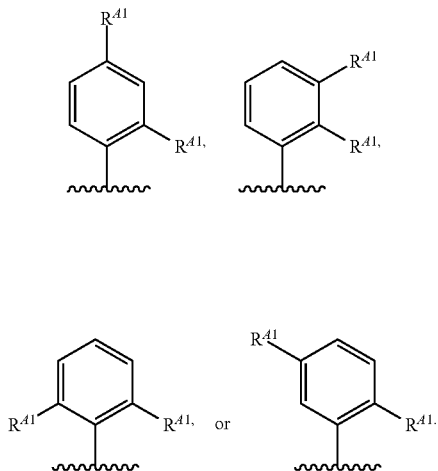

In certain certain embodiments, $R^A$ is of the formula:

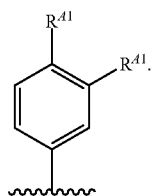

In certain embodiments, $R^A$ is

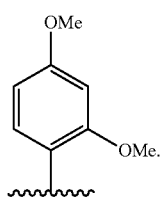 [SMILES: *c1ccc(OC)cc1OC]

In certain embodiments, $R^A$ is

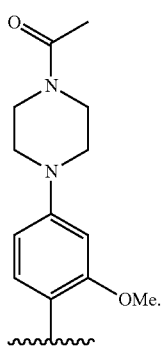 [SMILES: *c1ccc(N2CCN(C(C)=O)CC2)cc1OC]

In certain embodiments, k is 2. In certain embodiments, $R^A$ is of the formula:

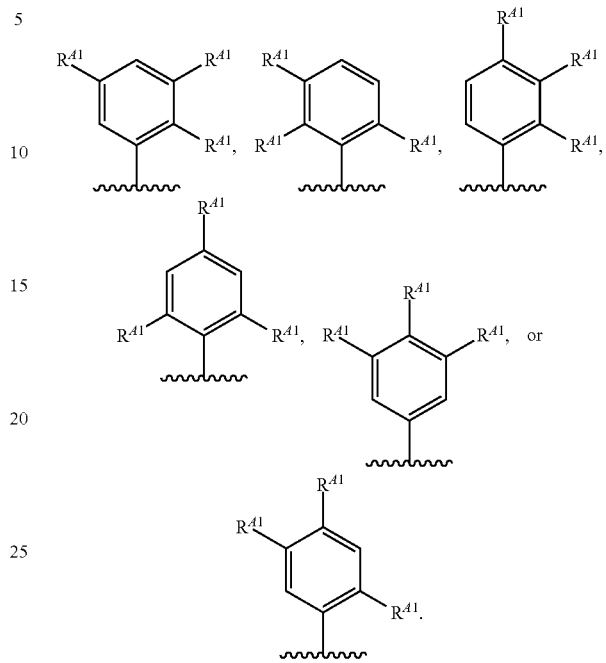

In certain embodiments, k is 3. In certain embodiments, $R^A$ is of the formula:

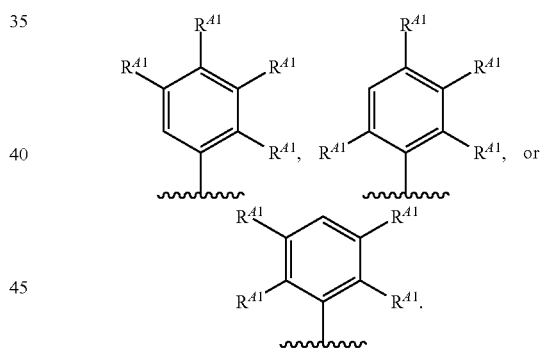

In certain embodiments, k is 4. In certain embodiments, $R^A$ is of the formula:

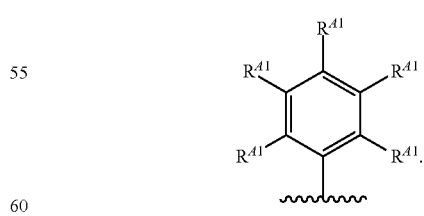

In certain embodiments, when $R^A$ is substituted phenyl, $R^A$ includes one or more $R^{A1}$ substituents. In certain embodiments, at least one instance of $R^{A1}$ is halogen (e.g., F, Cl, Br, or I). In certain embodiments, at least one $R^{A1}$ is substituted or unsubstituted alkyl (e.g., substituted or unsubstituted $C_{1-6}$ alkyl). In certain embodiments, at least one instance of $R^{A1}$ is substituted or unsubstituted methyl. In certain embodiments, at least one instance of $R^{41}$ is substituted or unsubstituted ethyl. In certain embodiments, at least one instance of $R^{41}$ is substituted or unsubstituted propyl. In certain embodiments, at least one instance of $R^{41}$ is substituted or unsubstituted alkenyl (e.g., substituted or unsubstituted $C_{2-6}$ alkenyl). In certain embodiments, at least one instance of $R^{41}$ is substituted or unsubstituted alkynyl (e.g., substituted or unsubstituted $C_{2-6}$ alkynyl). In certain embodiments, at least one instance of $R^{41}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{41}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{41}$ is substituted or unsubstituted piperazinyl. In certain embodiments, at least one instance of $R^{41}$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, at least one instance of $R^{41}$ is substituted or unsubstituted aryl (e.g., substituted or unsubstituted, 6- to 10-membered aryl). In certain embodiments, at least one instance of $R^{41}$ is benzyl. In certain embodiments, at least one instance of $R^{41}$ is substituted or unsubstituted phenyl. In certain embodiments, at least one instance of $R^{41}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{41}$ is —$OR^a$ (e.g., —OH or —OMe). In certain embodiments, at least one instance of $R^{41}$ is —$N(R^b)_2$, —$SR^a$, —CN, —SCN, —C(=$NR^b$)$R^a$, —C(=$NR^b$)$OR^a$, —C(=$NR^b$)N($R^b$)$_2$, —C(=O)$R^a$, —C(=O)$OR^a$, —C(=O)N($R^b$)$_2$, —$NO_2$, —$NR^b$C(=O)$R^a$, —$NR^b$C(=O)$OR^a$, —$NR^b$C(=O)N($R^b$)$_2$, —OC(=O)$R^a$, —OC(=O)$OR^a$, or —OC(=O)N($R^b$)$_2$.

In certain embodiments, at least one instance of $R^a$ is hydrogen. In certain embodiments, at least one instance of $R^a$ is halogen (e.g., F, Cl, Br, or I). In certain embodiments, at least one instance of $R^a$ is substituted or unsubstituted alkyl (e.g., substituted or unsubstituted $C_{1-6}$ alkyl). In certain embodiments, at least one instance of $R^a$ is substituted or unsubstituted methyl. In certain embodiments, at least one instance of $R^a$ is substituted or unsubstituted ethyl. In certain embodiments, at least one instance of $R^a$ is substituted or unsubstituted propyl. In certain embodiments, at least one instance of $R^a$ is substituted or unsubstituted alkenyl (e.g., substituted or unsubstituted $C_{2-6}$ alkenyl). In certain embodiments, at least one instance of $R^a$ is substituted or unsubstituted alkynyl (e.g., substituted or unsubstituted $C_{2-6}$ alkynyl). In certain embodiments, at least one instance of $R^a$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^a$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^a$ is substituted or unsubstituted aryl (e.g., substituted or unsubstituted, 6- to 10-membered aryl). In certain embodiments, at least one instance of $R^{41}$ is benzyl. In certain embodiments, at least one instance of $R^a$ is substituted or unsubstituted phenyl. In certain embodiments, at least one instance of $R^a$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^a$ is an oxygen protecting group when attached to an oxygen atom. In certain embodiments, at least one instance of $R^a$ is a sulfur protecting group when attached to a sulfur atom.

In certain embodiments, at least one instance of $R^b$ is hydrogen. In certain embodiments, at least one instance of $R^b$ is substituted or unsubstituted $C_{1-6}$ alkyl (e.g., substituted or unsubstituted methyl, ethyl, or propyl). In certain embodiments, at least one instance of $R^b$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of $R^b$ are taken together with their intervening atoms to form a substituted or unsubstituted heterocyclic or substituted or unsubstituted heteroaryl ring (e.g., substituted or unsubstituted, 5- to 10-membered monocyclic or bicyclic heterocyclic ring, wherein one or two atoms in the heterocyclic ring are independently nitrogen, oxygen, or sulfur; or substituted or unsubstituted, 5- to 6-membered, monocyclic heteroaryl, wherein one, two, three, or four atoms in the heteroaryl ring system are independently nitrogen, oxygen, or sulfur). In certain embodiments, two instances of $R^b$ are taken together with their intervening atoms to form substituted or unsubstituted piperazinyl. In certain embodiments, two instances of $R^b$ are taken together with their intervening atoms to form

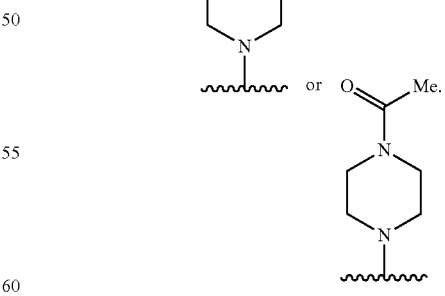

In certain embodiments, $R^A$ is substituted or unsubstituted heteroaryl. In certain embodiments, $R^A$ is substituted or unsubstituted, 5- to 6-membered, monocyclic heteroaryl, wherein one, two, three, or four atoms in the heteroaryl ring system are independently nitrogen, oxygen, or sulfur (e.g., furanyl, thiophenyl, pyridinyl, or pyrimidinyl, etc.) In certain embodiments, $R^A$ is substituted or unsubstituted furanyl. In certain embodiments, $R^A$ is substituted or unsubstituted thiophenyl. In certain embodiments, $R^A$ is substituted or unsubstituted pyridinyl. In certain embodiments, RA is of the formula:

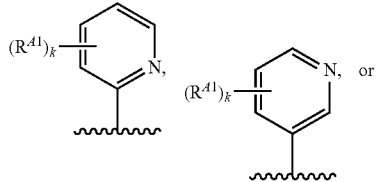

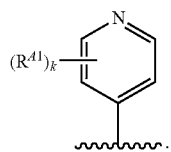

In certain embodiments, k is 0. In certain embodiments, $R^A$ is of the formula:

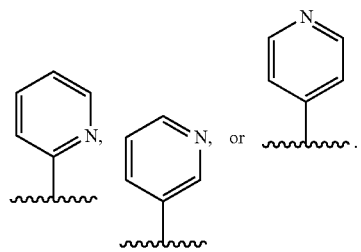

In certain embodiments, k is 1. In certain embodiments, $R^A$ is of the formula:

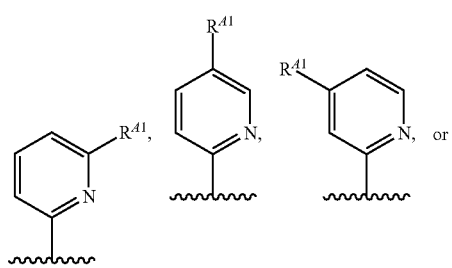

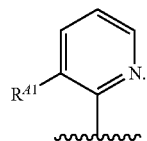

In certain embodiments, $R^A$ is of the formula:

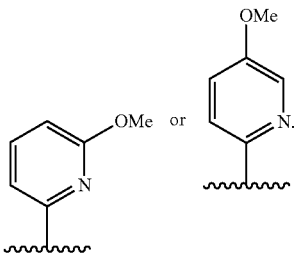 [SMILES: *c1cccc(OC)n1 ; *c1ccc(OC)cn1]

In certain embodiments, $R^A$ is of the formula:

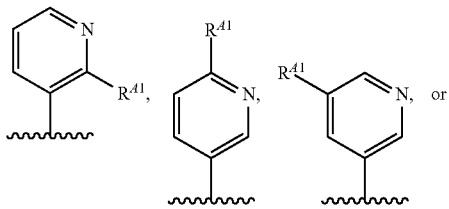

In certain embodiments, $R^A$ is of the formula:

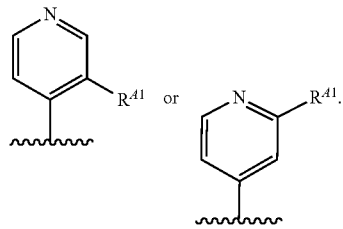

In certain embodiments, k is 2. In certain embodiments, $R^A$ is of the formula:

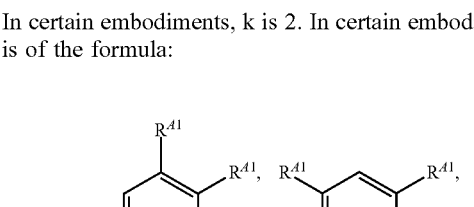

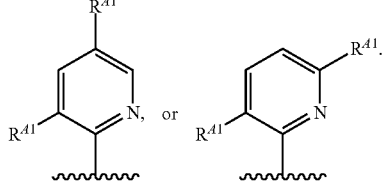

In certain embodiments $R^A$ is of the formula:

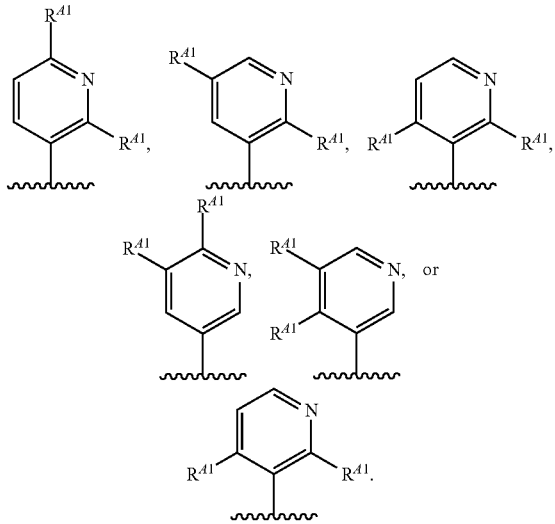

In certain embodiments, $R^A$ is of the formula:

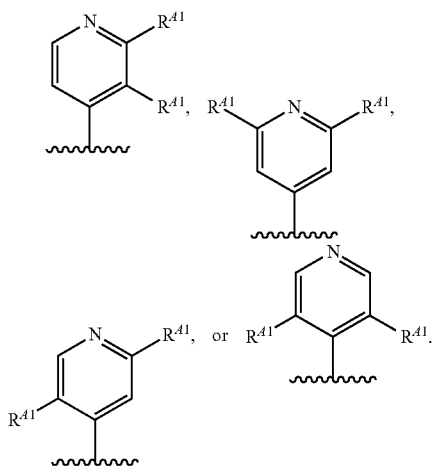

In certain embodiments, k is 3. In certain embodiments, $R^A$ is of the formula:

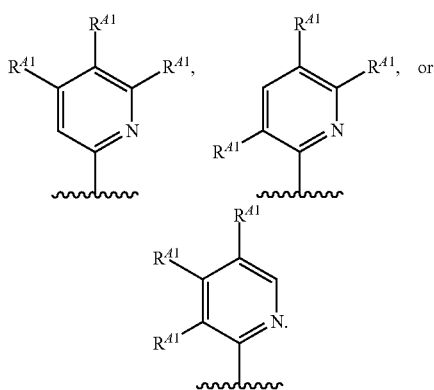

In certain embodiments, $R^A$ is of the formula:

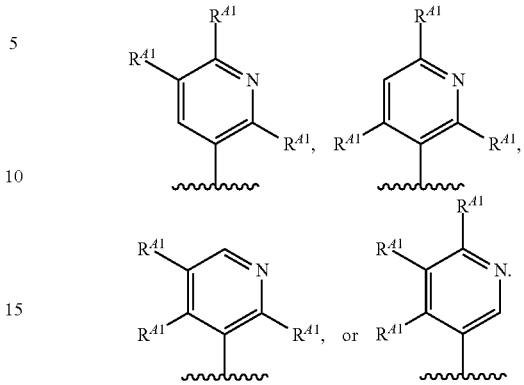

In certain embodiments, $R^A$ is of the formula:

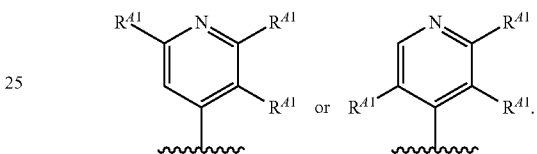

In certain embodiments, k is 4. In certain embodiments, $R^A$ is of the formula:

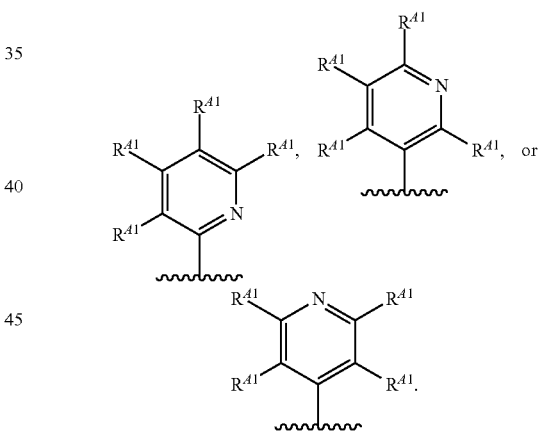

In certain embodiments, $R^A$ is not substituted or unsubstituted pyridinyl. In certain embodiments, $R^A$ is not substituted or unsubstituted 2-pyridinyl. In certain embodiments, $R^A$ is not substituted 2-pyridinyl. In certain embodiments, $R^A$ is substituted or unsubstituted pyrimidinyl. In certain embodiments, $R^A$ is substituted or unsubstituted pyrazinyl. In certain embodiments, $R^A$ is substituted or unsubstituted triazinyl. In certain embodiments, $R^A$ is substituted or unsubstituted, 9- to 10-membered, bicyclic heteroaryl, wherein one, two, three, or four atoms in the heteroaryl ring system are independently nitrogen, oxygen, or sulfur). In certain embodiments, $R^A$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur), In certain embodiments, $R^A$ is not substituted or unsubstituted 3-pyrrolidinyl. In certain embodiments, $R^A$ is substituted or unsubstituted tetrahydropyranyl. In certain embodiments, $R^A$ is unsubstituted tetrahydropyranyl. In certain embodiments, $R^A$ is piperidinyl. In certain embodiments, $R^A$ is substituted or unsubstituted morpholinyl. In certain embodiments, $R^A$ is substituted or unsubstituted piperazinyl.

Formula (II) includes Ring B. Ring B is described in the Detailed Description for Formula (IV) below.

Formula (II) includes substituents $R^C$, $R^D$, $R^E$, and $R^F$. Substituents $R^C$, $R^D$, $R^E$, and $R^F$ are described in the Detailed Description for Formula (IV) below.

Formula (II) includes Ring A and one or more instances of substituent $R^G$. Ring A and substituent $R^G$ are described in the Detailed Description for Formula (IV) below.

Formula (II) includes linker L that connects Ring A to substituent $R^H$. In certain embodiments, L is a substituted or unsubstituted $C_{1-6}$ hydrocarbon chain. In certain embodiments, one or more chain atoms of the hydrocarbon chain of L are independently replaced with —C(=O)—, —O—, —S—, —$NR^b$—, —N=, or =N—. In certain embodiments, L is an unsubstituted $C_{1-3}$ hydrocarbon chain.

In certain embodiments, L is of the formula:

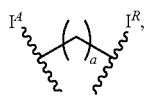

wherein a is 0, 1, 2, 3, 4, 5, or 6. In certain embodiments, a is 0. In certain embodiments, L is a bond. In certain embodiments, a is 1. In certain embodiments, a is 2. In certain embodiments, a is 3. In certain embodiments, a is 4. In certain embodiments, a is 5. In certain embodiments, a is 6. In certain embodiments, L is of the formula:

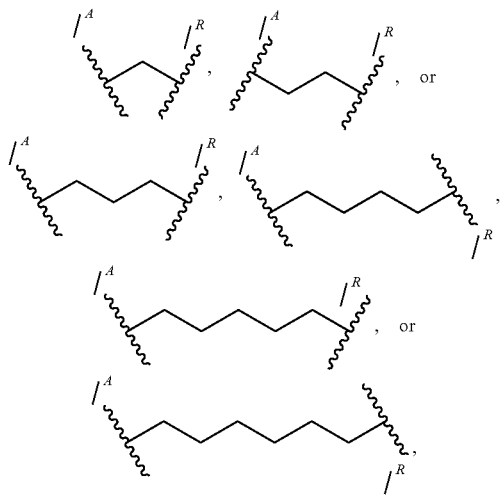

wherein $l^A$ indicates the point of attachment to Ring A, and $l^R$ indicates the point of attachment to $R^H$.

In certain embodiments, L is an unsubstituted $C_{1-3}$ hydrocarbon chain, wherein one or more chain atoms of the hydrocarbon chain are independently replaced with —O— or —$NR^b$—. In certain embodiments, L is an unsubstituted $C_{1-3}$ hydrocarbon chain, wherein one chain atom of the hydrocarbon chain is replaced with —O—. In certain embodiments, L is of the formula:

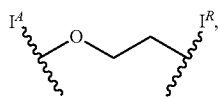

wherein $l^A$ indicates the point of attachment to Ring A, and $l^R$ indicates the point of attachment to $R^A$. In certain embodiments, L is of the formula:

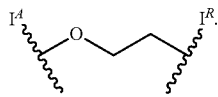

In certain embodiments, L is a substituted $C_{1-6}$ hydrocarbon chain, wherein one chain atom of the hydrocarbon chain is replaced with —N—. In certain embodiments, L is of the formula:

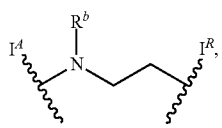

wherein $l^A$ indicates the point of attachment to Ring A, and $l^R$ indicates the point of attachment to $R^H$. In certain embodiments, L is of the formula:

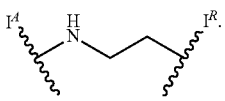

In certain embodiments, L is of the formula:

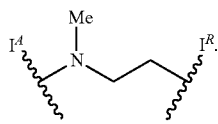

In certain embodiments, L is of the formula:

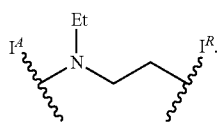

In certain embodiments, L is an unsubstituted $C_{1-3}$ hydrocarbon chain, wherein one chain atom of the hydrocarbon chain is replaced with —C(=O)—. In certain embodiments, L is an unsubstituted $C_{1-3}$ hydrocarbon chain, wherein one chain atom of the hydrocarbon chain is replaced with —S—. In certain embodiments, L is an unsubstituted $C_{1-3}$ hydrocarbon chain, wherein one chain atom of the hydrocarbon chain is replaced with —$NR^b$—. In certain embodiments, L is an unsubstituted $C_{1-3}$ hydrocarbon chain, wherein one chain atom of the hydrocarbon chain is replaced with —N=. In certain embodiments, L is an unsubstituted $C_{1-3}$ hydrocarbon chain, wherein one chain atom of the hydrocarbon chain is replaced with =N—.

Formula (II) includes substituent $R^H$. In certain embodiments, $R^H$ is substituted or unsubstituted $C_{1-6}$ alkyl (e.g., methyl, ethyl, or propyl). In certain embodiments, $R^H$ is methyl. In certain embodiments, $R^H$ is substituted or unsubstituted methyl. In certain embodiments, $R^H$ is substituted methyl. In certain embodiments, $R^H$ is

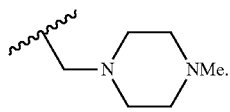

In certain embodiments, $R^H$ is unsubstituted methyl. In certain embodiments, $R^H$ is ethyl. In certain embodiments, $R^H$ is propyl. In certain embodiments, $R^H$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^H$ is substituted or unsubstituted tetrahydropyranyl, substituted or unsubstituted piperidinyl, substituted or unsubstituted morpholinyl, or substituted or unsubstituted piperazinyl. In certain embodiments, $R^H$ is of the formula:

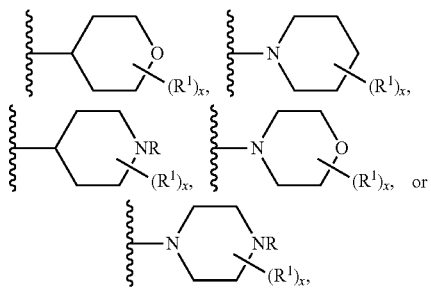

wherein $R^1$ is substituted or unsubstituted $C_{1-6}$ alkyl or —$OR^{x1}$, wherein R is hydrogen, substituted or unsubstituted $C_{1-6}$ alkyl or nitrogen protecting group; $R^{x1}$ is hydrogen or substituted or unsubstituted $C_{1-6}$ alkyl; and x is 0, 1, 2, or 3. In certain embodiments, $R^H$ is of the formula:

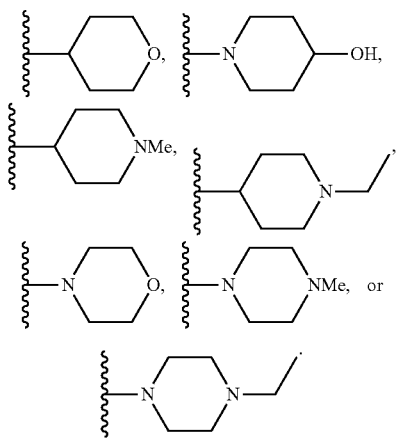

In certain embodiments, $R^H$ is —OH. In certain embodiments, $R^H$ is —$N(R^c)_2$. As generally described herein, $R^H$ may include substituent $R^c$. In certain embodiments, $R^c$ is hydrogen. In certain embodiments, $R^c$ is substituted or unsubstituted $C_{1-6}$ alkyl. In certain embodiments, $R^c$ is substituted or unsubstituted $C_{1-3}$ alkyl. In certain embodiments, $R^c$ is substituted or unsubstituted methyl. In certain embodiments, $R^c$ is methyl. In certain embodiments, $R^c$ is substituted or unsubstituted ethyl. In certain embodiments, $R^c$ is substituted or unsubstituted methyl. In certain embodiments, $R^c$ is a nitrogen protecting group. In certain embodiments, $R^H$ is —$NMe_2$. In certain embodiments, two instances of $R^c$ are taken together with their intervening atoms to form a substituted or unsubstituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, two instances of $R^c$ are taken together with their intervening atoms to form a substituted or unsubstituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, Ring A with linker L and substituent $R^H$ is of the formula:

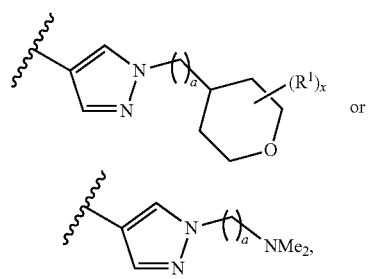

wherein a is 0, 1, 2, 3, 4, 5, or 6. In certain embodiments, Ring A with linker L and substituent $R^H$ is of the formula:

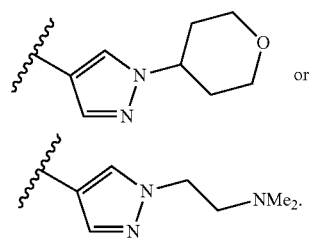

In certain embodiments, Ring A with linker L and substituent $R^H$ is of the formula:

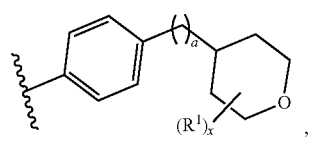

99
-continued
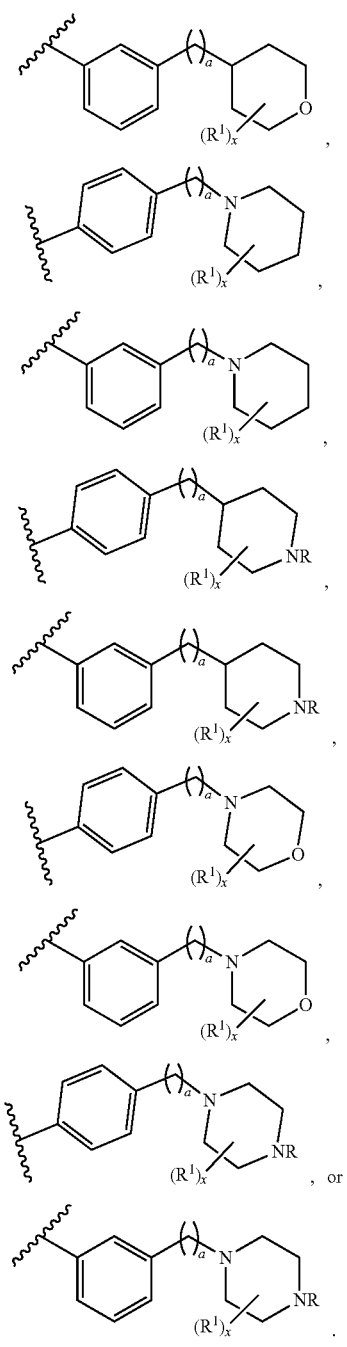
In certain embodiments, Ring A with linker L and substituent $R^H$ is not of the formula:
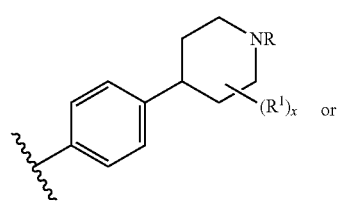
100
-continued
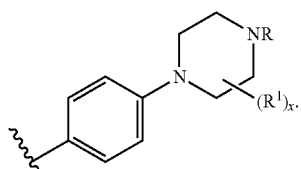
In certain embodiments, Ring A with linker L and substituent $R^H$ is of the formula:
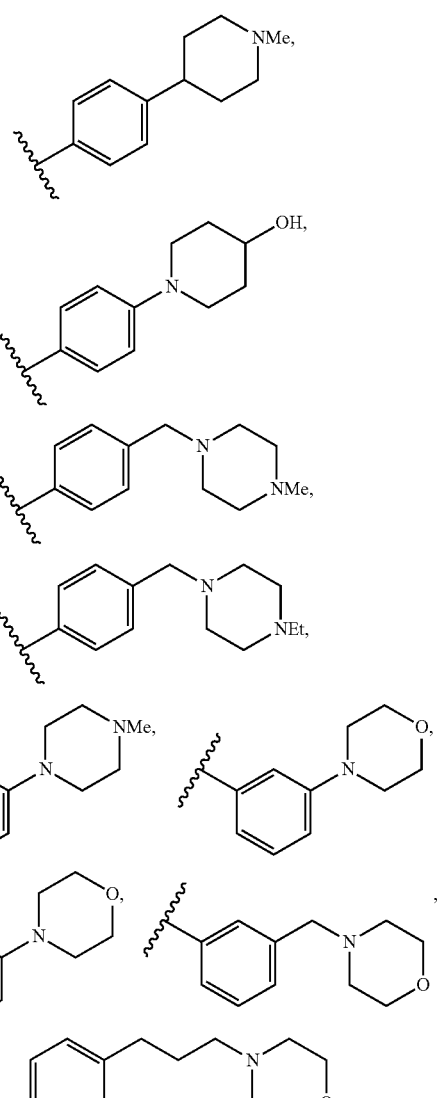

-continued

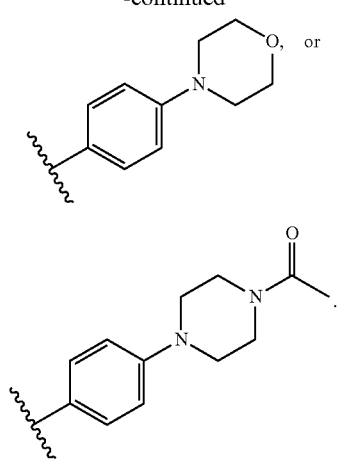

In certain embodiments, Ring A with linker L and substituent $R^H$ is not of the formula:

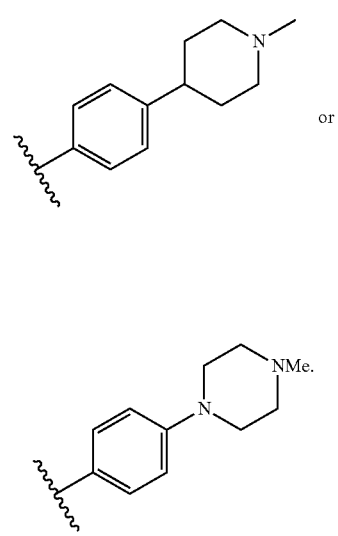

In certain embodiments, Ring A with linker L and substituent $R^H$ is of the formula:

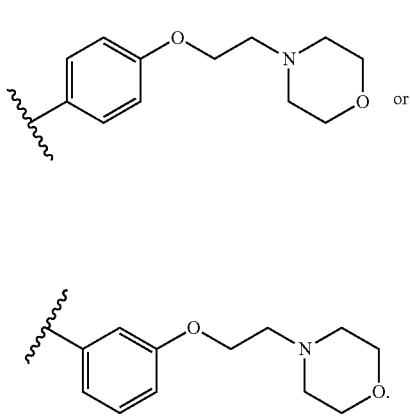

In certain embodiments, the compound of Formula (II) is of the formula

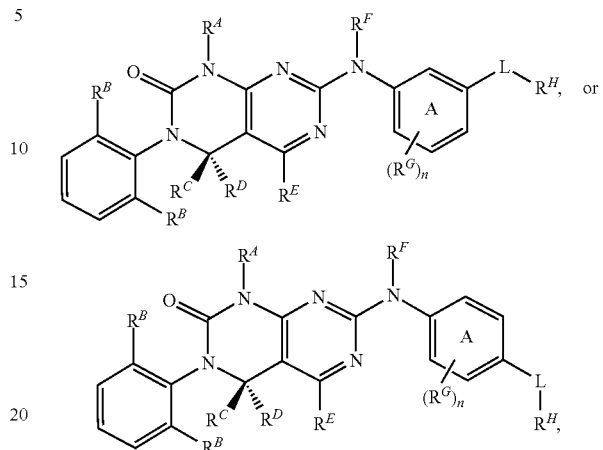

or a pharmaceutically acceptable salt, solvate, hydrate, polymorph, co-crystal, tautomer, stereoisomer, isotopically labeled derivative, or prodrug thereof.

In certain embodiments, the compound of Formula (II) useful in the present invention is of the formula:

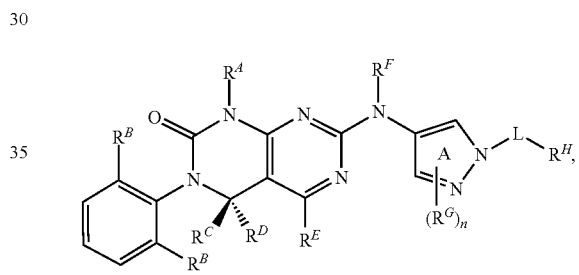

or a pharmaceutically acceptable salt, solvate, hydrate, polymorph, co-crystal, tautomer, stereoisomer, isotopically labeled derivative, or prodrug thereof.

In certain embodiments, the compound of Formula (II) useful in the present invention is of the formula:

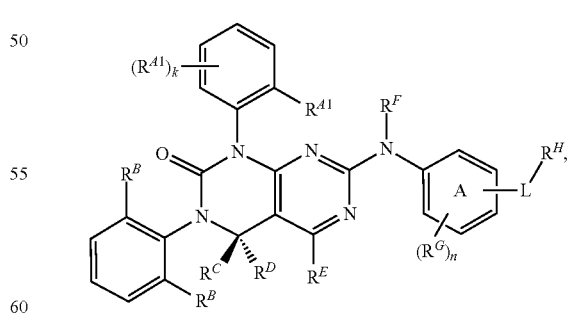

or a pharmaceutically acceptable salt, solvate, hydrate, polymorph, co-crystal, tautomer, stereoisomer, isotopically labeled derivative, or prodrug thereof.

In certain embodiments, the compound of Formula (II) useful in the present invention is of the formula:

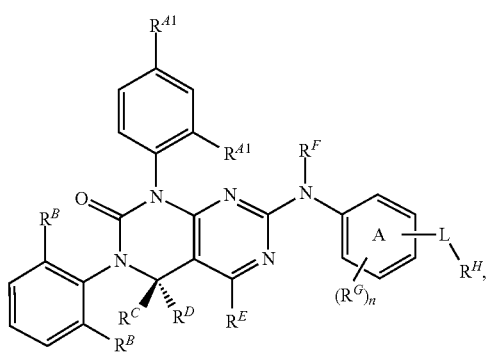

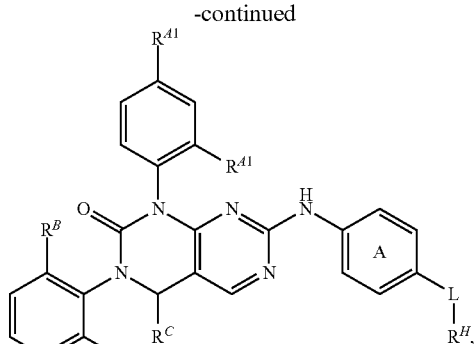

or a pharmaceutically acceptable salt, solvate, hydrate, polymorph, co-crystal, tautomer, stereoisomer, isotopically labeled derivative, or prodrug thereof.

In certain embodiments, the compound of Formula (II) useful in the present invention is of the formula:

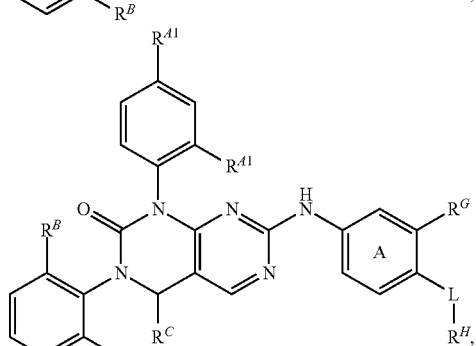

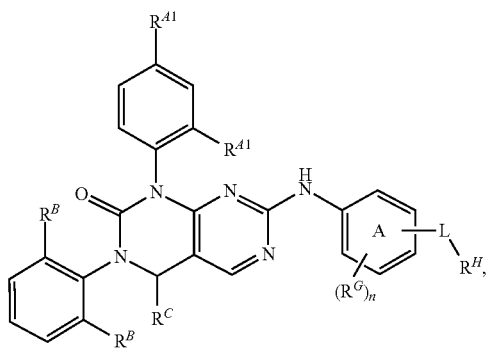

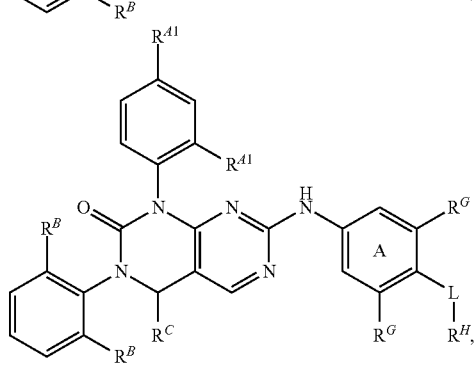

or a pharmaceutically acceptable salt, solvate, hydrate, polymorph, co-crystal, tautomer, stereoisomer, isotopically labeled derivative, or prodrug thereof.

In certain embodiments, the compound of Formula (II) useful in the present invention is of the formula:

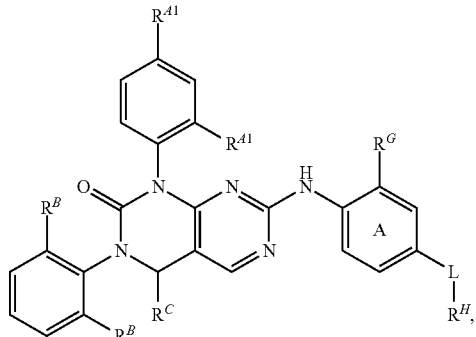

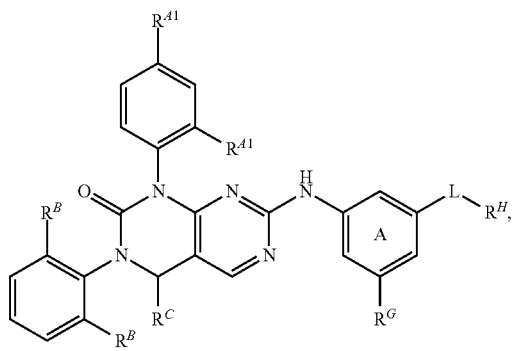

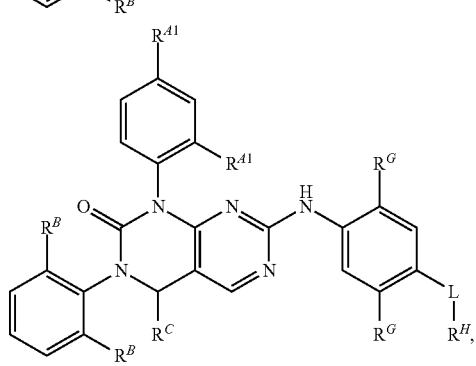

-continued

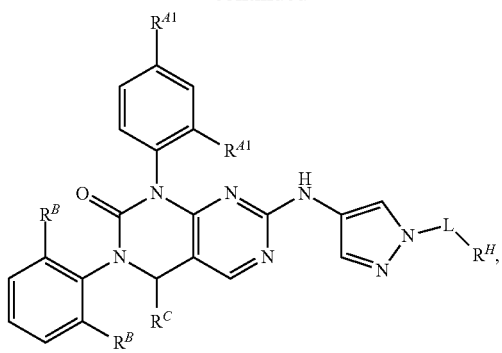

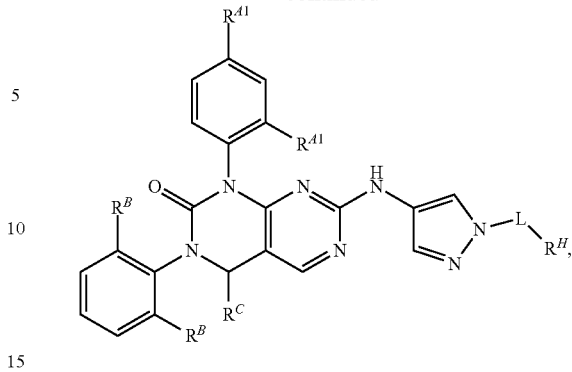

or a pharmaceutically acceptable salt, solvate, hydrate, polymorph, co-crystal, tautomer, stereoisomer, isotopically labeled derivative, or prodrug thereof.

In certain embodiments, the compound of Formula (II) useful in the present invention is of the formula:

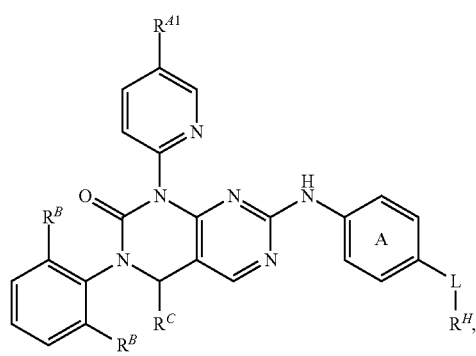

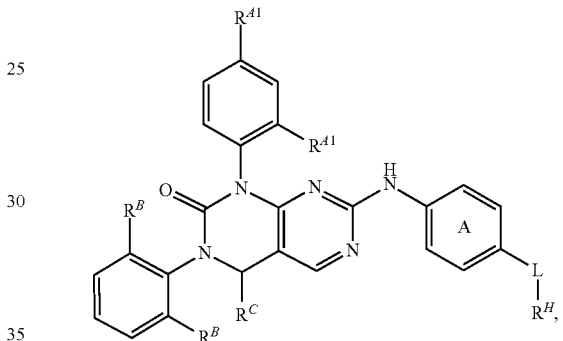

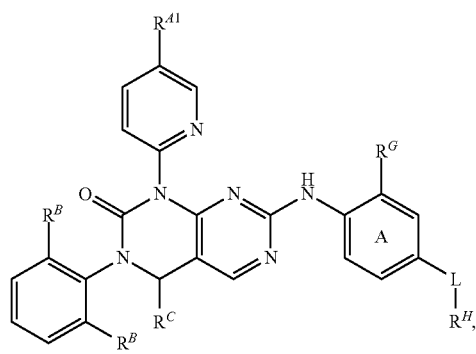

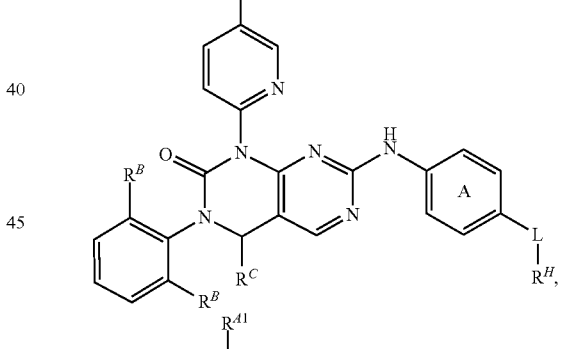

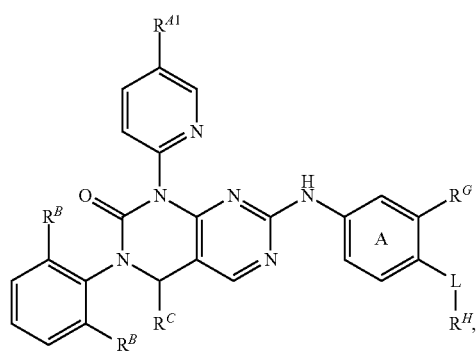

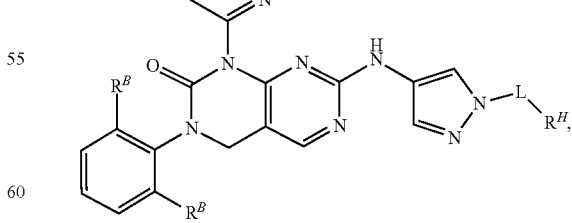

or a pharmaceutically acceptable salt, solvate, hydrate, polymorph, co-crystal, tautomer, stereoisomer, isotopically labeled derivative, or prodrug thereof.

In certain embodiments, the compound of Formula (II) useful in the present invention is of the formula:

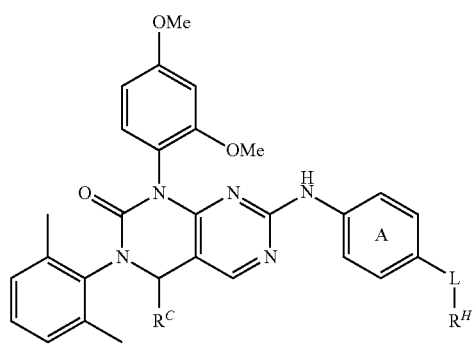
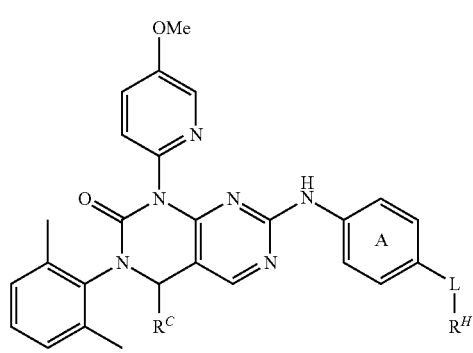
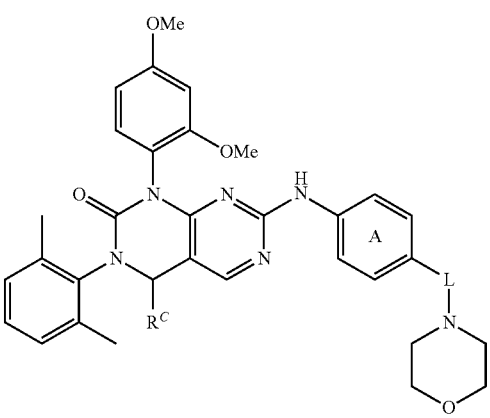
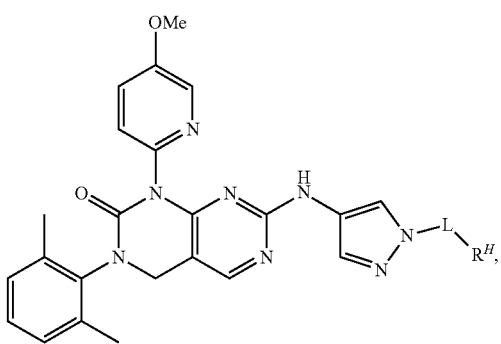
or a pharmaceutically acceptable salt, solvate, hydrate, polymorph, co-crystal, tautomer, stereoisomer, isotopically labeled derivative, or prodrug thereof.
In certain embodiments, the compound of Formula (II) useful in the present invention is of the formula:
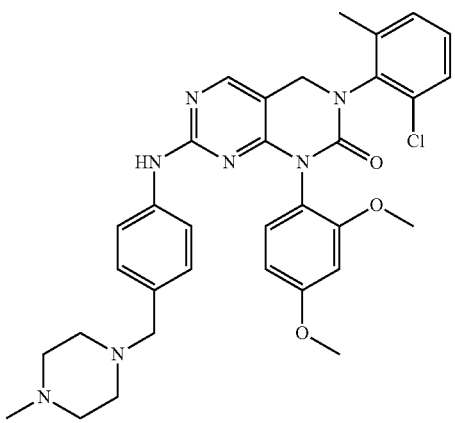
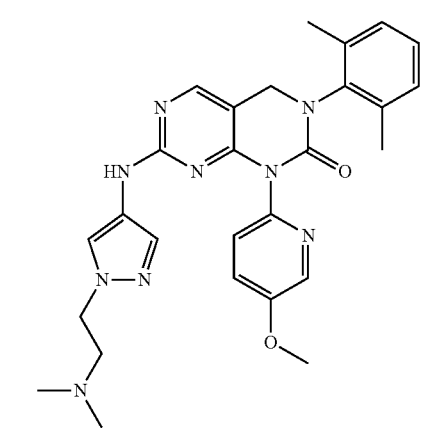
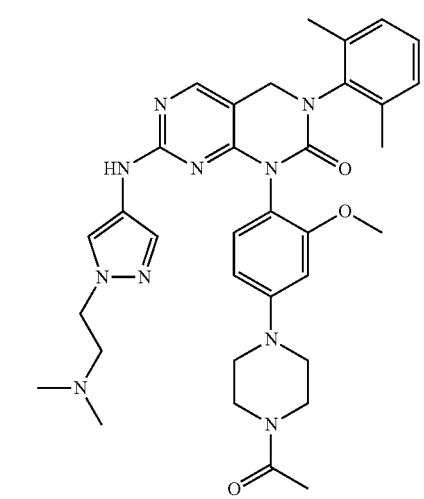

109
-continued
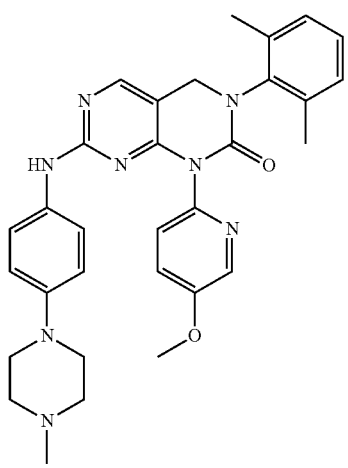
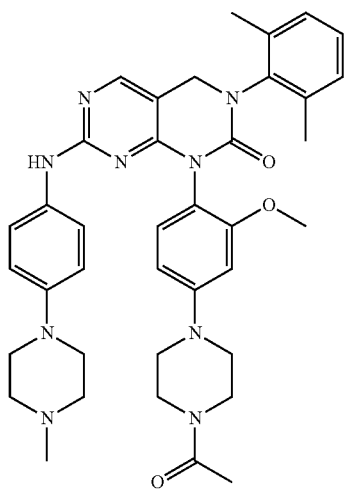
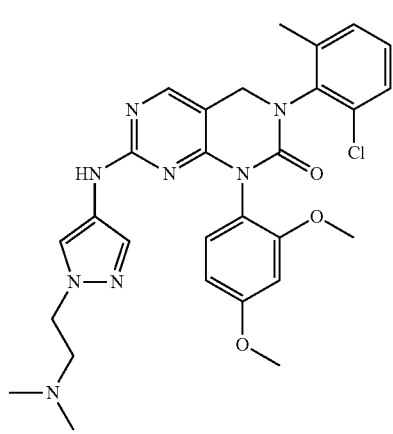
110
-continued
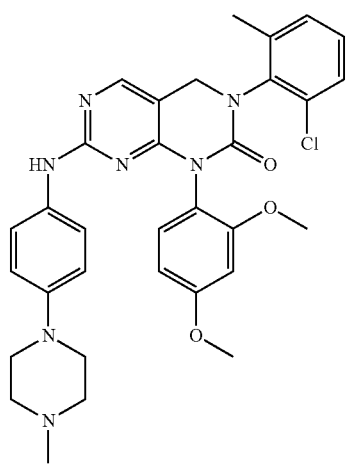
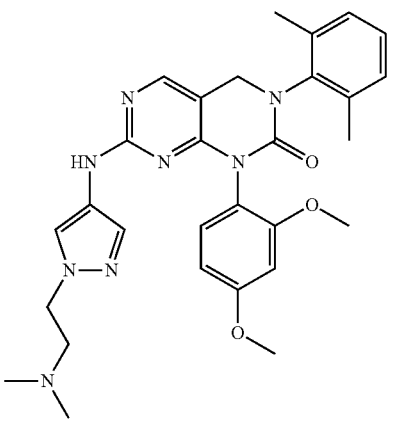
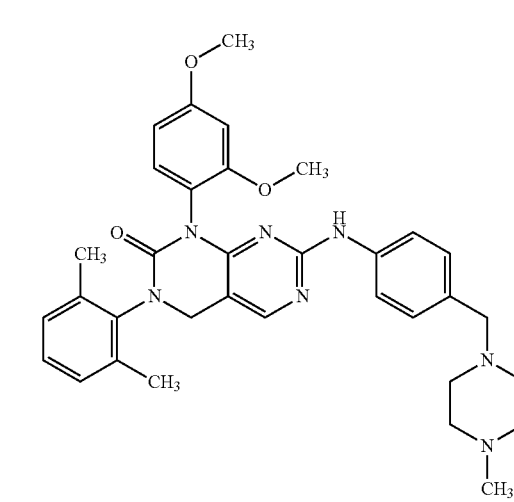

111
-continued
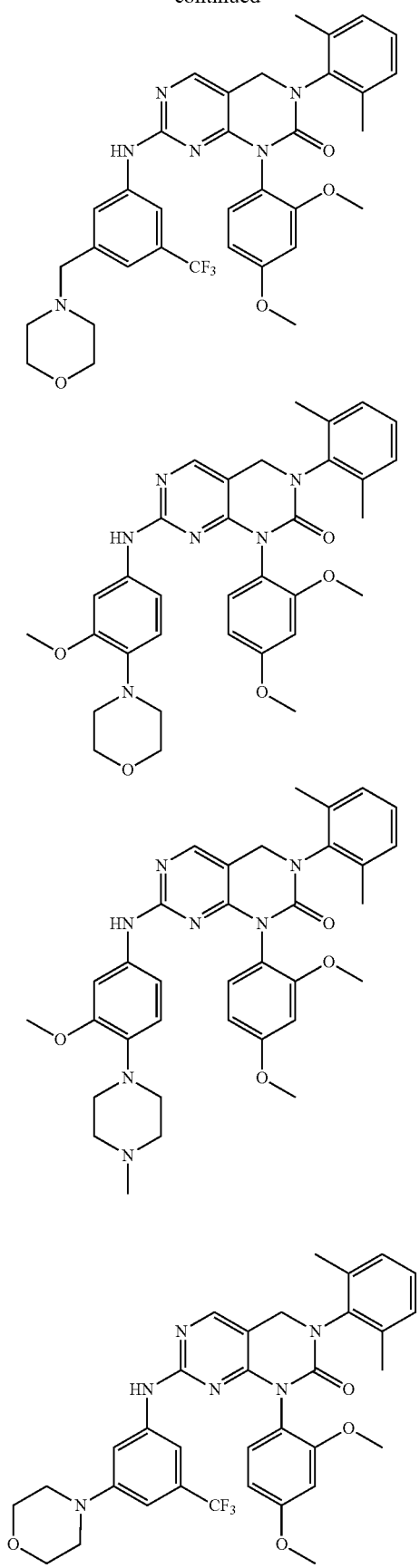
112
-continued
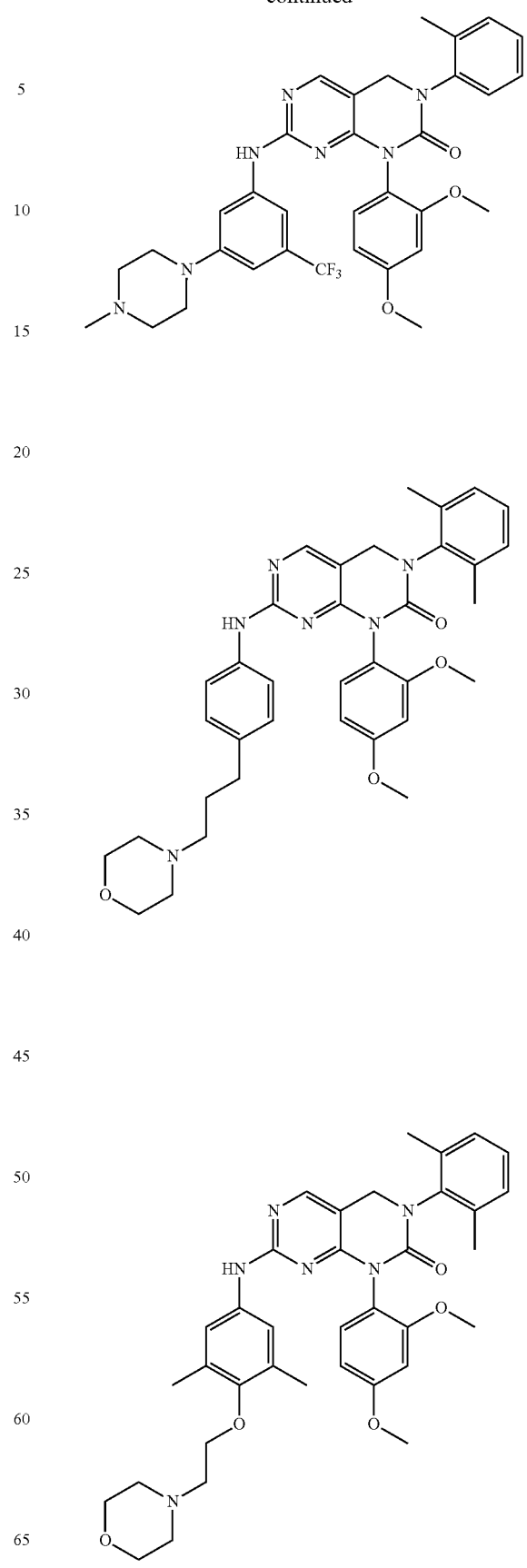

113
-continued
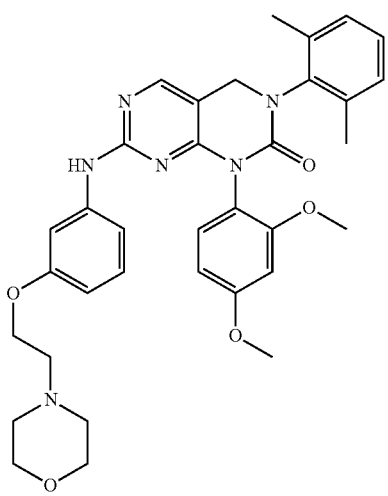
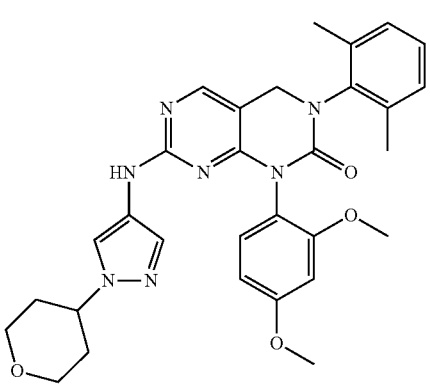
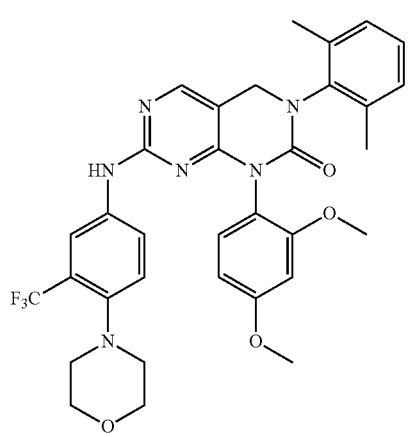
114
-continued
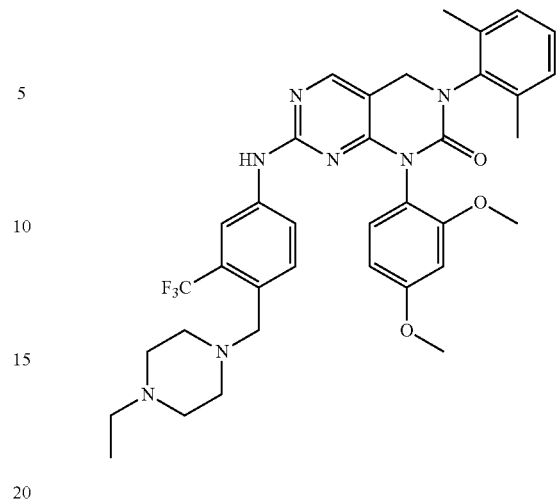
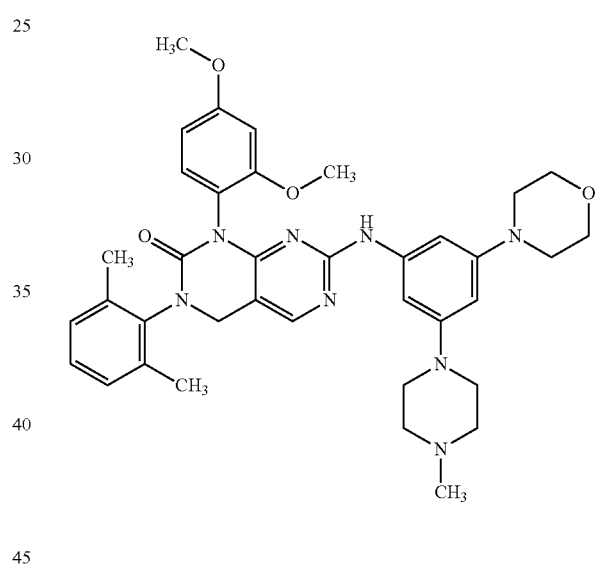
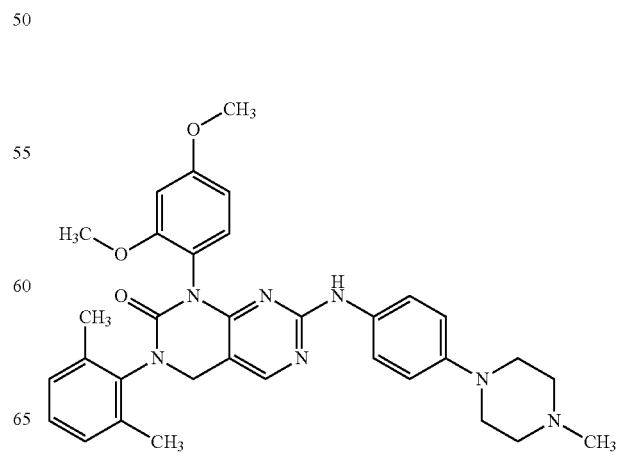

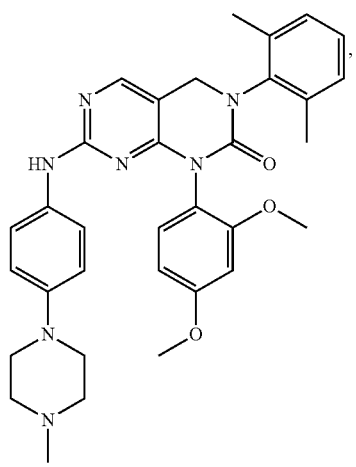
(115)

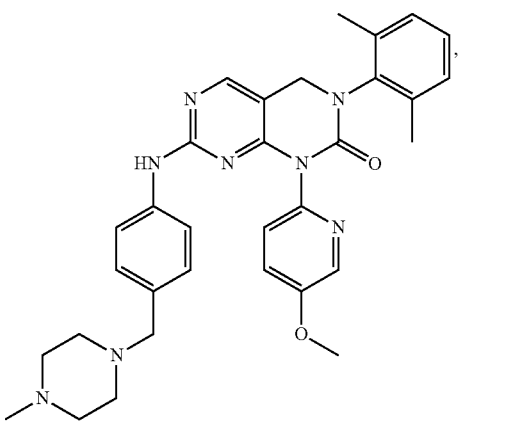
(YKL-04-136-10)

or a pharmaceutically acceptable salt, solvate, hydrate, polymorph, co-crystal, tautomer, stereoisomer, isotopically labeled derivative, or prodrug thereof.

In certain embodiments, the compounds of Formula (II) useful in the present invention include, but are not limited to:

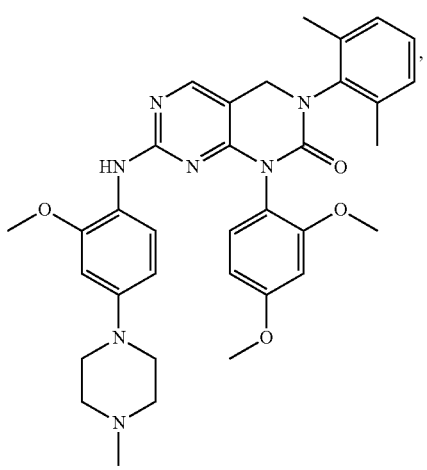
(HG-11-139-01)

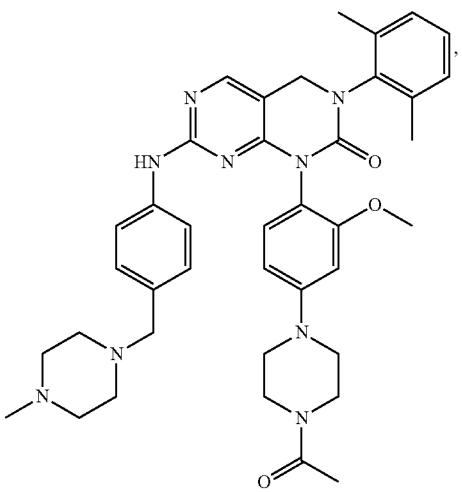
(YKL-04-136-11)

and pharmaceutically acceptable salts, solvates, hydrates, polymorphs, co-crystals, tautomers, stereoisomers, isotopically labeled derivatives, and prodrugs thereof.

In certain embodiments, the compounds of Formula (II) useful in the present invention include, but are not limited to:

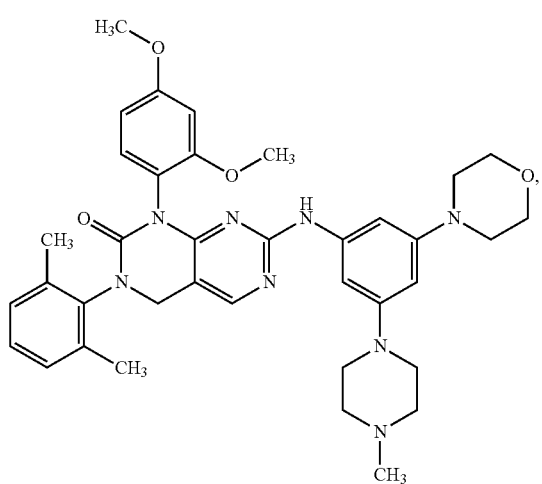
(HG-11-143-01)

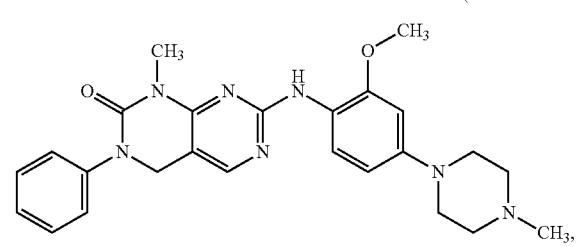
(HG-11-139-02)

-continued (HG-11-143-01)

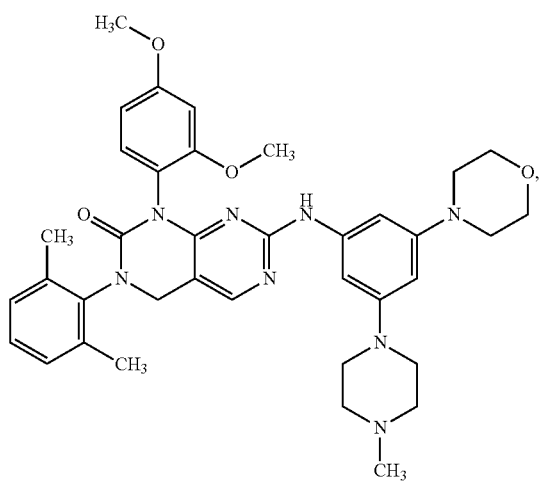

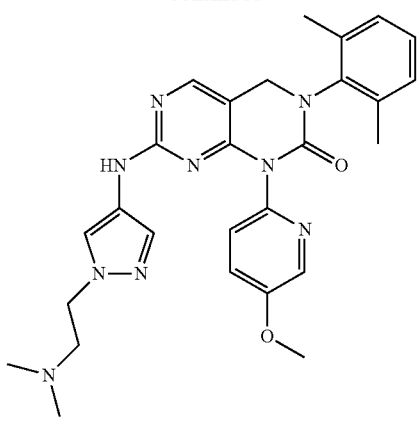

and pharmaceutically acceptable salts, solvates, hydrates, polymorphs, co-crystals, tautomers, stereoisomers, isotopically labeled derivatives, and prodrugs thereof.

In certain embodiments, the compounds of Formula (II) useful in the present invention include, but are not limited to:

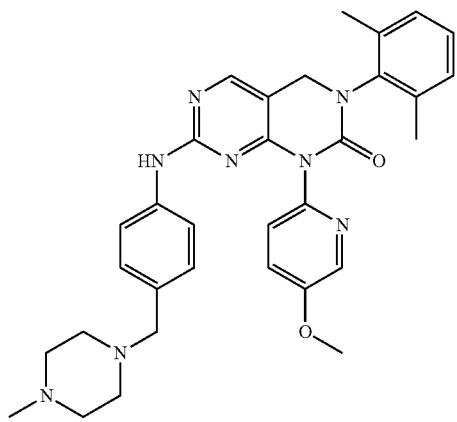

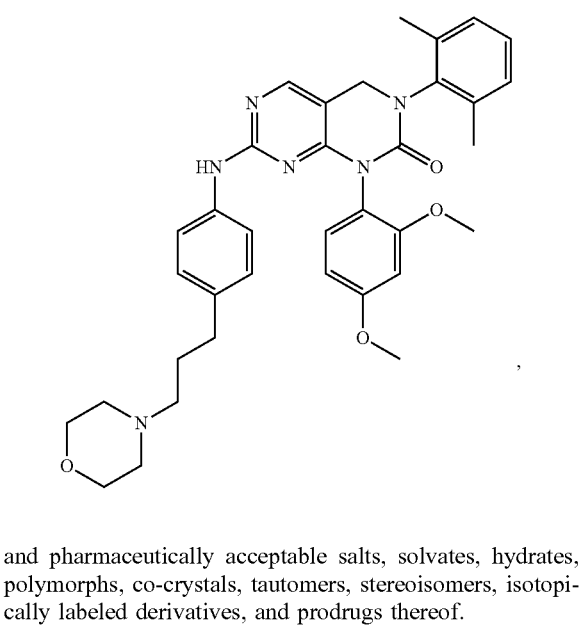

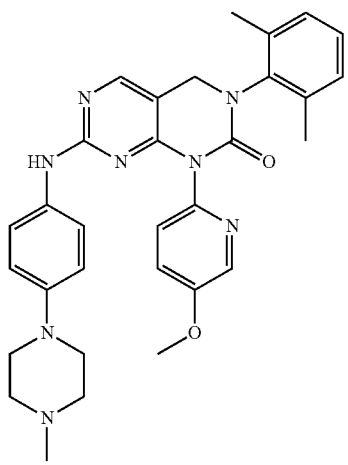

and pharmaceutically acceptable salts, solvates, hydrates, polymorphs, co-crystals, tautomers, stereoisomers, isotopically labeled derivatives, and prodrugs thereof.

In certain embodiments, the compounds of Formula (II) useful in the present invention include, but are not limited to:

(YKL-05-57)

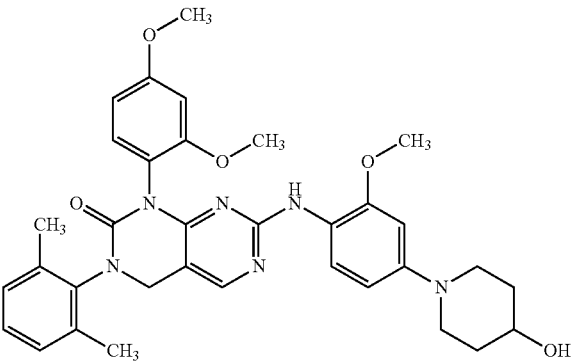

(YKL-05-58)
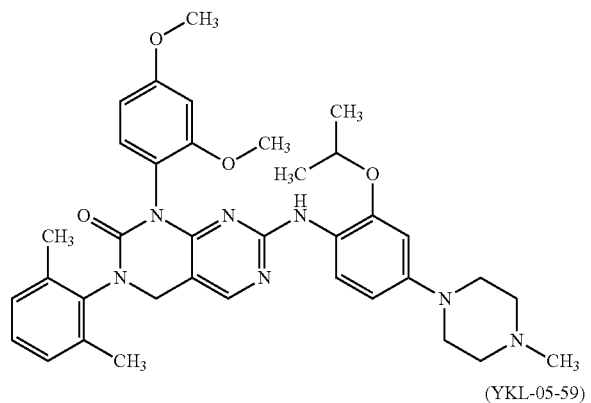
(YKL-05-59)
(YKL-05-60)
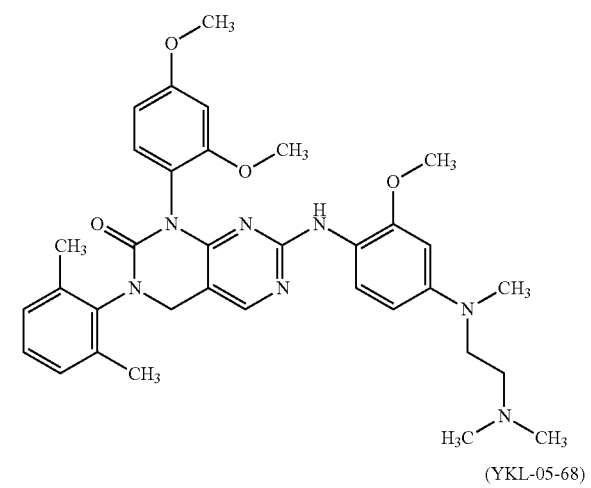
(YKL-05-68)
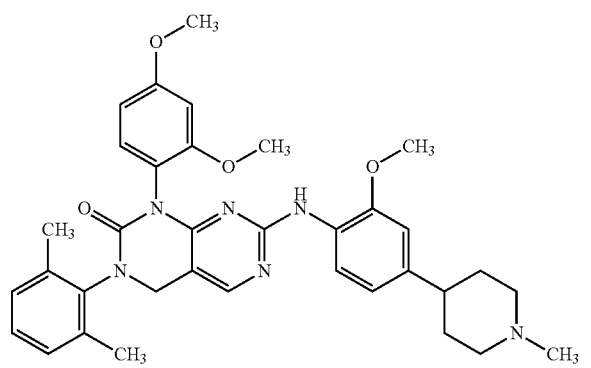
(YKL-05-69)
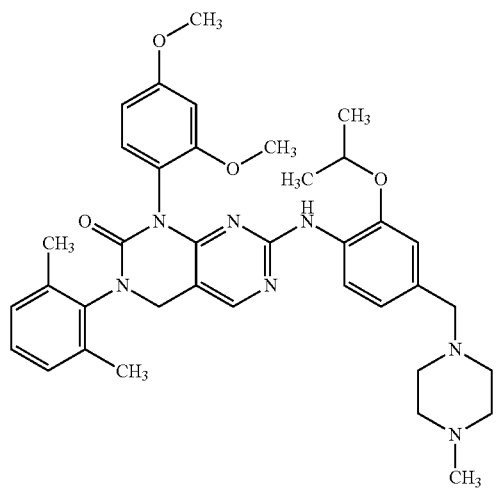
(YKL-05-70)
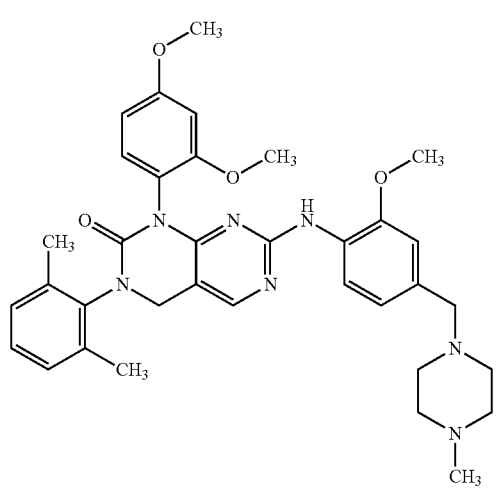
(YKL-05-74)
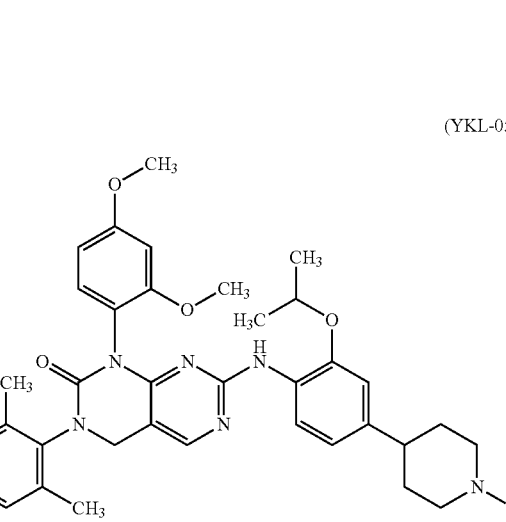

-continued
(YKL-05-76)
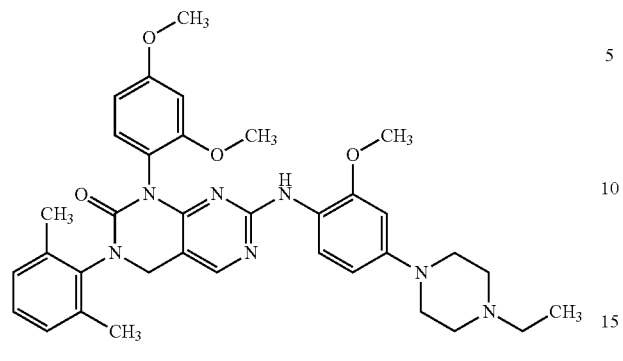
(YKL-05-77)
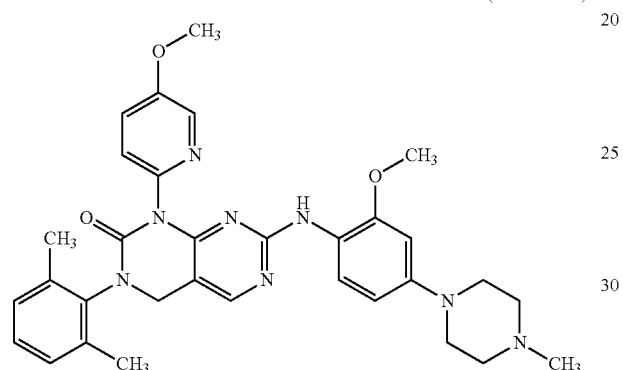
(YKL-05-88)
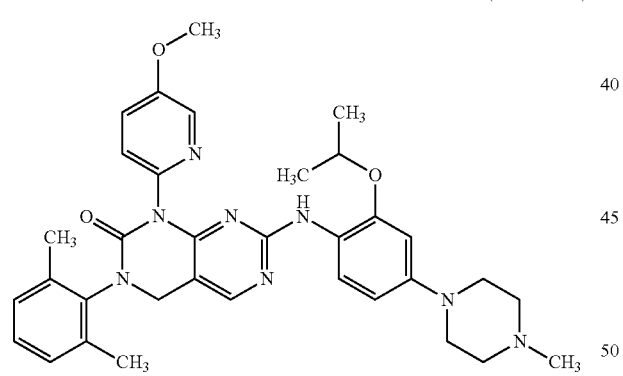
(YKL-05-89)
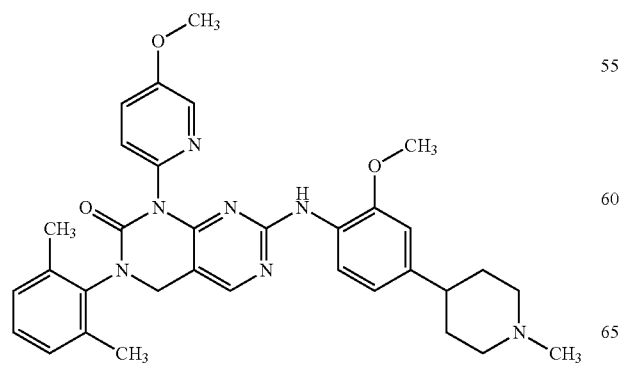
-continued
(YKL-05-90)
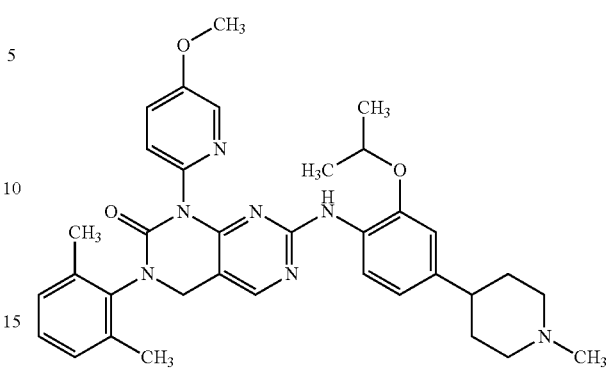
(YKL-05-91)
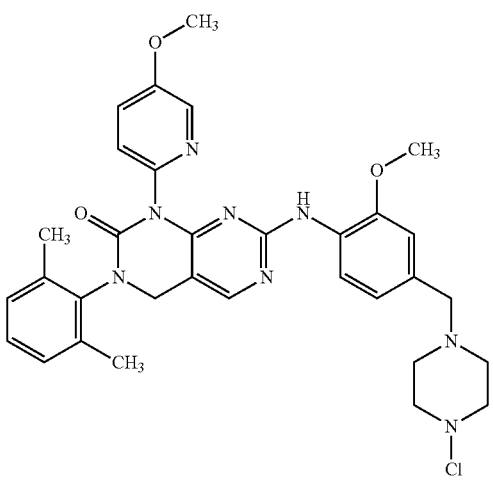
(YKL-05-92)
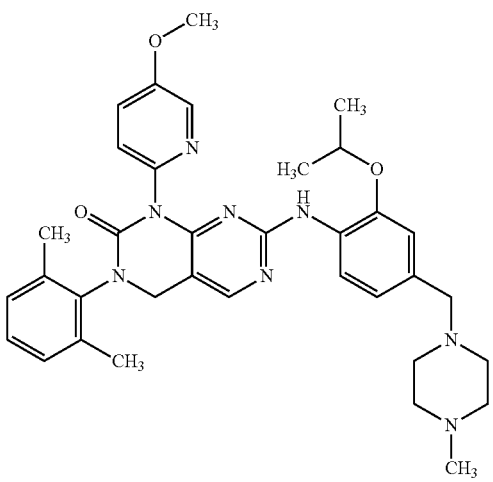

(YKL-05-93)
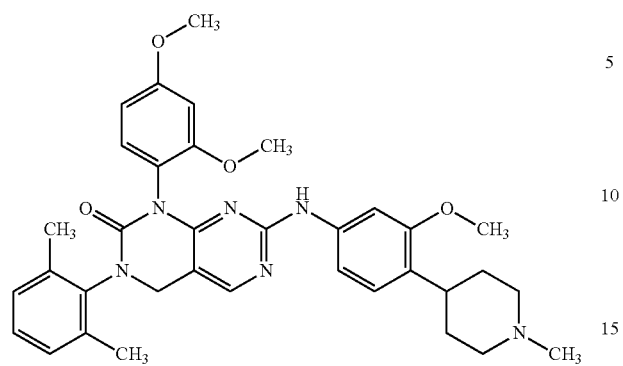
(YKL-05-94)
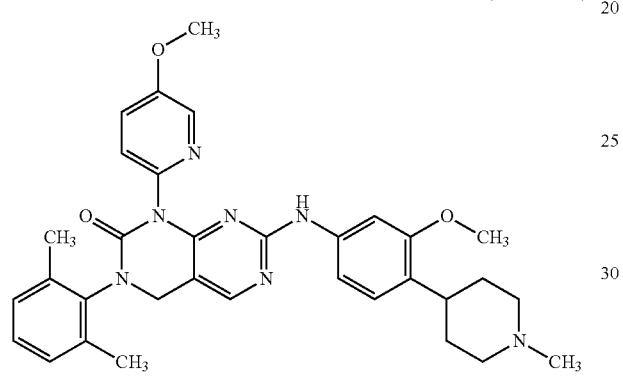
(YKL-05-95)
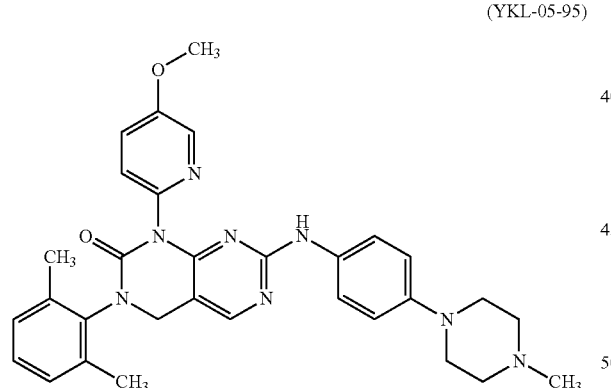
(YKL-05-96)
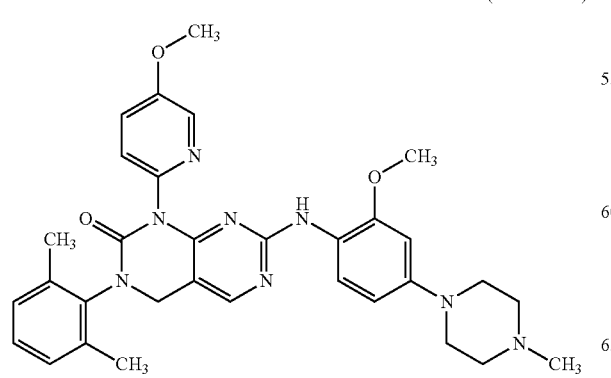
(YKL-05-97)
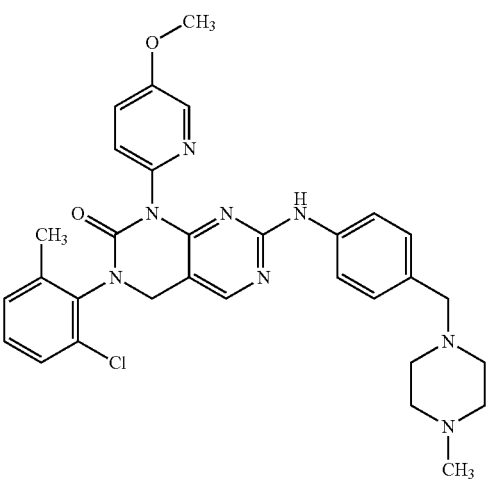
(YKL-05-98)
(YKL-05-99)
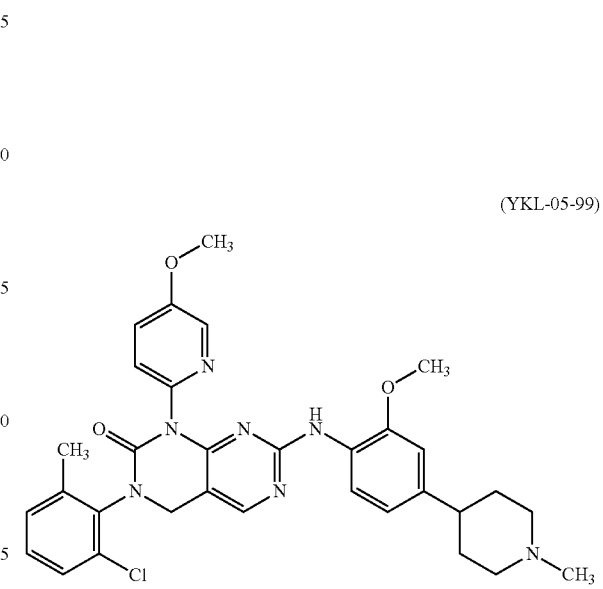

(YKL-05-100)
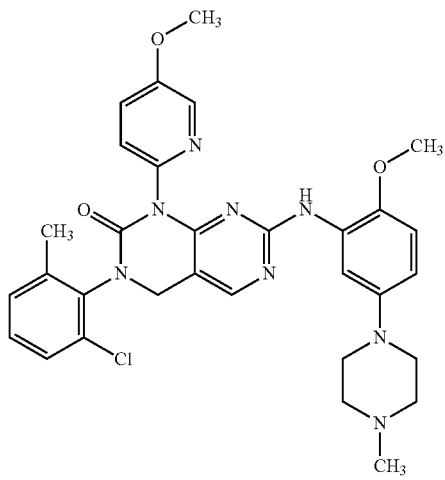
(YKL-05-151)
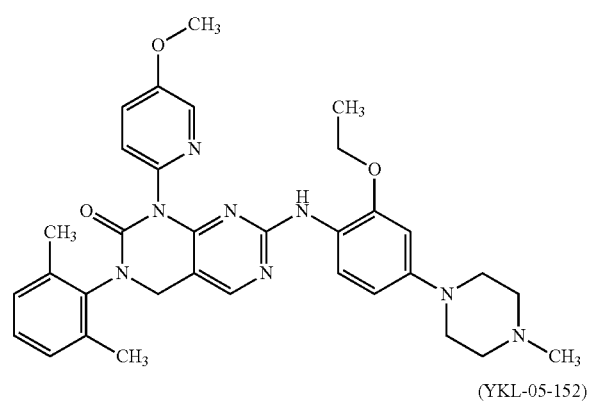
(YKL-05-152)
(YKL-05-153)
(YKL-05-154)
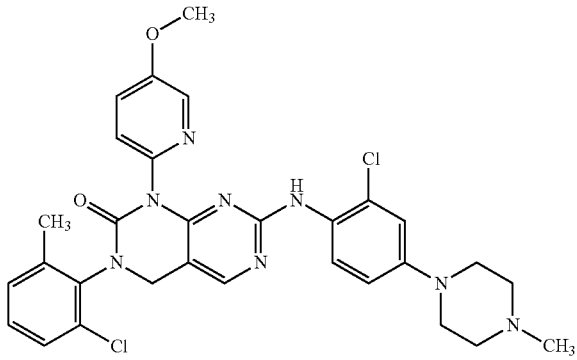
(YKL-05-155)
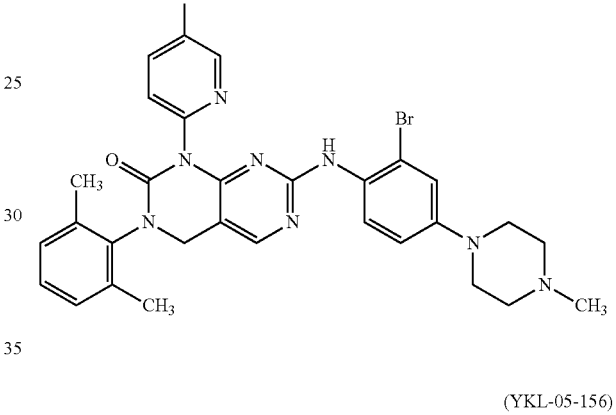
(YKL-05-156)
(YKL-05-163)
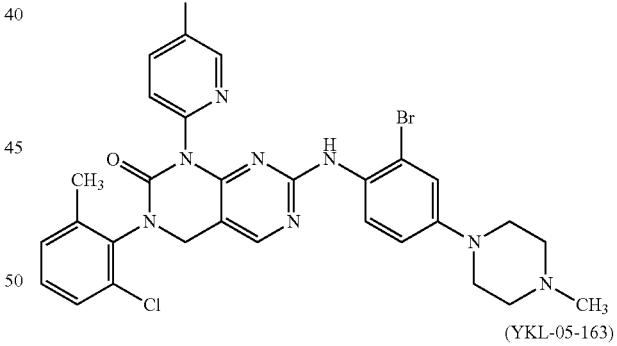
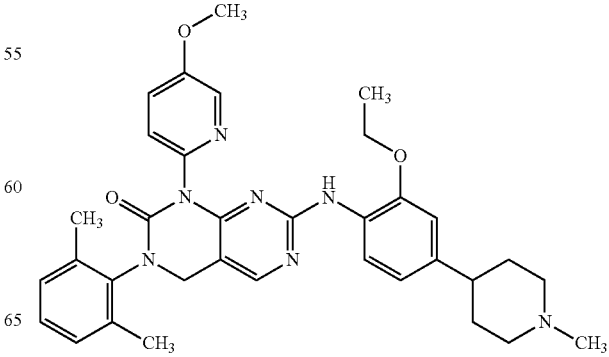

(YKL-05-164)
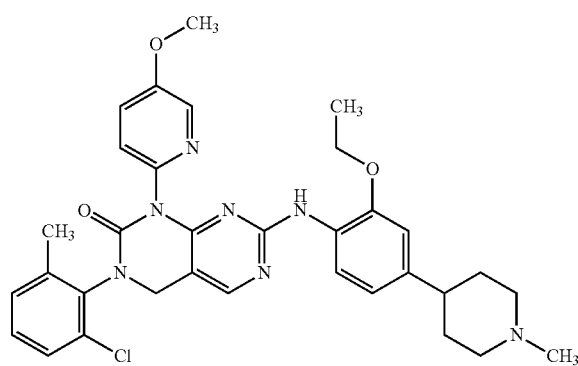
(YKL-05-179)
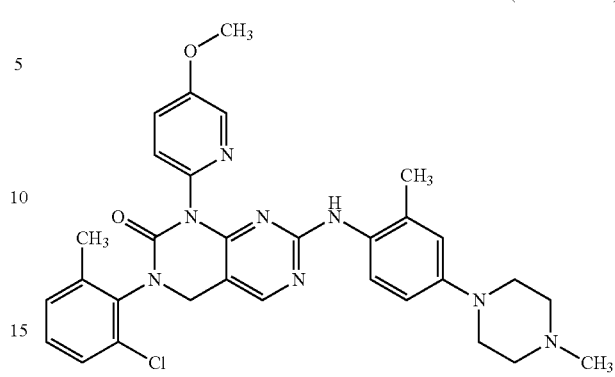
(YKL-05-165)
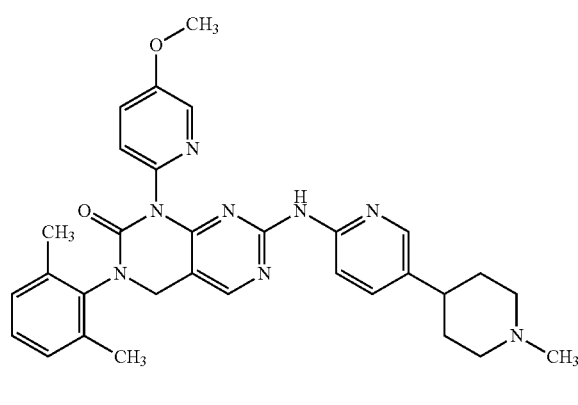
(YKL-05-180)
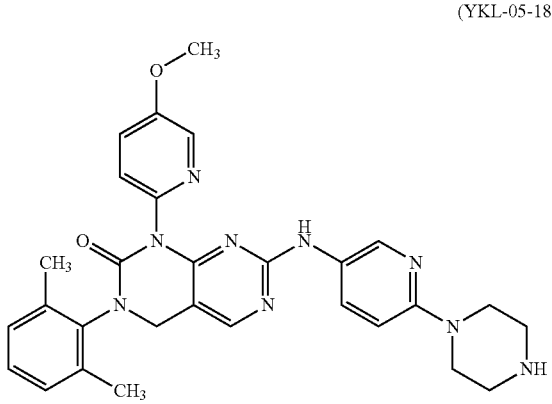
(YKL-05-166)
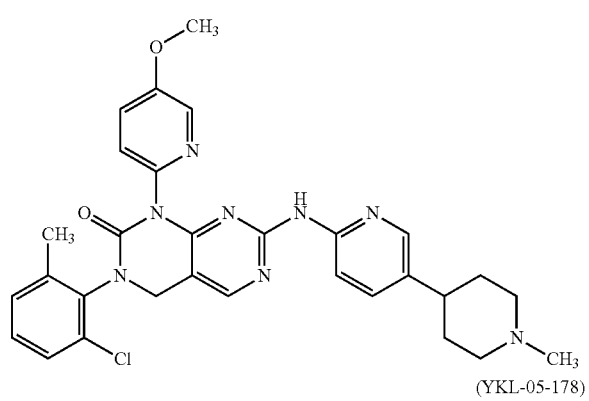
(YKL-05-181)
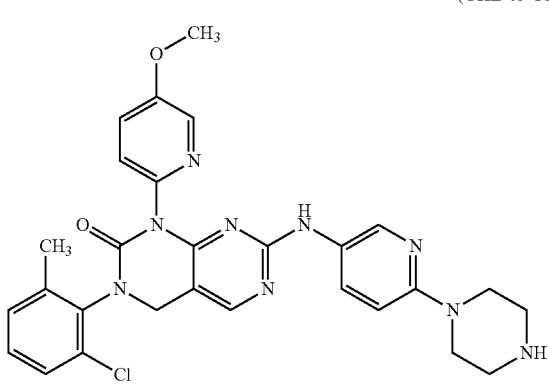
(YKL-05-178)
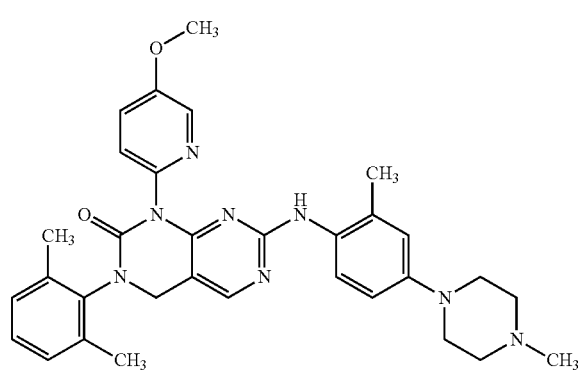
(YKL-05-182)
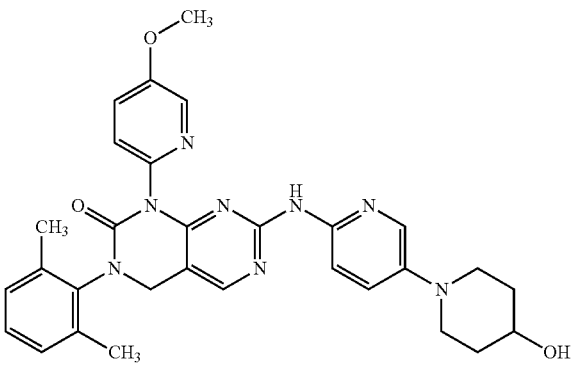

(YKL-05-183)
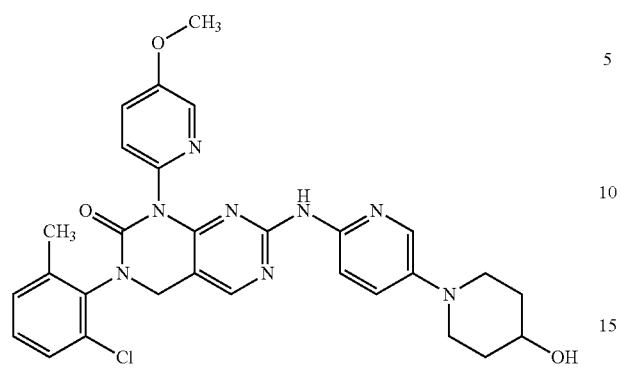
(SB1-D-09; YKL-04-136-6)
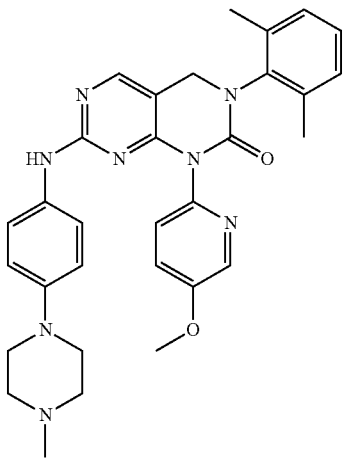
(Example 2)
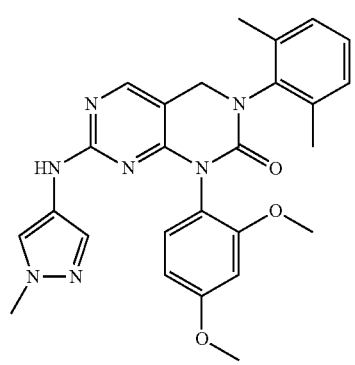
(SB1-D-10)
(YKL-04-136-1; SB1-D-01)
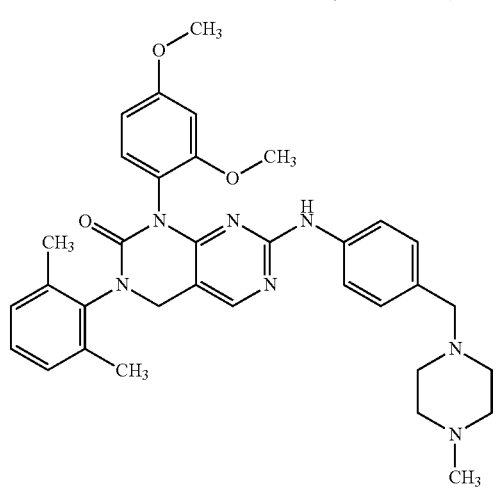
(YKL-04-136-10)
(SB1-D-11)
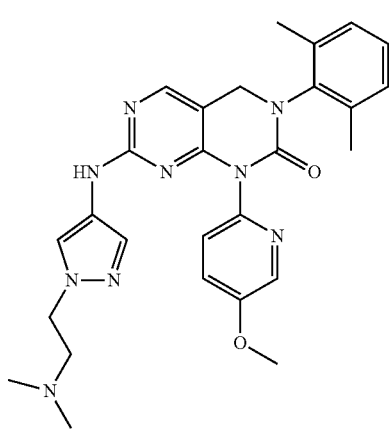
(YKL-04-136-8)

-continued
(YKL-06-038)
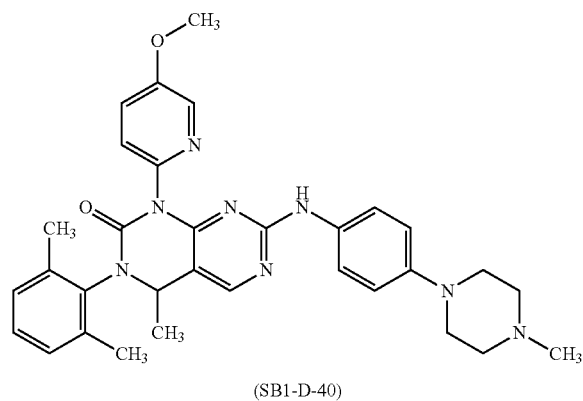
(SB1-D-40)
(YKL-06-039)
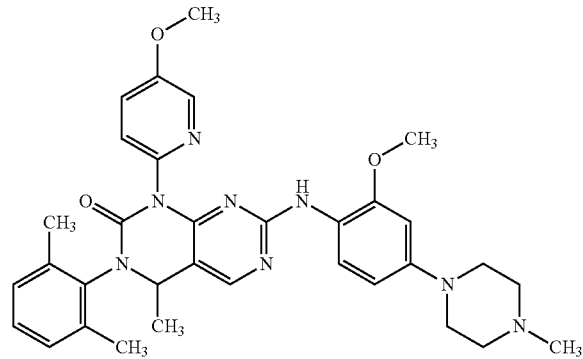
(SB1-D-42)
(YKL-06-040)
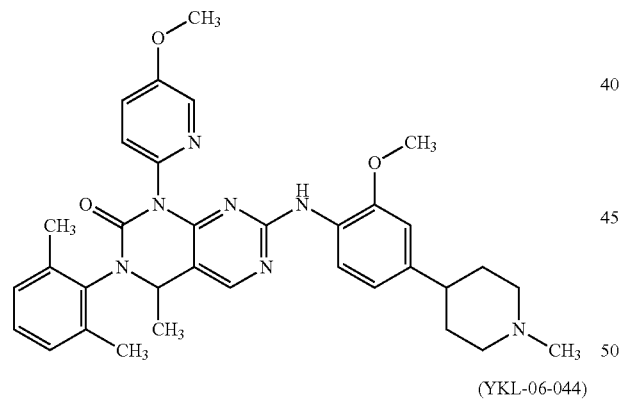
(YKL-06-044)
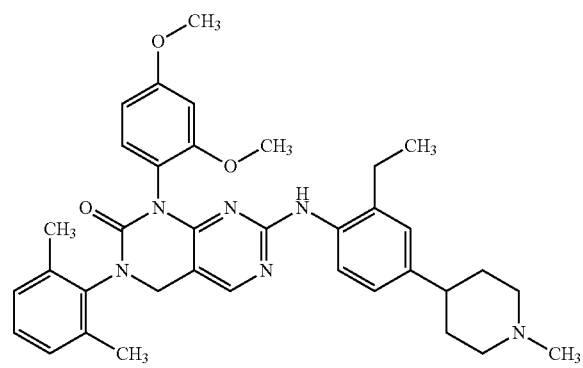
-continued
(YKL-06-045)
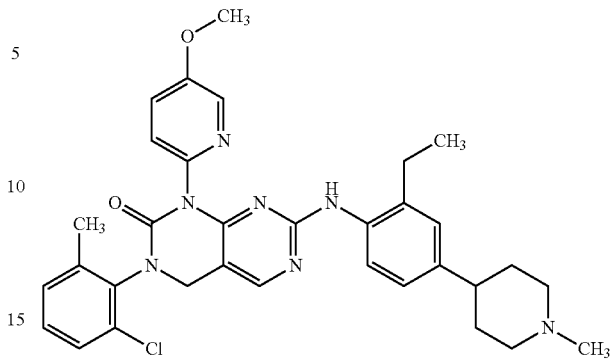
(YKL-06-051)
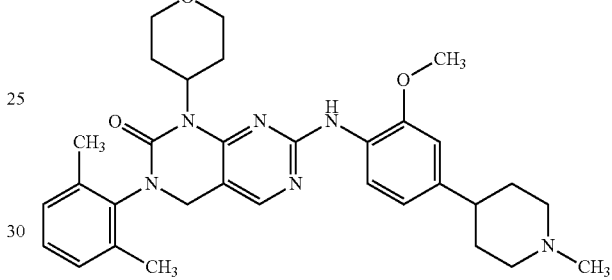
(YKL-06-054)
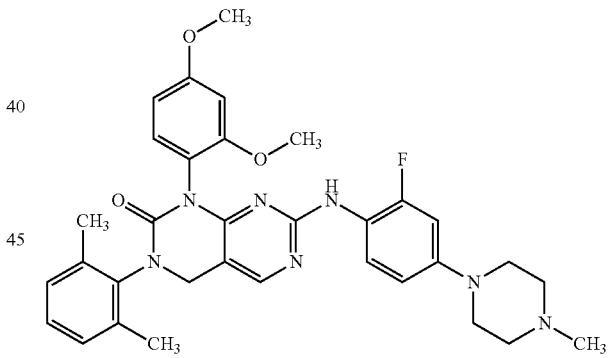
(YKL-06-055)
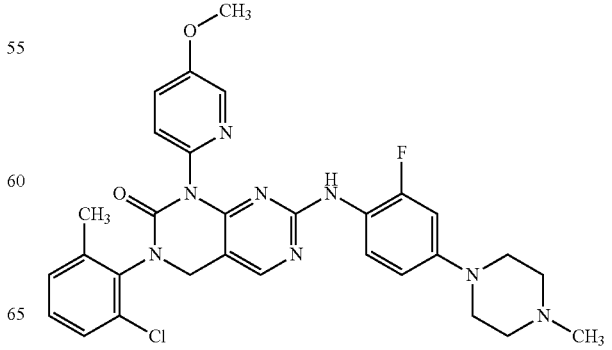

(YKL-06-056)

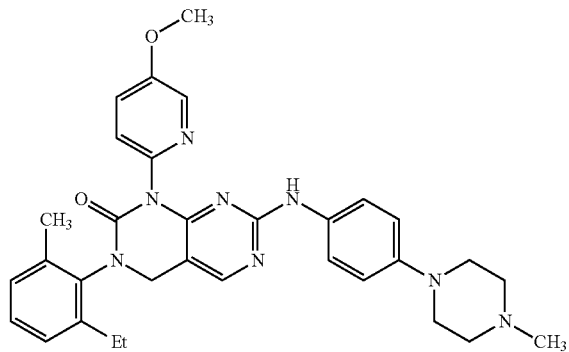

(YKL-06-080-1)

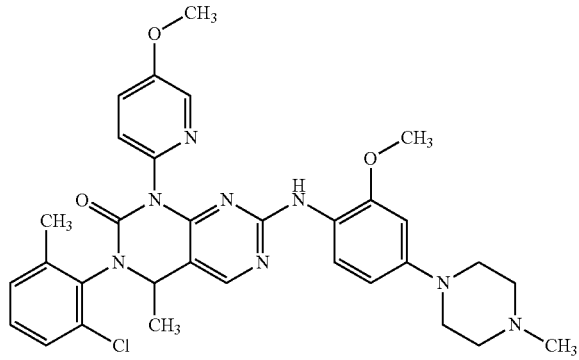

(YKL-06-057)

(SB1-D-60)

(YKL-06-081-1)

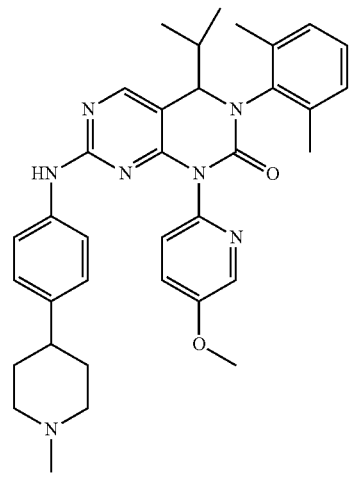

(SB1-D-43)

(SB1-D-61)

(YKL-06-077)

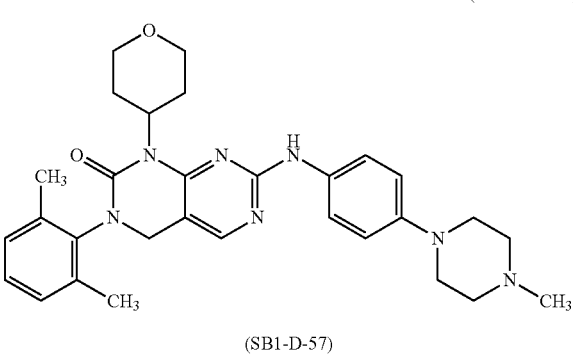

(YKL-06-082)

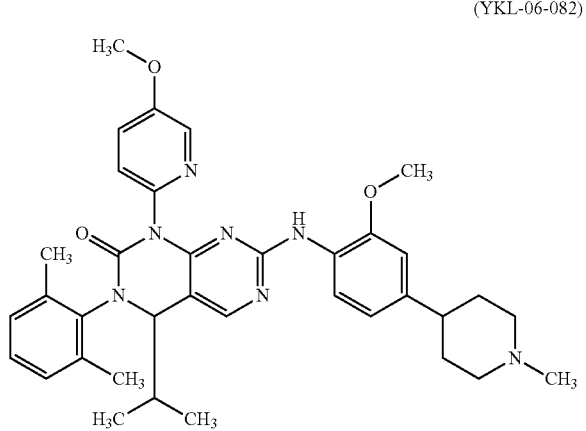

(SB1-D-57)

(SB1-D-62)

(YKL-06-078)

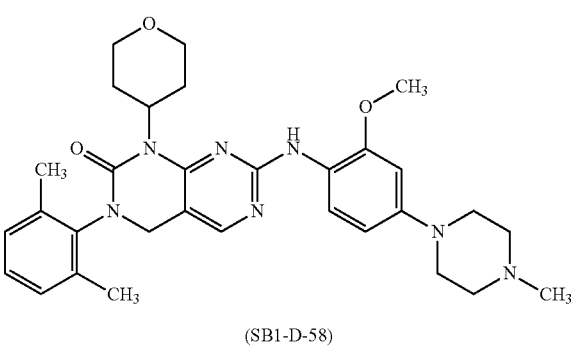

(SB1-D-58)

and pharmaceutically acceptable salts, solvates, hydrates, polymorphs, co-crystals, tautomers, stereoisomers, isotopically labeled derivatives, and prodrugs thereof.

In certain embodiments, the compound of Formula (II) useful in the present invention
or pharmaceutically acceptable salt, solvate, hydrate, polymorph, co-crystal, tautomer, stereoisomer, isotopically labeled derivative, or prodrug thereof.

In certain embodiments, the compound of Formula (II) useful in the present invention is not of the formula:

(YKL-05-95)

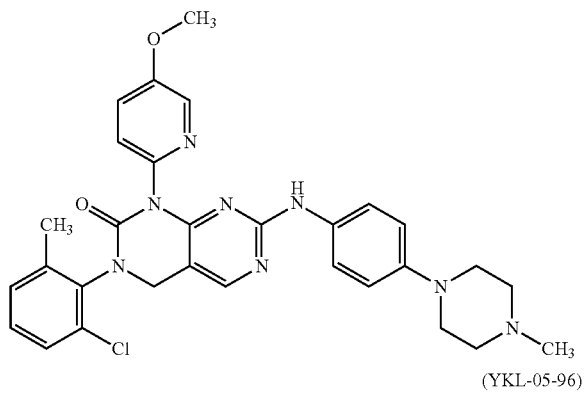

(YKL-05-96)

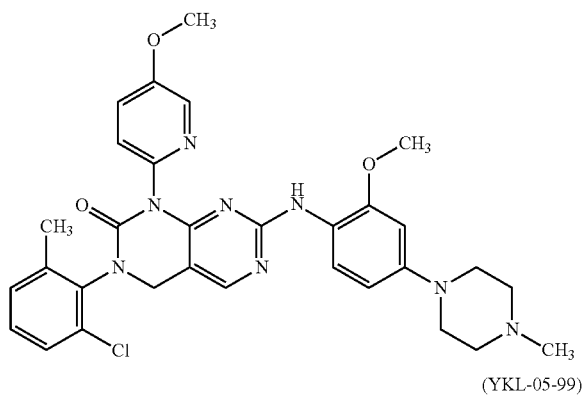

(YKL-05-99)

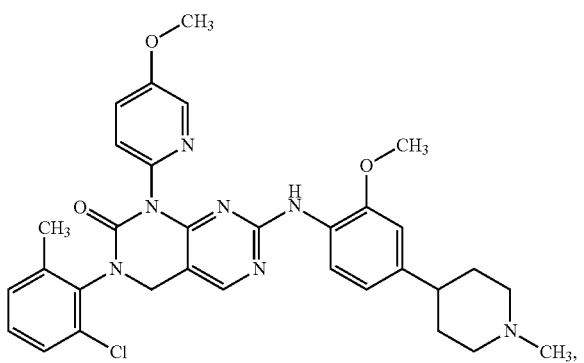

or a pharmaceutically acceptable salt, solvate, hydrate, polymorph, co-crystal, tautomer, stereoisomer, isotopically labeled derivative, or prodrug thereof.

In certain embodiments, the compound of Formula (II) useful in the present invention is not of the formula:

(HG-11-139-02)

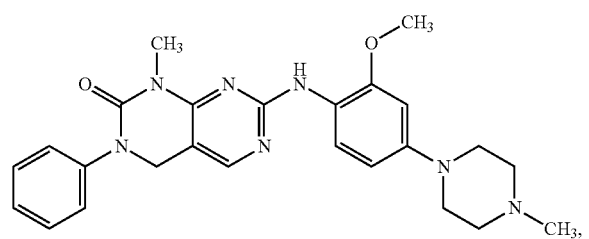

(HG-11-143-01)

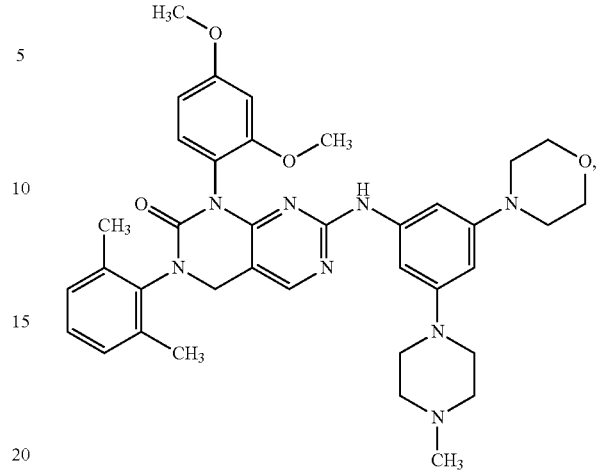

or a pharmaceutically acceptable salt, solvate, hydrate, polymorph, co-crystal, tautomer, stereoisomer, isotopically labeled derivative, or prodrug thereof.

Compounds of Formula (III)

In another aspect, the compound utilized in the present disclosure is of Formula (III):

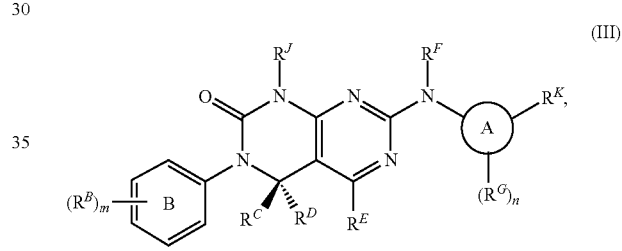

and pharmaceutically acceptable salts, solvates, hydrates, polymorphs, co-crystals, tautomers, stereoisomers, isotopically labeled derivatives, and prodrugs thereof, wherein:

$R^J$ is substituted or unsubstituted carbocyclyl;

each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —C(=$NR^b$)$R^a$, —C(=$NR^b$)$OR^a$, —C(=$NR^b$)N($R^b$)$_2$, —C(=O)$R^a$, —C(=O)$OR^a$, —C(=O)N($R^b$)$_2$, —$NO_2$, —$NR^b$C(=O)$R^a$, —$NR^b$C(=O)$OR^a$, —$NR^b$C(=O)N($R^b$)$_2$, —OC(=O)$R^a$, —OC(=O)$OR^a$, or —OC(=O)N($R^b$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom;

each instance of $R^b$ is independently hydrogen, substituted or unsubstituted $C_{1-6}$ alkyl, or a nitrogen protecting group, or optionally two instances of $R^b$ are taken together with their intervening atoms to form a substituted or unsubstituted heterocyclic or substituted or unsubstituted heteroaryl ring;

m is 0, 1, 2, 3, 4, or 5;

$R^C$ is hydrogen, halogen, or substituted or unsubstituted $C_{1-6}$ alkyl;

$R^D$ is hydrogen, halogen, or substituted or unsubstituted $C_{1-6}$ alkyl;

$R^E$ is hydrogen, halogen, or substituted or unsubstituted $C_{1-6}$ alkyl;

$R^F$ is hydrogen, substituted or unsubstituted $C_{1-6}$ alkyl, or a nitrogen protecting group;

Ring A is substituted or unsubstituted phenyl; substituted or unsubstituted, polycyclic aryl; substituted or unsubstituted, 5- or 6-membered, monocyclic heteroaryl; or substituted or unsubstituted, polycyclic heteroaryl;

each instance of $R^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —C(=$NR^b$)$R^a$, —C(=$NR^b$)$OR^a$, —C(=$NR^b$)N($R^b$)$_2$, —C(=O)$R^a$, —C(=O)$OR^a$, —C(=O)N($R^b$)$_2$, —$NO_2$, —$NR^b$C(=O)$R^a$, —$NR^b$C(=O)$OR^a$, —$NR^b$C(=O)N($R^b$)$_2$, —OC(=O)$R^a$, —OC(=O)$OR^a$, or —OC(=O)N($R^b$)$_2$;

n is 0, 1, 2, 3, or 4, as valency permits;

$R^K$ is unsubstituted methyl, substituted or unsubstituted heterocyclyl, —$OR^a$, or —$N(R^c)_2$, wherein each instance of $R^c$ is independently hydrogen, substituted or unsubstituted $C_{1-6}$ alkyl, or a nitrogen protecting group, or optionally two instances of $R^c$ are taken together with their intervening atoms to form a substituted or unsubstituted heterocyclic or substituted or unsubstituted heteroaryl ring.

Formula (III) includes substituent $R^J$. In certain embodiments, $R^J$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^J$ is substituted or unsubstituted, $C_{3-6}$ carbocyclyl. In certain embodiments, $R^J$ is substituted or unsubstituted cyclopropyl. In certain embodiments, $R^J$ is substituted or unsubstituted cyclobutyl. In certain embodiments, $R^J$ is cyclobutyl. In certain embodiments, $R^J$ is substituted or unsubstituted cyclopentyl. In certain embodiments, $R^J$ is cyclopentyl. In certain embodiments, $R^J$ is substituted or unsubstituted cyclohexyl. In certain embodiments, $R^J$ is cyclohexyl.

As generally defined herein, as applicable to Formula (II) and (III), Ring B is an unsubstituted phenyl ring (e.g., when m is 0) or a phenyl ring substituted with one or more substituents $R^B$ (e.g., when m is 1, 2, 3, 4, or 5). In certain embodiments, at least two instances of $R^B$ are different. In certain embodiments, all instances of $R^B$ are the same. In certain embodiments, m is 0. In certain embodiments, m is 1. In certain embodiments, m is 2. In certain embodiments, m is 3. In certain embodiments, m is 4. In certain embodiments, m is 5. In certain embodiments, Ring B is of the formula:

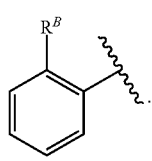

In certain embodiments, Ring B is of the formula:

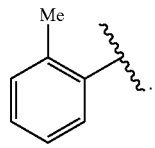

In certain embodiments, Ring B is of the formula:

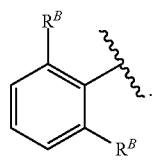

In certain embodiments, Ring B is of the formula:

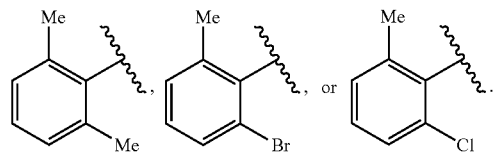

In certain embodiments, Ring B is not of the formula:

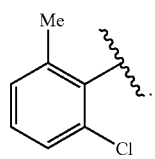

In certain embodiments, Ring B is of the formula:

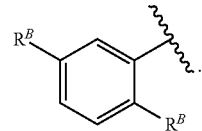

In certain embodiments, Ring B is of the formula:

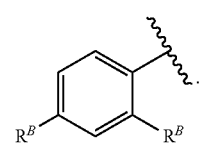

In certain embodiments, Ring B is of the formula:

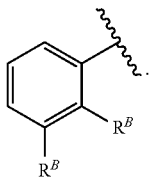

In certain embodiments, at least one instance of $R^B$ is halogen (e.g., F, Cl, Br, or I). In certain embodiments, at least one instance of $R^B$ is F. In certain embodiments, at least one instance of $R^B$ is Cl. In certain embodiments, at least one instance of $R^B$ is Br. In certain embodiments, at least one instance of $R^B$ is I. In certain embodiments, at least one $R^B$ is substituted or unsubstituted alkyl (e.g., substituted or unsubstituted $C_{1-6}$ alkyl). In certain embodiments, at least one instance of $R^B$ is substituted or unsubstituted methyl. In certain embodiments, at least one instance of $R^B$ is methyl. In certain embodiments, m is 2, and both instances of $R^B$ are methyl. In certain embodiments, m is 2, and one instance of $R^B$ is halogen, and the other instance of $R^B$ is methyl. In certain embodiments, m is 2, and one instance of $R^B$ is Cl, and the other instance of $R^B$ is methyl. In certain embodiments, at least one instance of $R^B$ is substituted or unsubstituted ethyl. In certain embodiments, at least one instance of $R^B$ is substituted or unsubstituted propyl. In certain embodiments, at least one instance of $R^B$ is substituted or unsubstituted alkenyl (e.g., substituted or unsubstituted $C_{2-6}$ alkenyl). In certain embodiments, at least one instance of $R^B$ is substituted or unsubstituted alkynyl (e.g., substituted or unsubstituted $C_{2-6}$ alkynyl). In certain embodiments, at least one instance of $R^B$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^B$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^B$ is substituted or unsubstituted aryl (e.g., substituted or unsubstituted, 6- to 10-membered aryl). In certain embodiments, at least one instance of $R^B$ is benzyl. In certain embodiments, at least one instance of $R^B$ is substituted or unsubstituted phenyl. In certain embodiments, at least one instance of $R^B$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^B$ is —$OR^a$ (e.g., —OH or —OMe). In certain embodiments, at least one instance of $R^B$ is —$N(R^b)_2$, —$SR^a$, —CN, —SCN, —$C(=NR^b)R^a$, —$C(=NR^b)OR^a$, —$C(=NR^b)N(R^b)_2$, —$C(=O)R^a$, —$C(=O)OR^a$, —$C(=O)N(R^b)_2$, —$NO_2$, —$NR^bC(=O)R^a$, —$NR^bC(=O)OR^a$, —$NR^bC(=O)N(R^b)_2$, —$OC(=O)R^a$, —$OC(=O)OR^a$, or —$OC(=O)N(R^b)_2$.

Formula (III) includes substituents $R^C$, $R^D$, $R^E$, and $R^F$. Substituents $R^C$, $R^D$, $R^E$, and $R^F$ are described in the Detailed Description for Formula (IV) below.

Formula (III) includes Ring A and one or more instances of substituent $R^G$. Ring A and substituent $R^G$ are described in the Detailed Description for Formula (IV) below.

As generally defined herein, Formula (III) includes substituent $R^K$ attached to Ring A. Substituent $R^K$ is described in the Detailed Description for Formula (IV) below.

In certain embodiments, Ring A with substituent $R^K$ is of the formula:

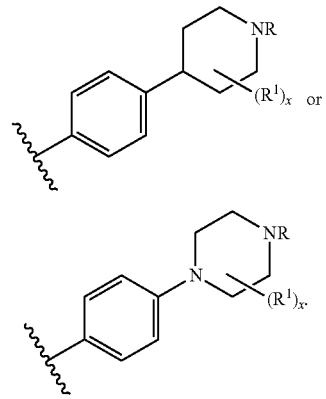

In certain embodiments, Ring A with substituent $R^K$ is of the formula:

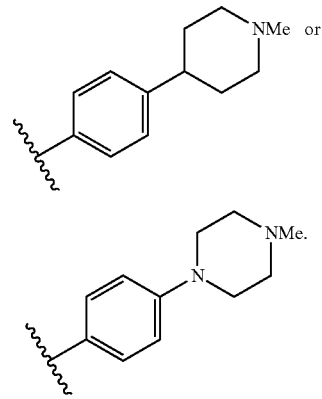

In certain embodiments, the compound of Formula (III) useful in the present invention is of the formula:

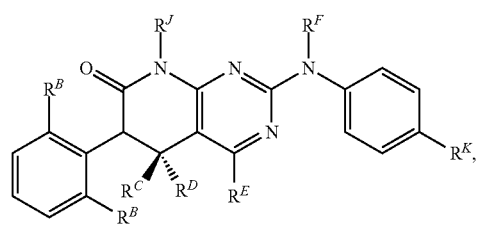

-continued

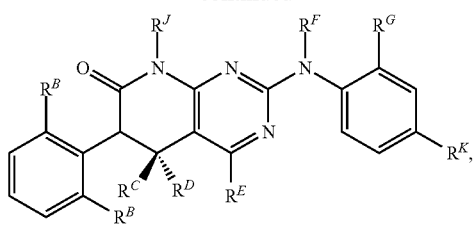

or a pharmaceutically acceptable salt, solvate, hydrate, polymorph, co-crystal, tautomer, stereoisomer, isotopically labeled derivative, or prodrug thereof.

In certain embodiments, the compound of Formula (III) useful in the present invention is of the formula:

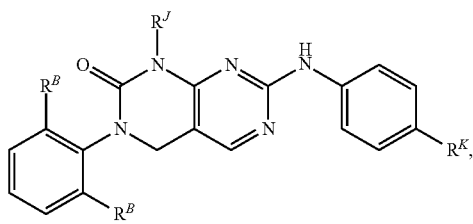

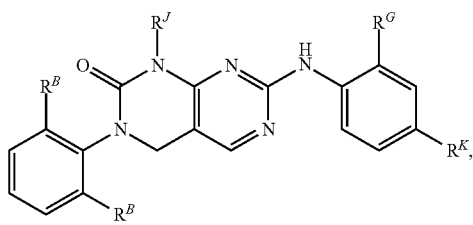

or a pharmaceutically acceptable salt, solvate, hydrate, polymorph, co-crystal, tautomer, stereoisomer, isotopically labeled derivative, or prodrug thereof.

In certain embodiments, the compound of Formula (III) useful in the present invention is of the formula:

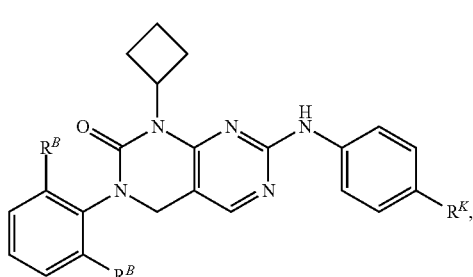

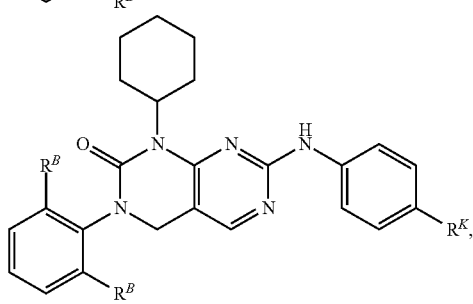

-continued

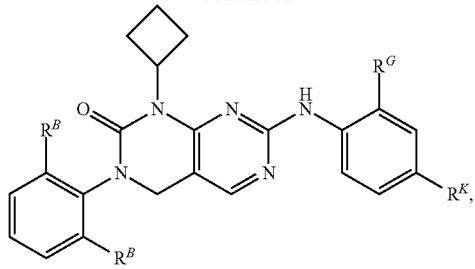

or a pharmaceutically acceptable salt, solvate, hydrate, polymorph, co-crystal, tautomer, stereoisomer, isotopically labeled derivative, or prodrug thereof.

In certain embodiments, the compound of Formula (III) useful in the present invention is of the formula:

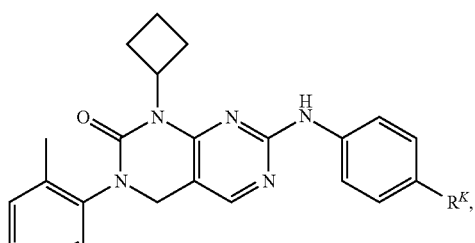

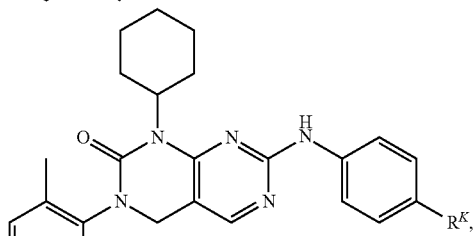

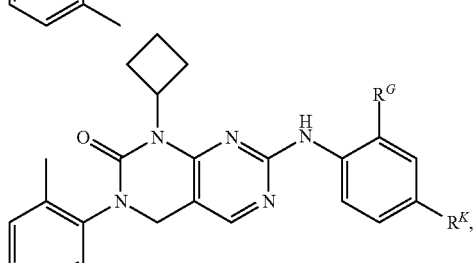

or a pharmaceutically acceptable salt, solvate, hydrate, polymorph, co-crystal, tautomer, stereoisomer, isotopically labeled derivative, or prodrug thereof.

In certain embodiments, the compound of Formula (III) useful in the present invention is of the formula:

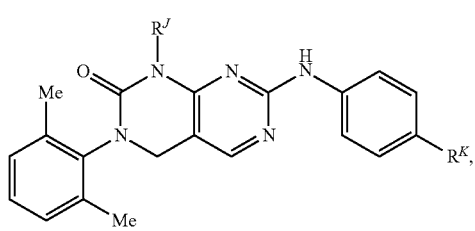

-continued

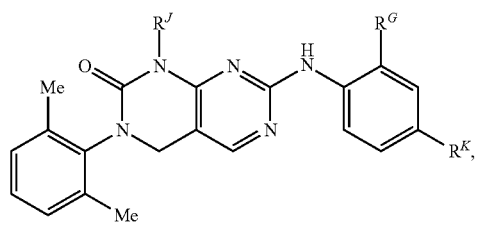

or a pharmaceutically acceptable salt, solvate, hydrate, polymorph, co-crystal, tautomer, stereoisomer, isotopically labeled derivative, or prodrug thereof.

In certain embodiments, the compound of Formula (III) useful in the present invention is of the formula:

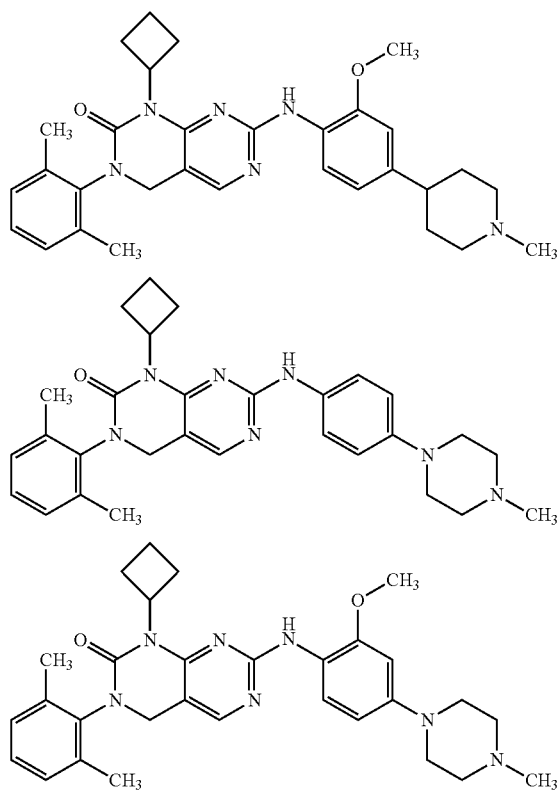

or a pharmaceutically acceptable salt, solvate, hydrate, polymorph, co-crystal, tautomer, stereoisomer, isotopically labeled derivative, or prodrug thereof.

In certain embodiments, the compound of Formula (III) useful in the present invention is of the formula:

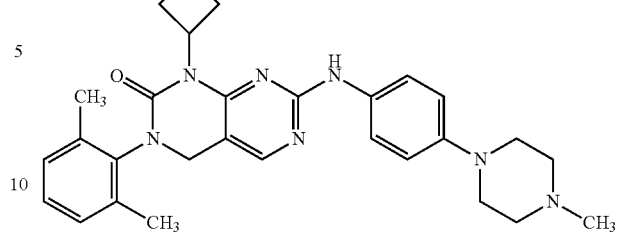

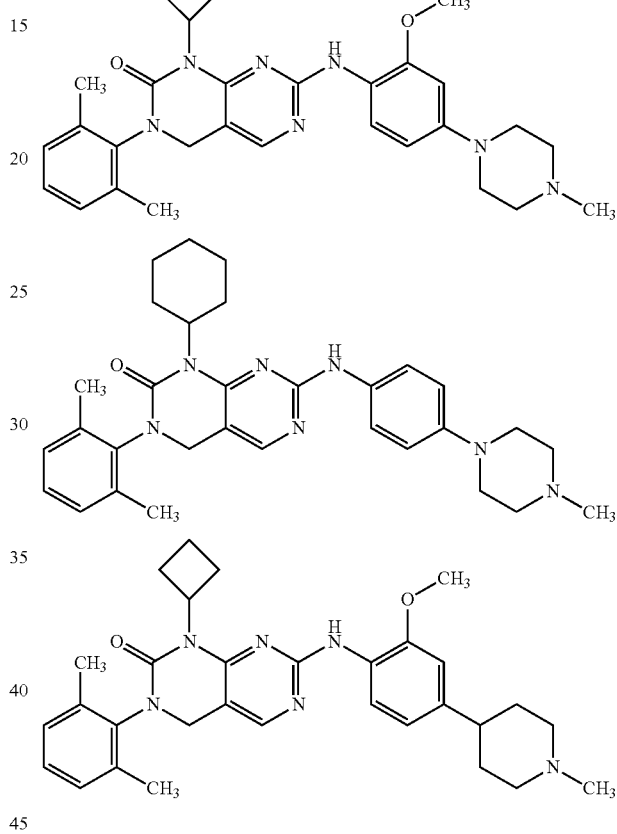

or a pharmaceutically acceptable salt, solvate, hydrate, polymorph, co-crystal, tautomer, stereoisomer, isotopically labeled derivative, or prodrug thereof.

In certain embodiments, the compound of Formula (III) useful in the present invention is of the formula:

(YKL-06-063)

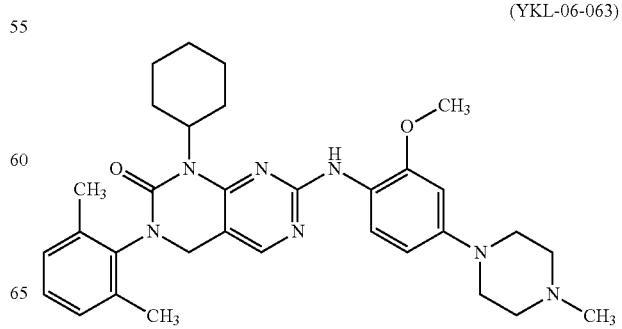

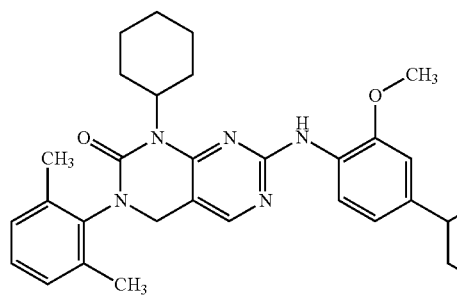
(YKL-06-064)

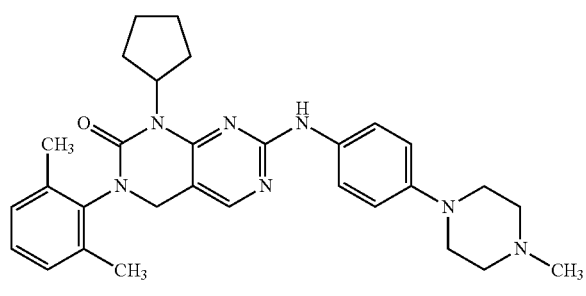
(YKL-06-075)

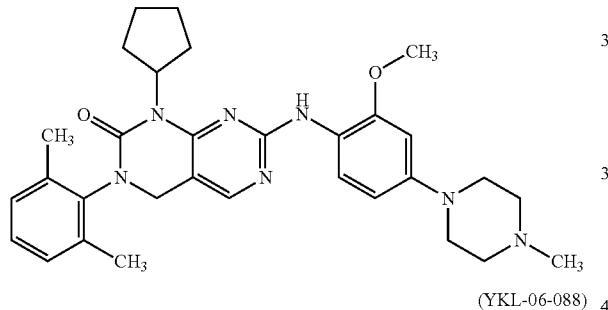
(YKL-06-076)

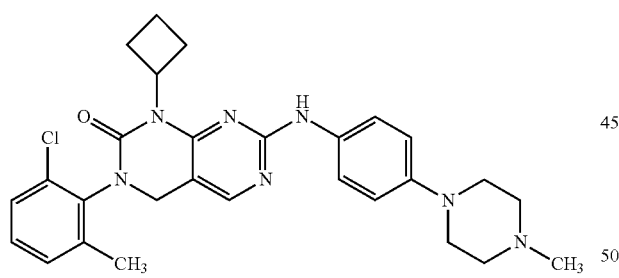
(YKL-06-088)

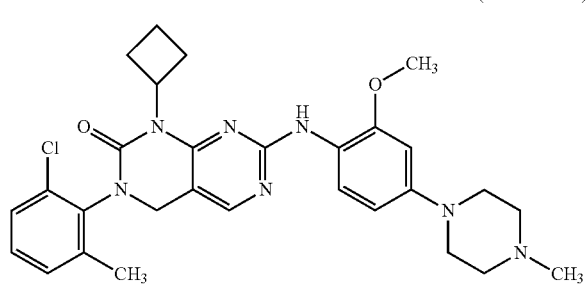
(YKL-06-089)

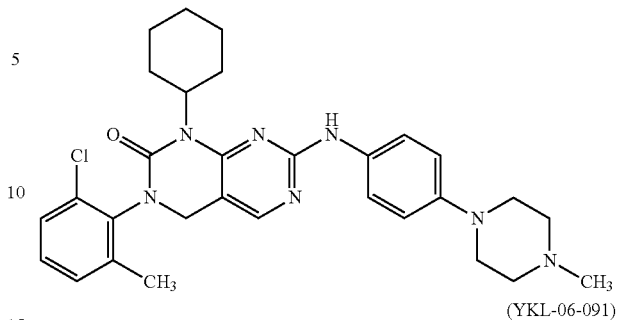
(YKL-06-090)

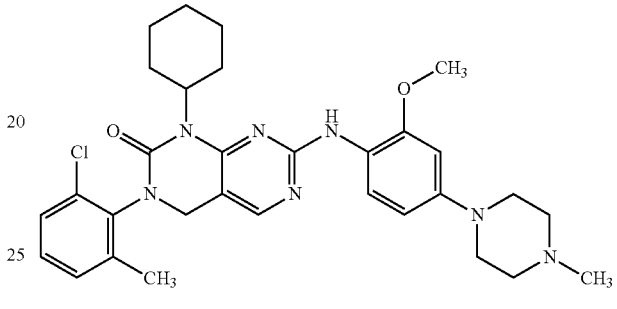
(YKL-06-091)

or a pharmaceutically acceptable salt, solvate, hydrate, polymorph, co-crystal, tautomer, stereoisomer, isotopically labeled derivative, or prodrug thereof.

Compounds of Formula (IV)

In another aspect, the compound utilized in the present disclosure is of Formula (IV):

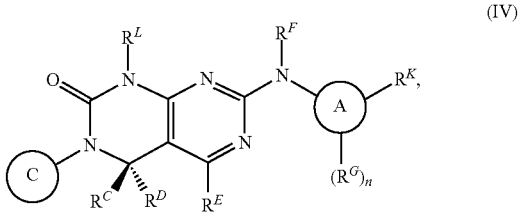

(IV)

and pharmaceutically acceptable salts, solvates, hydrates, polymorphs, co-crystals, tautomers, stereoisomers, isotopically labeled derivatives, and prodrugs thereof, wherein:

$R^L$ is substituted or unsubstituted alkyl;

Ring C is unsubstituted phenyl or of the formula:

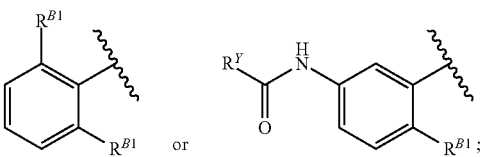

each instance of $R^{B1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^d$)$_2$, —SR$^a$, —CN, —SCN, —C(=NR$^d$)R$^a$, —C(=NR$^d$)OR$^a$, —C(=NR$^d$)N (R$^d$)$_2$, —C(=O)R$^a$, —C(=O)OR$^a$, —C(=O)N(R$^d$)$_2$, —NO$_2$, —NR$^d$C(=O)R$^a$, —NR$^d$C(=O)OR$^a$, —NR$^d$C(=O)N(R$^a$)$_2$, —OC(=O)R$^a$, —OC(=O)OR$^a$, or —OC(=O)N(R$^d$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom;

each instance of R$^d$ is independently hydrogen, —C(=O)R$^a$, substituted or unsubstituted C$_{1-6}$ alkyl, or a nitrogen protecting group, or optionally two instances of R$^d$ are taken together with their intervening atoms to form a substituted or unsubstituted heterocyclic or substituted or unsubstituted heteroaryl ring;

R$^C$ is hydrogen, halogen, or substituted or unsubstituted C$_{1-6}$ alkyl;

R$^D$ is hydrogen, halogen, or substituted or unsubstituted C$_{1-6}$ alkyl;

R$^E$ is hydrogen, halogen, or substituted or unsubstituted C$_{1-6}$ alkyl;

R$^F$ is hydrogen, substituted or unsubstituted C$_{1-6}$ alkyl, or a nitrogen protecting group;

Ring A is substituted or unsubstituted phenyl; substituted or unsubstituted, polycyclic aryl; substituted or unsubstituted, 5- or 6-membered, monocyclic heteroaryl; or substituted or unsubstituted, polycyclic heteroaryl;

each instance of R$^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, —SR$^a$, —CN, —SCN, —C(=NR$^b$)R$^a$, —C(=NR$^b$)OR$^a$, —C(=NR$^a$)N(R$^a$)$_2$, —C(=O)R$^a$, —C(=O)OR$^a$, —C(=O)N(R$^a$)$_2$, —NO$_2$, —NRbC(=O)R$^a$, —NR$^b$C(=O)OR$^a$, —NR$^b$C(=O)N(R$^a$)$_2$, —OC(=O)R$^a$, —OC(=O)OR$^a$, or —OC(=O)N(R$^b$)$_2$;

n is 0, 1, 2, 3, or 4, as valency permits;

R$^K$ is unsubstituted methyl, substituted or unsubstituted heterocyclyl, —OR$^a$, or —N(R$^a$)$_2$, wherein each instance of R$^c$ is independently hydrogen, substituted or unsubstituted C$_{1-6}$ alkyl, or a nitrogen protecting group, or optionally two instances of R$^c$ are taken together with their intervening atoms to form a substituted or unsubstituted heterocyclic or substituted or unsubstituted heteroaryl ring;

R$^Y$ is substituted phenyl.

Formula (IV) includes Ring C. In certain embodiments, Ring C is unsubstituted phenyl. In certain embodiments, Ring C is of the formula:

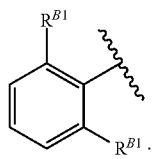

In certain embodiments, at least one instance of R$^{B1}$ is halogen. In certain embodiments, at least one instance of R$^{B1}$ is halogen. In certain embodiments, at least one instance of R$^{B1}$ is F. In certain embodiments, at least one instance of R$^{B1}$ is Cl. In certain embodiments, at least one instance of R$^{B1}$ is Br. In certain embodiments, at least one instance of R$^{B1}$ is I (iodine). In certain embodiments, at least one instance of R$^{B1}$ is substituted or unsubstituted C$_{1-6}$ alkyl (e.g., methyl, ethyl, or propyl). In certain embodiments, at least one instance of R$^{B1}$ is substituted or unsubstituted methyl. In certain embodiments, at least one instance of R$^{B1}$ is methyl. In certain embodiments, at least one instance of R$^{B1}$ is —N(R$^d$)$_2$, wherein each instance of R$^d$ is hydrogen or —C(=O)R$^a$. In certain embodiments, at least one instance of R$^{B1}$ is —NH(C(=O)R$^a$). In certain embodiments, at least one instance of R$^{B1}$ is —OR$^a$ (e.g., —OH or —OMe). In certain embodiments, at least one instance of R$^{B1}$ is —SR$^a$, —CN, —SCN, —C(=NR$^d$)R$^a$, —C(=NR$^d$)OR$^a$, —C(=NR$^d$)N(Rd)$_2$, —C(=O)R$^a$, —C(=O)OR$^a$, —C(=O)N(R$^a$)$_2$, —NO$_2$, —NR$^d$C(=O)R$^a$, —NR$^d$C(=O)OR$^a$, —NR$^d$C(=O)N(R$^a$)$_2$, —OC(=O)R$^a$, —OC(=O)OR$^a$, or —OC(=O)N(R$^d$)$_2$. In certain embodiments, Ring C is of the formula:

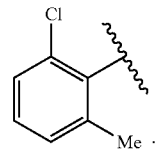

In certain embodiments, Ring C is of the formula:

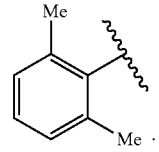

In certain embodiments, Ring C is of the formula:

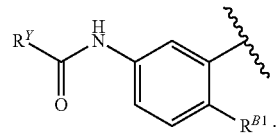

In certain embodiments, R$^Y$ is substituted phenyl. In certain embodiments, R$^Y$ is substituted phenyl. In certain embodiments, R$^Y$ is of the formula:

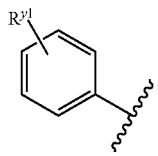

wherein R$^{y1}$ is halogen or substituted or unsubstituted C$_{1-6}$ alkyl. In certain embodiments, R$^{y1}$ is halogen (e.g., Br, Cl, F). In certain embodiments, R$^{y1}$ is substituted or unsubstituted C$_{1-6}$ alkyl (e.g., substituted or unsubstituted, methyl, ethyl, or propyl). In certain embodiments, R$^{y1}$ is substituted or unsubstituted methyl. In certain embodiments, R$^{y1}$ is substituted methyl. In certain embodiments, $R^{y1}$ is methyl. In certain embodiments, $R^{y1}$ is —$CF_3$. In certain embodiments, Ring C is of the formula:

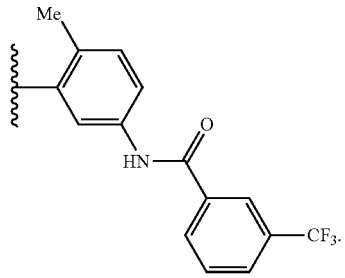 [SMILES: *c1cc(NC(=O)c2cccc(C(F)(F)F)c2)ccc1C]

In certain embodiments, Ring C is of the formula:

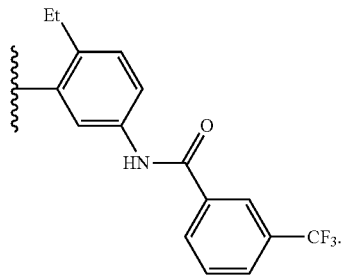 [SMILES: *c1cc(NC(=O)c2cccc(C(F)(F)F)c2)ccc1CC]

Formula (IV) includes substituent $R^L$. In certain embodiments, $R^L$ is substituted or unsubstituted alkyl (e.g., substituted or unsubstituted $C_{1-6}$ alkyl). In certain embodiments, $R^L$ is substituted or unsubstituted methyl. In certain embodiments, $R^L$ is methyl. In certain embodiments, $R^L$ is unsubstituted methyl. In certain embodiments, $R^L$ is substituted methyl. In certain embodiments, $R^L$ is substituted or unsubstituted ethyl. In certain embodiments, $R^L$ is ethyl. In certain embodiments, $R^L$ is unsubstituted ethyl. In certain embodiments, $R^L$ is substituted ethyl. In certain embodiments, $R^L$ is substituted or unsubstituted propyl. In certain embodiments, $R^L$ is propyl. In certain embodiments, $R^L$ is isopropyl. In certain embodiments, $R^L$ is substituted or unsubstituted butyl.

As generally defined herein, Formulae (III) and (IV) include substituent $R^K$ attached to Ring A. In certain embodiments, $R^K$ is unsubstituted methyl. In certain embodiments, $R^K$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^K$ is substituted or unsubstituted tetrahydropyranyl. In certain embodiments, $R^K$ is substituted or unsubstituted piperidinyl. In certain embodiments, $R^K$ is substituted or unsubstituted morpholinyl. In certain embodiments, $R^K$ is substituted or unsubstituted piperazinyl. In certain embodiments, $R^K$ is of the formula:

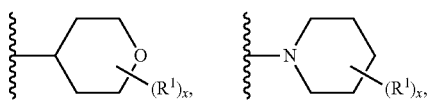

-continued

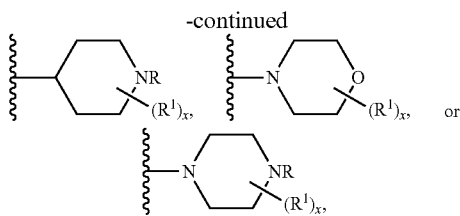

wherein $R^1$ is substituted or unsubstituted $C_{1-6}$ alkyl or —$OR^{x1}$, wherein R is hydrogen, substituted or unsubstituted $C_{1-6}$ alkyl, or nitrogen protecting group; $R^{x1}$ is hydrogen or substituted or unsubstituted $C_{1-6}$ alkyl; and x is 0, 1, 2, or 3. In certain embodiments, $R^K$ is of the formula:

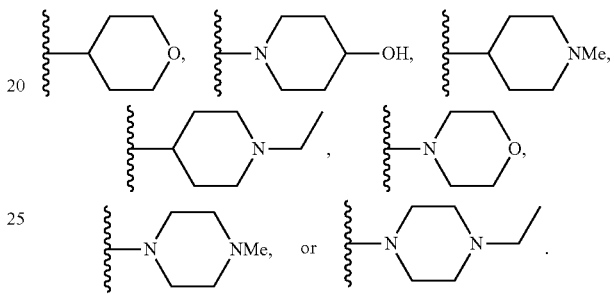

In certain embodiments, $R^K$ is —$OR^a$ (e.g., —OH or —OMe). In certain embodiments, $R^K$ is —$N(R^b)_2$. In certain embodiments, two instances of $R^c$ are taken together with their intervening atoms to form a substituted or unsubstituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, two instances of $R^c$ are taken together with their intervening atoms to form a substituted or unsubstituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^K$ is —$NMe_2$. In certain embodiments, $R^K$ is —$SR^a$, —CN, —SCN, —C(=$NR^b$)$R^a$, —C(=$NR^b$)$OR^a$, —C(=$NR^b$)$N(R^b)_2$, —C(=O)$R^a$, —C(=O)$OR^a$, —C(=O)$N(R^b)_2$, —$NO_2$, —$NR^bC$(=O) $R^a$, —$NR^bC$(=O)$OR^a$, —$NR^bC$(=O)$N(R^b)_2$, —OC(=O) $R^a$, —OC(=O)$OR^a$, or —OC(=O)$N(R^b)_2$.

As generally defined herein, Formulae (II), (III), and (IV) include substituent $R^C$. In certain embodiments, $R^C$ is hydrogen. In certain embodiments, $R^C$ is halogen (e.g., F, Cl, Br, or I). In certain embodiments, $R^C$ is substituted or unsubstituted $C_{1-6}$ alkyl (e.g., methyl, ethyl, or propyl). In certain embodiments, $R^C$ is substituted or unsubstituted methyl. In certain embodiments, $R^C$ is methyl. In certain embodiments, $R^C$ is substituted or unsubstituted ethyl. In certain embodiments, $R^C$ is ethyl. In certain embodiments, $R^C$ is substituted or unsubstituted propyl. In certain embodiments, $R^C$ is unsubstituted isopropyl.

As generally defined herein, Formulae (II), (III), and (IV) include substituent $R^D$. In certain embodiments, $R^D$ is hydrogen. In certain embodiments, $R^D$ is halogen (e.g., F, Cl, Br, or I). In certain embodiments, $R^D$ is substituted or unsubstituted $C_{1-6}$ alkyl (e.g., methyl, ethyl, or propyl). In certain embodiments, $R^D$ is substituted or unsubstituted methyl. In certain embodiments, $R^D$ is methyl. In certain embodiments, $R^D$ is substituted or unsubstituted ethyl. In certain embodiments, $R^D$ is ethyl. In certain embodiments, $R^D$ is substituted or unsubstituted propyl. In certain embodiments, $R^D$ is isopropyl.

As generally defined herein, Formulae (II), (III), and (IV) include substituent $R^E$. In certain embodiments, $R^E$ is hydrogen. In certain embodiments, $R^E$ is halogen (e.g., F, Cl, Br, or I). In certain embodiments, $R^E$ is substituted or unsubstituted $C_{1-6}$ alkyl (e.g., methyl, ethyl, or propyl). In certain embodiments, $R^E$ is substituted or unsubstituted methyl. In certain embodiments, $R^E$ is methyl. In certain embodiments, $R^E$ is substituted or unsubstituted ethyl. In certain embodiments, $R^E$ is ethyl. In certain embodiments, $R^E$ is substituted or unsubstituted propyl. In certain embodiments, $R^E$ is isopropyl.

As generally defined herein, Formulae (II), (III), and (IV) include substituent $R^F$. In certain embodiments, $R^F$ is hydrogen. In certain embodiments, $R^E$ is substituted or unsubstituted $C_{1-6}$ alkyl (e.g., methyl, ethyl, or propyl). In certain embodiments, $R^F$ is substituted or unsubstituted methyl. In certain embodiments, $R^F$ is methyl. In certain embodiments, $R^F$ is substituted or unsubstituted ethyl. In certain embodiments, $R^F$ is ethyl. In certain embodiments, $R^F$ is substituted or unsubstituted propyl. In certain embodiments, $R^F$ is isopropyl. In certain embodiments, $R^F$ is a nitrogen protecting group (e.g., a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, $R^C$, $R^D$, $R^E$, and $R^F$ are each hydrogen. In certain embodiments, at least one substituent selected from the group consisting of $R^C$, $R^D$, $R^E$, and $R^F$ is substituted or unsubstituted $C_{1-6}$ alkyl. In certain embodiments, $R^C$ is substituted or unsubstituted $C_{1-6}$ alkyl; and $R^D$, $R^E$, and $R^F$ are each hydrogen. In certain embodiments, $R^C$ is unsubstituted methyl; and $R^D$, $R^E$, and $R^F$ are each hydrogen. In certain embodiments, $R^C$ is unsubstituted isopropyl; and $R^D$, $R^E$, and $R^F$ are each hydrogen. In certain embodiments, $R^D$ is substituted or unsubstituted $C_{1-6}$ alkyl; and $R^C$, $R^E$, and $R^F$ are each hydrogen. In certain embodiments, $R^E$ is substituted or unsubstituted $C_{1-6}$ alkyl; and $R^C$, $R^D$, and $R^F$ are each hydrogen. In certain embodiments, $R^F$ is substituted or unsubstituted $C_{1-6}$ alkyl; and $R^C$, $R^D$, and $R^E$ are each hydrogen.

As generally defined herein, Formulae (II), (III), and (IV) include Ring A. In certain embodiments, Ring A is substituted or unsubstituted phenyl. In certain embodiments, Ring A is not substituted or unsubstituted phenyl. In certain embodiments, Ring A is not substituted phenyl. In certain embodiments, Ring A is not substituted phenyl. In certain embodiments, Ring A is unsubstituted phenyl. In certain embodiments, Ring A is phenyl, and includes one or more $R^G$ substituents. In certain embodiments, Ring A includes one $R^G$ substituent. In certain embodiments, Ring A includes two $R^G$ substituents. In certain embodiments, Ring A is substituted or unsubstituted polycyclic aryl (e.g., naphthalene or anthracene). In certain embodiments, Ring A is substituted or unsubstituted, 5- or 6-membered, monocyclic heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, Ring A is substituted or unsubstituted furan. In certain embodiments, Ring A is substituted or unsubstituted thiophene. In certain embodiments, Ring A is substituted or unsubstituted pyrrole. In certain embodiments, Ring A is substituted or unsubstituted pyrazole. In certain embodiments, Ring A is pyrazole. In certain embodiments, Ring A is substituted or unsubstituted pyridinyl. In certain embodiments, Ring A is pyridinyl. In certain embodiments, Ring A is substituted or unsubstituted polycyclic heteroaryl (e.g., substituted or unsubstituted, 9- to 10-membered, bicyclic heteroaryl, wherein one, two, three, or four atoms in the heteroaryl ring system are independently nitrogen, oxygen, or sulfur).

As generally defined herein, Formulae (II), (III), and (IV) include one or more instances of substituent $R^G$. In certain embodiments, n is 0. In certain embodiments, n is 1. In certain embodiments, n is 2. In certain embodiments, n is 3. In certain embodiments, n is 4. In certain embodiments, at least one instance of $R^G$ is halogen (e.g., F, Cl, Br, or I). In certain embodiments, at least one instance of $R^G$ is F. In certain embodiments, at least one instance of $R^G$ is Cl. In certain embodiments, at least one instance of $R^G$ is Br. In certain embodiments, at least one instance of $R^G$ is I. In certain embodiments, at least one $R^G$ is substituted or unsubstituted alkyl (e.g., substituted or unsubstituted $C_{1-6}$ alkyl). In certain embodiments, at least one instance of $R^G$ is substituted or unsubstituted $C_{1-3}$ alkyl. In certain embodiments, at least one instance of $R^G$ is substituted or unsubstituted methyl. In certain embodiments, at least one instance of $R^G$ is unsubstituted methyl. In certain embodiments, at least one instance of $R^G$ is substituted methyl. In certain embodiments, at least one instance of $R^G$ is —$CF_3$. In certain embodiments, at least one instance of $R^G$ is substituted or unsubstituted ethyl. In certain embodiments, at least one instance of $R^G$ is substituted ethyl. In certain embodiments, at least one instance of $R^G$ is unsubstituted ethyl. In certain embodiments, at least one instance of $R^G$ is substituted or unsubstituted propyl. In certain embodiments, at least one instance of $R^G$ is substituted or unsubstituted alkenyl (e.g., substituted or unsubstituted $C_{2-6}$ alkenyl). In certain embodiments, at least one instance of $R^G$ is substituted or unsubstituted alkynyl (e.g., substituted or unsubstituted $C_{2-6}$ alkynyl). In certain embodiments, at least one instance of $R^G$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^G$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^G$ is substituted or unsubstituted morpholinyl. In certain embodiments, at least one instance of $R^G$ is of the formula:

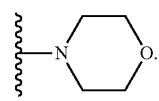

In certain embodiments, at least one instance of $R^G$ is substituted or unsubstituted piperazinyl. In certain embodiments, at least one instance of $R^G$ is of the formula:

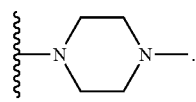

In certain embodiments, at least one instance of $R^G$ is of the formula:

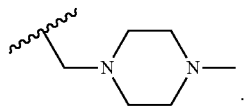 [SMILES: *CN1CCN(C)CC1]

In certain embodiments, at least one instance of $R^G$ is substituted or unsubstituted aryl (e.g., substituted or unsubstituted, 6- to 10-membered aryl). In certain embodiments, at least one instance of $R^G$ is benzyl. In certain embodiments, at least one instance of $R^G$ is substituted or unsubstituted phenyl. In certain embodiments, at least one instance of $R^B$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^G$ is —$OR^a$, wherein $R^a$ is hydrogen or substituted or unsubstituted $C_{1-6}$ alkyl (e.g., —OH or —OMe). In certain embodiments, at least one instance of $R^G$ is —OMe. In certain embodiments, at least one instance of $R^G$ is —OEt. In certain embodiments, at least one instance of $R^G$ is —O(Pr). In certain embodiments, at least one instance of $R^G$ is —O(iPr). In certain embodiments, at least one instance of $R^G$ is —$N(R^b)_2$, —$SR^a$, —CN, —SCN, —C(=$NR^b$)$R^a$, —C(=$NR^b$)$OR^a$, —C(=$NR^b$)$N(R^b)_2$, —C(=O)$R^a$, —C(=O)$OR^a$, —C(=O)$N(R^b)_2$, —$NO_2$, —$NR^bC$(=O)$R^a$, —$NR^bC$(=O)$OR^a$, —$NR^bC$(=O)$N(R^b)_2$, —OC(=O)$R^a$, —OC(=O)$OR^a$, or —OC(=O)$N(R^b)_2$.

In certain embodiments, Ring A with substituent $R^K$ is of the formula:

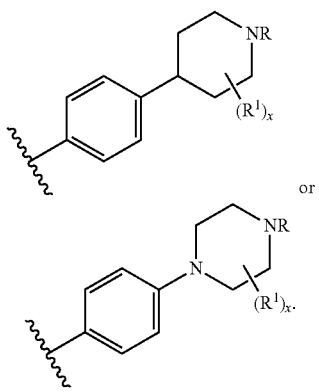

In certain embodiments, Ring A with substituent $R^K$ is of the formula:

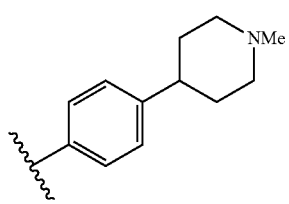

or

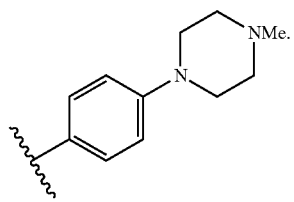

In certain embodiments, the compound of Formula (IV) useful in the present invention is of the formula:

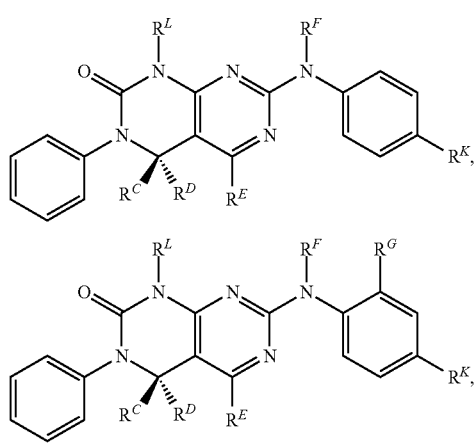

or a pharmaceutically acceptable salt, solvate, hydrate, polymorph, co-crystal, tautomer, stereoisomer, isotopically labeled derivative, or prodrug thereof.

In certain embodiments, the compound of Formula (IV) useful in the present invention is of the formula:

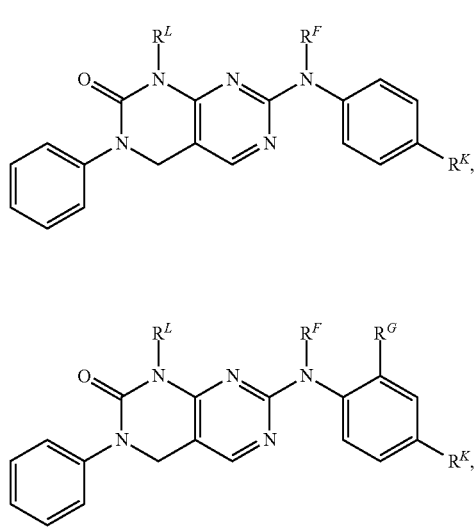

or a pharmaceutically acceptable salt, solvate, hydrate, polymorph, co-crystal, tautomer, stereoisomer, isotopically labeled derivative, or prodrug thereof.

In certain embodiments, the compound of Formula (IV) useful in the present invention is of the formula:

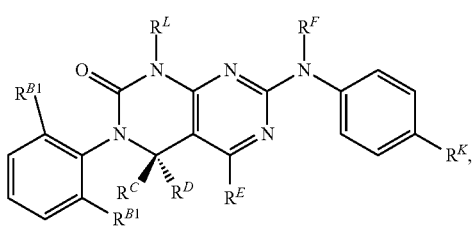

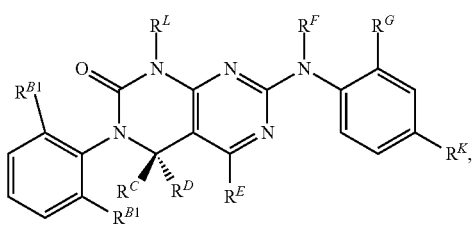

or a pharmaceutically acceptable salt, solvate, hydrate, polymorph, co-crystal, tautomer, stereoisomer, isotopically labeled derivative, or prodrug thereof.

In certain embodiments, the compound of Formula (IV) useful in the present invention is of the formula:

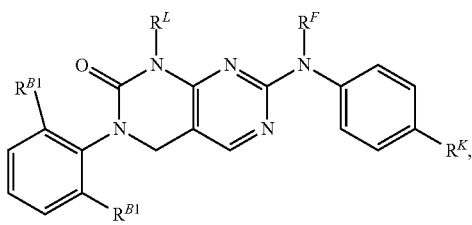

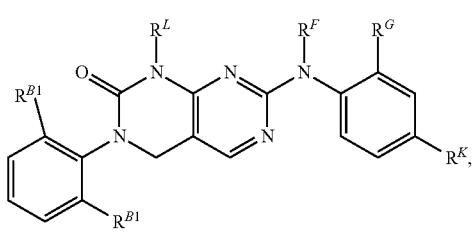

or a pharmaceutically acceptable salt, solvate, hydrate, polymorph, co-crystal, tautomer, stereoisomer, isotopically labeled derivative, or prodrug thereof.

In certain embodiments, the compound of Formula (IV) useful in the present invention is of the formula:

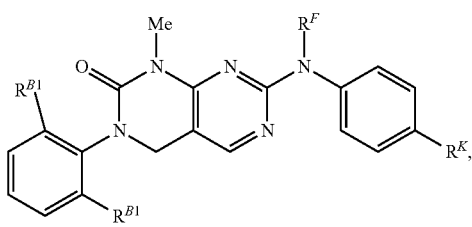

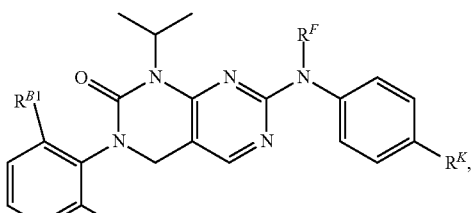

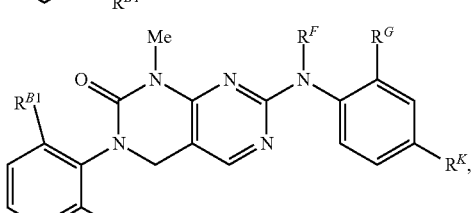

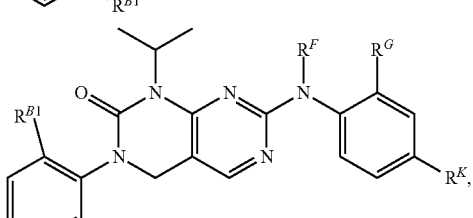

or a pharmaceutically acceptable salt, solvate, hydrate, polymorph, co-crystal, tautomer, stereoisomer, isotopically labeled derivative, or prodrug thereof.

In certain embodiments, the compound of Formula (IV) useful in the present invention is of the formula:

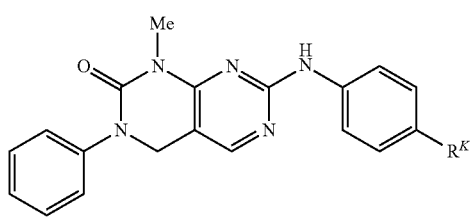

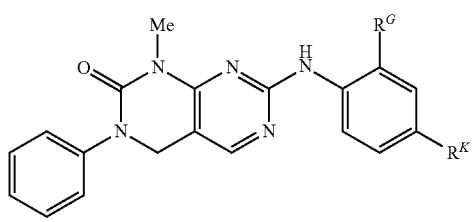

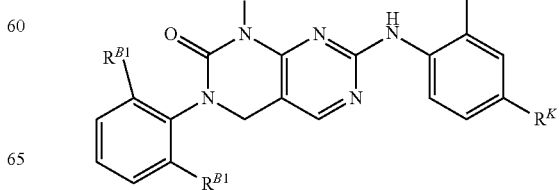

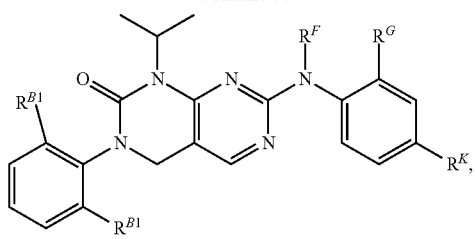

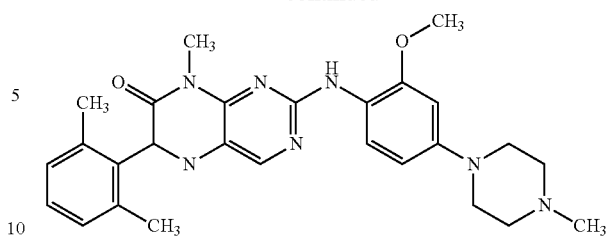

or a pharmaceutically acceptable salt, solvate, hydrate, polymorph, co-crystal, tautomer, stereoisomer, isotopically labeled derivative, or prodrug thereof.

In certain embodiments, the compound of Formula (IV) useful in the present invention is of the formula:

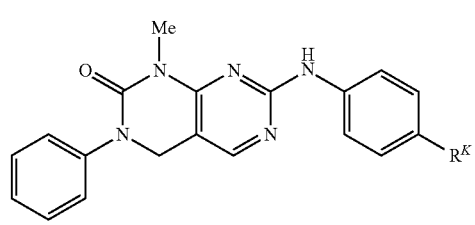

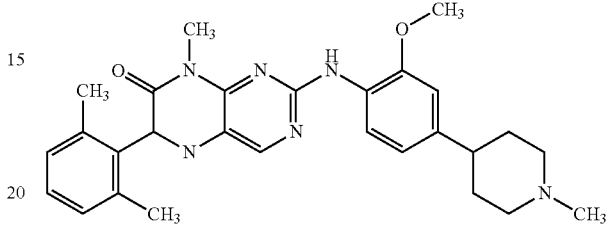

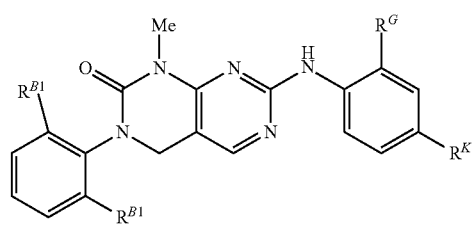

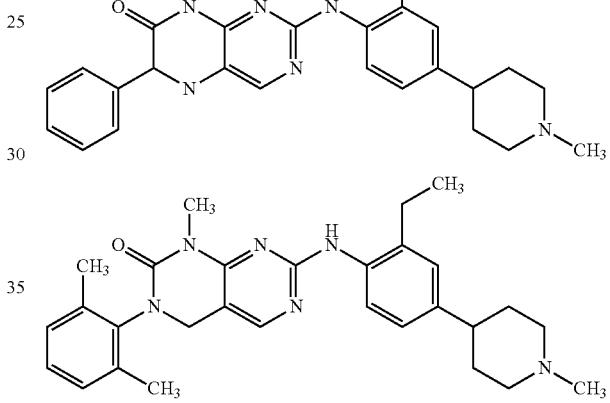

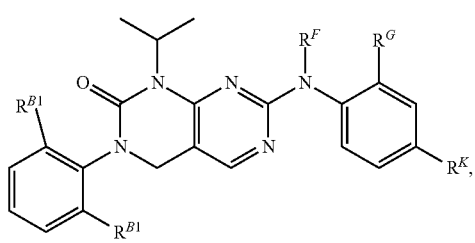

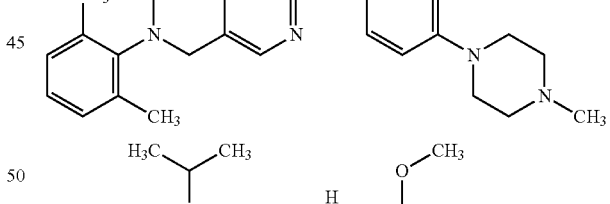

or a pharmaceutically acceptable salt, solvate, hydrate, polymorph, co-crystal, tautomer, stereoisomer, isotopically labeled derivative, or prodrug thereof.

In certain embodiments, the compound of Formula (IV) useful in the present invention is of the formula:

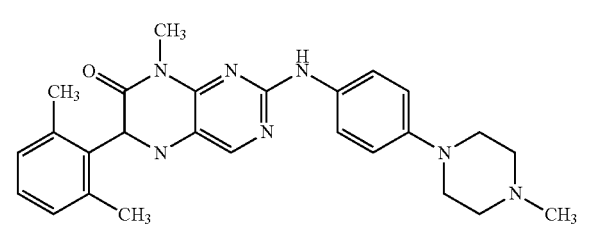

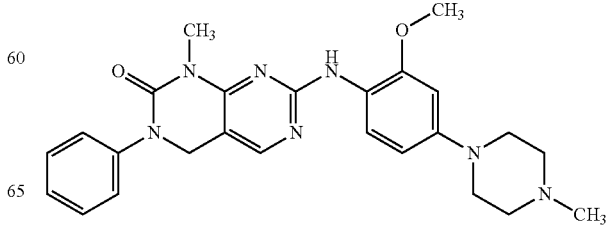

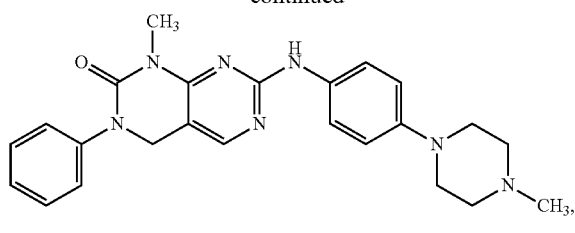

or a pharmaceutically acceptable salt, solvate, hydrate, polymorph, co-crystal, tautomer, stereoisomer, isotopically labeled derivative, or prodrug thereof.

In certain embodiments, the compound of Formula (IV) useful in the present invention is of the formula:

(HG-11-23-01)

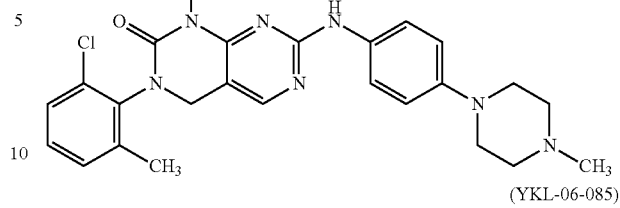

(YKL-06-084)

(YKL-06-085)

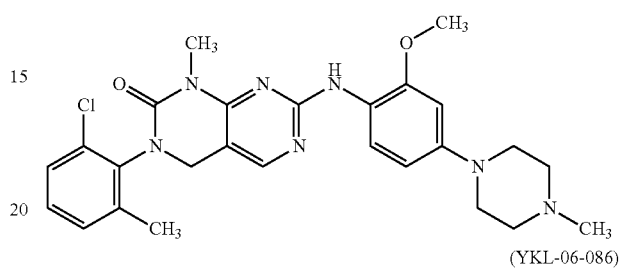

(YKL-06-086)

(YKL-06-087)

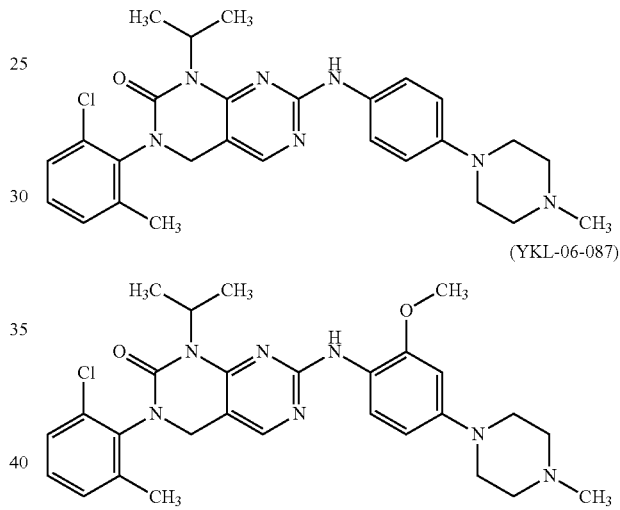

(HG-4-34-01)

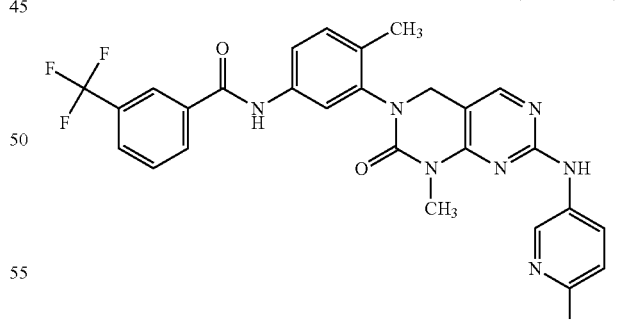

or a pharmaceutically acceptable salt, solvate, hydrate, polymorph, co-crystal, tautomer, stereoisomer, isotopically labeled derivative, or prodrug thereof.

In certain embodiments, the compound of Formula (IV) useful in the present invention is of the formula:

(HG-11-139-02)

or a pharmaceutically acceptable salt, solvate, hydrate, polymorph, co-crystal, tautomer, stereoisomer, isotopically labeled derivative, or prodrug thereof.

In certain embodiments, the compound of Formula (IV) useful in the present invention is of the formula:

or a pharmaceutically acceptable salt, solvate, hydrate, polymorph, co-crystal, tautomer, stereoisomer, isotopically labeled derivative, or prodrug thereof.

In certain embodiments, the compound of Formula (IV) useful in the present invention is of the formula:

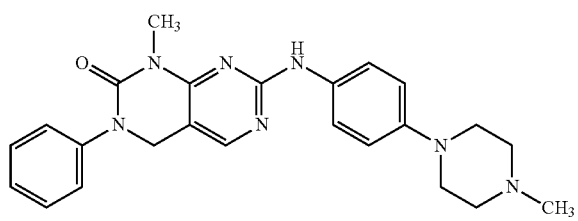
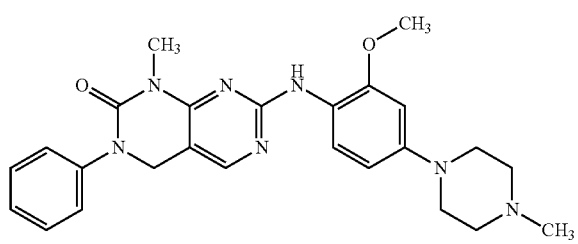
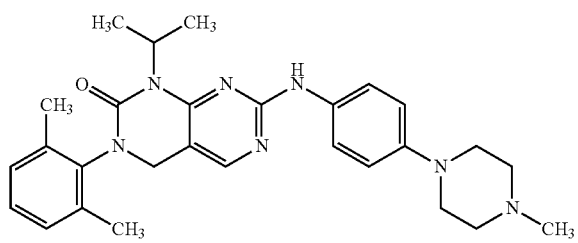
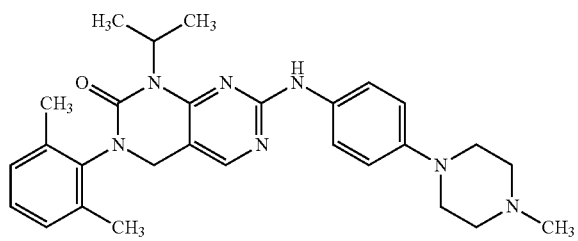
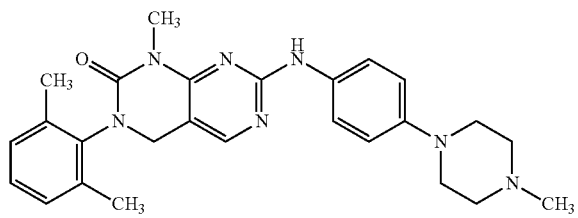
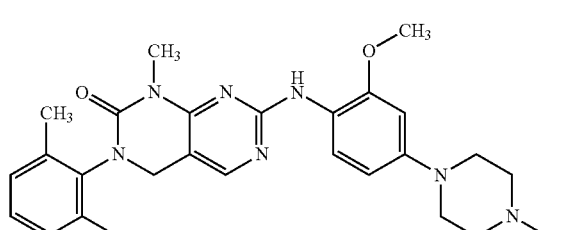
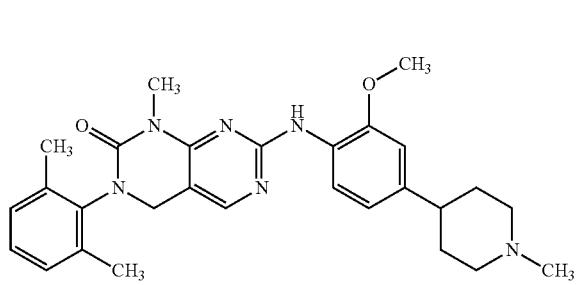

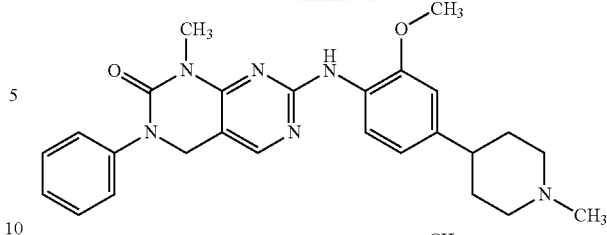
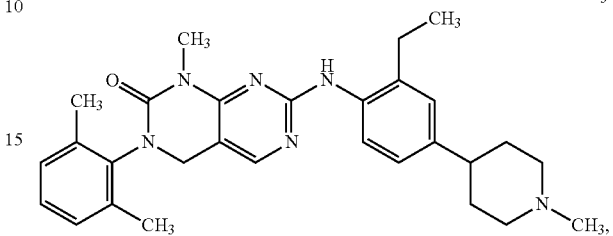

or a pharmaceutically acceptable salt, solvate, hydrate, polymorph, co-crystal, tautomer, stereoisomer, isotopically labeled derivative, or prodrug thereof.

In certain embodiments, the compound of Formula (IV) useful in the present invention is not of the formula:

(HG-11-139-02)

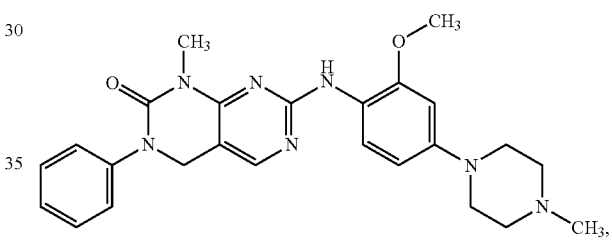

or a pharmaceutically acceptable salt, solvate, hydrate, polymorph, co-crystal, tautomer, stereoisomer, isotopically labeled derivative, or prodrug thereof.

Compounds of Formula (V)

In another aspect, the compound utilized in the present disclosure is of Formula (V):

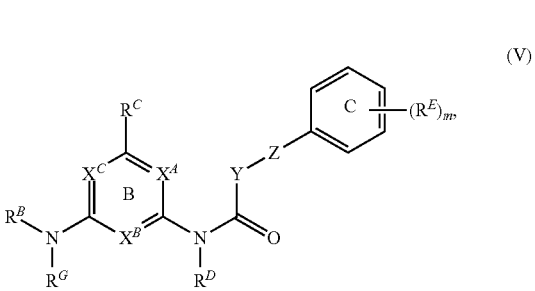

(V)

and pharmaceutically acceptable salts, solvates, hydrates, polymorphs, co-crystals, tautomers, stereoisomers, isotopically labeled derivatives, and prodrugs thereof, wherein:

$R^G$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaryl, or of the formula:

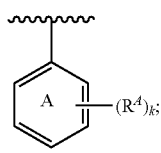

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=NR^a)R^a$, $-C(=NR^a)OR^a$, $-C(=NR^a)N(R^a)_2$, $-C(=O)R^a$, $-C(=O)OR^a$, $-C(=O)N(R^a)_2$, $-NO_2$, $-NR^aC(=O)R^a$, $-NR^aC(=O)OR^a$, $-NR^aC(=O)N(R^a)_2$, $-OC(=O)R^a$, $-OC(=O)OR^a$, or $-OC(=O)N(R^a)_2$, or two $R^A$ groups are joined to form a substituted or unsubstituted carbocyclic ring, substituted or unsubstituted heterocyclic ring, substituted or unsubstituted aryl ring, or substituted or unsubstituted heteroaryl ring;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^a$ groups are joined to form a substituted or unsubstituted heterocyclic or substituted or unsubstituted heteroaryl ring;

k is 0, 1, 2, 3, 4, or 5;

$R^B$ is hydrogen, substituted or unsubstituted acyl, substituted or unsubstituted $C_{1-6}$ alkyl, or a nitrogen protecting group;

each of $X^A$, $X^B$, and $X^C$ is independently N or $CR^X$, wherein each instance of $R^X$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=NR^a)R^a$, $-C(=NR^a)OR^a$, $-C(=NR^a)N(R^a)_2$, $-C(=O)R^a$, $-C(=O)OR^a$, $-C(=O)N(R^a)_2$, $-NO_2$, $-NR^aC(=O)R^a$, $-NR^aC(=O)OR^a$, $-NR^aC(=O)N(R^a)_2$, $-OC(=O)R^a$, $-OC(=O)OR^a$, or $-OC(=O)N(R^a)_2$;

or: $X^B$ is $CR^X$, and $R^G$ and $R^X$ of $X^B$ are joined to form a substituted or unsubstituted heterocyclic or substituted or unsubstituted heteroaryl ring;

$R^C$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=NR^a)R^a$, $-C(=NR^a)OR^a$, $-C(=NR^a)N(R^a)_2$, $-C(=O)R^a$, $-C(=O)OR^a$, $-C(=O)N(R^a)_2$, $-NO_2$, $-NR^aC(=O)R^a$, $-NR^aC(=O)OR^a$, $-NR^aC(=O)N(R^a)_2$, $-OC(=O)R^a$, $-OC(=O)OR^a$, or $-OC(=O)N(R^a)_2$;

$R^D$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

Y is $-O-$ or $-NR^Y-$, wherein $R^Y$ is hydrogen, substituted or unsubstituted acyl, substituted or unsubstituted $C_{1-6}$ alkyl, or a nitrogen protecting group;

Z is a bond or $-C(R^Z)_2-$, wherein each instance of $R^Z$ is independently hydrogen, halogen, or substituted or unsubstituted $C_{1-6}$ alkyl;

each instance of $R^E$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=NR^a)R^a$, $-C(=NR^a)OR^a$, $-C(=NR^a)N(R^a)_2$, $-C(=O)R^a$, $-C(=O)OR^a$, $-C(=O)N(R^a)_2$, $-NO_2$, $-NR^aC(=O)R^a$, $-NR^aC(=O)OR^a$, $-NR^aC(=O)N(R^a)_2$, $-NR^aS(=O)R^a$, $-NR^aS(=O)OR^a$, $-NR^aS(=O)N(R^a)_2$, $-NR^aS(=O)_2R^a$, $-NR^aS(=O)_2OR^a$, $-NR^aS(=O)_2N(R^a)_2$, $-OC(=O)R^a$, $-OC(=O)OR^a$, or $-OC(=O)N(R^a)_2$; and m is 0, 1, 2, 3, 4, or 5.

In certain embodiments, a compound of Formula (V) useful in the present invention is of Formula (V-A):

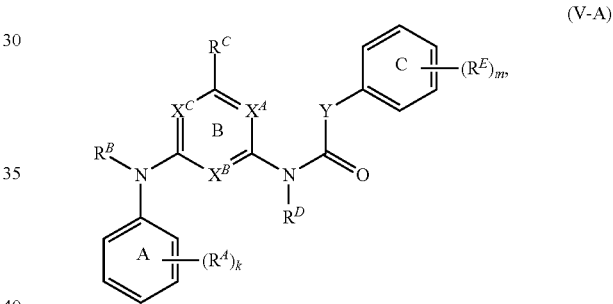

(V-A)

or a pharmaceutically acceptable salt, solvate, hydrate, polymorph, co-crystal, tautomer, stereoisomer, isotopically labeled derivative, or prodrug thereof, wherein:

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=NR^a)R^a$, $-C(=NR^a)OR^a$, $-C(=NR^a)N(R^a)_2$, $-C(=O)R^a$, $-C(=O)OR^a$, $-C(=O)N(R^a)_2$, $-NO_2$, $-NR^aC(=O)R^a$, $-NR^aC(=O)OR^a$, $-NR^aC(=O)N(R^a)_2$, $-OC(=O)R^a$, $-OC(=O)OR^a$, or $-OC(=O)N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^a$ groups are joined to form a substituted or unsubstituted heterocyclic or substituted or unsubstituted heteroaryl ring;

k is 0, 1, 2, 3, 4, or 5;

$R^B$ is hydrogen, substituted or unsubstituted acyl, substituted or unsubstituted $C_{1-6}$ alkyl, or a nitrogen protecting group;

each of $X^A$, $X^B$, and $X^C$ is independently N or $CR^X$, wherein each instance of $R^X$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —NO$_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

$R^C$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —NO$_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

$R^D$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

Y is —O— or —$NR^Y$—, wherein $R^Y$ is hydrogen, substituted or unsubstituted acyl, substituted or unsubstituted $C_{1-6}$ alkyl, or a nitrogen protecting group;

each instance of $R^E$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —NO$_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$; and m is 0, 1, 2, 3, 4, or 5.

Formula (V) includes substituent $R^G$. In certain embodiments, $R^G$ is hydrogen. In certain embodiments, $R^G$ is substituted or unsubstituted alkyl. In certain embodiments, $R^G$ is substituted $C_{1-6}$ alkyl (e.g., —$CF_3$, perfluoroethyl, perfluoropropyl, perfluorobutyl, Bn, or $C_{1-6}$ alkyl substituted with at least one instance of halogen and/or —$OR^a$)). In certain embodiments, $R^G$ is $C_{1-6}$ alkyl substituted with at least one instance of —$OR^a$, optionally wherein $R^a$ is hydrogen or substituted or unsubstituted $C_{1-6}$ alkyl. In certain embodiments, $R^G$ is of the formula:

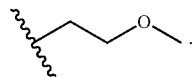 [SMILES: *CCOC]

In certain embodiments, $R^G$ is unsubstituted $C_{1-6}$ alkyl (e.g., Me, Et, Pr, or Bu). In certain embodiments, $R^G$ is substituted or unsubstituted alkenyl (e.g., substituted or unsubstituted $C_{1-6}$ alkenyl). In certain embodiments, $R^G$ is substituted or unsubstituted alkynyl (e.g., substituted or unsubstituted $C_{1-6}$ alkynyl). In certain embodiments, $R^G$ is substituted or unsubstituted carbocyclyl (e.g., substituted or unsubstituted, monocyclic, 3- to 7-membered carbocyclyl). In certain embodiments, $R^G$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, $R^G$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, $R^G$ is substituted or unsubstituted 2-pyridyl. In certain embodiments, $R^G$ is substituted or unsubstituted 3-pyridyl. In certain embodiments, $R^G$ is of the formula:

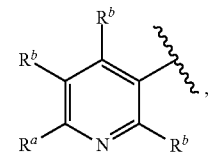

wherein $R^a$ is hydrogen, halogen, substituted or unsubstituted $C_{1-6}$ alkyl, —OH, —O(substituted or unsubstituted $C_{1-6}$ alkyl), or substituted or unsubstituted, monocyclic, 5- to 6-membered heterocyclyl, wherein one, two, or three atoms in the heterocyclic ring system are independently nitrogen, oxygen, or sulfur; and each instance of $R^b$ is independently hydrogen, halogen, substituted or unsubstituted $C_{1-6}$ alkyl, —OH, or —O(substituted or unsubstituted $C_{1-6}$ alkyl). In certain embodiments, $R^G$ is of the formula:

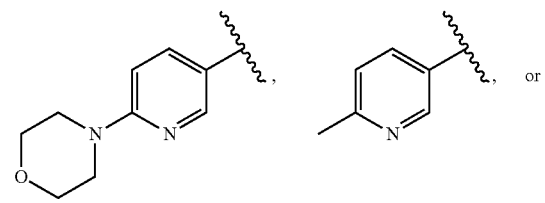

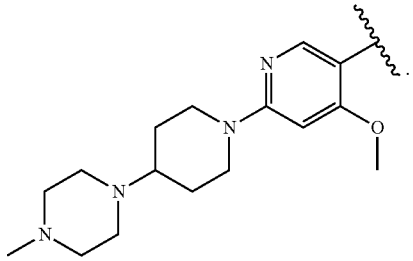

In certain embodiments, $R^G$ is substituted or unsubstituted 4-pyridyl. In certain embodiments, $R^G$ is substituted or unsubstituted 1-pyrazolyl. In certain embodiments, $R^G$ is substituted or unsubstituted 3-pyrazolyl. In certain embodiments, $R^G$ is substituted or unsubstituted 4-pyrazolyl. In certain embodiments, $R^G$ is of the formula:

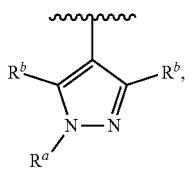

wherein $R^a$ is hydrogen, substituted or unsubstituted $C_{1-6}$ alkyl, a nitrogen protecting group, or -(substituted or unsubstituted $C_{1-6}$ alkylene)-(substituted or unsubstituted, monocyclic, 5- to 6-membered heterocyclyl, wherein one, two, or three atoms in the heterocyclic ring system are independently nitrogen, oxygen, or sulfur); and each instance of $R^b$ is independently hydrogen, halogen, substituted or unsubstituted $C_{1-6}$ alkyl, —OH, or —O(substituted or unsubstituted $C_{1-6}$ alkyl). In certain embodiments, $R^G$ is of the formula:

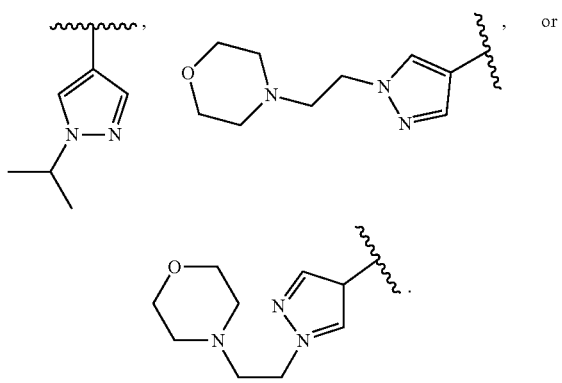

In certain embodiments, $R^G$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, substituted or unsubstituted isothiazolyl, or substituted or unsubstituted tetrazolyl. In certain embodiments, $R^G$ is substituted or unsubstituted pyrazinyl, substituted or unsubstituted pyrimidinyl, or substituted or unsubstituted pyridazinyl. In certain embodiments, $R^G$ is substituted or unsubstituted, bicyclic, 9- to 10-membered heteroaryl, wherein one, two, three, or four atoms in the heteroaryl ring system are independently nitrogen, oxygen, or sulfur.

In certain embodiments, $R^G$ is of the formula:

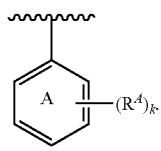

Ring A is unsubstituted (e.g., when k is 0) or substituted with one or more substituents $R^A$ (e.g., when k is 1, 2, 3, 4, or 5). In certain embodiments, Ring A is an unsubstituted phenyl ring. In certain embodiments, Ring A is a substituted phenyl ring. In certain embodiments, Ring A is of the formula:

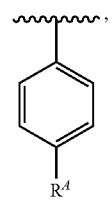

optionally wherein $R^A$ is substituted or unsubstituted, monocyclic, 5- to 6-membered heterocyclic ring, wherein one or two atoms in the heterocyclic ring system are independently nitrogen, oxygen, or sulfur. In certain embodiments, Ring A is of the formula:

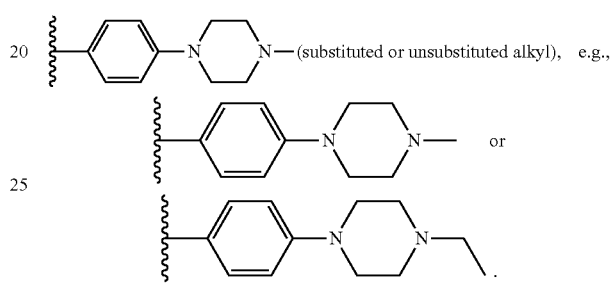

In certain embodiments, $R^G$ is

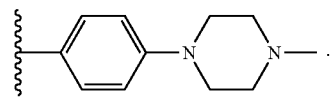 [SMILES: *c1ccc(N2CCN(C)CC2)cc1]

In certain embodiments, Ring A is of the formula:

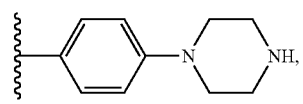

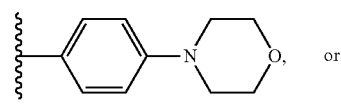

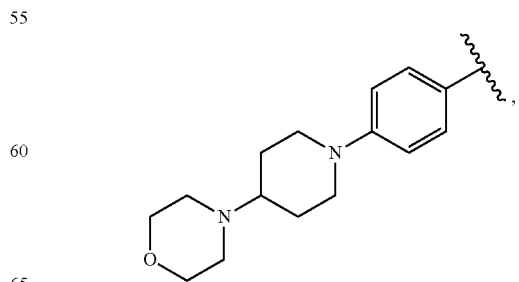

In certain embodiments, Ring A is of the formula:

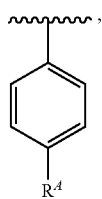

optionally wherein $R^A$ is halogen, substituted or unsubstituted $C_{1-6}$ alkyl, or —$OR^a$. In certain embodiments, Ring A is of the formula:

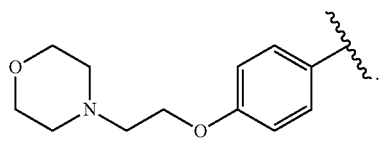 [SMILES: *c1ccc(OCCN2CCOCC2)cc1]

In certain embodiments, Ring A is of the formula:

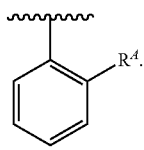

In certain embodiments, Ring A is of the formula:

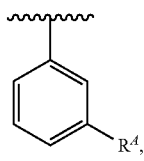

optionally wherein $R^A$ is halogen, substituted or unsubstituted $C_{1-6}$ alkyl, or —$OR^a$. In certain embodiments, Ring A is of the formula:

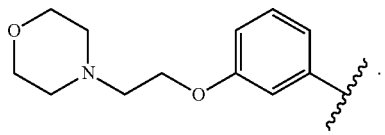 [SMILES: *c1cccc(OCCN2CCOCC2)c1]

In certain embodiments, Ring A is of the formula:

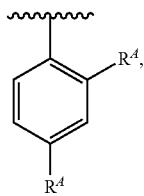

optionally wherein each instance of $R^A$ is independently halogen, substituted or unsubstituted $C_{1-6}$ alkyl, —$OR^a$, —$C(=O)R^a$, —$C(=O)OR^a$, —$C(=O)N(R^a)_2$, or substituted or unsubstituted, monocyclic, 5- to 6-membered heterocyclic ring, wherein one or two atoms in the heterocyclic ring system are independently nitrogen, oxygen, or sulfur. In certain embodiments, Ring A is of the formula:

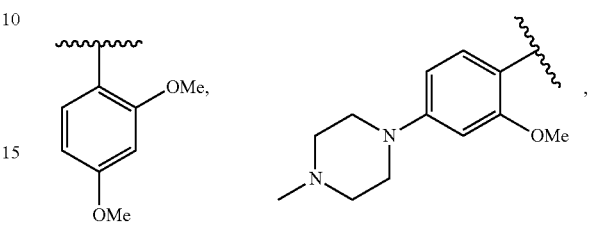

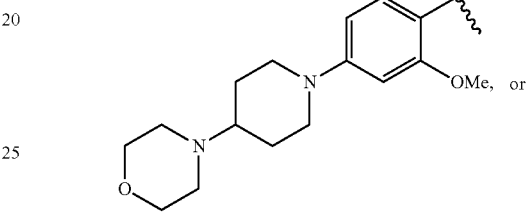

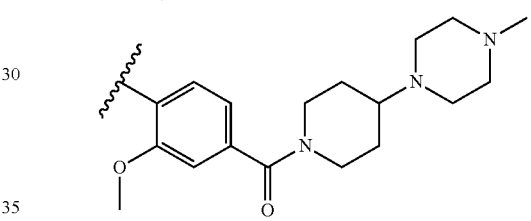

In certain embodiments, Ring A is of the formula:

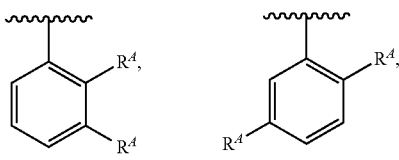

In certain embodiments, Ring A is of the formula:

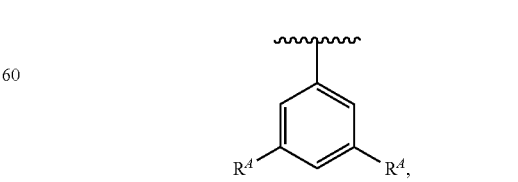

optionally wherein each instance of $R^A$ is independently halogen, substituted or unsubstituted $C_{1-6}$ alkyl, —$OR^a$, or substituted or unsubstituted, monocyclic, 5- to 6-membered heterocyclic ring, wherein one or two atoms in the heterocyclic ring system are independently nitrogen, oxygen, or sulfur. In certain embodiments, Ring A is of the formula:

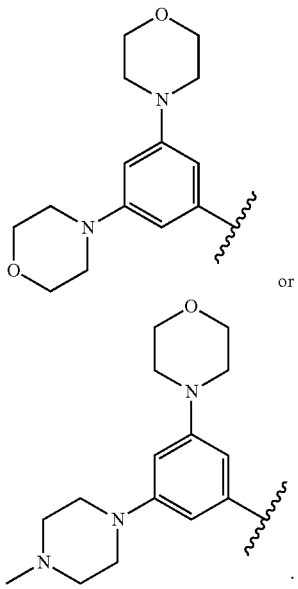

or

In certain embodiments, Ring A is of the formula:

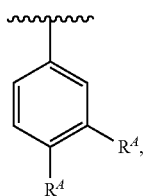

wherein the two instances of $R^A$ are joined to form a substituted or unsubstituted carbocyclic ring (e.g., substituted or unsubstituted, 3- to 7-membered, monocyclic carbocyclic ring), substituted or unsubstituted heterocyclic ring (e.g., substituted or unsubstituted, monocyclic, 5- to 6-membered heterocyclic ring, wherein one or two atoms in the heterocyclic ring system are independently nitrogen, oxygen, or sulfur), substituted or unsubstituted aryl ring (e.g., substituted or unsubstituted phenyl ring), or substituted or unsubstituted heteroaryl ring (e.g., substituted or unsubstituted, monocyclic, 5- to 6-membered heteroaryl ring, wherein one or two atoms in the heteroaryl ring system are independently nitrogen, oxygen, or sulfur). In certain embodiments, Ring A is of the formula:

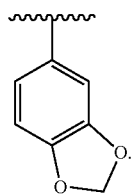

In certain embodiments, Ring A is of the formula:

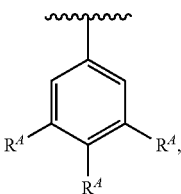

optionally wherein each instance of $R^A$ is independently halogen, substituted or unsubstituted $C_{1-6}$ alkyl, —$OR^a$, or substituted or unsubstituted, monocyclic, 5- to 6-membered heterocyclic ring, wherein one or two atoms in the heterocyclic ring system are independently nitrogen, oxygen, or sulfur. In certain embodiments, Ring A is of the formula:

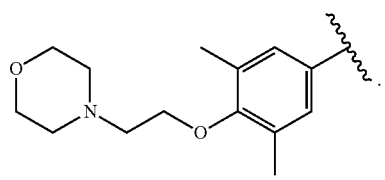 [SMILES: *c1cc(C)c(OCCN2CCOCC2)c(C)c1]

In certain embodiments, Ring A is of the formula:

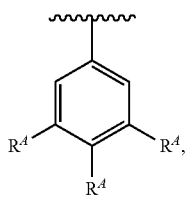

wherein each instance of $R^A$ is independently —$OR^a$. In certain embodiments, Ring A is of the formula:

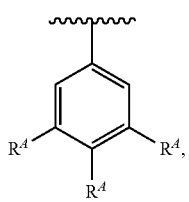

wherein each instance of $R^A$ is independently —O(substituted or unsubstituted alkyl). In certain embodiments, Ring A is of the formula:

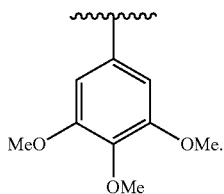

In certain embodiments, Ring A is of the formula:

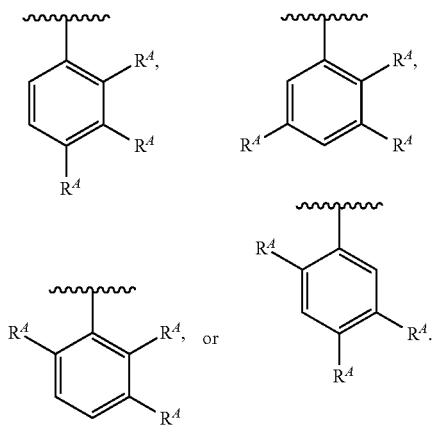

In Formula (V), Ring A may include one or more substituents $R^A$. In certain embodiments, all instances of $R^A$ are the same. In certain embodiments, at least two instances of $R^A$ are different. In certain embodiments, at least one instance of $R^A$ is halogen (e.g., F, Cl, Br, or I). In certain embodiments, at least one instance of $R^A$ is substituted or unsubstituted alkyl (e.g., substituted or unsubstituted $C_{1-6}$ alkyl). In certain embodiments, at least one instance of $R^A$ is —$CH_3$. In certain embodiments, at least one instance of $R^A$ is —$CF_3$, unsubstituted ethyl, perfluoroethyl, unsubstituted propyl, perfluoropropyl, unsubstituted butyl, perfluorobutyl, or Bn. In certain embodiments, at least one instance of $R^A$ is substituted or unsubstituted alkenyl (e.g., substituted or unsubstituted $C_{1-6}$ alkenyl). In certain embodiments, at least one instance of $R^A$ is substituted or unsubstituted alkynyl (e.g., substituted or unsubstituted $C_{1-6}$ alkynyl). In certain embodiments, at least one instance of $R^A$ is substituted or unsubstituted carbocyclyl (e.g., substituted or unsubstituted, monocyclic, 3- to 7-membered carbocyclyl). In certain embodiments, at least one instance of $R^A$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^A$ is of the formula:

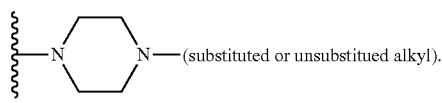

In certain embodiments, at least one instance of $R^A$ is of the formula:

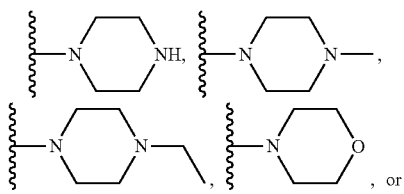

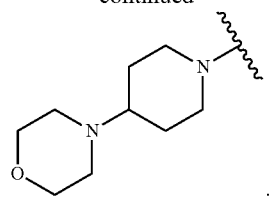

In certain embodiments, at least one instance of $R^A$ is substituted or unsubstituted aryl (e.g., substituted or unsubstituted, 6- to 10-membered aryl). In certain embodiments, at least one instance of $R^A$ is substituted or unsubstituted phenyl. In certain embodiments, at least one instance of $R^A$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^A$ is —$OR^a$. In certain embodiments, at least one instance of $R^A$ is —OH. In certain embodiments, at least one instance of $R^A$ is —O(substituted or unsubstituted alkyl), such as —O(substituted or unsubstituted $C_{1-6}$ alkyl) (e.g., —OMe, —OEt, —OPr, —OBu, —OBn, or

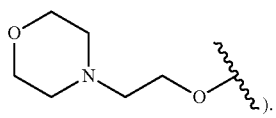 [SMILES: *OCCN1CCOCC1]

In certain embodiments, at least one instance of $R^A$ is —O(substituted or unsubstituted phenyl) (e.g., —OPh)). In certain embodiments, at least one instance of $R^A$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^A$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^A$ is —CN, —SCN, or —$NO_2$. In certain embodiments, at least one instance of $R^A$ is —C(=$NR^a$)$R^a$, —C(=$NR^a$)$OR^a$, or —C(=$NR^a$)N($R^a$)$_2$. In certain embodiments, at least one instance of $R^A$ is —C(=O)$R^a$ or —C(=O)$OR^a$. In certain embodiments, at least one instance of $R^A$ is —C(=O)N($R^a$)$_2$ (e.g., —C(=O)$NH_2$, —C(=O)NHMe, —C(=O)$NMe_2$, or

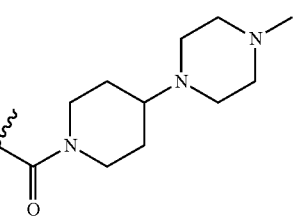

In certain embodiments, at least one instance of $R^A$ is —$NR^aC$(=O)$R^a$, —$NR^aC$(=O)$OR^a$, or —$NR^aC$(=O)N($R^a$)$_2$. In certain embodiments, at least one instance of $R^A$ is —OC(=O)$R^a$, —OC(=O)$OR^a$, or —OC(=O)N($R^a$)$_2$.

Each instance of $R^A$, $R^C$, $R^E$, and $R^X$ may independently include one or more substituents $R^a$. In certain embodiments, all instances of $R^a$ are the same. In certain embodiments, at least two instances of $R^a$ are different. In certain embodiments, at least one instance of $R^a$ is H. In certain embodiments, each instance of $R^a$ is H. In certain embodiments, at least one instance of $R^a$ is substituted or unsubstituted acyl (e.g., acetyl). In certain embodiments, at least one instance of $R^a$ is substituted or unsubstituted alkyl (e.g., substituted or unsubstituted $C_{1-6}$ alkyl). In certain embodiments, at least one instance of $R^a$ is —$CH_3$. In certain embodiments, at least one instance of $R^a$ is —$CF_3$, unsubstituted ethyl, perfluoroethyl, unsubstituted propyl, perfluoropropyl, unsubstituted butyl, perfluorobutyl, or Bn. In certain embodiments, at least one instance of $R^a$ is substituted or unsubstituted alkenyl (e.g., substituted or unsubstituted $C_{1-6}$ alkenyl). In certain embodiments, at least one instance of $R^a$ is substituted or unsubstituted alkynyl (e.g., substituted or unsubstituted $C_{1-6}$ alkynyl). In certain embodiments, at least one instance of $R^a$ is substituted or unsubstituted carbocyclyl (e.g., substituted or unsubstituted, monocyclic, 3- to 7-membered carbocyclyl). In certain embodiments, at least one instance of $R^a$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^a$ is substituted or unsubstituted aryl (e.g., substituted or unsubstituted, 6- to 10-membered aryl). In certain embodiments, at least one instance of $R^a$ is substituted or unsubstituted phenyl. In certain embodiments, at least one instance of $R^a$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^a$ is a nitrogen protecting group (e.g., Bn, Boc, Cbz, Fmoc, trifluoroacetyl, triphenylmethyl, acetyl, or Ts) when attached to a nitrogen atom. In certain embodiments, at least one instance of $R^a$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, at least one instance of $R^a$ is a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^a$ are joined to form a substituted or unsubstituted heterocyclic ring (e.g., substituted or unsubstituted, monocyclic, 5- to 6-membered heterocyclic ring, wherein one, two, or three atoms in the heterocyclic ring system are independently nitrogen, oxygen, or sulfur). In certain embodiments, two instances of $R^a$ are joined to form a substituted or unsubstituted heteroaryl ring (e.g., substituted or unsubstituted, monocyclic, 5- to 6-membered heteroaryl ring, wherein one, two, three, or four atoms in the heteroaryl ring system are independently nitrogen, oxygen, or sulfur).

In certain embodiments, k is 0. In certain embodiments, k is 1. In certain embodiments, k is 2. In certain embodiments, k is 3. In certain embodiments, k is 4. In certain embodiments, k is 5.

Formula (V) includes substituent $R^B$ on the nitrogen atom that connects Rings A and B. In certain embodiments, $R^B$ is hydrogen. In certain embodiments, $R^B$ is substituted or unsubstituted acyl (e.g., acetyl). In certain embodiments, $R^B$ is substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, perfluorobutyl, or Bn). In certain embodiments, $R^B$ is a nitrogen protecting group (e.g., Bn, Boc, Cbz, Fmoc, trifluoroacetyl, triphenylmethyl, acetyl, or Ts).

Formula (V) includes a heteroaryl ring as Ring B that includes moieties $X^A$, $X^B$, and $X^C$ in the heteroaryl ring system. In certain embodiments, $X^A$ is $CR^X$, and each of $X^B$ and $X^C$ is N. In certain embodiments, $X^A$ is CH, and each of $X^B$ and $X^C$ is N. In certain embodiments, $X^B$ is $CR^X$, and each of $X^A$ and $X^C$ is N. In certain embodiments, $X^B$ is CH, and each of $X^A$ and $X^C$ is N. In certain embodiments, $X^C$ is $CR^X$, and each of $X^A$ and $X^B$ is N. In certain embodiments, $X^C$ is CH, and each of $X^A$ and $X^B$ is N. In certain embodiments, $X^A$ is N, and each of $X^B$ and $X^C$ is independently $CR^X$. In certain embodiments, $X^A$ is N, and each of $X^B$ and $X^C$ is CH. In certain embodiments, $X^B$ is N, and each of $X^A$ and $X^C$ is independently $CR^X$. In certain embodiments, $X^B$ is N, and each of $X^A$ and $X^C$ is CH. In certain embodiments, $X^C$ is N, and each of $X^A$ and $X^B$ is independently $CR^X$. In certain embodiments, $X^C$ is N, and each of $X^A$ and $X^B$ is CH. In certain embodiments, each of $X^A$, $X^B$, and $X^C$ is independently $CR^X$. In certain embodiments, each of $X^A$, $X^B$, and $X^C$ is CH.

In certain embodiments, $X^B$ is $CR^X$, and $R^G$ and $R^X$ of $X^B$ are joined to form a substituted or unsubstituted heterocyclic ring (e.g., substituted or unsubstituted, monocyclic, 5- to 6-membered heterocyclic ring, wherein one or two atoms in the heterocyclic ring system are independently nitrogen, oxygen, or sulfur, further wherein at least one atom in the heterocyclic ring system is nitrogen). In certain embodiments, $X^B$ is $CR^X$, and $R^G$ and $R^X$ of $X^B$ are joined to form a substituted or unsubstituted heteroaryl ring (e.g., substituted or unsubstituted, monocyclic, 5- to 6-membered heteroaryl ring, wherein one or two atoms in the heterocyclic ring system are independently nitrogen, oxygen, or sulfur, further wherein at least one atom in the heteroaryl ring system is nitrogen). In certain embodiments, $X^B$ is $CR^X$, and $R^{G1}$ and $R^X$ of $X^B$ are joined to form substituted or unsubstituted pyrrolyl ring.

In certain embodiments, all instances of $R^X$ are the same. In certain embodiments, at least two instances of $R^X$ are different. In certain embodiments, at least one instance of $R^X$ is hydrogen. In certain embodiments, at least one instance of $R^X$ is halogen (e.g., F, Cl, Br, or I). In certain embodiments, at least one instance of $R^X$ is substituted or unsubstituted alkyl (e.g., substituted or unsubstituted $C_{1-6}$ alkyl). In certain embodiments, at least one instance of $R^X$ is —$CH_3$. In certain embodiments, at least one instance of $R^X$ is —$CF_3$, unsubstituted ethyl, perfluoroethyl, unsubstituted propyl, perfluoropropyl, unsubstituted butyl, perfluorobutyl, or Bn. In certain embodiments, at least one instance of $R^X$ is substituted or unsubstituted alkenyl (e.g., substituted or unsubstituted $C_{1-6}$ alkenyl). In certain embodiments, at least one instance of $R^X$ is substituted or unsubstituted alkynyl (e.g., substituted or unsubstituted $C_{1-6}$ alkynyl). In certain embodiments, at least one instance of $R^X$ is substituted or unsubstituted carbocyclyl (e.g., substituted or unsubstituted, monocyclic, 3- to 7-membered carbocyclyl). In certain embodiments, at least one instance of $R^X$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^X$ is substituted or unsubstituted aryl (e.g., substituted or unsubstituted, 6- to 10-membered aryl). In certain embodiments, at least one instance of $R^X$ is substituted or unsubstituted phenyl. In certain embodiments, at least one instance of $R^X$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^X$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^X$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^X$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^X$ is —CN, —SCN, or —$NO_2$. In certain embodiments, at least one instance of $R^X$ is —C(=$NR^a$)$R^a$, —C(=$NR^a$)$OR^a$, or —C(=$NR^a$)N($R^a$)$_2$. In certain embodiments, at least one instance of $R^X$ is —C(=O)$R^a$, —C(=O)$OR^a$, or —C(=O)N($R^a$)$_2$ (e.g., —C(=O)$NH_2$, —C(=O)NHMe, or —C(=O)$NMe_2$). In certain embodiments, at least one instance of $R^X$ is —$NR^aC$(=O)$R^a$, —$NR^aC$(=O)$OR^a$, or —$NR^aC$(=O)N($R^a$)$_2$. In certain embodiments, at least one instance of $R^X$ is —OC(=O)$R^a$, —OC(=O)$OR^a$, or —OC(=O)N($R^a$)$_2$.

Formula (V) includes substituent $R^C$ on Ring B. In certain embodiments, $R^C$ is hydrogen. In certain embodiments, $R^C$ is halogen (e.g., F, Cl, Br, or I). In certain embodiments, $R^C$ is substituted or unsubstituted alkyl (e.g., substituted or unsubstituted $C_{1-6}$ alkyl). In certain embodiments, $R^C$ is —$CH_3$. In certain embodiments, $R^C$ is —$CF_3$, unsubstituted ethyl, perfluoroethyl, unsubstituted propyl, perfluoropropyl, unsubstituted butyl, perfluorobutyl, or Bn. In certain embodiments, $R^C$ is substituted or unsubstituted alkenyl (e.g., substituted or unsubstituted $C_{1-6}$ alkenyl). In certain embodiments, $R^C$ is substituted or unsubstituted alkynyl (e.g., substituted or unsubstituted $C_{1-6}$ alkynyl). In certain embodiments, $R^C$ is substituted or unsubstituted carbocyclyl (e.g., substituted or unsubstituted, monocyclic, 3- to 7-membered carbocyclyl). In certain embodiments, $R^C$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, $R^C$ is substituted or unsubstituted aryl (e.g., substituted or unsubstituted, 6- to 10-membered aryl). In certain embodiments, $R^C$ is substituted or unsubstituted phenyl. In certain embodiments, $R^C$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, $R^C$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^C$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^C$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^C$ is —CN, —SCN, or —$NO_2$. In certain embodiments, $R^C$ is —C(=$NR^a$)$R^a$, —C(=$NR^a$)$OR^a$, or —C(=$NR^a$)N($R^a$)$_2$. In certain embodiments, $R^C$ is —C(=O)$R^a$, —C(=O)$OR^a$, or —C(=O)N($R^a$)$_2$ (e.g., —C(=O)$NH_2$, —C(=O)NHMe, or —C(=O)$NMe_2$). In certain embodiments, $R^C$ is —$NR^aC$(=O)$R^a$, —$NR^aC$(=O)$OR^a$, or —$NR^aC$(=O)N($R^a$)$_2$. In certain embodiments, $R^C$ is —OC(=O)$R^a$, —OC(=O)$OR^a$, or —OC(=O)N($R^a$)$_2$.

Formula (V) includes substituent $R^D$ on a nitrogen atom of the urea or carbamate moiety. In certain embodiments, $R^D$ is hydrogen. In certain embodiments, $R^D$ is substituted or unsubstituted alkyl, such as substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, perfluorobutyl, or Bn). In certain embodiments, $R^D$ is substituted or unsubstituted alkenyl (e.g., substituted or unsubstituted $C_{1-6}$ alkenyl). In certain embodiments, $R^D$ is substituted or unsubstituted alkynyl (e.g., substituted or unsubstituted $C_{1-6}$ alkynyl). In certain embodiments, $R^D$ is substituted or unsubstituted carbocyclyl (e.g., substituted or unsubstituted, monocyclic, 3- to 7-membered carbocyclyl). In certain embodiments, $R^D$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, $R^D$ is substituted or unsubstituted oxetanyl, substituted or unsubstituted azetidinyl, substituted or unsubstituted tetrahydrofuranyl, substituted or unsubstituted tetrahydropyranyl, substituted or unsubstituted pyrrolidinyl, substituted or unsubstituted piperidinyl, substituted or unsubstituted piperazinyl, or substituted or unsubstituted morpholinyl. In certain embodiments, $R^D$ is of the formula:

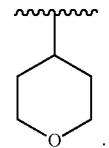

In certain embodiments, $R^D$ is substituted or unsubstituted aryl (e.g., substituted or unsubstituted, 6- to 10-membered aryl). In certain embodiments, $R^D$ is substituted or unsubstituted phenyl. In certain embodiments, $R^D$ is of the formula:

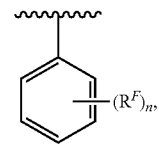

wherein each instance of $R^F$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^aC$(=O)$R^a$, —$NR^aC$(=O)$OR^a$, —$NR^aC$(=O)N($R^a$)$_2$, —OC(=O)$R^a$, —OC(=O)$OR^a$, or —OC(=O)N($R^a$)$_2$; and n is 0, 1, 2, 3, 4, or 5. In certain embodiments, $R^D$ is of the formula:

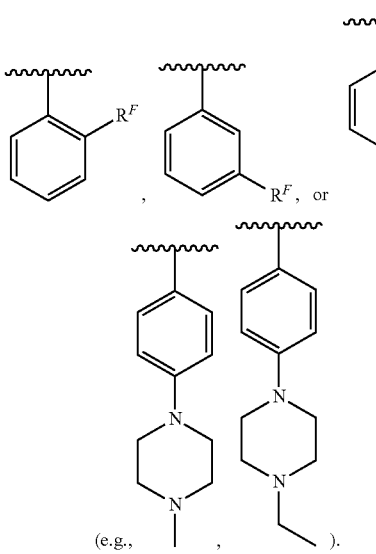

In certain embodiments, $R^D$ is of the formula:

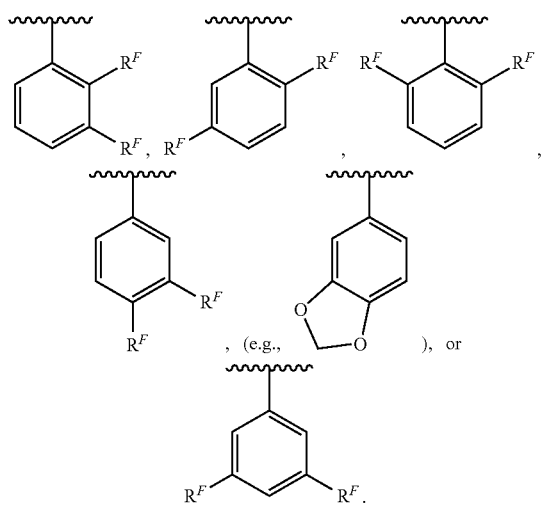

In certain embodiments, $R^D$ is of the formula

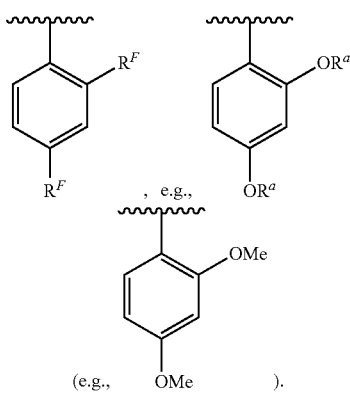

In certain embodiments, $R^D$ is of the formula

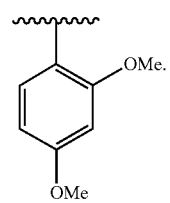 [SMILES: *c1ccc(OC)cc1OC]

In certain embodiments, $R^D$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, $R^D$ is substituted or unsubstituted 1-pyrazolyl, substituted or unsubstituted 3-pyrazolyl, or substituted or unsubstituted 4-pyrazolyl

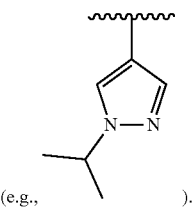 [SMILES: *c1cnn(C(C)C)c1]

In certain embodiments, $R^D$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, substituted or unsubstituted isothiazolyl, or substituted or unsubstituted tetrazolyl. In certain embodiments, $R^D$ is substituted or unsubstituted pyridyl, substituted or unsubstituted pyrazinyl, substituted or unsubstituted pyrimidinyl, or substituted or unsubstituted pyridazinyl.

In certain embodiments, $R^D$ is a nitrogen protecting group (e.g., Bn, Boc, Cbz, Fmoc, trifluoroacetyl, triphenylmethyl, acetyl, or Ts).

Formula (V) includes divalent moiety Y. In certain embodiments, Y is —O—. In certain embodiments, Y is —NR$^Y$—. In certain embodiments, Y is —NH—.

In certain embodiments, $R^Y$ is hydrogen. In certain embodiments, $R^Y$ is substituted or unsubstituted acyl (e.g., acetyl). In certain embodiments, $R^Y$ is substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, perfluorobutyl, or Bn). In certain embodiments, $R^Y$ is a nitrogen protecting group (e.g., Bn, Boc, Cbz, Fmoc, trifluoroacetyl, triphenylmethyl, acetyl, or Ts).

Formula (V) includes divalent moiety Z. In certain embodiments, Z is a bond. In certain embodiments, Z is —C(R$^Z$)$_2$—. In certain embodiments, Z is —CH$_2$—. In certain embodiments, Z is —CHF— or —CF$_2$-.

In certain embodiments, the two instances of $R^Z$ are the same. In certain embodiments, the two instances of $R^Z$ are not the same. In certain embodiments, at least one instance of $R^Z$ is hydrogen. In certain embodiments, each instance of $R^Z$ is hydrogen. In certain embodiments, at least one instance of $R^Z$ is halogen (e.g., F, Cl, Br, or I). In certain embodiments, at least one instance of $R^Z$ is substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, perfluorobutyl, or Bn).

In certain embodiments, —Y—Z— is —N($R^Y$)—. In certain embodiments, —Y—Z— is —NH—. In certain embodiments, —Y—Z— is —N(Me)-. In certain embodiments, —Y—Z— is —O—. In certain embodiments, —Y—Z— is —N($R^Y$)—C($R^Z$)$_2$— (e.g., —N($R^Y$)—$CH_2$—). In certain embodiments, —Y—Z— is —NH—$CH_2$—. In certain embodiments, —Y—Z— is —N(Me)-$CH_2$—. In certain embodiments, —Y—Z— is —O—C($R^Z$)$_2$— (e.g., —O—$CH_2$—).

Formula (V) includes a phenyl ring as Ring C, which is unsubstituted (e.g., when m is 0) or substituted with one or more substituents $R^E$ (e.g., when m is 1, 2, 3, 4, or 5). In certain embodiments, Ring C is an unsubstituted phenyl ring. In certain embodiments, Ring C is a substituted phenyl ring. In certain embodiments, Ring C is of the formula:

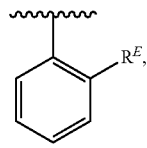

optionally wherein $R^E$ is halogen, substituted or unsubstituted $C_{1-6}$ alkyl, —$OR^a$, —$N(R^a)_2$, —$C(=O)R^a$, —$C(=O)OR^a$, —$C(=O)N(R^a)_2$, —$NR^aC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —$OC(=O)R^a$, —$OC(=O)OR^a$, —$OC(=O)N(R^a)_2$, —CN, —SCN, or —$NO_2$. In certain embodiments, Ring C is of the formula:

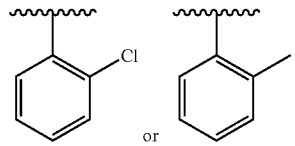

In certain embodiments, Ring C is of the formula:

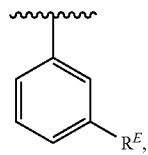

optionally wherein $R^E$ is halogen, substituted or unsubstituted $C_{1-6}$ alkyl, —$OR^a$, —$N(R^a)_2$, —$C(=O)R^a$, —$C(=O)OR^a$, —$C(=O)N(R^a)_2$, —$NR^aC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —$OC(=O)R^a$, —$OC(=O)OR^a$, —$OC(=O)N(R^a)_2$, —CN, —SCN, or —$NO_2$. In certain embodiments, Ring C is of the formula:

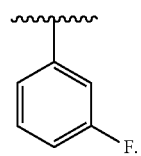

In certain embodiments, Ring C is of the formula:

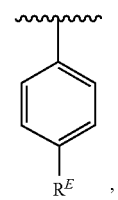

optionally wherein $R^E$ is halogen, substituted or unsubstituted $C_{1-6}$ alkyl, —$OR^a$, —$N(R^a)_2$, —$C(=O)R^a$, —$C(=O)OR^a$, —$C(=O)N(R^a)_2$, —$NR^aC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —$OC(=O)R^a$, —$OC(=O)OR^a$, —$OC(=O)N(R^a)_2$, —CN, —SCN, or —$NO_2$. In certain embodiments, Ring C is of the formula:

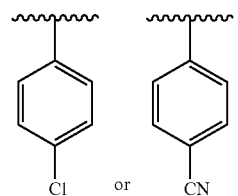

In certain embodiments, Ring C is of the formula:

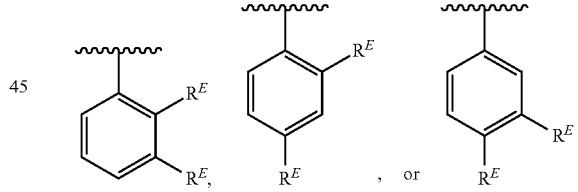

In certain embodiments, Ring C is of the formula:

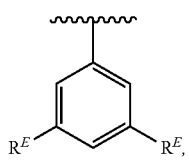

optionally wherein each instance of $R^E$ is independently halogen, substituted or unsubstituted $C_{1-6}$ alkyl, —$OR^a$, —$N(R^a)_2$, —$C(=O)R^a$, —$C(=O)OR^a$, —$C(=O)N(R^a)_2$, —$NR^aC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —$OC(=O)R^a$, —$OC(=O)OR^a$, OC(=O)N(R$^a$)$_2$, —CN, —SCN, or —NO$_2$. In certain embodiments, Ring C is of the formula:

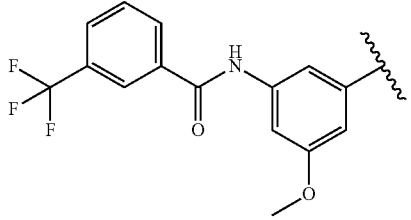

In certain embodiments, Ring C is of the formula:

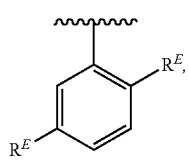

optionally wherein each instance of R$^E$ is independently halogen, substituted or unsubstituted C$_{1-6}$ alkyl, —OR$^a$, —N(R$^a$)$_2$, —C(=O)R$^a$, —C(=O)OR$^a$, —C(=O)N(R$^a$)$_2$, —NR$^a$C(=O)R$^a$, —NR$^a$C(=O)OR$^a$, —NR$^a$C(=O)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OC(=O)R$^a$, —OC(=O)OR$^a$, —OC(=O)N(R$^a$)$_2$, —CN, —SCN, or —NO$_2$. In certain embodiments, Ring C is of the formula:

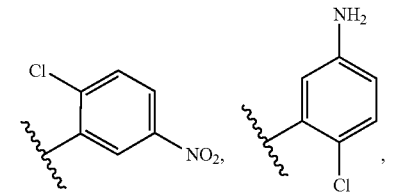

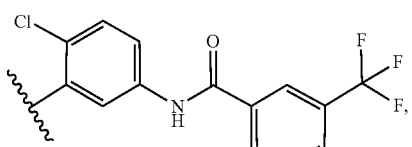

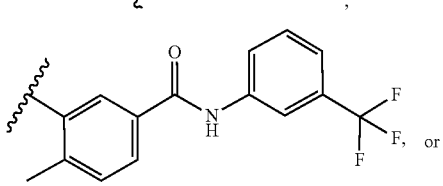, or

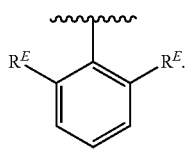

In certain embodiments, Ring C is of the formula:

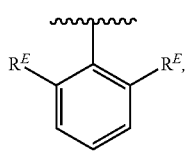

In certain embodiments, Ring C is of the formula:

wherein each instance of R$^E$ is independently substituted or unsubstituted alkyl. In certain embodiments, Ring C is of the formula:

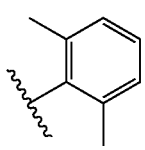

wherein each instance of R$^E$ is independently halogen, substituted or unsubstituted C$_{1-6}$ alkyl, —OR$^a$, —N(R$^a$)$_2$, —C(=O)R$^a$, —C(=O)OR$^a$, —C(=O)N(R$^a$)$_2$, —NR$^a$C(=O)R$^a$, —NR$^a$C(=O)OR$^a$, —NR$^a$C(=O)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OC(=O)R$^a$, —OC(=O)OR$^a$, —OC(=O)N(R$^a$)$_2$, —CN, —SCN, or —NO$_2$. In certain embodiments, Ring C is of the formula:

In certain embodiments, Ring C is of the formula:

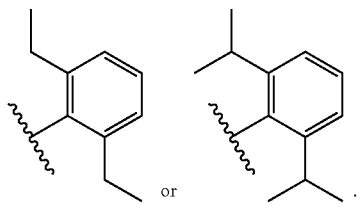

or

In certain embodiments, Ring C is of the formula:

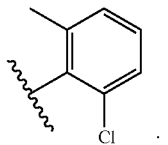 [SMILES: *c1c(C)cccc1Cl]

In certain embodiments, Ring C is of the formula:

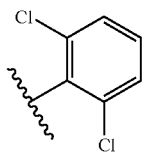

In certain embodiments, Ring C is of the formula:

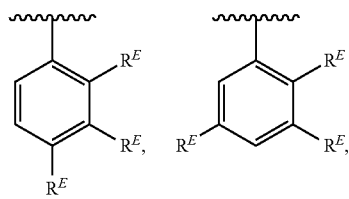

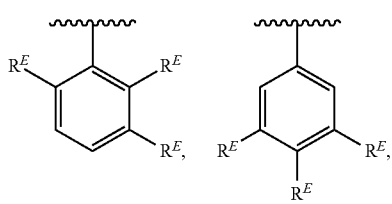

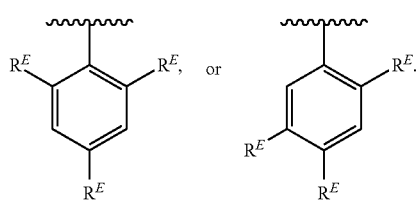

In certain embodiments, Ring C is of the formula:

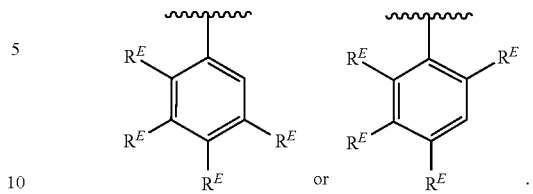

or

In certain embodiments, Ring C is of the formula:

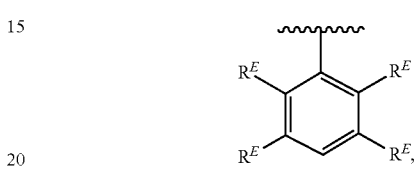

optionally wherein each instance of $R^E$ is independently halogen, substituted or unsubstituted $C_{1-6}$ alkyl, —$OR^a$, —$N(R^a)_2$, —$C(=O)R^a$, —$C(=O)OR^a$, —$C(=O)N(R^a)_2$, —$NR^aC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —$OC(=O)R^a$, —$OC(=O)OR^a$, —$OC(=O)N(R^a)_2$, —CN, —SCN, or —$NO_2$. In certain embodiments, Ring C is of the formula:

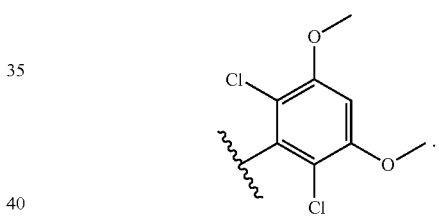

In certain embodiments, Ring C is of the formula:

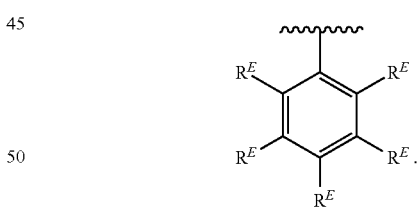

In Formula (V), Ring C may include one or more substituents $R^E$. In certain embodiments, all instances of $R^E$ are the same. In certain embodiments, at least two instances of $R^E$ are different. In certain embodiments, at least one instance of $R^E$ is halogen (e.g., F, Cl, Br, or I). In certain embodiments, at least one instance of $R^E$ is substituted or unsubstituted alkyl (e.g., substituted or unsubstituted $C_{1-6}$ alkyl). In certain embodiments, at least one instance of $R^E$ is —$CH_3$. In certain embodiments, at least one instance of $R^E$ is —$CF_3$, unsubstituted ethyl, perfluoroethyl, unsubstituted propyl, perfluoropropyl, unsubstituted butyl, perfluorobutyl, or Bn. In certain embodiments, at least one instance of $R^E$ is substituted or unsubstituted alkenyl (e.g., substituted or unsubstituted $C_{1-6}$ alkenyl). In certain embodiments, at least one instance of RE is substituted or unsubstituted alkynyl (e.g., substituted or unsubstituted $C_{1-6}$ alkynyl). In certain embodiments, at least one instance of $R^E$ is substituted or unsubstituted carbocyclyl (e.g., substituted or unsubstituted, monocyclic, 3- to 7-membered carbocyclyl). In certain embodiments, at least one instance of $R^E$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^E$ is substituted or unsubstituted aryl (e.g., substituted or unsubstituted, 6- to 10-membered aryl). In certain embodiments, at least one instance of $R^E$ is substituted or unsubstituted phenyl. In certain embodiments, at least one instance of $R^E$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^E$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^E$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^E$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^E$ is —CN, —SCN, or —$NO_2$. In certain embodiments, at least one instance of $R^E$ is —C(=$NR^a$)$R^a$, —C(=$NR^a$)$OR^a$, or —C(=$NR^a$)N($R^a$)$_2$. In certain embodiments, at least one instance of $R^E$ is —C(=O)$R^a$, —C(=O)$OR^a$, or —C(=O)N($R^a$)$_2$ (e.g., —C(=O)$NH_2$, —C(=O)NHMe, or —C(=O)$NMe_2$). In certain embodiments, at least one instance of $R^E$ is —$NR^a$C(=O)$R^a$, optionally wherein each instance of $R^a$ is independently H, substituted or unsubstituted $C_{1-6}$ alkyl, substituted or unsubstituted phenyl, or a nitrogen protecting group when attached to a nitrogen atom. In certain embodiments, at least one instance of $R^E$ is —NHC(=O)$R^a$, wherein $R^a$ is substituted or unsubstituted phenyl. In certain embodiments, at least one instance of $R^E$ is of the formula:

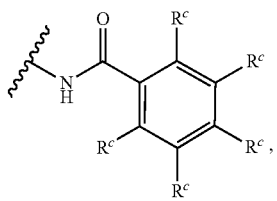

optionally wherein each instance of $R^c$ is independently H, halogen, substituted or unsubstituted $C_{1-6}$ alkyl, —OH, or —O(substituted or unsubstituted $C_{1-6}$ alkyl). In certain embodiments, at least one instance of $R^E$ is of the formula:

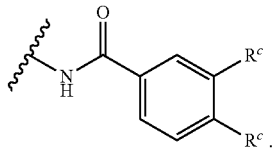

In certain embodiments, at least one instance of $R^E$ is —$NR^a$C(=O)$OR^a$ or —$NR^a$C(=O)N($R^a$)$_2$. In certain embodiments, at least one instance of $R^E$ is —OC(=O)$R^a$, —OC(=O)$OR^a$, or —OC(=O)N($R^a$)$_2$. In certain embodiments, at least one instance of $R^E$ is —$NR^a$S(=O)$R^a$, —$NR^a$S(=O)$OR^a$, or —$NR^a$S(=O)N($R^a$)$_2$, optionally wherein each instance of $R^a$ is independently H, substituted or unsubstituted $C_{1-6}$ alkyl, nitrogen protecting group when attached to a nitrogen atom, or an oxygen protecting group when attached to an oxygen atom. In certain embodiments, at least one instance of $R^E$ is —$NR^a$S(=O)$_2R^a$, —$NR^a$S(=O)$_2OR^a$, or —$NR^a$S(=O)$_2$N($R^a$)$_2$, optionally wherein each instance of $R^a$ is independently H, substituted or unsubstituted $C_{1-6}$ alkyl, nitrogen protecting group when attached to a nitrogen atom, or an oxygen protecting group when attached to an oxygen atom. In certain embodiments, at least one instance of $R^E$ is —NHS(=O)$_2R^a$, optionally wherein $R^a$ is substituted or unsubstituted $C_{1-6}$ alkyl. In certain embodiments, at least one instance of $R^E$ is —NHS(=O)$_2$Me.

In certain embodiments, m is 0. In certain embodiments, m is 1. In certain embodiments, m is 2. In certain embodiments, m is 3. In certain embodiments, m is 4. In certain embodiments, m is 5.

In certain embodiments, the compound of Formula (V) useful in the present invention is of the formula:

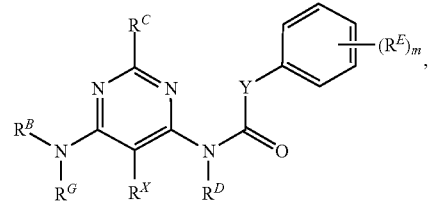

or a pharmaceutically acceptable salt, solvate, hydrate, polymorph, co-crystal, tautomer, stereoisomer, isotopically labeled derivative, or prodrug thereof.

In certain embodiments, the compound of Formula (V) useful in the present invention is of the formula:

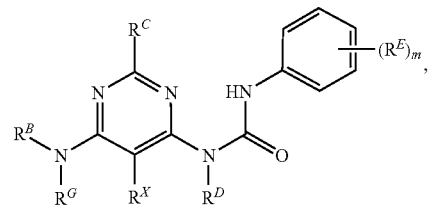

or a pharmaceutically acceptable salt, solvate, hydrate, polymorph, co-crystal, tautomer, stereoisomer, isotopically labeled derivative, or prodrug thereof.

In certain embodiments, the compound of Formula (V) useful in the present invention is of the formula:

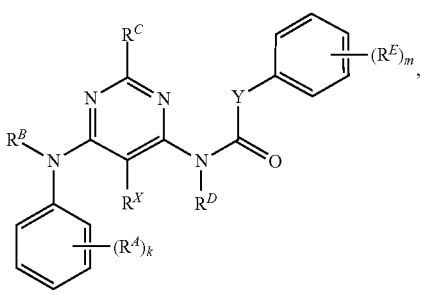

or a pharmaceutically acceptable salt, solvate, hydrate, polymorph, co-crystal, tautomer, stereoisomer, isotopically labeled derivative, or prodrug thereof.

In certain embodiments, the compound of Formula (V) useful in the present invention is of the formula:

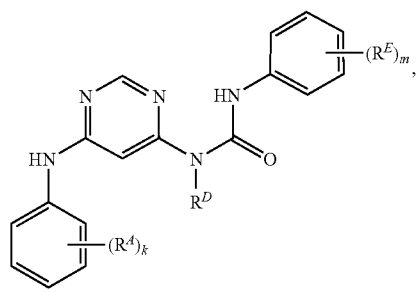

or a pharmaceutically acceptable salt, solvate, hydrate, polymorph, co-crystal, tautomer, stereoisomer, isotopically labeled derivative, or prodrug thereof.

In certain embodiments, the compound of Formula (V) useful in the present invention is not of the formula:

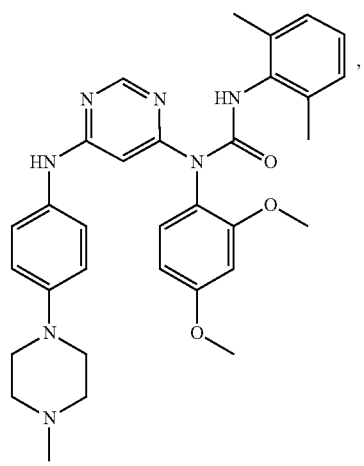 [SMILES: COc1ccc(N(C(=O)Nc2c(C)cccc2C)c2cc(Nc3ccc(N4CCN(C)CC4)cc3)ncn2)c(OC)c1]

or a pharmaceutically acceptable salt, solvate, hydrate, polymorph, co-crystal, tautomer, stereoisomer, isotopically labeled derivative, or prodrug thereof.

In certain embodiments, the compound of Formula (V) useful in the present invention is of the formula:

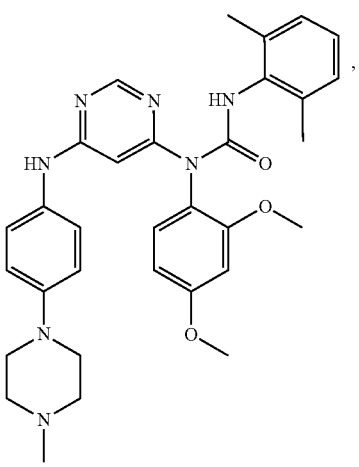

(HG-9-91-01)

or a pharmaceutically acceptable salt, solvate, hydrate, polymorph, co-crystal, tautomer, stereoisomer, isotopically labeled derivative, or prodrug thereof.

Compounds of Formula (VI)

In another aspect, the compound utilized in the present disclosure is of Formula (VI):

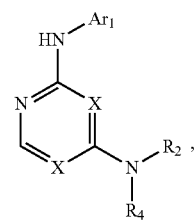

(VI)

and pharmaceutically acceptable salts, solvates, hydrates, polymorphs, co-crystals, tautomers, stereoisomers, isotopically labeled derivatives, and prodrugs thereof, wherein:

$Ar_1$ is a 5- or 6-membered hetero- or homo-cyclic aromatic ring optionally having a $C_1$-$C_4$ alkyl, or saturated heterocyclic or methyl-heterocyclic substituent;

X is separately N or CH;

$R_2$ is

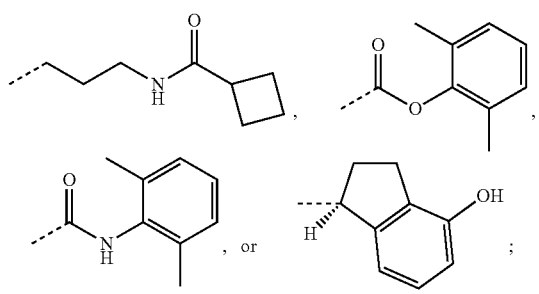

, or ;

$R_4$ is hydrogen,

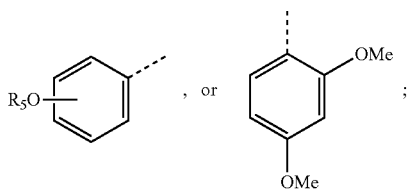

and $R_5$ is H or a $C_1$-$C_4$ alkyl.

In another aspect, the compound utilized in the present disclosure is of Formula (VI-A):

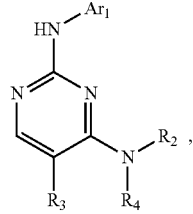

(VI-A)

and pharmaceutically acceptable salts, solvates, hydrates, polymorphs, co-crystals, tautomers, stereoisomers, isotopically labeled derivatives, and prodrugs thereof, wherein:

$Ar_1$ is a 5- or 6-membered hetero- or homo-cyclic aromatic ring optionally having a $C_1$-$C_4$ alkyl, or saturated heterocyclic or methyl-heterocyclic substituent;

$R_2$ is

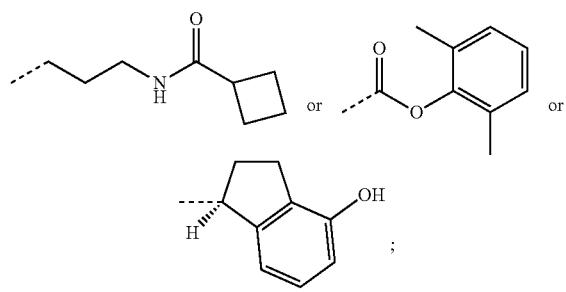

$R_3$ is hydrogen or

and $R_4$ is hydrogen,

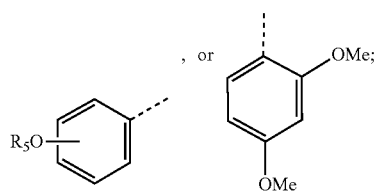

$R_5$ is H or a $C_1$-$C_4$ alkyl; or $R_3$ and $R_4$ are joined together with the intervening atoms to form a pyrrolidine ring where one or both of the free carbons are substituted with an alkyl or oxygen-containing substituent.

In certain embodiments, in Formula (VI) or (VI-A), Ar is a 5- or 6-membered hetero- or homo-cyclic aromatic ring optionally having a $C_1$-$C_4$ alkyl, or saturated heterocyclic or methyl-heterocyclic substituent. In certain embodiments, a hetero-cyclic aromatic ring is a heteroaryl ring. In certain embodiments, a homo-cyclic aromatic ring is an aryl ring. In certain embodiments, in Formula (VI) or (VI-A), Ar is optionally substituted 5- or 6-membered heteroaryl or aryl. In certain embodiments, Ar₁ is optionally substituted with a $C_1$-$C_4$ alkyl, or saturated heterocyclic or methyl-heterocyclic substituent. In certain embodiments, Ar is optionally substituted aryl. In certain embodiments, Ar₁ is optionally substituted phenyl. In certain embodiments, Ar is unsubstituted phenyl. In certain embodiments, Ar is optionally substituted 5- or 6-membered heteroaryl. In certain embodiments, Ar₁ is optionally substituted 5-membered heteroaryl. In certain embodiments, Ar₁ is optionally substituted pyrazole. In certain embodiments, Ar₁ is optionally substituted 6-membered heteroaryl. In certain embodiments, Ar₁ is optionally substituted heterocyclyl. In certain embodiments, Ar₁ is optionally substituted 5-10 membered heterocyclyl with 1-4 ring heteroatoms, wherein each heteroatom is independently selected from nitrogen, oxygen, and sulfur. In certain embodiments, Ar₁ is a saturated heterocyclic or methyl-heterocyclic substituent.

In certain embodiments, X is separately N or CH. In certain embodiments, at least one instance of X is N. In certain embodiments, at least one instance of X is CH. In certain embodiments, one instance of X is N and the other instance of X is CH.

In certain embodiments, $R_2$ is

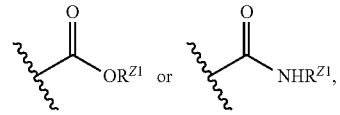

wherein $R^{Z1}$ is hydrogen, optionally substituted alkyl, optionally substituted aryl, optionally substituted heterocyclyl, or optionally substituted heteroaryl. In certain embodiments, $R_2$ is

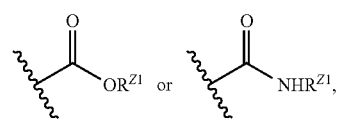

wherein $R^{Z1}$ is optionally substituted alkyl, optionally substituted aryl. In certain embodiments, $R_2$ is

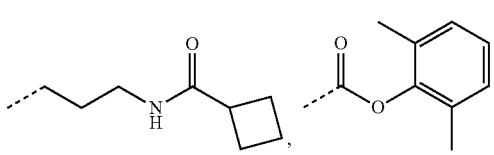

-continued

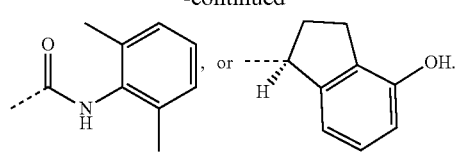

In certain embodiments, $R_2$ is

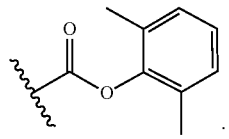

In certain embodiments, $R_2$ is

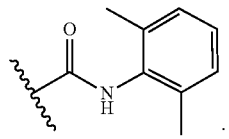

In certain embodiments, $R_2$ is

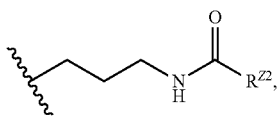

where $R^{Z2}$ is optionally substituted alkyl, optionally substituted aryl, optionally substituted carbocyclyl, or optionally substituted heterocyclyl. In certain embodiments, $R_2$ is

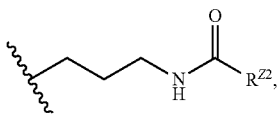

where $R^{Z2}$ is optionally substituted carbocyclyl. In certain embodiments, $R_2$ is

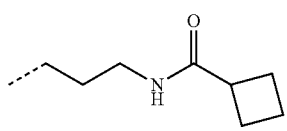

In certain embodiments, $R_2$ is optionally substituted carbocyclyl. In certain embodiments, $R_2$ is optionally substituted $C_{3-14}$ carbocyclyl. In certain embodiments, $R_2$ is optionally substituted $C_{5-10}$ carbocyclyl. In certain embodiments, $R_2$ is

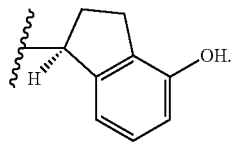 [SMILES: *[C@H]1CCc2c(O)cccc21]

In certain embodiments, in Formula (VI-A), $R_3$ is hydrogen or

In certain embodiments, in Formula (VI-A), $R_3$ is hydrogen. In certain embodiments, $R_3$ is optionally substituted carbocyclyl. In certain embodiments, $R_3$ is optionally substituted $C_{3-14}$ carbocyclyl. In certain embodiments, $R_3$ is optionally substituted $C_{3-10}$ carbocyclyl. In certain embodiments, $R_3$ is optionally substituted $C_{3-8}$ carbocyclyl. In certain embodiments, $R_3$ is

In certain embodiments, $R_4$ is optionally substituted aryl (e.g., optionally substituted phenyl or benzyl). In certain embodiments, $R_4$ is optionally substituted phenyl. In certain embodiments, $R_4$ is hydrogen. In certain embodiments, $R_4$ is

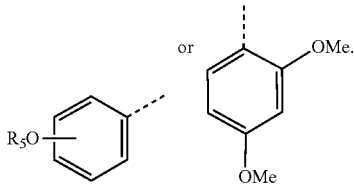

In certain embodiments, $R_5$ is H or optionally substituted alkyl. In certain embodiments, $R_4$ is

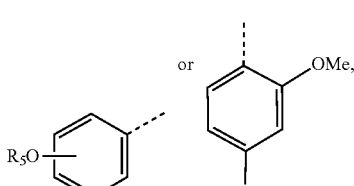

where $R_5$ is H or optionally substituted alkyl. In certain embodiments, $R_4$ is hydrogen,

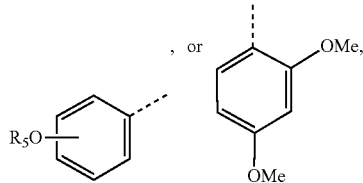

where $R_5$ is H or a $C_1$-$C_4$ alkyl.

In certain embodiments, $R_3$ and $R_4$ are joined together with the intervening atoms to form a pyrrolidine ring where at least one the free carbons is substituted with optionally substituted alkyl, optionally substituted heterocyclyl, optionally substituted heteroaryl, or —$OR^{Z1}$, wherein $R^{Z1}$ is hydrogen, optionally substituted alkyl, optionally substituted aryl, optionally substituted heterocyclyl, or optionally substituted heteroaryl. In certain embodiments, $R_3$ and $R_4$ are joined together with the intervening atoms to form a pyrrolidine ring where one or both of the free carbons are substituted with an alkyl or oxygen-containing substituent. In certain embodiments, $R_3$ and $R_4$ are joined together with the intervening atoms to form a pyrrolidine ring where both of the free carbons are substituted with optionally substituted alkyl. In certain embodiments, $R_3$ and $R_4$ are joined together with the intervening atoms to form a pyrrolidine ring where both of the free carbons are substituted with optionally substituted $C_{1-6}$ alkyl. In certain embodiments, $R_3$ and $R_4$ are joined together with the intervening atoms to form a pyrrolidine ring where both of the free carbons are substituted with unsubstituted methyl.

In certain embodiments, the compound of Formula (VI) or (VI-A) useful in the present invention is of the formula:

(MRT67307)

(MRT68771)

(MRT199665)

(KIN112)

or a pharmaceutically acceptable salt, solvate, hydrate, polymorph, co-crystal, tautomer, stereoisomer, isotopically labeled derivative, or prodrug thereof.

Compounds of Formula (VII)

In another aspect, the compound utilized in the present disclosure is of Formula (VII):

(VII)

and pharmaceutically acceptable salts, solvates, hydrates, polymorphs, co-crystals, tautomers, stereoisomers, isotopically labeled derivatives, and prodrugs thereof, wherein:

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —CN, —SCN, —$C(=NR^{A1})R^{A1}$, —$C(=NR^{A1})OR^{A1}$, —C(=NR$^{A1}$)N(R$^{A1}$)$_2$, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$C(=O)N(R$^{A1}$)$_2$, —OC(=O)R$^{A1}$, —OC(=O)OR$^{A1}$, or —OC(=O)N(R$^{A1}$)$_2$, wherein each instance of R$^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{A1}$ are joined to form a substituted or unsubstituted heterocyclic or substituted or unsubstituted heteroaryl ring;

j is 0, 1, or 2;

R$^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

R$^C$ is hydrogen, substituted or unsubstituted acyl, substituted or unsubstituted C$_{1-6}$ alkyl, or a nitrogen protecting group;

each instance of R$^D$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{D1}$, —N(R$^{D1}$)$_2$, —SR$^{D1}$, —CN, —SCN, —C(=NR$^{D1}$)R$^{D1}$, —C(=NR$^{D1}$)OR$^{D1}$, —C(=NR$^{D1}$)N(R$^{D1}$)$_2$, —C(=O)R$^{D1}$, —C(=O)OR$^{D1}$, —C(=O)N(R$^{D1}$)$_2$, —NO$_2$, —NR$^{D1}$C(=O)R$^{D1}$, —NR$^{D1}$C(=O)OR$^{D1}$, —NR$^{D1}$C(=O)N(R$^{D1}$)$_2$, —OC(=O)R$^{D1}$, —OC(=O)OR$^{D1}$, or —OC(=O)N(R$^{D1}$)$_2$, wherein each instance of R$^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{D1}$ are joined to form a substituted or unsubstituted heterocyclic or substituted or unsubstituted heteroaryl ring;

m is 0, 1, or 2;

R$^E$ is hydrogen, substituted or unsubstituted acyl, substituted or unsubstituted C$_{1-6}$ alkyl, or a nitrogen protecting group;

each instance of R$^F$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{F1}$, —N(R$^{F1}$)$_2$, —SR$^{F1}$, —CN, —SCN, —C(=NR$^{F1}$)R$^{F1}$, —C(=NR$^{F1}$)OR$^{F1}$, —C(=NR$^{F1}$)N(R$^{F1}$)$_2$, —C(=O)R$^{F1}$, —C(=O)OR$^{F1}$, —C(=O)N(R$^{F1}$)$_2$, —NO$_2$, —NR$^{F1}$C(=O)R$^{F1}$, —NR$^{F1}$C(=O)OR$^{F1}$, —NR$^{F1}$C(=O)N(R$^{F1}$)$_2$, —OC(=O)R$^{F1}$, —OC(=O)OR$^{F1}$, or —OC(=O)N(R$^{F1}$)$_2$, wherein each instance of R$^{F1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{F1}$ are joined to form a substituted or unsubstituted heterocyclic or substituted or unsubstituted heteroaryl ring; and n is 0, 1, 2, 3, 4, or 5.

Formula (VII) includes as Ring A a pyrimidinyl ring that is unsubstituted (e.g., when j is 0) or substituted with one or two substituents R$^A$ (e.g., when j is 1 or 2). In certain embodiments, the two instances of R$^A$ are different. In certain embodiments, both instances of R$^A$ are the same. In certain embodiments, at least one instance of R$^A$ is halogen. In certain embodiments, at least one instance of R$^A$ is F. In certain embodiments, at least one instance of R$^A$ is Cl. In certain embodiments, at least one instance of R$^A$ is Br. In certain embodiments, at least one instance of R$^A$ is I (iodine). In certain embodiments, at least one instance of R$^A$ is substituted alkyl. In certain embodiments, at least one instance of R$^A$ is unsubstituted alkyl. In certain embodiments, at least one instance of R$^A$ is unsubstituted C$_{1-6}$ alkyl. In certain embodiments, both instances of R$^A$ are unsubstituted C$_{1-6}$ alkyl. In certain embodiments, at least one instance of R$^A$ is substituted C$_{1-6}$ alkyl. In certain embodiments, at least one instance of R$^A$ is C$_{1-6}$ alkyl substituted with at least one halogen. In certain embodiments, at least one instance of R$^A$ is —CH$_3$. In certain embodiments, at least one instance of R$^A$ is substituted methyl. In certain embodiments, at least one instance of R$^A$ is —CH$_2$F. In certain embodiments, at least one instance of R$^A$ is —CHF$_2$. In certain embodiments, at least one instance of R$^A$ is —CF$_3$. In certain embodiments, at least one instance of R$^A$ is ethyl. In certain embodiments, at least one instance of R$^A$ is propyl. In certain embodiments, at least one instance of R$^A$ is butyl. In certain embodiments, at least one instance of R$^A$ is pentyl. In certain embodiments, at least one instance of R$^A$ is hexyl. In certain embodiments, at least one instance of R$^A$ is halogen or substituted or unsubstituted C$_{1-6}$ alkyl. In certain embodiments, at least one instance of R$^A$ is substituted alkenyl. In certain embodiments, at least one instance of R$^A$ is unsubstituted alkenyl. In certain embodiments, at least one instance of R$^A$ is substituted alkynyl. In certain embodiments, at least one instance of R$^A$ is unsubstituted alkynyl. In certain embodiments, at least one instance of R$^A$ is substituted carbocyclyl. In certain embodiments, at least one instance of R$^A$ is unsubstituted carbocyclyl. In certain embodiments, at least one instance of R$^A$ is saturated carbocyclyl. In certain embodiments, at least one instance of R$^A$ is unsaturated carbocyclyl. In certain embodiments, at least one instance of R$^A$ is monocyclic carbocyclyl. In certain embodiments, at least one instance of R$^A$ is 3- to 7-membered, monocyclic carbocyclyl. In certain embodiments, at least one instance of R$^A$ is substituted heterocyclyl. In certain embodiments, at least one instance of R$^A$ is unsubstituted heterocyclyl. In certain embodiments, at least one instance of R$^A$ is saturated heterocyclyl. In certain embodiments, at least one instance of R$^A$ is unsaturated heterocyclyl. In certain embodiments, at least one instance of R$^A$ is heterocyclyl, wherein one, two, or three atoms of the heterocyclic ring system are independently selected from the group consisting of nitrogen, oxygen, and sulfur. In certain embodiments, at least one instance of R$^A$ is monocyclic heterocyclyl. In certain embodiments, at least one instance of R$^A$ is 3- to 7-membered, monocyclic heterocyclyl. In certain embodiments, at least one instance of $R^A$ is substituted aryl. In certain embodiments, at least one instance of $R^A$ is unsubstituted aryl. In certain embodiments, at least one instance of $R^A$ is 6- to 10-membered aryl. In certain embodiments, at least one instance of $R^A$ is substituted phenyl. In certain embodiments, at least one instance of $R^A$ is unsubstituted phenyl. In certain embodiments, at least one instance of $R^A$ is substituted heteroaryl. In certain embodiments, at least one instance of $R^A$ is unsubstituted heteroaryl. In certain embodiments, at least one instance of $R^A$ is heteroaryl, wherein one, two, three, or four atoms of the heteroaryl ring system are independently selected from the group consisting of nitrogen, oxygen, and sulfur. In certain embodiments, at least one instance of $R^A$ is monocyclic heteroaryl. In certain embodiments, at least one instance of $R^A$ is 5-membered, monocyclic heteroaryl. In certain embodiments, at least one instance of $R^A$ is 6-membered, monocyclic heteroaryl. In certain embodiments, at least one instance of $R^A$ is bicyclic heteroaryl, wherein the point of attachment may be on any atom of the bicyclic heteroaryl ring system, as valency permits. In certain embodiments, at least one instance of $R^A$ is 9- or 10-membered, bicyclic heteroaryl. In certain embodiments, at least one instance of $R^A$ is —$OR^{A1}$. In certain embodiments, at least one instance of $R^A$ is —OH. In certain embodiments, at least one instance of $R^A$ is —O(substituted or unsubstituted $C_{1-6}$ alkyl). In certain embodiments, at least one instance of $R^A$ is —OMe. In certain embodiments, at least one instance of $R^A$ is —OEt. In certain embodiments, at least one instance of $R^A$ is —OPr. In certain embodiments, at least one instance of $R^A$ is —OBu. In certain embodiments, at least one instance of $R^A$ is —OBn. In certain embodiments, at least one instance of $R^A$ is —OPh. In certain embodiments, at least one instance of $R^A$ is —$SR^{A1}$. In certain embodiments, at least one instance of $R^A$ is —SH. In certain embodiments, at least one instance of $R^A$ is —SMe. In certain embodiments, at least one instance of $R^A$ is —$N(R^{A1})_2$. In certain embodiments, at least one instance of $R^A$ is —$NH_2$. In certain embodiments, at least one instance of $R^A$ is —NHMe. In certain embodiments, at least one instance of $R^A$ is —$NMe_2$. In certain embodiments, at least one instance of $R^A$ is —CN. In certain embodiments, at least one instance of $R^A$ is —SCN. In certain embodiments, at least one instance of $R^A$ is —$C(=NR^{A1})R^{A1}$, —$C(=NR^{A1})OR^{A1}$, or —$C(=NR^{A1})N(R^{A1})_2$. In certain embodiments, at least one instance of $R^A$ is —$C(=O)R^{A1}$ or —$C(=O)OR^{A1}$. In certain embodiments, at least one instance of $R^A$ is —$C(=O)N(R^{A1})_2$. In certain embodiments, at least one instance of $R^A$ is —$C(=O)NMe_2$, —$C(=O)NHMe$, or —$C(=O)NH_2$. In certain embodiments, at least one instance of $R^A$ is —$NO_2$. In certain embodiments, at least one instance of $R^A$ is —$NR^{A1}C(=O)R^{A1}$, —$NR^{A1}C(=O)OR^{A1}$, or —$NR^{A1}C(=O)N(R^{A1})_2$. In certain embodiments, at least one instance of $R^A$ is —$OC(=O)R^{A1}$, —$OC(=O)OR^{A1}$, or —$OC(=O)N(R^{A1})_2$.

In certain embodiments, at least one instance of $R^{A1}$ is H. In certain embodiments, at least one instance of $R^{A1}$ is substituted acyl. In certain embodiments, at least one instance of $R^{A1}$ is unsubstituted acyl. In certain embodiments, at least one instance of $R^{A1}$ is acetyl. In certain embodiments, at least one instance of $R^{A1}$ is substituted alkyl. In certain embodiments, at least one instance of $R^{A1}$ is unsubstituted alkyl. In certain embodiments, at least one instance of $R^{A1}$ is unsubstituted $C_{1-6}$ alkyl. In certain embodiments, at least one instance of $R^{A1}$ is methyl. In certain embodiments, at least one instance of $R^{A1}$ is ethyl. In certain embodiments, at least one instance of $R^{A1}$ is propyl. In certain embodiments, at least one instance of $R^{A1}$ is butyl. In certain embodiments, at least one instance of $R^{A1}$ is pentyl. In certain embodiments, at least one instance of $R^{A1}$ is hexyl. In certain embodiments, at least one instance of $R^{A1}$ is substituted alkenyl. In certain embodiments, at least one instance of $R^{A1}$ is unsubstituted alkenyl. In certain embodiments, at least one instance of $R^{A1}$ is substituted alkynyl. In certain embodiments, at least one instance of $R^{A1}$ is unsubstituted alkynyl. In certain embodiments, at least one instance of $R^{A1}$ is substituted or unsubstituted carbocyclyl. In certain embodiments, at least one instance of $R^{A1}$ is saturated carbocyclyl. In certain embodiments, at least one instance of $R^{A1}$ is unsaturated carbocyclyl. In certain embodiments, at least one instance of $R^{A1}$ is 3- to 7-membered, monocyclic carbocyclyl. In certain embodiments, at least one instance of $R^{A1}$ is substituted or unsubstituted heterocyclyl. In certain embodiments, at least one instance of $R^{A1}$ is saturated heterocyclyl. In certain embodiments, at least one instance of $R^{A1}$ is unsaturated heterocyclyl. In certain embodiments, at least one instance of $R^{A1}$ is heterocyclyl, wherein one, two, or three atoms of the heterocyclic ring system are independently selected from the group consisting of nitrogen, oxygen, and sulfur. In certain embodiments, at least one instance of $R^{A1}$ is 3- to 7-membered, monocyclic heterocyclyl. In certain embodiments, at least one instance of $R^{A1}$ is substituted or unsubstituted aryl. In certain embodiments, at least one instance of $R^{A1}$ is 6- to 10-membered aryl. In certain embodiments, at least one instance of $R^{A1}$ is monocyclic aryl. In certain embodiments, at least one instance of $R^{A1}$ is substituted phenyl. In certain embodiments, at least one instance of $R^{A1}$ is unsubstituted phenyl. In certain embodiments, at least one instance of $R^{A1}$ is bicyclic aryl. In certain embodiments, at least one instance of $R^A$ is substituted or unsubstituted heteroaryl. In certain embodiments, at least one instance of $R^{A1}$ is heteroaryl, wherein one, two, three, or four atoms of the heteroaryl ring system are independently selected from the group consisting of nitrogen, oxygen, and sulfur. In certain embodiments, at least one instance of $R^{A1}$ is monocyclic heteroaryl. In certain embodiments, at least one instance of $R^{A1}$ is 5- or 6-membered, monocyclic heteroaryl. In certain embodiments, at least one instance of RA is bicyclic heteroaryl, wherein the point of attachment may be on any atom of the bicyclic heteroaryl ring system, as valency permits. In certain embodiments, at least one instance of $R^{A1}$ is a nitrogen protecting group when attached to a nitrogen atom. In certain embodiments, at least one instance of $R^{A1}$ is Bn, Boc, Cbz, Fmoc, trifluoroacetyl, triphenylmethyl, acetyl, or Ts when attached to a nitrogen atom. In certain embodiments, $R^{A1}$ is an oxygen protecting group when attached to an oxygen atom. In certain embodiments, $R^{A1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A1}$ is a sulfur protecting group when attached to a sulfur atom. In certain embodiments, $R^{A1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{A1}$ are joined to form a substituted or unsubstituted heterocyclic ring. In certain embodiments, two instances of $R^{A1}$ are joined to form a saturated or unsaturated heterocyclic ring. In certain embodiments, two instances of $R^{A1}$ are joined to form a heterocyclic ring, wherein one, two, or three atoms of the heterocyclic ring system are independently selected from the group consisting of nitrogen, oxygen, and sulfur. In certain embodiments, two instances of $R^{A1}$ are joined to form a 3- to 7-membered, monocyclic heterocyclic ring. In certain embodiments, two instances of $R^{A1}$ are joined to form a substituted or unsubstituted heteroaryl ring. In certain embodiments, two instances of $R^{A1}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, j is 0. In certain embodiments, j is 1. In certain embodiments, j is 2.

Formula (VII) includes substituent $R^B$ on a nitrogen atom. In certain embodiments, $R^B$ is H. In certain embodiments, $R^B$ is substituted acyl. In certain embodiments, $R^B$ is unsubstituted acyl. In certain embodiments, $R^B$ is acetyl. In certain embodiments, $R^B$ is substituted alkyl. In certain embodiments, $R^B$ is unsubstituted alkyl. In certain embodiments, $R^B$ is unsubstituted $C_{1-6}$ alkyl. In certain embodiments, $R^B$ is substituted $C_{1-6}$ alkyl. In certain embodiments, $R^B$ is $C_{1-6}$ alkyl substituted with at least one halogen. In certain embodiments, $R^B$ is —$CH_3$. In certain embodiments, $R^B$ is substituted methyl. In certain embodiments, $R^B$ is —$CH_2F$. In certain embodiments, $R^B$ is —$CHF_2$. In certain embodiments, $R^B$ is —$CF_3$. In certain embodiments, $R^B$ is ethyl. In certain embodiments, $R^B$ is propyl. In certain embodiments, $R^B$ is butyl. In certain embodiments, $R^B$ is pentyl. In certain embodiments, $R^B$ is hexyl. In certain embodiments, $R^B$ is —$(CH_2)_{1-4}$-(Ring F), wherein Ring F is a substituted or unsubstituted, 3- to 7-membered, monocyclic heterocyclic ring. In certain embodiments, $R^B$ is —$(CH_2)_{1-4}$-(substituted or unsubstituted pyrrolidinyl). In certain embodiments, $R^B$ is of the formula:

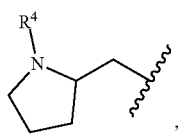

wherein $R^4$ is H, substituted or unsubstituted $C_{1-6}$ alkyl, or a nitrogen protecting group. In certain embodiments, $R^B$ is of the formula:

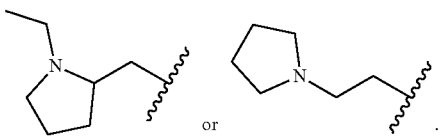

In certain embodiments, $R^B$ is —$(CH_2)_{1-4}$-(Ring F), wherein Ring F is a substituted or unsubstituted oxetanyl, substituted or unsubstituted azetidinyl, substituted or unsubstituted tetrahydrofuranyl, substituted or unsubstituted tetrahydropyranyl, substituted or unsubstituted piperidinyl, substituted or unsubstituted piperazinyl, or substituted or unsubstituted morpholinyl ring. In certain embodiments, $R^B$ is substituted alkenyl. In certain embodiments, $R^B$ is unsubstituted alkenyl. In certain embodiments, $R^B$ is substituted alkynyl. In certain embodiments, $R^B$ is unsubstituted alkynyl. In certain embodiments, $R^B$ is substituted carbocyclyl. In certain embodiments, $R^B$ is unsubstituted carbocyclyl. In certain embodiments, $R^B$ is saturated carbocyclyl. In certain embodiments, $R^B$ is unsaturated carbocyclyl. In certain embodiments, $R^B$ is monocyclic carbocyclyl. In certain embodiments, $R^B$ is 3- to 7-membered, monocyclic carbocyclyl. In certain embodiments, $R^B$ is unsubstituted cyclopropyl. In certain embodiments, $R^B$ is substituted cyclopropyl. In certain embodiments, $R^B$ is substituted heterocyclyl. In certain embodiments, $R^B$ is unsubstituted heterocyclyl. In certain embodiments, $R^B$ is saturated heterocyclyl. In certain embodiments, $R^B$ is unsaturated heterocyclyl. In certain embodiments, $R^B$ is heterocyclyl, wherein one, two, or three atoms of the heterocyclic ring system are independently selected from the group consisting of nitrogen, oxygen, and sulfur. In certain embodiments, $R^B$ is monocyclic heterocyclyl. In certain embodiments, $R^B$ is 3- to 7-membered, monocyclic heterocyclyl. In certain embodiments, $R^B$ is substituted aryl. In certain embodiments, $R^B$ is unsubstituted aryl. In certain embodiments, $R^B$ is 6- to 10-membered aryl. In certain embodiments, $R^B$ is substituted phenyl. In certain embodiments, $R^B$ is unsubstituted phenyl. In certain embodiments, $R^B$ is substituted or unsubstituted, 5- to 6-membered, monocyclic heteroaryl, wherein one, two, three, or four atoms of the heteroaryl ring system are independently nitrogen, oxygen, or sulfur. In certain embodiments, $R^B$ is substituted or unsubstituted pyrazolyl. In certain embodiments, $R^B$ is of the formula:

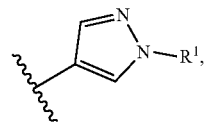

wherein $R^1$ is H, substituted or unsubstituted $C_{1-6}$ alkyl, or a nitrogen protecting group. In certain embodiments, $R^B$ is of the formula:

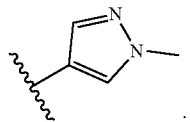 [SMILES: *c1cnn(C)c1]

In certain embodiments, $R^B$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, $R^B$ is substituted or unsubstituted pyridyl, substituted or unsubstituted pyrazinyl, substituted or unsubstituted pyrimidinyl, or substituted or unsubstituted pyridazinyl. In certain embodiments, $R^B$ is substituted or unsubstituted, 9- to 10-membered, bicyclic heteroaryl, wherein one, two, three, or four atoms of the heteroaryl ring system are independently nitrogen, oxygen, or sulfur. In certain embodiments, $R^B$ is a nitrogen protecting group. In certain embodiments, $R^B$ is Bn, Boc, Cbz, Fmoc, trifluoroacetyl, triphenylmethyl, acetyl, or Ts.

Formula (VII) includes substituent $R^C$ on a nitrogen atom. In certain embodiments, $R^C$ is H. In certain embodiments, $R^C$ is substituted acyl. In certain embodiments, $R^C$ is unsubstituted acyl. In certain embodiments, $R^C$ is acetyl. In certain embodiments, $R^C$ is unsubstituted $C_{1-6}$ alkyl. In certain embodiments, $R^C$ is substituted $C_{1-6}$ alkyl. In certain embodiments, $R^C$ is $C_{1-6}$ alkyl substituted with at least one halogen. In certain embodiments, $R^C$ is unsubstituted methyl. In certain embodiments, $R^C$ is substituted methyl. In certain embodiments, $R^C$ is —$CH_2F$. In certain embodiments, $R^C$ is —$CHF_2$. In certain embodiments, $R^C$ is —$CF_3$.

In certain embodiments, $R^C$ is ethyl. In certain embodiments, $R^C$ is propyl. In certain embodiments, $R^C$ is butyl. In certain embodiments, $R^C$ is pentyl. In certain embodiments, $R^C$ is hexyl. In certain embodiments, $R^C$ is a nitrogen protecting group. In certain embodiments, $R^C$ is Bn, Boc, Cbz, Fmoc, trifluoroacetyl, triphenylmethyl, acetyl, or Ts.

In certain embodiments, $R^B$ is substituted or unsubstituted $C_{1-6}$ alkyl, and $R^C$ is H. In certain embodiments, $R^B$ is —$(CH_2)_{1-4}$-(Ring F), wherein Ring F is a substituted or unsubstituted, 3- to 7-membered, monocyclic heterocyclic ring; and $R^C$ is H. In certain embodiments, $R^B$ is substituted or unsubstituted phenyl (e.g., para-substituted phenyl), and $R^C$ is H. In certain embodiments, $R^B$ is substituted or unsubstituted, 5- to 6-membered, monocyclic heteroaryl, wherein one, two, three, or four atoms of the heteroaryl ring system are independently nitrogen, oxygen, or sulfur; and $R^C$ is H. In certain embodiments, $R^B$ is substituted or unsubstituted pyrazolyl, and $R^C$ is H. In certain embodiments, $R^B$ is substituted or unsubstituted, 3- to 7-membered, monocyclic carbocyclyl; and $R^C$ is H. In certain embodiments, $R^B$ is substituted or unsubstituted cyclopropyl, and $R^C$ is H.

Formula (VII) includes as Ring B an imidazolyl ring that is unsubstituted (e.g., when m is 0) or substituted with one or two substituents $R^D$ (e.g., when m is 1 or 2). In certain embodiments, Ring B does not include substituents $R^D$, that is, m is 0. In certain embodiments, the two instances of $R^D$ are different. In certain embodiments, both instances of $R^D$ are the same. In certain embodiments, at least one instance of $R^D$ is halogen. In certain embodiments, at least one instance of $R^D$ is F. In certain embodiments, at least one instance of $R^D$ is Cl. In certain embodiments, at least one instance of $R^D$ is Br. In certain embodiments, at least one instance of $R^D$ is I (iodine). In certain embodiments, at least one instance of $R^D$ is substituted alkyl. In certain embodiments, at least one instance of $R^D$ is unsubstituted alkyl. In certain embodiments, at least one instance of $R^D$ is unsubstituted $C_{1-6}$ alkyl. In certain embodiments, both instances of $R^D$ are unsubstituted $C_{1-6}$ alkyl. In certain embodiments, at least one instance of $R^D$ is substituted $C_{1-6}$ alkyl. In certain embodiments, at least one instance of $R^D$ is $C_{1-6}$ alkyl substituted with at least one halogen. In certain embodiments, at least one instance of $R^D$ is —$CH_3$. In certain embodiments, at least one instance of $R^D$ is substituted methyl. In certain embodiments, at least one instance of $R^D$ is —$CH_2F$. In certain embodiments, at least one instance of $R^D$ is —$CHF_2$. In certain embodiments, at least one instance of $R^D$ is —$CF_3$. In certain embodiments, at least one instance of $R^D$ is ethyl. In certain embodiments, at least one instance of $R^D$ is propyl. In certain embodiments, at least one instance of $R^D$ is butyl. In certain embodiments, at least one instance of $R^D$ is pentyl. In certain embodiments, at least one instance of $R^D$ is hexyl. In certain embodiments, at least one instance of $R^D$ is halogen or substituted or unsubstituted $C_{1-6}$ alkyl. In certain embodiments, at least one instance of $R^D$ is substituted alkenyl. In certain embodiments, at least one instance of $R^D$ is unsubstituted alkenyl. In certain embodiments, at least one instance of $R^D$ is substituted alkynyl. In certain embodiments, at least one instance of $R^D$ is unsubstituted alkynyl. In certain embodiments, at least one instance of $R^D$ is substituted carbocyclyl. In certain embodiments, at least one instance of $R^D$ is unsubstituted carbocyclyl. In certain embodiments, at least one instance of $R^D$ is saturated carbocyclyl. In certain embodiments, at least one instance of $R^D$ is unsaturated carbocyclyl. In certain embodiments, at least one instance of $R^D$ is monocyclic carbocyclyl. In certain embodiments, at least one instance of $R^D$ is 3- to 7-membered, monocyclic carbocyclyl. In certain embodiments, at least one instance of $R^D$ is substituted heterocyclyl. In certain embodiments, at least one instance of $R^D$ is unsubstituted heterocyclyl. In certain embodiments, at least one instance of $R^D$ is saturated heterocyclyl. In certain embodiments, at least one instance of $R^D$ is unsaturated heterocyclyl. In certain embodiments, at least one instance of $R^D$ is heterocyclyl, wherein one, two, or three atoms of the heterocyclic ring system are independently selected from the group consisting of nitrogen, oxygen, and sulfur. In certain embodiments, at least one instance of $R^D$ is monocyclic heterocyclyl. In certain embodiments, at least one instance of $R^D$ is 3- to 7-membered, monocyclic heterocyclyl. In certain embodiments, at least one instance of $R^D$ is substituted aryl. In certain embodiments, at least one instance of $R^D$ is unsubstituted aryl. In certain embodiments, at least one instance of $R^D$ is 6- to 10-membered aryl. In certain embodiments, at least one instance of $R^D$ is substituted phenyl. In certain embodiments, at least one instance of $R^D$ is unsubstituted phenyl. In certain embodiments, at least one instance of $R^D$ is substituted heteroaryl. In certain embodiments, at least one instance of $R^D$ is unsubstituted heteroaryl. In certain embodiments, at least one instance of $R^D$ is heteroaryl, wherein one, two, three, or four atoms of the heteroaryl ring system are independently selected from the group consisting of nitrogen, oxygen, and sulfur. In certain embodiments, at least one instance of $R^D$ is monocyclic heteroaryl. In certain embodiments, at least one instance of $R^D$ is 5-membered, monocyclic heteroaryl. In certain embodiments, at least one instance of $R^D$ is 6-membered, monocyclic heteroaryl. In certain embodiments, at least one instance of $R^D$ is bicyclic heteroaryl, wherein the point of attachment may be on any atom of the bicyclic heteroaryl ring system, as valency permits. In certain embodiments, at least one instance of $R^D$ is 9- or 10-membered, bicyclic heteroaryl. In certain embodiments, at least one instance of $R^D$ is —$OR^{D1}$. In certain embodiments, at least one instance of $R^D$ is —OH. In certain embodiments, at least one instance of $R^D$ is —O(substituted or unsubstituted $C_{1-6}$ alkyl). In certain embodiments, at least one instance of $R^D$ is —OMe. In certain embodiments, at least one instance of $R^D$ is —OEt. In certain embodiments, at least one instance of $R^D$ is —OPr. In certain embodiments, at least one instance of $R^D$ is —OBu. In certain embodiments, at least one instance of $R^D$ is —OBn. In certain embodiments, at least one instance of $R^D$ is —OPh. In certain embodiments, at least one instance of $R^D$ is —$SR^{D1}$. In certain embodiments, at least one instance of $R^D$ is —SH. In certain embodiments, at least one instance of $R^D$ is —SMe. In certain embodiments, at least one instance of $R^D$ is —$N(R^{D1})_2$. In certain embodiments, at least one instance of $R^D$ is —$NH_2$. In certain embodiments, at least one instance of $R^D$ is —NHMe. In certain embodiments, at least one instance of $R^D$ is —$NMe_2$. In certain embodiments, at least one instance of $R^D$ is —CN. In certain embodiments, at least one instance of $R^D$ is —SCN. In certain embodiments, at least one instance of $R^D$ is —$C(=NR^{D1})R^{D1}$, —$C(=NR^{D1})OR^{D1}$, or —$C(=NR^{D1})N(R^{D1})_2$. In certain embodiments, at least one instance of $R^D$ is —$C(=O)R^{D1}$ or —$C(=O)OR^{D1}$. In certain embodiments, at least one instance of $R^D$ is —$C(=O)N(R^{D1})_2$. In certain embodiments, at least one instance of $R^B$ is —$C(=O)NMe_2$, —$C(=O)NHMe$, or —$C(=O)NH_2$. In certain embodiments, at least one instance of $R^{D1}$ is —$NO_2$. In certain embodiments, at least one instance of $R^D$ is —$NR^{D1}C(=O)R^{D1}$, —$NR^{D1}C(=O)OR^{D1}$, or —$NR^{D1}C(=O)N(R^{D1})_2$. In certain embodiments, at least one instance of $R^D$ is —OC(=O)$R^{D1}$, —OC(=O)O$R^{D1}$, or —OC(=O)N($R^{D1}$)$_2$.

In certain embodiments, at least one instance of $R^{D1}$ is H. In certain embodiments, at least one instance of $R^{D1}$ is substituted acyl. In certain embodiments, at least one instance of $R^{D1}$ is unsubstituted acyl. In certain embodiments, at least one instance of $R^{D1}$ is acetyl. In certain embodiments, at least one instance of $R^{D1}$ is substituted alkyl. In certain embodiments, at least one instance of $R^{D1}$ is unsubstituted alkyl. In certain embodiments, at least one instance of $R^{D1}$ is unsubstituted $C_{1-6}$ alkyl. In certain embodiments, at least one instance of $R^{D1}$ is methyl. In certain embodiments, at least one instance of $R^{D1}$ is ethyl. In certain embodiments, at least one instance of $R^{D1}$ is propyl. In certain embodiments, at least one instance of $R^{D1}$ is butyl. In certain embodiments, at least one instance of $R^{D1}$ is pentyl. In certain embodiments, at least one instance of $R^{D1}$ is hexyl. In certain embodiments, at least one instance of $R^{D1}$ is substituted alkenyl. In certain embodiments, at least one instance of $R^{D1}$ is unsubstituted alkenyl. In certain embodiments, at least one instance of $R^{D1}$ is substituted alkynyl. In certain embodiments, at least one instance of $R^{D1}$ is unsubstituted alkynyl. In certain embodiments, at least one instance of $R^{D1}$ is substituted or unsubstituted carbocyclyl. In certain embodiments, at least one instance of $R^{D1}$ is saturated carbocyclyl. In certain embodiments, at least one instance of $R^{D1}$ is unsaturated carbocyclyl. In certain embodiments, at least one instance of $R^{D1}$ is 3- to 7-membered, monocyclic carbocyclyl. In certain embodiments, at least one instance of $R^{D1}$ is substituted or unsubstituted heterocyclyl. In certain embodiments, at least one instance of $R^{D1}$ is saturated heterocyclyl. In certain embodiments, at least one instance of $R^{D1}$ is unsaturated heterocyclyl. In certain embodiments, at least one instance of $R^{D1}$ is heterocyclyl, wherein one, two, or three atoms of the heterocyclic ring system are independently selected from the group consisting of nitrogen, oxygen, and sulfur. In certain embodiments, at least one instance of $R^{D1}$ is 3- to 7-membered, monocyclic heterocyclyl. In certain embodiments, at least one instance of $R^{D1}$ is substituted or unsubstituted aryl. In certain embodiments, at least one instance of $R^{D1}$ is 6- to 10-membered aryl. In certain embodiments, at least one instance of $R^{D1}$ is monocyclic aryl. In certain embodiments, at least one instance of $R^{D1}$ is substituted phenyl. In certain embodiments, at least one instance of $R^{D1}$ is unsubstituted phenyl. In certain embodiments, at least one instance of $R^{D1}$ is bicyclic aryl. In certain embodiments, at least one instance of $R^{D1}$ is substituted or unsubstituted heteroaryl. In certain embodiments, at least one instance of $R^{D1}$ is heteroaryl, wherein one, two, three, or four atoms of the heteroaryl ring system are independently selected from the group consisting of nitrogen, oxygen, and sulfur. In certain embodiments, at least one instance of $R^{D1}$ is monocyclic heteroaryl. In certain embodiments, at least one instance of $R^{D1}$ is 5- or 6-membered, monocyclic heteroaryl. In certain embodiments, at least one instance of $R^{D1}$ is bicyclic heteroaryl, wherein the point of attachment may be on any atom of the bicyclic heteroaryl ring system, as valency permits. In certain embodiments, at least one instance of $R^{D1}$ is a nitrogen protecting group when attached to a nitrogen atom. In certain embodiments, at least one instance of $R^{D1}$ is Bn, Boc, Cbz, Fmoc, trifluoroacetyl, triphenylmethyl, acetyl, or Ts when attached to a nitrogen atom. In certain embodiments, $R^{D1}$ is an oxygen protecting group when attached to an oxygen atom. In certain embodiments, $R^{D1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D1}$ is a sulfur protecting group when attached to a sulfur atom. In certain embodiments, $R^{D1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{D1}$ are joined to form a substituted or unsubstituted heterocyclic ring. In certain embodiments, two instances of $R^{D1}$ are joined to form a saturated or unsaturated heterocyclic ring. In certain embodiments, two instances of $R^{D1}$ are joined to form a heterocyclic ring, wherein one, two, or three atoms of the heterocyclic ring system are independently selected from the group consisting of nitrogen, oxygen, and sulfur. In certain embodiments, two instances of $R^{D1}$ are joined to form a 3- to 7-membered, monocyclic heterocyclic ring. In certain embodiments, two instances of $R^{D1}$ are joined to form a substituted or unsubstituted heteroaryl ring. In certain embodiments, two instances of $R^{D1}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, m is 0. In certain embodiments, m is 1. In certain embodiments, m is 2.

Formula (VII) includes substituent $R^E$ on a nitrogen atom. In certain embodiments, $R^E$ is H. In certain embodiments, $R^E$ is substituted acyl. In certain embodiments, $R^E$ is unsubstituted acyl. In certain embodiments, $R^E$ is acetyl. In certain embodiments, $R^E$ is unsubstituted $C_{1-6}$ alkyl. In certain embodiments, $R^E$ is substituted $C_{1-6}$ alkyl. In certain embodiments, $R^E$ is $C_{1-6}$ alkyl substituted with at least one halogen. In certain embodiments, $R^E$ is unsubstituted methyl. In certain embodiments, $R^E$ is substituted methyl. In certain embodiments, $R^E$ is —CH$_2$F. In certain embodiments, $R^E$ is —CHF$_2$. In certain embodiments, $R^E$ is —CF$_3$. In certain embodiments, $R^E$ is ethyl. In certain embodiments, $R^E$ is propyl. In certain embodiments, $R^E$ is butyl. In certain embodiments, $R^E$ is pentyl. In certain embodiments, $R^E$ is hexyl. In certain embodiments, $R^E$ is a nitrogen protecting group. In certain embodiments, $R^E$ is Bn, Boc, Cbz, Fmoc, trifluoroacetyl, triphenylmethyl, acetyl, or Ts.

In certain embodiments, each of $R^C$ and $R^E$ is H.

Formula (VII) includes as Ring C a phenyl ring that is unsubstituted (e.g., when n is 0) or substituted with one or more substituents $R^F$ (e.g., when n is 1, 2, 3, 4, or 5). In certain embodiments, Ring C is of the formula:

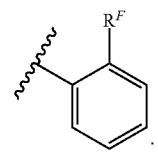

In certain embodiments, Ring C is of the formula:

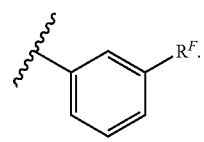

In certain embodiments, Ring C is of the formula:

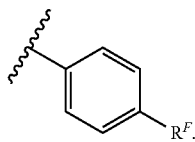

In certain embodiments, Ring C is of the formula:

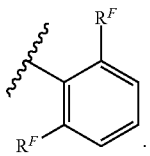

In certain embodiments, Ring C is of the formula:

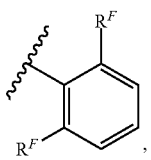

wherein each instance of $R^F$ is independently halogen or substituted or unsubstituted $C_{1-6}$ alkyl. In certain embodiments, Ring C is of the formula:

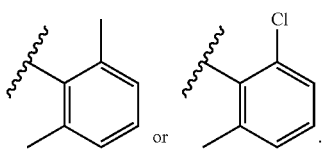

In certain embodiments, Ring C is of the formula:

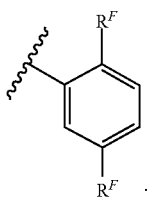

In certain embodiments, Ring C is of the formula:

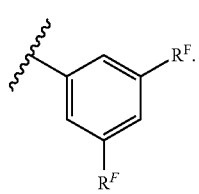

In certain embodiments, Ring C is of the formula:

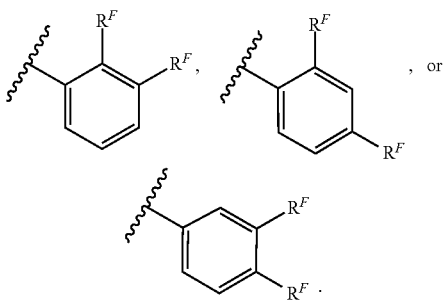

In certain embodiments, at least two instances of $R^F$ are different. In certain embodiments, all instances of $R^F$ are the same. In certain embodiments, at least one instance of $R^F$ is halogen. In certain embodiments, at least one instance of $R^F$ is F. In certain embodiments, at least one instance of $R^F$ is Cl. In certain embodiments, at least one instance of $R^F$ is Br. In certain embodiments, at least one instance of $R^F$ is I (iodine). In certain embodiments, at least one instance of $R^F$ is substituted alkyl. In certain embodiments, at least one instance of $R^F$ is unsubstituted alkyl. In certain embodiments, at least one instance of $R^F$ is unsubstituted $C_{1-6}$ alkyl. In certain embodiments, all instances of $R^F$ are unsubstituted $C_{1-6}$ alkyl. In certain embodiments, at least one instance of $R^F$ is substituted $C_{1-6}$ alkyl. In certain embodiments, at least one instance of $R^F$ is $C_{1-6}$ alkyl substituted with at least one halogen. In certain embodiments, at least one instance of $R^F$ is —$CH_3$. In certain embodiments, all instances of $R^F$ are —$CH_3$. In certain embodiments, at least one instance of $R^F$ is substituted methyl. In certain embodiments, at least one instance of $R^F$ is —$CH_2F$. In certain embodiments, at least one instance of $R^F$ is —$CHF_2$. In certain embodiments, at least one instance of $R^F$ is —$CF_3$. In certain embodiments, at least one instance of $R^F$ is ethyl. In certain embodiments, at least one instance of $R^F$ is propyl. In certain embodiments, at least one instance of $R^F$ is butyl. In certain embodiments, at least one instance of $R^F$ is pentyl. In certain embodiments, at least one instance of $R^F$ is hexyl. In certain embodiments, at least one instance of $R^F$ is substituted alkenyl. In certain embodiments, at least one instance of $R^F$ is unsubstituted alkenyl. In certain embodiments, at least one instance of $R^F$ is substituted alkynyl. In certain embodiments, at least one instance of $R^F$ is unsubstituted alkynyl. In certain embodiments, at least one instance of $R^F$ is substituted carbocyclyl. In certain embodiments, at least one instance of $R^F$ is unsubstituted carbocyclyl. In certain embodiments, at least one instance of $R^F$ is saturated carbocyclyl. In certain embodiments, at least one instance of $R^F$ is unsaturated carbocyclyl. In certain embodiments, at least one instance of $R^F$ is monocyclic carbocyclyl. In certain embodiments, at least one instance of $R^F$ is 3- to 7-membered, monocyclic carbocyclyl. In certain embodiments, at least one instance of $R^F$ is substituted heterocyclyl. In certain embodiments, at least one instance of $R^F$ is unsubstituted heterocyclyl. In certain embodiments, at least one instance of $R^F$ is saturated heterocyclyl. In certain embodiments, at least one instance of $R^F$ is unsaturated heterocyclyl. In certain embodiments, at least one instance of $R^F$ is heterocyclyl, wherein one, two, or three atoms of the heterocyclic ring system are independently selected from the group consisting of nitrogen, oxygen, and sulfur. In certain embodiments, at least one instance of $R^F$ is monocyclic heterocyclyl. In certain embodiments, at least one instance of $R^F$ is 3- to 7-membered, monocyclic heterocyclyl. In certain embodiments, at least one instance of $R^F$ is substituted aryl. In certain embodiments, at least one instance of $R^F$ is unsubstituted aryl. In certain embodiments, at least one instance of $R^F$ is 6- to 10-membered aryl. In certain embodiments, at least one instance of $R^F$ is substituted phenyl. In certain embodiments, at least one instance of $R^F$ is unsubstituted phenyl. In certain embodiments, at least one instance of $R^F$ is substituted heteroaryl. In certain embodiments, at least one instance of $R^F$ is unsubstituted heteroaryl. In certain embodiments, at least one instance of $R^F$ is heteroaryl, wherein one, two, three, or four atoms of the heteroaryl ring system are independently selected from the group consisting of nitrogen, oxygen, and sulfur. In certain embodiments, at least one instance of $R^F$ is monocyclic heteroaryl. In certain embodiments, at least one instance of $R^F$ is 5-membered, monocyclic heteroaryl. In certain embodiments, at least one instance of $R^F$ is 6-membered, monocyclic heteroaryl. In certain embodiments, at least one instance of $R^F$ is bicyclic heteroaryl, wherein the point of attachment may be on any atom of the bicyclic heteroaryl ring system, as valency permits. In certain embodiments, at least one instance of $R^F$ is 9- or 10-membered, bicyclic heteroaryl. In certain embodiments, at least one instance of $R^F$ is —$OR^{F1}$. In certain embodiments, at least one instance of $R^F$ is —OH. In certain embodiments, at least one instance of $R^F$ is —O(substituted or unsubstituted $C_{1-6}$ alkyl). In certain embodiments, at least one instance of $R^F$ is —OMe. In certain embodiments, at least one instance of $R^F$ is —OEt. In certain embodiments, at least one instance of $R^F$ is —OPr. In certain embodiments, at least one instance of $R^F$ is —OBu. In certain embodiments, at least one instance of $R^F$ is —OBn. In certain embodiments, at least one instance of $R^F$ is —OPh. In certain embodiments, at least one instance of $R^F$ is —$SR^{F1}$. In certain embodiments, at least one instance of $R^F$ is —SH. In certain embodiments, at least one instance of $R^F$ is —SMe. In certain embodiments, at least one instance of $R^F$ is —$N(R^{F1})_2$. In certain embodiments, at least one instance of $R^F$ is —$NH_2$. In certain embodiments, at least one instance of $R^F$ is —NHMe. In certain embodiments, at least one instance of $R^F$ is —$NMe_2$. In certain embodiments, at least one instance of $R^F$ is —CN. In certain embodiments, at least one instance of $R^F$ is —SCN. In certain embodiments, at least one instance of $R^F$ is —$C(=NR^{F1})R^{F1}$, —$C(=NR^{F1})OR^{F1}$, or —$C(=NR^{F1})N(R^{F1})_2$. In certain embodiments, at least one instance of $R^F$ is —$C(=O)R^{F1}$ or —$C(=O)OR^{F1}$. In certain embodiments, at least one instance of $R^F$ is —$C(=O)N(R^{F1})_2$.

In certain embodiments, at least one instance of $R^F$ is —$C(=O)N(R^{F1})_2$, wherein each instance of $R^{F1}$ is independently hydrogen, substituted or unsubstituted $C_{1-6}$ alkyl, substituted or unsubstituted phenyl, or a nitrogen protecting group. In certain embodiments, at least one instance of $R^F$ is —$C(=O)NHR^{F1}$, wherein $R^{F1}$ is substituted or unsubstituted phenyl. In certain embodiments, at least one instance of $R^F$ is —$C(=O)NHR^{F1}$, wherein $R^{F1}$ is phenyl substituted with one, two, three, four, or five substituents independently selected from the group consisting of halogen and substituted or unsubstituted $C_{1-6}$ alkyl. In certain embodiments, at least one instance of $R^F$ is —$C(=O)NMeR^{F1}$, wherein $R^{F1}$ is substituted or unsubstituted phenyl. In certain embodiments, at least one instance of $R^F$ is —$C(=O)NMeR^{F1}$, wherein $R^{F1}$ is phenyl substituted with one, two, three, four, or five substituents independently selected from the group consisting of halogen and substituted or unsubstituted $C_{1-6}$ alkyl. In certain embodiments, at least one instance of $R^F$ is —$C(=O)NMe_2$, —$C(=O)NHMe$, or —$C(=O)NH_2$. In certain embodiments, at least one instance of $R^F$ is —$NO_2$. In certain embodiments, at least one instance of $R^F$ is —$NR^{F1}C(=O)R^{F1}$, —$NR^{F1}C(=O)OR^{F1}$, or —$NR^{F1}C(=O)N(R^{F1})_2$. In certain embodiments, at least one instance of $R^F$ is —$OC(=O)R^{F1}$, —$OC(=O)OR^{F1}$, or —$OC(=O)N(R^{F1})_2$.

In certain embodiments, at least one instance of $R^F$ is halogen, substituted or unsubstituted $C_{1-6}$ alkyl, or —$OR^{F1}$. In certain embodiments, at least one instance of $R^F$ is halogen, substituted or unsubstituted $C_{1-6}$ alkyl, or —$OR^{F1}$, wherein $R^{F1}$ is hydrogen, substituted or unsubstituted $C_{1-6}$ alkyl, or an oxygen protecting group. In certain embodiments, at least one instance of $R^F$ is halogen, unsubstituted $C_{1-6}$ alkyl, or —$OR^{F1}$, wherein $R^{F1}$ is unsubstituted $C_{1-6}$ alkyl. In certain embodiments, at least one instance of $R^F$ is —$CH_3$ or Cl.

In certain embodiments, at least one instance of $R^{F1}$ is H. In certain embodiments, at least one instance of $R^{F1}$ is substituted acyl. In certain embodiments, at least one instance of $R^{F1}$ is unsubstituted acyl. In certain embodiments, at least one instance of $R^{F1}$ is acetyl. In certain embodiments, at least one instance of $R^{F1}$ is substituted alkyl. In certain embodiments, at least one instance of $R^{F1}$ is unsubstituted alkyl. In certain embodiments, at least one instance of $R^{F1}$ is unsubstituted $C_{1-6}$ alkyl. In certain embodiments, at least one instance of $R^{F1}$ is methyl. In certain embodiments, at least one instance of $R^{F1}$ is ethyl. In certain embodiments, at least one instance of $R^{F1}$ is propyl. In certain embodiments, at least one instance of $R^{F1}$ is butyl. In certain embodiments, at least one instance of $R^{F1}$ is pentyl. In certain embodiments, at least one instance of $R^{F1}$ is hexyl. In certain embodiments, at least one instance of $R^{F1}$ is substituted alkenyl. In certain embodiments, at least one instance of $R^{F1}$ is unsubstituted alkenyl. In certain embodiments, at least one instance of $R^{F1}$ is substituted alkynyl. In certain embodiments, at least one instance of $R^{F1}$ is unsubstituted alkynyl. In certain embodiments, at least one instance of $R^{F1}$ is substituted or unsubstituted carbocyclyl. In certain embodiments, at least one instance of $R^{F1}$ is saturated carbocyclyl. In certain embodiments, at least one instance of $R^{F1}$ is unsaturated carbocyclyl. In certain embodiments, at least one instance of $R^{F1}$ is 3- to 7-membered, monocyclic carbocyclyl. In certain embodiments, at least one instance of $R^{F1}$ is substituted or unsubstituted heterocyclyl. In certain embodiments, at least one instance of $R^{F1}$ is saturated heterocyclyl. In certain embodiments, at least one instance of $R^{F1}$ is unsaturated heterocyclyl. In certain embodiments, at least one instance of $R^{F1}$ is heterocyclyl, wherein one, two, or three atoms of the heterocyclic ring system are independently selected from the group consisting of nitrogen, oxygen, and sulfur. In certain embodiments, at least one instance of $R^{F1}$ is 3- to 7-membered, monocyclic heterocyclyl. In certain embodiments, at least one instance of $R^{F1}$ is substituted or unsubstituted aryl. In certain embodiments, at least one instance of $R^{F1}$ is 6- to 10-membered aryl. In certain embodiments, at least one instance of $R^{F1}$ is monocyclic aryl. In certain embodiments, at least one instance of $R^{F1}$ is substituted phenyl. In certain embodiments, at least one instance of $R^{F1}$ is unsubstituted phenyl. In certain embodiments, at least one instance of $R^{F1}$ is bicyclic aryl. In certain embodiments, at least one instance of $R^{F1}$ is substituted or unsubstituted heteroaryl. In certain embodiments, at least one instance of $R^{F1}$ is heteroaryl, wherein one, two, three, or four atoms of the heteroaryl ring system are independently selected from the group consisting of nitrogen, oxygen, and sulfur. In certain embodiments, at least one instance of $R^{F1}$ is monocyclic heteroaryl. In certain embodiments, at least one instance of $R^{F1}$ is 5- or 6-membered, monocyclic heteroaryl. In certain embodiments, at least one instance of $R^{F1}$ is bicyclic heteroaryl, wherein the point of attachment may be on any atom of the bicyclic heteroaryl ring system, as valency permits. In certain embodiments, at least one instance of $R^{F1}$ is a nitrogen protecting group when attached to a nitrogen atom. In certain embodiments, at least one instance of $R^{F1}$ is Bn, Boc, Cbz, Fmoc, trifluoroacetyl, triphenylmethyl, acetyl, or Ts when attached to a nitrogen atom. In certain embodiments, $R^{F1}$ is an oxygen protecting group when attached to an oxygen atom. In certain embodiments, $R^{F1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{F1}$ is a sulfur protecting group when attached to a sulfur atom. In certain embodiments, $R^{F1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{F1}$ are joined to form a substituted or unsubstituted heterocyclic ring. In certain embodiments, two instances of $R^{F1}$ are joined to form a saturated or unsaturated heterocyclic ring. In certain embodiments, two instances of $R^{F1}$ are joined to form a heterocyclic ring, wherein one, two, or three atoms of the heterocyclic ring system are independently selected from the group consisting of nitrogen, oxygen, and sulfur. In certain embodiments, two instances of $R^{F1}$ are joined to form a 3- to 7-membered, monocyclic heterocyclic ring. In certain embodiments, two instances of $R^{F1}$ are joined to form a substituted or unsubstituted heteroaryl ring. In certain embodiments, two instances of $R^{F1}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, n is 0. In certain embodiments, n is 1. In certain embodiments, n is 2. In certain embodiments, n is 3. In certain embodiments, n is 4. In certain embodiments, n is 5.

In certain embodiments, n is 1; and $R^F$ is —C(=O)N($R^{F1}$)$_2$. In certain embodiments, n is 1; and $R^F$ is —C(=O)N($R^{F1}$)$_2$, wherein each instance of $R^{F1}$ is independently hydrogen, substituted or unsubstituted $C_{1-6}$ alkyl, substituted or unsubstituted phenyl, or a nitrogen protecting group. In certain embodiments, n is 2; and each instance of $R^F$ is independently halogen or substituted or unsubstituted $C_{1-6}$ alkyl. In certain embodiments, n is 2; and each instance of $R^F$ is independently halogen or unsubstituted $C_{1-6}$ alkyl (e.g., —CH$_3$). In certain embodiments, n is 2; and each instance of $R^F$ is independently halogen, substituted or unsubstituted $C_{1-6}$ alkyl, —OR$^{F1}$, or —C(=O)N($R^{F1}$)$_2$. In certain embodiments, n is 2; and each instance of $R^F$ is independently halogen, substituted or unsubstituted $C_{1-6}$ alkyl, —OR$^{F1}$, or —C(=O)N($R^{F1}$)$_2$, wherein each instance of $R^{F1}$ is independently hydrogen, substituted or unsubstituted $C_{1-6}$ alkyl, substituted or unsubstituted phenyl, an oxygen protecting group when attached to an oxygen atom, or a nitrogen protecting group when attached to a nitrogen atom.

In certain embodiments, the compound of Formula (VII) is of Formula (VII-A):

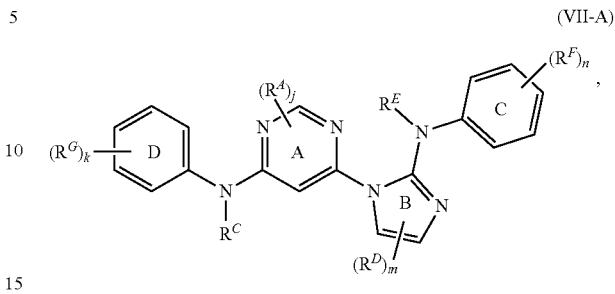

(VII-A)

or a pharmaceutically acceptable salt, solvate, hydrate, polymorph, co-crystal, tautomer, stereoisomer, isotopically labeled derivative, or prodrug thereof, wherein:

each instance of $R^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{G1}$, —N($R^{G1}$)$_2$, —SR$^{G1}$, —CN, —SCN, —C(=NR$^{G1}$)R$^{G1}$, —C(=NR$^{G1}$)OR$^{G1}$, —C(=NR$^{G1}$)N($R^{G1}$)$_2$, —C(=O)R$^{G1}$, —C(=O)OR$^{G1}$, —C(=O)N($R^{G1}$)$_2$, —NO$_2$, —NR$^{G1}$C(=O)R$^{G1}$, —NR$^{G1}$C(=O)OR$^{G1}$, —NR$^{G1}$C(=O)N(RGI)$_2$, —OC(=O)R$^{G1}$, —OC(=O)OR$^{G1}$, or —OC(=O)N($R^{G1}$)$_2$, wherein each instance of $R^{G1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{G1}$ are joined to form a substituted or unsubstituted heterocyclic or substituted or unsubstituted heteroaryl ring; and k is 0, 1, 2, 3, 4, or 5.

Formula (VII-A) includes as Ring D a phenyl ring that is unsubstituted (e.g., when k is 0) or substituted with one or more substituents $R^G$ (e.g., when k is 1, 2, 3, 4, or 5). In certain embodiments, Ring D is of the formula:

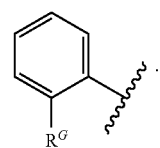

In certain embodiments, Ring D is of the formula:

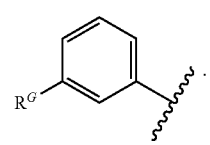

In certain embodiments, Ring D is of the formula:

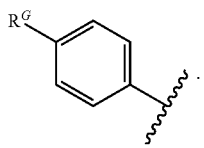

In certain embodiments, Ring D is of the formula:

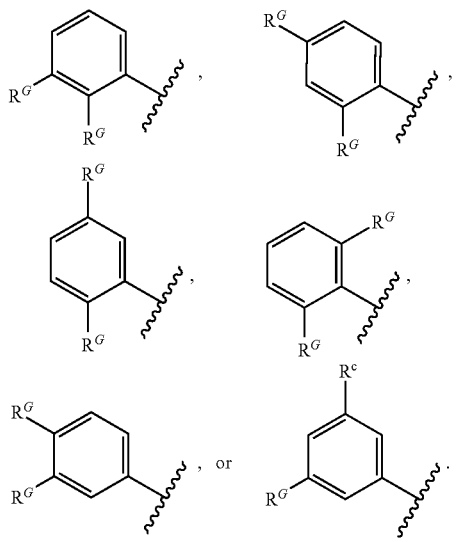

In certain embodiments, at least two instances of $R^G$ are different. In certain embodiments, all instances of $R^G$ are the same. In certain embodiments, at least one instance of $R^G$ is halogen. In certain embodiments, at least one instance of $R^G$ is F. In certain embodiments, at least one instance of $R^G$ is Cl. In certain embodiments, at least one instance of $R^G$ is Br. In certain embodiments, at least one instance of $R^G$ is I (iodine). In certain embodiments, at least one instance of $R^G$ is substituted alkyl. In certain embodiments, at least one instance of $R^G$ is unsubstituted alkyl. In certain embodiments, at least one instance of $R^G$ is unsubstituted $C_{1-6}$ alkyl. In certain embodiments, all instances of $R^G$ are unsubstituted $C_{1-6}$ alkyl. In certain embodiments, at least one instance of $R^G$ is substituted $C_{1-6}$ alkyl. In certain embodiments, at least one instance of $R^G$ is $C_{1-6}$ alkyl substituted with at least one halogen. In certain embodiments, at least one instance of $R^G$ is —$CH_3$. In certain embodiments, all instances of $R^G$ are —$CH_3$. In certain embodiments, at least one instance of $R^G$ is substituted methyl. In certain embodiments, at least one instance of $R^G$ is —$CH_2F$. In certain embodiments, at least one instance of $R^G$ is —$CHF_2$. In certain embodiments, at least one instance of $R^G$ is —$CF_3$. In certain embodiments, at least one instance of $R^G$ is ethyl. In certain embodiments, at least one instance of $R^G$ is propyl. In certain embodiments, at least one instance of $R^G$ is butyl. In certain embodiments, at least one instance of $R^G$ is pentyl. In certain embodiments, at least one instance of $R^G$ is hexyl. In certain embodiments, at least one instance of $R^G$ is substituted alkenyl. In certain embodiments, at least one instance of $R^G$ is unsubstituted alkenyl. In certain embodiments, at least one instance of $R^G$ is substituted alkynyl. In certain embodiments, at least one instance of $R^G$ is unsubstituted alkynyl. In certain embodiments, at least one instance of $R^G$ is substituted carbocyclyl. In certain embodiments, at least one instance of $R^G$ is unsubstituted carbocyclyl. In certain embodiments, at least one instance of $R^G$ is saturated carbocyclyl. In certain embodiments, at least one instance of $R^G$ is unsaturated carbocyclyl. In certain embodiments, at least one instance of $R^G$ is monocyclic carbocyclyl. In certain embodiments, at least one instance of $R^G$ is 3- to 7-membered, monocyclic carbocyclyl. In certain embodiments, at least one instance of $R^G$ is substituted heterocyclyl. In certain embodiments, at least one instance of $R^G$ is unsubstituted heterocyclyl. In certain embodiments, at least one instance of $R^G$ is saturated heterocyclyl. In certain embodiments, at least one instance of $R^G$ is unsaturated heterocyclyl. In certain embodiments, at least one instance of $R^G$ is heterocyclyl, wherein one, two, or three atoms of the heterocyclic ring system are independently selected from the group consisting of nitrogen, oxygen, and sulfur. In certain embodiments, at least one instance of $R^G$ is monocyclic heterocyclyl. In certain embodiments, at least one instance of $R^G$ is 3- to 7-membered, monocyclic heterocyclyl. In certain embodiments, at least one instance of $R^G$ is substituted or unsubstituted piperazinyl. In certain embodiments, at least one instance of $R^G$ is of the formula:

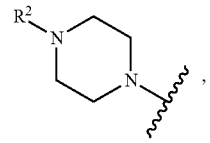

wherein $R^2$ is H, substituted or unsubstituted $C_{1-6}$ alkyl, or a nitrogen protecting group. In certain embodiments, at least one instance of $R^G$ is of the formula:

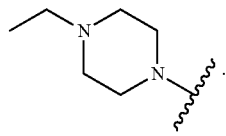

In certain embodiments, at least one instance of $R^G$ is substituted aryl. In certain embodiments, at least one instance of $R^G$ is unsubstituted aryl. In certain embodiments, at least one instance of $R^G$ is 6- to 10-membered aryl. In certain embodiments, at least one instance of $R^G$ is substituted phenyl. In certain embodiments, at least one instance of $R^G$ is unsubstituted phenyl. In certain embodiments, at least one instance of $R^G$ is substituted heteroaryl. In certain embodiments, at least one instance of $R^G$ is unsubstituted heteroaryl. In certain embodiments, at least one instance of $R^G$ is heteroaryl, wherein one, two, three, or four atoms of the heteroaryl ring system are independently selected from the group consisting of nitrogen, oxygen, and sulfur. In certain embodiments, at least one instance of $R^G$ is monocyclic heteroaryl. In certain embodiments, at least one instance of $R^G$ is 5-membered, monocyclic heteroaryl. In certain embodiments, at least one instance of $R^G$ is 6-membered, monocyclic heteroaryl. In certain embodiments, at least one instance of $R^G$ is bicyclic heteroaryl, wherein the point of attachment may be on any atom of the bicyclic heteroaryl ring system, as valency permits. In certain embodiments, at least one instance of $R^G$ is 9- or 10-membered, bicyclic heteroaryl. In certain embodiments, at least one instance of $R^G$ is —$OR^{G1}$. In certain embodiments, at least one instance of $R^G$ is —OH. In certain embodiments, at least one instance of $R^G$ is —O(substituted or unsubstituted $C_{1-6}$ alkyl). In certain embodiments, at least one instance of $R^G$ is —O—$(CH_2)_{2-4}$—O-(substituted or unsubstituted $C_{1-6}$ alkyl). In certain embodiments, at least one instance of $R^G$ is —O—$(CH_2)_2$—OMe. In certain embodiments, at least one instance of $R^G$ is —OMe. In certain embodiments, at least one instance of $R^G$ is —OEt. In certain embodiments, at least one instance of $R^G$ is —OPr. In certain embodiments, at least one instance of $R^G$ is —OBu. In certain embodiments, at least one instance of $R^G$ is —OBn. In certain embodiments, at least one instance of $R^G$ is —OPh. In certain embodiments, at least one instance of $R^G$ is —$SR^{G1}$. In certain embodiments, at least one instance of $R^G$ is —SH. In certain embodiments, at least one instance of $R^G$ is —SMe. In certain embodiments, at least one instance of $R^G$ is —$N(R^{G1})_2$. In certain embodiments, at least one instance of $R^G$ is —$N(R^{G1})_2$, wherein each instance of $R^{G1}$ is independently hydrogen, substituted or unsubstituted $C_{1-6}$ alkyl, or a nitrogen protecting group, or two instances of $R^{G1}$ are joined to form a substituted or unsubstituted, 3- to 7-membered, monocyclic heterocyclic ring. In certain embodiments, at least one instance of $R^G$ is —$NH_2$. In certain embodiments, at least one instance of $R^G$ is —NHMe. In certain embodiments, at least one instance of $R^G$ is —$NMe_2$. In certain embodiments, at least one instance of $R^G$ is —CN. In certain embodiments, at least one instance of $R^G$ is —SCN. In certain embodiments, at least one instance of $R^G$ is —$C(=NR^{G1})R^{G1}$, —$C(=NR^{G1})OR^{G1}$, or —$C(=NR^{G1})N(R^{G1})_2$. In certain embodiments, at least one instance of $R^G$ is —$C(=O)R^{G1}$ or —$C(=O)OR^{G1}$. In certain embodiments, at least one instance of $R^G$ is —$C(=O)N(R^{G1})_2$. In certain embodiments, at least one instance of $R^G$ is —$C(=O)NMe_2$, —$C(=O)NHMe$, or —$C(=O)NH_2$. In certain embodiments, at least one instance of $R^G$ is —$NO_2$. In certain embodiments, at least one instance of $R^G$ is —$NR^{G1}C(=O)R^{G1}$, —$NR^{G1}C(=O)OR^{G1}$, or —$NR^{G1}C(=O)N(R^{G1})_2$. In certain embodiments, at least one instance of $R^G$ is —$OC(=O)R^{G1}$, —$OC(=O)OR^{G1}$, or —$OC(=O)N(R^{G1})_2$.

In certain embodiments, at least one instance of $R^G$ is —$OR^{G1}$, —$N(R^{G1})_2$, or substituted or unsubstituted, 3- to 7-membered, monocyclic heterocyclyl, wherein one, two, or three atoms of the heterocyclic ring system are independently nitrogen, oxygen, or sulfur.

In certain embodiments, at least one instance of $R^{G1}$ is H. In certain embodiments, at least one instance of $R^{G1}$ is substituted acyl. In certain embodiments, at least one instance of RGI is unsubstituted acyl. In certain embodiments, at least one instance of $R^{G1}$ is acetyl. In certain embodiments, at least one instance of $R^{G1}$ is substituted alkyl. In certain embodiments, at least one instance of $R^{G1}$ is unsubstituted alkyl. In certain embodiments, at least one instance of $R^{G1}$ is unsubstituted $C_{1-6}$ alkyl. In certain embodiments, at least one instance of $R^{G1}$ is methyl. In certain embodiments, at least one instance of $R^{G1}$ is ethyl. In certain embodiments, at least one instance of $R^{G1}$ is propyl. In certain embodiments, at least one instance of $R^{G1}$ is butyl. In certain embodiments, at least one instance of $R^{G1}$ is pentyl. In certain embodiments, at least one instance of $R^{G1}$ is hexyl. In certain embodiments, at least one instance of $R^{G1}$ is substituted alkenyl. In certain embodiments, at least one instance of $R^{G1}$ is unsubstituted alkenyl. In certain embodiments, at least one instance of $R^{G1}$ is substituted alkynyl. In certain embodiments, at least one instance of $R^{G1}$ is unsubstituted alkynyl. In certain embodiments, at least one instance of $R^{G1}$ is substituted or unsubstituted carbocyclyl. In certain embodiments, at least one instance of $R^{G1}$ is saturated carbocyclyl. In certain embodiments, at least one instance of $R^{G1}$ is unsaturated carbocyclyl. In certain embodiments, at least one instance of $R^{G1}$ is 3- to 7-membered, monocyclic carbocyclyl. In certain embodiments, at least one instance of $R^{G1}$ is substituted or unsubstituted heterocyclyl. In certain embodiments, at least one instance of $R^{G1}$ is saturated heterocyclyl. In certain embodiments, at least one instance of $R^{G1}$ is unsaturated heterocyclyl. In certain embodiments, at least one instance of $R^{G1}$ is heterocyclyl, wherein one, two, or three atoms of the heterocyclic ring system are independently selected from the group consisting of nitrogen, oxygen, and sulfur. In certain embodiments, at least one instance of $R^{G1}$ is 3- to 7-membered, monocyclic heterocyclyl. In certain embodiments, at least one instance of $R^{G1}$ is substituted or unsubstituted aryl. In certain embodiments, at least one instance of $R^{G1}$ is 6- to 10-membered aryl. In certain embodiments, at least one instance of $R^{G1}$ is monocyclic aryl. In certain embodiments, at least one instance of $R^{G1}$ is substituted phenyl. In certain embodiments, at least one instance of $R^{G1}$ is unsubstituted phenyl. In certain embodiments, at least one instance of $R^{G1}$ is bicyclic aryl. In certain embodiments, at least one instance of $R^{G1}$ is substituted or unsubstituted heteroaryl. In certain embodiments, at least one instance of $R^{G1}$ is heteroaryl, wherein one, two, three, or four atoms of the heteroaryl ring system are independently selected from the group consisting of nitrogen, oxygen, and sulfur. In certain embodiments, at least one instance of $R^{G1}$ is monocyclic heteroaryl. In certain embodiments, at least one instance of $R^{G1}$ is 5- or 6-membered, monocyclic heteroaryl. In certain embodiments, at least one instance of $R^{G1}$ is bicyclic heteroaryl, wherein the point of attachment may be on any atom of the bicyclic heteroaryl ring system, as valency permits. In certain embodiments, at least one instance of $R^{G1}$ is a nitrogen protecting group when attached to a nitrogen atom. In certain embodiments, at least one instance of $R^{G1}$ is Bn, Boc, Cbz, Fmoc, trifluoroacetyl, triphenylmethyl, acetyl, or Ts when attached to a nitrogen atom. In certain embodiments, $R^{G1}$ is an oxygen protecting group when attached to an oxygen atom. In certain embodiments, $R^{G1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{G1}$ is a sulfur protecting group when attached to a sulfur atom. In certain embodiments, $R^{G1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{G1}$ are joined to form a substituted or unsubstituted heterocyclic ring. In certain embodiments, two instances of $R^{G1}$ are joined to form a saturated or unsaturated heterocyclic ring. In certain embodiments, two instances of $R^{G1}$ are joined to form a heterocyclic ring, wherein one, two, or three atoms of the heterocyclic ring system are independently selected from the group consisting of nitrogen, oxygen, and sulfur. In certain embodiments, two instances of $R^{G1}$ are joined to form a 3- to 7-membered, monocyclic heterocyclic ring. In certain embodiments, two instances of $R^{G1}$ are joined to form a substituted or unsubstituted heteroaryl ring. In certain embodiments, two instances of $R^{G1}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, k is 0. In certain embodiments, k is 1. In certain embodiments, k is 2. In certain embodiments, k is 3. In certain embodiments, k is 4. In certain embodiments, k is 5.

In certain embodiments, k is 1; and $R^G$ is —$OR^{G1}$, —$N(R^{G1})_2$, or substituted or unsubstituted, 3- to 7-membered, monocyclic heterocyclyl, wherein one, two, or three atoms of the heterocyclic ring system are independently nitrogen, oxygen, or sulfur. In certain embodiments, k is 1; and $R^G$ is —$OR^{G1}$, —$N(R^{G1})_2$, or substituted or unsubstituted, 3- to 7-membered, monocyclic heterocyclyl, wherein one, two, or three atoms of the heterocyclic ring system are independently nitrogen, oxygen, or sulfur; and each instance of $R^{G1}$ is independently H, substituted or unsubstituted $C_{1-6}$ alkyl, an oxygen protecting group when attached to an oxygen atom, or a nitrogen protecting group when attached to a nitrogen group.

In certain embodiments, the compound of Formula (VII) is of the formula:

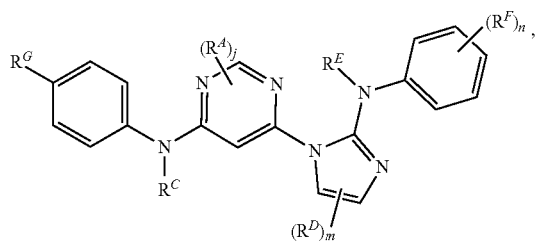

or a pharmaceutically acceptable salt, solvate, hydrate, polymorph, co-crystal, tautomer, stereoisomer, isotopically labeled derivative, or prodrug thereof.

In certain embodiments, the compound of Formula (VII) is of the formula:

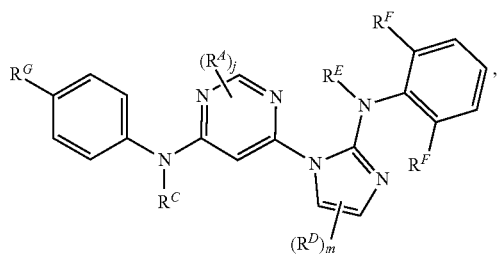

or a pharmaceutically acceptable salt, solvate, hydrate, polymorph, co-crystal, tautomer, stereoisomer, isotopically labeled derivative, or prodrug thereof.

In certain embodiments, the compound of Formula (VII) is of the formula:

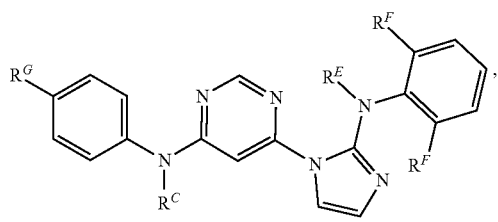

or a pharmaceutically acceptable salt, solvate, hydrate, polymorph, co-crystal, tautomer, stereoisomer, isotopically labeled derivative, or prodrug thereof.

In certain embodiments, the compound of Formula (VII) is of the formula:

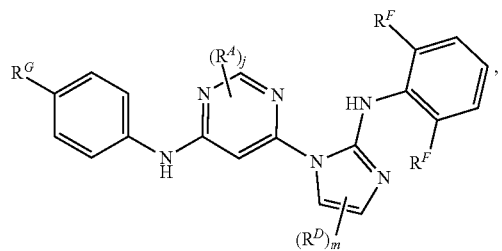

or a pharmaceutically acceptable salt, solvate, hydrate, polymorph, co-crystal, tautomer, stereoisomer, isotopically labeled derivative, or prodrug thereof.

In certain embodiments, the compound of Formula (VII) is of the formula:

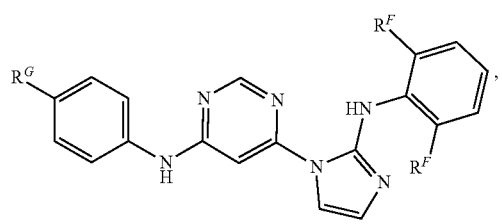

or a pharmaceutically acceptable salt, solvate, hydrate, polymorph, co-crystal, tautomer, stereoisomer, isotopically labeled derivative, or prodrug thereof.

In certain embodiments, the compound of Formula (VII) is of Formula (VII-B):

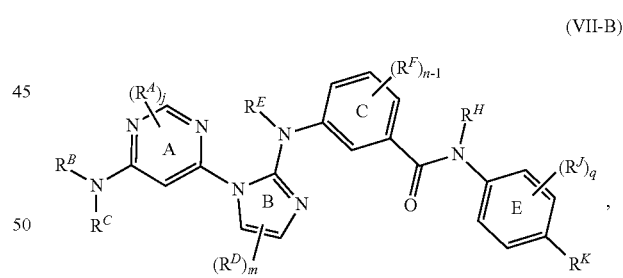

(VII-B)

or a pharmaceutically acceptable salt, solvate, hydrate, polymorph, co-crystal, tautomer, stereoisomer, isotopically labeled derivative, or prodrug thereof, wherein:

$R^H$ is hydrogen, substituted or unsubstituted acyl, substituted or unsubstituted $C_{1-6}$ alkyl, or a nitrogen protecting group;

each instance of $R^J$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{J1}$, —$N(R^{J1})_2$, —$SR^{J1}$, —CN, —SCN, —C(=$NR^{J1}$)$R^{J1}$, —C(=$NR^{J1}$)$OR^{J1}$, —C(=$NR^{J1}$)$N(R^{J1})_2$, —C(=O)$R^{J1}$, —C(=O)$OR^{J1}$, —C(=O)N(R$^{J1}$)$_2$, —NO$_2$, —NR$^{J1}$C(=O)R$^{J1}$, —NR$^{J1}$C(=O)OR$^{J1}$, —NR$^{J1}$C(=O)N(R$^{J1}$)$_2$, —OC(=O)R$^{J1}$, —OC(=O)OR$^{J1}$, or —OC(=O)N(R$^{J1}$)$_2$, wherein each instance of R$^{J1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{J1}$ are joined to form a substituted or unsubstituted heterocyclic or substituted or unsubstituted heteroaryl ring;

q is 0, 1, 2, 3, or 4; and

R$^K$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{K1}$, —N(R$^{K1}$)$_2$, —SR$^{K1}$, —CN, —SCN, —C(=NR$^{K1}$)R$^{K1}$, —C(=NR$^{K1}$)OR$^K$, —C(=NR$^{K1}$)N(R$^{K1}$)$_2$, —C(=O)R$^{K1}$, —C(=O)OR$^{K1}$, —C(=O)N(R$^{K1}$)$_2$, —NO$_2$, —NR$^{K1}$C(=O)R$^{K1}$, —NR$^{K1}$C(=O)OR$^{K1}$, —NR$^{K1}$C(=O)N(R$^{K1}$)$_2$, —OC(=O)R$^{K1}$, —OC(=O)OR$^{K1}$, or —OC(=O)N(R$^{K1}$)$_2$, wherein each instance of R$^{K1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{K1}$ are joined to form a substituted or unsubstituted heterocyclic or substituted or unsubstituted heteroaryl ring.

In certain embodiments, a compound of Formula (VII) is of Formula (VII-B), wherein when R$^C$ is hydrogen, R$^B$ is not unsubstituted cyclopropyl or

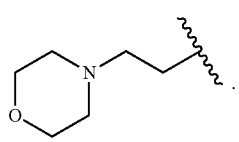 [SMILES: *CCN1CCOCC1]

Formula (VII-B) includes substituent R$^H$ on a nitrogen atom. In certain embodiments, R$^H$ is H. In certain embodiments, R$^H$ is not H. In certain embodiments, R$^H$ is substituted acyl. In certain embodiments, R$^H$ is unsubstituted acyl. In certain embodiments, R$^H$ is acetyl. In certain embodiments, R$^H$ is unsubstituted C$_{1-6}$ alkyl. In certain embodiments, R$^H$ is substituted C$_{1-6}$ alkyl. In certain embodiments, R$^H$ is C$_{1-6}$ alkyl substituted with at least one halogen. In certain embodiments, R$^H$ is unsubstituted methyl. In certain embodiments, R$^H$ is substituted methyl. In certain embodiments, R$^H$ is —CH$_2$F. In certain embodiments, R$^H$ is —CHF$_2$. In certain embodiments, R$^H$ is —CF$_3$. In certain embodiments, R$^H$ is ethyl. In certain embodiments, R$^H$ is propyl. In certain embodiments, R$^H$ is butyl. In certain embodiments, R$^H$ is pentyl. In certain embodiments, R$^H$ is hexyl. In certain embodiments, R$^H$ is a nitrogen protecting group. In certain embodiments, R$^H$ is Bn, Boc, Cbz, Fmoc, trifluoroacetyl, triphenylmethyl, acetyl, or Ts. In certain embodiments, R$^H$ is hydrogen or unsubstituted C$_{1-6}$ alkyl.

Formula (VII-B) includes as Ring E a phenyl ring that is substituted with R$^K$ and optionally one or more substituents R$^J$. In certain embodiments, Ring E is of the formula:

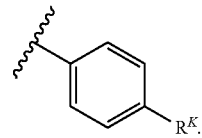

In certain embodiments, Ring E is of the formula:

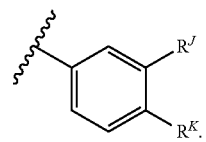

In certain embodiments, Ring E is of the formula:

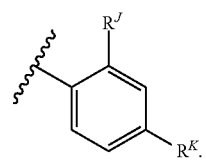

In certain embodiments, Ring E is of the formula:

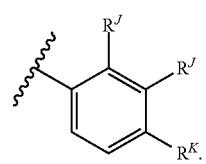

In certain embodiments, Ring E is of the formula:

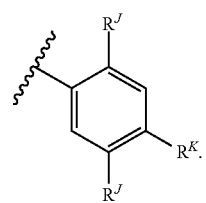

In certain embodiments, Ring E is of the formula:

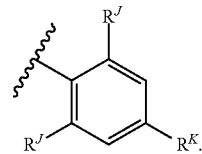

In certain embodiments, Ring E is of the formula:

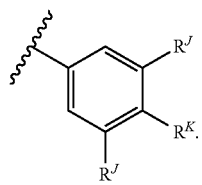

In certain embodiments, $R^K$ is H. In certain embodiments, $R^K$ is halogen. In certain embodiments, $R^K$ is F. In certain embodiments, $R^K$ is Cl. In certain embodiments, $R^K$ is Br. In certain embodiments, $R^K$ is I (iodine). In certain embodiments, $R^K$ is substituted alkyl. In certain embodiments, $R^K$ is unsubstituted alkyl. In certain embodiments, $R^K$ is unsubstituted $C_{1-6}$ alkyl. In certain embodiments, $R^K$ is substituted $C_{1-6}$ alkyl. In certain embodiments, $R^K$ is $C_{1-6}$ alkyl substituted with at least one halogen. In certain embodiments, $R^K$ is —$CH_3$. In certain embodiments, $R^K$ is substituted methyl. In certain embodiments, $R^K$ is —$CH_2F$. In certain embodiments, $R^K$ is —$CHF_2$. In certain embodiments, $R^K$ is —$CF_3$. In certain embodiments, $R^K$ is ethyl. In certain embodiments, $R^K$ is propyl. In certain embodiments, $R^K$ is butyl. In certain embodiments, $R^K$ is pentyl. In certain embodiments, $R^K$ is hexyl. In certain embodiments, $R^K$ is substituted alkenyl. In certain embodiments, $R^K$ is unsubstituted alkenyl. In certain embodiments, $R^K$ is substituted alkynyl. In certain embodiments, $R^K$ is unsubstituted alkynyl. In certain embodiments, $R^K$ is substituted carbocyclyl. In certain embodiments, $R^K$ is unsubstituted carbocyclyl. In certain embodiments, $R^K$ is saturated carbocyclyl. In certain embodiments, $R^K$ is unsaturated carbocyclyl. In certain embodiments, $R^K$ is monocyclic carbocyclyl. In certain embodiments, $R^K$ is 3- to 7-membered, monocyclic carbocyclyl. In certain embodiments, $R^K$ is substituted heterocyclyl. In certain embodiments, $R^K$ is unsubstituted heterocyclyl. In certain embodiments, $R^K$ is saturated heterocyclyl. In certain embodiments, $R^K$ is unsaturated heterocyclyl. In certain embodiments, $R^K$ is heterocyclyl, wherein one, two, or three atoms of the heterocyclic ring system are independently selected from the group consisting of nitrogen, oxygen, and sulfur. In certain embodiments, $R^K$ is monocyclic heterocyclyl. In certain embodiments, $R^K$ is 3- to 7-membered, monocyclic heterocyclyl. In certain embodiments, $R^K$ is substituted aryl. In certain embodiments, $R^K$ is unsubstituted aryl. In certain embodiments, $R^K$ is 6- to 10-membered aryl. In certain embodiments, $R^K$ is substituted phenyl. In certain embodiments, $R^K$ is unsubstituted phenyl. In certain embodiments, $R^K$ is substituted heteroaryl. In certain embodiments, $R^K$ is unsubstituted heteroaryl. In certain embodiments, $R^K$ is heteroaryl, wherein one, two, three, or four atoms of the heteroaryl ring system are independently selected from the group consisting of nitrogen, oxygen, and sulfur. In certain embodiments, $R^K$ is monocyclic heteroaryl. In certain embodiments, $R^K$ is 5-membered, monocyclic heteroaryl. In certain embodiments, $R^K$ is not substituted imidazolyl. In certain embodiments, $R^K$ is 6-membered, monocyclic heteroaryl. In certain embodiments, $R^K$ is bicyclic heteroaryl, wherein the point of attachment may be on any atom of the bicyclic heteroaryl ring system, as valency permits. In certain embodiments, $R^K$ is 9- or 10-membered, bicyclic heteroaryl. In certain embodiments, $R^K$ is —$OR^{K1}$. In certain embodiments, $R^K$ is —OH. In certain embodiments, $R^K$ is —O(substituted or unsubstituted $C_{1-6}$ alkyl). In certain embodiments, $R^K$ is —OMe. In certain embodiments, $R^K$ is —OEt. In certain embodiments, $R^K$ is —OPr. In certain embodiments, $R^K$ is —OBu. In certain embodiments, $R^K$ is —OBn. In certain embodiments, $R^K$ is —OPh. In certain embodiments, $R^K$ is —$SR^{K1}$. In certain embodiments, $R^K$ is —SH. In certain embodiments, $R^K$ is —SMe. In certain embodiments, $R^K$ is —$N(R^{K1})_2$. In certain embodiments, $R^K$ is —$NH_2$. In certain embodiments, $R^K$ is —NHMe. In certain embodiments, $R^K$ is —$NMe_2$. In certain embodiments, $R^K$ is —CN. In certain embodiments, $R^K$ is —SCN. In certain embodiments, $R^K$ is —$C(=NR^{K1})R^{K1}$, —$C(=NR^{K1})OR^{K1}$, or —$C(=NR^{K1})N(R^{K1})_2$. In certain embodiments, $R^K$ is —$C(=O)R^{K1}$ or —$C(=O)OR^{K1}$. In certain embodiments, $R^K$ is —$C(=O)N(R^{K1})_2$. In certain embodiments, $R^K$ is —$C(=O)NMe_2$, —$C(=O)NHMe$, or —$C(=O)NH_2$. In certain embodiments, $R^K$ is —$NO_2$. In certain embodiments, $R^K$ is —$NR^{K1}C(=O)R^{K1}$, —$NR^{K1}C(=O)OR^{K1}$, or —$NR^{K1}C(=O)N(R^{K1})_2$. In certain embodiments, $R^K$ is —$OC(=O)R^{K1}$, —$OC(=O)OR^{K1}$, or —$OC(=O)N(R^{K1})_2$.

In certain embodiments, $R^K$ is —$(CH_2)_{1-3}$-(Ring G), wherein Ring G is a substituted or unsubstituted, 3- to 7-membered, monocyclic heterocyclic ring. In certain embodiments, $R^K$ is —$(CH_2)_{1-3}$-(substituted or unsubstituted piperazinyl). In certain embodiments, $R^K$ is of the formula:

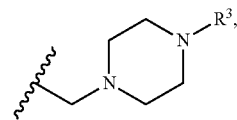

wherein $R^3$ is H, substituted or unsubstituted $C_{2-6}$ alkyl, substituted methyl, or a nitrogen protecting group. In certain embodiments, $R^K$ is of the formula:

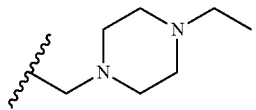

In certain embodiments, $R^K$ is not of the formula:

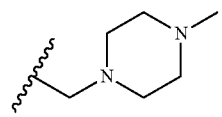

In certain embodiments, $R^K$ is —$(CH_2)_{1-3}$-(Ring G), wherein Ring G is a substituted or unsubstituted oxetanyl, substituted or unsubstituted azetidinyl, substituted or unsubstituted tetrahydrofuranyl, substituted or unsubstituted pyrrolidinyl, substituted or unsubstituted tetrahydropyranyl, substituted or unsubstituted piperidinyl, or substituted or unsubstituted morpholinyl ring.

In certain embodiments, $R^{K1}$ is H. In certain embodiments, $R^{K1}$ is substituted acyl. In certain embodiments, $R^{K1}$ is unsubstituted acyl. In certain embodiments, $R^{K1}$ is acetyl. In certain embodiments, $R^{K1}$ is substituted alkyl. In certain embodiments, $R^{K1}$ is unsubstituted alkyl. In certain embodiments, $R^{K1}$ is unsubstituted $C_{1-6}$ alkyl. In certain embodiments, $R^{K1}$ is methyl. In certain embodiments, $R^{K1}$ is ethyl.

In certain embodiments, $R^{K1}$ is propyl. In certain embodiments, $R^{K1}$ is butyl. In certain embodiments, $R^{K1}$ is pentyl. In certain embodiments, $R^{K1}$ is hexyl. In certain embodiments, $R^{K1}$ is substituted alkenyl. In certain embodiments, $R^{K1}$ is unsubstituted alkenyl. In certain embodiments, $R^{K1}$ is substituted alkynyl. In certain embodiments, $R^{K1}$ is unsubstituted alkynyl. In certain embodiments, $R^{K1}$ is substituted or unsubstituted carbocyclyl. In certain embodiments, $R^{K1}$ is saturated carbocyclyl. In certain embodiments, $R^{K1}$ is unsaturated carbocyclyl. In certain embodiments, $R^{K1}$ is 3- to 7-membered, monocyclic carbocyclyl. In certain embodiments, $R^{K1}$ is substituted or unsubstituted heterocyclyl. In certain embodiments, $R^{K1}$ is saturated heterocyclyl. In certain embodiments, $R^{K1}$ is unsaturated heterocyclyl. In certain embodiments, $R^{K1}$ is heterocyclyl, wherein one, two, or three atoms of the heterocyclic ring system are independently selected from the group consisting of nitrogen, oxygen, and sulfur. In certain embodiments, $R^{K1}$ is 3- to 7-membered, monocyclic heterocyclyl. In certain embodiments, $R^{K1}$ is substituted or unsubstituted aryl. In certain embodiments, $R^{K1}$ is 6- to 10-membered aryl. In certain embodiments, $R^{K1}$ is monocyclic aryl. In certain embodiments, $R^{K1}$ is substituted phenyl. In certain embodiments, $R^{K1}$ is unsubstituted phenyl. In certain embodiments, $R^{K1}$ is bicyclic aryl. In certain embodiments, $R^{K1}$ is substituted or unsubstituted heteroaryl. In certain embodiments, $R^{K1}$ is heteroaryl, wherein one, two, three, or four atoms of the heteroaryl ring system are independently selected from the group consisting of nitrogen, oxygen, and sulfur. In certain embodiments, $R^{K1}$ is monocyclic heteroaryl. In certain embodiments, $R^{K1}$ is 5- or 6-membered, monocyclic heteroaryl. In certain embodiments, $R^{K1}$ is bicyclic heteroaryl, wherein the point of attachment may be on any atom of the bicyclic heteroaryl ring system, as valency permits. In certain embodiments, $R^{K1}$ is a nitrogen protecting group when attached to a nitrogen atom. In certain embodiments, $R^{K1}$ is Bn, Boc, Cbz, Fmoc, trifluoroacetyl, triphenylmethyl, acetyl, or Ts when attached to a nitrogen atom. In certain embodiments, $R^{K1}$ is an oxygen protecting group when attached to an oxygen atom. In certain embodiments, $R^{K1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{K1}$ is a sulfur protecting group when attached to a sulfur atom. In certain embodiments, $R^{K1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{K1}$ are joined to form a substituted or unsubstituted heterocyclic ring. In certain embodiments, two instances of $R^{K1}$ are joined to form a saturated or unsaturated heterocyclic ring. In certain embodiments, two instances of $R^{K1}$ are joined to form a heterocyclic ring, wherein one, two, or three atoms of the heterocyclic ring system are independently selected from the group consisting of nitrogen, oxygen, and sulfur. In certain embodiments, two instances of $R^{K1}$ are joined to form a 3- to 7-membered, monocyclic heterocyclic ring. In certain embodiments, two instances of $R^{K1}$ are joined to form a substituted or unsubstituted heteroaryl ring. In certain embodiments, two instances of $R^{K1}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

Ring E of Formula (VII-B) may include one or more substituents $R^J$. In certain embodiments, at least two instances of $R^J$ are different. In certain embodiments, all instances of $R^J$ are the same. In certain embodiments, at least one instance of $R^J$ is halogen. In certain embodiments, at least one instance of $R^J$ is F. In certain embodiments, at least one instance of $R^J$ is Cl. In certain embodiments, at least one instance of $R^J$ is Br. In certain embodiments, at least one instance of $R^J$ is I (iodine). In certain embodiments, at least one instance of $R^J$ is substituted alkyl. In certain embodiments, at least one instance of $R^J$ is unsubstituted alkyl. In certain embodiments, at least one instance of $R^J$ is unsubstituted $C_{1-6}$ alkyl. In certain embodiments, all instances of $R^J$ are unsubstituted $C_{1-6}$ alkyl. In certain embodiments, at least one instance of $R^J$ is substituted $C_{1-6}$ alkyl. In certain embodiments, at least one instance of $R^J$ is $C_{1-6}$ alkyl substituted with at least one halogen. In certain embodiments, at least one instance of $R^J$ is —$CH_3$. In certain embodiments, all instances of $R^J$ are —$CH_3$. In certain embodiments, at least one instance of $R^J$ is substituted methyl. In certain embodiments, at least one instance of $R^J$ is —$CH_2F$. In certain embodiments, at least one instance of $R^J$ is —$CHF_2$. In certain embodiments, at least one instance of $R^J$ is —$CF_3$. In certain embodiments, at least one instance of $R^J$ is ethyl. In certain embodiments, at least one instance of $R^J$ is propyl. In certain embodiments, at least one instance of $R^J$ is butyl. In certain embodiments, at least one instance of $R^J$ is pentyl. In certain embodiments, at least one instance of $R^J$ is hexyl. In certain embodiments, at least one instance of $R^J$ is halogen or substituted or unsubstituted $C_{1-6}$ alkyl. In certain embodiments, at least one instance of $R^J$ is substituted alkenyl. In certain embodiments, at least one instance of $R^J$ is unsubstituted alkenyl. In certain embodiments, at least one instance of $R^J$ is substituted alkynyl. In certain embodiments, at least one instance of $R^J$ is unsubstituted alkynyl. In certain embodiments, at least one instance of $R^J$ is substituted carbocyclyl. In certain embodiments, at least one instance of $R^J$ is unsubstituted carbocyclyl. In certain embodiments, at least one instance of $R^J$ is saturated carbocyclyl. In certain embodiments, at least one instance of $R^J$ is unsaturated carbocyclyl. In certain embodiments, at least one instance of $R^J$ is monocyclic carbocyclyl. In certain embodiments, at least one instance of $R^J$ is 3- to 7-membered, monocyclic carbocyclyl. In certain embodiments, at least one instance of $R^J$ is substituted heterocyclyl. In certain embodiments, at least one instance of $R^J$ is unsubstituted heterocyclyl. In certain embodiments, at least one instance of $R^J$ is saturated heterocyclyl. In certain embodiments, at least one instance of $R^J$ is unsaturated heterocyclyl. In certain embodiments, at least one instance of $R^J$ is heterocyclyl, wherein one, two, or three atoms of the heterocyclic ring system are independently selected from the group consisting of nitrogen, oxygen, and sulfur. In certain embodiments, at least one instance of $R^J$ is monocyclic heterocyclyl. In certain embodiments, at least one instance of $R^J$ is 3- to 7-membered, monocyclic heterocyclyl. In certain embodiments, at least one instance of $R^J$ is substituted aryl. In certain embodiments, at least one instance of $R^J$ is unsubstituted aryl. In certain embodiments, at least one instance of $R^J$ is 6- to 10-membered aryl. In certain embodiments, at least one instance of $R^J$ is substituted phenyl. In certain embodiments, at least one instance of $R^J$ is unsubstituted phenyl. In certain embodiments, at least one instance of $R^J$ is substituted heteroaryl. In certain embodiments, at least one instance of $R^J$ is unsubstituted heteroaryl. In certain embodiments, at least one instance of $R^J$ is heteroaryl, wherein one, two, three, or four atoms of the heteroaryl ring system are independently selected from the group consisting of nitrogen, oxygen, and sulfur. In certain embodiments, at least one instance of $R^J$ is monocyclic heteroaryl. In certain embodiments, at least one instance of $R^J$ is 5-membered, monocyclic heteroaryl. In certain embodiments, no instance of $R^J$ is substituted imidazolyl. In certain embodiments, at least one instance of $R^J$ is 6-membered, monocyclic heteroaryl. In certain embodiments, at least one instance of $R^J$ is bicyclic heteroaryl, wherein the point of attachment may be on any atom of the bicyclic heteroaryl ring system, as valency permits. In certain embodiments, at least one instance of $R^J$ is 9- or 10-membered, bicyclic heteroaryl. In certain embodiments, at least one instance of $R^J$ is —$OR^{J1}$. In certain embodiments, at least one instance of $R^J$ is —OH. In certain embodiments, at least one instance of $R^J$ is —O(substituted or unsubstituted $C_{1-6}$ alkyl). In certain embodiments, at least one instance of $R^J$ is —OMe. In certain embodiments, at least one instance of $R^J$ is —OEt. In certain embodiments, at least one instance of $R^J$ is —OPr. In certain embodiments, at least one instance of $R^J$ is —OBu. In certain embodiments, at least one instance of $R^J$ is —OBn. In certain embodiments, at least one instance of $R^J$ is —OPh. In certain embodiments, at least one instance of $R^J$ is —$SR^{J1}$. In certain embodiments, at least one instance of $R^J$ is —SH. In certain embodiments, at least one instance of $R^J$ is —SMe. In certain embodiments, at least one instance of $R^J$ is —$N(R^{J1})_2$. In certain embodiments, at least one instance of $R^J$ is —$NH_2$. In certain embodiments, at least one instance of $R^J$ is —NHMe. In certain embodiments, at least one instance of $R^J$ is —$NMe_2$. In certain embodiments, at least one instance of $R^J$ is —CN. In certain embodiments, at least one instance of $R^J$ is —SCN. In certain embodiments, at least one instance of $R^J$ is —$C(=NR^{J1})R^{J1}$, —$C(=NR^{J1})OR^{J1}$, or —$C(=NR^{J1})N(R^{J1})_2$. In certain embodiments, at least one instance of $R^J$ is —$C(=O)R^{J1}$ or —$C(=O)OR^{J1}$. In certain embodiments, at least one instance of $R^J$ is —$C(=O)N(R^{J1})_2$. In certain embodiments, at least one instance of $R^J$ is —$C(=O)NMe_2$, —$C(=O)NHMe$, or —$C(=O)NH_2$. In certain embodiments, at least one instance of $R^J$ is —$NO_2$. In certain embodiments, at least one instance of $R^J$ is —$NR^{J1}C(=O)R^{J1}$, —$NR^{J1}C(=O)OR^{J1}$, or —$NR^{J1}C(=O)N(R^{J1})_2$. In certain embodiments, at least one instance of $R^J$ is —$OC(=O)R^{J1}$, —$OC(=O)OR^{J1}$, or —$OC(=O)N(R^{J1})_2$.

In certain embodiments, at least one instance of $R^J$ is halogen or substituted or unsubstituted $C_{1-6}$ alkyl. In certain embodiments, at least one instance of $R^J$ is halogen, unsubstituted $C_{1-6}$ alkyl, or $C_{1-6}$ alkyl substituted with at least one halogen.

In certain embodiments, at least one instance of $R^{J1}$ is H. In certain embodiments, at least one instance of $R^{J1}$ is substituted acyl. In certain embodiments, at least one instance of $R^{J1}$ is unsubstituted acyl. In certain embodiments, at least one instance of $R^{J1}$ is acetyl. In certain embodiments, at least one instance of $R^{J1}$ is substituted alkyl. In certain embodiments, at least one instance of $R^{J1}$ is unsubstituted alkyl. In certain embodiments, at least one instance of $R^{J1}$ is unsubstituted $C_{1-6}$ alkyl. In certain embodiments, at least one instance of $R^{J1}$ is methyl. In certain embodiments, at least one instance of $R^{J1}$ is ethyl. In certain embodiments, at least one instance of $R^{J1}$ is propyl. In certain embodiments, at least one instance of $R^{J1}$ is butyl. In certain embodiments, at least one instance of $R^{J1}$ is pentyl. In certain embodiments, at least one instance of $R^{J1}$ is hexyl. In certain embodiments, at least one instance of $R^{J1}$ is substituted alkenyl. In certain embodiments, at least one instance of $R^{J1}$ is unsubstituted alkenyl. In certain embodiments, at least one instance of $R^{J1}$ is substituted alkynyl. In certain embodiments, at least one instance of $R^{J1}$ is unsubstituted alkynyl. In certain embodiments, at least one instance of $R^{J1}$ is substituted or unsubstituted carbocyclyl. In certain embodiments, at least one instance of $R^{J1}$ is saturated carbocyclyl. In certain embodiments, at least one instance of $R^{J1}$ is unsaturated carbocyclyl. In certain embodiments, at least one instance of $R^{J1}$ is 3- to 7-membered, monocyclic carbocyclyl. In certain embodiments, at least one instance of $R^{J1}$ is substituted or unsubstituted heterocyclyl. In certain embodiments, at least one instance of $R^{J1}$ is saturated heterocyclyl. In certain embodiments, at least one instance of $R^{J1}$ is unsaturated heterocyclyl. In certain embodiments, at least one instance of $R^{J1}$ is heterocyclyl, wherein one, two, or three atoms of the heterocyclic ring system are independently selected from the group consisting of nitrogen, oxygen, and sulfur. In certain embodiments, at least one instance of $R^{J1}$ is 3- to 7-membered, monocyclic heterocyclyl. In certain embodiments, at least one instance of $R^{J1}$ is substituted or unsubstituted aryl. In certain embodiments, at least one instance of $R^{J1}$ is 6- to 10-membered aryl. In certain embodiments, at least one instance of $R^{J1}$ is monocyclic aryl. In certain embodiments, at least one instance of $R^{J1}$ is substituted phenyl. In certain embodiments, at least one instance of $R^{J1}$ is unsubstituted phenyl. In certain embodiments, at least one instance of $R^{J1}$ is bicyclic aryl. In certain embodiments, at least one instance of $R^{J1}$ is substituted or unsubstituted heteroaryl. In certain embodiments, at least one instance of $R^{J1}$ is heteroaryl, wherein one, two, three, or four atoms of the heteroaryl ring system are independently selected from the group consisting of nitrogen, oxygen, and sulfur. In certain embodiments, at least one instance of $R^{J1}$ is monocyclic heteroaryl. In certain embodiments, at least one instance of $R^{J1}$ is 5- or 6-membered, monocyclic heteroaryl. In certain embodiments, at least one instance of $R^{J1}$ is bicyclic heteroaryl, wherein the point of attachment may be on any atom of the bicyclic heteroaryl ring system, as valency permits. In certain embodiments, at least one instance of $R^{J1}$ is a nitrogen protecting group when attached to a nitrogen atom. In certain embodiments, at least one instance of $R^{J1}$ is Bn, Boc, Cbz, Fmoc, trifluoroacetyl, triphenylmethyl, acetyl, or Ts when attached to a nitrogen atom. In certain embodiments, $R^{J1}$ is an oxygen protecting group when attached to an oxygen atom. In certain embodiments, $R^{J1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{J1}$ is a sulfur protecting group when attached to a sulfur atom. In certain embodiments, $R^{J1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{J1}$ are joined to form a substituted or unsubstituted heterocyclic ring. In certain embodiments, two instances of $R^{J1}$ are joined to form a saturated or unsaturated heterocyclic ring. In certain embodiments, two instances of $R^{J1}$ are joined to form a heterocyclic ring, wherein one, two, or three atoms of the heterocyclic ring system are independently selected from the group consisting of nitrogen, oxygen, and sulfur. In certain embodiments, two instances of $R^{J1}$ are joined to form a 3- to 7-membered, monocyclic heterocyclic ring. In certain embodiments, two instances of $R^{J1}$ are joined to form a substituted or unsubstituted heteroaryl ring. In certain embodiments, two instances of $R^{J1}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, q is 0. In certain embodiments, q is 1. In certain embodiments, q is 2. In certain embodiments, q is 3. In certain embodiments, q is 4.

In certain embodiments, no instance of $R^J$ and $R^K$ is substituted or unsubstituted heteroaryl. In certain embodiments, no instance of $R^J$ and $R^K$ is substituted or unsubstituted imidazolyl. In certain embodiments, no instance of $R^J$ and $R^K$ is substituted imidazolyl.

In certain embodiments, the compound of Formula (VII) is of the formula:

In certain embodiments, the compound of Formula (VII) is of the formula:

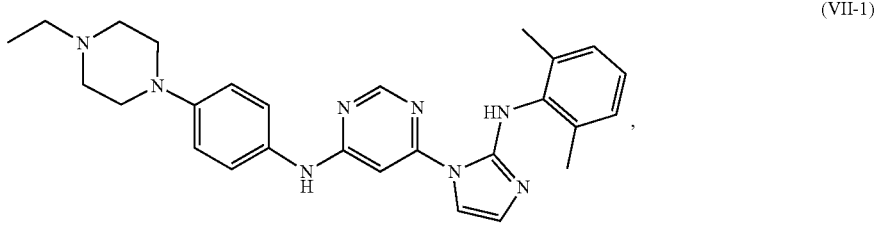
(VII-1)

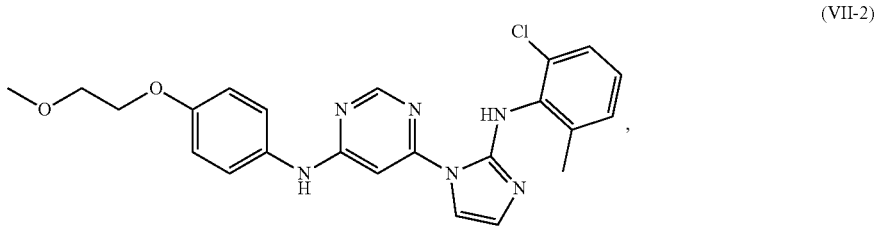
(VII-2)

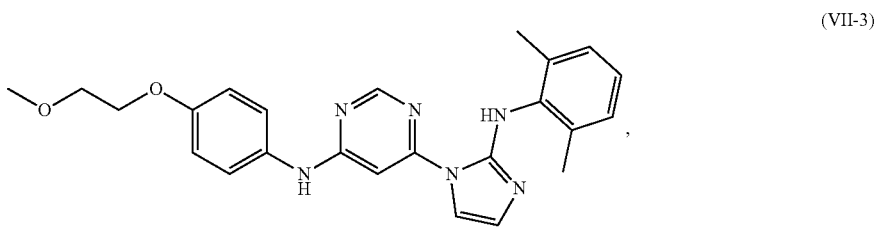
(VII-3)

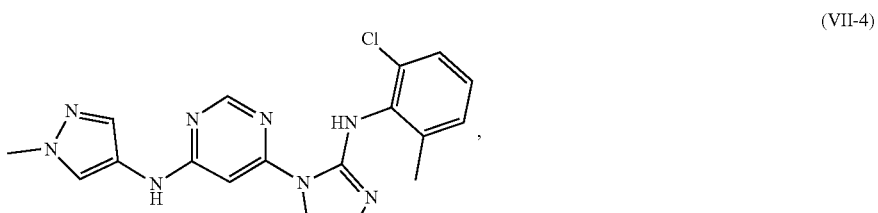
(VII-4)

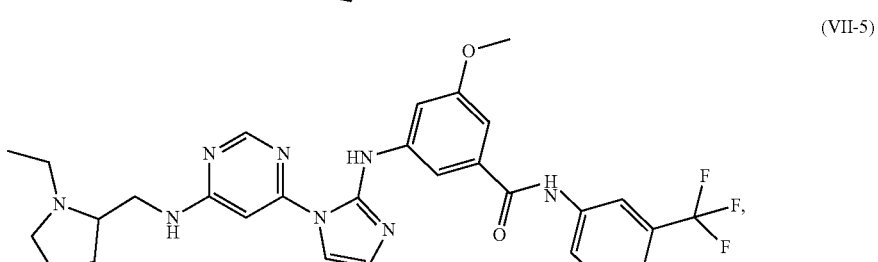
(VII-5)

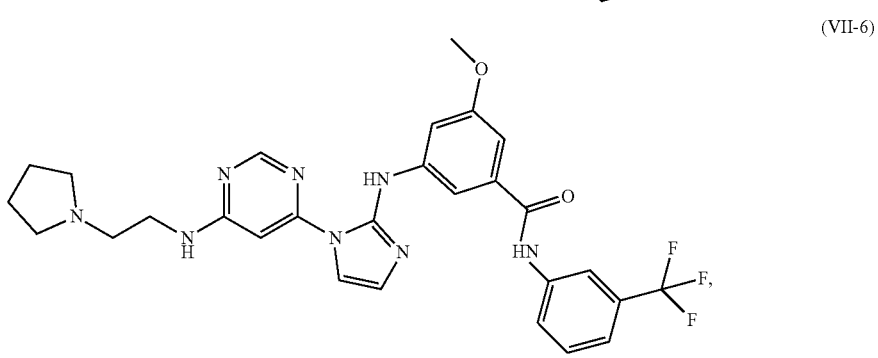
(VII-6)

(VII-7)
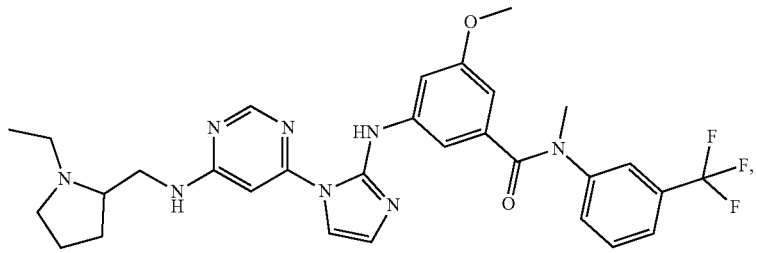
(VII-8)
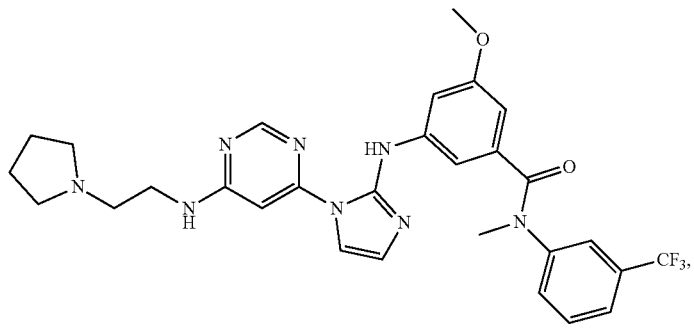
(VII-9)
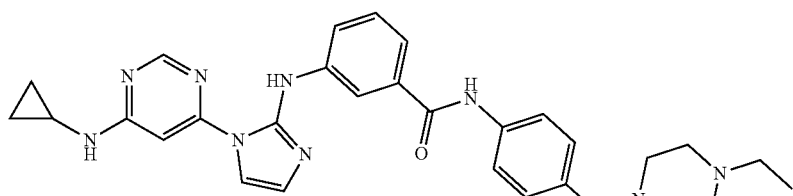
(VII-10)
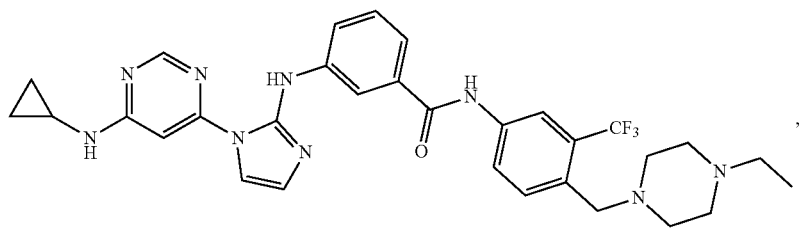
(VII-11)
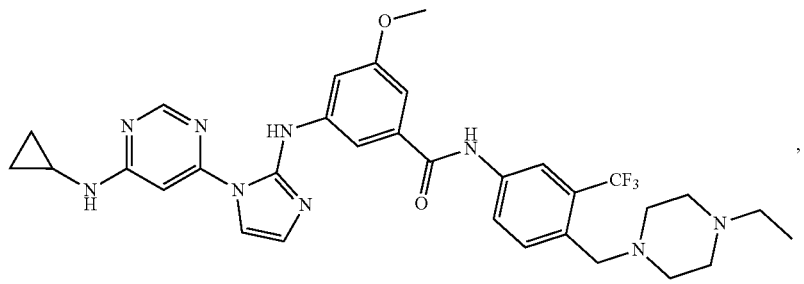
(VII-12)
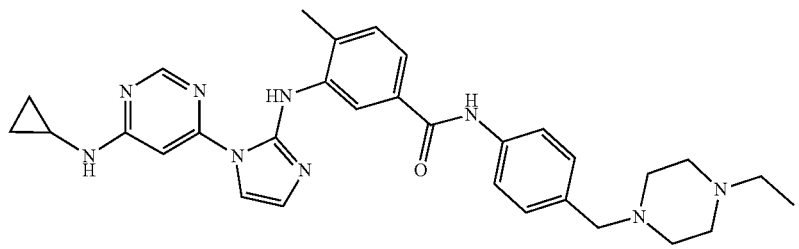

or a pharmaceutically acceptable salt, solvate, hydrate, polymorph, co-crystal, tautomer, stereoisomer, isotopically labeled derivative, or prodrug thereof.
In certain embodiments, a compound of Formula (VII) is not of the formula:
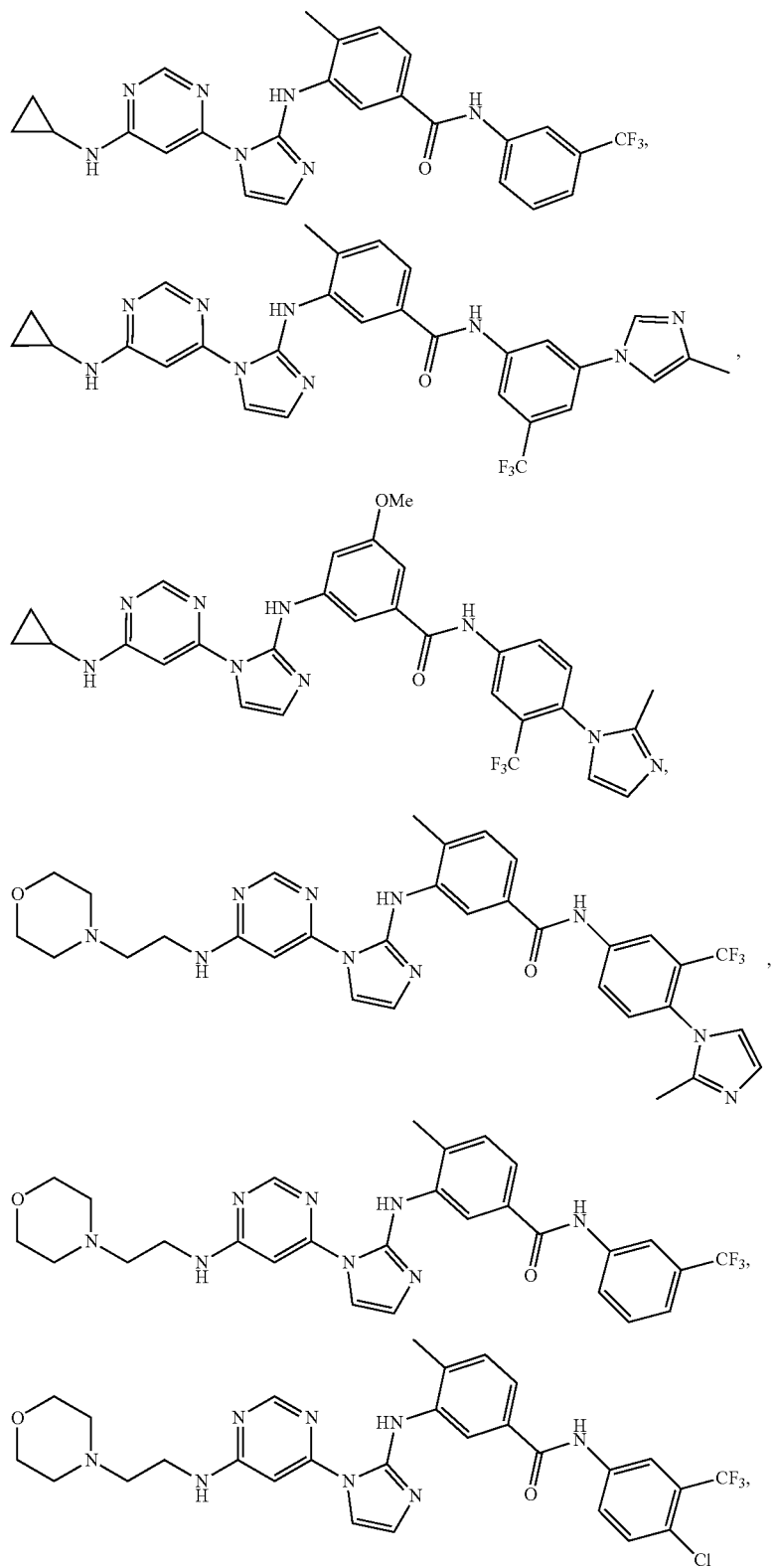

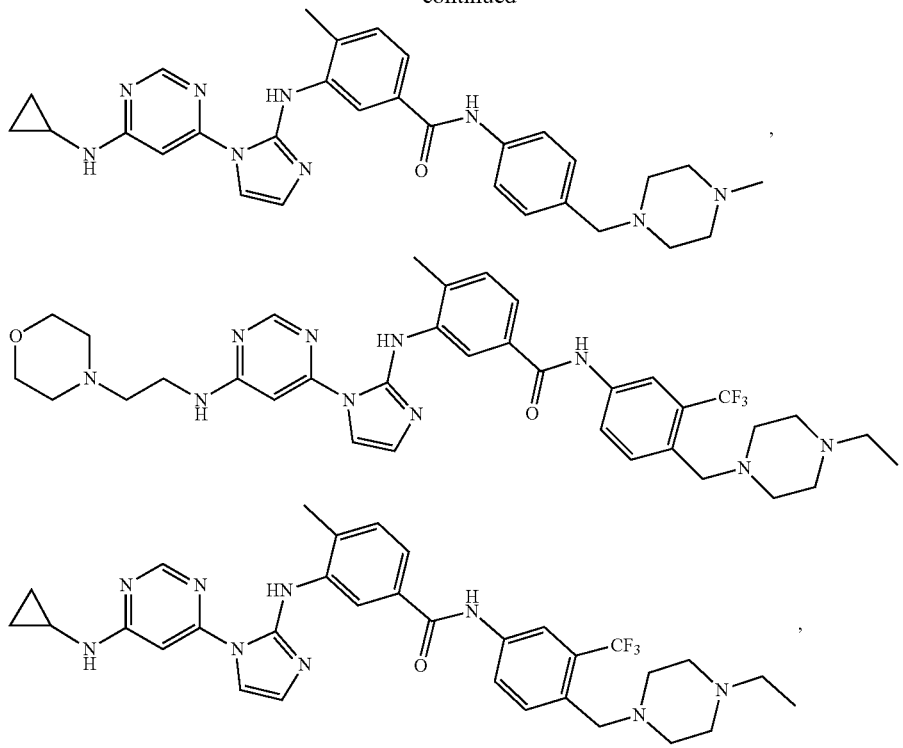

In certain embodiments, the compound utilized in the present disclosure is of Formula (VII):

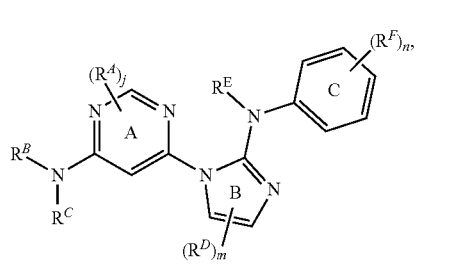

(VII)

or a pharmaceutically acceptable salt, solvate, hydrate, polymorph, co-crystal, or tautomer thereof. each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A1}$, $-N(R^{A1})_2$, $-SR^{A1}$, $-CN$, $-SCN$, $-C(=NR^{A1})R^{A1}$, $-C(=NR^{A1})OR^{A1}$, $-C(=NR^{A1})N(R^{A1})_2$, $-C(=O)R^{A1}$, $-C(=O)OR^{A1}$, $-C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, or $-OC(=O)N(R^{A1})_2$, wherein each instance of $R^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1}$ are joined to form a substituted or unsubstituted heterocyclic or substituted or unsubstituted heteroaryl ring;

j is 0, 1, or 2;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^C$ is hydrogen, substituted or unsubstituted acyl, substituted or unsubstituted $C_{1-6}$ alkyl, or a nitrogen protecting group;

each instance of $R^D$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{D1}$, $-N(R^{D1})_2$, $-SR^{D1}$, $-CN$, $-SCN$, $-C(=NR^{D1})R^{D1}$, $-C(=NR^{D1})OR^{D1}$, $-C(=NR^{D1})N(R^{D1})_2$, $-C(=O)R^{D1}$, $-C(=O)OR^{D1}$, $-C(=O)N(R^{D1})_2$, $-NO_2$, $-NR^{D1}C(=O)R^{D1}$, $-NR^{D1}C(=O)OR^{D1}$, $-NR^{D1}C(=O)N(R^{D1})_2$, $-OC(=O)R^{D1}$, $-OC(=O)OR^{D1}$, or $-OC(=O)N(R^{D1})_2$, wherein each instance of $R^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{D1}$ are joined to form a substituted or unsubstituted heterocyclic or substituted or unsubstituted heteroaryl ring;

m is 0, 1, or 2;

$R^E$ is hydrogen, substituted or unsubstituted acyl, substituted or unsubstituted $C_{1-6}$ alkyl, or a nitrogen protecting group;

each instance of $R^F$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{F1}$, —$N(R^{F1})_2$, —$SR^{F1}$, —CN, —SCN, —$C(=NR^{F1})R^{F1}$, —$C(=NR^{F1})OR^{F1}$, —$C(=NR^{F1})N(R^{F1})_2$, —$C(=O)R^{F1}$, —$C(=O)OR^{F1}$, —$C(=O)N(R^{F1})_2$, —$NO_2$, —$NR^{F1}C(=O)R^{F1}$, —$NR^{F1}C(=O)OR^{F1}$, —$NR^{F1}C(=O)N(R^{F1})_2$, —$OC(=O)R^{F1}$, —$OC(=O)OR^{F1}$, or —$OC(=O)N(R^{F1})_2$, wherein each instance of $R^{F1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{F1}$ are joined to form a substituted or unsubstituted heterocyclic or substituted or unsubstituted heteroaryl ring; and n is 0, 1, 2, 3, 4, or 5;

provided that the compound is not of the formula:

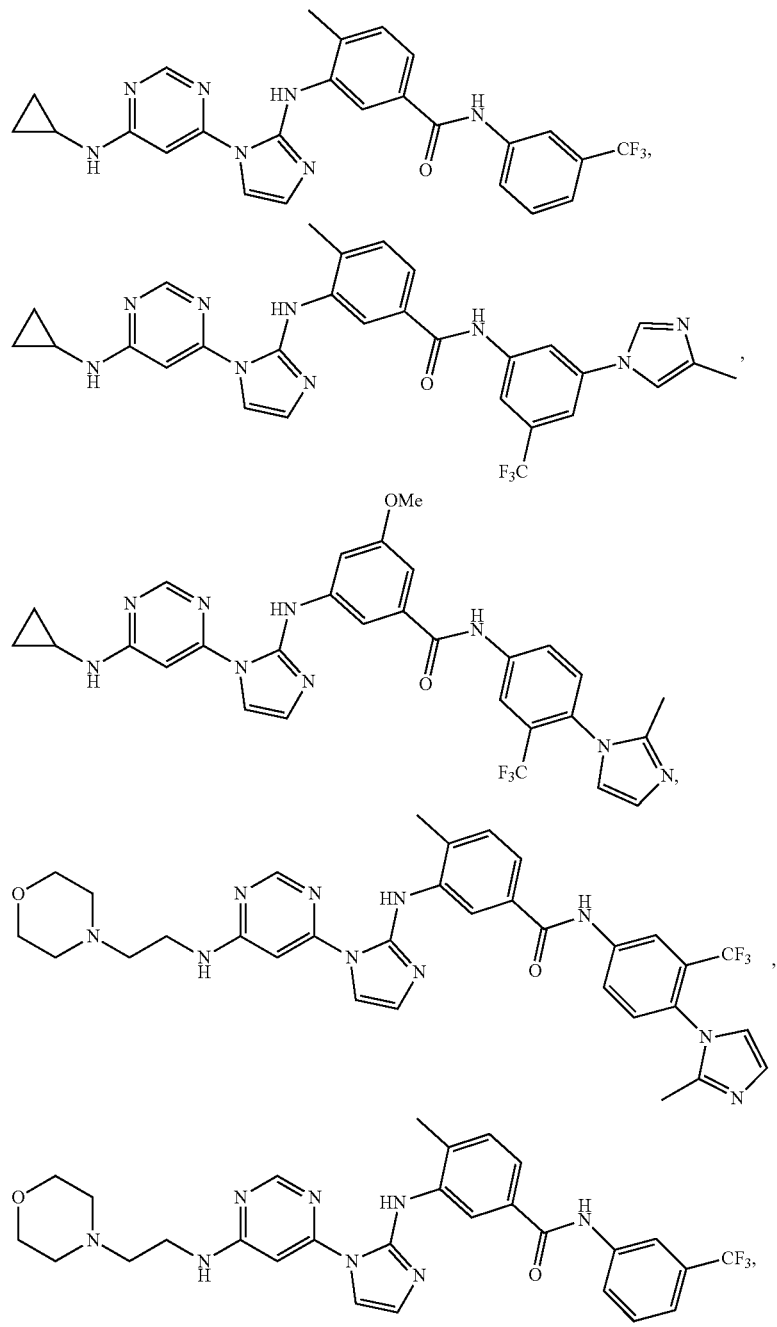

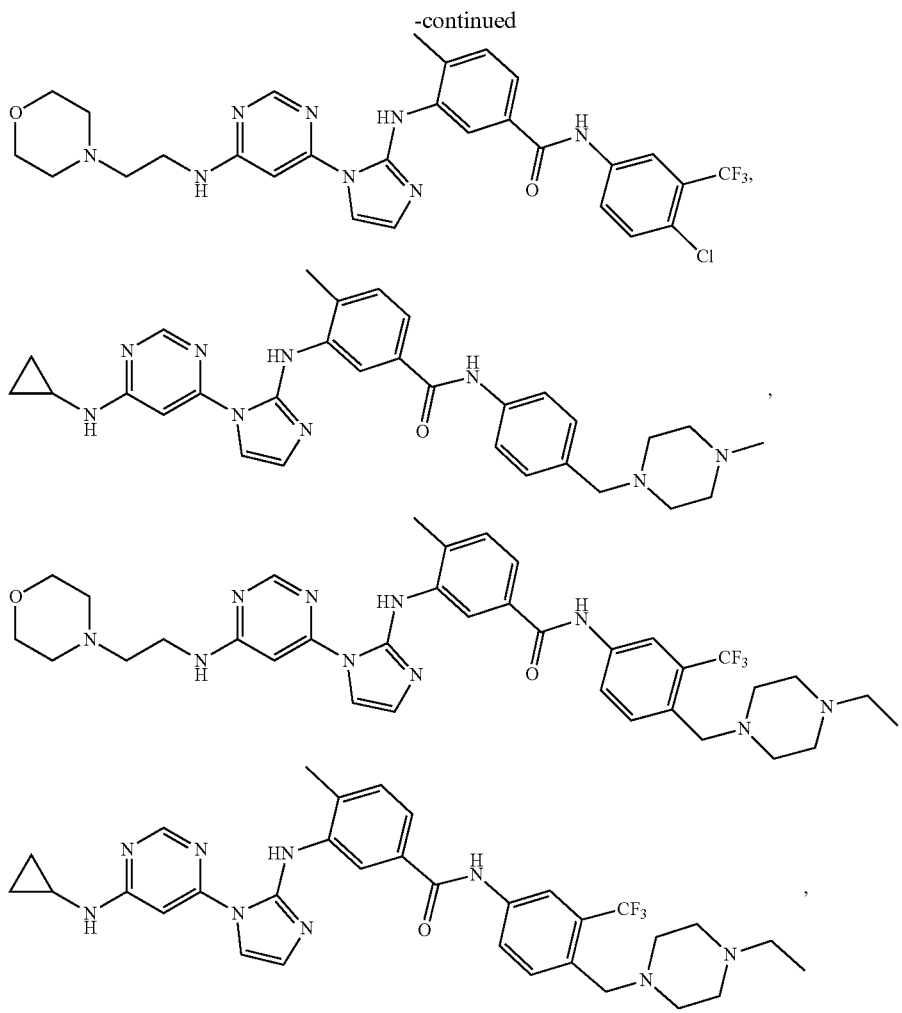

or a pharmaceutically acceptable salt thereof.

Pharmaceutical Compositions and Administration

In certain embodiments, a SIK inhibitor for use in the invention described herein is a compound of Formula (I), (II), (III), (IV), (V), (VI), (VI-A), or (VII), or a pharmaceutically acceptable salt, solvate, hydrate, polymorph, co-crystal, tautomer, stereoisomer, isotopically labeled derivative, or prodrug thereof. In certain embodiments, the compound described herein is provided in an effective amount in the pharmaceutical composition. In certain embodiments, the effective amount is a prophylactically effective amount. In certain embodiments, the effective amount is an amount effective for increasing skin pigmentation in a subject in need thereof. In certain embodiments, the effective amount is an amount effective for increasing skin pigmentation in a subject in need thereof for cosmetic purposes. In certain embodiments, the effective amount is an amount effective for increasing skin pigmentation in a subject in need thereof for treating polymorphic light eruption (e.g., sun hypersensitivity). In certain embodiments, the effective amount is an amount effective for reducing the risk of skin cancer in a subject in need thereof. In certain embodiments, the effective amount is an amount effective for inhibiting the activity of a SIK, (e.g., SIK1, SIK2, or SIK3)) in a subject or cell (e.g., the skin of a subject or in skin cells).

In certain embodiments, the subject being administered a compound or composition described herein is an animal. The animal may be of either sex and may be at any stage of development. In certain embodiments, the subject described herein is a human. In certain embodiments, the subject is a non-human animal. In certain embodiments, the subject is a mammal.

An effective amount of a compound described herein may vary from about 0.001 mg/kg to about 1000 mg/kg in one or more dose administrations for one or several days (depending on the mode of administration), wherein mg/kg is mg of compound to kg weight of the subject. In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

In certain embodiments, the effective amount is an amount effective for inhibiting the activity of a SIK by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of a SIK by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of a SIK by a range between a percentage described in this paragraph and another percentage described in this paragraph, inclusive.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the skin of a subject. In certain embodiments, the compound or pharmaceutical composition described herein is suitable for transdermal administration to the skin of a subject. In certain embodiments, the compound or pharmaceutical composition described herein is suitable for administration to the skin cells of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 pg and 1 pg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

A SIK inhibitor or composition, as described herein, can be administered in combination with one or more additional pharmaceutical agents (e.g., therapeutically and/or prophylactically active agents) useful in increasing skin pigmentation and/or reducing the risk of skin cancer. The compounds or compositions can be administered in combination with additional pharmaceutical agents that improve their activity (e.g., activity (e.g., potency and/or efficacy) in increasing skin pigmentation and/or reducing the risk of skin cancer in a subject in need thereof, and/or in inhibiting the activity of SIK in a subject), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a SIK inhibitor described herein and an additional pharmaceutical agent shows a synergistic effect that is absent in a pharmaceutical composition including one of the SIK inhibitor and the additional pharmaceutical agent, but not both.

The SIK inhibitor or composition can be administered concurrently with, prior to, or subsequent to one or more additional pharmaceutical agents, which are different from the compound or composition and may be useful as, e.g., combination therapies in increasing skin pigmentation and/or reducing the risk of skin cancer. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for increasing skin pigmentation and/or reducing the risk of skin cancer. Each additional pharmaceutical agent may be administered at a dose and/or on a time schedule determined for that pharmaceutical agent. The additional pharmaceutical agents may also be administered together with each other and/or with the SIK inhibitor or composition described herein in a single dose or administered separately in different doses. The particular combination to employ in a regimen will take into account compatibility of the SIK inhibitor described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-musculoskeletal disease agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-musculoskeletal disease agent. In certain embodiments, the additional pharmaceutical agent is an anti-cancer agent. In certain embodiments, the additional pharmaceutical agent is an anti-viral agent. In certain embodiments, the additional pharmaceutical agent is an binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy. In certain embodiments, the additional pharmaceutical agent is an agent for increasing skin pigmentation in a subject. In certain embodiments, the additional pharmaceutical agent is an agent for reducing the risk of skin cancer in a subject. In certain embodiments, the additional pharmaceutical agent is an agent for inducing eumelanin synthesis, inducing melanosomal maturation, export, and localization, or inducing microphthalmia-associated transcription factor (MITF) expression.

Methods of Treatment and Uses

The present disclosure provides methods of inhibiting the activity of SIK (e.g., SIK1, SIK2, or SIK3) in a subject or cell. The present disclosure also provides methods for increasing skin pigmentation and/or reducing the risk of skin cancer in a subject in need thereof. The present disclosure provides methods for increasing skin pigmentation for cosmetic purposes. In certain embodiments, provided herein are methods of increasing the appearance of skin darkening in a subject in need thereof using the described compounds (e.g., via topical administration of the described compounds). In certain embodiments, the present disclosure provides methods of increasing the appearance of skin pigmentation in a subject, the methods comprising administering topically to the subject's skin an effective amount of a salt inducible kinase (SIK) inhibitor of any one of Formulae (I), (II), (III), (IV), (V), (VI), (VI-A), and (VII), or a pharmaceutically acceptable salt, solvate, hydrate, tautomer, or stereoisomer thereof, or a pharmaceutical composition thereof.

In certain embodiments, the present disclosure provides methods of treating polymorphic light eruption (e.g., sun hypersensitivity). The present disclosure provides methods of inducing eumelanin synthesis. The present disclosure provides methods of inducing melanosomal maturation, export, and localization. In certain embodiments, the present disclosure provides methods of inducing (e.g., temporarily and reversibly inducing) microphthalmia-associated transcription factor (MITF) expression. In certain embodiments, the present disclosure provides methods of inducing increased microphthalmia-associated transcription factor (MITF) expression. In certain embodiments, inducing MITF expression comprises temporarily and reversibly inducing MITF expression.

In another aspect, the present disclosure provides methods of inhibiting the activity of SIK, (e.g., SIK1, SIK2, or SIK3) in a subject. In certain embodiments, the activity of a SIK, (e.g., SIK1, SIK2, or SIK3) in a subject is inhibited by a method described herein by at least about 1%, at least about 3%, at least about 10%, at least about 20%, at least about 30%, at least about 40%, at least about 50%, at least about 60%, at least about 70%, at least about 80%, or at least about 90%. In some embodiments, the activity of SIK, (e.g., SIK1, SIK2, or SIK3) in a subject is selectively inhibited by the method. In some embodiments, the activity of SIK2 in a subject is selectively inhibited by the method. In another aspect, the present disclosure provides methods of inhibiting SIK in the skin of a subject.

Another aspect of the present disclosure relates to methods of treating a disease associated with SIK, (e.g., SIK1, SIK2, or SIK3).

In still another aspect, the present disclosure provides methods of preventing skin cancer described herein in a subject in need thereof.

In another aspect, the present disclosure provides methods of increasing skin pigmentation and/or reducing the risk of skin cancer in a subject in need thereof, the method comprising administering topically to the subject's skin an effective amount of a salt inducible kinase (SIK) inhibitor of any one of Formulae (I), (II), (III), (IV), (V), (VI), (VI-A), and (VII), or a pharmaceutically acceptable salt, solvate, hydrate, tautomer, or stereoisomer thereof, or a pharmaceutical composition thereof. In certain embodiments, provided are methods of reversibly increasing skin pigmentation and/or reducing the risk of skin cancer in a subject in need thereof, the method comprising administering topically to the subject's skin an effective amount of a SIK inhibitor of compounds described herein. In certain embodiments, increasing skin pigmentation comprises reversibly increasing skin pigmentation.

In certain embodiments, the methods of the disclosure include administering to a subject in need thereof an effective amount of a compound or pharmaceutical composition described herein. In certain embodiments, the subject being administered a compound or pharmaceutical composition described herein is a human. In certain embodiments, the subject being administered a compound or pharmaceutical composition described herein is a non-human animal. In certain embodiments, the effective amount is an amount effective for inhibiting the activity of a SIK by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of a SIK by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of a SIK by a range between a percentage described in this paragraph and another percentage described in this paragraph, inclusive.

In certain embodiments, the methods of the disclosure include administering to a subject in need thereof an effective amount of a compound or pharmaceutical composition described herein. In certain embodiments, the methods of the disclosure include topically administering to a subject in need thereof an effective amount of a compound or pharmaceutical composition described herein. In certain embodiments, the methods of the disclosure include administering to a subject in need thereof a prophylactically effective amount of a compound or pharmaceutical composition described herein. In certain embodiments, the methods of the disclosure include topically administering to a subject in need thereof a prophylactically effective amount of a compound or pharmaceutical composition described herein.

In another aspect, the present disclosure provides the compounds described herein for use in a method described herein (e.g., method of inhibiting SIK, (e.g., SIK1, SIK2, or SIK3)), or a method of increasing skin pigmentation and/or reducing the risk of skin cancer in a subject in need thereof. The compounds provided may be used in a method of inducing a skin condition in a subject in need thereof. In certain embodiments, provided is a method of increasing skin pigmentation by administering the compounds described herein. In certain embodiments, provided is a method of increasing skin pigmentation and/or reducing the risk of skin cancer by topically administering the compounds described herein to a subject's skin on a body part. In certain embodiments, the body part is the face of the subject. In certain embodiments, the body part is the neck of the subject. In certain embodiments, the body part is the chest of the subject. In certain embodiments, the body part is the back of the subject. In certain embodiments, the skin on the body part is skin on the arms of the subject. In certain embodiments, the skin on the body part is skin on the legs of the subject. In certain embodiments, the skin is on the torso of the subject. In another aspect, the present disclosure provides methods of inhibiting SIK in the skin of a subject. In another aspect, the present disclosure provides methods of inducing eumelanin synthesis. In certain embodiments, the present disclosure provides methods of inducing melanosomal maturation, export, and localization. In certain embodiments, the present disclosure provides methods of inducing microphthalmia-associated transcription factor (MITF) expression. In certain embodiments, the present disclosure provides methods of inducing increased microphthalmia-associated transcription factor (MITF) expression.

In still another aspect, the present disclosure provides the pharmaceutical compositions described herein for use in a method described herein (e.g., a method of inhibiting SIK, (e.g., SIK1, SIK2, or SIK3)), or method of increasing skin pigmentation in a subject in need thereof. In still another aspect, the present disclosure provides the compounds described herein, or a topical formulation thereof, for use in a method of inducing a condition (e.g., increasing skin pigmentation) in a subject in need thereof.

EXAMPLES

In order that the disclosure may be more fully understood, the following examples are set forth. The examples described in this application are offered to illustrate the compounds, pharmaceutical compositions, uses, and methods provided herein and are not to be construed in any way as limiting their scope.

Methods

Materials. Salt inducible kinase inhibitors were dissolved in 30% propylene glycol+70% ethanol.

Kinome Profiling. Kinome profiling was performed using KinomeScan ScanMAX at compound concentration of 1 µM. Protocols are available from DiscoverX®.

Kinase activity in vitro assay. The biochemical activities against SIK2 were measured by Caliper-based mobility shift assay (PerkinElmer®). For these experiments, full length His6-MBP-tagged hSIK2 (4 nM) was incubated with HG-9-91-01 derivatives in buffer containing 100 mM HEPES 7.5, 10 mM $MgCl_2$, 2.5 mM DTT, 0.004% Tween20, 0.003% Brij-35, 30 µM ATP and 1.5 µM ProfilerPro FL-Peptide 10 (5-FAMKKKVSRSGLYRSPSMPENLNRPR-COOH (SEQ ID NO: 1), PerkinElmer®, Catalog No. 760354) at room temperature. Reactions were quenched by adding 20 mM EDTA (pH 8) after 1 hour, and percentage of substrate conversion was measured by LabChip EZ Reader II (PerkinElmer®). IC50's for SIK2 inhibition were calculated using SmartFit nonlinear regression in Genedata® Screener software suite (Genedata®).

All other in vitro kinase assay were conducted using the SelectScreen Kinase Profiling Service at Thermo Fisher Scientific® (Madison, Wis.). The protocols are available from Thermo Fisher Scientific® website.

Cell Culture. UACC257 and UACC62 cells were grown in RPM1+1% penicillin and streptomycin+5% fetal bovine serum. Normal human melanocytes were grown in TIVA, and starved 24 hours in HAM's F-12+1% penicillin and streptomycin before all molecular experiments.

qPCR. mRNA was extracted from cells using the RNeasy Mini Kit (Qiagen®). KAPA SYBR® FAST Universal One-Step qRT-PCR Kit (KAPA BIOSYSTEMS®) was used to prepare mRNA samples for qPCR and samples were analyzed using the 7500 Fast Real Time PCR System (Applied Biosystems®). The relative expression of each gene was calculated by 7500 Fast System Software program, which utilizes Ct normalized to mRNA levels of RPL11 to calculate relative expression. Results are reported relative to control cells.

Cell pelleting experiments. $1 \times 10^5$ UACC257 cells were plated per well in a 6-well plate. Cells were treated daily (1x/day) with 4 uM of SIK inhibitors HG 9-91-01, YKL 06-061, or YKL 06-062 or vehicle control. After 3 days, cells were trypsinized with 0.25% trypsin, resuspended in RPMI media, and pelleted. Pellets were washed 1x with PBS and allowed to dry before imaging.

Mice. C57BL/6J $Mc1r^{e/e}$ mice were crossed with K14—Scf transgenic mice. C57BL/6J $Tyr^{c2j/c2j}$ were crossed with K14—Scf transgenic mice. (Kunisada et al. 1998; D'Orazio et al. 2006).

Photos. Photos were taken using a Nikon® D50 DSLR with a Nikon® Nikkor 40 mm f/2.8 DX G AF-S. Shutter speed ranged from 1/40 to 1/250 and aperture ranged from F3-F8. Ott-Lite Model L139AB were used to create uniform lighting for photos.

Mouse pigmentation experiments. Animals were treated with vehicle control or 37.5 mM HG 9-9-01 until uniform gross darkening was visible as stated in figure legends. Daily differences in darkening of the skin were measured by reflective colorimetry. Skin was harvested, fixed, and processed for paraffin embedding. Sections were cut from paraffin blocks, and sections were stained utilizing hematoxylin and eosin (morphology) and Fontana-Masson (melanin). Melanin dissolution was conducted utilizing NaOH lysis method (Wakamatsu and Ito 2002).

Human pigmentation experiments. Full thickness human breast skin explants were cultured in petri dishes with a solid phase and liquid phase phenol red free DMEM medium with 20% penicillin streptomycin, 5% fungizone (Gibco®), and 10% FBS. Explants were treated daily with vehicle or SIK inhibitor as indicated in figure legends. Passive application refers to simply applying the treatment to skin without further rubbing or manipulation. Mechanical application refers to application of agents to skin with further rubbing of treatment with 10 clockwise turns of a gloved cotton swab applicator. Skin was harvested, fixed, and processed for paraffin embedding. Sections were cut from paraffin blocks, and sections were stained utilizing hematoxylin and eosin (morphology) and Fontana-Masson (melanin).

Colorimeter Measurements: Differences in darkening of the skin were measured by reflective colorimetry (CIE L* white-black color axis) utilizing a CR-400 Colorimeter (Minolta®) calibrated by a calibration plate (C: Y 93.1, x 0.3133, y 0.3194) before each set of measurements.

Statistical Analysis. Data are presented as the mean±SD. Statistical significance of differences between experimental groups for dose curve experiments were assessed by one-way ANOVA with Dunnet post test. Statistical significance of differences between experimental groups for time course experiments were assessed by two-way ANOVA with Dunnet post test. Multiplicity adjusted P values were reported for each comparison, and differences of means were considered significant if P<0.05.

Example I. Preparation and Characterization of Exemplary Compounds

Unless otherwise noted, reagents and solvents were used as received from commercial suppliers. Proton nuclear magnetic resonance spectra ($^1$H NMR) were obtained on Bruker AVANCE spectrometer at 400 MHz for proton. Spectra are given in ppm (δ) and coupling constants, J, are reported in Hertz. The solvent peak was used as the reference peak for proton spectra. LC-MS spectra were obtained on Agilent 1100 HPLC LC-MS ion trap electrospray ionization (ESI) mass spectrometer.

Synthesis of YKL-04-114 and YKL-05-093

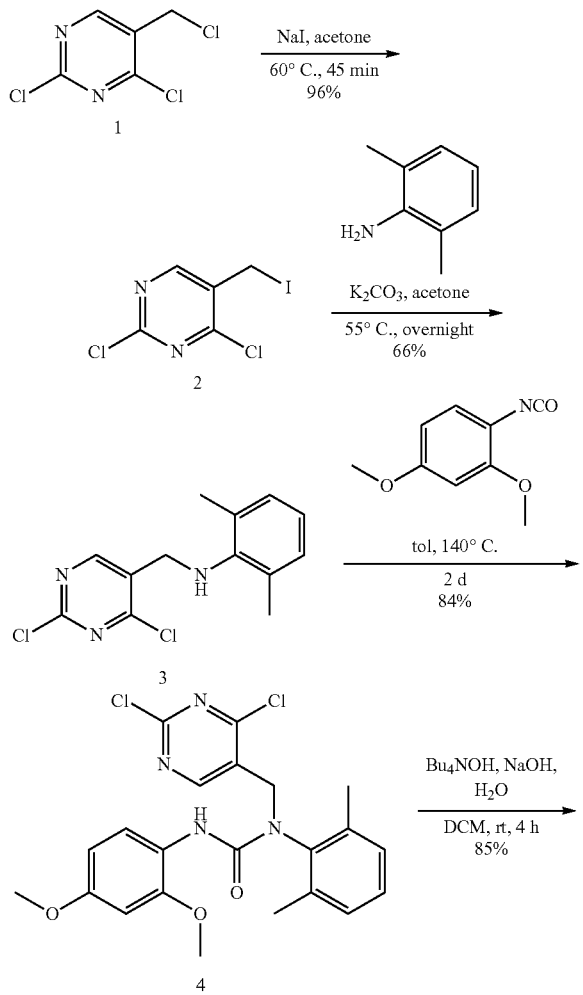

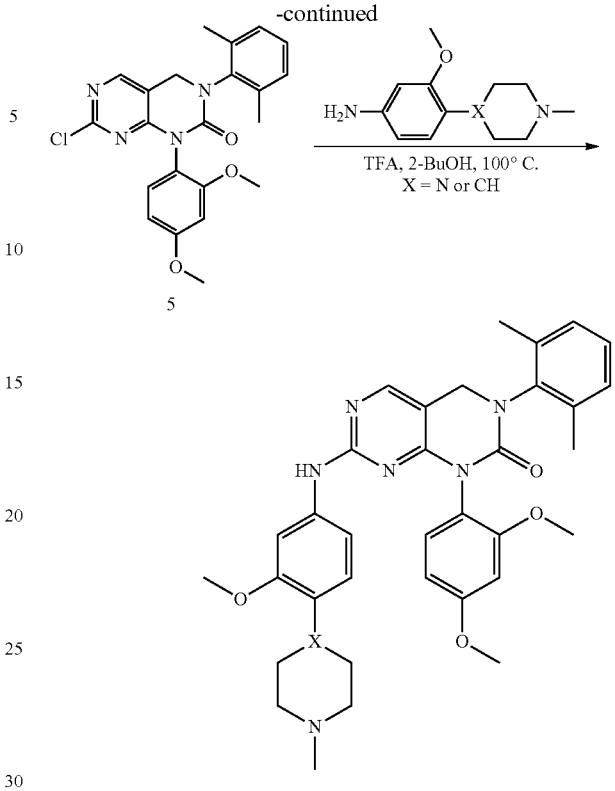

YKL-04-114, X = N
YKL-05-093, X = CH 2,4-dichloro-5-(iodomethyl)pyrimidine (2)

A mixture of 2,4-dichloro-5-(chloromethyl)pyrimidine (15.0 g, 76.0 mmol), NaI (13.7 g, 91.4 mmol) in acetone was stirred at 60° C. for 45 min. The resulting precipitate (NaCl) was removed by filtration and washed with acetone. The combined filtrate was concentrated to give light yellow solid, which was purified by column chromatography on silica gel (eluting with DCM) to obtain 2,4-dichloro-5-(iodomethyl)pyrimidine 2 as a light yellow solid (30.8 g, yield 96%). LCMS (m/z): 289.3 [M+H]$^+$.

N-((2,4-dichloropyrimidin-5-yl)methyl)-2,6-dimethylaniline (3)

A mixture of 2,4-dichloro-5-(iodomethyl)pyrimidine 2 (7.0 g, 24.2 mmol), 2,6-dimethylaniline (3.8 g, 31.4 mmol), K$_2$CO$_3$ (5.0 g, 36.2 mmol) in acetone (60 mL) was stirred at 55° C. overnight. The solvent was removed and the residue was extracted with EtOAc (150 mL×3). The combined organic phase was washed with brine (80 mL×3), dried with Na$_2$SO$_4$, filtered, and concentrated. The residue was purified by column chromatography on silica gel (petroleum ether/EtOAc=8/1, 4/1, 1/1) to get N-((2,4-dichloropyrimidin-5-yl)methyl)-2,6-dimethylaniline 3 as a light brown solid (4.5 g, yield 66%). LCMS (m/z): 282.3 [M+H]$^+$.

1-((2,4-dichloropyrimidin-5-yl)methyl)-3-(2,4-dimethoxyphenyl)-1-(2,6-dimethylphenyl)urea (4)

A round bottomed flask with a Dean-Stark apparatus was charged with N-((2,4-dichloropyrimidin-5-yl)methyl)-2,6-dimethylaniline 3 (3.0 g, 10.6 mmol), 1-isocyanato-2,4- dimethoxybenzene (2.5 g, 14.0 mmol), toluene (3 mL). The mixture was stirred at 130° C. for 2 d, cooled to rt, and concentrated. The residue was purified by column chromatography on silica gel (petroleum ether/EtOAc=4/1, 2/1, 1/1, EA) to get 1-((2,4-dichloropyrimidin-5-yl)methyl)-3-(2,4-dimethoxyphenyl)-1-(2,6-dimethylphenyl)urea 4 as a light brown solid (4.1 g, yield 84%). LCMS (m/z): 461.4 [M+H]$^+$.

7-chloro-1-(2,4-dimethoxyphenyl)-3-(2,6-dimethylphenyl)-3,4-dihydropyrimido[4,5-d]pyrimidin-2 (1H)-one (5)

To the solution of -((2,4-dichloropyrimidin-5-yl)methyl)-3-(2,4-dimethoxyphenyl) 1-(2,6-dimethylphenyl) urea 4 (3.1 g, 6.7 mmol) in DCM (20 mL) was added Bu$_4$NOH (174 mg, 0.67 mmol), NaOH (474 mg, in 2 mL H$_2$O, 11.8 mmol). The mixture was stirred at rt for 4 h. The final mixture was diluted with H$_2$O (20 mL), extracted with DCM (80 mL×3). The combined organic phase was washed with brine (50 mL×2), dried with Na$_2$SO$_4$, filtered, and concentrated. The residue was purified by column chromatography on silica gel (eluting with DCM/MeOH=20/1) to give 7-chloro-1-(2,4-dimethoxyphenyl)-3-(2,6-dimethylphenyl)-3,4-dihydropyrimido[4,5-d]pyrimidin-2(1H)-one 5 as an off-white solid (2.4 g, yield 85%). $^1$H NMR (DMSO-d$_6$, 400 MHz): δ 8.37 (s, 1H), 7.16-7.19 (m, 4H), 6.68 (d, J=2.4 Hz, 1H), 6.58 (dd, J=8.8, 2.4 Hz, 1H), 4.74 (dd, J=5.5, 1.6 Hz, 2H), 3.81 (s, 3H), 3.70 (s, 3H), 2.25 (s, 3H), 2.20 (s, 3H); LCMS (m/z): 425.4 [M+H]$^+$.

YKL-04-114

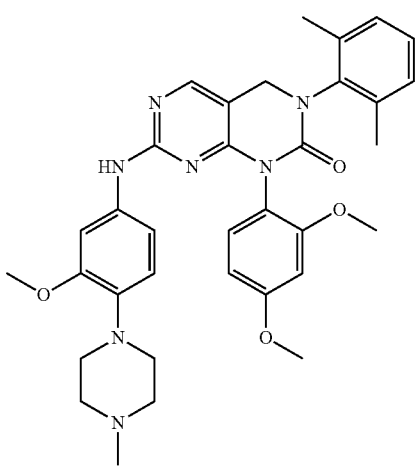

A mixture of 7-chloro-1-(2,4-dimethoxyphenyl)-3-(2,6-dimethylphenyl)-3,4-dihydropyrimido[4,5-d]pyrimidin-2 (1H)-one 5 (10 mg, 0.024 mmol), 3-methoxy-4-(4-methylpiperazin-1-yl)aniline (7.8 mg, 0.035 mmol), and TFA (5.5 mg, 0.048 mmol) in 2-BuOH (0.5 mL) was stirred at 100° C. overnight. The reaction was cooled and concentrated. The residue was purified by prep-HPLC (MeOH/H$_2$O 5:95-100: 0), followed by column chromatography on silica gel (0-10% MeOH in DCM) to afford YKL-04-114 as a white solid (8.0 mg, 56%). $^1$H NMR (DMSO-d$_6$, 400 MHz): δ 9.21 (s, 1H), 8.20 (s, 1H), 7.25-7.22 (m, 4H), 7.03 (d, J=8.4 Hz, 1H), 6.98 (s, 1H), 6.77 (d, J=2.8 Hz, 1H), 6.68 (dd, J=8.8, 2.8 Hz, 1H), 6.51 (d, J=8.4 Hz, 1H), 4.73 (d, J=14.4 Hz, 1H), 4.59 (d, J=14.4 Hz, 1H), 3.91 (s, 3H), 3.73 (s, 3H), 3.68 (s, 3H), 2.94 (m, 4H), 2.58 (m, 4H), 2.34 (s, 3H), 2.32 (s, 3H), 2.29 (s, 3H); LCMS (m/z): 610.7 [M+H]$^+$.

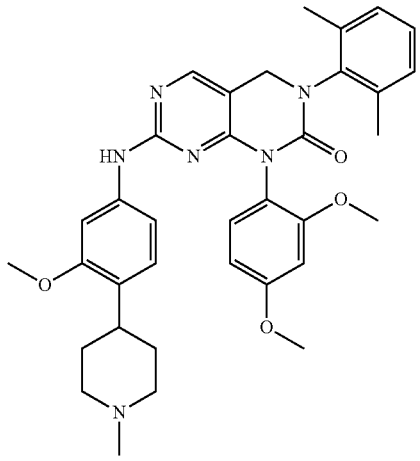 [SMILES: COc1ccc(N2C(=O)N(c3c(C)cccc3C)Cc3cnc(Nc4ccc(N5CCN(C)CC5)c(OC)c4)nc32)c(OC)c1]

A mixture of 7-chloro-1-(2,4-dimethoxyphenyl)-3-(2,6-dimethylphenyl)-3,4-dihydropyrimido[4,5-d]pyrimidin-2 (1H)-one 5 (100 mg, 0.24 mmol), 3-methoxy-4-(1-methylpiperidin-4-yl)aniline (78 mg, 0.35 mmol), and TFA (55 mg, 0.48 mmol) in 2-BuOH (5 mL) was stirred at 100° C. overnight. The reaction was cooled and concentrated. The residue was purified by prep-HPLC (MeOH/H$_2$O 5:95-100: 0), followed by column chromatography on silica gel (0-10% MeOH in DCM) to afford YKL-05-093 as a white solid (127 mg, 89%). $^1$H NMR (DMSO-d$_6$, 400 MHz): δ 9.16 (s, 1H), 8.09 (s, 1H), 7.12-7.09 (m, 4H), 6.95 (d, J=8.0 Hz, 1H), 6.86 (s, 1H), 6.65-6.62 (m, 2H), 6.55 (dd, J=8.4, 2.4 Hz, 1H), 4.60 (d, J=14.8 Hz, 1H), 4.47 (d, J=14.8 Hz, 1H), 3.78 (s, 3H), 3.60 (s, 3H), 3.54 (s, 3H), 2.81 (m, 2H), 2.66-2.57 (m, 1H), 2.19 (s, 3H), 2.16 (s, 3H), 2.15 (s, 3H), 1.95-1.90 (m, 2H), 1.56-1.46 (m, 4H); LCMS (m/z): 609.7 [M+H]$^+$.

Synthesis of YKL-06-061

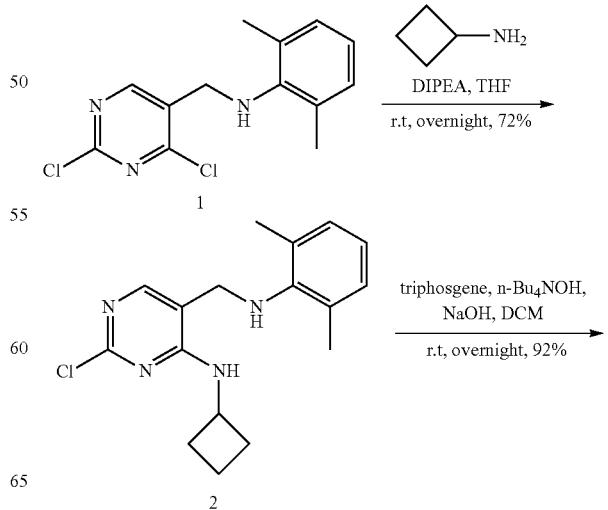

-continued

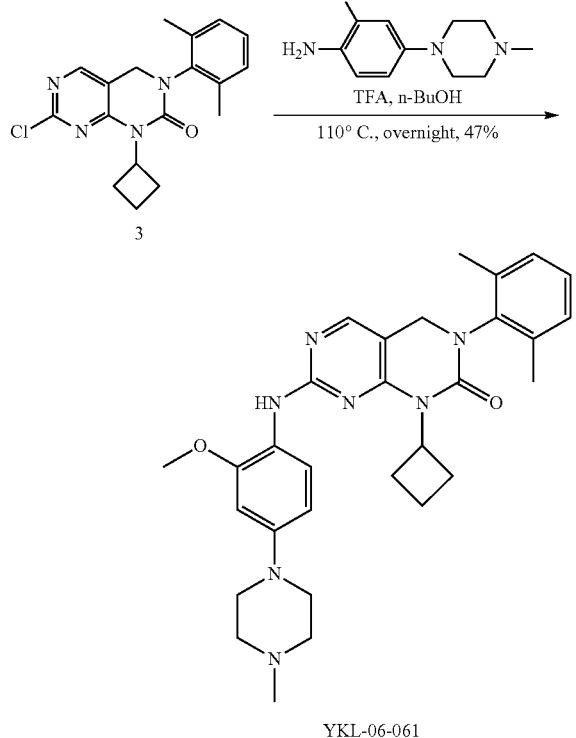

YKL-06-061

2-chloro-N-cyclobutyl-5-((2,6-dimethylphenylamino)methyl)pyrimidin-4-amine (2)

A mixture of N-((2,4-dichloropyrimidin-5-yl)methyl)-2,6-dimethylaniline (1) (1.10 g, 3.91 mmol), cyclobutanamine (1.67 g, 23.49 mmol) and DIPEA (6 mL) in THF (100 mL) was stirred at room temperature overnight. Then the mixture was concentrated, the residue was purified by flash column (eluting with ethyl acetate/PE=0-15%) to give 2-chloro-N-cyclobutyl-5-((2,6-dimethylphenylamino)methyl)pyrimidin-4-amine (2) as white solid (0.90 g, yield 72%). LCMS (m/z): 317 [M+H]$^+$.

7-chloro-1-cyclobutyl-3-(2,6-dimethylphenyl)-3,4-dihydropyrimido[4,5-d]pyrimidin-2(1H)-one (3)

A mixture of 2-chloro-N-cyclobutyl-5-((2,6-dimethylphenylamino)methyl)pyrimidin-4-amine (2) (0.75 g, 2.37 mmol) and triphosgene (1.05 g, 3.56 mmol) in DCM (100 mL) was stirred at room temperature for 1 hour, the a solution of NaOH (1.90 g, 47.5 mmol) and n-Bu$_4$NOH (78 mg, 0.301 mmol) in H$_2$O (24 mL) was added, the resulting mixture was stirred at room temperature overnight. The organic layer was washed with H$_2$O (50 mL×2), dried with Na$_2$SO$_4$, filtered and concentrated, the residue was purified by flash column (eluting with ethyl acetate/PE=0-15%) to give 7-chloro-1-cyclobutyl-3-(2,6-dimethylphenyl)-3,4-dihydropyrimido[4,5-d] pyrimidin-2(1H)-one (3) as white solid (750 mg, yield 92%). LCMS (m/z): 343 [M+H]$^+$. $^1$H-NMR (CDCl$_3$, 400 MHz): δ 8.11 (s, 1H), 7.11-7.18 (m, 3H), 4.83-4.92 (m, 1H), 4.47 (d, J=0.8 Hz, 2H), 2.52-2.59 (m, 4H), 2.22 (s, 6H), 1.74-1.92 (m, 2H).

1-cyclobutyl-3-(2,6-dimethylphenyl)-7-(2-methoxy-4-(4-methylpiperazin-1-yl)phenylamino)-3,4-dihydropyrimido[4,5-d]pyrimidin-2(1H)-one (YKL-06-061)

A mixture of 7-chloro-1-cyclobutyl-3-(2,6-dimethylphenyl)-3,4-dihydropyrimido[4,5-d]pyrimidin-2(1H)-one (3) (70 mg, 0.204 mmol), 2-methoxy-4-(4-methylpiperazin-1-yl)aniline (66 mg, 0.298 mmol) and TFA (0.5 mL) in n-BuOH (5 mL) was stirred at 110° C. overnight, the mixture was concentrated, the residue was purified by prep-HPLC (0.05% NH$_4$HCO$_3$ in CH$_3$CN—H$_2$O) to give YKL-06-061 as white solid (50 mg, yield 47%). LCMS (m/z): 528 [M+H]$^+$. $^1$H-NMR (CDCl$_3$, 400 MHz): δ 8.22 (d, J=8.4 Hz, 1H), 7.95 (s, 1H), 7.36 (s, 1H), 7.09-7.16 (m, 3H), 6.56-6.60 (m, 2H), 4.90-4.98 (m, 1H), 4.37 (s, 2H), 3.90 (s, 3H), 3.20 (t, J=5.2 Hz, 4H), 2.58-2.68 (m, 6H), 2.46-2.54 (m, 2H), 2.38 (s, 3H), 2.23 (s, 6H), 1.74-1.89 (m, 2H).

Synthesis of YKL-06-062

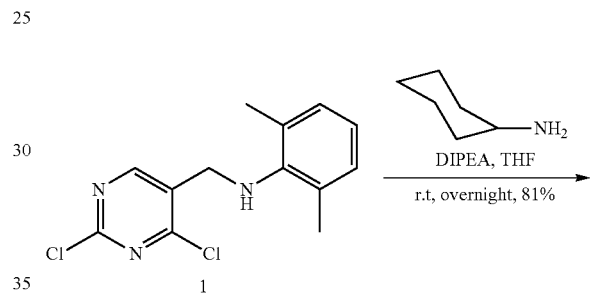

1

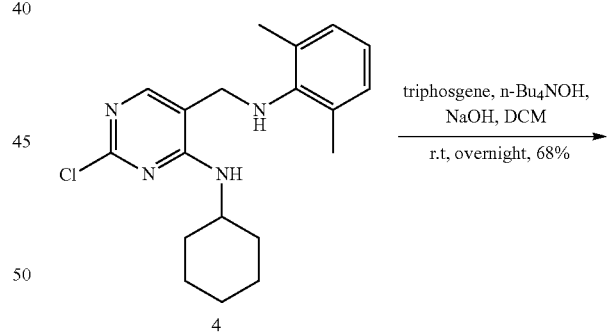

4

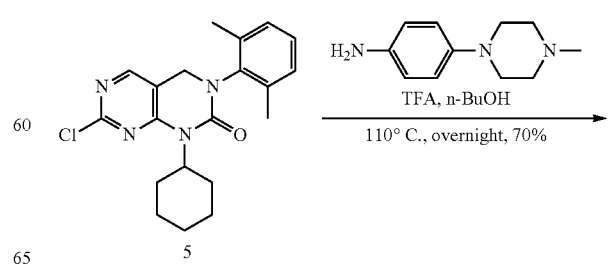

5

-continued

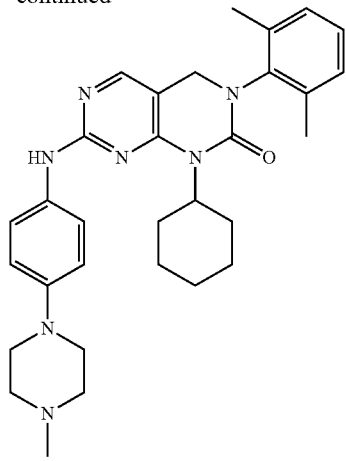

YKL-06-062

2-chloro-N-cyclohexyl-5-((2,6-dimethylphenylamino)methyl)pyrimidin-4-amine (4)

A mixture of A mixture of N-((2,4-dichloropyrimidin-5-yl)methyl)-2,6-dimethylaniline (1) (1.5 g, 5.34 mmol), cyclohexanamine (3.17 g, 32.0 mmol) and DIPEA (6 mL) was stirred at room temperature overnight. Then the mixture was concentrated, the residue was purified by flash column (eluting with ethyl acetate/PE=0-12%) to give 2-chloro-N-cyclohexyl-5-((2,6-dimethylphenylamino)methyl)pyrimidin-4-amine (4) as white solid (1.5 g, yield 81%). LCMS (m/z): 345 [M+H]$^+$.

7-chloro-1-cyclohexyl-3-(2,6-dimethylphenyl)-3,4-dihydropyrimido[4,5-d]pyrimidin-2(1H)-one (5)

A mixture of 2-chloro-N-cyclohexyl-5-((2,6-dimethylphenylamino)methyl)pyrimidin-4-amine (4) (1.50 g, 4.36 mmol) and triphosgene (1.94 g, 6.54 mmol) in DCM (100 mL) was stirred at room temperature for 30 minutes, then a solution of NaOH (3.49 g, 87.3 mmol) and n-Bu$_4$NOH (78 mg, 0.301 mmol) in H$_2$O (43 mL) was added, the resulting mixture was stirred at room temperature overnight. The organic layer was washed with H$_2$O (50 mL×2), dried with Na$_2$SO$_4$, filtered and concentrated to give crude product, then purified by flash column (eluting with ethyl acetate/PE=0-20%) to give 7-chloro-1-cyclohexyl-3-(2,6-dimethylphenyl)-3,4-dihydro-pyrimido[4,5-d]pyrimidin-2(1H)-one (5) as white solid (1.1 g, yield 68%). LCMS (m/z): 371 [M+H]$^+$. $^1$H-NMR (CDCl$_3$, 400 MHz): δ 8.08 (s, 1H), 7.11-7.18 (m, 3H), 4.63-4.71 (m, 1H), 4.49 (d, J=0.8 Hz, 2H), 2.45-2.56 (m, 2H), 2.22 (s, 6H), 1.65-1.86 (m, 5H), 1.34-1.43 (m, 2H), 1.17-1.28 (m, 1H).

1-cyclohexyl-3-(2,6-dimethylphenyl)-7-(4-(4-methylpiperazin-1-yl)phenylamino)-3,4-dihydropyrimido[4,5-d]pyrimidin-2(1H)-one (YKL-06-062)

A mixture of 7-chloro-1-cyclohexyl-3-(2,6-dimethylphenyl)-3,4-dihydropyrimido[4,5-d]pyrimidin-2(1H)-one (5) (94 mg, 0.254 mmol), 4-(4-methylpiperazin-1-yl)aniline (97 mg, 0.508 mmol) and TFA (0.5 mL) in n-BuOH (8 mL) was stirred at 110° C. overnight. The mixture was concentrated, the residue was purified by prep-HPLC (0.05% NH$_4$HCO$_3$ in CH$_3$CN—H$_2$O) to give YKL-06-062 as light yellow solid (94 mg, yield 70%). LCMS (m/z): 526 [M+H]$^+$. $^1$H-NMR (CDCl$_3$, 400 MHz): δ 7.92 (s, 1H), 7.46-7.50 (m, 2H), 7.09-7.15 (m, 3H), 7.02 (s, 1H), 6.93-6.96 (m, 2H), 4.61-4.69 (m, 1H), 4.38 (s, 2H), 3.19 (t, J=5.2 Hz, 4H), 2.61 (t, J=5.2 Hz, 4H), 2.43-2.53 (m, 2H), 2.36 (s, 3H), 2.23 (s, 6H), 1.76-1.86 (m, 4H), 1.66 (d, J=12.4 Hz, 1H), 1.32-1.43 (m, 2H), 1.14-1.23 (m, 1H).

TABLE 1

| Exemplary Compounds of Formula (I), (II), (III), (IV), and (V) | |
|---|---|
| Compound Number | Compound Structure |
| YKL 05-120 | ![structure] |
| YKL 05-200-01 | ![structure] |

TABLE 1-continued
Exemplary Compounds of Formula (I), (II), (III), (IV), and (V)
Compound Number | Compound Structure
YKL 05-200-02
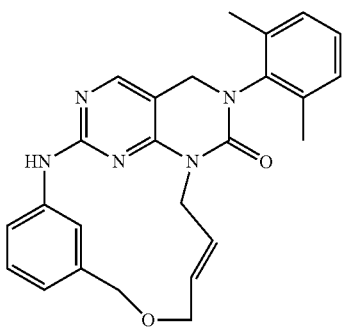 [SMILES: Cc1cccc(C)c1N1Cc2cnc3nc2N(C/C=C/COCc2cccc(c2)N3)C1=O]
YKL 05-201-1
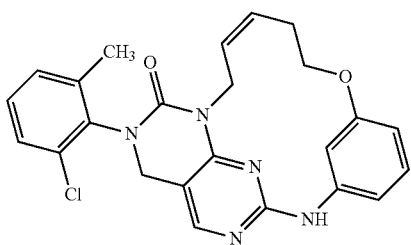 [SMILES: Cc1cccc(Cl)c1N1Cc2cnc3nc2N(C/C=C\CCOc2cccc(c2)N3)C1=O]
YKL 05-201-2
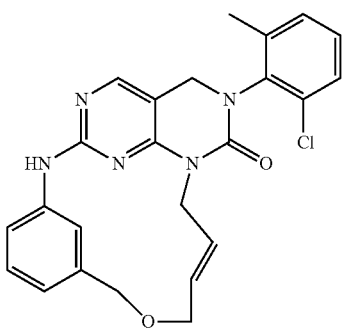 [SMILES: Cc1cccc(Cl)c1N1Cc2cnc3nc2N(C/C=C/COCc2cccc(c2)N3)C1=O]
YKL 05-203-1
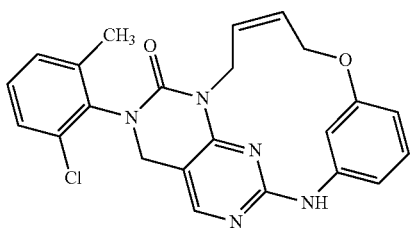 [SMILES: Cc1cccc(Cl)c1N1Cc2cnc3nc2N(C/C=C\COc2cccc(c2)N3)C1=O]
YKL 05-203-2
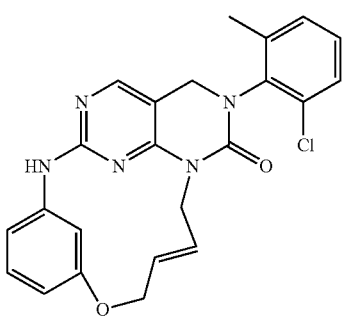 [SMILES: Cc1cccc(Cl)c1N1Cc2cnc3nc2N(C/C=C/COc2cccc(c2)N3)C1=O]

TABLE 1-continued
Exemplary Compounds of Formula (I), (II), (III), (IV), and (V)
| Compound Number | Compound Structure |
| --- | --- |
| YKL 05-204-1 | 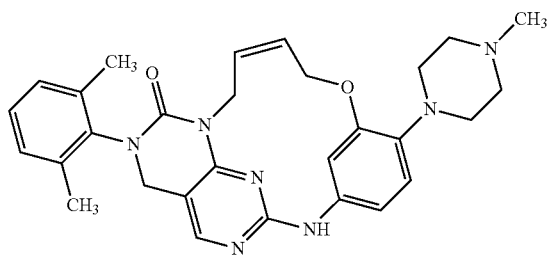 [SMILES: Cc1cccc(C)c1N1Cc2cnc3nc2N(C/C=C\COc2cc(ccc2N2CCN(C)CC2)N3)C1=O] |
| YKL 05-204-2 | 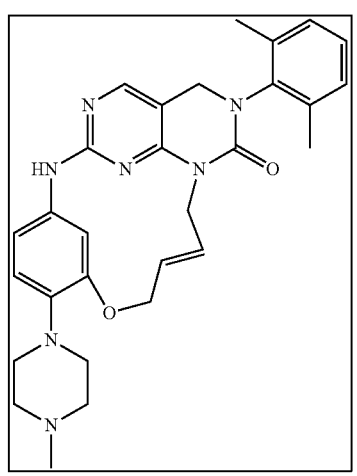 [SMILES: Cc1cccc(C)c1N1Cc2cnc3nc2N(C/C=C/COc2cc(ccc2N2CCN(C)CC2)N3)C1=O] |
| YKL 06-029 | 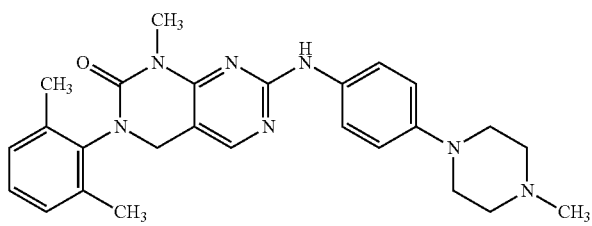 [SMILES: Cc1cccc(C)c1N1Cc2cnc(Nc3ccc(N4CCN(C)CC4)cc3)nc2N(C)C1=O] |
| YKL 06-030 | 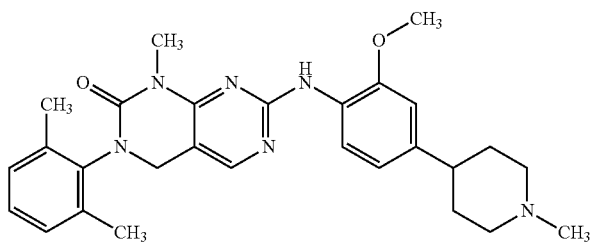 [SMILES: COc1cc(C2CCN(C)CC2)ccc1Nc1ncc2c(n1)N(C)C(=O)N(c1c(C)cccc1C)C2] |
| YKL 06-031 | 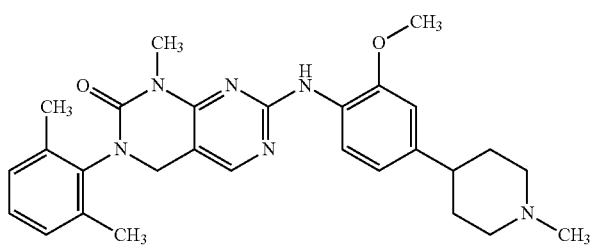 |

TABLE 1-continued
Exemplary Compounds of Formula (I), (II), (III), (IV), and (V)
| Compound Number | Compound Structure |
|---|---|
| YKL 06-033 | 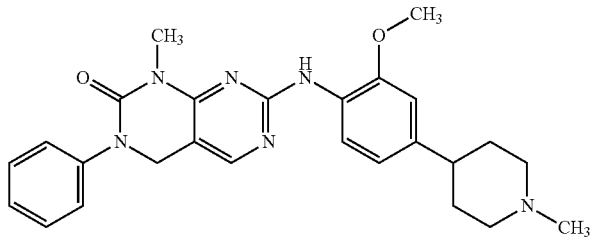 [SMILES: COc1cc(C2CCN(C)CC2)ccc1Nc1ncc2c(n1)N(C)C(=O)N(c1ccccc1)C2] |
| YKL 06-046 | 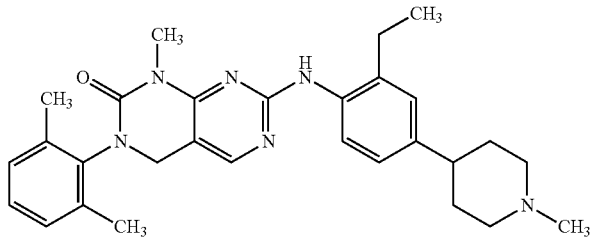 [SMILES: CCc1cc(C2CCN(C)CC2)ccc1Nc1ncc2c(n1)N(C)C(=O)N(c1c(C)cccc1C)C2] |
| YKL 06-050 | 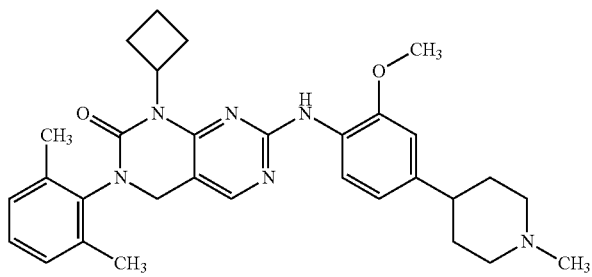 [SMILES: COc1cc(C2CCN(C)CC2)ccc1Nc1ncc2c(n1)N(C1CCC1)C(=O)N(c1c(C)cccc1C)C2] |
| YKL 06-058 | 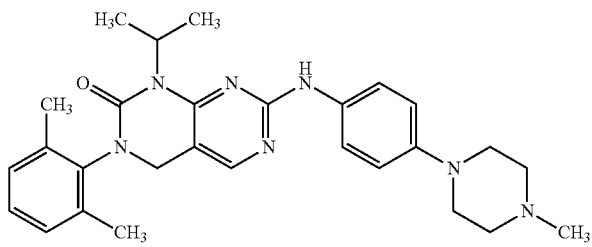 [SMILES: Cc1cccc(C)c1N1Cc2cnc(Nc3ccc(N4CCN(C)CC4)cc3)nc2N(C(C)C)C1=O] |
| YKL 06-059 | 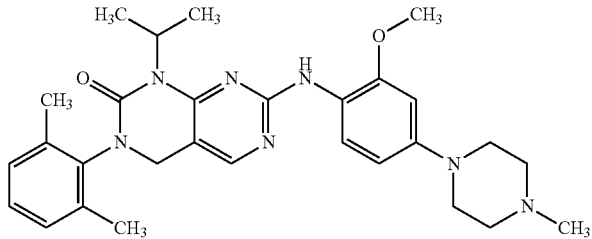 |
| YKL 06-059 | 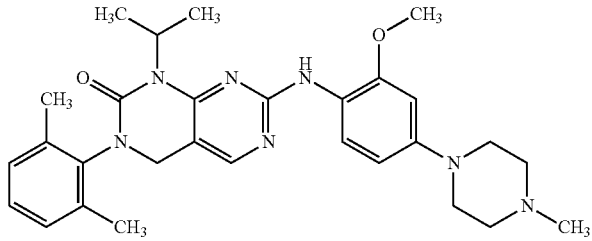 [SMILES: COc1cc(N2CCN(C)CC2)ccc1Nc1ncc2c(n1)N(C(C)C)C(=O)N(c1c(C)cccc1C)C2] |

TABLE 1-continued
Exemplary Compounds of Formula (I), (II), (III), (IV), and (V)
Compound Number   Compound Structure
YKL 06-060
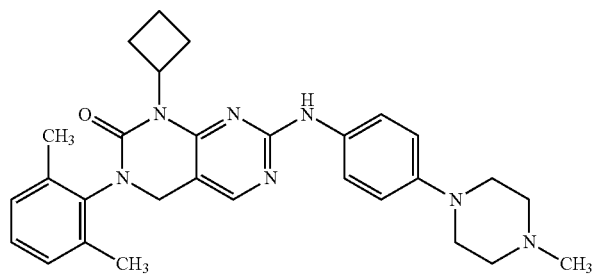 [SMILES: Cc1cccc(C)c1N1Cc2cnc(Nc3ccc(N4CCN(C)CC4)cc3)nc2N(C2CCC2)C1=O]
YKL 06-061
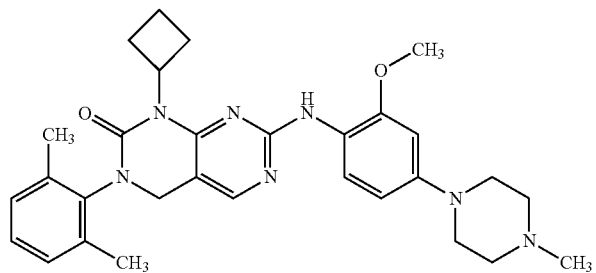 [SMILES: COc1cc(N2CCN(C)CC2)ccc1Nc1ncc2c(n1)N(C1CCC1)C(=O)N(c1c(C)cccc1C)C2]
YKL 06-062
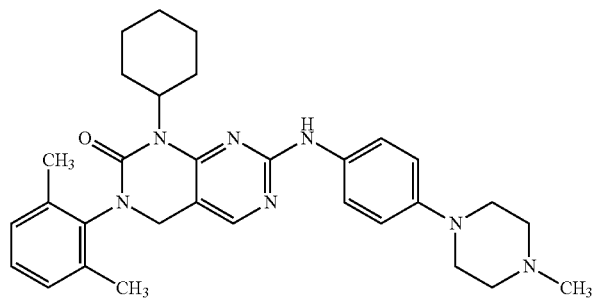 [SMILES: Cc1cccc(C)c1N1Cc2cnc(Nc3ccc(N4CCN(C)CC4)cc3)nc2N(C2CCCCC2)C1=O]
YKL-04-136-8
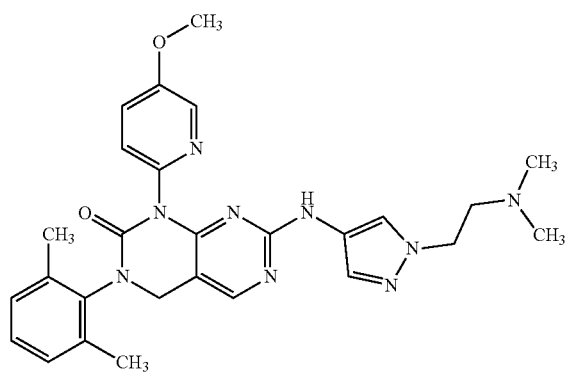 [SMILES: COc1ccc(N2C(=O)N(c3c(C)cccc3C)Cc3cnc(Nc4cnn(CCN(C)C)c4)nc32)nc1]

TABLE 1-continued
Exemplary Compounds of Formula (I), (II), (III), (IV), and (V)
| Compound Number | Compound Structure |
|---|---|
| YKL-04-136-7 | 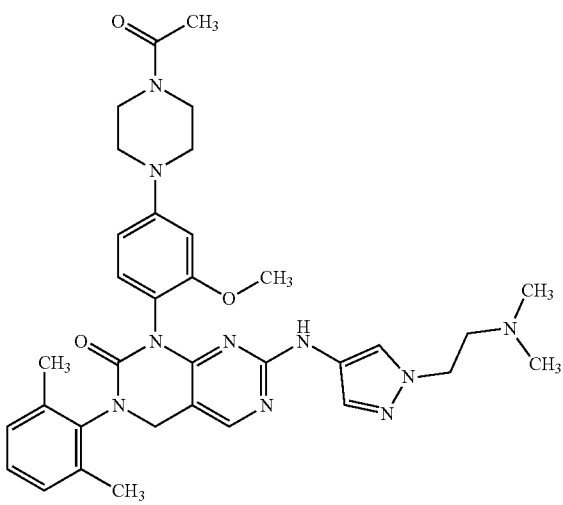 [SMILES: COc1cc(N2CCN(C(C)=O)CC2)ccc1N1C(=O)N(c2c(C)cccc2C)Cc2cnc(Nc3cnn(CCN(C)C)c3)nc21] |
| YKL-04-136-6 | 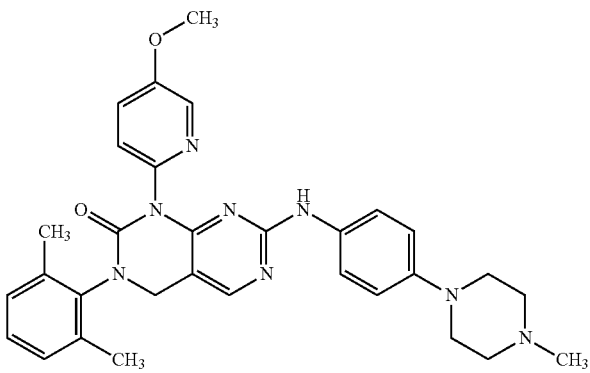 [SMILES: COc1ccc(N2C(=O)N(c3c(C)cccc3C)Cc3cnc(Nc4ccc(N5CCN(C)CC5)cc4)nc32)nc1] |
| YKL-04-136-5 | 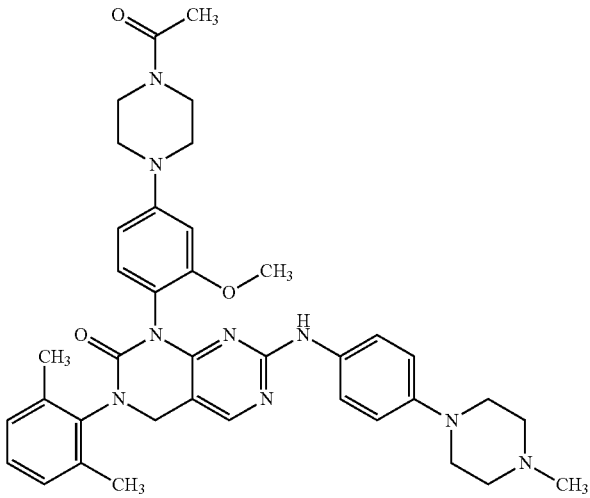 [SMILES: COc1cc(N2CCN(C(C)=O)CC2)ccc1N1C(=O)N(c2c(C)cccc2C)Cc2cnc(Nc3ccc(N4CCN(C)CC4)cc3)nc21] |

TABLE 1-continued
Exemplary Compounds of Formula (I), (II), (III), (IV), and (V)
Compound Number  Compound Structure
YKL-04-136-4
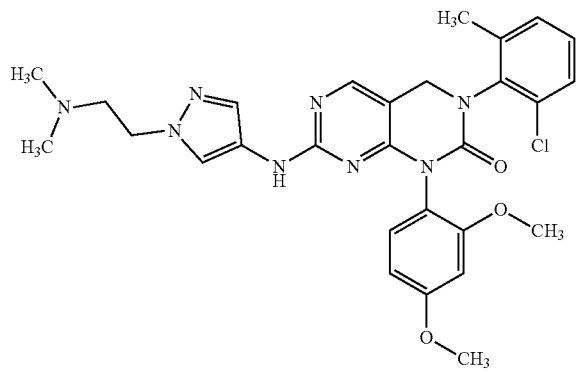 [SMILES: COc1ccc(N2C(=O)N(c3c(C)cccc3Cl)Cc3cnc(Nc4cnn(CCN(C)C)c4)nc32)c(OC)c1]
YKL-04-136-3
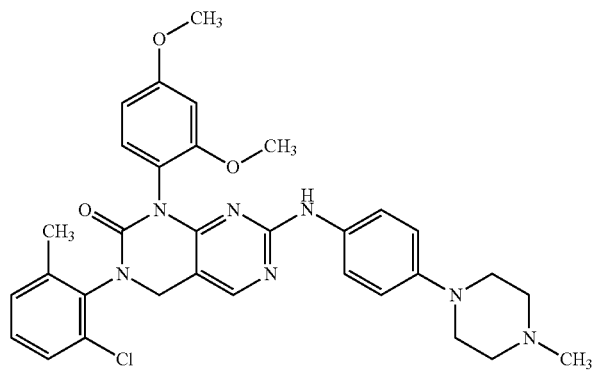 [SMILES: COc1ccc(N2C(=O)N(c3c(C)cccc3Cl)Cc3cnc(Nc4ccc(N5CCN(C)CC5)cc4)nc32)c(OC)c1]
YKL-04-136-2
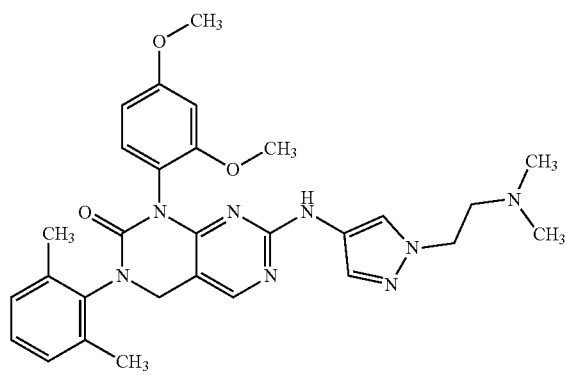 [SMILES: COc1ccc(N2C(=O)N(c3c(C)cccc3C)Cc3cnc(Nc4cnn(CCN(C)C)c4)nc32)c(OC)c1]

TABLE 1-continued
Exemplary Compounds of Formula (I), (II), (III), (IV), and (V)
Compound Number  Compound Structure
YKL-04-136-1
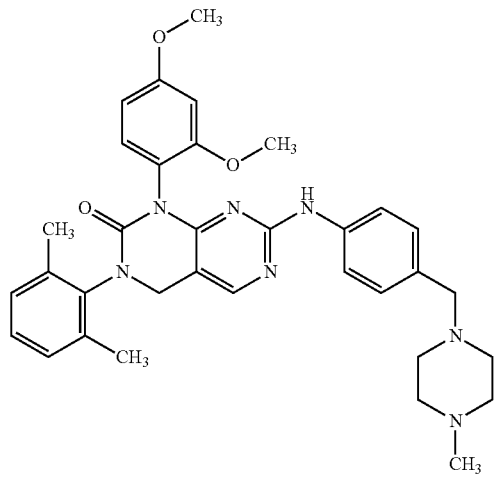 [SMILES: COc1ccc(N2C(=O)N(c3c(C)cccc3C)Cc3cnc(Nc4ccc(CN5CCN(C)CC5)cc4)nc32)c(OC)c1]
YKL-04-125
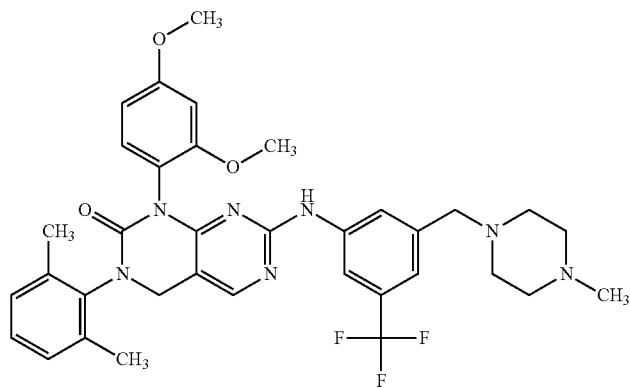 [SMILES: COc1ccc(N2C(=O)N(c3c(C)cccc3C)Cc3cnc(Nc4cc(CN5CCN(C)CC5)cc(C(F)(F)F)c4)nc32)c(OC)c1]
YKL-04-118
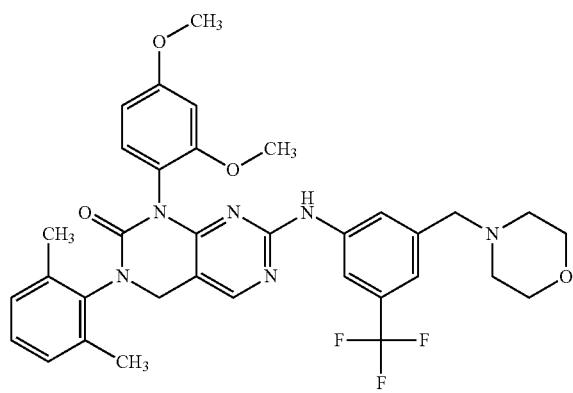 [SMILES: COc1ccc(N2C(=O)N(c3c(C)cccc3C)Cc3cnc(Nc4cc(CN5CCOCC5)cc(C(F)(F)F)c4)nc32)c(OC)c1]

TABLE 1-continued
Exemplary Compounds of Formula (I), (II), (III), (IV), and (V)
Compound Number  Compound Structure
YKL-04-115 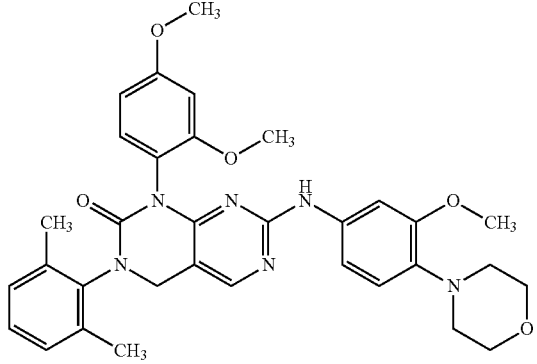 [SMILES: COc1ccc(N2C(=O)N(c3c(C)cccc3C)Cc3cnc(Nc4ccc(N5CCOCC5)c(OC)c4)nc32)c(OC)c1]
YKL-04-114 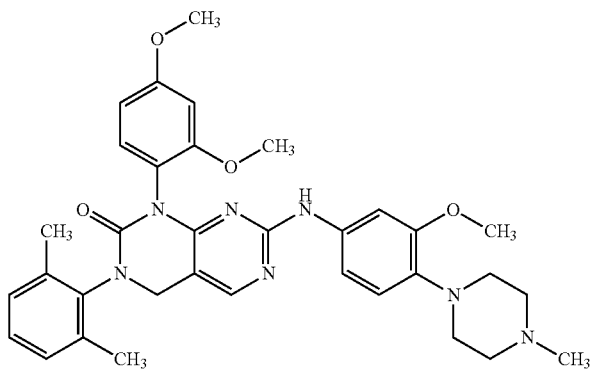 [SMILES: COc1ccc(N2C(=O)N(c3c(C)cccc3C)Cc3cnc(Nc4ccc(N5CCN(C)CC5)c(OC)c4)nc32)c(OC)c1]
YKL-04-113 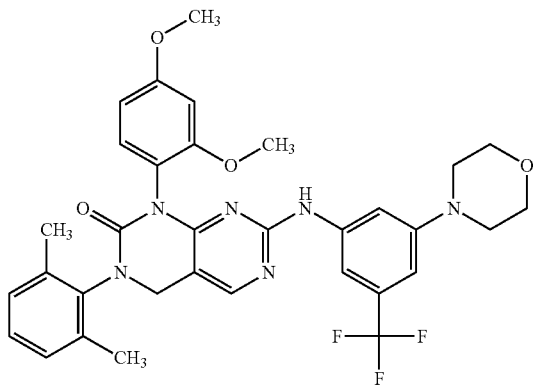 [SMILES: COc1ccc(N2C(=O)N(c3c(C)cccc3C)Cc3cnc(Nc4cc(N5CCOCC5)cc(C(F)(F)F)c4)nc32)c(OC)c1]
YKL-04-112 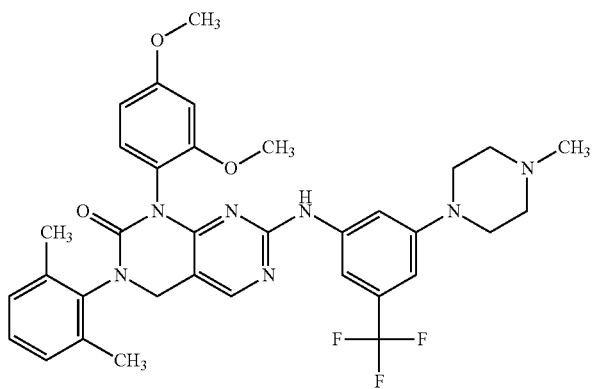 [SMILES: COc1ccc(N2C(=O)N(c3c(C)cccc3C)Cc3cnc(Nc4cc(N5CCN(C)CC5)cc(C(F)(F)F)c4)nc32)c(OC)c1]

TABLE 1-continued
Exemplary Compounds of Formula (I), (II), (III), (IV), and (V)
Compound Number   Compound Structure
YKL-04-108
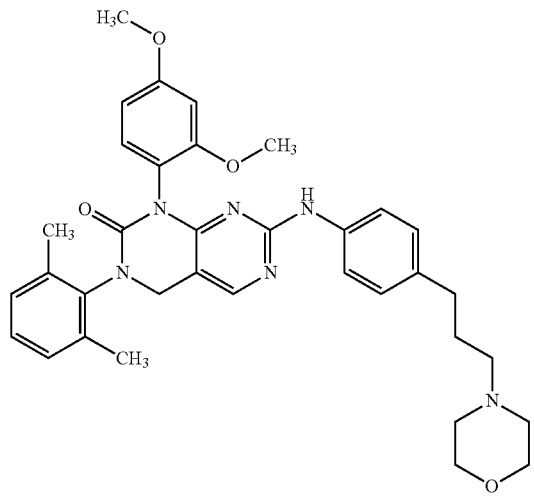 [SMILES: COc1ccc(N2C(=O)N(c3c(C)cccc3C)Cc3cnc(Nc4ccc(CCCN5CCOCC5)cc4)nc32)c(OC)c1]
YKL-04-107
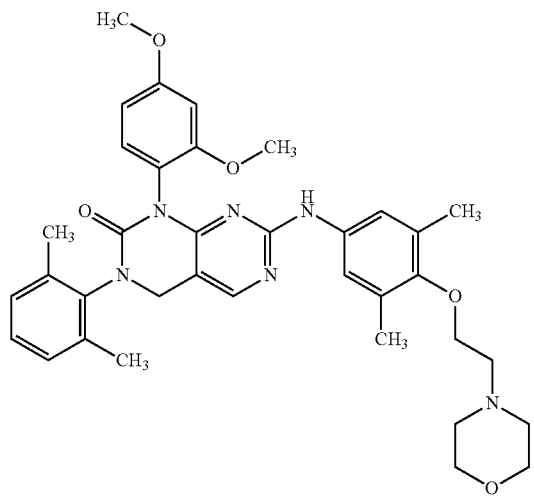 [SMILES: COc1ccc(N2C(=O)N(c3c(C)cccc3C)Cc3cnc(Nc4cc(C)c(OCCN5CCOCC5)c(C)c4)nc32)c(OC)c1]
YKL-04-106
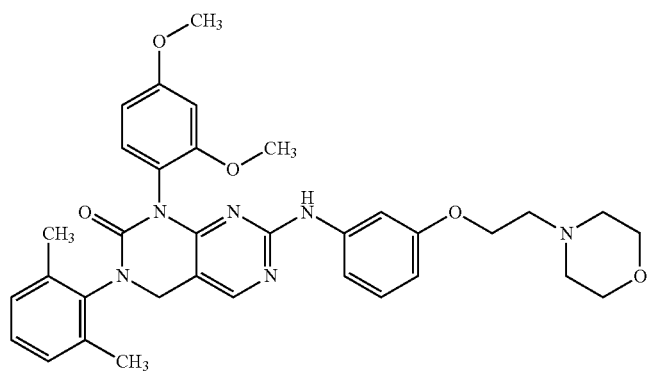 [SMILES: COc1ccc(N2C(=O)N(c3c(C)cccc3C)Cc3cnc(Nc4cccc(OCCN5CCOCC5)c4)nc32)c(OC)c1]

TABLE 1-continued
Exemplary Compounds of Formula (I), (II), (III), (IV), and (V)
Compound Number  Compound Structure
YKL-04-105
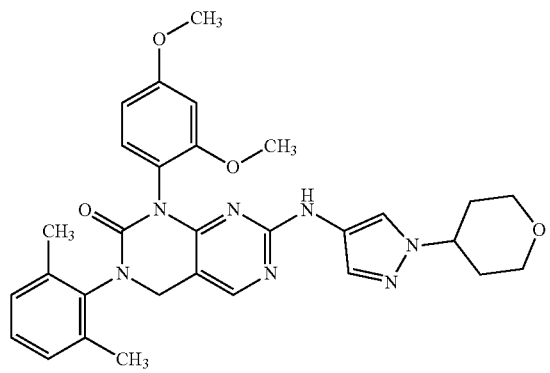 [SMILES: COc1ccc(N2C(=O)N(c3c(C)cccc3C)Cc3cnc(Nc4cnn(C5CCOCC5)c4)nc32)c(OC)c1]
YKL-04-104
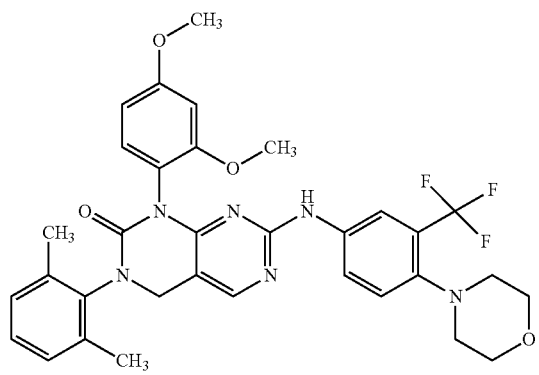 [SMILES: COc1ccc(N2C(=O)N(c3c(C)cccc3C)Cc3cnc(Nc4ccc(N5CCOCC5)c(C(F)(F)F)c4)nc32)c(OC)c1]
YKL-04-103
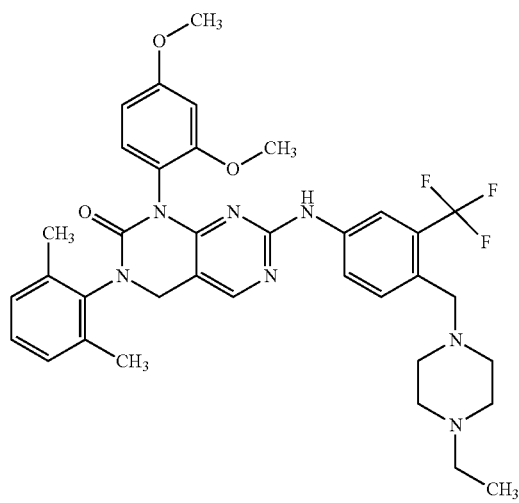 [SMILES: CCN1CCN(Cc2ccc(Nc3ncc4c(n3)N(c3ccc(OC)cc3OC)C(=O)N(c3c(C)cccc3C)C4)cc2C(F)(F)F)CC1]

TABLE 1-continued

Exemplary Compounds of Formula (I), (II), (III), (IV), and (V)

| Compound Number | Compound Structure |
| --- | --- |
| HG-11-136-01 | 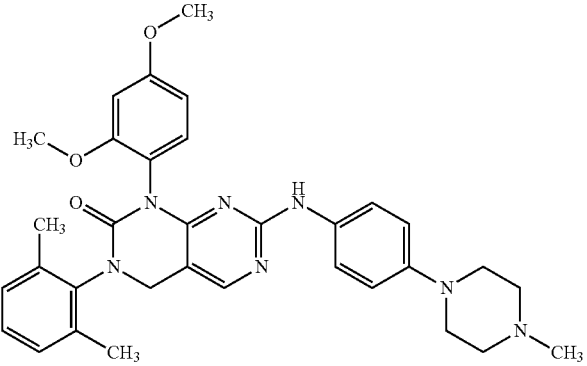 [SMILES: COc1ccc(N2C(=O)N(c3c(C)cccc3C)Cc3cnc(Nc4ccc(N5CCN(C)CC5)cc4)nc32)c(OC)c1] |
| HG 9-91-01 | 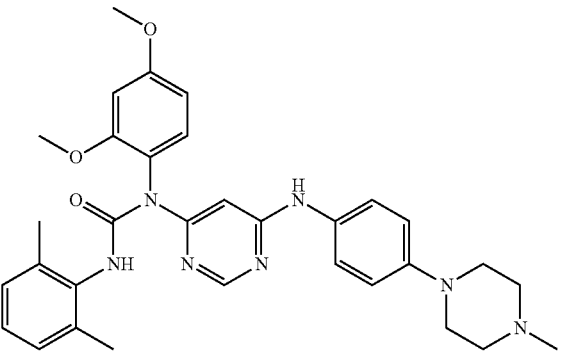 [SMILES: COc1ccc(N(C(=O)Nc2c(C)cccc2C)c2cc(Nc3ccc(N4CCN(C)CC4)cc3)ncn2)c(OC)c1] |
| HG 11-139-02 | 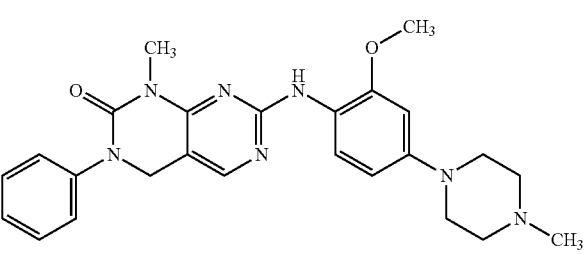 |
| HG 11-137-01 | 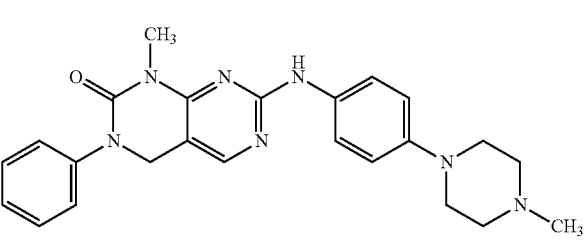 [SMILES: CN1CCN(c2ccc(Nc3ncc4c(n3)N(C)C(=O)N(c3ccccc3)C4)cc2)CC1] |

Example 2. A UV Independent Topical Small Molecule Approach for Melanin Production in Human Skin Small Molecule Inhibition of SIK Induces Mitf Expression In Vitro.

Figure 1A:
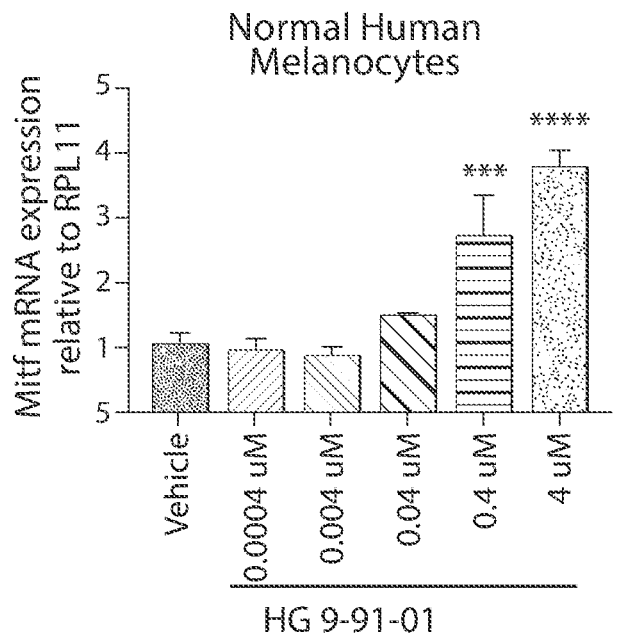
FIG. 1 shows that inhibition of SIK by HG 9-91-01 promotes Mitf transcription and pigmentation in vitro. Panel A shows mRNA expression of Mitf relative to Rpl11 (control ribosomal gene) mRNA quantified by QPCR in normal human melanocytes 3 hours after HG 9-91-01 or vehicle control (70% ethanol; 30% propylene glycol) treatment (n=3, mean±SD). Panel B shows mRNA expression of Mitf and Panel C shows Mitf-dependent gene, TRPM1 over 24 hours after 4 uM HG 9-91-01 treatment, relative to Rpl11 and vehicle control (70% ethanol; 30% propylene glycol) Mitf or TRPM1 mRNA expression, respectively, in normal human melanocytes quantified by QPCR (n=3, mean±SD). Panel D shows cell pellets of UACC257 melanoma cells after 3 days of treatment with vehicle control (70% ethanol; 30% propylene glycol) or 4 uM of SIK inhibitor HG 9-91-01 (n=3). For all graphs, statistical significance is reported as follows: *P<0.001, **P<0.0001.
Figure 1B:
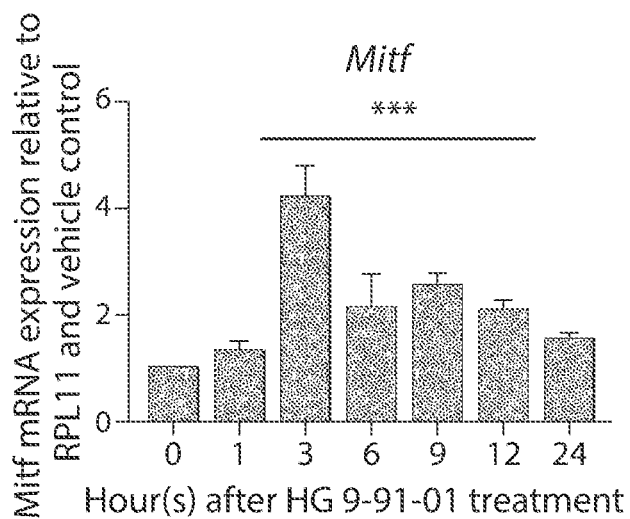
Figure 1C:
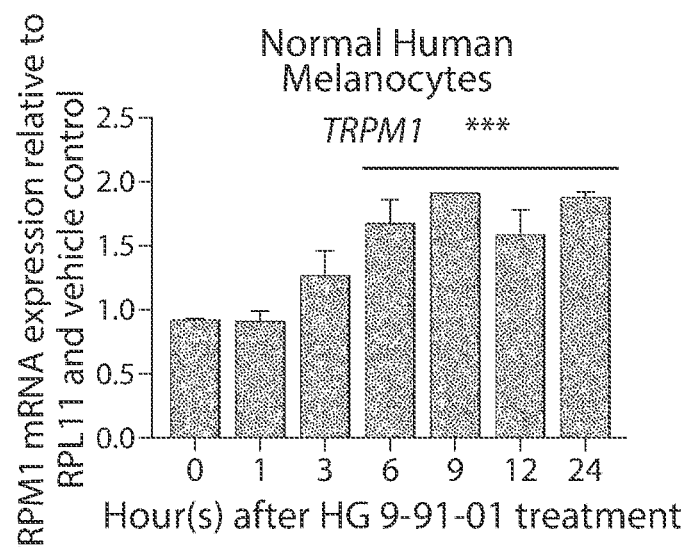
Figure 1D:
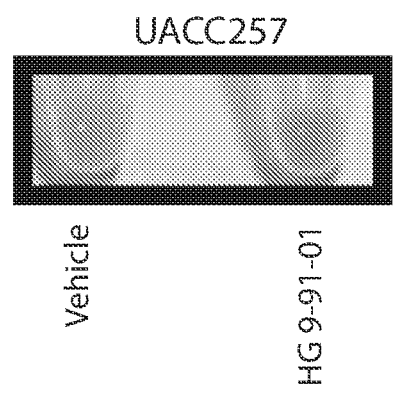
Figure 7G:
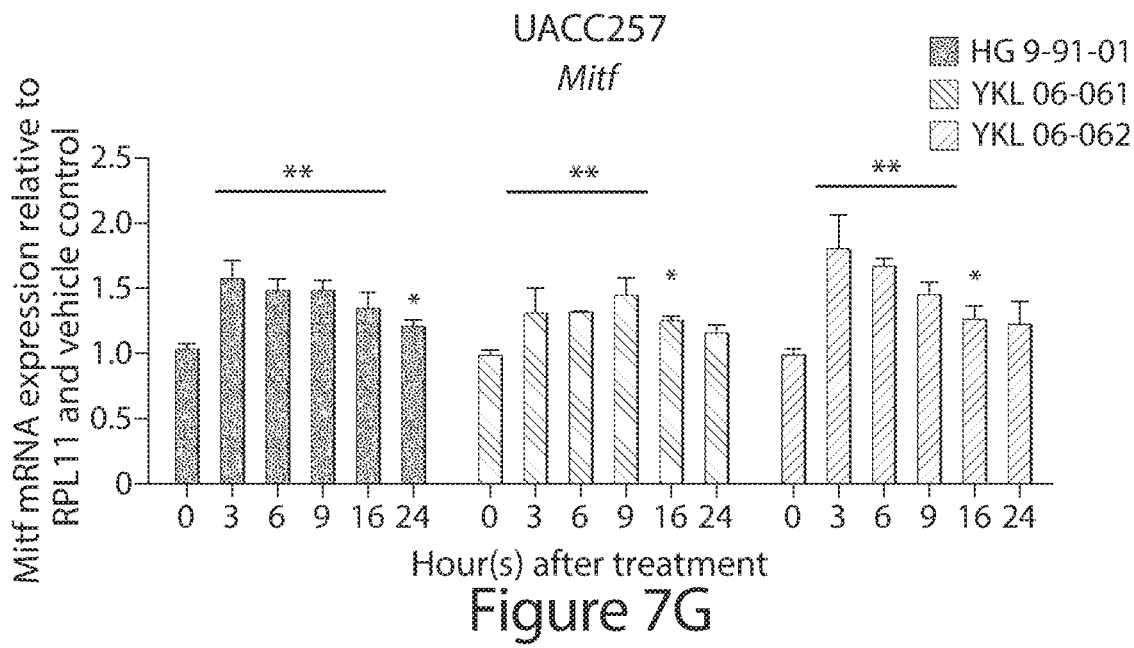
Figure 7H:
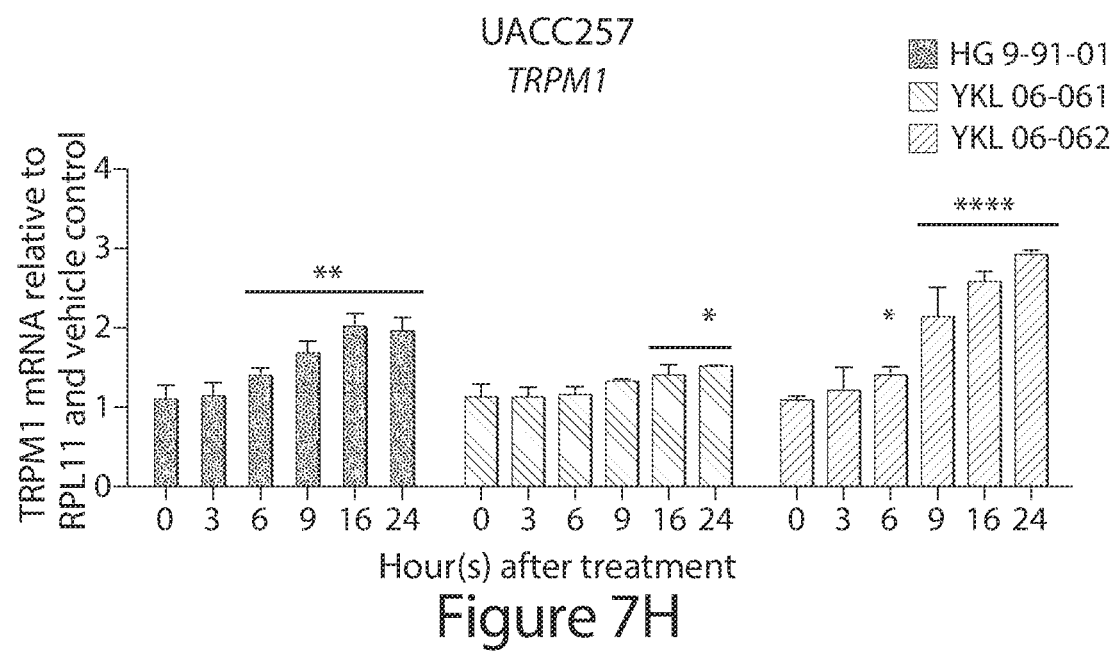

To test regulation of the pigmentation pathway by the SIK inhibitor HG 9-91-01 (HG) in vitro, normal human melanocytes, UACC62 melanoma cells, and UACC257 melanoma cells were treated. Dose-dependent increases in expression of MITF were observed in these cells (See FIG. 1A; FIGS. 7A, 7B, 7G). RNA levels of the MITF gene target TRPM1 (Miller et al) were also increased and followed the anticipated delayed kinetics relative to MITF induction in normal human melanocytes (See FIG. 1B, 1C) and UACC257 cells (FIG. 7G, 7H). Gross pigmentation was observed in cell pellets of UACC257 cells after 3 days of HG 9-91-01 treatment (See FIG. 1D). These data suggest that small molecule SIK inhibition may stimulate the pigmentation pathway in vitro.

Tables 2 to 5 below show the effects of exemplary K inhibitor compounds on skin darkening, including an in vitro test of MITF induction following the same protocol as described above in paragraph 333, wherein exemplary SIK inhibitor compounds were tested for their in vitro induction of MITF.

TABLE 2

Effects of exemplary SIK inhibitor compounds on skin darkening

| Compound Name | Type of Test | Type of Cells | Results |
|---|---|---|---|
| HG-10-32-01 | In vitro MITF induction | B16 | |
| HG-10-88-02 | In vitro MITF induction | B16 | |
| HG-10-93-01 | In vitro MITF induction | B16 | |
| HG-11-123-01 | In vitro MITF induction | B16 | |
| HG-11-136-01 | In vitro MITF induction | B16 | |
| HG-11-137-01 | In vitro MITF induction | B16 | |
| HG-11-139-01 | In vitro MITF induction | B16 | |
| HG-11-139-02 | In vitro MITF induction | B16 | |
| HG-11-143-01 | In vitro MITF induction | B16 | |
| HG-9-91-01 | In vitro MITF induction | B16 | |
| YKL-04-103 | In vitro MITF induction | B16 | |
| YKL-04-104 | In vitro MITF induction | B16 | |
| YKL-04-105 | In vitro MITF induction | B16 | |
| YKL-04-106 | In vitro MITF induction | B16 | |
| YKL-04-107 | In vitro MITF induction | B16 | |
| YKL-04-108 | In vitro MITF induction | B16 | |
| YKL-04-112 | In vitro MITF induction | B16 | |
| YKL-04-113 | In vitro MITF induction | B16 | |
| YKL-04-114 | In vitro MITF induction | B16 | |
| YKL-04-115 | In vitro MITF induction | B16 | |
| YKL-04-118 | In vitro MITF induction | B16 | |
| YKL-04-125 | In vitro MITF induction | B16 | |
| YKL-04-136-1 | In vitro MITF induction | B16 | |
| YKL-04-136-10 | In vitro MITF induction | B16 | |
| YKL-04-136-11 | In vitro MITF induction | B16 | |
| YKL-04-136-2 | In vitro MITF induction | B16 | |
| YKL-04-136-3 | In vitro MITF induction | B16 | |
| YKL-04-136-4 | In vitro MITF induction | B16 | |
| YKL-04-136-5 | In vitro MITF induction | B16 | |
| YKL-05-120 | Human Skin Explants | | Slight Darkening |
| YKL-05-200-1 | Human Skin Explants | | Slight Darkening |
| YKL-05-200-2 | Human Skin Explants | | Darkens |
| YKL-05-201-1 | Human Skin Explants | | Darkens |
| YKL-05-201-2 | Human Skin Explants | | Slight Darkening |
| YKL-05-203-1 | Human Skin Explants | | Slight Darkening |
| YKL-05-203-2 | Human Skin Explants | | Slight Darkening |
| YKL-05-204-1 | Human Skin Explants | | Darkens |
| YKL-05-204-2 | Human Skin Explants | | Darkens |
| YKL-06-029 | In vitro MITF induction | UACC62 | |
| YKL-06-058 | Human Skin Explants | | Darkens |
| YKL-06-059 | Human Skin Explants | | Darkens |
| YKL-06-060 | Human Skin Explants | | Darkens |
| YKL-06-061 | Human Skin Explants | | Darkens |
| YKL-06-062 | Human Skin Explants | | Darkens |
| YKL-06-29 | Human Skin Explants | | Darkens |
| YKL-06-30 | Human Skin Explants | | Slight Darkening |
| YKL-06-31 | Human Skin Explants | | Slight Darkening |
| YKL-06-33 | Human Skin Explants | | Slight Darkening |
| YKL-06-46 | Human Skin Explants | | Slight Darkening |
| YKL-06-50 | Human Skin Explants | | Slight Darkening |

TABLE 3

Effects of exemplary SIK inhibitor compounds on skin darkening

| Compound Name | Type of Test | Type of Cells | Results |
|---|---|---|---|
| HG-11-137-01 | Human Skin Explants | | Darkens |
| HG-11-139-02 | Human Skin Explants | | No Darkening |
| HG-9-91-01 | Human Skin Explants | | Darkens |
| YKL-04-108 | Human Skin Explants | | Darkens |
| YKL-05-200-2 | In vitro MITF induction | UACC62 | |
| YKL-05-201-1 | In vitro MITF induction | UACC62 | |
| YKL-05-204-1 | In vitro MITF induction | UACC62 | |
| YKL-06-029 | In vitro MITF induction | UACC62 | |
| YKL-06-059 | In vitro MITF induction | UACC62 | |
| YKL-06-060 | In vitro MITF induction | UACC62 | |
| YKL-06-061 | In vitro MITF induction | UACC62 | |
| YKL-06-062 | In vitro MITF induction | UACC62 | |

TABLE 4

Effects of exemplary SIK inhibitor compounds on skin darkening

| Compound Name | Type of Test | Results |
|---|---|---|
| HG-11-137-01 | Human Skin Explants | Slight Darkening |
| HG-11-139-02 | Human Skin Explants | Slight Darkening |
| HG-9-91-01 | Human Skin Explants | Darkens |
| YKL-05-120 | Human Skin Explants | Slight Darkening |
| YKL-05-200-1 | Human Skin Explants | Slight Darkening |
| YKL-05-200-2 | Human Skin Explants | Darkens |
| YKL-05-201-1 | Human Skin Explants | Darkens |
| YKL-05-201-2 | Human Skin Explants | Slight Darkening |
| YKL-05-203-1 | Human Skin Explants | Slight Darkening |
| YKL-05-203-2 | Human Skin Explants | Slight Darkening |
| YKL-05-204-1 | Human Skin Explants | Darkens |
| YKL-05-204-2 | Human Skin Explants | Darkens |
| YKL-06-058 | Human Skin Explants | Darkens |
| YKL-06-059 | Human Skin Explants | Darkens |
| YKL-06-060 | Human Skin Explants | Darkens |
| YKL-06-061 | Human Skin Explants | Darkens |
| YKL-06-062 | Human Skin Explants | Darkens |
| YKL-06-29 | Human Skin Explants | Darkens |
| YKL-06-30 | Human Skin Explants | Slight Darkening |
| YKL-06-31 | Human Skin Explants | Slight Darkening |
| YKL-06-33 | Human Skin Explants | Slight Darkening |
| YKL-06-46 | Human Skin Explants | Slight Darkening |
| YKL-06-50 | Human Skin Explants | Slight Darkening |

Table 5 below additionally provides characteristics of exemplary SIK inhibitor compounds, MITF induction in B16 cells, $EC_{50}$, log P, and experimental conditions for skin darkening experiments in mice and humans.

TABLE 5

Effects of exemplary SIK inhibitor compounds on skin darkening; and characteristics of exemplary SIK inhibitor compounds

| Compound Name | Molecular weight (g/mol) | Highest fold mitf induction in B16 cells | H-bond donors | H-bond acceptors | Concentration highest induction observed (uM) | EC50 (uM) | logP | Days Treated Mouse | [ ] Mouse | Darkening (Mouse) | Days Treated Human | [ ] Human | Darkening (Human) |
|---|---|---|---|---|---|---|---|---|---|---|---|---|---|
| YKL-04-118 | | 1.1 | | | 0.08 | 1424.000 | 6.36 | | | | | | |
| YKL-04-136-07 | | 2.4 | | | 0.4 | 0.127 | 3.38 | | | | | | |
| HG-9-91-01 | | 2.5 | | | 0.06 | 0.016 | 6.01 | 2 | 25 mM | Darkens | 5 | 25 mM | No darkening |
| YKL-04-107 | | 3.6 | | | 0.4 | 0.015 | 6.43 | | | | | | |
| YKL-04-136-08 | | 4.1 | | | 0.4 | 0.014 | 3.57 | | | | | | |
| YKL-04-112 | | 5.2 | | | 0.4 | 0.215 | 6.59 | | | | | | |
| HG-11-136-01 | | 6.1 | | | 0.06 | 0.000 | 5.55 | 12 | 25 mM | Darkens | 16 | 75 mM | No Darkening |
| YKL-04-136-03 | | 6.2 | | | 0.08 | 0.025 | 5.8 | | | | | | |
| HG-11-143-01 | | 6.8 | | | 0.4 | 0.057 | 5.6 | 12 | 25 mM (4 days) −130 mM (8 days) | No Darkening | | | No Darkening |
| YKL-04-104 | | 8.0 | | | 0.4 | 0.021 | 6.52 | | | | | | |
| YKL-04-136-05 | | 8.9 | | | 0.4 | 0.042 | 5.05 | | | | | | |
| YKL-04-106 | | 9.0 | | | 0.4 | 0.074 | 5.4 | | | | | | |
| YKL-04-136-04 | | 9.2 | | | 0.08 | 0.015 | 4.13 | | | | | | |
| YKL-04-136-01 | | 9.7 | | | 0.4 | 0.053 | 5.55 | | | | | | |
| YKL-04-125 | | 9.7 | | | 0.4 | 0.133 | 6.42 | | | | | | |
| YKL-04-105 | | 9.9 | | | 0.08 | 0.005 | 4.15 | | | | | | |
| YKL-04-115 | | 10.1 | | | 0.08 | 0.024 | 5.49 | | | | | | |
| YKL-04-103 | | 10.2 | | | 0.08 | 0.001 | 6.78 | | | | | | |
| YKL-04-114 | | 10.4 | | | 0.4 | 0.067 | 5.55 | | | | | | |
| YKL-04-113 | | 11.2 | | | 0.4 | 0.657 | 6.52 | | | | | | |
| YKL-04-108 | | 13.9 | | | 0.08 | 0.014 | 6.21 | | | | | | |

TABLE 5-continued

Effects of exemplary SIK inhibitor compounds on skin darkening; and characteristics of exemplary SIK inhibitor compounds

| Compound Name | Molecular weight (g/mol) | Highest fold mitf induction in B16 cells | H-bond donors | H-bond acceptors | Concentration highest induction observed (uM) | EC50 (uM) | logP | Days Treated Mouse | [ ] Mouse | Darkening (Mouse) | Days Treated Human | [ ] Human | Darkening (Human) |
|---|---|---|---|---|---|---|---|---|---|---|---|---|---|
| YKL-04-136-02 | | 16.1 | | | 0.08 | 0.021 | 4.04 | | | | | | |
| YKL-04-136-09 | | 16.5 | | | 0.4 | 0.007 | 5.64 | | | | | | |
| YKL-04-136-06 | | 26.9 | | | 0.08 | 0.009 | 5.25 | | | | | | |
| HG-10-32-01 | 401.461 | 2.4 | 2 | 5 | | | 4.91 | | | | | | |
| YKL-04-136-10 | 564.681 | 16.28 | 1 | 8 | | | 5.08 | | | | | | |
| YKL-04-136-11 | 689.849 | 9.58 | 1 | 9 | | | 4.89 | | | | | | |
| YKL-04-193-1 | 465.593 | 2.02 | 2 | 7 | | | 5.92 | | | | | | |
| YKL-04-193-2 | 428.533 | 2.65 | 2 | 7 | | | 4.41 | | | | | | |
| HG-11-137-01 | 429.518 | 4.82 | 1 | 6 | | | 3.34 | | | | | | |
| HG-11-139-02 | 459.544 | 5.76 | 1 | 7 | | | 3.19 | | | | | | |
| Control | | | | | | | | 2 | | No darkening | 16 | | No darkening |

Table 6 below provides characteristics of exemplary SIK inhibitor compounds, highest fold MITF induction, and log P. Table 7 below provides characteristics of exemplary SIK inhibitor compounds and log P

TABLE 6

Characteristics of exemplary SIK inhibitor compounds, and effects of exemplary SIK inhibitor compounds on MITF induction

| Compound Name | Molecular weight (g/mol) | log P | H-bond donors | H-bond acceptors | Highest fold Mitf induction |
|---|---|---|---|---|---|
| HG-10-32-01 | 401.461 | 4.91 | 2 | 5 | 2.4 |
| YKL-04-136-10 | 564.681 | 5.08 | 1 | 8 | 16.28 |
| YKL-04-136-11 | 689.849 | 4.89 | 1 | 9 | 9.58 |
| YKL-04-193-1 | 465.593 | 5.92 | 2 | 7 | 2.02 |
| YKL-04-193-2 | 428.533 | 4.41 | 2 | 7 | 2.65 |
| HG-11-137-01 | 429.518 | 3.34 | 1 | 6 | 4.82 |
| HG-11-139-02 | 459.544 | 3.19 | 1 | 7 | 5.76 |

TABLE 7

Characteristics of exemplary SIK inhibitor compounds

| Molecule Name | Molecular weight (g/mol) | log P | H-bond donors | H-bond acceptors |
|---|---|---|---|---|
| HG-9-91-01 | 567.681 | 6.01 | 2 | 8 |
| HG-11-137-01 | 429.518 | 3.34 | 1 | 6 |
| HG-11-139-02 | 459.544 | 3.19 | 1 | 7 |
| YKL-05-200-2 | 427.498 | 4.65 | 1 | 5 |
| YKL-05-201-1 | 447.917 | 4.74 | 1 | 5 |
| YKL-05-204-1 | 511.618 | 4.57 | 1 | 7 |
| YKL-06-029 | 457.571 | 4.37 | 1 | 6 |
| YKL-06-059 | 515.65 | 4.99 | 1 | 7 |
| YKL-06-060 | 497.634 | 5.28 | 1 | 6 |
| YKL-06-061 | 527.66 | 5.12 | 1 | 7 |
| YKL-06-062 | 525.688 | 6.17 | 1 | 6 |

HG 9-91-01 Rescues Melanogenesis in Mice with Inactive Melanocortin 1 Receptor.

Figure 2B:
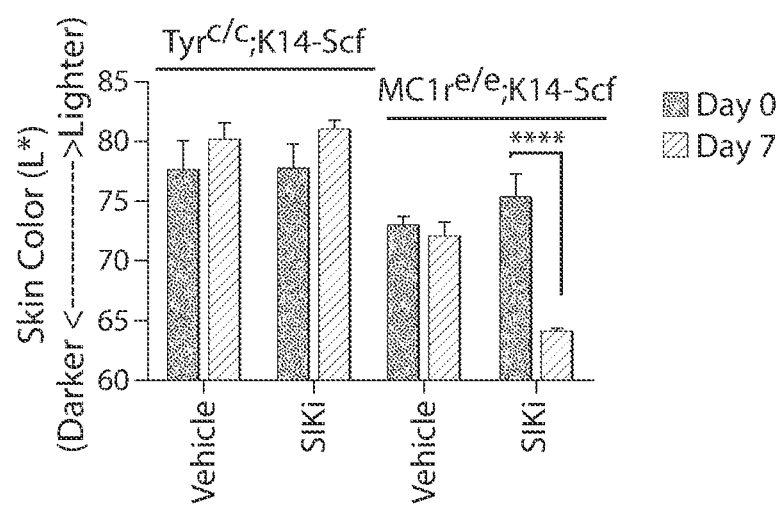
Figure 2C:
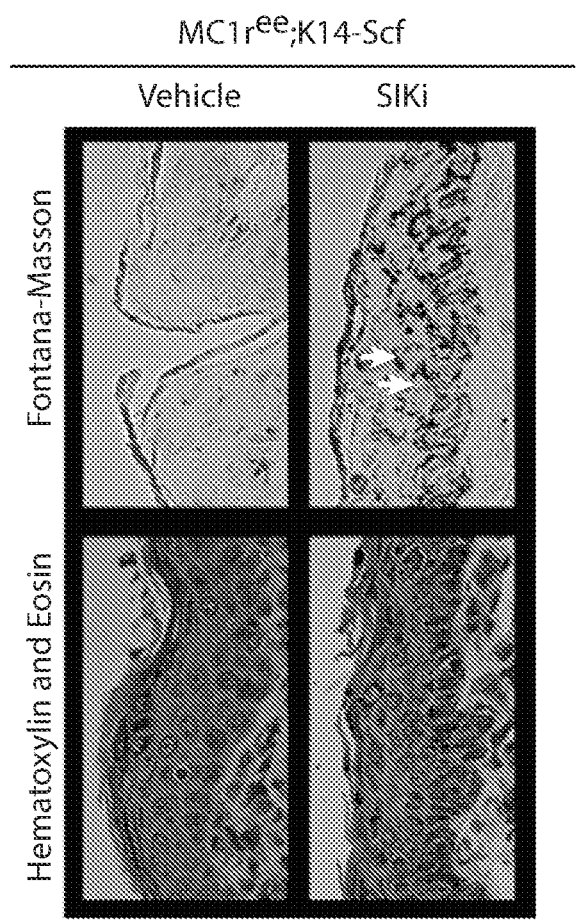
Figure 2D:
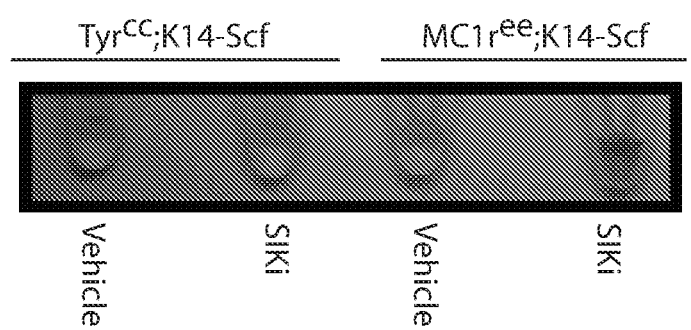
Figure 3A:
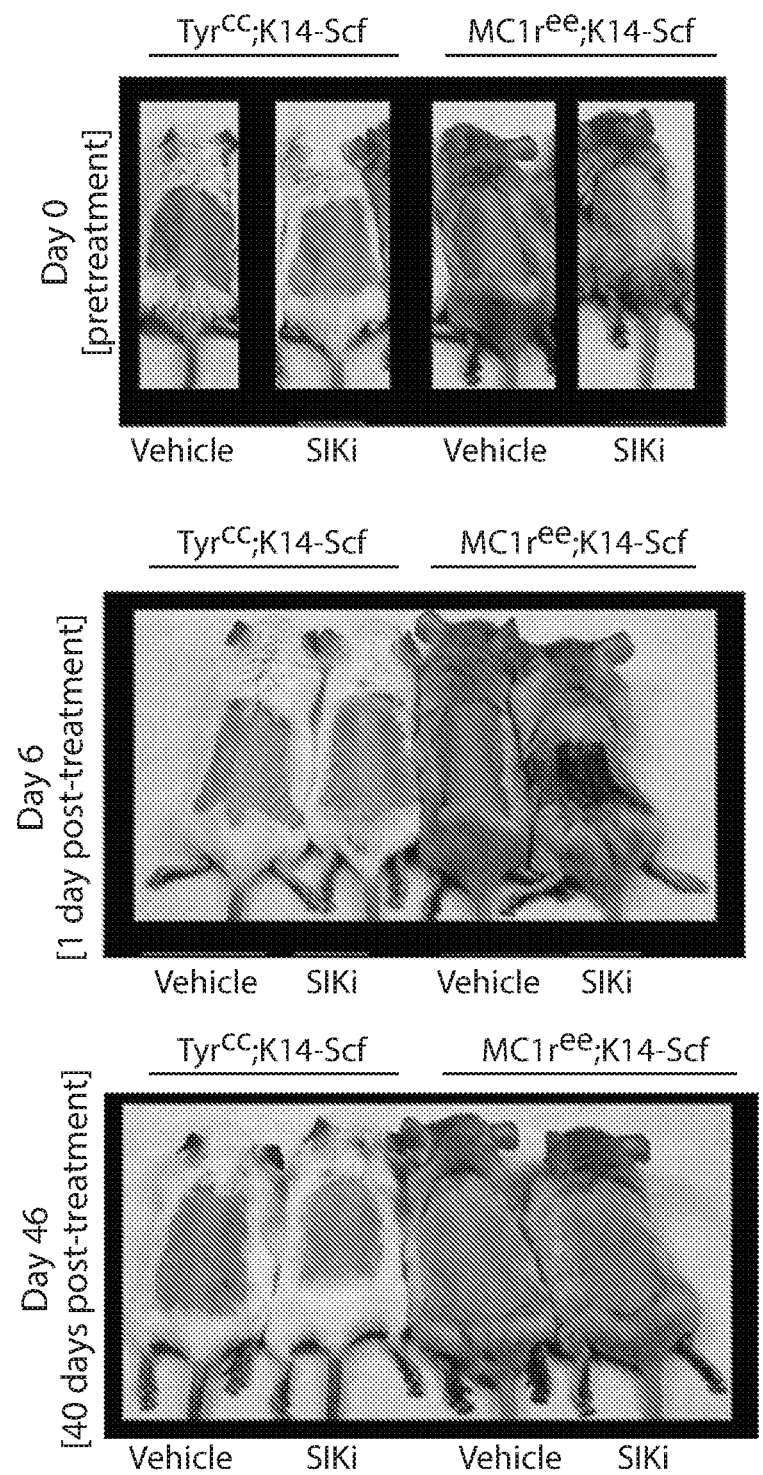
FIG. 3 shows that darkening induced by topical application of SIK inhibitor HG 9-91-01 (labeled "SIKi" in FIG. 3) to MC1R$^{e/e}$;K14-Scf mice is progressive and reversible. Panel A shows MC1R$^{e/e}$;K14-Scf mice and Tyr$^{c/c}$;K14-Scf mice after treatment with 30 uL of vehicle control (70% ethanol; 30% propylene glycol) or 37.5 mM HG 9-91-01: before treatment (Day 0) and after 6 days of treatment (Day 6), and 40 days post-treatment (Day 46) (vehicle mouse in Day 46 photo is different from Day 0 and Day 6 photo). In Panel A, for Tyr$^{c/c}$;K14-Scf (albino) mice vehicle: n=3 (Day 0-10), n=2 (Day 11-20); for Tyr$^{c/c}$;K14-Scf mice HG 9-91-01: n=3; for MC1R$^{e/e}$;K14-Scf mice vehicle: n=5 (Day 0-19), n=4 (Day 24-34). In Panel A, for MC1R$^{e/e}$;K14-Scf mice HG 9-91-01: n=3 mean±SD. Panels B and C show reflective colorimetry measurements (CIE L* white-black color axis) of MC1R$^{e/e}$;K14-Scf mice (Panel B) and Tyr$_{c/c}$; K14-Scf mice (Panel C) described in Panel A above. For all graphs, statistical significance is reported as follows: *P<0.05, P<0.01, *P<0.001, ****P<0.0001.
Figure 3B:
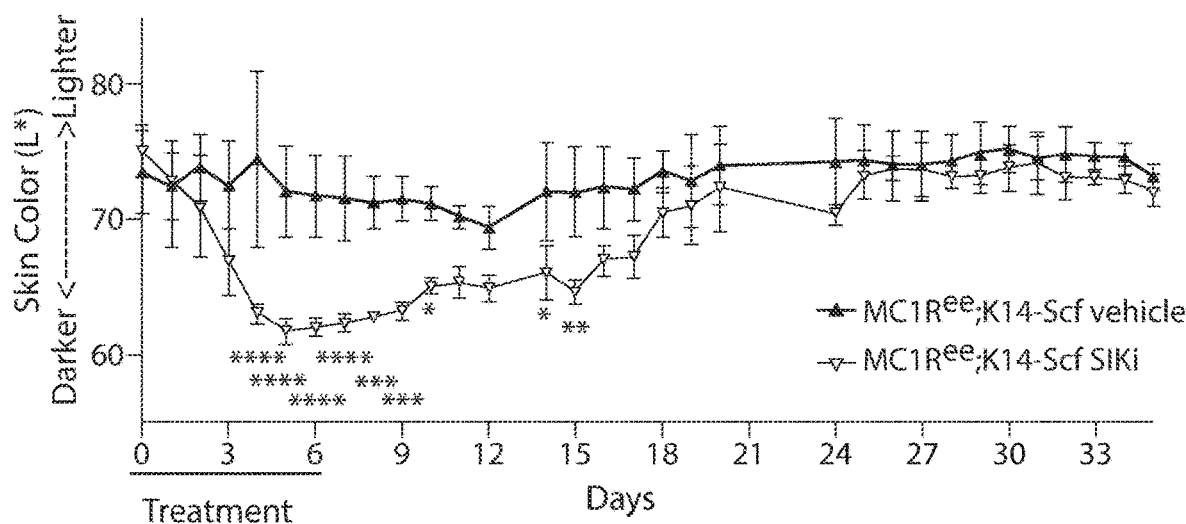
Figure 3C:
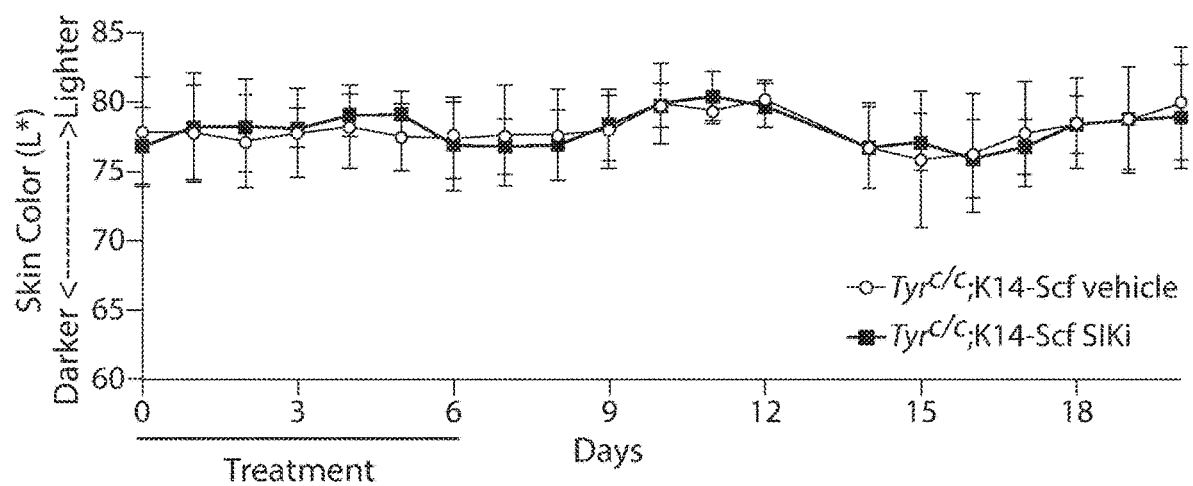
Figure 8A:
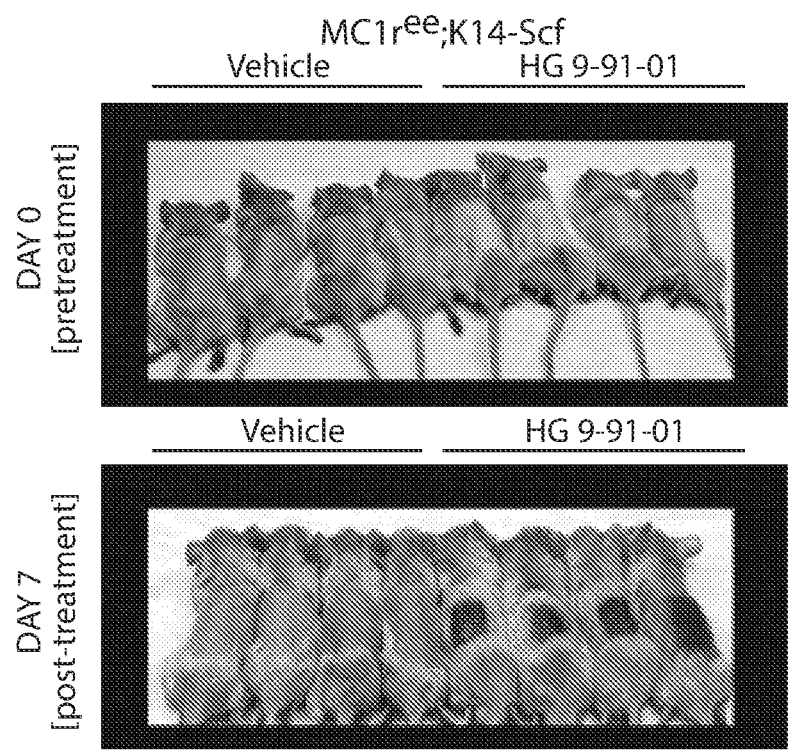
Figure 8B:
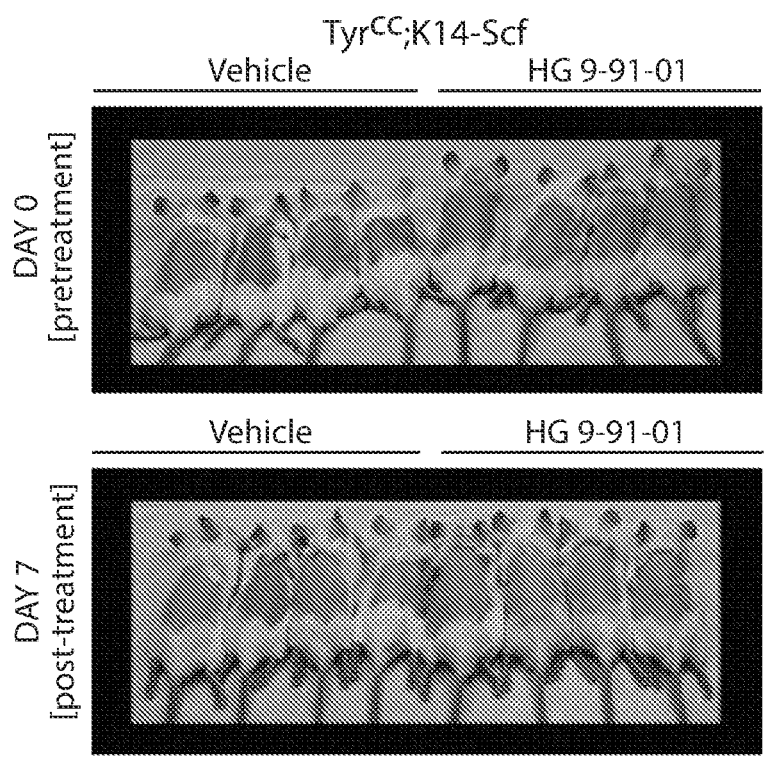
Figure 8C:
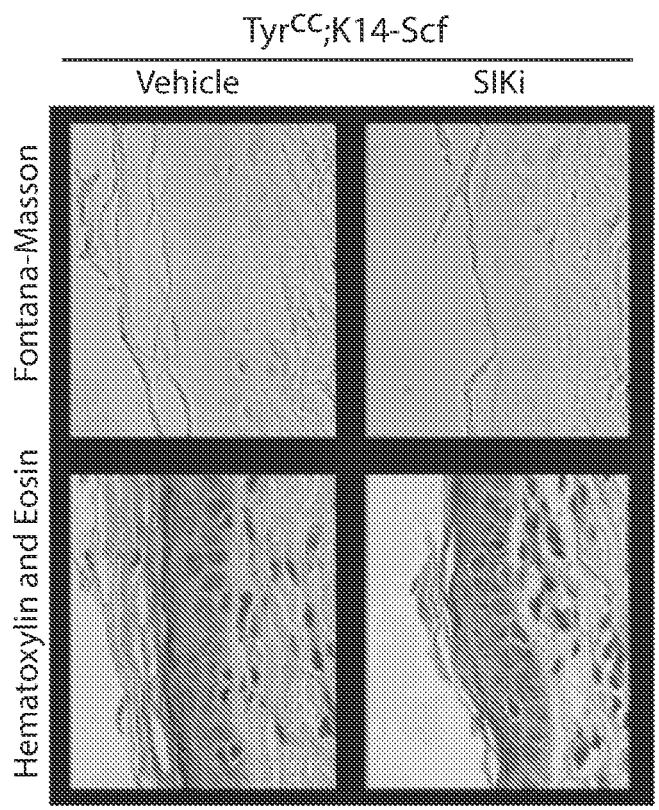
Figure 8D:
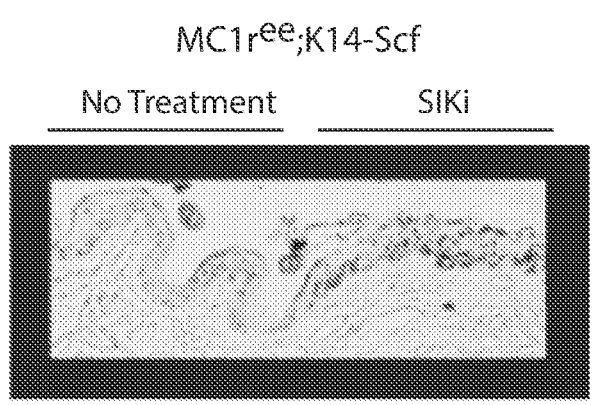
Figure 8E:
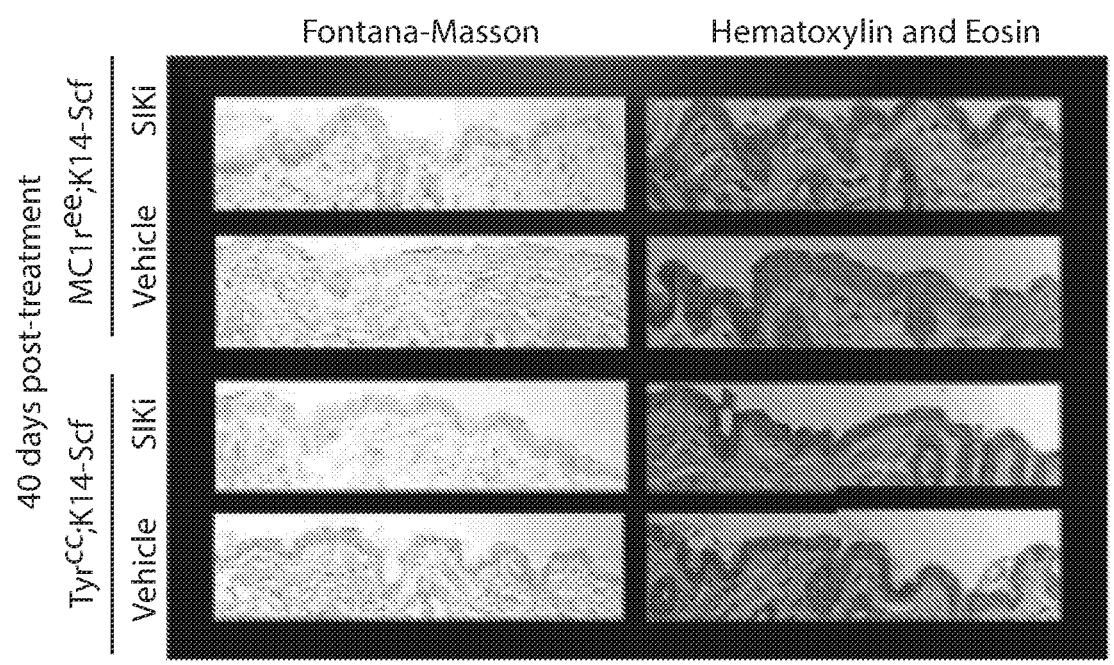

Since the in vitro results demonstrated that inhibition of SIK by HG 9-91-01 positively regulated the CRTC-CREB-MITF pathway, it was next evaluated whether topical application of this compound could induce pigmentation independent of Mc1r in vivo. To test this, a previously described mouse "redhair" model was utilized which carries the inactivating Mc1r$^{e/e}$ mutant allele and a transgene, K14—SCF, in which Stem Cell Factor expression is driven by the Keratin-14 promoter allowing for epidermal homing of melanocytes (Kunisada et al. 1998; D'Orazio et al. 2006). Albino mice harboring a mutation in the tyrosinase gene were combined with the K14—Scf transgene (tyr$^{c/c}$;K14—Scf mice) and served as controls to evaluate whether the pigmentation afforded by topical SIK inhibitor was dependent upon the canonical tyrosinase-melanin pathway. Daily application of the SIK inhibitor HG 9-91-01 for 6 days, caused robust darkening in Mc1r$_{e/e}$;K14—Scf mice (FIG. 2A; FIG. 8A). No visible change in skin pigmentation was observed in Mc1r$^{e/e}$;K14—Scf mice treated with vehicle or Tyr$^{c/c}$;K14—Scf mice treated with vehicle or HG 9-91-01 (FIG. 2A; FIG. 8A, 8B). Reflective colorimetry analysis (CIE L* white-black color axis (Park, Suh, and Youn 1999)) revealed significant darkening in Mc1r$^{e/e}$;K14—Scf mice treated with SIK inhibitor, but not in vehicle treated Mc1r$^{e/e}$;K14—Scf mice or Tyr$^{c/c}$;K14—Scf mice treated with either SIK inhibitor or vehicle control (FIG. 2B). Fontana-Masson staining, a specialized melanin stain, revealed strong induction of melanin production in Mc1r$^{e/e}$;K14—Scf mice in areas treated with HG 9-91-01, (FIG. 2C; FIG. 8D) but no pigment induction in Mc1r$^{e/e}$; K14—Scf mice treated with vehicle or in albino (Tyr$^{c/c}$; K14—Scf) mice treated with either vehicle or SIK inhibitor (FIG. 8C). Nuclear capping of melanin-laden melanosomes was observed within epidermal keratinocytes in Mc1r$^{e/e}$; K14—Scf mice treated with HG 9-91-01 (indicated by white arrows) and represents a known subcellular localization typical of physiologic skin pigmentation (Kobayashi et al. 1998) (FIG. 2C). This feature suggests that SIK inhibitor treatment not only stimulates melanocytic pigment synthesis, but also export of melanin in a fashion that closely mimics the known pathway of UV melanogenesis. Hematoxylin and eosin staining revealed normal morphology of HG 9-91-01 treated Mc1r$^{e/e}$;K14—Scf mice (FIG. 2C) and Tyr$^{c/c}$;K14—Scf epidermis (FIG. 8C). Additionally, NaOH lysis of skin samples (Wakamatsu and Ito 2002) revealed a visible increase in extractable eumelanin from Mc1r$^{e/e}$; K14—Scf mice treated with HG 9-91-01 compared to all other treatment groups (FIG. 2D). The darkening induced by topical application of HG 9-91-01 to Mc1r$^{e/e}$;K14—Scf mice was progressive over 6 days of treatment and reversible by 10 days after treatment was stopped (FIG. 3A, 3B). Skin pigmentation remained in its pretreatment state over the next 30 days (FIG. 3A; 3B). No change was observed in Tyr$^{c/c}$;K14—Scf mice during treatment or 14 days after treatment was stopped (FIG. 3C). Fontana-Masson staining of skin sections revealed no differences in either treatment group for Mc1r$^{e/e}$;K14—Scf mice or Tyr$^{c/c}$;K14—Scf mice and hematoxylin and eosin stain illustrated normal morphology for all mice 40 days after treatment (FIG. 8E). These findings combined with the small molecule and lipophilic nature of the SIK inhibitors led us to investigate the use of SIK inhibitors for topical eumelanization of human skin.

Second Generation SIK Inhibitors are as Efficacious in Inducing the Pigmentation Pathway as HG 9-91-01.

Since there are limitations to topical delivery of drugs into human skin epidermis, novel SIK inhibitors designed to enhance epidermal permeation by reducing the size and increasing the lipophilicity (c Log P) to develop second generation SIK inhibitors YKL 06-061 and YKL 06-062 were derived (FIG. 6) (Bos and Meinardi 2000; Hadgraft and Pugh 1998). They had comparable IC50 values for inhibition of SIKs (FIG. 6). To assess the kinome selectivity information of new analogs, YKL-06-061 was screened across a panel of 468 human kinases at a concentration of 1 pM using the KinomeScan methodology (DiscoverX). YKL-06-061 exhibited a S(1) score of 0.02 with 16 kinases displaying tight binding to it (Ambit scores of less than or equal to 1). As the KinomeScan assays measure binding, enzymatic assays for these targets were also performed either in-house or using the SelectScreen Kinase Profiling Service at Thermo Fisher Scientific (Madison, Wis.). YKL-06-061 only inhibited one kinase (FRK) stronger than SIKs, which demonstrates its high overall selectivity. It was anticipated that YKL-06-062 had similar kinase selectivity considering their high structural similarity.

Figure 4A:
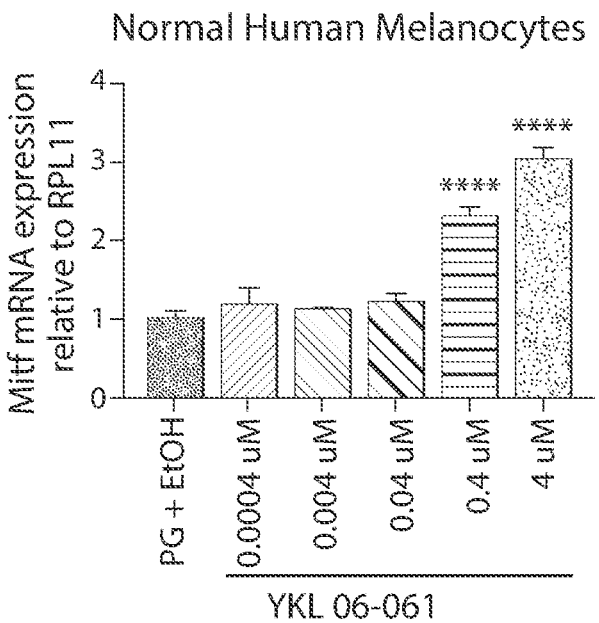
FIG. 4 shows that second generation SIK inhibitors (YKL 06-061 and YKL 06-062) are as efficacious in inducing the pigmentation pathway as HG 9-91-01. Panels A and B show mRNA expression of Mitf relative to Rpl11 mRNA quantified by QPCR in normal human melanocytes, treated with YKL 06-061 (Panel A) YKL 06-062 (Panel B) (n=3, mean±SD). Panels C and D show mRNA expression of Mitf (Panel C) and Mitf-dependent gene, TRPM1 (Panel D), relative to Rpl11 and vehicle control (70% ethanol; 30% propylene glycol) treatment's Mitf or TRPM1 mRNA expression, respectively, in normal human melanocytes treated with 4 uM of SIK inhibitor quantified by QPCR. For all graphs, statistical significance is reported as follows: *P<0.05, P<0.01, *P<0.001, ****P<0.0001.
Figure 4B:
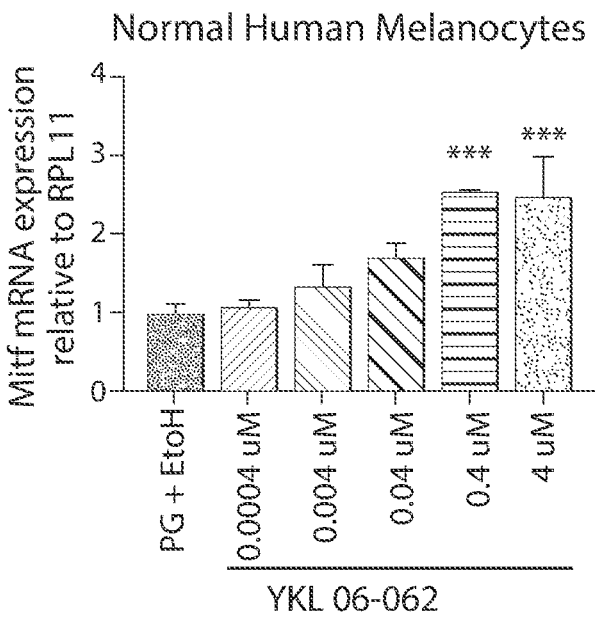
Figure 4C:
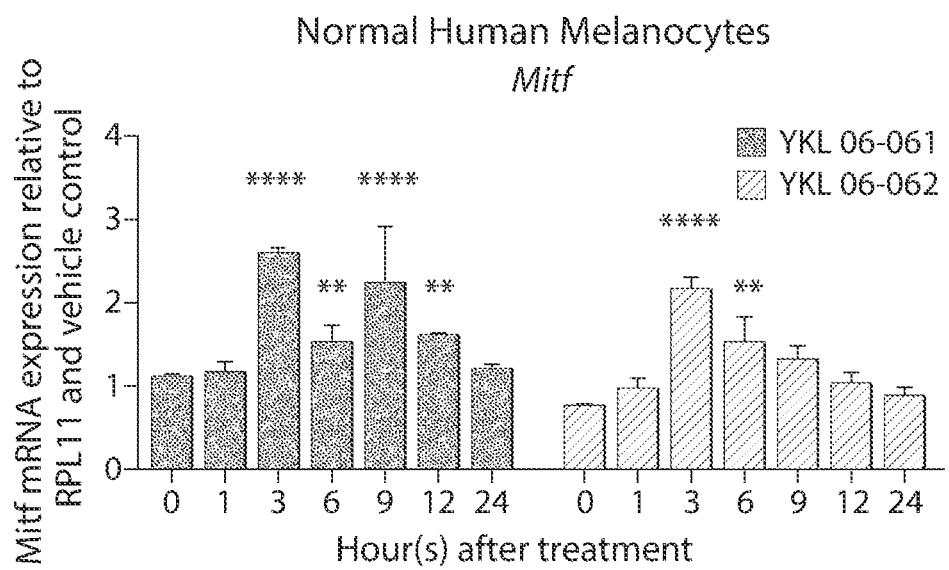
Figure 4D:
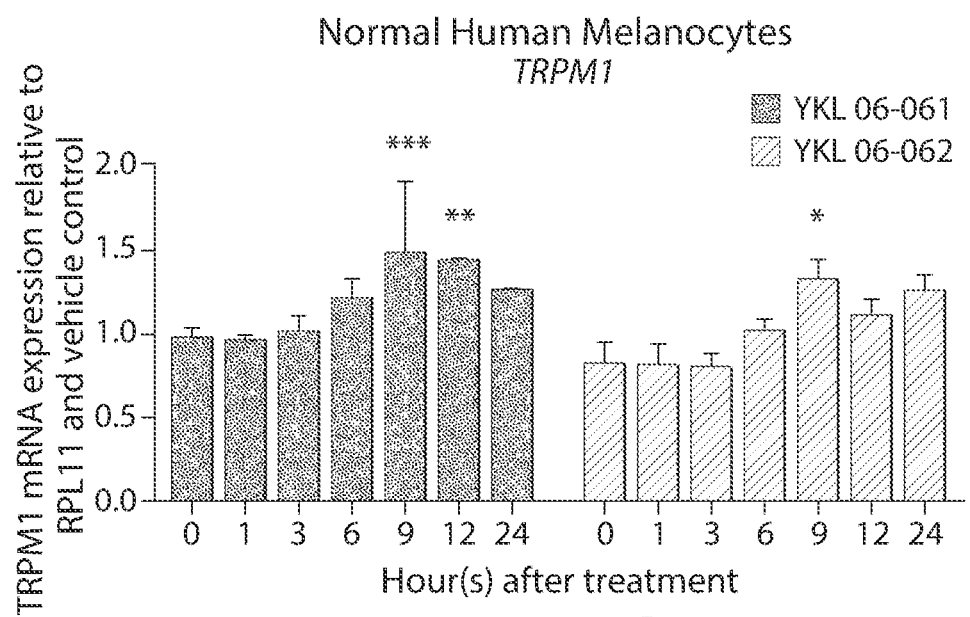

Similar to observations with HG 9-91-01, after 3 hours of treatment of normal human melanocytes (FIG. 4A, B), UACC62, and UACC257 cells (FIG. 7C-F), there was a dose dependent increase in MITF mRNA expression for YKL 06-061 and YKL 06-062. Levels of TRPM1 mRNA increased after MITF induction with agents these cells (Figure C-D; FIG. 7G, 7H).

Topical SIK Inhibitors Induce Human Skin Eumelanization

Figure 5A:
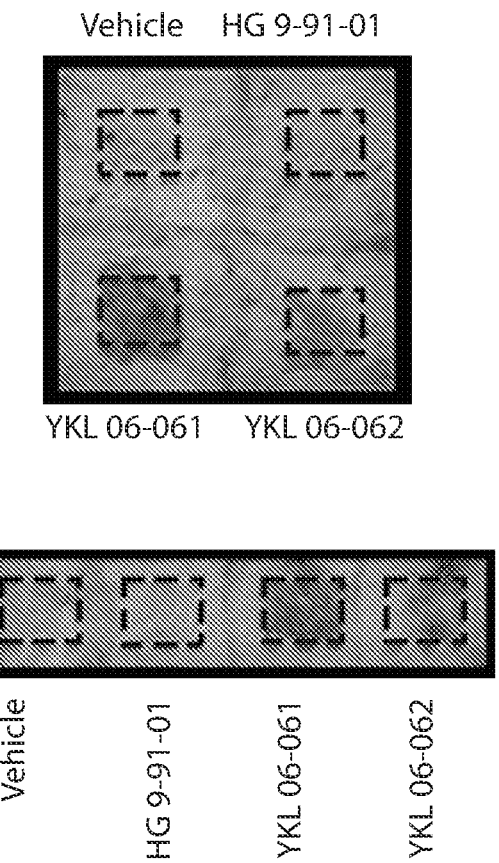
FIG. 5 shows that treatment of human skin explants with 37.5 mM of SIK inhibitor induces pigmentation. Human breast skin explants were treated with passive application of vehicle control (70% ethanol; 30% propylene glycol) or 37.5 mM of SIK inhibitors YKL 06-061, YKL 06-062, or HG 9-91-01 for 8 days (10 uL; Ix/day). Panel A shows an image taken 2 days after the end of treatment (n=3). Panel B shows hematoxylin and eosin (bottom panel) and Fontana-masson (top panel) staining (×400 magnification) (Panel B) of breast skin described in Panel A. Human breast skin explants were treated with a passive application of vehicle control (70% ethanol; 30% propylene glycol) or 37.5 mM of SIK inhibitors YKL 06-061, YKL 06-062, or HG 9-91-01 for 5 days (10 uL; 2×/day). Panel C shows an image taken 1 day after end of treatment (n=1). Panel D shows human breast skin explants treated with passive application of control (70% ethanol; 30% propylene glycol) or 37.5 mM of SIK inhibitors YKL 06-061, YKL 06-062, or HG 9-91-01 for 6 days (10 uL; 2×/day). The image was taken 1 day after end of treatment (n=1). Panel E shows human breast skin explants treated with mechanical application of vehicle control (70% ethanol; 30% propylene glycol) or 50 mM (50 uL for 1 day; 1×/day) or 25 mM (50 ul for 3 days; 3×/day)) of HG 9-91-01
Figure 5B:
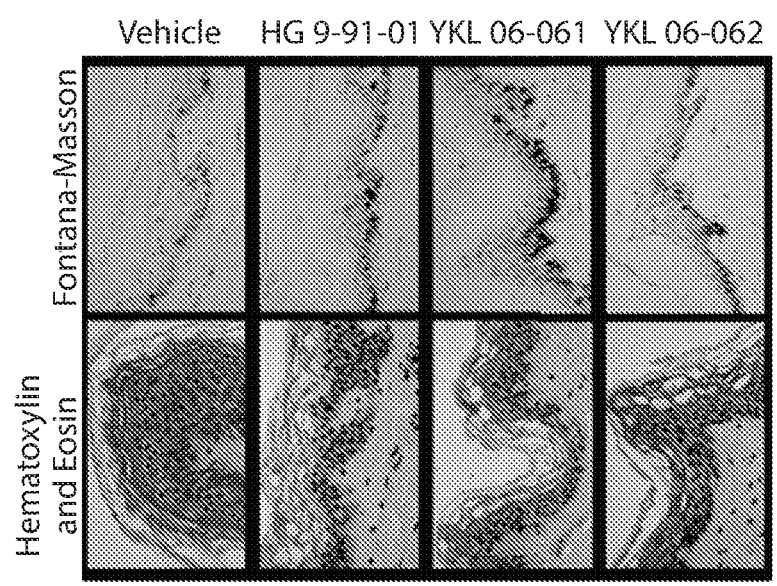
Figure 5C:
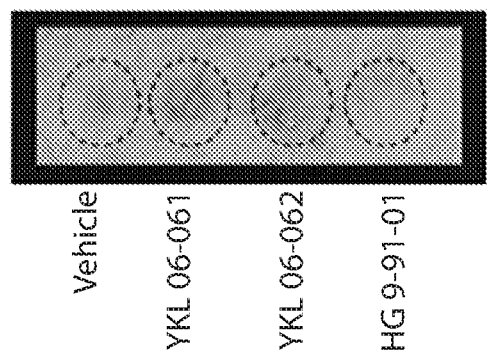
Figure 5D:
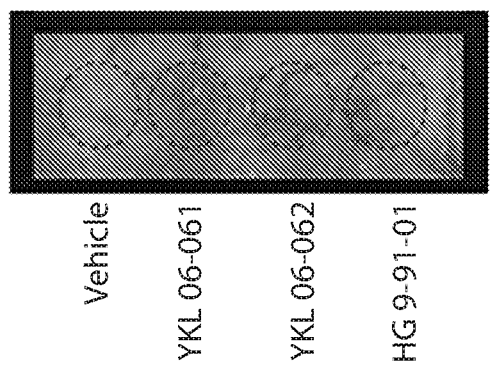
Figure 5E:
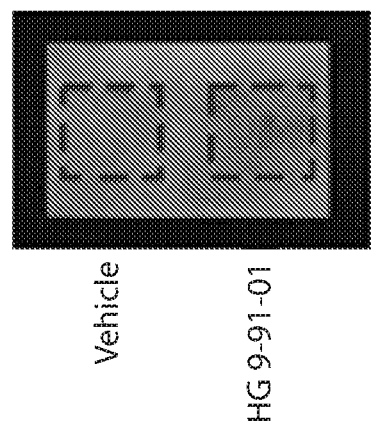
Figure 5F:
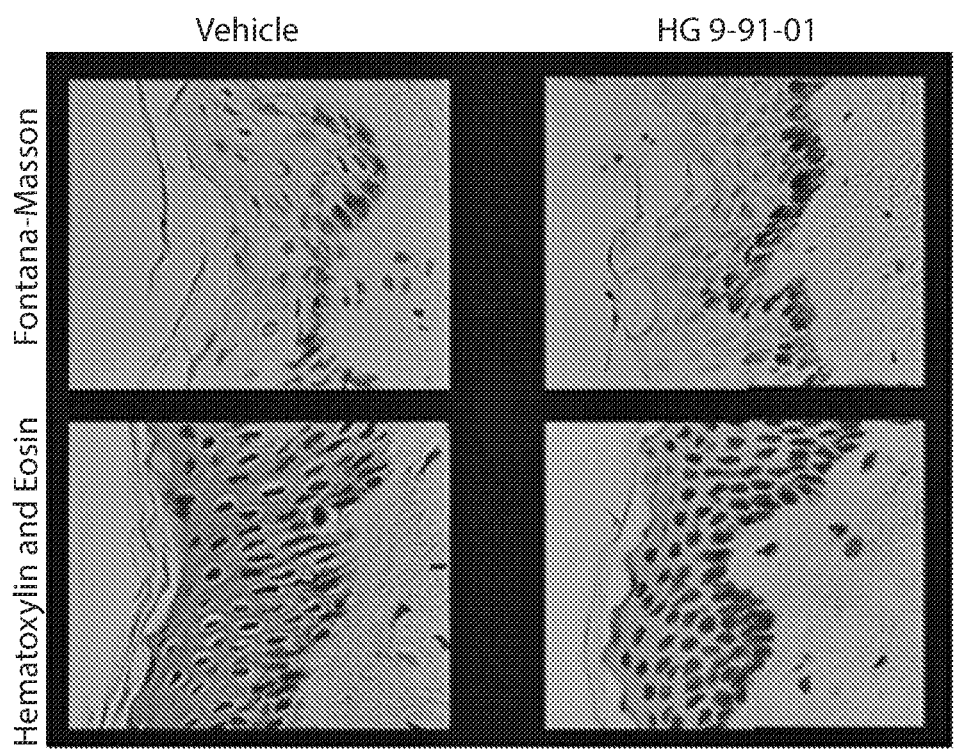
Figure 6A:
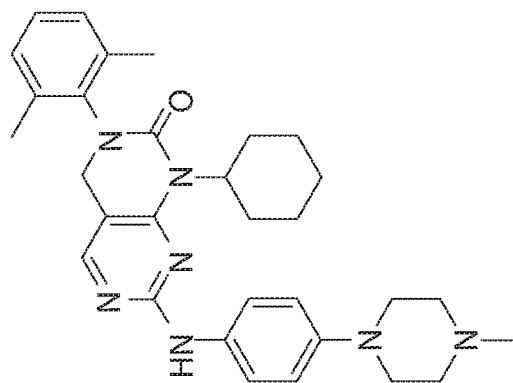
Figure 6A:
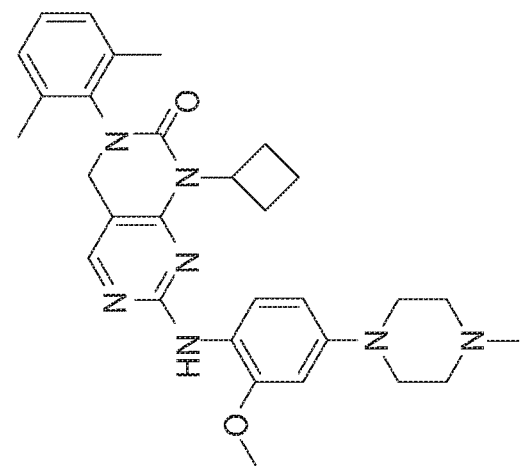
Figure 6A:
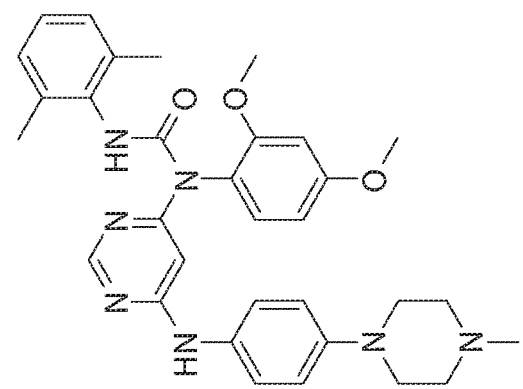
Figures 6B, 6C:
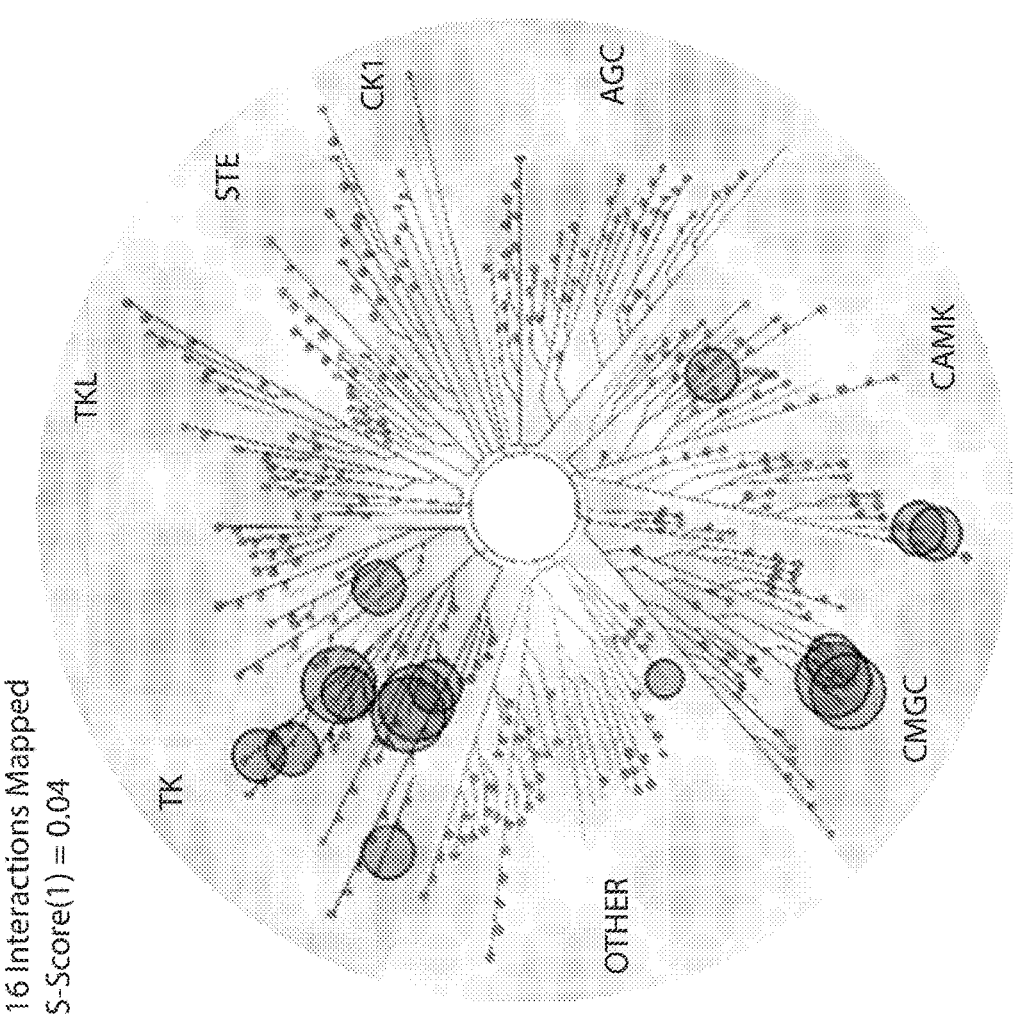

Treatment of human skin explants with passive topical application of the second generation SIK inhibitors, YKL 06-061 and YKL 06-062, induced significant pigmentation without any additional treatments after 8 days (1x/day) of treatment, but no significant gross pigmentation was observed in skin treated with HG 9-91-01 (FIG. 5A). Fontanna Mason staining revealed increased melanin content in skin treated with YKL 06-061 and YKL 06-062 and marginally increased melanin in skin treated with HG 9-91-01 as compared to control (FIG. 5B). This effect was reproducible with independent preparations of synthesized drugs applied passively to different human skin donors (FIG. 5C; 5D). Mechanical application of the first generation SIK inhibitor HG 9-91-01 (by rubbing via an applicator) induced significant gross pigmentation (FIG. 5E), and increased melanin content was observed upon Fontana Masson staining of skin sections (FIG. 5F), suggesting HG 9-91-01's human skin limited penetration can be at least partially overcome through mechanical application. YKL 06-061 and YKL 06-062 did not require mechanical application (rubbing) to induce significant human epidermal darkening. Human skin explants were treated with passive topical application of the exemplary SIK inhibitors shown in Tables 2-5 above. Whether the exemplary SIK inhibitors induced pigmentation without any additional treatments after 8 days (1x/day) of treatment is shown in Tables 2-5 above. Fontanna Mason staining further illustrated whether exemplary SIK inhibitors induced pigmentation in the human skin explants. See Tables 2-5.

These results illustrate, but are not limited to, the development and successful application of small molecule SIK inhibitors for topical induction of skin pigmentation independently of UV irradiation in human skin. SIK inhibitors were shown to induce enhanced expression of the MITF transcription factor which is known to regulate expression of numerous pigment enzymes that promote biosynthesis of eumelanin. A new generation of SIK inhibitors was developed, based upon strategies designed to enhance likelihood of skin penetration through increased lipophilicity. Two such SIK targeted inhibitors, YKL 06-061 and YKL 06-062, were shown to induce similar responses both in vitro and when applied to human skin explants. In addition to upregulating mRNA levels of MITF and TRPM1, topical SIK inhibitors were seen to trigger transfer of melanosomes into epidermal keratinocytes in a manner which recapitulates the perinuclear capping (subcellular localization) that is seen in normal human epidermal pigmentation. Thus SIK inhibitor treatments appear to induce not only synthesis of melanin, but also melanosomal maturation, export, and localization features, even after import into keratinocytes. These features closely resemble the previously observed behavior of forskolin treatment in redhaired mice (D'Orazio et al. 2006).

For example, the induction of dark pigmentation is associated with the lowest risk of most skin cancers in humans, and this pigment synthesis is believed to be dependent upon MITF. Yet fixed genomic mutation or amplification of the MITF gene can be oncogenic in certain contexts (Garraway et al; Yokoyama et al; Bertollotto et al). Reversible upregulation of MITF as reported here, is also likely to occur in routine instances of UV-tanning, or to be constitutively elevated in skin of individuals with darker pigmentation levels, and would not be anticipated to trigger genomic mutation of the MITF gene. Analogously, transient administration of recombinant hematopoietic growth factors has not been associated with formation of oncogenic transformation or leukemias. In mice, topical forskolin's pigmentary rescue in "redheads" resulted in significant protection from UV carcinogenesis without apparent associated toxicities over many months of treatment (D'Orazio et al). A recent study has utilized injections of the synthetic alpha-MSH analogue, afamelanotide, for treatment of photosensitivity associated with erythropoietic protoporphyria (Langendonk et al 2015). In this work systemic elevations in MSH downstream signals were induced, and pigmented lesions/melanoma were carefully evaluated and reported not to occur at elevated risk.

The half-life of melanin in skin is thought to be several weeks and primarily diminishes only after superficial keratinocyte sloughing. Most epidermal melanin resides within keratinocytes after transfer of melanosomes from melanocytes. Therefore it is possible that small molecule approaches like that described here, but not limited to these exemplary approaches, might be achievable, or maintained, through intermittent dosing strategies. In conclusion, these studies describe an exemplary small molecule topical approach to the rescue of eumelanin synthesis in a UV-independent manner. The applications of the strategy could be significant in a number of UV-protection related settings.

REFERENCES

1. Armstrong, B. K., and A. Kricker. 2001. 'The epidemiology of UV induced skin cancer', *J Photochem Photobiol B*, 63: 8-18.
2. Bertolotto, C., P. Abbe, T. J. Hemesath, K. Bille, D. E. Fisher, J. P. Ortonne, and R. Ballotti. 1998. 'Microphthalmia gene product as a signal transducer in cAMP-induced differentiation of melanocytes', *J Cell Biol*, 142: 827-35.
3. Bos, J. D., and M. M. Meinardi. 2000. 'The 500 Dalton rule for the skin penetration of chemical compounds and drugs', *Exp Dermatol*, 9: 165-9.
4. Clark, K., K. F. MacKenzie, K. Petkevicius, Y. Kristariyanto, J. Zhang, H. G. Choi, M. Peggie, L. Plater, P. G. Pedrioli, E. McIver, N. S. Gray, J. S. Arthur, and P. Cohen. 2012. 'Phosphorylation of CRTC3 by the salt-inducible kinases controls the interconversion of classically activated and regulatory macrophages', *Proc Natl Acad Sci USA*, 109: 16986-91.
5. Cui, R., H. R. Widlund, E. Feige, J. Y. Lin, D. L. Wilensky, V. E. Igras, J. D'Orazio, C. Y. Fung, C. F. Schanbacher, S. R. Granter, and D. E. Fisher. 2007. 'Central role of p53 in the suntan response and pathologic hyperpigmentation', *Cell*, 128: 853-64.
6. D'Orazio, J. A., T. Nobuhisa, R. Cui, M. Arya, M. Spry, K. Wakamatsu, V. Igras, T. Kunisada, S. R. Granter, E. K. Nishimura, S. Ito, and D. E. Fisher. 2006. 'Topical drug rescue strategy and skin protection based on the role of Mclr in UV-induced tanning', *Nature*, 443: 340-4.
7. Dentin, R., Y. Liu, S. H. Koo, S. Hedrick, T. Vargas, J. Heredia, J. Yates, 3rd, and M. Montminy. 2007. 'Insulin modulates gluconeogenesis by inhibition of the coactivator TORC2', *Nature*, 449: 366-9.
8. Gandini, S., F. Sera, M. S. Cattaruzza, P. Pasquini, O. Picconi, P. Boyle, and C. F. Melchi. 2005. 'Meta-analysis of risk factors for cutaneous melanoma: II. Sun exposure', *Eur J Cancer*, 41: 45-60.
9. Hadgraft, J., and W. J. Pugh. 1998. 'The selection and design of topical and transdermal agents: a review', *J Investig Dermatol Symp Proc*, 3: 131-5.
10. Harms, J. H., S. Lautenschlager, C. E. Minder, and E. I. Minder. 2009. 'Mitigating photosensitivity of erythropoietic protoporphyria patients by an agonistic analog of alpha-melanocyte stimulating hormone', *Photochem Photobiol*, 85: 1434-9.
11. Horike, N., A. Kumagai, Y. Shimono, T. Onishi, Y. Itoh, T. Sasaki, K. Kitagawa, O. Hatano, H. Takagi, T. Susumu, H. Teraoka, K. Kusano, Y. Nagaoka, H. Kawahara, and H. Takemori. 2010. 'Downregulation of SIK2 expression promotes the melanogenic program in mice', *Pigment Cell Melanoma Res*, 23: 809-19.
12. Kennedy, C., C. D. Bajdik, R. Willemze, F. R. De Gruijl, and J. N. Bouwes Bavinck. 2003. 'The influence of painful sunburns and lifetime sun exposure on the risk of actinic keratoses, seborrheic warts, melanocytic nevi, atypical nevi, and skin cancer', *J Invest Dermatol*, 120: 1087-93.
13. Khaled, M., C. Levy, and D. E. Fisher. 2010. 'Control of melanocyte differentiation by a MITF-PDE4D3 homeostatic circuit', *Genes Dev*, 24: 2276-81.
14. Kobayashi, N., A. Nakagawa, T. Muramatsu, Y. Yamashina, T. Shirai, M. W. Hashimoto, Y. Ishigaki, T. Ohnishi, and T. Mori. 1998. 'Supranuclear melanin caps reduce ultraviolet induced DNA photoproducts in human epidermis', *J Invest Dermatol*, 110: 806-10.
15. Kumagai, A., N. Horike, Y. Satoh, T. Uebi, T. Sasaki, Y. Itoh, Y. Hirata, K. Uchio-Yamada, K. Kitagawa, S. Uesato, H. Kawahara, H. Takemori, and Y. Nagaoka. 2011. 'A potent inhibitor of SIK2, 3, 3', 7-trihydroxy-4'-methoxyflavon (4'-O-methylfisetin), promotes melanogenesis in B16F10 melanoma cells', *PLoS One*, 6: e26148.
16. Kunisada, T., S. Z. Lu, H. Yoshida, S. Nishikawa, S. Nishikawa, M. Mizoguchi, S. Hayashi, L. Tyrrell, D. A. Williams, X. Wang, and B. J. Longley. 1998. 'Murine cutaneous mastocytosis and epidermal melanocytosis induced by keratinocyte expression of transgenic stem cell factor', *J Exp Med*, 187: 1565-73.
17. Lim, H. W., W. D. James, D. S. Rigel, M. E. Maloney, J. M. Spencer, and R. Bhushan. 2011. 'Adverse effects of ultraviolet radiation from the use of indoor tanning equipment: time to ban the tan', *J Am Acad Dermatol*, 64: 893-902.
18. Newton, R. A., S. E. Smit, C. C. Barnes, J. Pedley, P. G. Parsons, and R. A. Sturm. 2005. 'Activation of the cAMP pathway by variant human MC1R alleles expressed in HEK and in melanoma cells', *Peptides*, 26: 1818-24.
19. Oancea, E., J. Vriens, S. Brauchi, J. Jun, I. Splawski, and D. E. Clapham. 2009. 'TRPM1 forms ion channels associated with melanin content in melanocytes', *Sci Signal*, 2: ra21.
20. Park, S. B., D. H. Suh, and J. I. Youn. 1999. 'A long-term time course of colorimetric evaluation of ultraviolet light-induced skin reactions', *Clin Exp Dermatol*, 24: 315-20.
21. Pennello, G., S. Devesa, and M. Gail. 2000. 'Association of surface ultraviolet B radiation levels with melanoma and nonmelanoma skin cancer in United States blacks', *Cancer Epidemiol Biomarkers Prev*, 9: 291-7.
22. Prevention, Centers for Disease Control and. 21 Jun. 2016. 'Skin Cancer Statistics'. https://www.cdc.gov/cancer/skin/statistics/.

23. Price, E. R., M. A. Horstmann, A. G. Wells, K. N. Weilbaecher, C. M. Takemoto, M. W. Landis, and D. E. Fisher. 1998. 'alpha-Melanocyte-stimulating hormone signaling regulates expression of microphthalmia, a gene deficient in Waardenburg syndrome', *J Biol Chem*, 273: 33042-7.
24. Rogers, H. W., M. A. Weinstock, S. R. Feldman, and B. M. Coldiron. 2015. 'Incidence Estimate of Nonmelanoma Skin Cancer (Keratinocyte Carcinomas) in the U.S. Population, 2012', *JAMA Dermatol*, 151: 1081-6.
25. Ryerson, A. B., C. R. Eheman, S. F. Altekruse, J. W. Ward, A. Jemal, R. L. Sherman, S. J. Henley, D. Holtzman, A. Lake, A. M. Noone, R. N. Anderson, J. Ma, K. N. Ly, K. A. Cronin, L. Penberthy, and B. A. Kohler. 2016. 'Annual Report to the Nation on the Status of Cancer, 1975-2012, featuring the increasing incidence of liver cancer', *Cancer*, 122: 1312-37.
26. Tsatmalia, M., K. Wakamatsu, A. J. Graham, and A. J. Thody. 1999. 'Skin POMC peptides. Their binding affinities and activation of the human MC1 receptor', *Ann NY Acad Sci*, 885: 466-9.
27. Valverde, P., E. Healy, I. Jackson, J. L. Rees, and A. J. Thody. 1995. 'Variants of the melanocyte-stimulating hormone receptor gene are associated with red hair and fair skin in humans', *Nat Genet*, 11: 328-30.
28. Wakamatsu, K., and S. Ito. 2002. 'Advanced chemical methods in melanin determination', *Pigment Cell Res*, 15: 174-83.
29. Watson, M., A. C. Geller, M. A. Tucker, G. P. Guy, Jr., and M. A. Weinstock. 2016. 'Melanoma burden and recent trends among non-Hispanic whites aged 15-49 years, United States', *Prev Med*, 91: 294-98.
30. Wu, S., J. Han, R. A. Vleugels, R. Puett, F. Laden, D. J. Hunter, and A. A. Qureshi. 2014. 'Cumulative ultraviolet radiation flux in adulthood and risk of incident skin cancers in women', *Br J Cancer*, 110: 1855-61.
31. Altarejos, J. Y., and Montminy, M. (2011) CREB and the CRTC co-activators: sensors for hormonal and metabolic signals. *Nat. Rev. Mol. Cell Biol.* 12, 141-151.
32. Patel, K., Foretz, M., Marion, A., Campbell, D. G., Gourlay, R., Boudaba, N., Tournier, E., Titchenell, P., Peggie, M., Deak, M., Wan, M., Kaestner, K. H., Goransson, O., Viollet, B., Gray, N. S., Birnbaum, M. J., Sutherland, C., and Sakamoto, K. (2014) The LKB1-salt-inducible kinase pathway functions as a key gluconeogenic suppressor in the liver, *Nat. Commun.*, 5.
33. Park, J., Yoon, Y. S., Han, H. S., Kim, Y. H., Ogawa, Y., Park, K. G., Lee, C. H., Kim, S. T., and Koo, S. H. (2014) SIK2 Is Critical in the Regulation of Lipid Homeostasis and Adipogenesis In Vivo. *Diabetes*, 63, 3659-3673.
34. Henriksson, E., Sall, J., Gormand, A., Wasserstrom, S., Morrice, N. A., Fritzen, A. M., Foretz, M., Campbell, D. G., Sakamoto, K., Ekelund, M., Degerman, E., Stenkula, K. G., and Goransson, O. (2015) SIK2 regulates CRTCs, HDAC4 and glucose uptake in adipocytes. *J. Cell Sci.*, 128, 472-486.
35. Kumagai et al., PLOS One, Oct. 13, 2011.
36. Horike et al., Pigment Cell Melanoma Res. 23; 809-819 (2010).
37. Langendonk J G et al., (2015). Afamelanotide for Erythropoietic Protoporphyria. *New Eng J Med.* 373 (1): 48-59.
38. Yasumoto et al., Molecular Cell Biology. 1994, 8058-70.
39. Pfeifer et al., Mutation Research. 2005, 571, 19-31.

EQUIVALENTS AND SCOPE

1. In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

2. Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

3. This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

4. Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of increasing skin pigmentation in a subject, the method comprising administering topically to the subject's skin an effective amount of a compound of Formula (II), (III), or (IV):

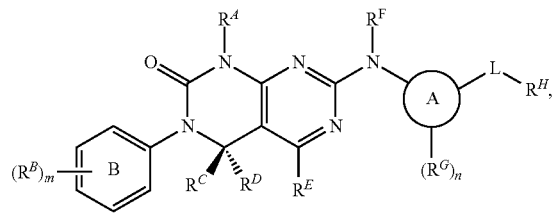

(II)

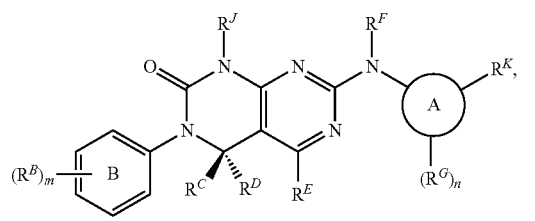

(III)

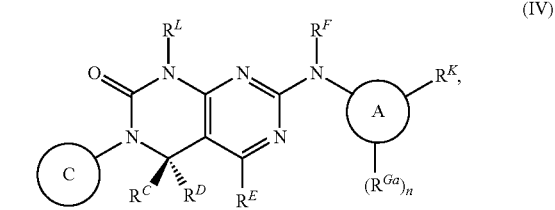

(IV)

or a pharmaceutically acceptable salt, solvate, hydrate, tautomer, stereoisomer, isotopically labeled derivative, or prodrug thereof, or a pharmaceutical composition thereof, wherein:

$R^A$ is substituted or unsubstituted alkenyl, substituted or unsubstituted alkynyl,

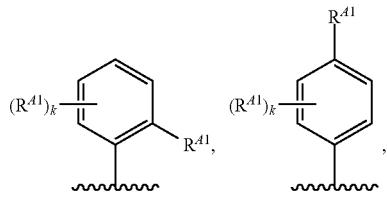

substituted or unsubstituted heteroaryl, or substituted or unsubstituted heterocyclyl;

each instance of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —$C(=NR^b)R^a$, —$C(=NR^b)OR^a$, —$C(=NR^b)N(R^b)_2$, —$C(=O)R^a$, —$C(=O)OR^a$, —$C(=O)N(R^b)_2$, —$NO_2$, —$NR^bC(=O)R^a$, —$NR^bC(=O)OR^a$, —$NR^bC(=O)N(R^b)_2$, —$OC(=O)R^a$, —$OC(=O)OR^a$, or —$OC(=O)N(R^b)_2$;

$R^J$ is substituted or unsubstituted carbocyclyl;
$R^L$ is substituted or unsubstituted alkyl;
Ring C is unsubstituted phenyl or of the formula:

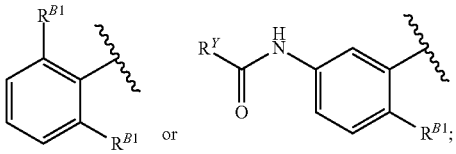

each instance of $R^{B1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^d)_2$, —$SR^a$, —CN, —SCN, —$C(=NR^d)R^a$, —$C(=NR^d)OR^a$, —$C(=NR^d)N(Rd)_2$, —$C(=O)R^a$, —$C(=O)OR^a$, —$C(=O)N(R^d)_2$, —$NO_2$, —$NR^dC(=O)R^a$, —$NR^dC(=O)OR^a$, —$NR^dC(=O)N(R^d)_2$, —$OC(=O)R^a$, —$OC(=O)OR^a$, or —$OC(=O)N(R^d)_2$;

each instance of $R^d$ is independently hydrogen, —C(=O)$R^a$, substituted or unsubstituted $C_{1-6}$ alkyl, or a nitrogen protecting group, or optionally two instances of $R^d$ are taken together with their intervening atoms to form a substituted or unsubstituted heterocyclic or substituted or unsubstituted heteroaryl ring;

$R^Y$ is substituted phenyl;

each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, —SR$^a$, —CN, —SCN, —C(=NR$^b$)R$^a$, —C(=NR$^b$)OR$^a$, —C(=NR$^b$)N(R$^b$)$_2$, —C(=O)R$^a$, —C(=O)OR$^a$, —C(=O)N(R$^b$)$_2$, —NO$_2$, —NR$^b$C(=O)R$^a$, —NR$^b$C(=O)OR$^a$, —NR$^b$C(=O)N(R$^b$)$_2$, —OC(=O)R$^a$, —OC(=O)OR$^a$, or —OC(=O)N(R$^b$)$_2$;

m is 0, 1, 2, 3, 4, or 5;

$R^C$ is hydrogen, halogen, or substituted or unsubstituted $C_{1-6}$ alkyl;

$R^D$ is hydrogen, halogen, or substituted or unsubstituted $C_{1-6}$ alkyl;

$R^E$ is hydrogen, halogen, or substituted or unsubstituted $C_{1-6}$ alkyl;

$R^F$ is hydrogen, substituted or unsubstituted $C_{1-6}$ alkyl, or a nitrogen protecting group;

Ring A is phenyl or 5- or 6-membered, monocyclic heteroaryl;

each instance of $R^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, —OR$^a$, —N(R$^b$)$_2$, —SR$^a$, —CN, —SCN, —C(=NR$^b$)R$^a$, —C(=NR$^b$)OR$^a$, —C(=NR$^b$)N(R$^b$)$_2$, —C(=O)R$^a$, —C(=O)OR$^a$, —C(=O)N(R$^b$)$_2$, —NO$_2$, —NR$^b$C(=O)R$^a$, —NR$^b$C(=O)OR$^a$, —NR$^b$C(=O)N(R$^b$)$_2$, —OC(=O)R$^a$, —OC(=O)OR$^a$, or —OC(=O)N(R$^b$)$_2$;

each instance of $R^{Ga}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, —OR$^a$, —N(R$^b$)$_2$, —SR$^a$, —CN, —SCN, —C(=NR$^b$)R$^a$, —C(=NR$^b$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^b$C(=O)R$^a$, —NR$^b$C(=O)OR$^a$, —NR$^b$C(=O)N(R$^a$)$_2$, —OC(=O)R$^a$, —OC(=O)OR$^a$, or —OC(=O)N(R$^b$)$_2$;

n is 0, 1, 2, 3, or 4, as valency permits;

L is a bond or a substituted or unsubstituted Cl-6 hydrocarbon chain, optionally wherein one or more chain atoms of the hydrocarbon chain are independently replaced with —C(=O)—, —O—, —S—, —NR$^b$—, —N=, or =N—;

$R^H$ is substituted or unsubstituted $C_{1-6}$ alkyl, substituted or unsubstituted heterocyclyl, —OH, or —N(R$^c$)$_2$;

$R^K$ is unsubstituted methyl, substituted or unsubstituted heterocyclyl, —OR$^a$, or —N(R$^4$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom;

each instance of $R^b$ is independently hydrogen, substituted or unsubstituted $C_{1-6}$ alkyl, or a nitrogen protecting group, or optionally two instances of $R^b$ are taken together with their intervening atoms to form a substituted or unsubstituted heterocyclic or substituted or unsubstituted heteroaryl ring; and each instance of $R^c$ is independently hydrogen, substituted or unsubstituted $C_{1-6}$ alkyl, or a nitrogen protecting group, or optionally two instances of $R^c$ are taken together with their intervening atoms to form a substituted or unsubstituted heterocyclic or substituted or unsubstituted heteroaryl ring;

wherein the subject does not suffer from eczema, dermatitis, inflammatory dermatosis, pemphigus or psoriasis.

2. A method of increasing the appearance of skin pigmentation in a subject, the method comprising administering topically to the subject's skin an effective amount of a compound of Formula (II), (III), or (IV):

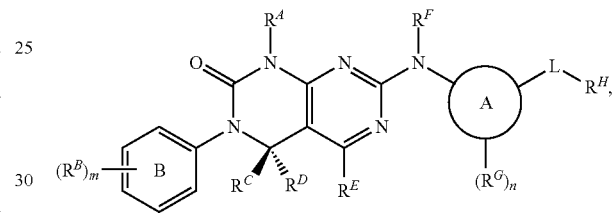

(II)

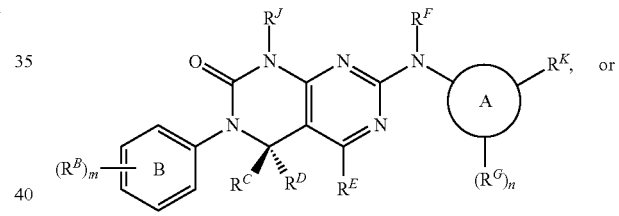

(III)

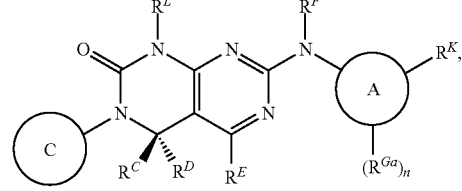

(IV)

or a pharmaceutically acceptable salt, solvate, hydrate, tautomer, stereoisomer, isotopically labeled derivative, or prodrug thereof, or a pharmaceutical composition thereof, wherein:

$R^A$ is substituted or unsubstituted alkenyl, substituted or unsubstituted alkynyl,

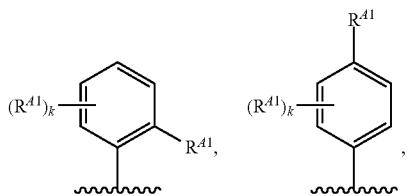

substituted or unsubstituted heteroaryl, or substituted or unsubstituted heterocyclyl;

each instance of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —$C(=NR^b)R^a$, —$C(=NR^b)OR^a$, —$C(=NR^b)N(R^b)_2$, —$C(=O)R^a$, —$C(=O)OR^a$, —$C(=O)N(R^b)_2$, —$NO_2$, —$NR^bC(=O)R^a$, —$NR^bC(=O)OR^a$, —$NR^bC(=O)N(R^b)_2$, —$OC(=O)R^a$, —$OC(=O)OR^a$, or —$OC(=O)N(R^b)_2$;

$R^J$ is substituted or unsubstituted carbocyclyl;

$R^L$ is substituted or unsubstituted alkyl;

Ring C is unsubstituted phenyl or of the formula:

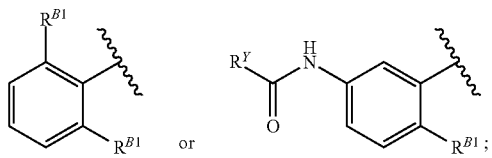

each instance of $R^{B1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^d)_2$, —$SR^a$, —CN, —SCN, —$C(=NR^d)R^a$, —$C(=NR^d)OR^a$, —$C(=NR^d)N(Rd)_2$, —$C(=O)R^a$, —$C(=O)OR^a$, —$C(=O)N(Rd)_2$, —$NO_2$, —$NRdC(=O)R^a$, —$NR^dC(=O)OR^a$, —$NR^dC(=O)N(R^a)_2$, —$OC(=O)R^a$, —$OC(=O)OR^a$, or —$OC(=O)N(R^d)_2$;

each instance of $R^d$ is independently hydrogen, —$C(=O)R^a$, substituted or unsubstituted $C_{1-6}$ alkyl, or a nitrogen protecting group, or optionally two instances of $R^d$ are taken together with their intervening atoms to form a substituted or unsubstituted heterocyclic or substituted or unsubstituted heteroaryl ring;

$R^Y$ is substituted phenyl;

each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —$C(=NR^b)R^a$, —$C(=NR^b)OR^a$, —$C(=NR^b)N(R^b)_2$, —$C(=O)R^a$, —$C(=O)OR^a$, —$C(=O)N(R^b)_2$, —$NO_2$, —$NR^bC(=O)R^a$, —$NR^bC(=O)OR^a$, —$NR^bC(=O)N(R^b)_2$, —$OC(=O)R^a$, —$OC(=O)OR^a$, or —$OC(=O)N(R^b)_2$;

m is 0, 1, 2, 3, 4, or 5;

$R^C$ is hydrogen, halogen, or substituted or unsubstituted $C_{1-6}$ alkyl;

$R^D$ is hydrogen, halogen, or substituted or unsubstituted $C_{1-6}$ alkyl;

$R^E$ is hydrogen, halogen, or substituted or unsubstituted $C_{1-6}$ alkyl;

$R^F$ is hydrogen, substituted or unsubstituted $C_{1-6}$ alkyl, or a nitrogen protecting group;

Ring A is phenyl or 5- or 6-membered, monocyclic heteroaryl;

each instance of $R^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, —$OR^a$, —$N(R^b)_2$, —$SR^a$, —CN, —SCN, —$C(=NR^b)R^a$, —$C(=NR^b)OR^a$, —$C(=NR^b)N(R^b)_2$, —$C(=O)R^a$, —$C(=O)OR^a$, —$C(=O)N(R^b)_2$, —$NO_2$, —$NR^bC(=O)R^a$, —$NR^bC(=O)OR^a$, —$NR^bC(=O)N(R^b)_2$, —$OC(=O)R^a$, —$OC(=O)OR^a$, or —$OC(=O)N(R^b)_2$;

each instance of $R^{Ga}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, —$OR^a$, —$N(R^b)_2$, —$SR^a$, —CN, —SCN, —$C(=NR^b)R^a$, —$C(=NR^b)OR^a$, —$C(=NR^a)N(R^a)_2$, —$C(=O)R^a$, —$C(=O)OR^a$, —$C(=O)N(R^a)_2$, —$NO_2$, —$NR^bC(=O)R^a$, —$NR^bC(=O)OR^a$, —$NR^bC(=O)N(R^a)_2$, —$OC(=O)R^a$, —$OC(=O)OR^a$, or —$OC(=O)N(R^b)_2$;

n is 0, 1, 2, 3, or 4, as valency permits;

L is a bond or a substituted or unsubstituted $C_{1-6}$ hydrocarbon chain, optionally wherein one or more chain atoms of the hydrocarbon chain are independently replaced with —$C(=O)$—, —O—, —S—, —$NR^b$—, —N=, or =N—;

$R^H$ is substituted or unsubstituted $C_{1-6}$ alkyl, substituted or unsubstituted heterocyclyl, —OH, or —$N(R^c)_2$;

$R^K$ is unsubstituted methyl, substituted or unsubstituted heterocyclyl, —$OR^a$, or —$N(R^c)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom;

each instance of $R^b$ is independently hydrogen, substituted or unsubstituted $C_{1-6}$ alkyl, or a nitrogen protecting group, or optionally two instances of $R^b$ are taken together with their intervening atoms to form a substituted or unsubstituted heterocyclic or substituted or unsubstituted heteroaryl ring; and each instance of $R^c$ is independently hydrogen, substituted or unsubstituted $C_{1-6}$ alkyl, or a nitrogen protecting group, or optionally two instances of $R^c$ are taken together with their intervening atoms to form a substituted or unsubstituted heterocyclic or substituted or unsubstituted heteroaryl ring;

wherein the subject does not suffer from eczema, dermatitis, inflammatory dermatosis, pemphigus or psoriasis.

3. The method of claim 1, wherein the compound is of Formula (II), or a pharmaceutically acceptable salt, solvate, hydrate, tautomer, stereoisomer, isotopically labeled derivative, or prodrug thereof.

4. The method of claim 1, wherein the compound is of Formula (III), or a pharmaceutically acceptable salt, solvate, hydrate, tautomer, stereoisomer, isotopically labeled derivative, or prodrug thereof.

5. The method of claim 4, wherein $R^J$ is substituted or unsubstituted cyclobutyl, substituted or unsubstituted cyclopentyl, or substituted or unsubstituted cyclohexyl.

6. The method of claim 4, wherein $R^K$ is substituted or unsubstituted piperidinyl or substituted or unsubstituted piperazinyl.

7. The method of claim 4, wherein

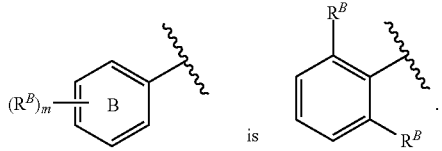

is

8. The method of claim 7, wherein at least one instance of $R^B$ is halogen or substituted or unsubstituted $C_{1-6}$ alkyl.

9. The method of claim 1, wherein $R^C$ is hydrogen, and $R^D$ is hydrogen.

10. The method of claim 1, wherein $R^E$ is hydrogen.

11. The method of claim 1, wherein $R^F$ is hydrogen.

12. The method of claim 4, wherein

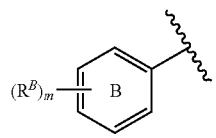

is of the formula

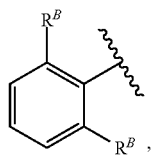

$R^C$, $R^D$, $R^E$, and $R^F$ are each hydrogen, $R^G$ is —$OR^a$, $R^J$ is substituted or unsubstituted, 4- to 6-membered carbocyclyl, and $R^K$ is substituted or unsubstituted piperidinyl, or substituted or unsubstituted piperazinyl.

13. The method of claim 4, wherein

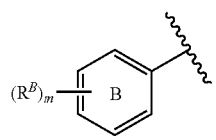

is of the formula:

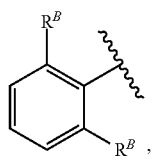

$R^C$, $R^D$, $R^E$, and $R^F$ are each hydrogen, n is 0, $R^J$ is substituted or unsubstituted, 4- to 6-membered carbocyclyl, and $R^K$ is substituted or unsubstituted piperidinyl, or substituted or unsubstituted piperazinyl.

14. The method of claim 4, wherein the compound is of the formula:

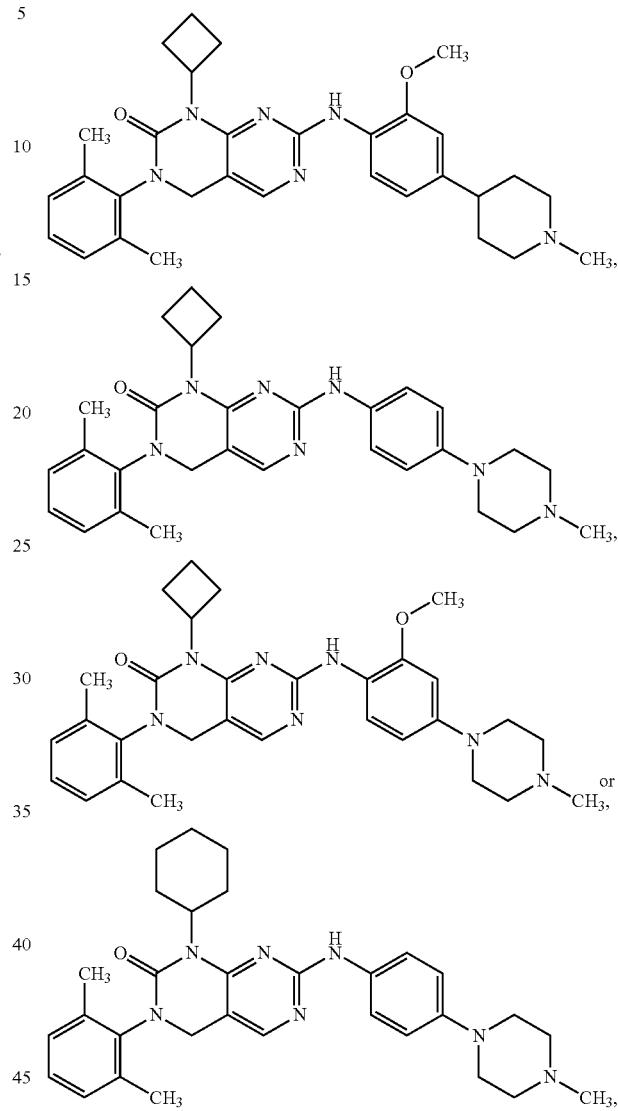

or a pharmaceutically acceptable salt, solvate, hydrate, tautomer, stereoisomer, isotopically labeled derivative, or prodrug thereof.

15. The method of claim 4, wherein the compound is of the formula:

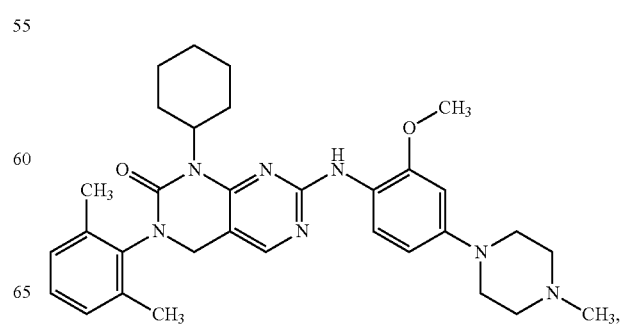

301
-continued

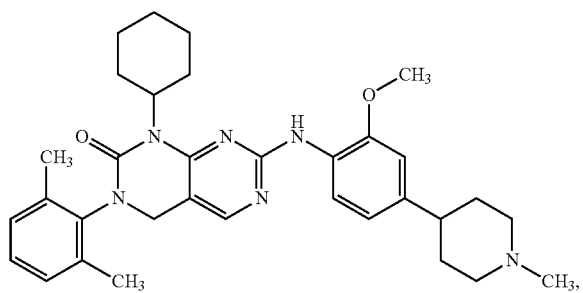
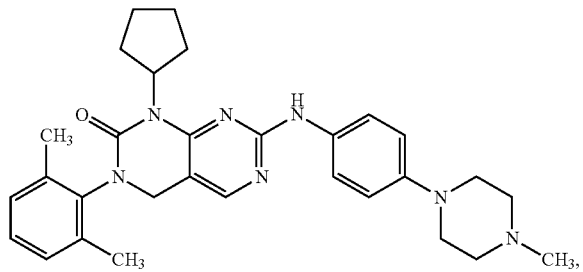
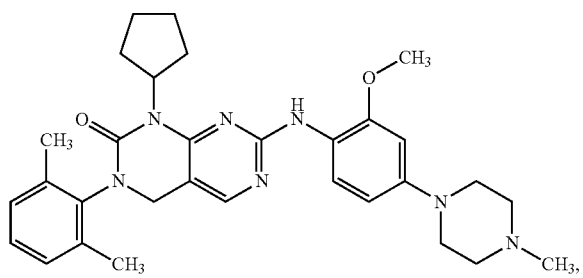
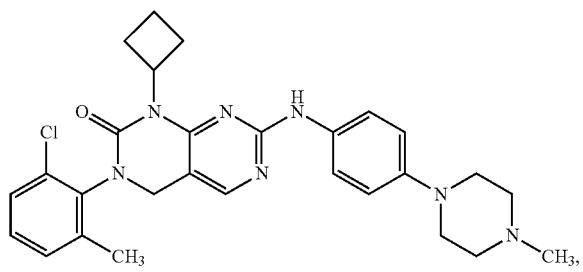
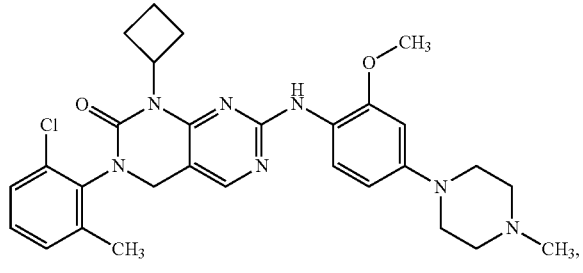
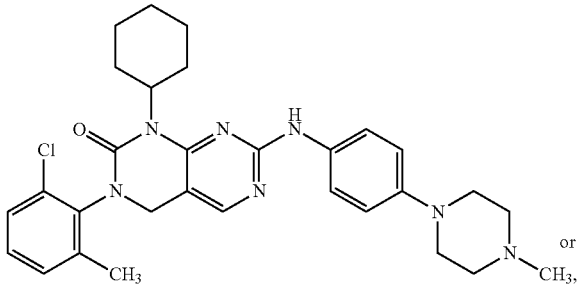

302
-continued

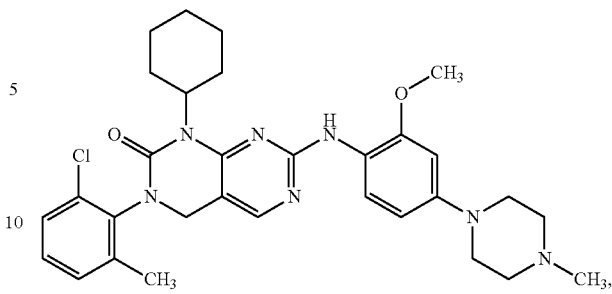

or a pharmaceutically acceptable salt, solvate, hydrate, tautomer, stereoisomer, isotopically labeled derivative, or prodrug thereof.

16. The method of claim 1, wherein the compound is of Formula (IV), or a pharmaceutically acceptable salt, solvate, hydrate, tautomer, stereoisomer, isotopically labeled derivative, or prodrug thereof.

17. The method of claim 1, wherein Ring A is phenyl.

18. The method of claim 4, wherein at least one instance of $R^G$ is substituted or unsubstituted $C_{1-6}$ alkyl or —O-(substituted or unsubstituted $C_{1-6}$ alkyl).

19. The method of claim 4, wherein the compound is of Formula (III), or a pharmaceutically acceptable salt or tautomer thereof.

20. The method of claim 4, wherein the compound is of the formula:

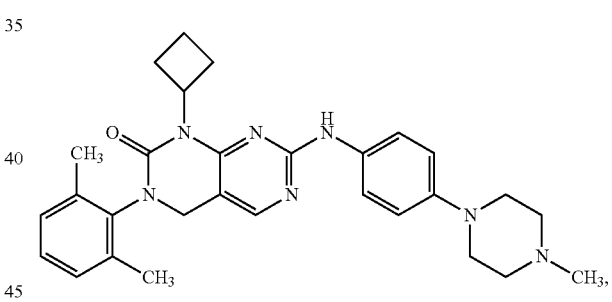

or a pharmaceutically acceptable salt or tautomer thereof.

21. The method of claim 4, wherein the compound is of the formula:

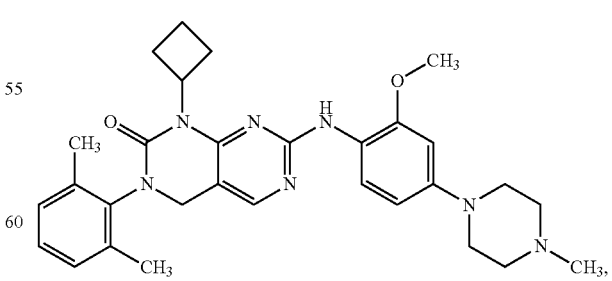

or a pharmaceutically acceptable salt or tautomer thereof.

22. The method of claim 4, wherein the compound is of the formula:

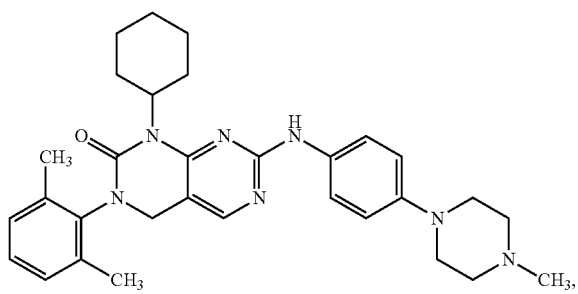

or a pharmaceutically acceptable salt or tautomer thereof.

23. The method of claim 16, wherein the compound is of Formula (IV), or a pharmaceutically acceptable salt or tautomer thereof.

24. The method of claim 16, wherein $R^L$ is unsubstituted $C_{1-6}$ alkyl.

25. The method of claim 16, wherein Ring C is unsubstituted phenyl or

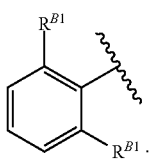

26. The method of claim 16, wherein at least one instance of $R^{B1}$ is halogen or substituted or unsubstituted $C_{1-6}$ alkyl.

27. The method of claim 16, wherein $R^K$ is substituted or unsubstituted heterocyclyl.

28. The method of claim 16, wherein $R^K$ is substituted or unsubstituted tetrahydropyranyl, substituted or unsubstituted piperidinyl, substituted or unsubstituted morpholinyl, or substituted or unsubstituted piperazinyl.

29. The method of claim 16, wherein at least one instance of $R^{Ga}$ is substituted or unsubstituted $C_{1-6}$ alkyl or —O-(substituted or unsubstituted $C_{1-6}$ alkyl).

30. The method of claim 16, wherein the compound is of the formula:

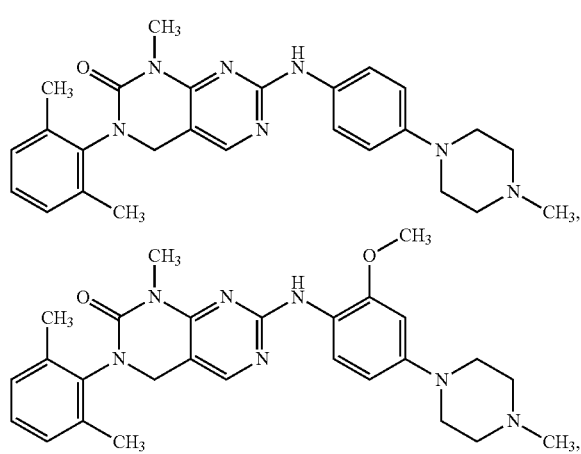

-continued

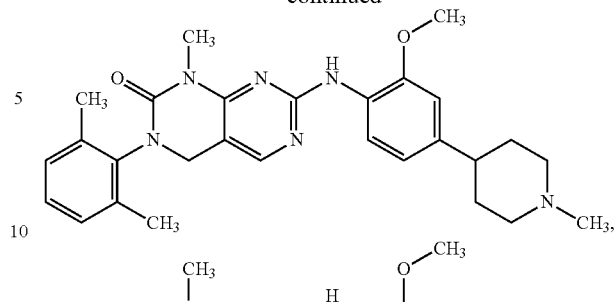

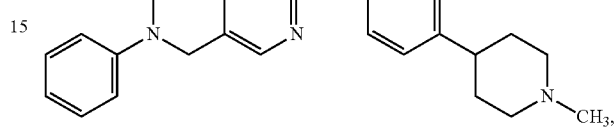

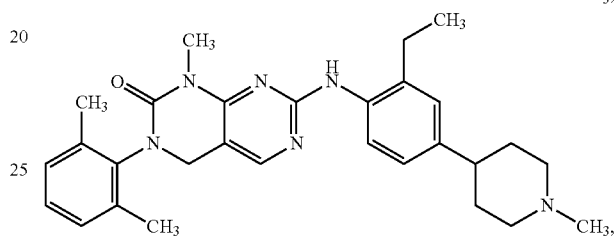

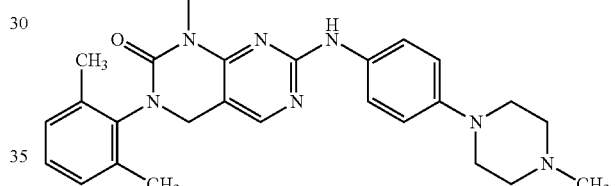

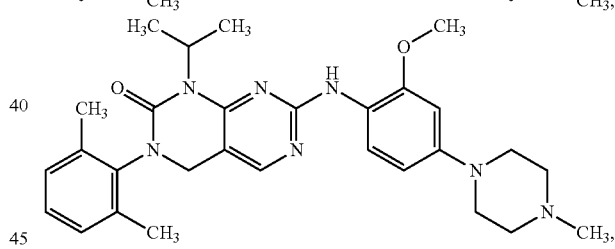

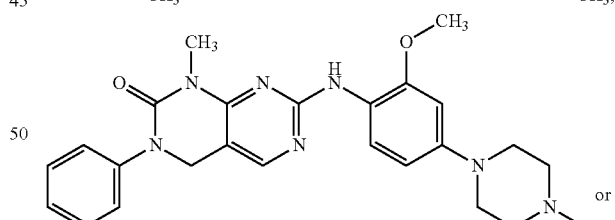

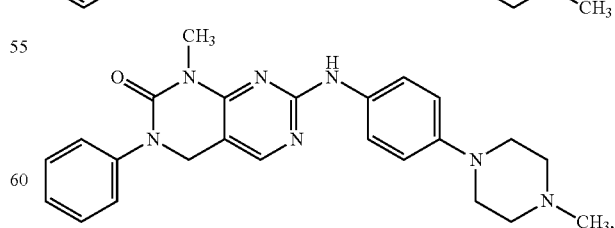

or a pharmaceutically acceptable salt or tautomer thereof.

31. The method of claim 16, wherein the compound is of the formula:

305

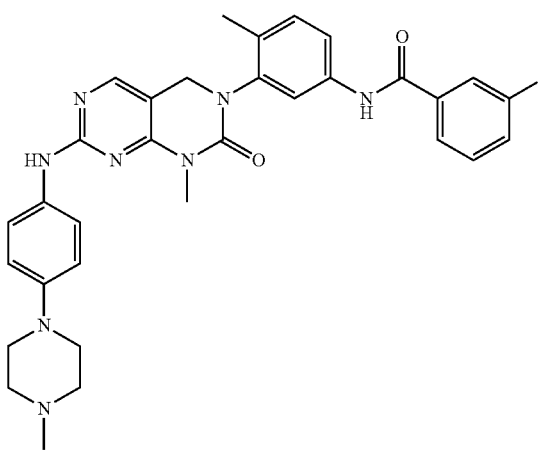

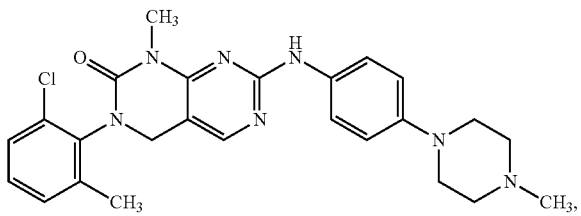

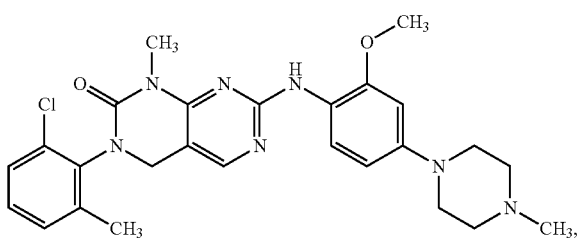 [SMILES: COc1cc(N2CCN(C)CC2)ccc1Nc1ncc2c(n1)N(C)C(=O)N(c1ccccc1)C2]

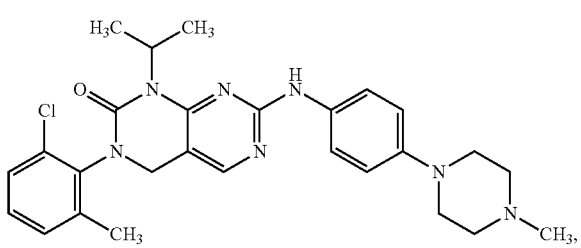

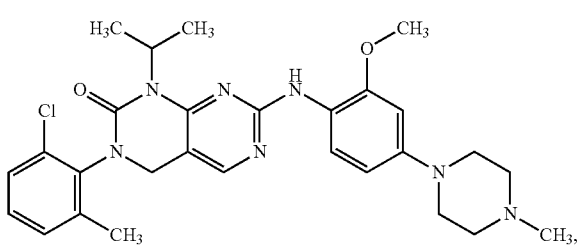

306

-continued

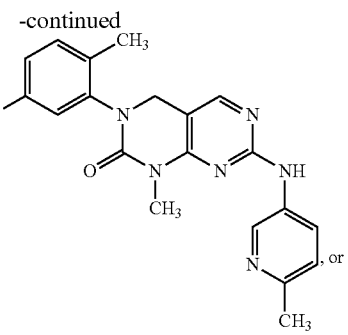

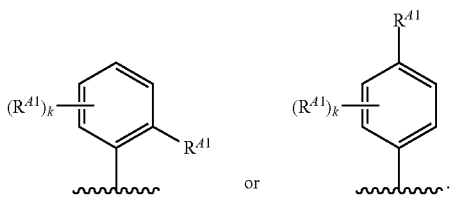

or a pharmaceutically acceptable salt or tautomer thereof.

32. The method of claim 16, wherein:
Ring C is unsubstituted phenyl or

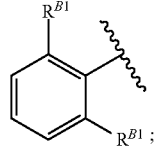

$R^C$, $R^D$, $R^E$, and $R^F$ are each hydrogen;
$R^L$ is unsubstituted alkyl;
Ring A is phenyl; and
$R^K$ is substituted or unsubstituted piperidinyl or substituted or unsubstituted piperazinyl.

33. The method of claim 3, wherein the compound is of Formula (II), or a pharmaceutically acceptable salt or tautomer thereof.

34. The method of claim 3, wherein $R^A$ is

35. The method of claim 3, wherein $R^A$ is substituted or unsubstituted pyridinyl.

36. The method of claim 3, wherein

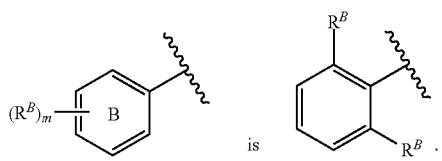

is

37. The method of claim 3, wherein at least one instance of $R^B$ is halogen or substituted or unsubstituted $C_{1-6}$ alkyl.

38. The method of claim 3, wherein Ring A is phenyl, pyrazolyl, or pyridinyl.

39. The method of claim 3, wherein L is a bond.

40. The method of claim 3, wherein L is an unsubstituted $C_{1-3}$ hydrocarbon chain, optionally wherein one chain atom of the hydrocarbon chain is replaced with —O— or —NR$^b$—.

41. The method of claim 3, wherein $R^H$ is substituted or unsubstituted heterocyclyl.

42. The method of claim 3, wherein $R^H$ is substituted or unsubstituted tetrahydropyranyl, substituted or unsubstituted piperidinyl, substituted or unsubstituted morpholinyl, or substituted or unsubstituted piperazinyl.

43. The method of claim 3, wherein $R^H$ is —N(R$^c$)$_2$.

44. The method of claim 3, wherein at least one instance of $R^G$ is substituted or unsubstituted $C_{1-6}$ alkyl or —O-(substituted or unsubstituted $C_{1-6}$ alkyl).

45. The method of claim 3, wherein:

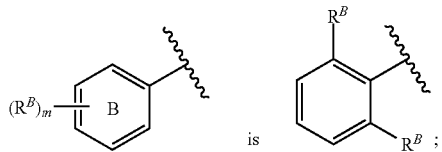

is $R^C$, $R^D$, $R^E$, and $R^F$ are each hydrogen;
$R^A$ is

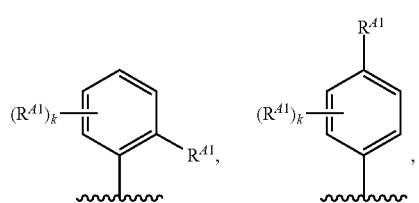

or substituted or unsubstituted pyridinyl;
Ring A is phenyl, pyrazolyl, or pyridinyl;
L is a bond or an unsubstituted $C_{1-3}$ hydrocarbon chain, optionally wherein one chain atom of the hydrocarbon chain is replaced with —O— or —NR$^b$—; and $R^H$ is substituted or unsubstituted tetrahydropyranyl, substituted or unsubstituted piperidinyl, substituted or unsubstituted morpholinyl, substituted or unsubstituted piperazinyl, or —N(R$^c$)$_2$.

46. The method of claim 3, wherein the compound is of the formula:

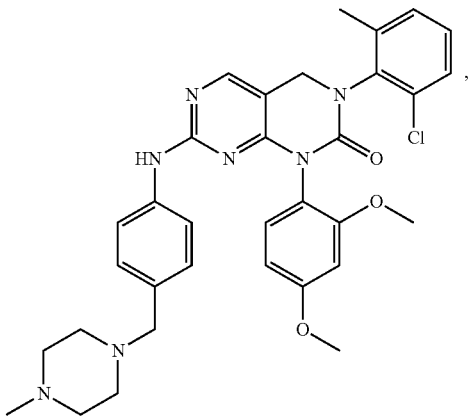

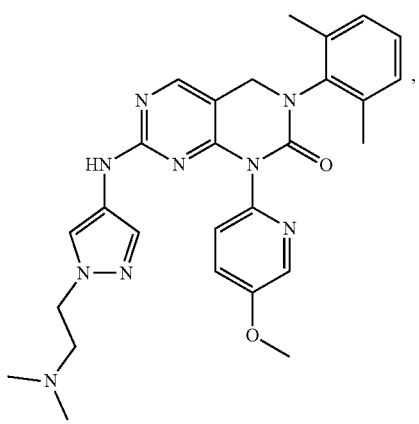

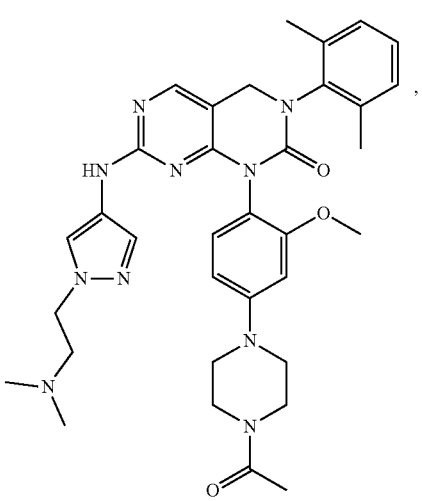

309 -continued
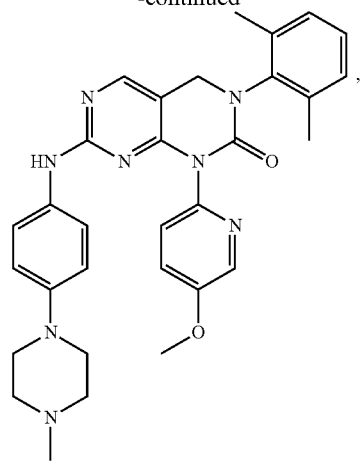
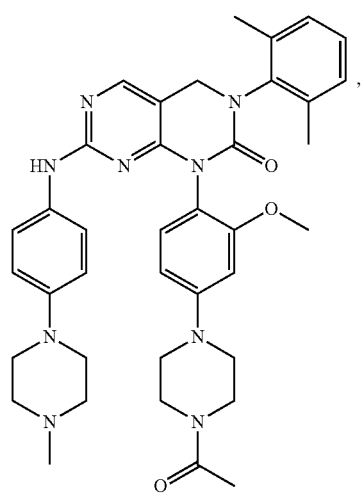
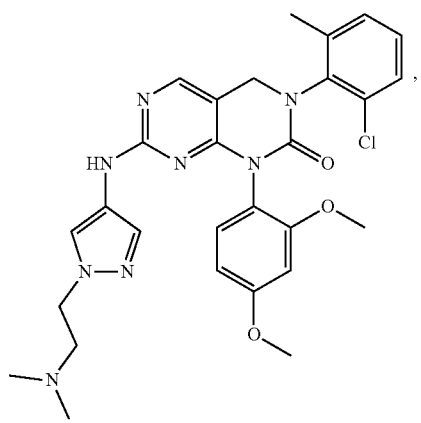
310 -continued
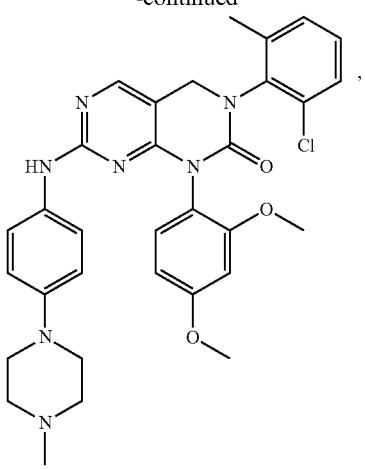
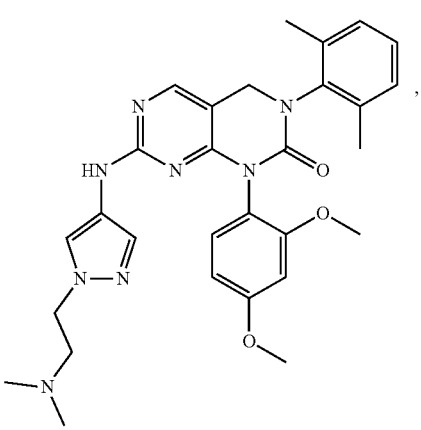
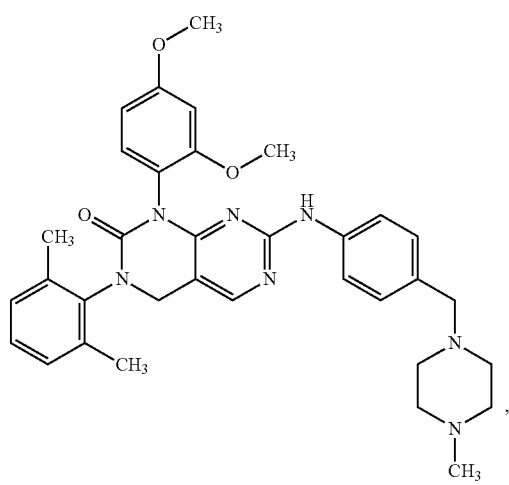

311
-continued
312
-continued
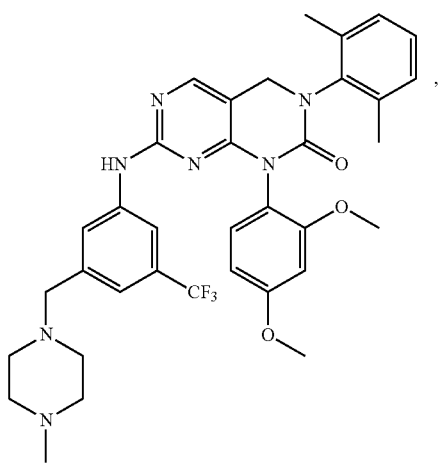
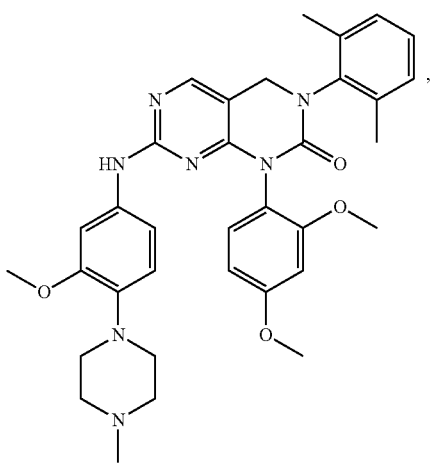
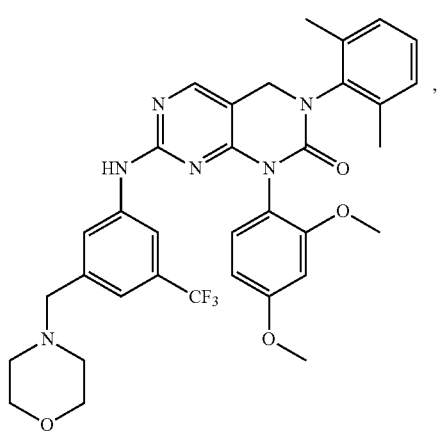
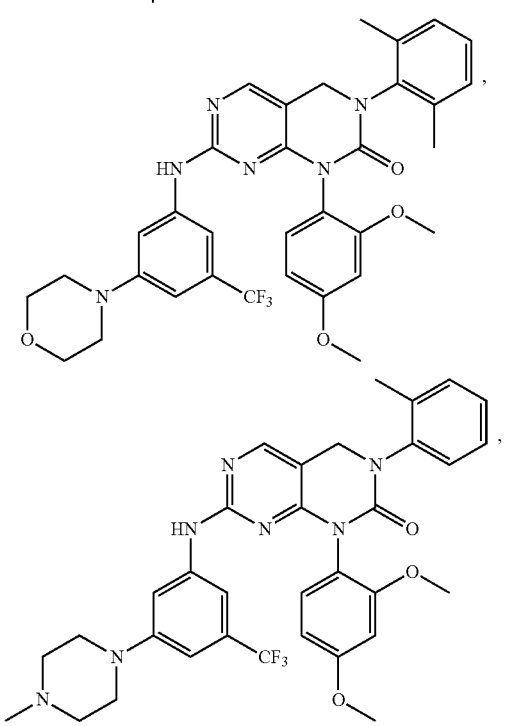
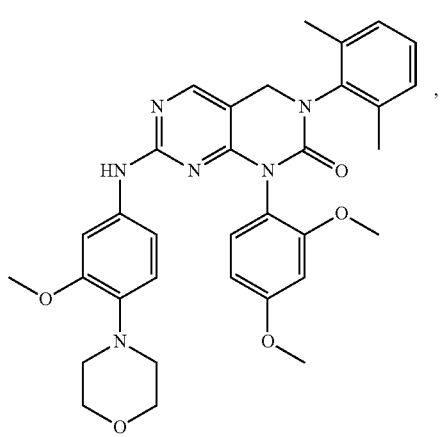
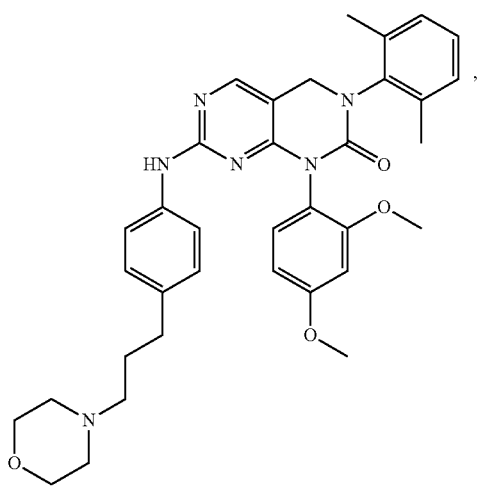

313
-continued
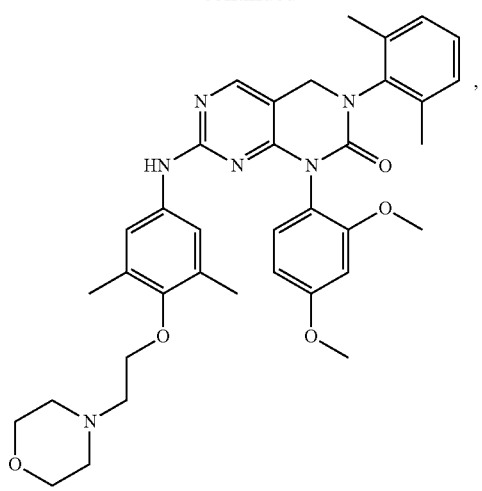
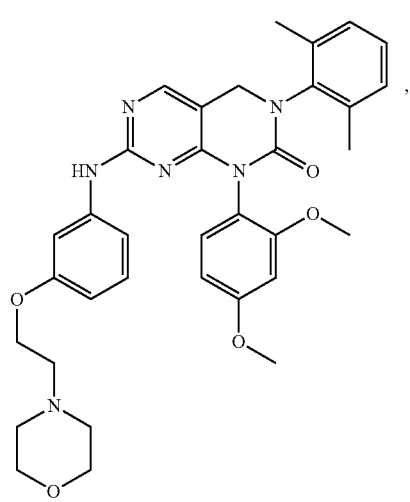
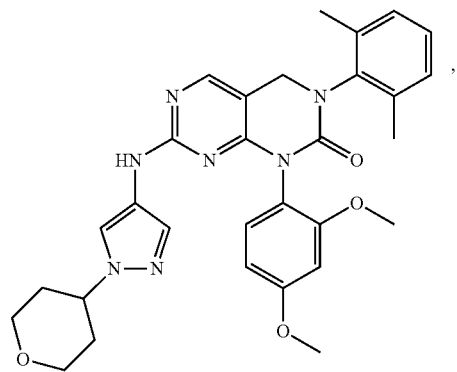
314
-continued
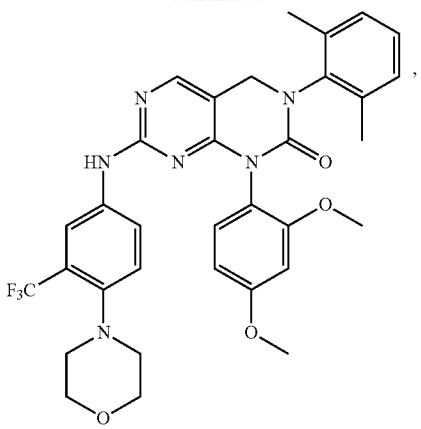
, or 315
-continued
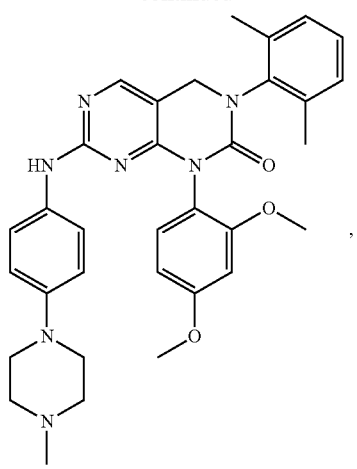
or a pharmaceutically acceptable salt or tautomer thereof.
47. The method of claim 3, wherein the compound is of the formula:
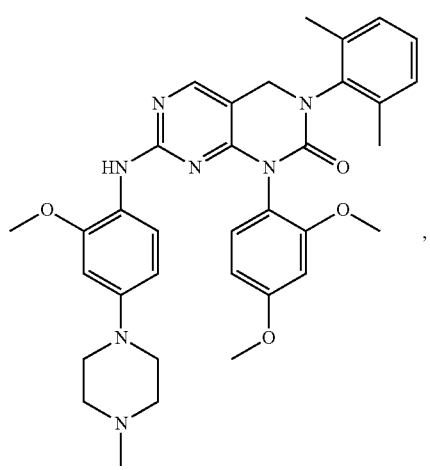
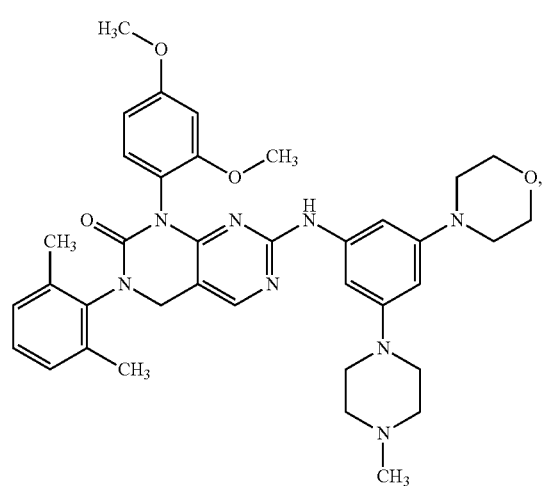
316
-continued
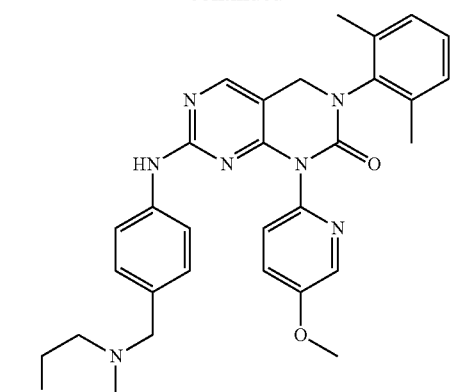
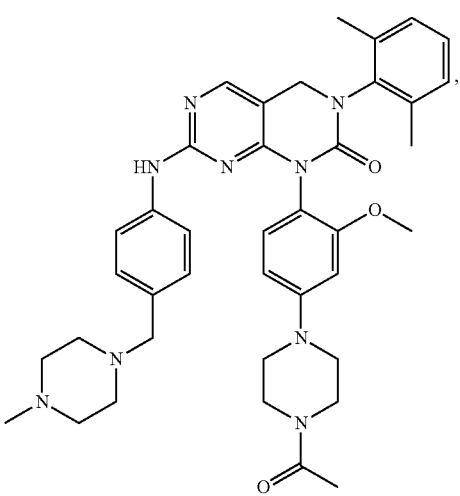
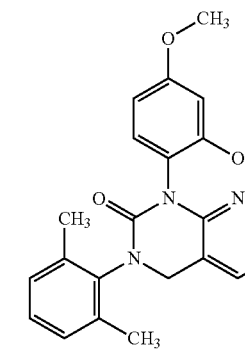
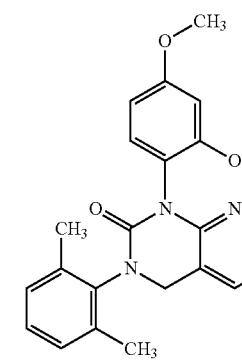

317
-continued
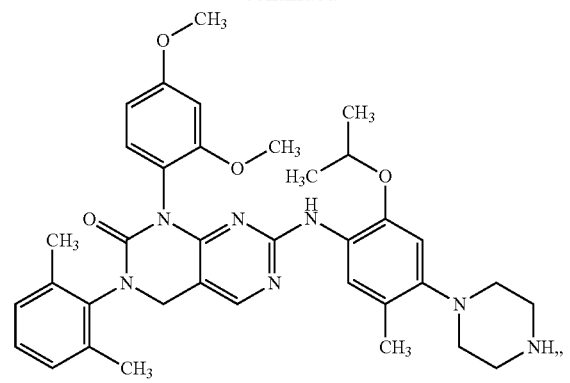
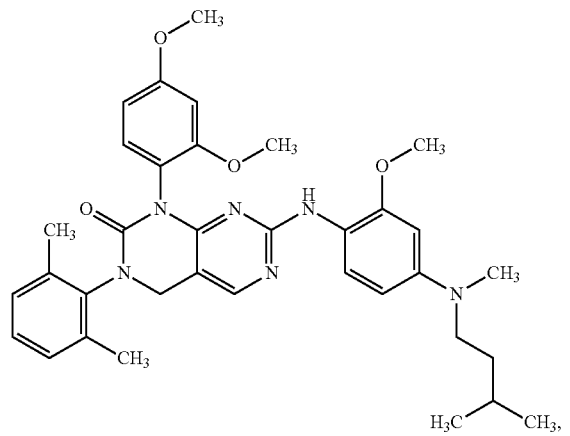
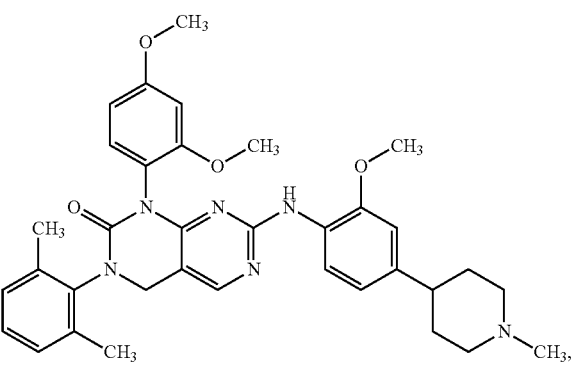
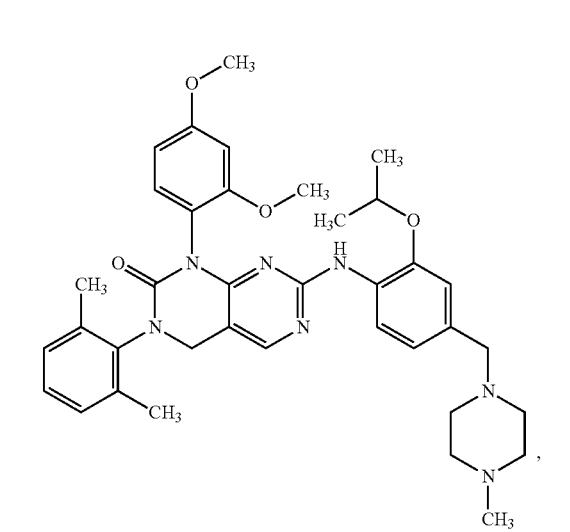
318
-continued
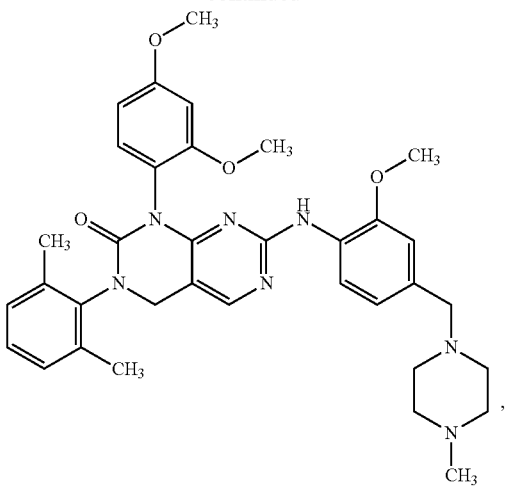
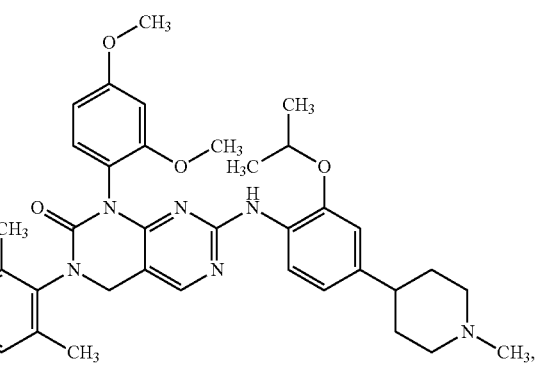
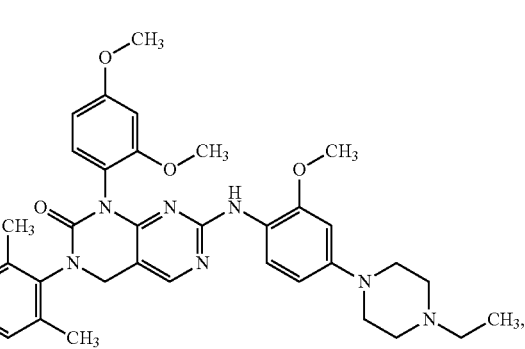
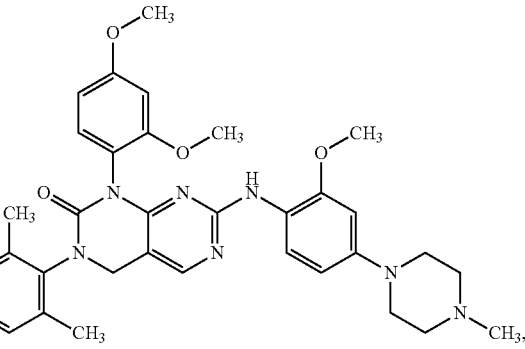

-continued
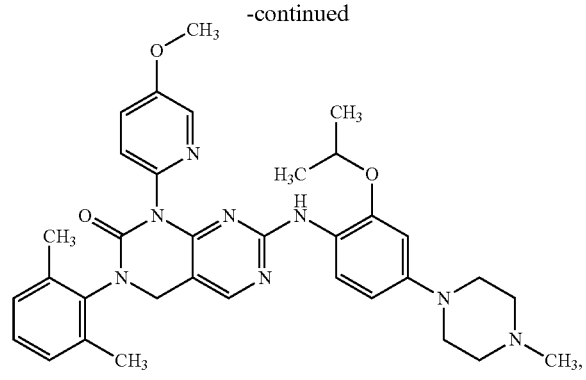
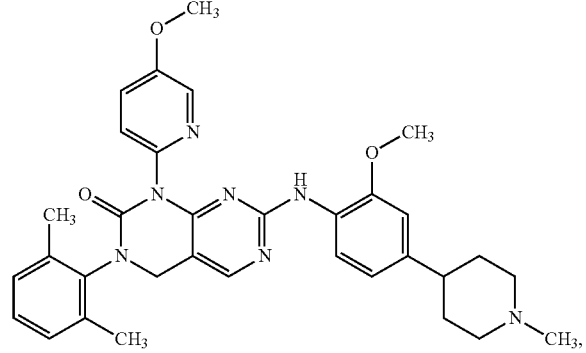
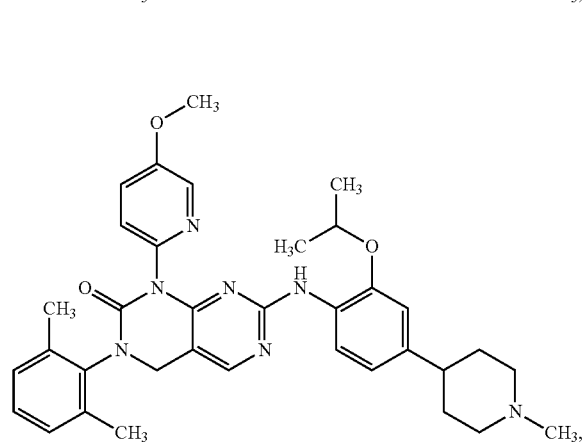
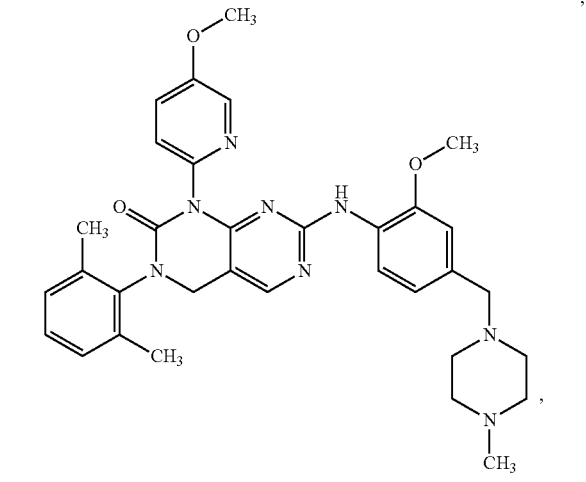
-continued
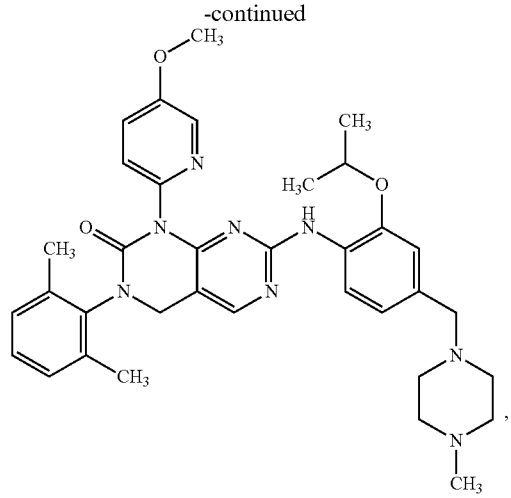
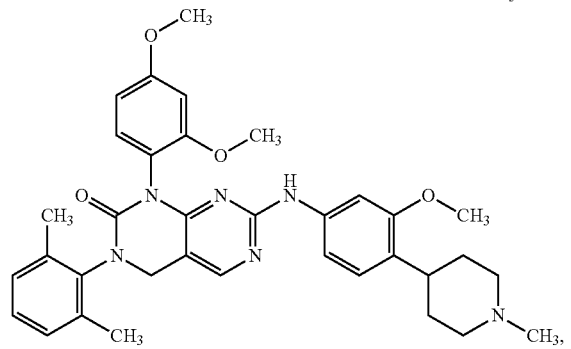
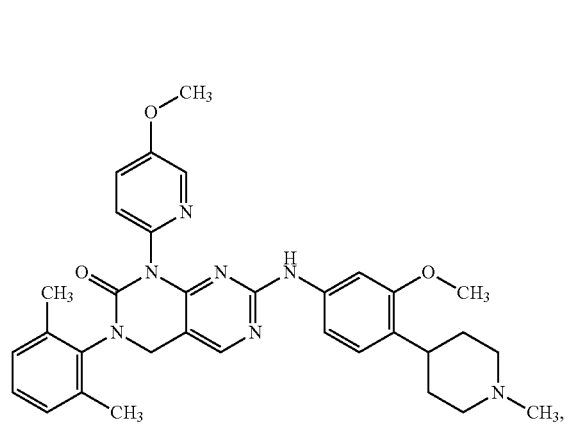
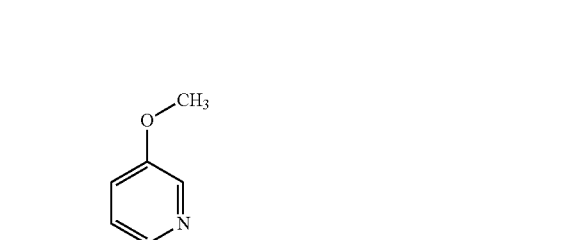
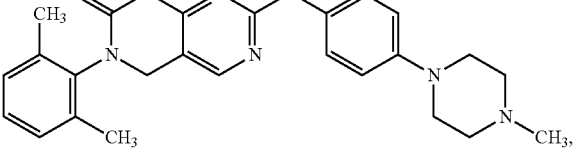

321
-continued
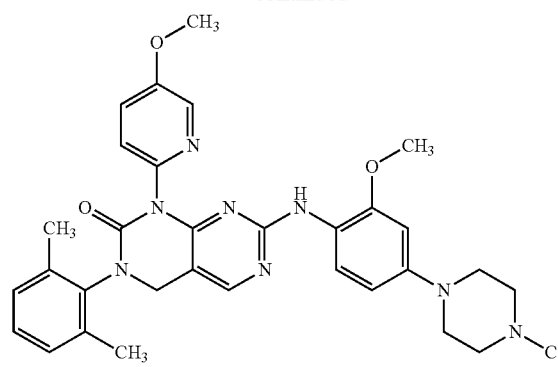
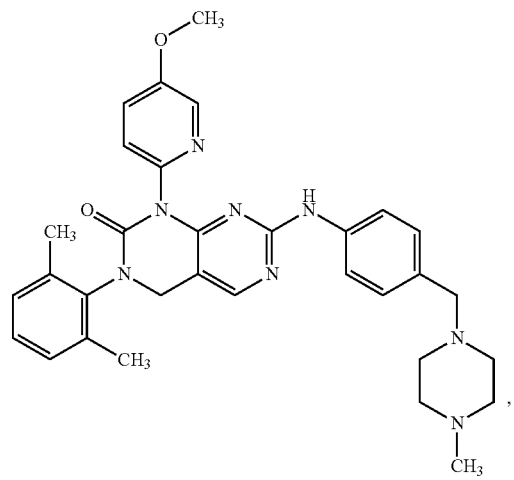
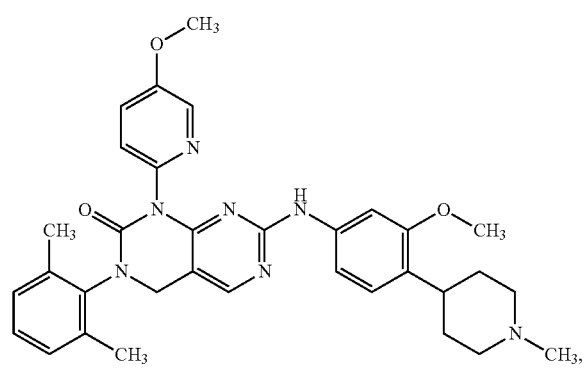
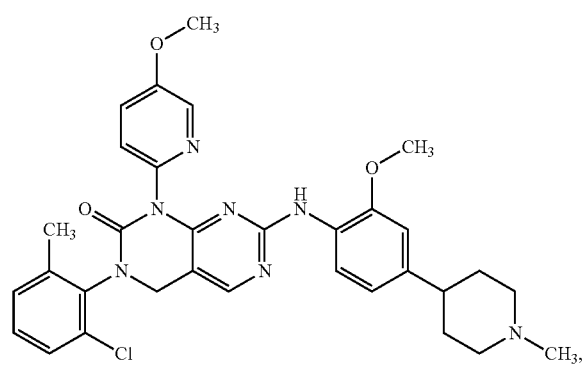
322
-continued
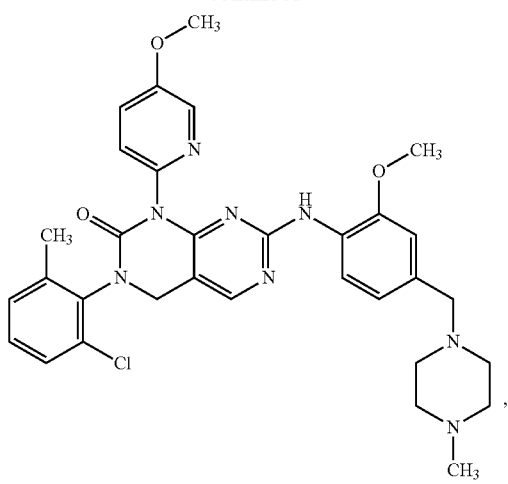
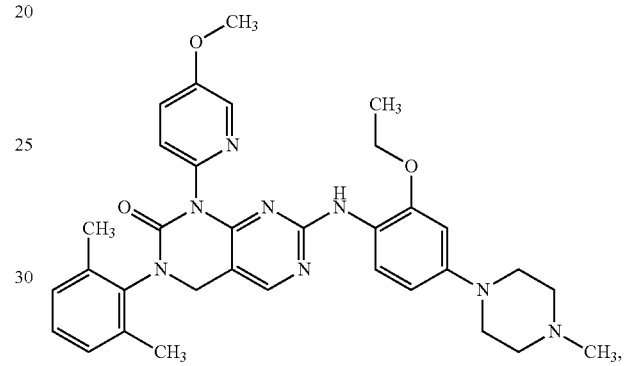
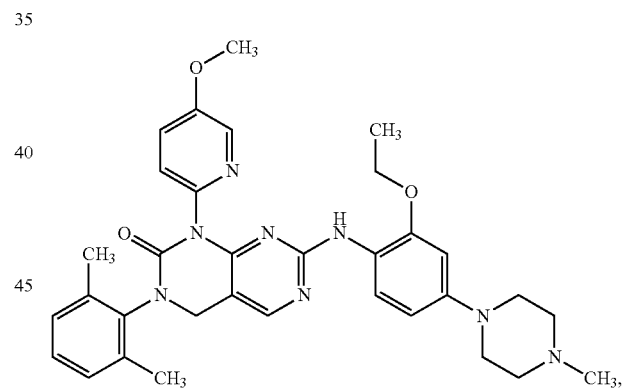
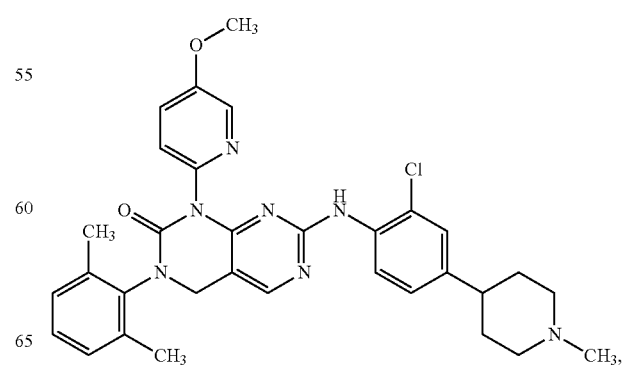

323
-continued
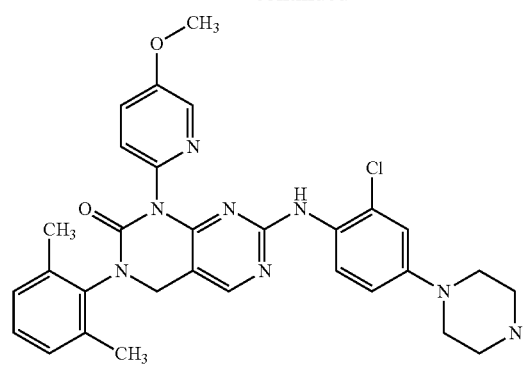
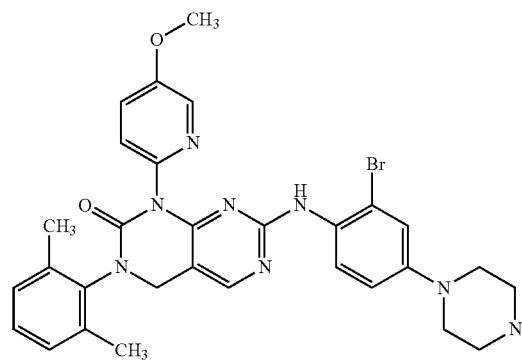
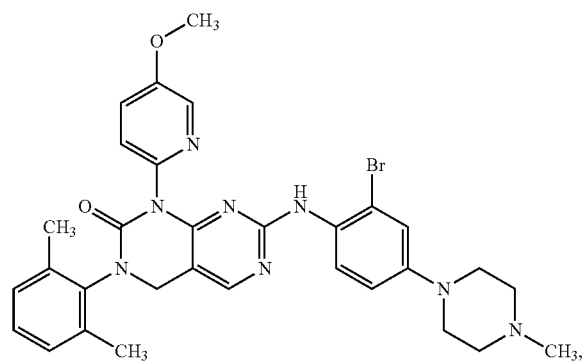
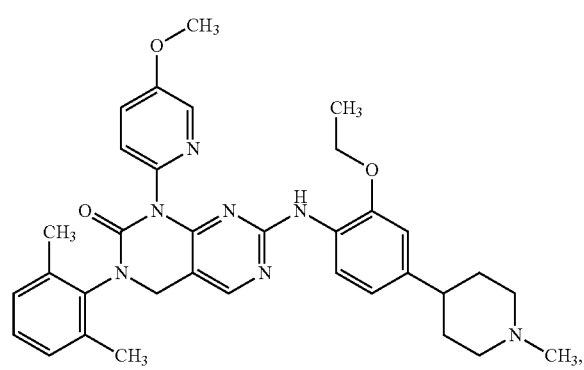
324
-continued
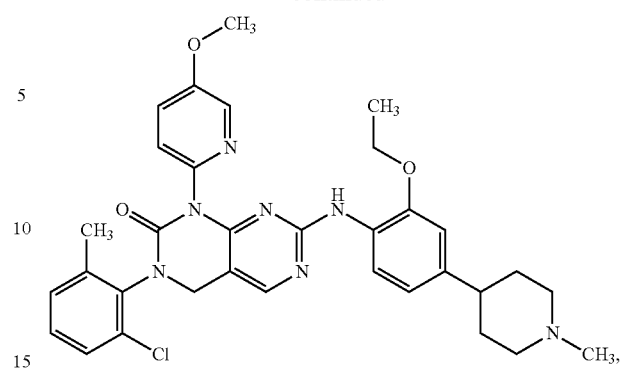
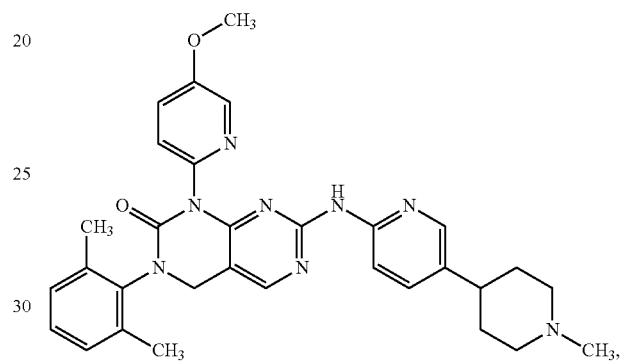
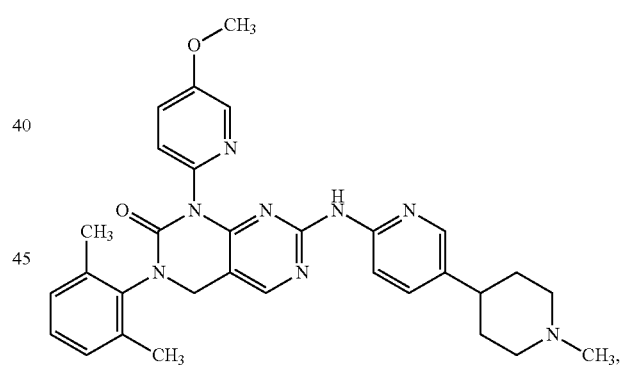
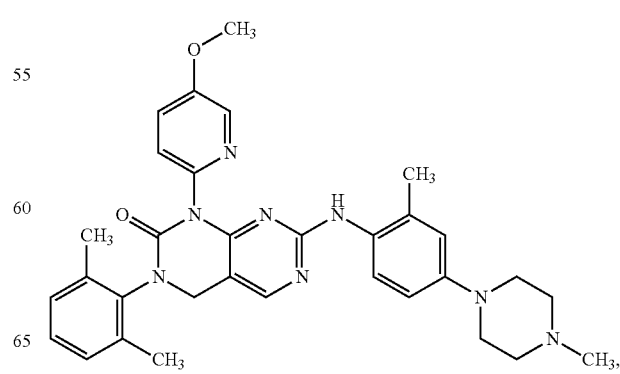

325
-continued
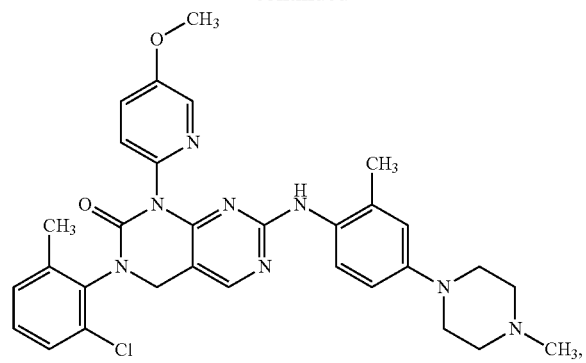
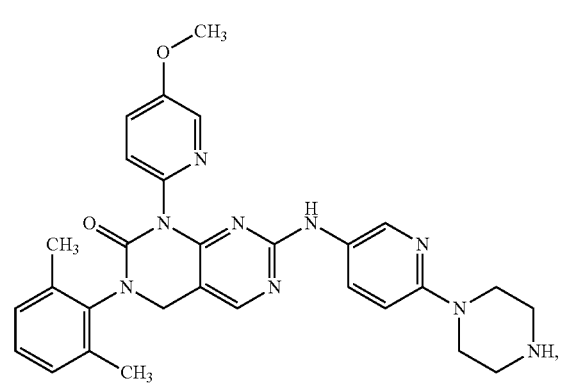
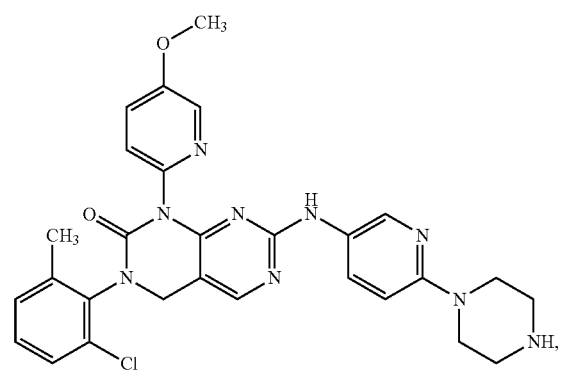
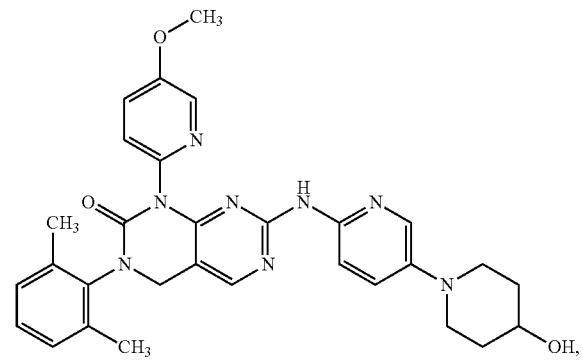
326
-continued
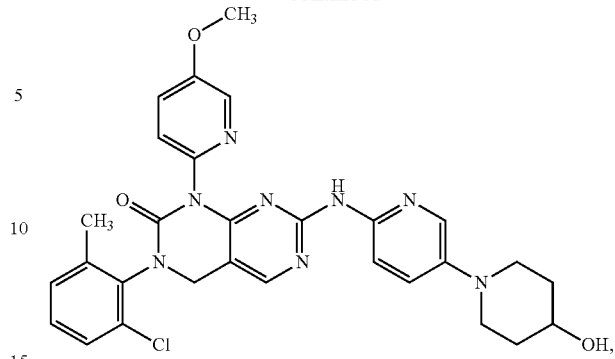
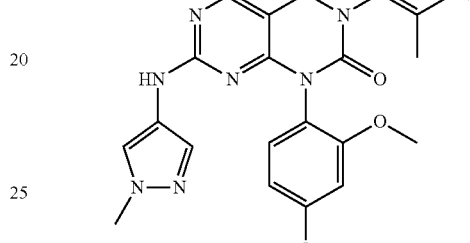
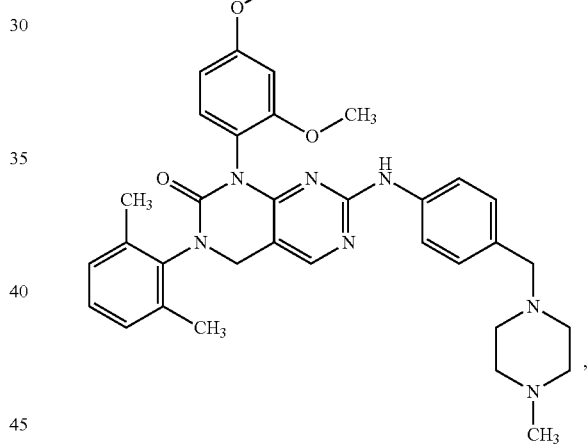
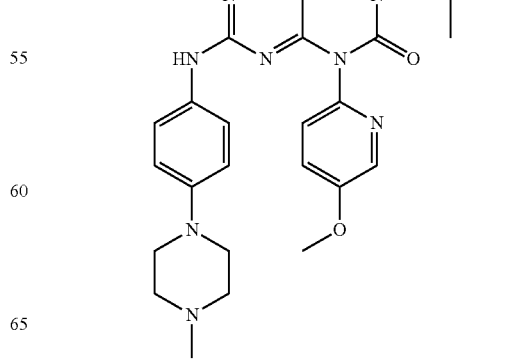

327
-continued
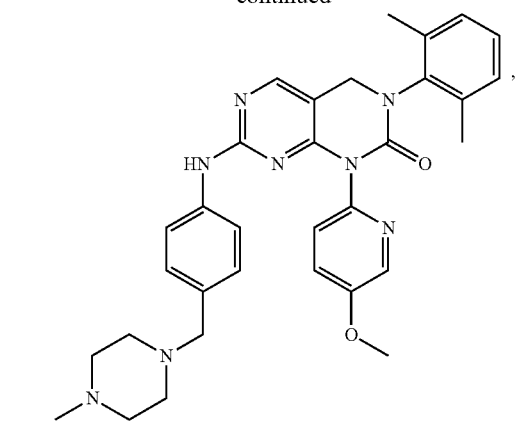
,
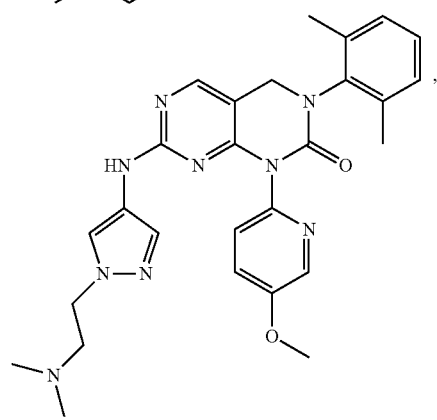
,
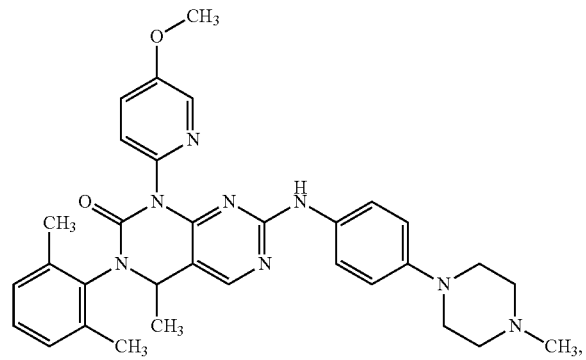
,
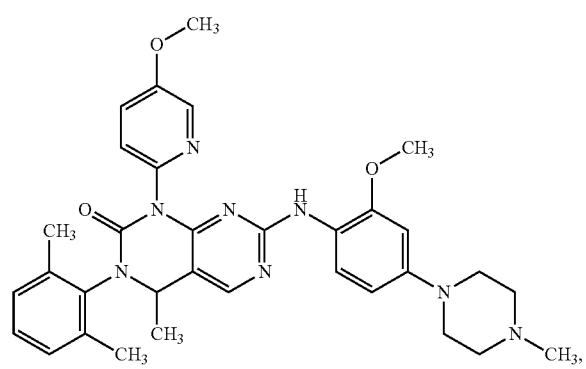
,
328
-continued
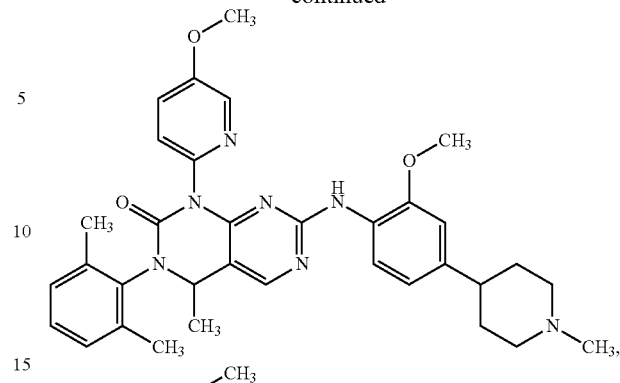
,
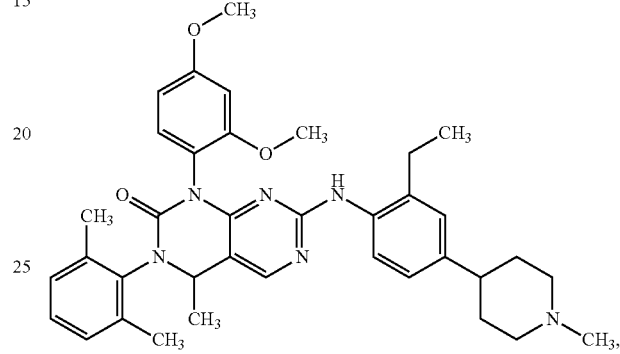
,
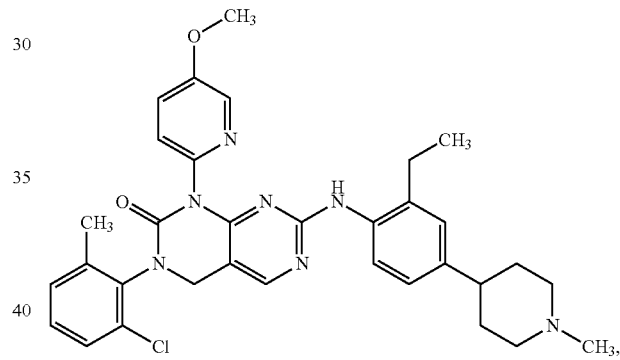
,
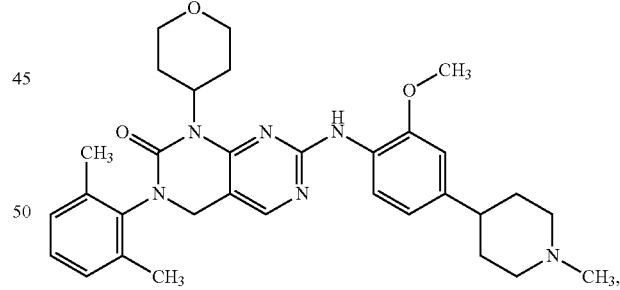
,
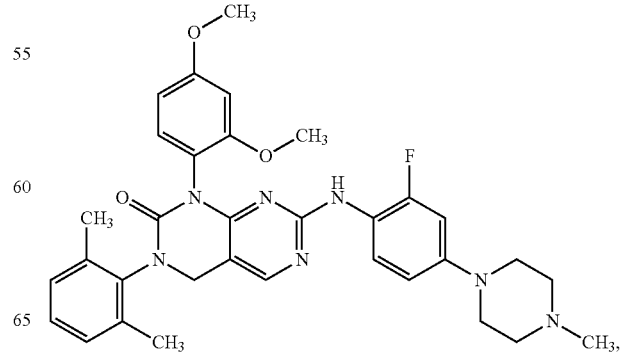
,

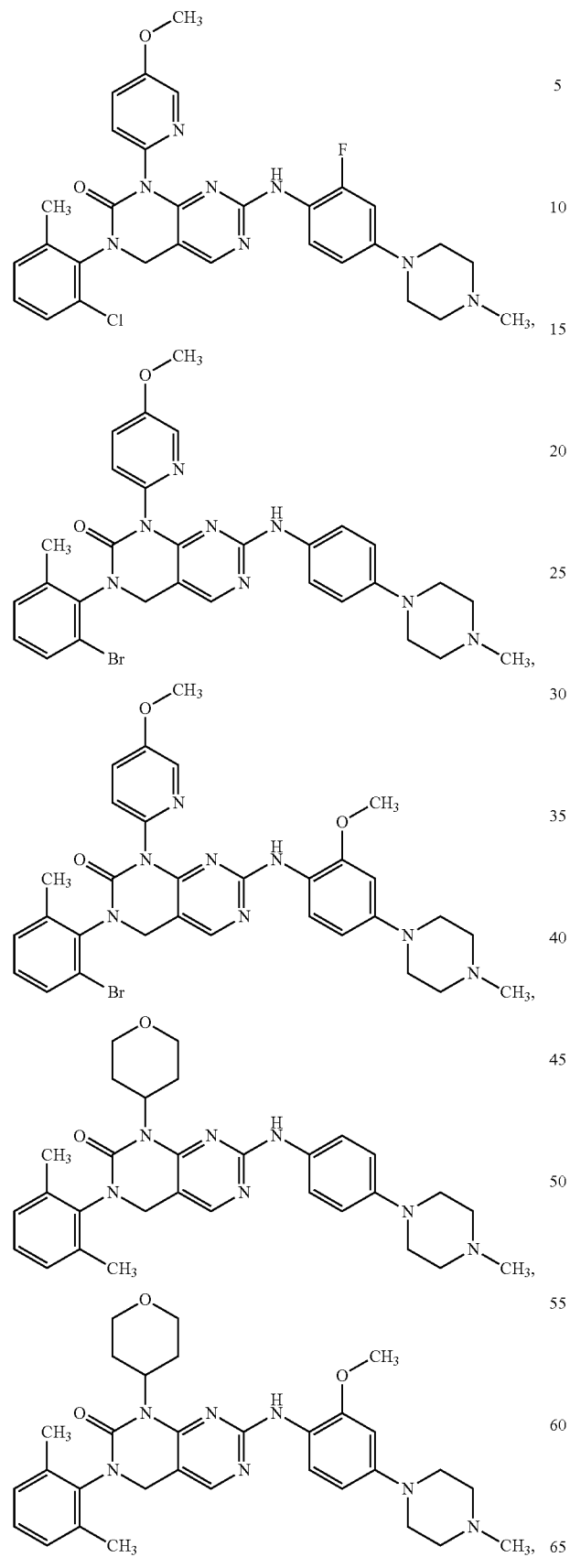
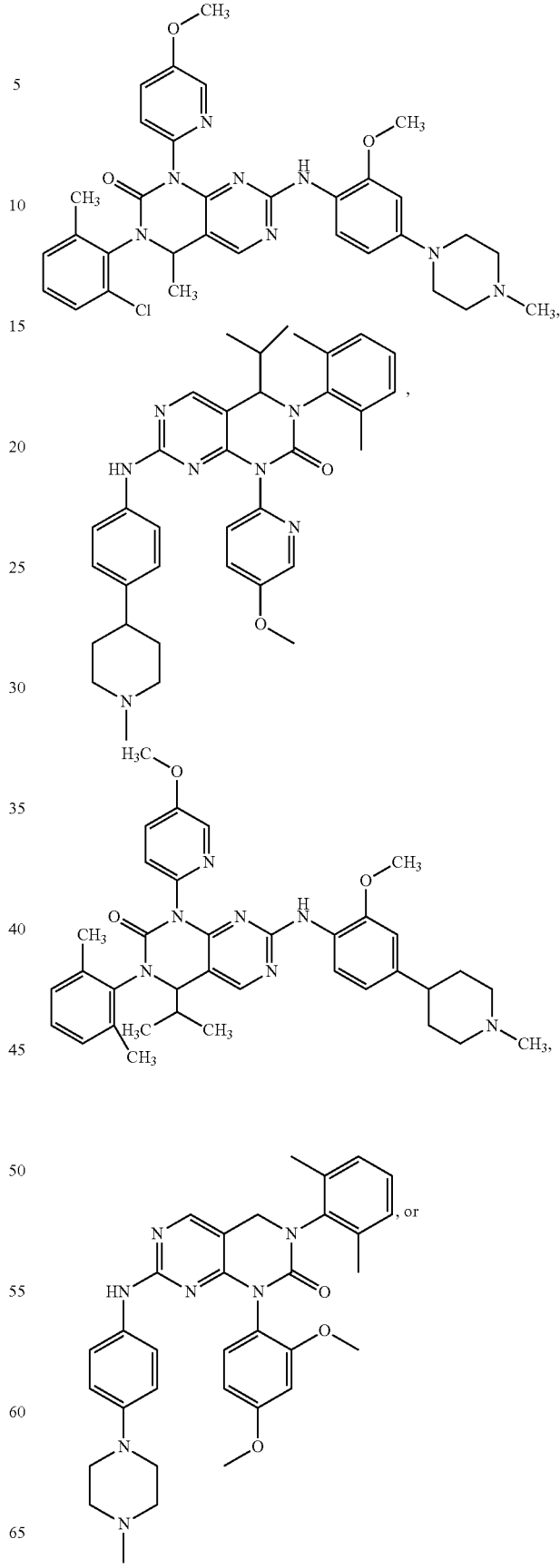

-continued
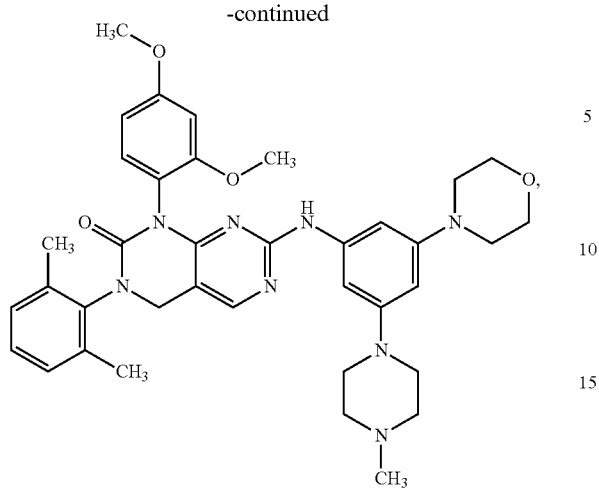
* * * * *

UNITED STATES PATENT AND TRADEMARK OFFICE
CERTIFICATE OF CORRECTION

PATENT NO. : 11,285,158 B2
APPLICATION NO. : 16/489462
DATED : March 29, 2022
INVENTOR(S) : David E. Fisher et al.

Page 1 of 8

It is certified that error appears in the above-identified patent and that said Letters Patent is hereby corrected as shown below:

In the Claims

In Column 318, Line 55:
Delete the following structure:

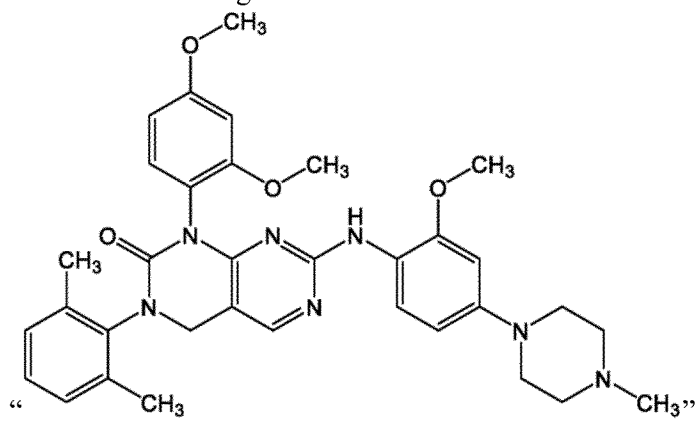

Replace with the following structure:

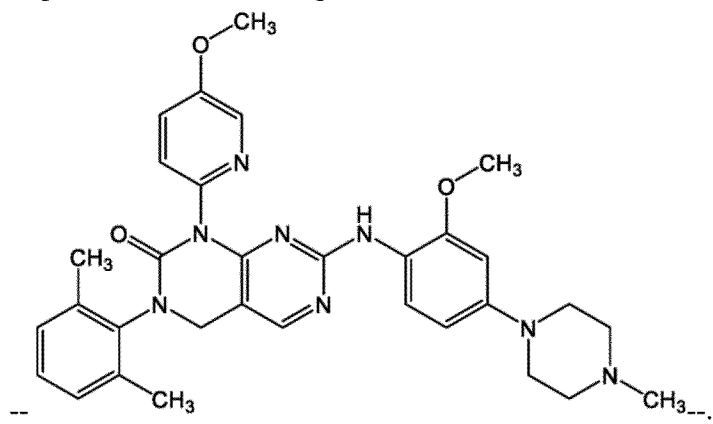

Signed and Sealed this
Eleventh Day of October, 2022

Katherine Kelly Vidal
*Director of the United States Patent and Trademark Office*

CERTIFICATE OF CORRECTION (continued)
U.S. Pat. No. 11,285,158 B2

In Column 320, Line 55:
Delete the following structure:

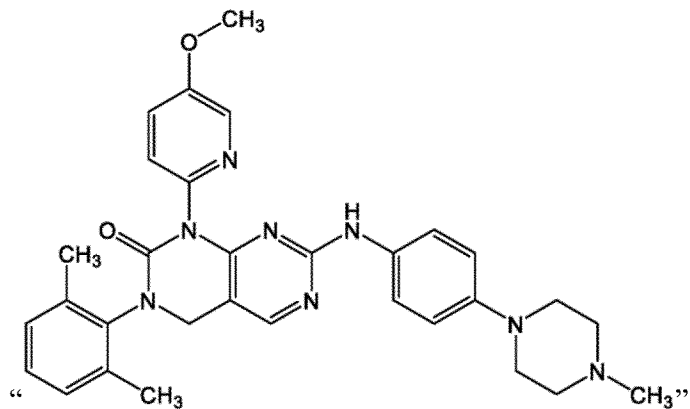

"

Replace with the following structure:

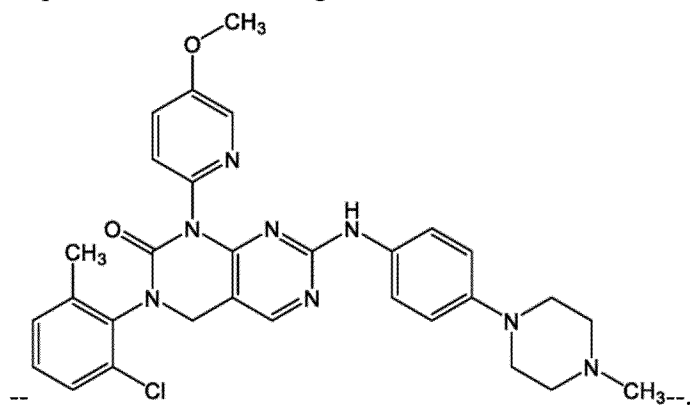

--.

In Column 321, Line 1:
Delete the following structure:

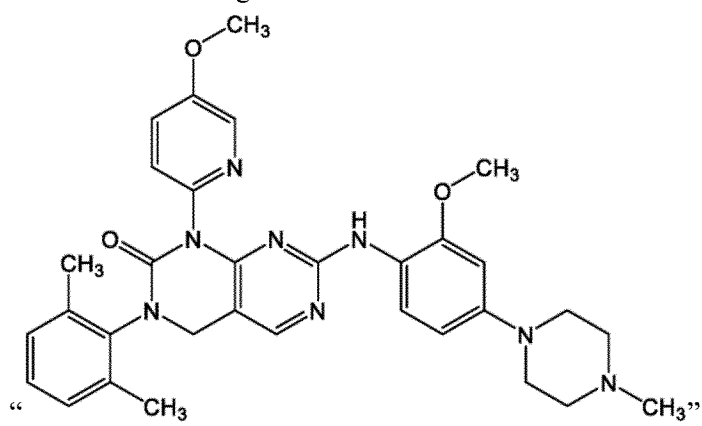

"

Replace with the following structure:
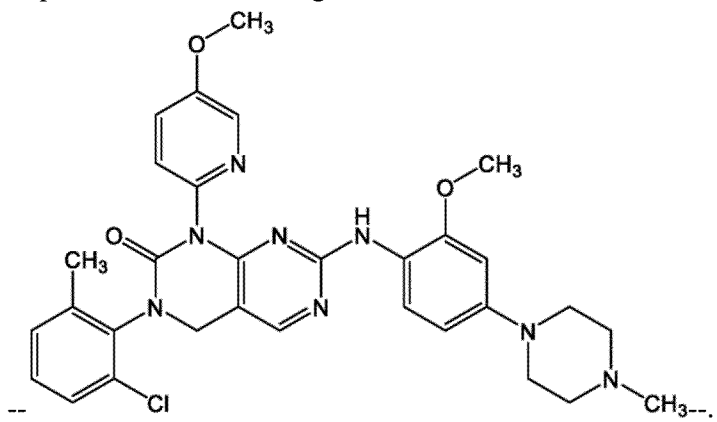
In Column 321, Line 20:
Delete the following structure:
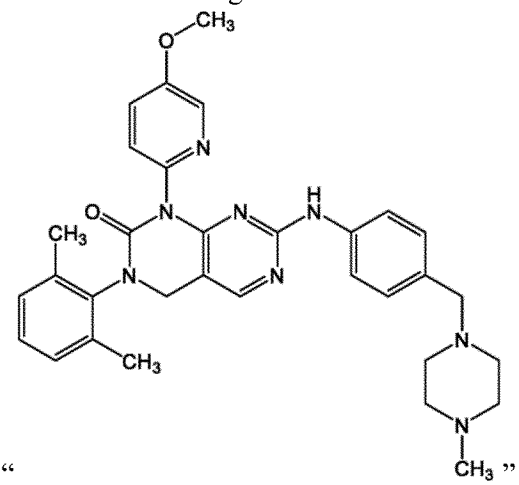
"  "
Replace with the following structure:
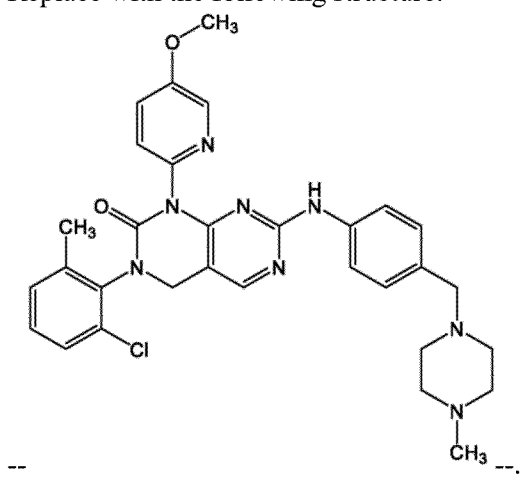

In Column 321, Line 40:
Delete the following structure:
"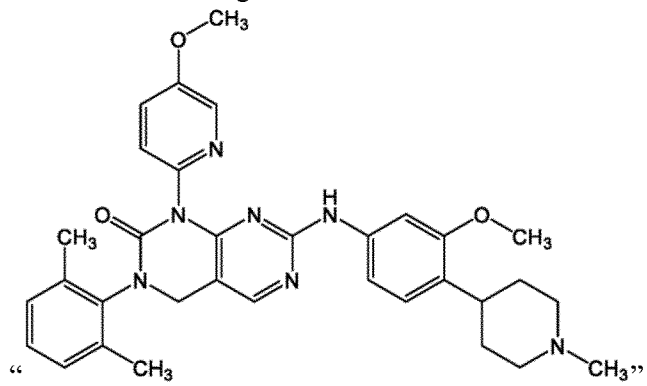"
Replace with the following structure:
--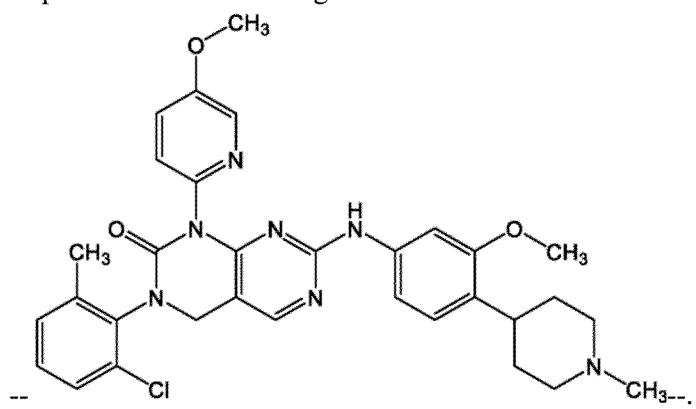--.
In Column 322, Line 40:
Delete the following structure:
"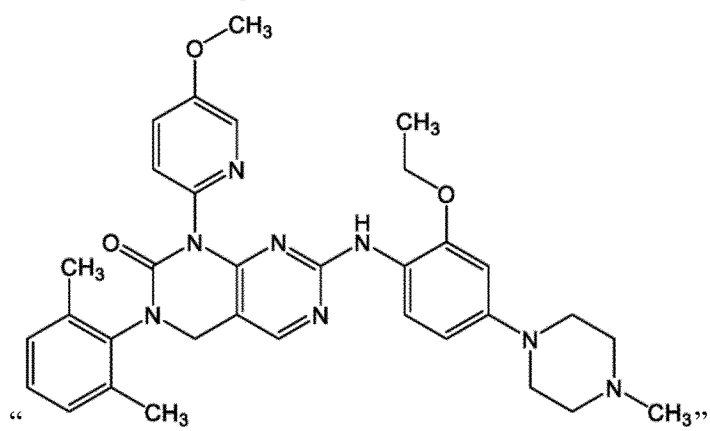"

Replace with the following structure:
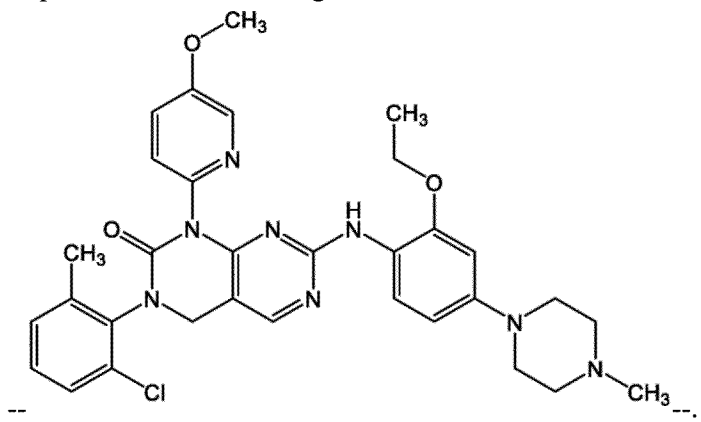
In Column 322, Line 55:
Delete the following structure:
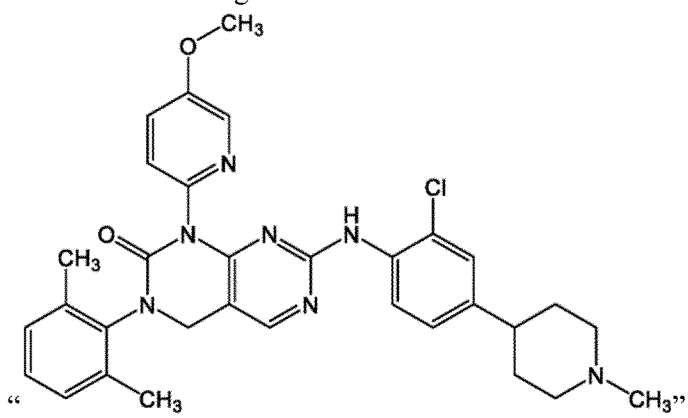
Replace with the following structure:
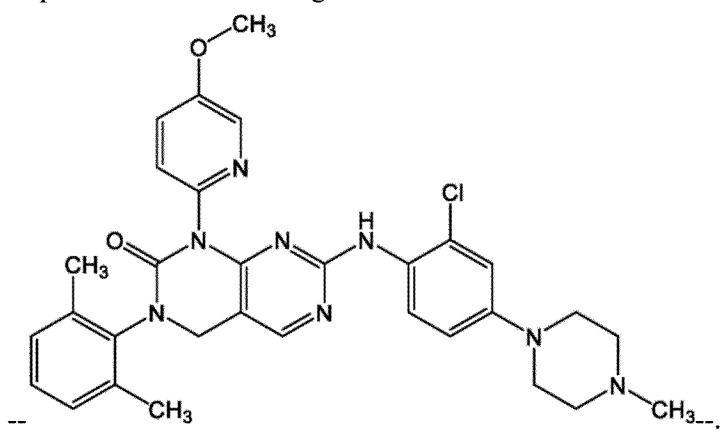

In Column 323, Line 1:
Delete the following structure:
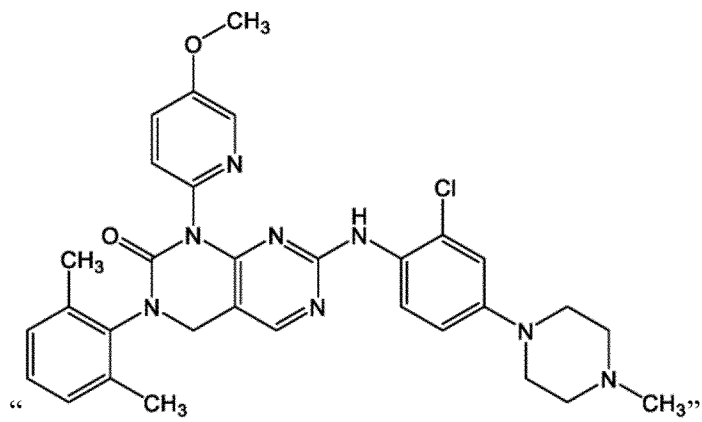
"
Replace with the following structure:
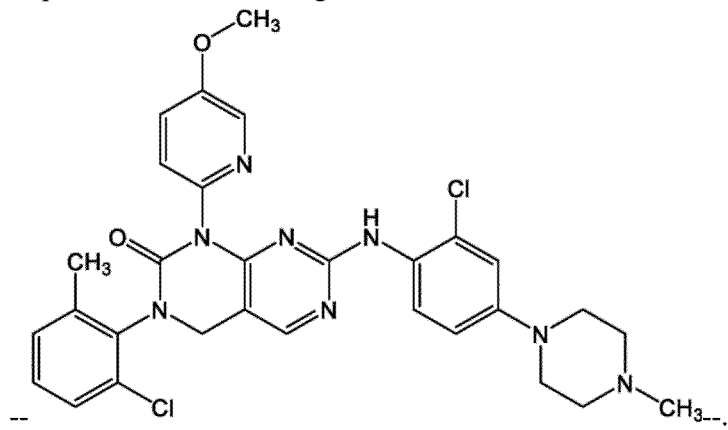
--.
In Column 323, Line 40:
Delete the following structure:
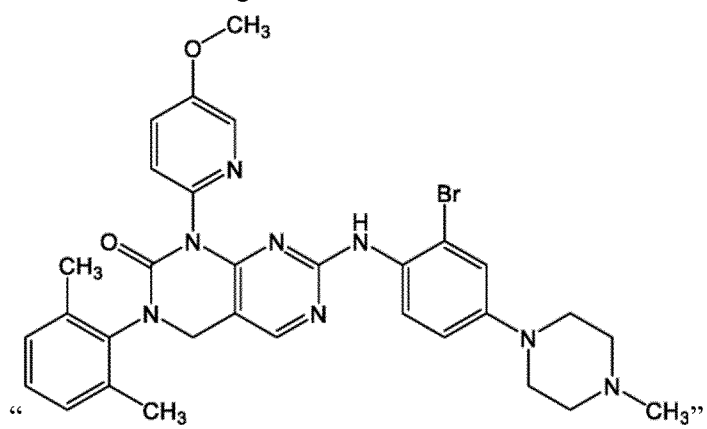
"

Replace with the following structure:
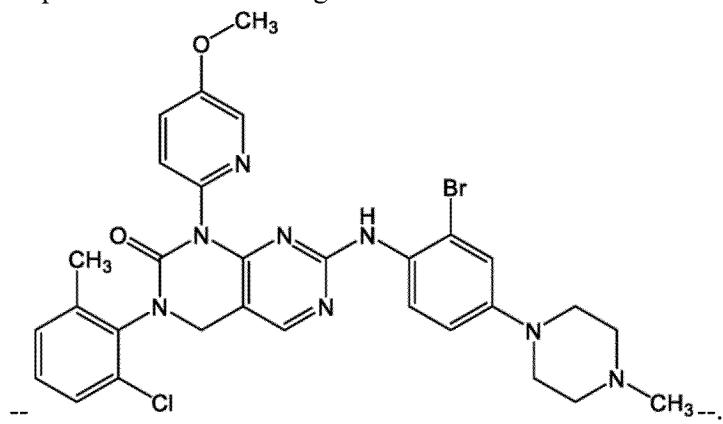
--
In Column 324, Line 40:
Delete the following structure:
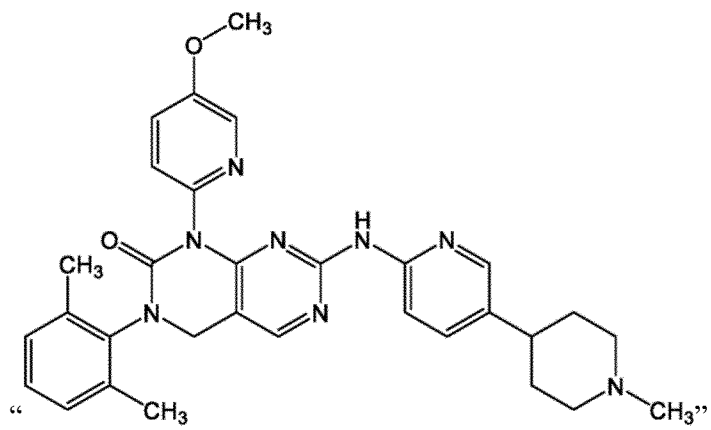
"
Replace with the following structure:
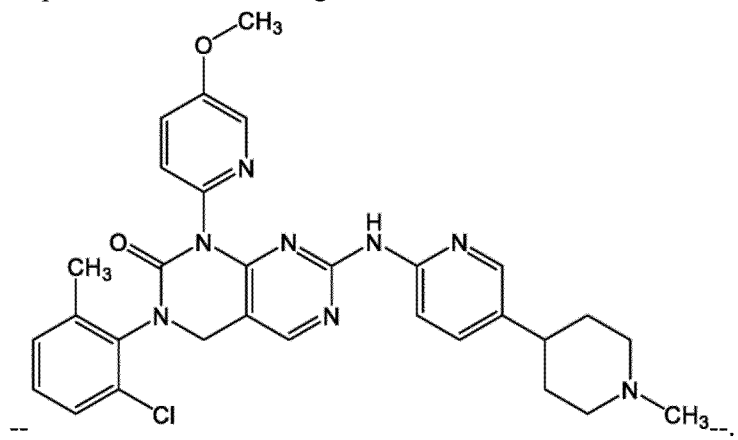
--

In Column 328, Line 40:
Delete the following structure:
"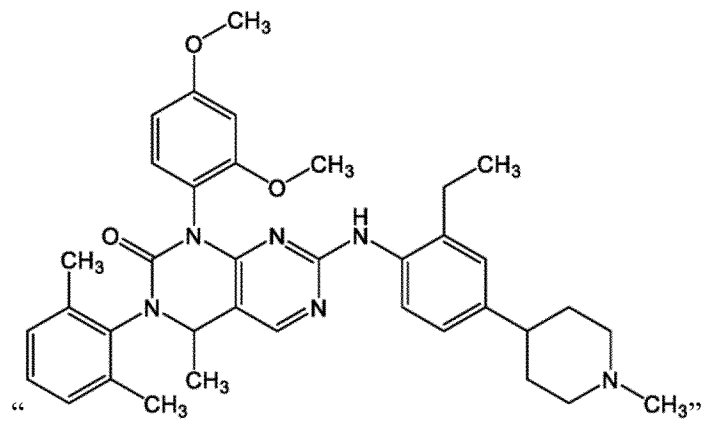"
Replace with the following structure:
--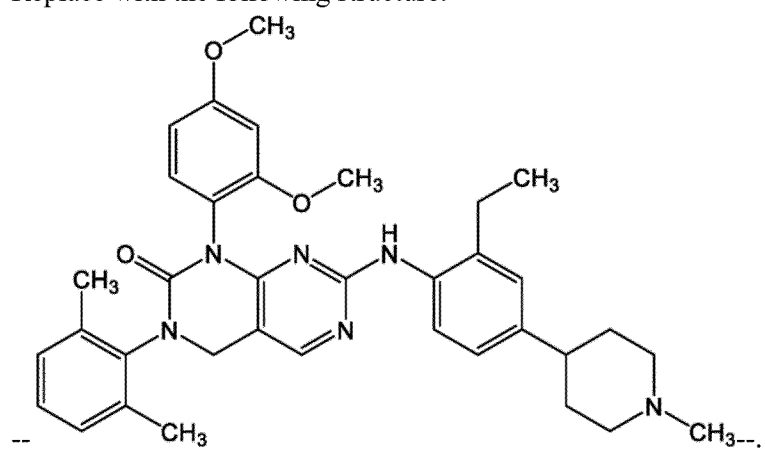--.

SEQUENCE LISTING

```
<160> NUMBER OF SEQ ID NOS: 1

<210> SEQ ID NO 1
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 1

Phe Ala Met Lys Lys Lys Val Ser Arg Ser Gly Leu Tyr Arg Ser Pro
1               5                   10                  15

Ser Met Pro Glu Asn Leu Asn Arg Pro Arg
            20                  25
```